United States Patent
Ogawa et al.

(10) Patent No.: US 8,017,638 B2
(45) Date of Patent: Sep. 13, 2011

(54) ISOXAZOLE DERIVATIVE AND ISOTHIAZOLE DERIVATIVE HAVING INHIBITORY ACTIVITY ON 11β-HYDROXYSTEROID DEHYDROGENASE TYPE 1

(75) Inventors: Tomoyuki Ogawa, Osaka (JP); Nobuo Chomei, Osaka (JP); Koji Masuda, Osaka (JP); Satoru Tanaka, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 147 days.

(21) Appl. No.: 12/293,246

(22) PCT Filed: Mar. 28, 2007

(86) PCT No.: PCT/JP2007/056538
§ 371 (c)(1),
(2), (4) Date: Sep. 16, 2008

(87) PCT Pub. No.: WO2007/114124
PCT Pub. Date: Oct. 11, 2007

(65) Prior Publication Data
US 2009/0131491 A1     May 21, 2009

(30) Foreign Application Priority Data
Mar. 30, 2006 (JP) ................. 2006-094057
Oct. 16, 2006 (JP) ................. 2006-280893

(51) Int. Cl.
*A61K 31/42* (2006.01)
*C07D 261/06* (2006.01)

(52) U.S. Cl. ........................ 514/380; 548/243
(58) Field of Classification Search .................. 514/380; 548/243
See application file for complete search history.

(56) References Cited

U.S. PATENT DOCUMENTS

| 4,562,187 A | 12/1985 | Tegeler et al. |
| 5,001,124 A | 3/1991 | Patterson et al. |
| 2005/0245532 A1 | 11/2005 | Hoff et al. |
| 2005/0245533 A1 | 11/2005 | Hoff et al. |
| 2005/0261302 A1 | 11/2005 | Hoff et al. |
| 2006/0148871 A1 | 7/2006 | Rohde et al. |

FOREIGN PATENT DOCUMENTS

| EP | 0 067 436 A2 | 12/1982 |
| EP | 1 460 071 A1 | 9/2004 |
| EP | 1 894 919 A1 | 3/2008 |
| EP | 1 953 145 A1 | 8/2008 |
| JP | 59-128306 A | 7/1984 |
| JP | 59-128326 A | 7/1984 |
| JP | 6-340641 | 12/1994 |
| JP | 2002-69061 A | 3/2002 |
| JP | 2005-509675 | 4/2005 |
| WO | WO 03/006454 A2 | 1/2003 |
| WO | WO 03/013517 A1 | 2/2003 |
| WO | WO 03/043999 A1 | 5/2003 |
| WO | 2004/058741 | 7/2004 |
| WO | WO 2004/056744 A1 | 7/2004 |
| WO | WO 2004/056745 A2 | 7/2004 |
| WO | WO 2004/058255 A1 | 7/2004 |
| WO | WO 2004/065351 A1 | 8/2004 |
| WO | WO 2004/089470 A2 | 10/2004 |
| WO | WO 2005/016877 A2 | 2/2005 |
| WO | WO 2005/097764 A1 | 10/2005 |
| WO | WO 2005/108359 A1 | 11/2005 |
| WO | WO 2005/108361 A1 | 11/2005 |
| WO | WO 2005/108368 A1 | 11/2005 |
| WO | WO 2006/002361 A2 | 1/2006 |
| WO | WO 2006/012227 A2 | 2/2006 |
| WO | WO 2006/024627 A2 | 3/2006 |
| WO | WO 2006/048750 A2 | 5/2006 |
| WO | WO 2006/074244 A2 | 7/2006 |
| WO | WO 2006/074330 A2 | 7/2006 |
| WO | WO 2006/024628 A1 | 9/2006 |
| WO | WO 2006/100502 A1 | 9/2006 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
International Search Report of PCT/JP2007/056538, dated Jun. 5, 2007.

(Continued)

*Primary Examiner* — Rebecca Anderson
*Assistant Examiner* — Samantha L Shterengarts
(74) *Attorney, Agent, or Firm* — Hamre, Schumann, Mueller & Larson, P.C.

(57) ABSTRACT

Disclosed is a compound useful as an inhibitor of 11β-hydroxysteroid dehydrogenase type 1.
A compound represented by the formula:

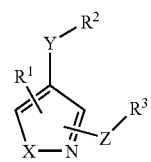

a pharmaceutically acceptable salt or solvate thereof,
wherein
$R^1$ is a group of the formula: —C(=O)NR$^4$R$^5$,
(wherein $R^4$ and $R^5$ are each independently, hydrogen, optionally substituted alkyl or the like) or
a group of the formula: —NR$^6$C(=O)R$^7$,
(wherein $R^6$ and $R^7$ are each independently, hydrogen, optionally substituted alkyl or the like),
X and Y are each independently —O— or the like,
Z is a bond or the like,
$R^2$ is optionally substituted alkyl, optionally substituted alkenyl or the like,
$R^3$ is optionally substituted alkyl, optionally substituted alkenyl or the like.

25 Claims, No Drawings

OTHER PUBLICATIONS

Stewart "11β-Hydroxysteroid dehydrogenase: implications for clinical medicine." Clinical Endocrinology, 44, 1994, pp. 493-499.

Kotelevtsev et al. "11β-Hydroxysteroid dehydrogenase type 1 knockout mice show attenuated glucocorticoid-inducible responses and resist hyperglycemia on obesity or stress." Proc.Natl. Acad. Sci. USA, vol. 94, Dec. 1997, pp. 14924-14929.

Walker et al. "Carbenoxolone Increases Hepatic Insulin Sensitivity in Man: A Novel Role for 11-Oxosteroid Reductase in Enhancing Glucocorticoid Receptor Activation." Journal of Clinical Endocrinology and Metabolism, vol. 80(11), 1995, pp. 3155-3159.

Bujalska et al. "Does central obesity reflect 'Cushing's disease of the omentum'?" The Lancet, vol. 349, Apr. 26, 1997, pp. 1210-1213.

Klötzer et al. "Reaktionen des 4-Methoxy-3, 5-dicarbomethoxy-isoxazols (v. Pechmann-Ester)." Monatschefte fuer Chemie, vol. 95(1), 1964, pp. 102-115.

Aβmann et al. "3-Mehtyl-4, 6-diphenylfuro[3,4-$d$]isoxazol—Ein nucs heterocyclisches System." Chem. Ber., 124, 1991, pp. 2481-2488.

Montori et al., "Waking up from the DREAM of preventing diabetes with drugs," 2007, BMJ, vol. 334, pp. 882-884.

* cited by examiner

ISOXAZOLE DERIVATIVE AND ISOTHIAZOLE DERIVATIVE HAVING INHIBITORY ACTIVITY ON 11β-HYDROXYSTEROID DEHYDROGENASE TYPE 1

FIELD OF THE INVENTION

This invention relates to a pharmaceutically useful compound with an inhibitory activity on 11β-hydroxysteroid dehydrogenase type 1, hereinafter referred to as 11β-HSD-1.

BACKGROUND ART

11β-HSD-1 is an enzyme that converts inactive steroids, 11β-dehydrosteroid into its active steroids and is considered to be important in the basal metabolic rate in the living body (Non-patent Document 1). Moreover, 11β-HSD-1 knockout mice have the resistance to hyperglycemia induced by obesity or stress (Non-patent Document 2). In addition, a similar phenomenon was observed in human on administration of 11β-HSD-1 inhibitor, carbenoxolone (Non-patent Document 3). These facts suggest that the 11β-HSD-1 inhibitors could be useful as drugs for the treatment of insulin independent diabetes or obesity (Non-patent Document 4).

The compounds having an isoxazole group have been described in Patent Document 1 as a useful compound for the treatment of hypertension as well as inflammation and the structures of them are limited to that without substituent at 4-position on an isoxazole group, and no compounds having the substituent on an isoxazole group such as the present compound have been described.

Patent Documents 2 to 4 disclose various compounds that have the inhibitory activity on 11β-hydroxysteroid dehydrogenase type 1.

Patent Documents 2 and 3 mainly disclose the compounds that have a phenyl group, but do not disclose the compounds that have an isoxazole group described in the present invention.

Patent Document 4 does not disclose the compounds having an isoxazole group described in the present invention.

Patent Documents 5 and 6 mainly disclose the compounds that have a phenyl group, but do not disclose the compounds that have an isoxazole group described in the present invention.

Patent Document 7 does not disclose the compounds having an isoxazole group described in the present invention.

[Patent Document 1] U.S. Pat. No. 4,562,187
[Patent Document 2] WO04/056744
[Patent Document 3] WO04/056745
[Patent Document 4] WO04/065351
[Patent Document 5] WO06/002361
[Patent Document 6] WO06/012227
[Patent Document 7] WO05/108368
[Non-patent Document 1] Clin. Endocrinol, 1996, 44, 493
[Non-patent Document 2] Proc. Nat. Acad. Sci. USA, 1997, 94, 14924
[Non-patent Document 3] J. Clin. Endocrinol. Metab. 1995, 80, 3155
[Non-patent Document 4] Lancet, 1997, 349, 1210

DISCLOSURE OF INVENTION

Problems to be Solved by the Invention

The present invention provides useful compounds having an inhibitory activity on 11β-hydroxysteroid dehydrogenase type 1.

Means for Solving the Problem

The present invention provides;
(1) A compound represented by the formula (I):

[Formula 1]

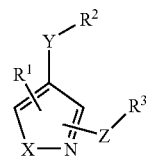

a pharmaceutically acceptable salt or a solvate thereof,
wherein
$R^1$ is a group of the formula: —C(=O)NR$^4$R$^5$,
   wherein $R^4$ and $R^5$ are each independently, hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^4$ and $R^5$ taken together with the adjacent nitrogen atom to which they are attached may form an optionally substituted ring or
a group of the formula: —NR$^6$C(=O)R$^7$,
   wherein $R^6$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted aralkyl or a group of the formula:—C(=O)R$^8$,
   $R^7$ and $R^8$ are each independently, hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^7$ and $R^8$ taken together with the adjacent carbon atom to which they are attached may form an optionally substituted ring,
X and Y are each independently, —O— or —S—,
Z is a bond, —O— or —S—,
$R^2$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl or optionally substituted carbamoyl,
$R^3$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted amino, optionally substituted sulfamoyl or a group of the formula: —R$^9$—C(R$^{10}$R$^{11}$)—R$^{12}$—R$^{13}$,
$R^9$ is —(CH$_2$)m-, wherein m is an integer of 0 to 3,
$R^{10}$ and $R^{11}$ are each independently, hydrogen, optionally substituted alkyl or halogen;
or $R^{10}$ and $R^{11}$ taken together with the adjacent carbon atom to which they are attached may form an optionally substituted ring, R[12] is —(CH$_2$)n-, wherein n is an integer of 0 to 3, R[13] is hydrogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkoxycarbonyl, optionally substituted aralkylcarbonyl, optionally substituted carbamoyl, optionally substituted thiocarbamoyl, optionally substituted alkylsulfonyl, optionally substituted arylsulfonyl, optionally substituted sulfamoyl, optionally substituted amino, optionally substituted carbamoyloxy, optionally substituted alkoxy, optionally substituted alkylthio, a group of the formula: —C(=O)—NR[14]R[15], wherein R[14] and R[15] are each independently, hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted arylsulfonyl, optionally substituted heteroarylsulfonyl or optionally substituted heterocyclesulfonyl; or R[14] and R[15] taken together with the adjacent nitrogen atom to which they are attached may form an optionally substituted ring or a group of the formula: —NR[16]R[17], wherein R[16] and R[17] are each independently, hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl or optionally substituted sulfamoyl; or R[16] and R[17] taken together with the adjacent nitrogen atom to which they are attached may form an optionally substituted ring, provided that, when R[2] encompasses a cyclic group and Y is —S—, then the compound is any one of compounds shown as follows,

[Formula 2]

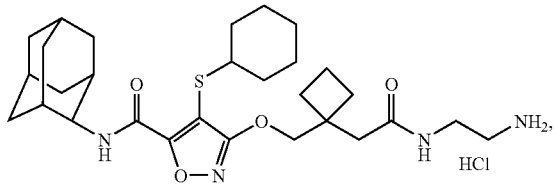

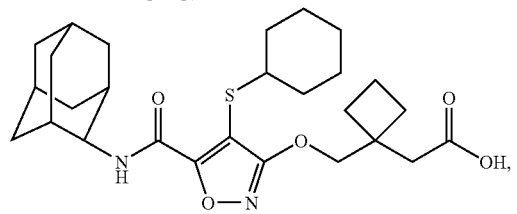

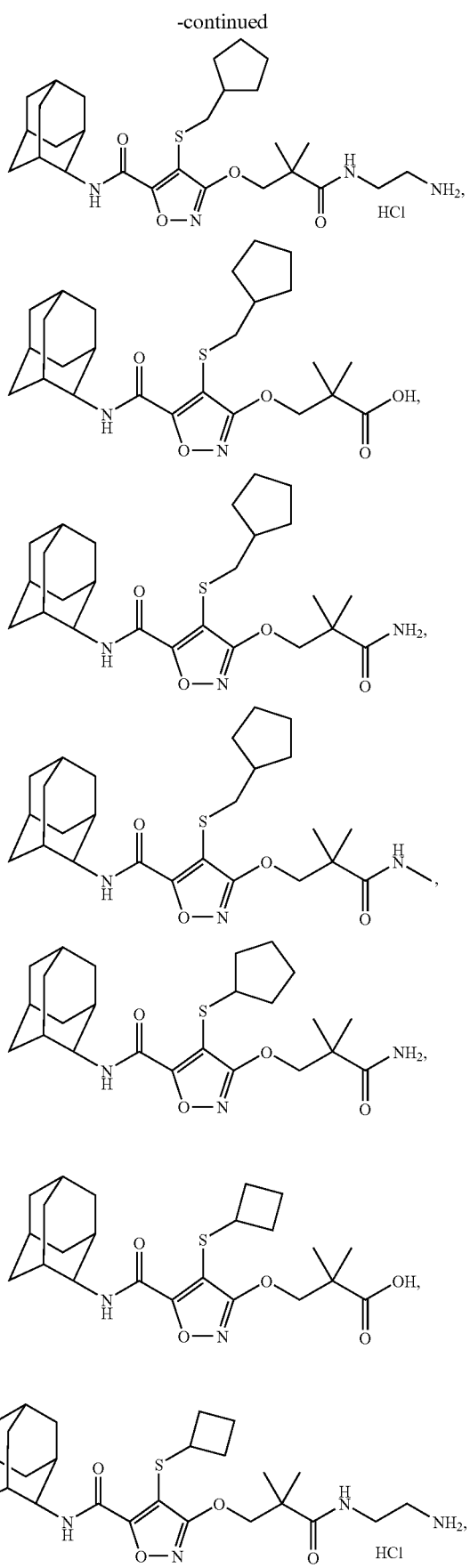

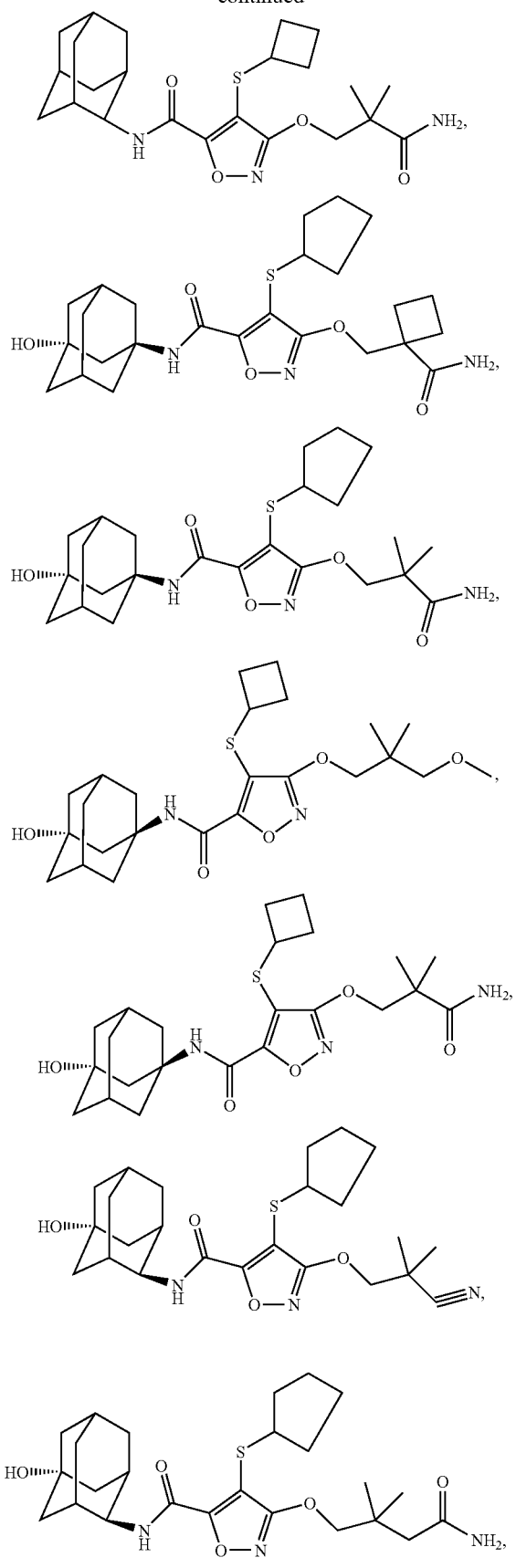
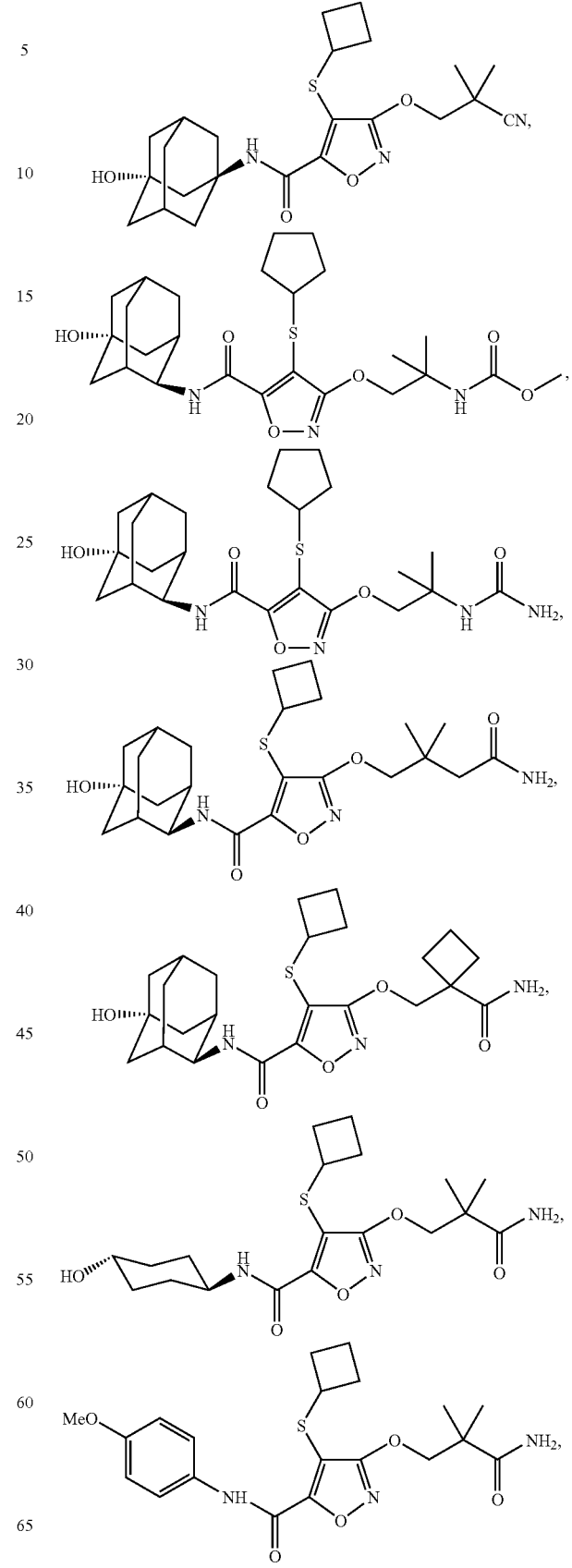

-continued

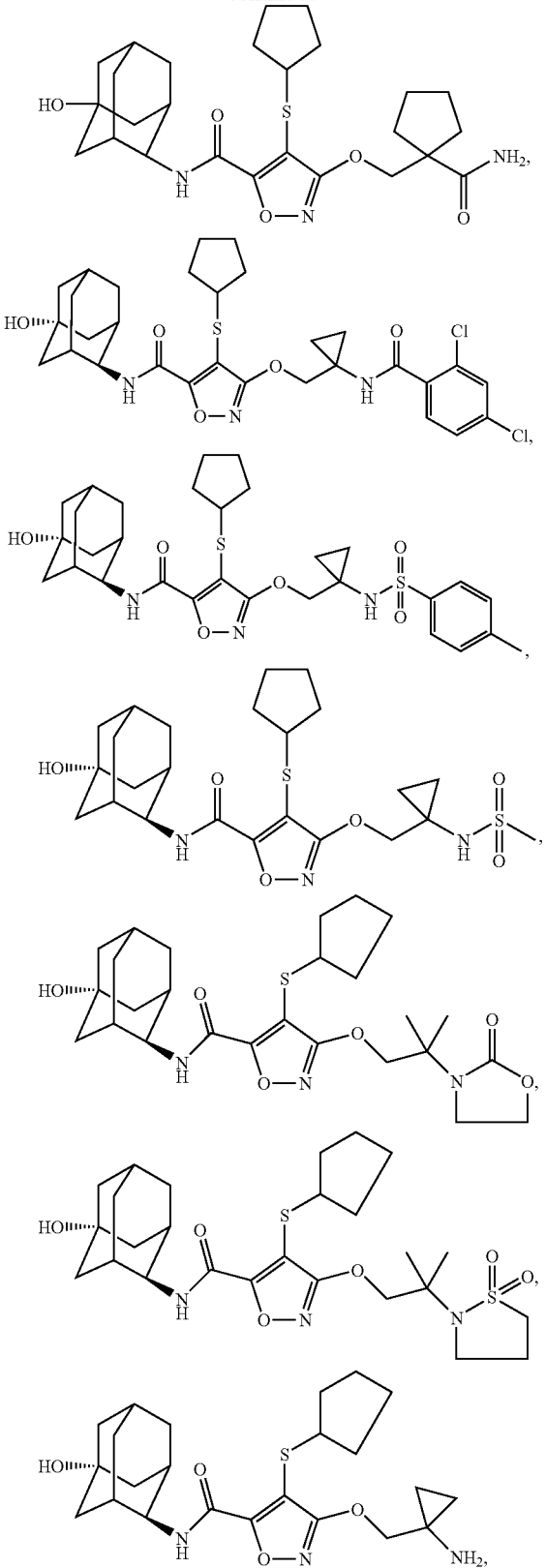

(2) The compound according to the above (1), a pharmaceutically acceptable salt or a solvate thereof, wherein the compound of the formula (I):

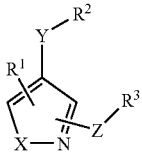

is a compound of the formula (II) represented below,

[Formula 5]

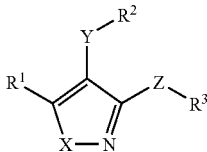

(3) The compound according to the above (2), a pharmaceutically acceptable salt or a solvate thereof, wherein $R^1$ is a group of the formula: —C(=O)$NR^4R^5$, wherein $R^4$ and $R^5$ have the same meaning as defined in the above (1), Y is —S— and z is 0, (4) The compound according to the above (1) or (2), a pharmaceutically acceptable salt or a solvate thereof, wherein $R^1$ is a group of the formula: —C(=O)$NR^4R^5$, wherein $R^4$ and $R^5$ have the same meaning as defined in the above (1), (5) The compound according to the above (3) or (4), a pharmaceutically acceptable salt or a solvate thereof, wherein either one of $R^4$ and $R^5$ is optionally substituted cycloalkyl, (6) The compound according to the above (5), a pharmaceutically acceptable salt or a solvate thereof, wherein either one of $R^4$ and $R^5$ is optionally substituted adamantly, (7) The compound according to the above (3) or (4), a pharmaceutically acceptable salt or a solvate thereof, wherein $R^1$ is a group of the formula (III):

[Formula 6]

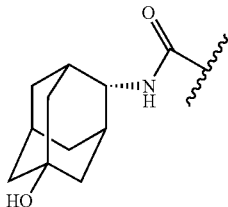

(8) The compound according to any one of the above (1) to (3), a pharmaceutically acceptable salt or a solvate thereof, wherein $R^2$ is optionally substituted alkyl, optionally substituted cycloalkyl, optionally substituted aryl, optionally substituted heteroaryl or optionally substituted heterocycle, (9) The compound according to the above (8), a pharmaceutically acceptable salt or a solvate thereof, wherein $R^2$ is optionally substituted alkyl wherein the substituent of said optionally substituted alkyl does not encompass a cyclic group, optionally substituted alkenyl wherein the substituent of said optionally substituted alkenyl does not encompass a cyclic group, optionally substituted alkynyl wherein the substituent of said optionally substituted alkynyl does not encompass a cyclic group, optionally substituted acyl wherein the substituent of said optionally substituted acyl does not encompass a cyclic group or optionally substituted carbamoyl wherein the substituent of said optionally substituted carbamoyl does not encompass a cyclic group,

(10) The compound according to the above (9), a pharmaceutically acceptable salt or a solvate thereof, wherein $R^2$ is optionally substituted alkyl wherein the substituent of said optionally substituted alkyl does not encompass a cyclic group,

(11) The compound according to the above (10), a pharmaceutically acceptable salt or a solvate thereof, wherein $R^2$ is branched alkyl,

(12) The compound according to any one of the above (1) to (3), a pharmaceutically acceptable salt or a solvate thereof, wherein $R^3$ is a group of the formula: —$R^9$—C($R^{10}R^{11}$)—$R^{12}$—$R^{13}$, wherein $R^9$, $R^{10}$, $R^{11}$, $R^{12}$ and $R^{13}$ have the same meaning as defined in the above (1),

(13) The compound according to the above (12), a pharmaceutically acceptable salt or a solvate thereof, wherein $R^9$ is —$CH_2$—,

(14) The compound according to the above (12) or (13), a pharmaceutically acceptable salt or a solvate thereof, wherein $R^{10}$ and $R^{11}$ are each independently, optionally substituted alkyl; or $R^{10}$ and $R^{11}$ taken together with the adjacent carbon atom to which they are attached may form an optionally substituted ring,

(15) The compound according to any one of the above (12) to (14), a pharmaceutically acceptable salt or a solvate thereof, wherein $R^{12}$ is —(CH$_2$)n- wherein n is an integer of 0 or 1,

(16) The compound according to any one of the above (12) to (15), a pharmaceutically acceptable salt or a solvate thereof, wherein $R^{13}$ is carboxy, cyano or heterocycle,

(17) The compound according to any one of the above (12) to (15), a pharmaceutically acceptable salt or a solvate thereof, wherein $R^{13}$ is a group of the formula: —C(=O)—$NR^{14}R^{15}$ wherein $R^{14}$ and $R^{15}$ are each independently hydrogen, optionally substituted alkyl, optionally substituted aryl, optionally substituted cycloalkyl, optionally substituted alkylsulfonyl, optionally substituted arylsulfonyl, optionally substituted heteroarylsulfonyl, optionally substituted heterocyclesulfonyl or optionally substituted heterocycle; or $R^{14}$ and $R^{15}$ taken together with the adjacent nitrogen atom to which they are attached may form an optionally substituted ring,

(18) The compound according to any one of the above (12) to (15), a pharmaceutically acceptable salt or a solvate thereof, wherein $R^{13}$ is a group of the formula: —$NR^{16}R^{17}$, wherein $R^{16}$ and $R^{17}$ have the same meaning as defined in the above (1),

(19) The compound according to the above (18), a pharmaceutically acceptable salt or a solvate thereof, wherein $R^{16}$ is a group of the formula: —C(=O)R', wherein R' is optionally substituted alkyl, optionally substituted alkenyl, optionally substituted cycloalkyl, optionally substituted aryl, optionally substituted amino or optionally substituted alkoxy,

(20) The compound according to any one of the above (1) to (3), a pharmaceutically acceptable salt or a solvate thereof, wherein X and/or Z is(are)-O—,

(21) The compound according to any one of the above (1) to (3), a pharmaceutically acceptable salt or a solvate thereof, wherein Y is —S—,

(22) A pharmaceutical composition which comprises the compound according to any one of the above (1) to (21), a pharmaceutically acceptable salt or a solvate thereof,

(23) The pharmaceutical composition according to the above (22) which has an inhibitory activity on 11β-hydroxysteroid dehydrogenase type 1,

(24) The pharmaceutical composition according to the above (22) or (23) for treating and/or preventing diabetes,

(25) A method for treating and/or preventing diabetes, comprising administering the compound of any one of the above (1) to (21), a pharmaceutically acceptable salt or a solvate thereof,

(26) A use of the compound of any one of the above (1) to (21), a pharmaceutically acceptable salt or a solvate thereof for the manufacture of a pharmaceutical composition for treating and/or preventing diabetes.

EFFECT OF THE INVENTION

The compounds of the present invention possess an inhibitory activity on 11β-hydroxysteroid dehydrogenase type 1 and the pharmaceutical compositions comprising them are very useful for a medicament, especially a medicament for treating and/or preventing hyperlipidemia, diabetes, obesity, arteriosclerosis, atherosclerosis, hyperglycemia and/or syndrome X. Moreover, the compounds of the present invention selectively inhibit 11β-hydroxysteroid dehydrogenase type 1. The preferable compounds in the present compounds have a high metabolic stability, a weak drug metabolizing enzyme induction, a weak drug metabolizing enzyme inhibition or a high oral absorption, and they are especially useful for a medicament. In addition, the present invention includes compounds having a low clearance and a long half-life period for exhibiting the drug activity.

BEST MODE FOR CARRYING OUT THE INVENTION

Terms used in the present specification are explained below. Each term has the following meanings alone or together with other terms.

"Alkyl" means a C1 to C10 straight or branched alkyl group, for example, methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferred is a C1 to C6 alkyl or a C1 to C4 alkyl, for example, methyl, ethyl, n-propyl, isopropyl, n-butyl, isobutyl, sec-butyl, tert-butyl, n-pentyl, isopentyl, neopentyl, n-hexyl, isohexyl.

"Alkenyl" means a C2 to C8 straight or branched alkenyl group, which includes a group having one or more double bond(s) in the above "alkyl". Exemplified is vinyl, 1-propenyl, 2-propenyl, 1-butenyl, 2-butenyl, 3-butenyl, 1,3-butadienyl, 3-methyl-2-butenyl or the like.

"Alkynyl" means a C2 to C8 straight or branched alkynyl group, which includes a group having one or more triple bond(s) in the above "alkyl". Exemplified is ethynyl, propynyl, butynyl or the like.

"Cycloalkyl" means a C3 to C15 saturated cyclic hydrocarbon group. Bridged cyclic hydrocarbon group is also included. Exemplified is cyclopropyl, cyclobutyl, cyclopentyl, cyclohexyl, cycloheptyl, cyclooctyl or bridged cyclic hydrocarbon group, exemplified as follows. Preferred is cyclopropyl, cyclobutyl, cyclopentyl, cyclohexyl, bridged cyclic hydrocarbon group, exemplified as follows or the like.

[Formula 7]

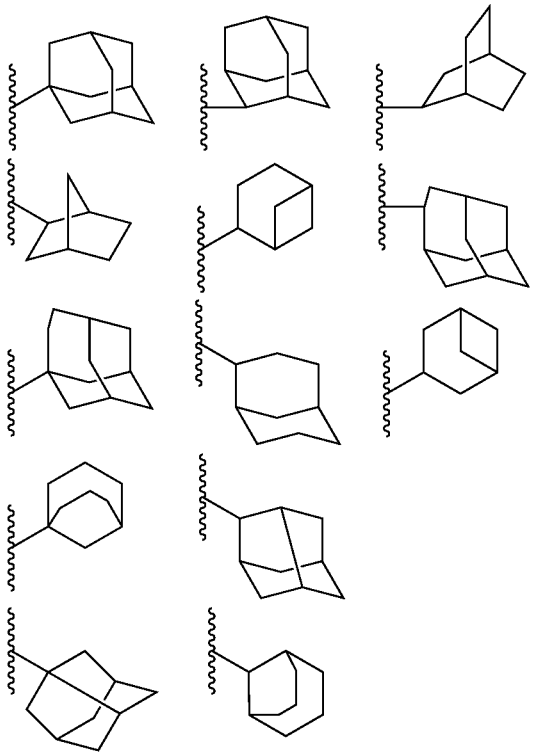

"Cycloalkenyl" means a C3 to C15 cyclic unsaturated aliphatic hydrocarbon group. Exemplified is cyclopropenyl, cyclobutenyl, cyclopentenyl, cyclohexenyl or cycloheptenyl. Preferred is cyclopropenyl, cyclobutenyl, cyclopentenyl or cyclohexenyl. Cycloalkenyl includes a bridged cyclic hydrocarbon group having unsaturated bond in the ring. Exemplified is a group having one or two double bond(s) in the above exemplified bridged cyclic hydrocarbon group.

"Aryl" means a monocyclic aromatic hydrocarbon group (e.g., phenyl) or a fused aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc.). Preferred is phenyl or naphthyl (1-naphthyl, 2-naphthyl) or the like.

"Heteroaryl" means a monocyclic aromatic heterocyclic group or fused aromatic heterocyclic group.

The monocyclic aromatic heterocyclic group means a group derived from 5 to 8-membered aromatic ring which may contain 1 to 4 oxygen, sulfur and/or nitrogen atom(s) in the ring. The binding bond can be at any substitutable position.

The fused aromatic heterocyclic group means a group derived from 5 to 8-membered aromatic ring which may contain 1 to 4 oxygen, sulfur and/or nitrogen atom(s) in the ring fused with one to four of 5 to 8-membered aromatic carbocycle(s) or other 5 to 8-membered aromatic heterocycle(s). The binding bond can be at any substitutable position.

"Heteroaryl" includes, for example, furyl (e.g., furan-2-yl or furan-3-yl), thienyl (e.g., thiophene-2-yl or thiophene-3-yl), pyrrolyl (e.g., pyrrole-1-yl, pyrrole-2-yl or pyrrole-3-yl), imidazolyl (e.g., imidazole-1-yl, imidazole-2-yl or imidazole-4-yl), pyrazolyl (e.g., pyrazole-1-yl, pyrazole-3-yl or pyrazole-4-yl), triazolyl (e.g., 1,2,4-triazole-1-yl, 1,2,4-triazole-3-yl or 1,2,4-triazole-4-yl), tetrazolyl (e.g., tetrazole-1-yl, tetrazole-2-yl or tetrazole-5-yl), oxazolyl (e.g., oxazole-2-yl, oxazole-4-yl or oxazole-5-yl), isoxazolyl (e.g., isoxazole-3-yl, isoxazole-4-yl or isoxazole-5-yl), thiazolyl (e.g., thiazole-2-yl, thiazole-4-yl or thiazole-5-yl), thiadiazolyl, isothiazolyl (e.g., isothiazole-3-yl, isothiazole-4-yl or isothiazole-5-yl), pyridyl (e.g., pyridine-2-yl, pyridine-3-yl or pyridine-4-yl), pyridazinyl (e.g., pyridazine-3-yl or pyridazine-4-yl), pyrimidinyl (e.g., pyrimidine-2-yl, pyrimidine-4-yl or pyrimidine-5-yl), furazanyl (e.g., furazan-3-yl), pyrazinyl (e.g., pyrazine-2-yl), oxadiazolyl (e.g., 1,3,4-oxadiazole-2-yl), benzofuryl (e.g., benzo[b]furan-2-yl, benzo[b]furan-3-yl, benzo[b]furan-4-yl, benzo[b]furan-5-yl, benzo[b]furan-6-yl or benzo[b]furan-7-yl), benzothienyl (e.g., benzo[b]thiophene-2-yl, benzo[b]thiophene-3-yl, benzo[b]thiophene-4-yl, benzo[b]thiophene-5-yl, benzo[b]thiophene-6-yl or benzo[b]thiophene-7-yl), benzimidazolyl (e.g., benzimidazole-1-yl, benzimidazole-2-yl, benzimidazole-4-yl or benzimidazole-5-yl), dibenzofuryl, benzoxazolyl, quinoxalyl (e.g., quinoxaline-2-yl, quinoxaline-5-yl or quinoxaline-6-yl), cinnolyl (e.g., cinnoline-3-yl, cinnoline-4-yl, cinnoline-5-yl, cinnoline-6-yl, cinnoline-7-yl or cinnoline-8-yl), quinazolyl (e.g., quinazoline-2-yl, quinazoline-4-yl, quinazoline-5-yl, quinazoline-6-yl, quinazoline-7-yl or quinazoline-8-yl), quinolyl (e.g., quinoline-2-yl, quinoline-3-yl, quinoline-4-yl, quinoline-5-yl, quinoline-6-yl, quinoline-7-yl or quinoline-8-yl), phthalazinyl (e.g., phthalazine-1-yl, phthalazine-5-yl or phthalazine-6-yl), isoquinolyl (e.g., isoquinoline-1-yl, isoquinoline-3-yl, isoquinoline-4-yl, isoquinoline-5-yl, isoquinoline-6-yl, isoquinoline-7-yl or isoquinoline-8-yl), puryl, pteridinyl (e.g., pteridine-2-yl, pteridine-4-yl, pteridine-6-yl or pteridine-7-yl), carbazolyl, phenanthridinyl, acridinyl (e.g., acridine-1-yl, acridine-2-yl, acridine-3-yl, acridine-4-yl or acridine-9-yl), indolyl (e.g., indole-1-yl, indole-2-yl, indole-3-yl, indole-4-yl, indole-5-yl, indole-6-yl or indole-7-yl), isoindolyl, phenazinyl (e.g., phenazine-1-yl or phenazine-2-yl), phenothiazinyl (e.g., phenothiazine-1-yl, phenothiazine-2-yl, phenothiazine-3-yl or phenothiazine-4-yl) or the like.

"Heterocycle" means a nonaromatic heterocycle group which may contain 1 to 4 oxygen, sulfur and/or nitrogen atom(s) in the ring. The binding bond can be at any substitutable position. Moreover, the nonaromatic heterocycle group can be bridged with a C1 to C4 alkyl chain or can be fused with cycloalkane (preferred is 5 to 6-membered ring) or benzene ring. Heterocycle can be saturated or unsaturated, as long as it is nonaromatic. Preferred is 5 to 8-membered ring. Exemplified is 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, or the following groups.

[Formula 8]

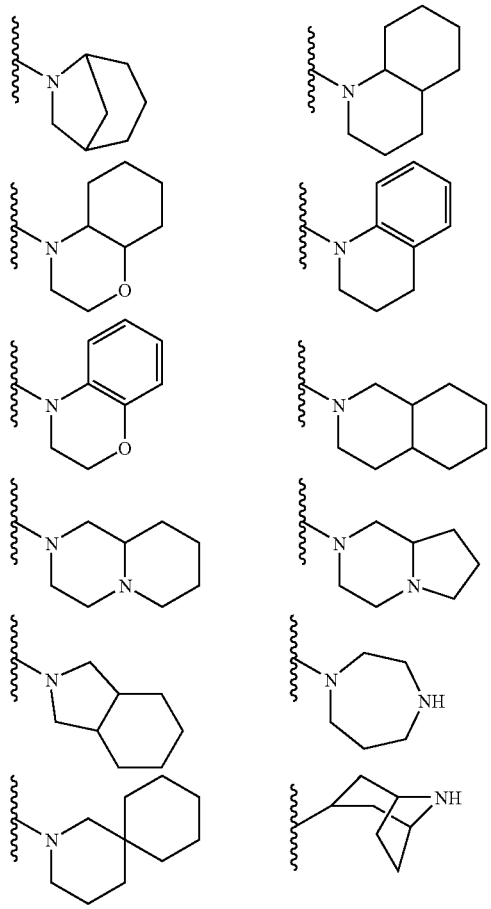

[Formula 9]

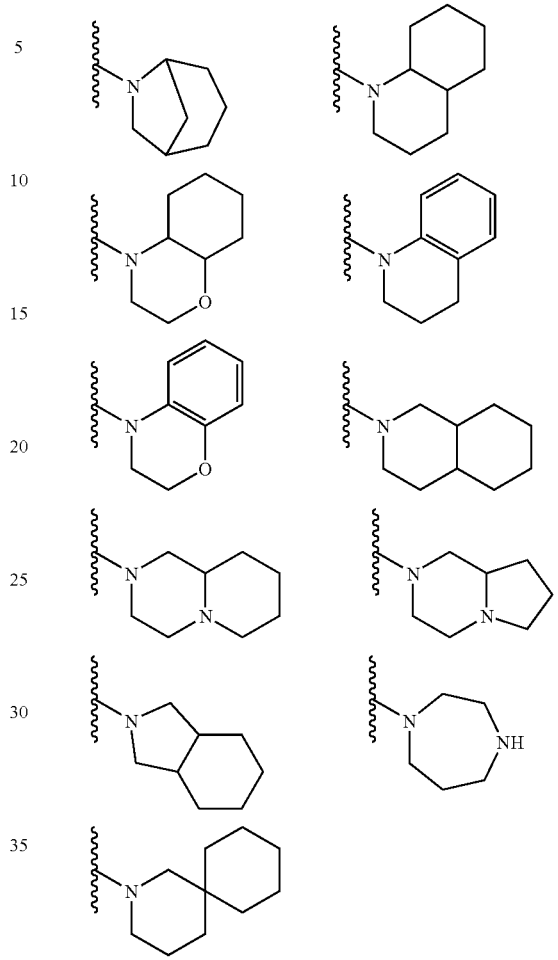

The alkyl part of "alkoxy" and "alkylthio" is the same as the above "alkyl".

"Aralkyl" means the above alkyl substituted with 1 to 3 of the above aryl.

"Acyl" means formyl, optionally substituted alkylcarbonyl, optionally substituted alkenylcarbonyl, optionally substituted cycloalkylcarbonyl, optionally substituted cycloalkenylcarbonyl, optionally substituted arylcarbonyl, optionally substituted heteroarylcarbonyl or optionally substituted heterocyclecarbonyl.

"Halogen" means F, Cl, Br or I. Preferred is F or Cl.

"A ring formed by taking together $R^4$ and $R^5$ with the adjacent nitrogen atom to which they are attached" means 3 to 15-membered nonaromatic hetero ring which may contain 1 to 4 oxygen, sulfur, and/or nitrogen atom(s) besides the above nitrogen atom in the ring. The nonaromatic hetero ring can be bridged with C1 to C4 alkyl chain and can be fused with cycloalkane (preferred is 5 to 6-membered ring) or benzene ring. The ring can be saturated or unsaturated, as long as it is nonaromatic. Preferred is 5 to 8-membered ring. For example, a group of the formula: —$NR^4R^5$ wherein $R^4$ and $R^5$ taken together with the adjacent nitrogen atom to which they are attached may form an optionally substituted ring are exemplified as follows. 1-Pyrrolinyl, 1-pyrrolidinyl, 1-imidazolinyl, 1-imidazolidinyl, 1-pyrazolinyl, 1-pyrazolidinyl, piperidino, morpholino and the following group are exemplified.

"A ring formed by taking together $R^7$ and $R^8$ with the adjacent carbon atom to which they are attached" means nonaromatic hetero ring which may contain 1 to 4 oxygen, sulfer, and/or nitrogen atom(s) besides the nitrogen atom in the ring. The nonaromatic hetero ring can be fused with cycloalkane (preferred is 5 to 6-membered ring) or cycloalkene (preferred is 5 to 6-membered ring) and be bridged with C1 to C4 alkyl chain or hetero atom. The ring can be saturated or unsaturated, as long as it is nonaromatic. For example, a group of the formula: —N(—C(=O)$R^7$)(—C(=O)$R^8$) wherein $R^7$ and $R^8$ taken together with the adjacent carbon atom to which they are attached may form an optionally substituted ring are exemplified as follows.

[Formula 10]

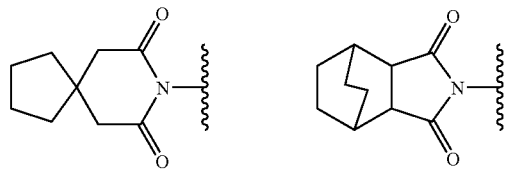

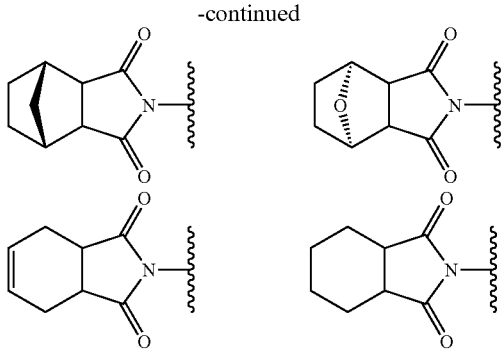

"A ring formed by taking together $R^{10}$ and $R^{11}$ with the adjacent carbon atom to which they are attached" means 3 to 15-membered saturated or unsaturated hydrocarbon ring or 3 to 15-membered saturated or unsaturated hetero ring containing 1 to 4 oxygen, sulfer, and/or nitrogen atom(s) in said hydrocarbon ring. Preferred is nonaromatic ring, for example, cyclopropane, cyclobutane, cyclopentane, cyclohexane, cycloheptane, cyclooctane, cyclopropene, cyclobutene, cyclopentene, cyclohexene, cycloheptene, or the like. Exemplified is saturated or unsaturated hetero ring containing 1 to 4 oxygen, sulfur, and/or nitrogen atom(s) in the hydrocarbon ring.

For example, a group of the formula: $-C(R^{10}R^{11})-$, wherein $R^{10}$ and $R^{11}$ taken together with the adjacent carbon atom to which they are attached may form an optionally substituted ring, is exemplified as follows.

[Formula 11]

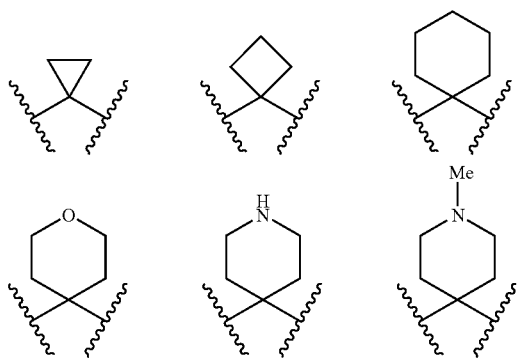

"A ring formed by taking together $R^{14}$ and $R^{15}$ with the adjacent nitrogen atom to which they are attached" and "a ring formed by taking together $R^{16}$ and $R^{17}$ with the adjacent nitrogen atom to which they are attached" mean 3 to 15-membered nonaromatic hetero ring which may contain 1 to 4 oxygen, sulfer, and/or nitrogen atom(s) besides the above nitrogen atom in the ring. The nonaromatic hetero ring can be bridged with C1 to C4 alkyl chain and be fused with cycloalkane (preferred is 5 to 6-membered ring) or benzene ring. The ring can be saturated or unsaturated, as long as it is nonaromatic. Preferred is 5 to 8-membered ring. For example, a group of the formula: $-NR^{14}R^{15}$ wherein $R^{14}$ and $R^{15}$ taken together with the adjacent nitrogen atom to which they are attached may form an optionally substituted ring and a group of the formula: $-NR^{16}R^{17}$ wherein $R^{16}$ and $R^{17}$ taken together with the adjacent nitrogen atom to which they are attached may form an optionally substituted ring are exemplified as follows. 1-Pyrrolinyl, 1-pyrrolidinyl, 1-imidazolinyl, 1-imidazolidinyl, 1-pyrazolinyl, 1-pyrazolidinyl, piperidino, morpholino and the following group are exemplified.

[Formula 12]

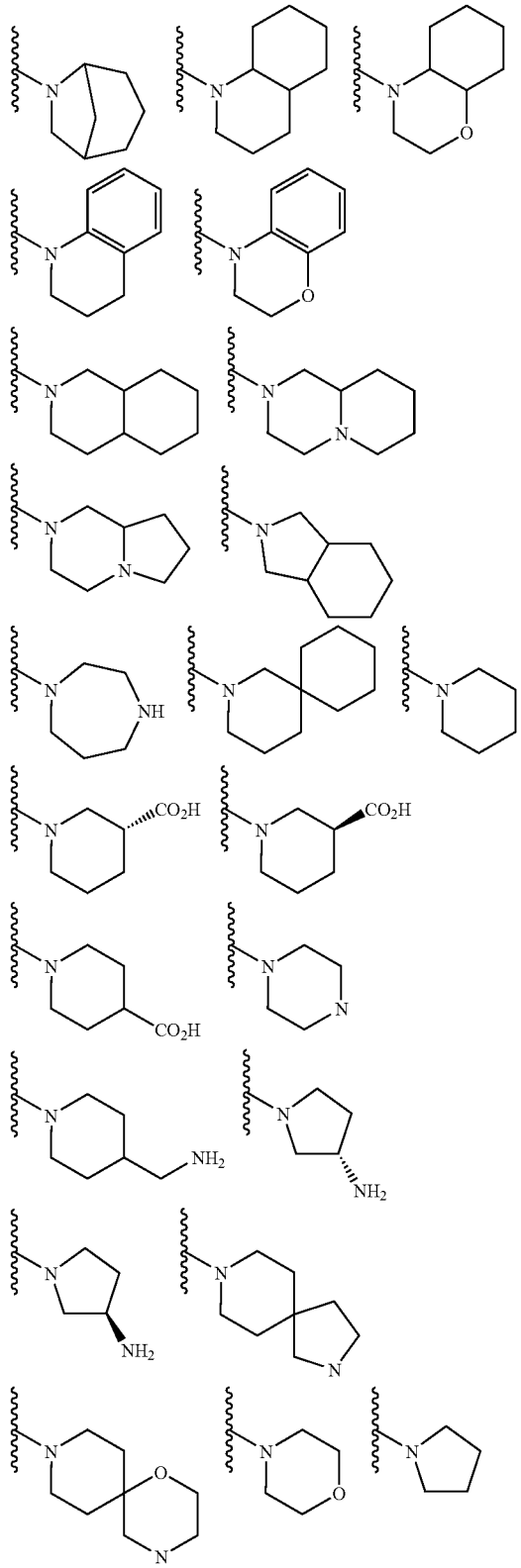

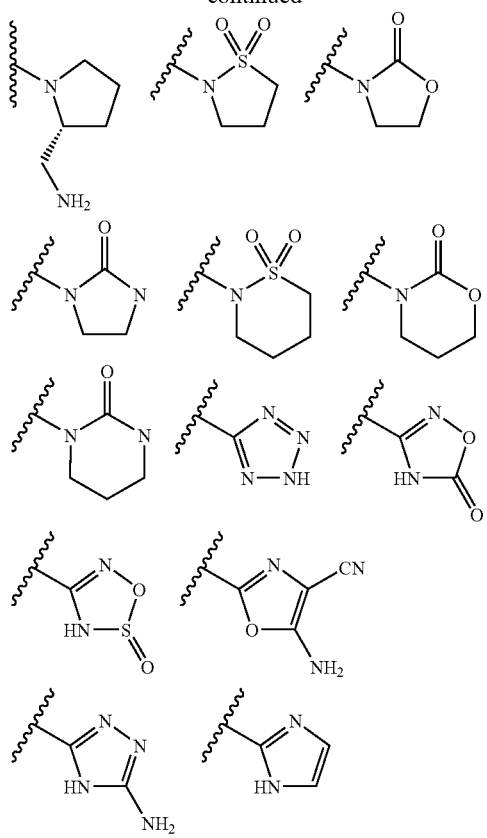

"Optionally substituted alkyl", "optionally substituted alkenyl", "optionally substituted alkynyl", "optionally substituted cycloalkyl", "optionally substituted cycloalkenyl", "optionally substituted aryl", "optionally substituted heteroaryl", "optionally substituted heterocycle", "optionally substituted acyl", "optionally substituted alkoxycarbonyl", "optionally substituted aralkylcarbonyl", "optionally substituted alkoxy", "optionally substituted alkylthio", "optionally substituted alkylsulfonyl", "optionally substituted arylsulfonyl", "a ring formed by taking together $R^4$ and $R^5$ with the adjacent nitrogen atom to which they are attached", "a ring formed by taking together $R^7$ and $R^8$ with the adjacent carbon atom to which they are attached", "a ring formed by taking together $R^{10}$ and $R^{11}$ with the adjacent carbon atom to which they are attached", "a ring formed by taking together $R^{14}$ and $R^{15}$ with the adjacent nitrogen atom to which they are attached" and "a ring formed by taking together $R^{16}$ and $R^{17}$ with the adjacent nitrogen atom to which they are attached" may be substituted with 1 to 4 substituent(s) selected from a group consisting of, for example, hydroxy, carboxy, halogen, halogenated alkyl (e.g.: —$CF_3$, —$CH_2CF_3$, —$CH_2CCl_3$),
alkyl (e.g.: methyl, ethyl, isopropyl, tert-butyl),
alkenyl (e.g.: vinyl),
alkynyl (e.g.: ethynyl),
cycloalkyl (e.g.: cyclopropyl),
cycloalkenyl (e.g.: cyclopropenyl),
alkoxy (e.g.: methoxy, ethoxy, propoxy, butoxy),
alkenyloxy (e.g.: vinyloxy, allyloxy),
alkoxycarbonyl (e.g.: methoxycarbonyl, ethoxycarbonyl, tert-butoxycarbonyl), nitro, nitroso,
optionally substituted amino (e.g.: alkylamino (e.g.: methylamino, ethylamino, dimethylamino), acylamino (e.g.: acetylamino, benzoylamino), aralkylamino (e.g.: benzylamino, tritylamino), hydroxyamino, alkyloxycarbonylamino, alkylsulfonylamino, optionally substituted carbamoylamino, heterocyclecarbonylamino, arylsulfonylamino), azide,
aryl (e.g.: phenyl),
aralky (e.g.: benzyl),
cyano, isocyano, isocyanate, thiocyanate, isothiocyanate, mercapto, alkylthio (e.g.: methylthio),
alkylsulfonyl (e.g.: methanesulfonyl, ethanesulfonyl),
optionally substituted carbamoyl (e.g.: alkylcarbamoyl (e.g.: methylcarbamoyl, ethylcarbamoyl, dimethylcarbamoyl), alkylsulfonylcarbamoyl),
sulfamoyl,
acyl (e.g.: formyl, acetyl),
formyloxy, haloformyl, oxalo, thioformyl, thiocarboxy, dithiocarboxy, thiocarbamoyl, sulfino, sulfo, sulfoamino, hydrazino, azide, ureido, amidino,
guanidino, phthalimide, oxo,
optionally substituted heteroaryl, heterocycle,
alkylene,
alkylenedioxy (—O—$CH_2$—O—, —O—$CH_2$—$CH_2$—O—, —O—$CH_2$—$CH_2$—$CH_2$—O—, or the like), sulfonyl, sulfinyl, alkylcarbonyloxy, arylcarbonyloxy, heteroarylcarbonyloxy, heterocyclecarbonyloxy,
alkylcarbonyl, arylcarbonyl, heteroarylcarbonyl, heterocyclecarbonyl, alkyloxycarbonyl, aryloxycarbonyl, heteroaryloxycarbonyl, heterocycleoxycarbonyl.

A substituent of "optionally substituted amino", "optionally substituted carbamoyl", "optionally substituted thiocarbamoyl" and "optionally substituted sulfamoyl" includes alkyl, alkenyl, aryl, heteroaryl, alkylcarbonyl, arylcarbonyl, heteroarylcarbonyl, heterocyclecarbonyl, alkyloxycarbonyl, aryloxycarbonyl, heteroaryloxycarbonyl, heterocycleoxycarbonyl, sulfamoyl, alkylsulfonyl, carbamoyl, cycloalkylsulfonyl, arylsulfonyl, heteroarylsulfonyl, heterocyclesulfonyl, acyl, hydroxy, sulfonyl, sulfinyl, amino or the like.

Among compounds of the present invention, the following embodiments are preferable.

A compound represented by the formula (I):

[Formula 13]

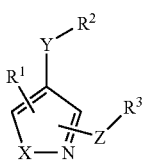

(I)

is preferably a compound represented by the formula (II):

[Formula 14]

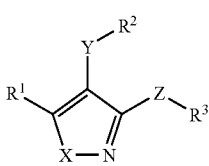

(II)

$R^1$ is a group of the formula: —C(=O)$NR^4R^5$,
wherein $R^4$ and $R^5$ are each independently, hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^4$ and $R^5$ taken together with the adjacent nitrogen atom to which they are attached may form an optionally substituted ring or a group of the formula: —$NR^6C(=O)R^7$,
wherein $R^6$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted aralkyl or a group of the formula:—$C(=O)R^8$, $R^7$ and $R^8$ are each independently, hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^7$ and $R^8$ taken together with the adjacent carbon atom to which they are attached may form an optionally substituted ring.

Preferably $R^1$ is a group of the formula: —$C(=O)NR^4R^5$ wherein $R^4$ and $R^5$ have the same meaning as defined in the above.

More concretely $R^1$ is preferably a group of the formula: —$C(=O)NR^4R^5$ wherein one of $R^4$ and $R^5$ is optionally substituted cycloalkyl, a group of the formula: —$C(=O)NR^4R^5$ wherein one of $R^4$ and $R^5$ is optionally substituted adamantyl or a group represented by the formula (III):

[Formula 15]

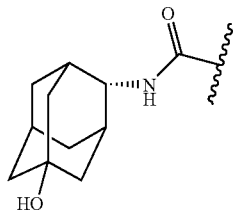

(III)

$R^2$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl or optionally substituted carbamoyl.

$R^2$ is preferably optionally substituted alkyl, optionally substituted cycloalkyl, optionally substituted aryl, optionally substituted heteroaryl or optionally substituted heterocycle.

More preferably $R^2$ is optionally substituted alkyl wherein the substituent of said optionally substituted alkyl does not encompass a cyclic group,
optionally substituted alkenyl wherein the substituent of said optionally substituted alkenyl does not encompass a cyclic group,
optionally substituted alkynyl wherein the substituent of said optionally substituted alkynyl does not encompass a cyclic group,
optionally substituted acyl wherein the substituent of said optionally substituted acyl does not encompass a cyclic group or optionally substituted carbamoyl wherein the substituent of said optionally substituted carbamoyl does not encompass a cyclic group.

Most preferably $R^2$ is optionally substituted alkyl wherein the substituent of said optionally substituted alkyl does not encompass a cyclic group or branched alkyl.

$R^3$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted amino, optionally substituted sulfamoyl or a group of the formula: —$R^9$—$C(R^{10}R^{11})$—$R^{12}$—$R^{13}$, $R^9$ is —$(CH_2)m$-, wherein m is an integer of 0 to 3, $R^{10}$ and $R^{11}$ are each independently, hydrogen, optionally substituted alkyl or halogen;

or $R^{10}$ and $R^{11}$ taken together with the adjacent carbon atom to which they are attached may form an optionally substituted ring, $R^{12}$ is —$(CH_2)n$-, wherein n is an integer of 0 to 3, $R^{13}$ is hydrogen, hydroxy, carboxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkoxycarbonyl, optionally substituted aralkylcarbonyl, optionally substituted carbamoyl, optionally substituted thiocarbamoyl, optionally substituted alkylsulfonyl, optionally substituted arylsulfonyl, optionally substituted sulfamoyl, optionally substituted amino, optionally substituted carbamoyloxy, optionally substituted alkoxy, optionally substituted alkylthio, a group of the formula: —$C(=O)$—$NR^{14}R^{15}$,
wherein $R^{14}$ and $R^{15}$ are each independently, hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^{14}$ and $R^{15}$ taken together with the adjacent nitrogen atom to which they are attached may form an optionally substituted ring or a group of the formula: —$NR^{16}R^{17}$,
wherein $R^{16}$ and $R^{17}$ are each independently, hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl or optionally substituted sulfamoyl; or $R^{16}$ and $R^{17}$ taken together with the adjacent nitrogen atom to which they are attached may form an optionally substituted ring.

$R^{13}$ is preferably a group of the formula: —$C(=O)$—$NR^{14}R^{15}$
wherein $R^{14}$ and $R^{15}$ are each independently, hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^{14}$ and $R^{15}$ taken together with the adjacent nitrogen atom to which they are attached may form an optionally substituted ring or a group of the formula: —NR$^{16}$R$^{17}$, wherein $R^{16}$ and $R^{17}$ are each independently, hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl or optionally substituted sulfamoyl; or $R^{16}$ and $R^{17}$ taken together with the adjacent nitrogen atom to which they are attached may form an optionally substituted ring.

More preferably $R^{13}$ is a group of the formula: —C(=O)—NR$^{14}$R$^{15}$ wherein $R^{14}$ and $R^{15}$ are each independently, hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^{14}$ and $R^{15}$ taken together with the adjacent nitrogen atom to which they are attached may form an optionally substituted ring.

X is —O— or —S—.

Especially preferred as X is —O—.

Y is —O— or —S—.

Especially preferred as Y is —S—.

Z is a bond, —O— or —S—.

Z is preferably —O— or —S—, more preferably —O—.

As to a compound represented by the formula (I), the following embodiments are particularly preferable.

[Formula 16]

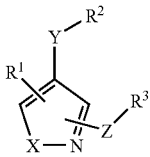

(I)

$R^1$ is one selected from a group consisting of the substituent of the following formula:

[Formula 17]

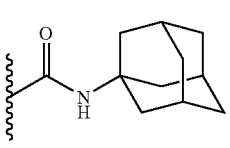

-continued

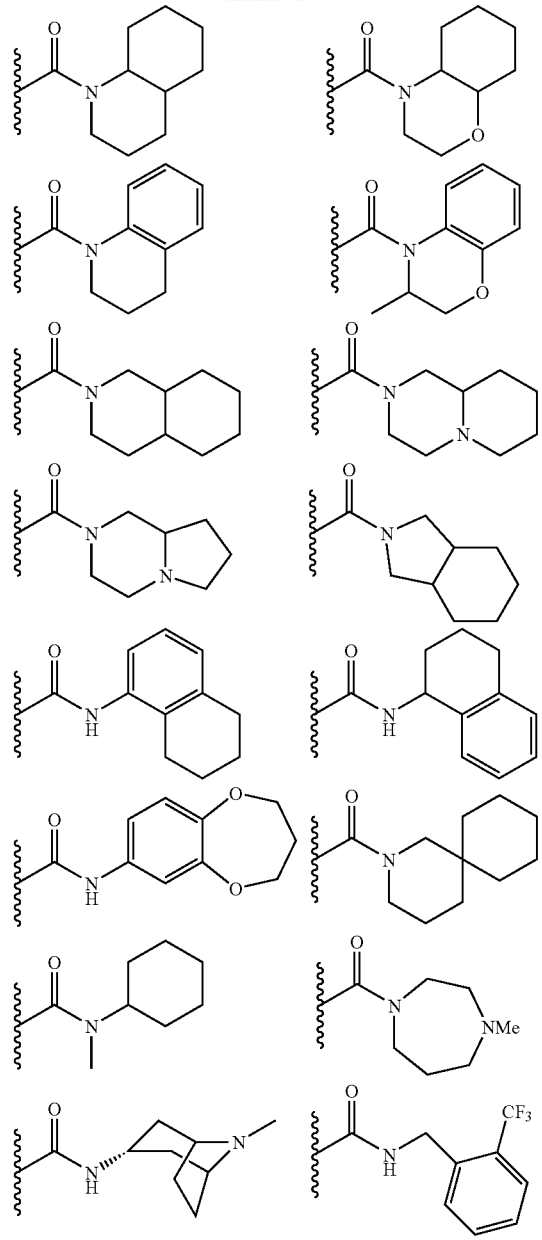

Moreover, $R^1$ is a group of the formula: —C(=O)NR$^4$R$^5$
wherein one of $R^4$ and $R^5$ is preferably optionally substituted cycloalkyl, more preferably one selected from a group consisting of the substituent of the following formula:

[Formula 18]

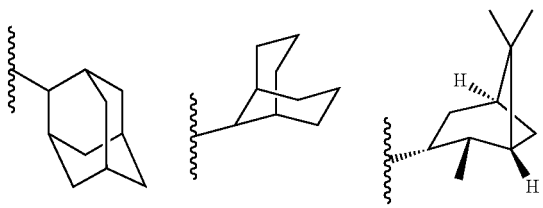

23
-continued
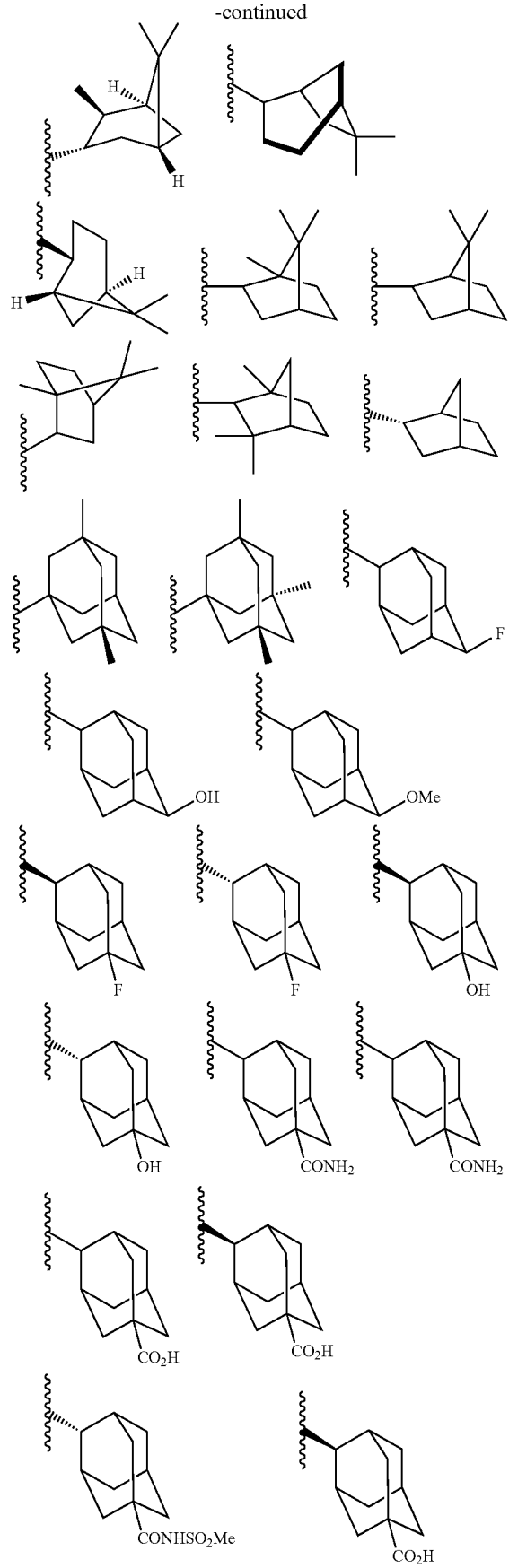
24
-continued
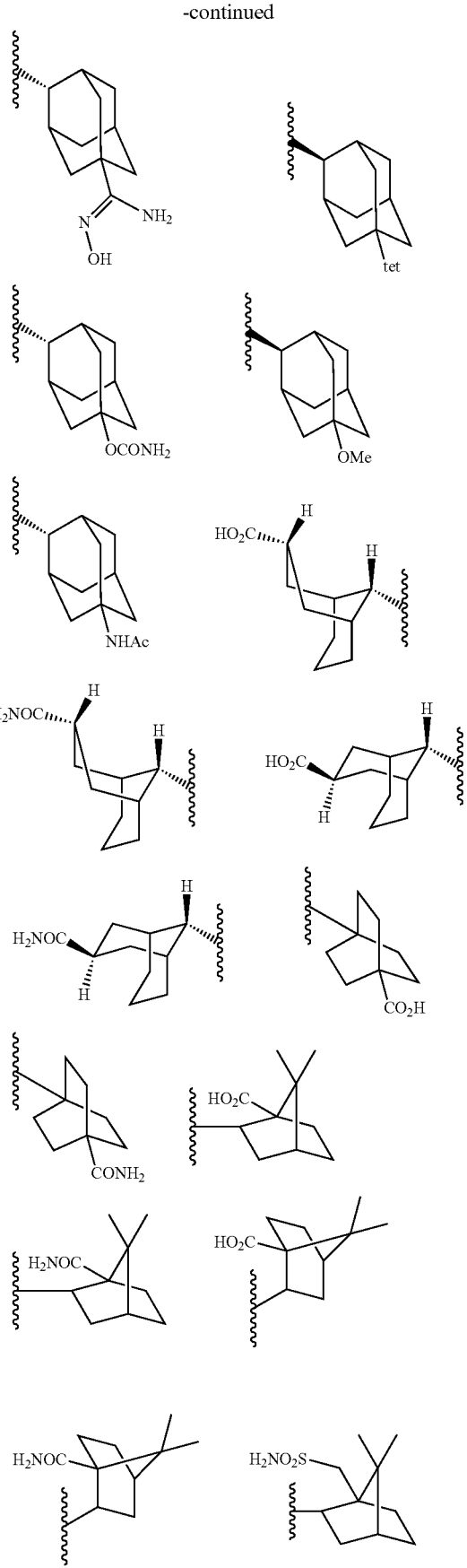

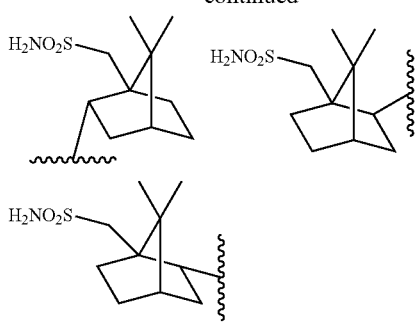

R² is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl or optionally substituted carbamoyl, R² is preferably optionally substituted alkyl, optionally substituted cycloalkyl or optionally substituted aryl, More preferably R² is methyl, ethyl, n-propyl, isopropyl, n-butyl, isobutyl, —CH₂CH(CH₂CH₃)₂, —CH₂CF₃, cyclopentyl, cyclohexyl or phenyl, R³ is one selected from a group consisting of the substituent of the following formula:

[Formula 19]

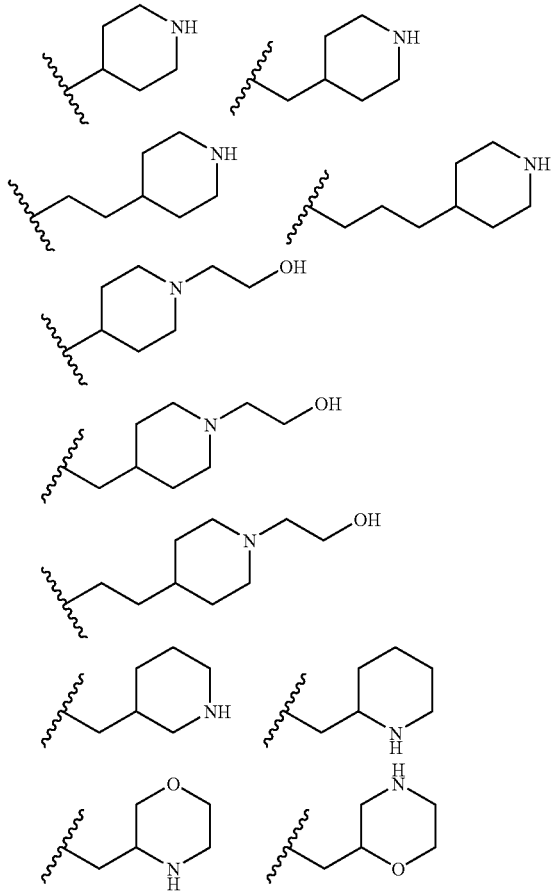

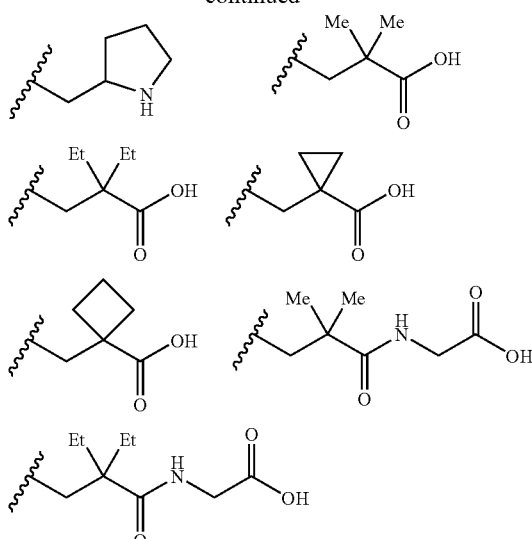

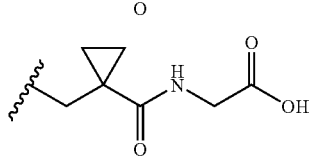

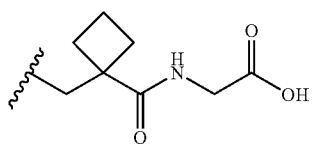

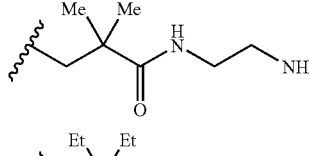

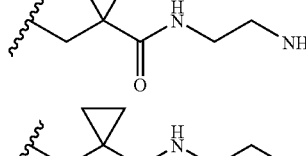

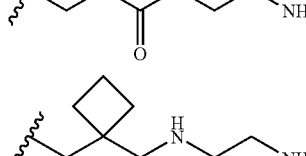

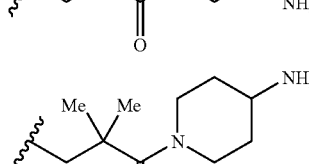

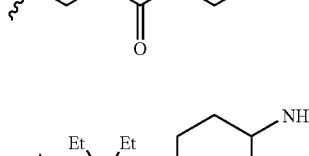

-continued
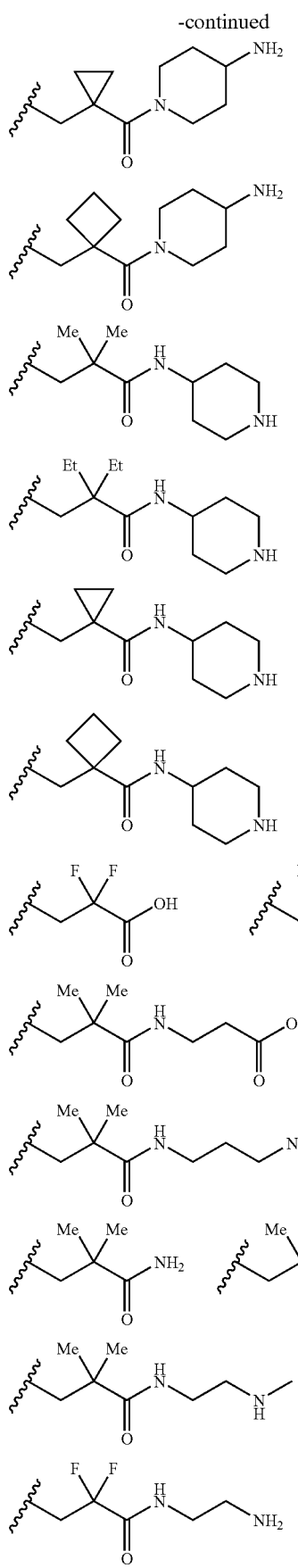
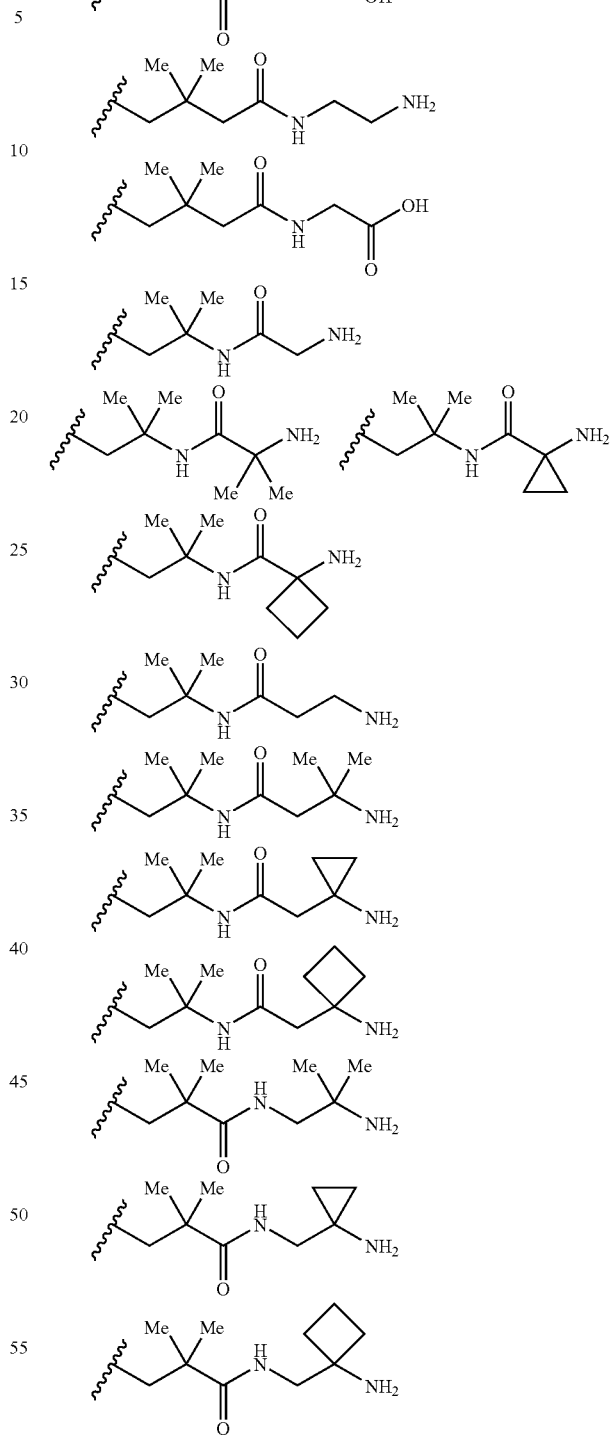
X and Y are each independently —O— or —S—,
Z is a bond, —O— or —S—,
preferably X is —O— or —S—, Y is —S—, and Z is —O—.
Pharmaceutically acceptable salts of the compounds of the present invention are exemplified as follows. Basic salts, for example, are salts of alkali metal such as sodium, potassium or the like; salts of alkaline-earth metal such as calcium, magnesium or the like; salts of ammonium; salts of aliphatic amine such as trimethylamine, triethylamine, dicyclohexylamine, ethanolamine, diethanolamine, triethanolamine, procaine, meglumine, diethanol amine, ethylenediamine or the like; salts of arylalkyl amine such as N,N-dibenzylethylenediamine, benetamine or the like; salts of hetero aromatic amine such as pyridine, picoline, quinoline, isoquinoline or the like; salts of quaternary ammonium such as tetramethylammonium, tetraethylammonium, benzyltrimethylammonium, benzyltriethylammonium, benzyltributylammonium, methyltrioctylammonium, tetrabutylammonium or the like; salts of basic amino acid such as arginine, lysine or the like.

Acidic salts, for example, are salts of inorganic acid such as hydrochloric acid, sulfuric acid, nitric acid, phosphoric acid, carbonic acid, hydrogen carbonic acid, perchloric acid or the like; salts of organic acid such as acetic acid, propionic acid, lactic acid, maleic acid, fumaric acid, tartaric acid, malic acid, citric acid or ascorbic acid; salts of sulfonic acid such as methansulfonic acid, isethionic acid, benzenesulfonic acid, p-toluenesulfonic acid or the like; salts of acidic amino acid such as aspartic acid, glutamic acid or the like.

Solvate means a solvate of a compound of the present invention or a pharmaceutically acceptable salt thereof, for example, alcohol (e.g., ethanol) solvate, hydrate or the like. As to hydrate, monohydrate, dihydrate or the like are exemplified.

A general method for producing a compound of the present invention is explained below. Each symbol is the same meanings as the above (1). In addition, the treatment of the conventional organic synthesis such as extraction, purification and the like can be used for the synthesis of a compound of the present invention.

[Formula 20]

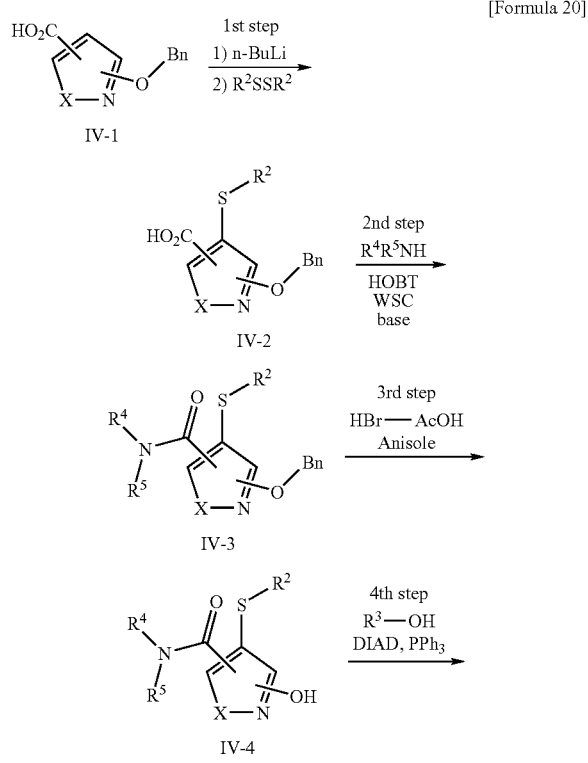

-continued

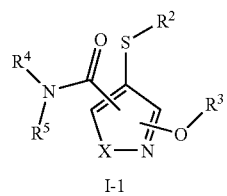

I-1

Each symbol in the above scheme is the same meanings as the above. As to compound (IV-1), well known compounds and compounds, which are lead from well-known compounds by usual methods, can be used. Bn is benzyl group.

1$^{st}$ Step

1$^{st}$ step is a process for manufacturing a compound of the formula (IV-2) which comprises reacting a compound of the formula (IV-1) with $R^2SSR^2$ in the presence of a base.

This reaction can be performed in a solvent of N-dimethylformamide, dimethyl sulfoxide, aromatic hydrocarbon group (for example, toluene, benzene, xylene or the like), saturated hydrocarbon group (for example, cyclohexane, hexane or the like), halogenated hydrocarbon group (for example, dichloromethane, chloroform, 1,2-dichloroethane or the like), ether group (for example, tetrahydrofuran, diethyl ether, dioxane, 1,2-dimethoxyethane or the like), ketone group (for example, acetone, methyl ethylketone or the like), nitryl group (for example, acetonitrile or the like), alcohol group (for example, methanol, ethanol, t-butanol or the like), water, a mixed solvent thereof or the like under the presence of n-BuLi, $R^2SSR^2$.

This reaction can be preferably performed in a solvent of ether group (e.g., tetrahydrofuran, diethyl ether, dioxane or the like) as a solvent at −78° C.-20° C. for 0.5-5 hours.

2$^{nd}$ Step

2$^{nd}$ step is a process for manufacturing a compound of the formula (IV-3) which comprises amidating a compound of the formula (IV-2).

This reaction can be performed in an appropriate solvent under the presence of HOBT, WSC, a base, $R^4R^5NH$.

As the solvent, the same solvent described in the above 1$^{st}$ step can be used.

The base is, for example, metal hydride (for example, sodium hydride or the like), metal hydroxide (for example, sodium hydroxide, potassium hydroxide, lithium hydroxide, barium hydroxide or the like), metal carbonate (for example, sodium carbonate, calcium carbonate, cesium carbonate or the like), metal alkoxide (for example, sodium methoxide, sodium ethoxide, potassium tert-butoxide or the like), sodium hydrogen carbonate, metallic sodium, organic amine (for example, triethylamine, diisopropylethylamine, DBU, 2,6-lutidine or the like) or the like.

Preferably this reaction can be performed in a solvent of N-dimethylformamide, ether group (e.g., tetrahydrofuran, diethyl ether, dioxane or the like) as a solvent under the presence of organic amine (for example, triethylamine, diisopropylethylamine or the like) at 20° C.-100° C. for 0.5-24 hours.

3$^{rd}$ Step

3$^{rd}$ step is a process for manufacturing a compound of the formula (IV-4) which comprises deprotecting a protective group of a compound of the formula (IV-3).

This reaction can be performed under the presence of a mixture of hydrogen bromide and acetic acid, anisole at 0° C.-50° C. for 0.5-24 hours.

4th Step

4th step is a process for manufacturing a compound of the formula (I-1) which comprises putting a compound of the formula (IV-4) in Mitsunobu reaction.

This reaction can be performed in an appropriate solvent under the presence of $R^3$—OH, DIAD and $PPh_3$.

As the solvent, the same solvent described in the above 1st step can be used.

Preferably this reaction can be performed in a solvent of ether group (e.g., tetrahydrofuran, diethyl ether, dioxane or the like) as a solvent at −30° C.-80° C. for 0.5-24 hours.

[Formula 21]

[Reaction scheme showing IV-5 → IV-6 → IV-7 → IV-8 → IV-9 → IV-10 → I-2 with the following steps:

5th step: 1) n-BuLi, 2) MeSSMe
6th step: $R^4R^5NH$, HOBT, WSC
7th step: $NaIO_4$
8th step: 1) 2,6-lutidine, $Tf_2O$, 2) base
9th step: $R^2$—Hal, base
10th step: 1) deprotection, 2) $R^3$—OH, DIAD, $PPh_3$]

Pro is a protecting group and the other symbols are the same meanings as the above. As to compound (IV-5), well known compounds and compounds, which are lead from well-known compounds by usual methods, can be used. Pro is benzyl group, triphenylmethyl group or the like.

5th Step

5th step is a process for manufacturing a compound of the formula (IV-6) which comprises putting a compound of the formula (IV-5) in the same reaction as the above 1st step.

As the solvent, the same solvent described in the above 1st step can be used.

Preferably this reaction can be performed in a solvent of ether group (e.g., tetrahydrofuran, diethyl ether, dioxane or the like) as a solvent at −78° C.-20° C. for 0.5-5 hours.

6th Step

6th step is a process for manufacturing a compound of the formula (IV-7) which comprises putting a compound of the formula (IV-6) in the same reaction as the above 2nd step.

As the solvent, the same solvent described in the above 1st step can be used.

As the base, the same base described in the above 2nd step can be used.

Preferably this reaction can be performed in a solvent of N-dimethylformamide, ether group (e.g., tetrahydrofuran, diethyl ether, dioxane or the like) as a solvent under the presence of organic amine (for example, triethylamine, diisopropylethylamine or the like) as a base at 20° C.-100° C. for 0.5-24 hours.

7th Step

7th step is a process for manufacturing a compound of the formula (IV-8) which comprises oxidizing a compound of the formula (IV-7).

This reaction can be performed in an appropriate solvent under the presence of sodium periodate.

As the solvent, the same solvent described in the above 1st step can be used.

Preferably this reaction can be performed in a mixed solvent of dioxane, methanol and water as a solvent at 20° C.-80° C. for 0.5-72 hours.

8th Step

8th step is a process for manufacturing a compound of the formula (IV-9) which comprises putting a compound of the formula (IV-8) in Pummerer rearrangement.

This reaction can be performed in an appropriate solvent under the presence of 2,6-lutidine, trifluoroacetic anhydride, base.

As the solvent, the same solvent described in the above 1st step can be used.

As the base, the same base described in the above 2nd step can be used.

Preferably this reaction can be performed in a solvent of halogenated hydrocarbon group (for example, dichloromethane, chloroform or the like) as a solvent or without any solvent under the presence of organic amine (for example, triethylamine, diisopropylethylamine or the like) as a base at −30° C.-80° C. for 0.5-24 hours.

9th Step

9th step is a process for manufacturing a compound of the formula (IV-10) which comprises alkylating a compound of the formula (IV-9).

This reaction can be performed in an appropriate solvent under the presence of $R^2$-Hal, a base.

As the solvent, the same solvent described in the above 1st step can be used.

As the base, the same base described in the above 2nd step can be used.

Preferably this reaction can be performed in a solvent of N-dimethylformamide, acetonitrile, acetone or a mixed solvent thereof as a solvent under the presence of metal carbonate (for example, calcium carbonate, cesium carbonate or the like) as a base at −30° C.-100° C. for 0.5-24 hours.

10$^{th}$ Step

10$^{th}$ step is a process for manufacturing a compound of the formula (I-2) which comprises deprotecting a protective group of a compound of the formula (IV-10) and then putting in Mitsunobu reaction.

Deprotection reaction and Mitsunobu reaction can be performed by a well-known method, preferably by the method described in the above 3$^{rd}$ step and 4$^{th}$ step.

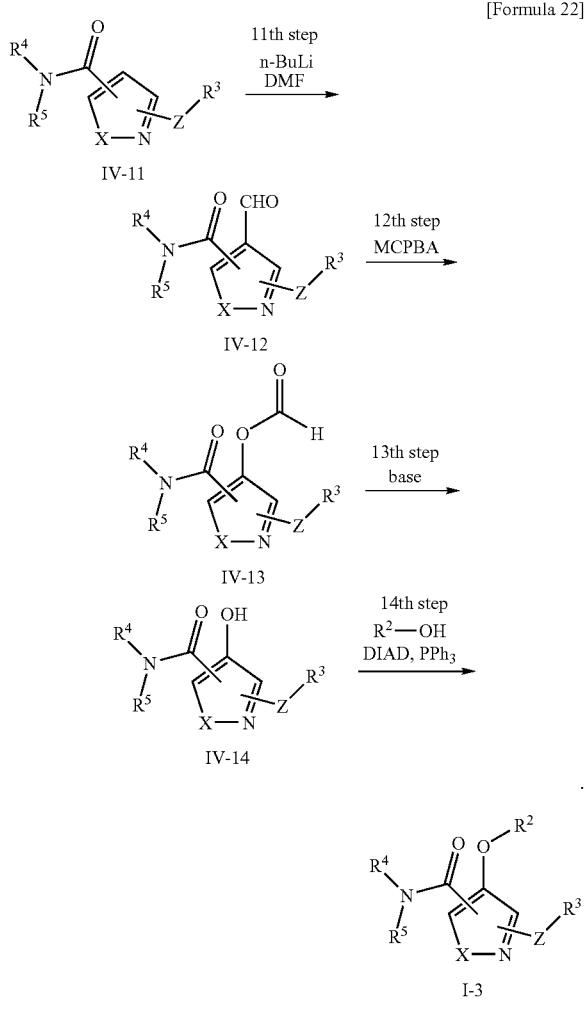

[Formula 22]

11$^{th}$ Step

11$^{th}$ step is a process for manufacturing a compound of the formula (IV-12) which comprises formylating a compound of the formula (IV-11).

This reaction can be performed in an appropriate solvent under the presence of n-BuLi and DMF.

As the solvent, the same solvent described in the above 1$^{st}$ step can be used.

Preferably this reaction can be performed in a solvent of N-dimethylformamide, ether group (e.g., tetrahydrofuran, diethyl ether, dioxane or the like) as a solvent at −78° C.-30° C. for 0.5-24 hours.

12$^{th}$ Step

12$^{th}$ step is a process for manufacturing a compound of the formula (IV-13) which comprises putting a compound of the formula (IV-12) in Baeyer-Villiger oxidation.

This reaction can be performed in an appropriate solvent under the presence of oxidant such as MCPBA, hydrogen peroxide solution or the like.

As the solvent, the same solvent described in the above 1$^{st}$ step can be used.

Preferably this reaction can be performed in a solvent of alcohol group (for example, methanol, ethanol or the like), water, halogenated hydrocarbon group (for example, dichloromethane, chloroform or the like) as a solvent at −78° C.-30° C. for 0.5-24 hours.

13$^{th}$ Step

13$^{th}$ step is a process for manufacturing a compound of the formula (IV-14) which comprises hydrolyzing a compound of the formula (IV-13).

This reaction can be performed in an appropriate solvent under the presence of a base.

As the solvent, the same solvent described in the above 1$^{st}$ step can be used.

Preferably this reaction can be performed in a solvent of alcohol group (for example, methanol, ethanol or the like), water as a solvent under the presence of metal hydroxide (for example, sodium hydroxide, potassium hydroxide or the like) as a base at 0° C.-100° C. for 0.5-24 hours.

14$^{th}$ Step

14$^{th}$ step is a process of manufacturing a compound of the formula (I-3) which comprises putting a compound of the formula (IV-14) in Mitsunobu reaction.

Mitsunobu reaction can be performed by a well-known method, preferably by the method described in the above 4$^{th}$ step.

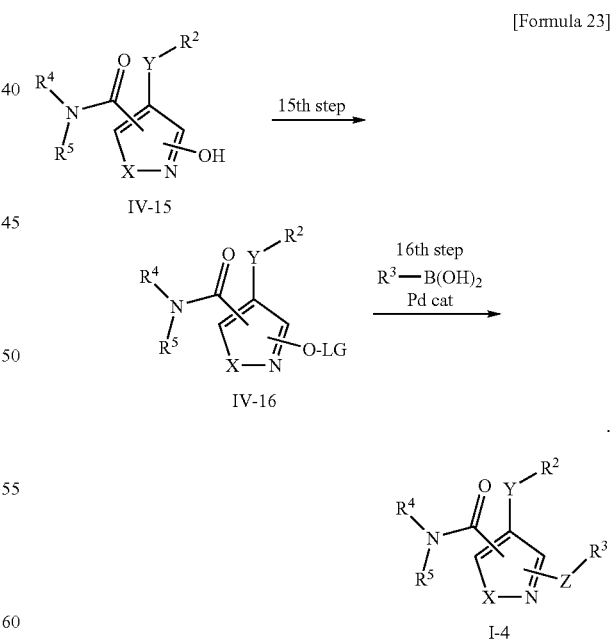

[Formula 23]

wherein LG is a leaving group and the other symbols are the same meanings as the above. As to compound (IV-15), well known compounds and compounds, which are lead from well-known compounds by usual methods, can be used. LG is, for example, mesyl group, tosyl group or the like.

Each symbol in the above scheme is the same meanings as the above. As to compound (IV-11), well known compounds and compounds, which are lead from well-known compounds by usual methods, can be used.

15th Step

15th step is a process for manufacturing a compound of the formula (IV-16) which comprises introducing a leaving group into a compound of the formula (IV-15).

This reaction can be performed in an appropriate solvent under the presence of Tf$_2$O, MsCl or the like.

As the solvent, the same solvent described in the above 1st step can be used.

Preferably this reaction can be performed in a solvent of halogenated hydrocarbon group (for example, dichloromethane, chloroform or the like) as a solvent at −78° C.-30° C. for 0.5-24 hours.

16th Step

16th step is a process for manufacturing a compound of the formula (I-4) which comprises putting a compound of the formula (IV-16) in Suzuki-coupling.

This reaction can be performed in an appropriate solvent under the presence of R$^3$—B(OH)$_2$, palladium catalyst (for example, Pd(PPh$_3$)$_4$ or the like).

As the solvent, the same solvent described in the above 1st step can be used.

Preferably this reaction can be performed in a solvent of N-dimethylformamide, 1,2-dimethoxyethane, alcohol group (for example, methanol, ethanol or the like), water or a mixed solvent thereof as a solvent at 20° C.-100° C. for 0.5-24 hours.

[Formula 24]

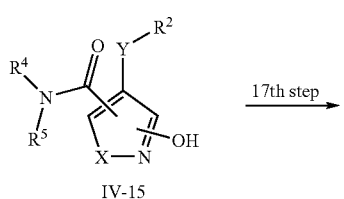

IV-15

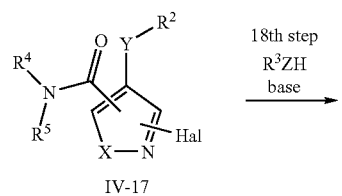

IV-17

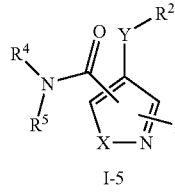

I-5

Each symbol in the above scheme is the same meanings as the above. As to compound (IV-15), well known compounds and compounds, which are lead from well-known compounds by usual methods, can be used.

17th Step

17th step is a process for manufacturing a compound of the formula (IV-17) which comprises halogenating a compound of the formula (IV-15).

This reaction can be performed in an appropriate solvent under the presence of phosphorous[phosphorus]oxychloride, sulfonyl chloride, carbon tetrabromide or the like.

As the solvent, the same solvent described in the above 1st step can be used.

Preferably this reaction can be performed in a solvent of halogenated hydrocarbon group (for example, dichloromethane, chloroform or the like) as a solvent or without any solvent at −30° C.-150° C. for 0.5-24 hours.

18th Step

18th step is a process for manufacturing a compound of the formula (I-5) which comprises reacting a compound of the formula (IV-17) with R$^3$ZH.

This reaction can be performed in an appropriate solvent under the presence of R$^3$ZH and a base.

As the solvent, the same solvent described in the above 1st step can be used.

As the base, the same base described in the above 2nd step can be used.

Preferably this reaction can be performed in a solvent of N-dimethylformamide, ether group (e.g., tetrahydrofuran, diethyl ether, dioxane or the like) as a solvent under the presence of metal hydride (for example, sodium hydride or the like), metal alkoxide (for example, sodium methoxide, sodium ethoxide, potassium tert-butoxide or the like), as a base at −78° C.-80° C. for 0.5-24 hours.

[Formula 25]

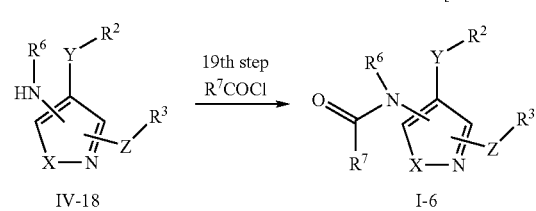

Each symbol in the above scheme is the same meanings as the above. As to compound (IV-18), well known compounds and compounds, which are lead from well-known compounds by usual methods, can be used.

19th Step

19th step is a process for manufacturing a compound of the formula (I-6) which comprises reacting a compound of the formula (IV-18) with R$^7$COCl.

This reaction can be performed in an appropriate solvent under the presence of R$^7$COCl.

As the solvent, the same solvent described in the above 1st step can be used.

Preferably this reaction can be performed in a solvent of halogenated hydrocarbon group (for example, dichloromethane, chloroform or the like), ether group (for example, tetrahydrofuran, diethyl ether, dioxane or the like), N-dimethylformamide as a solvent at −30° C.-100° C. for 0.5-24 hours.

The abbreviations used in the each stage are as follows.

| | |
|---|---|
| DBU | 1,8-Diazabicyclo[5.4.0]undec-7-ene |
| n-BuLi | n-Butyllithium |
| HOBT | 1-Hydroxybenzotriazole |
| WSC | 1-(3-Dimethylaminopropyl)-3-ethylcarbodiimide |
| DIAD | Azodicarboxylic acid diisopropyl |
| PPh$_3$ | Triphenylphosphine |
| Tf$_2$O | Trifluoroacetic anhydride |
| MCPBA | m-chloroperbenzoic acid |

If necessary, after hydroxy or thiol group of a compound is protected by the usual method at an appropriate step, it is subjected to the reaction and then deprotected by the usual method at an appropriate step.

As a protecting group, alkyl (methyl, ethyl or the like), aralkyl (benzyl, p-methoxybenzyl, triphenylmethyl or the like), trialkyl silyl (t-butyldimethylsilyl, t-butyldiphenylsilyl or the like), acetyl group or the like can be used.

Various substituent of a compound of the present invention can be introduced referring to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS, or the like.

A compound of the present invention has a high inhibitory activity on 11β-hydroxysteroid dehydrogenase type 1. Therefore, a compound of the present invention can be used for treating and/or preventing a disease concerning 11β-hydroxysteroid dehydrogenase type 1, especially, hyperlipidemia, diabetes, obesity, arteriosclerosis, atherosclerosis, hyperglycemia and/or syndrome X. Especially, a compound of the present invention is useful for treating and/or preventing diabetes.

A compound of the present invention can be administrated orally or parenterally. For oral administration, the compound of the present invention can be used in any form of the conventional pharmaceutical formulations, for example, solid formulations such as tablets, powders, granules, capsules or the like; aqueous formulations; oleaginous suspensions; or solution formulations such as syrup or elixir. For parenteral administration, the compound of the present invention can be used as an aqueous or oleaginous suspension injections or nose drops. In the preparation of such formulations, the conventional pharmaceutical excipients, binding agents, lubricants, aqueous solvents, oleaginous solvents, emulsifying agents, suspending agents, preservatives, stabilizers, and the like can be optionally used. Especially, a compound of the present invention is preferably used as oral agents.

A formulation according to the present invention can be manufactured by combining (e.g., admixing) a curatively effective amount of a compound of the present invention with a pharmaceutically acceptable carrier or diluent. The formulation can be manufactured by using of well-known and easily available ingredients in accordance with a known method.

A dosage of a compound of the present invention depends on the administration route, age, body weight, conditions of the patient, and kind of disease, but in case of oral administration, the daily dosage for an adult can be between approximately 0.05 mg~3000 mg, preferably approximately 0.1 mg~1000 mg. The daily dosage can be administered in divisions. When a compound of the present invention is administrated parenterally, the daily dosage for an adult can be between approximately 0.01 mg~1000 mg, preferably approximately 0.05 mg~500 mg. Moreover, a compound of the present invention can be administrated with other curative agents.

Examples are shown below for further detail explanation of the present invention, but are not intended to limit the scope of the present invention.

The abbreviations used in the examples are as follows.

Boc t-Butoxycarbonyl
TEA Triethylamine
TFA Trifluoroacetic acid
BnBr Benzyl bromide

EXAMPLE 1

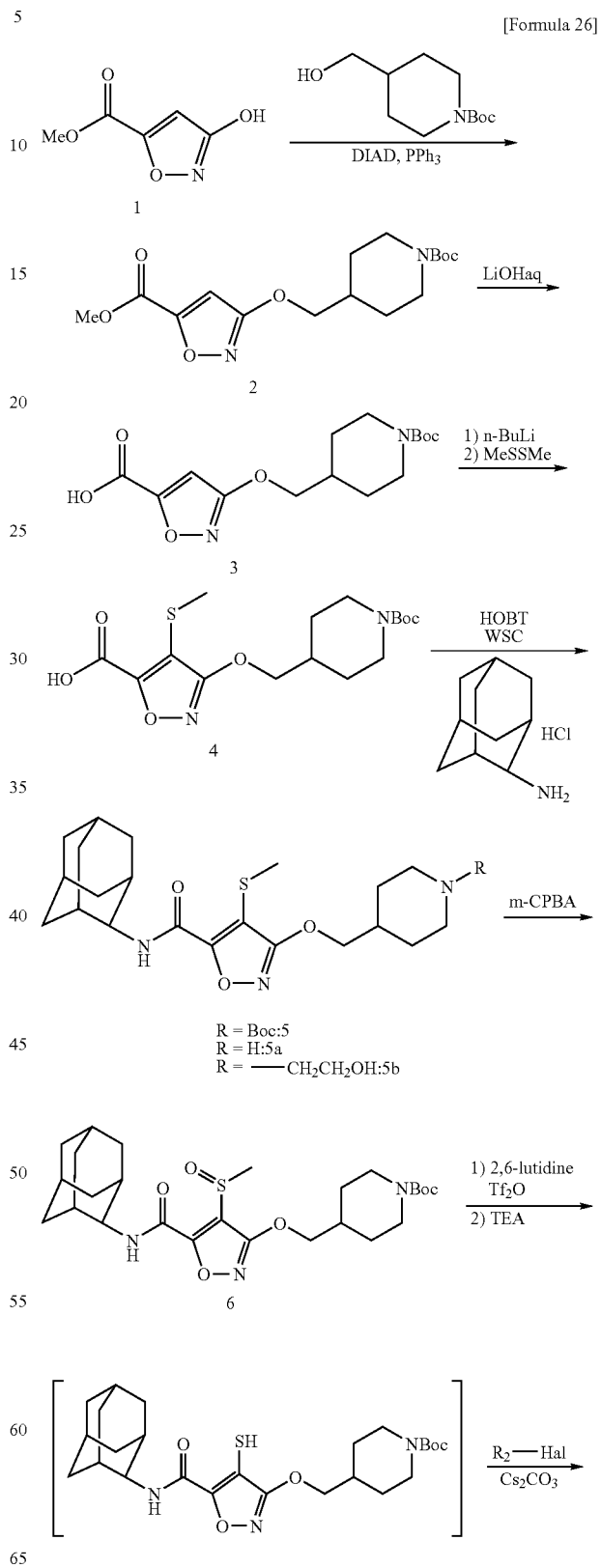

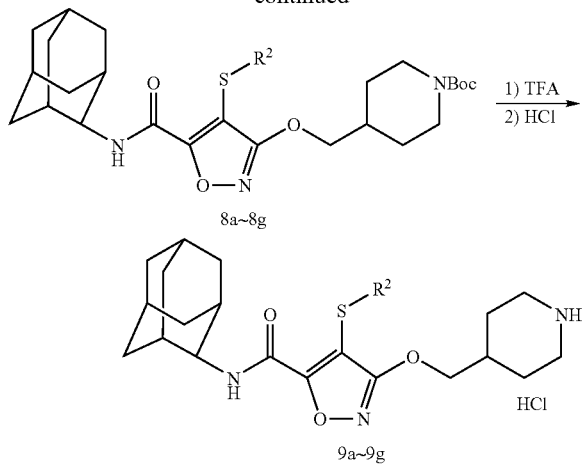

8a~8g

9a~9g

To a solution of Compound 1 (12 g) in tetrahydrofuran (240 ml) were added N-Boc-4-piperidinemethanol (18 g) and triphenylphosphine (22 g). Azodicarboxylic acid diisopropyl (16.5 ml) was added dropwisely to the solution, then the reaction solution was stirred at room temperature for 2 hrs. After termination of the reaction, the solvent was removed and the residue was purified by silicagel columnchromatography to give Compound 2. According to the above procedure, the obtained 2 was dissolved in tetrahydrofuran (200 ml) and methanol (100 ml), and then 2N LiOH aqueous soln. (65 ml) was added to the resulting solution. The solution was stirred at room temperature for 1 hr. After termination of the reaction, tetrahydrofuran and methanol were removed. The solution was diluted with $H_2O$ and the aqueous layer was washed with diethylether. The mixture was acidified with 2N HCl aqueous soln., and extracted with ethyl acetate. The organic layer was washed with brine and dried with sodium sulfate and concentrated to give Compound 3 (21.6 g).

To a solution of Compound 3 (21.6 g) in tetrahydrofuran (500 ml) was added n-butyllithium (1.57M in hexane, 100 ml) dropwisely at −78° C. After stirring at −78° C. for 10 min, the whole mixture was stirred at room temperature for 30 min. After cooling again to −78° C., dimethyl disulfide (6.9 ml) was added dropwisely to the solution and the reaction solution was stirred at room temperature for 3 hrs. After termination of the reaction, conc. HCl (14 ml) was added to the reaction solution and the solution was stirred for 10 min. The solution was adjusted to pH 8 by 2N NaOH aqueous soln. And washed with diethylether. The aqueous layer was acidified with conc. $H_2SO_4$, and extracted with ethyl acetate. The organic layer was washed with brine and dried with sodium sulfate and concentrated to give Compound 4 (23.9 g).

Under $N_2$ atmosphere, to a solution of Compound 4 (23.9 g) in dimethylformamide (400 ml) was added 2-adamantanamine hydrochloride (13.3 g), 1-(3-dimethylaminopropyl)-3-ethylcarbodiimide hydrochloride (14.8 g) and 1-hydroxybenzotriazole (9.2 g), then triethylamine (23.2 ml) was slowly added dropwisely to the solution. The resulting solution was stirred at room temperature for 24 hrs. After termination of the reaction, the solution was poured into 2N HCl aqueous soln. (400 ml) and ice (300 ml), then extracted with ethyl acetate. The extraction was washed with sat. sodium hydrogencarbonate soln. and brine successively, then dried with sodium sulfate and concentrated. The residue was purified by silicagel columnchromatography to give Compound 5 (28.2 g). Compound 5a was obtained by deprotecting Compound 5 under acid condition. The reaction of Compound 5a with bromoethanol gave Compound 5b.

5a: $^1$H-NMR (CDCl$_3$): 1.65-2.1 (m, 19H), 2.20 (m, 1H), 2.46 (s, 3H), 2.96 (m, 2H), 3.58 (brd, J=16.4 Hz, 1H), 4.27 (d, J=8.4 Hz, 2H), 7.64 (d, J=6.8 Hz, 1H), 9.47 (m, 1H), 9.73 (m, 1H)

5b: $^1$H-NMR (CDCl$_3$): 1.4-1.6 (m, 2H), 1.65-2.1 (m, 18H), 2.17 (dt, J=2.1, 11.7 Hz, 2H), 2.46 (s, 3H), 2.59 (t, J=5.4 Hz, 2H), 2.7 (brs, 1H), 3.02 (brd, J=11.7 Hz, 2H), 3.65 (t, J=5.4 Hz, 2H), 4.21 (d, J=6.6 Hz, 2H), 4.27 (brd, J=8.1 Hz, 1H), 7.64 (d, J=8.4 Hz, 1H)

To a solution of Compound 5 (7.83 g) in chloroform (60 ml) was added m-chloroperbenzoic acid (content of about 70%, 3.8 g), then the resulting mixture was stirred at room temperature for 30 min. After termination of the reaction, the organic layer was washed with sat. sodium hydrogencarbonate soln. and brine successively, and dried with sodium sulfate and concentrated to give Compound 6 (7.67 g).

To a solution of Compound 6 (19.7 g) in chloroform (100 ml) was added 2,6-lutidine (24.3 g) under $N_2$ atmosphere, and trifluoroacetic anhydride (21.3 ml) was added dropwisely to the resulting mixture under ice-cooling. The solution was stirred at 50° C. for 1 hr, and chloroform was removed. Methanol (80 ml) and triethylamine (20 ml) were added to the residue, and the solution was stirred at room temperature for 1 hr. After termination of the reaction, the solution was acidified with 2N HCl aqueous soln., and extracted with ethyl acetate. The organic layer was washed with brine and dried with magnesium sulfate and concentrated. The residue (7) was dissolved in dimethylformamide (120 ml), and isopropyl bromide (18.5 g) and cesium carbonate (48.6 g) were added to the solution. The solution was stirred at room temperature for 14 hrs. After termination of the reaction, the solution was poured into ice-cold water and extracted with ethyl acetate. The organic layer was washed with brine and dried with magnesium sulfate and concentrated. The residue was purified by silicagel columnchromatography to give Compound 8b (14.2 g).

To a solution of Compound 8b (7.31 g) in chloroform (70 ml) was added trifluoroacetic acid (10 ml), and the resulting mixture was stirred at room temperature for 2 hrs. After termination of the reaction, the solvent was removed and the residue was diluted with ethyl acetate. The organic layer was washed with sodium carbonate soln. and brine successively, and dried with magnesium sulfate and concentrated. The residue was dissolved in diethylether, and hydrochloride was formed by adding 0.02M HCl (diethylether soln.) to the solution. The resulting powder was collected by filtration and dried to give Compound 9b (3.91 g).

The above-mentioned examples are concerning Compound 9b. Compounds 9a, 9c~9g were synthesized in accordance with the method shown in the above examples.

TABLE 1

| No. | $R^2$ | NMR |
|---|---|---|
| 9a | Et | (DMSO-d6); 1.14 (t, J = 7.2 Hz, 3H), 1.45-2.05 (m, 16H), 2.14 (m, 1H), 2.84 (m, 2H), 2.90 (m, 2H), 3.30 (m, 2H), 4.03 (brs, 1H), 4.19 (d, J = 6.0 Hz, 2H), 8.39 (d, J = 7.2 Hz, 1H), 8.86 (m, 1H), 9.16 (m, 1H) |

TABLE 1-continued

| No. | $R^2$ | NMR |
|---|---|---|
| 9b | i-Pr | (DMSO-d6); 1.29 (d, J = 6.4 Hz, 6H), 1.45-2.05 (m, 18H), 2.14 (m, 1H), 2.88 (m, 2H), 3.28 (m, 2H), 4.03 (brs, 1H), 4.19 (d, J = 5.2 Hz, 2H), 8.43(d, J = 7.6 Hz, 1H), 8.81 (m, 1H), 9.09 (m, 1H) |
| 9c | n-Pr | (DMSO-d6); 0.91 (t, J = 7.2 Hz, 3H), 1.4-2.05 (m, 22H), 2.16 (m, 1H), 2.81 (t, J = 7.2 Hz, 2H), 2.90 (m, 2H), 4.03 (brs, 1H), 4.20 (d, J = 6.0 Hz 2H), 8.40 (d, J = 6.8 Hz, 1H), 8.61 (m, 1H), 8.92 (m, 1H) |
| 9d | n-Bu | (DMSO-d6); 0.83 (t, J = 7.2 Hz, 3H), 1.33 (m, 2H), 1.4-2.05 (m, 16H), 2.12 (m, 1H), 2.83 (t, J = 6.8 Hz, 2H), 2.90 (m, 2H), 3.29 (m, 2H), 4.03 (brs, 1H), 4.19 (d, J = 6.0 Hz, 2H), 8.38(d, J = 6.4 Hz, 1H), 8.73 (m, 1H), 9.07 (m, 1H) |
| 9e | —$CH_2CF_3$ | (DMSO-d6); 1.45-2.1 (m, 20H), 2.16 (m, 1H), 2.90 (m, 2H), 3.80 (m, 2H), 4.02 (brs, 1H), 4.19 (d, J = 6.4 Hz, 2H), 8.44 (d, J = 7.2 Hz, 1H), 8.69 (m, 1H), 8.96 (m, 1H) |
| 9f | i-Bu | (DMSO-d6); 0.92 (d, J = 6.8 Hz, 6H) 1.45-2.05 (m, 15H), 2.15 (m, 1H), 2.73 (d, J = 6.4 Hz, 2H), 2.91 (m, 2 H ), 3.28 (brd J = 11.6 Hz, 2H), 3.78 (m, 1H), 4.03 (m, 1H), 4.19 (d, J = 6.0 Hz, 2H), 8.39 (d, J = 6.8 Hz, 1H), 8.84 (m, 1H), 9.12 (m, 1H) |
| 9g | —$CH_2CH(CH_2CH_3)_2$ | (DMSO-d6); 0.79 (d, J = 6.8 Hz, 6H) 1.25-2.05 (m, 23H), 2.15 (m, 1H), 2.82 (d, J = 4.8 Hz, 2H), 2.90 (m, 2H), 3.29 (m, 2H), 4.02 (brs, 1H), 4.19 (d, J = 6.0 Hz, 2H), 8.37 (d, J = 7.6 Hz, 1H), 8.71 (m, 1H), 9.01 (m, 1H) |

EXAMPLE 2

[Formula 27]

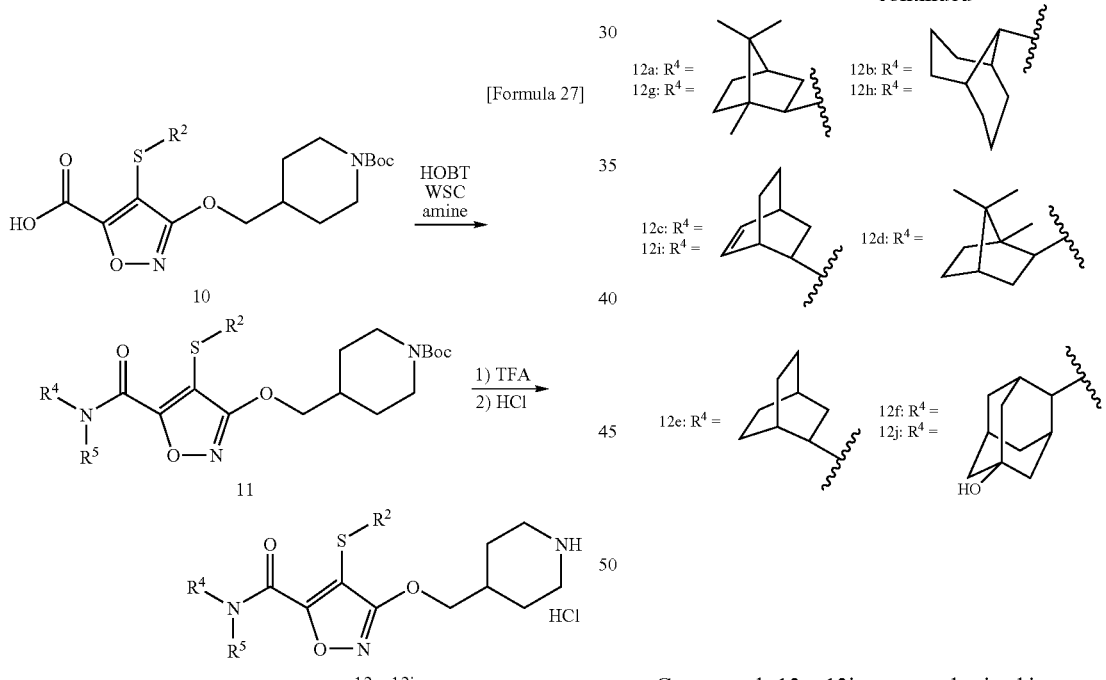

Compounds 12a~12j were synthesized in accordance with the above-mentioned scheme.

TABLE 2

| No. | $R^2$ | $R^5$ | NMR |
|---|---|---|---|
| 12a | i-Pr | H | (DMSO-d6); 0.82 (s, 3H), 0.85 (s, 3H), 0.97 (s, 3H), 1.18 (t, J = 7.6 Hz, 6H), 1.45-2.0 (m, 12H), 2.14 (m, 1H), 2.91 (m, 2H), 3.30 (m, 2H), 3.91 (brs, 1H), 4.17 (d, J = 5.6 Hz, 2H), 7.99 (d, J = 7.6 Hz, 1H), 8.72 (m, 1H), 9.00 (m, 1H) |
| 12b | i-Pr | H | (DMSO-d6); 1.20 (d, J = 6.8 Hz, 6H), 1.53 (brt, J = 13.2 Hz, 6H) 1.80-1.89 (m, 13H), 2.14 (m, 1H), 2.88 (m, 2H), 3.30 (m, 2H), 3.86 (m, 1H), 4.18 (d, J = 6.8 Hz, 2H), 8.37 (brd, J = 7.2 Hz, 1H), 8.87 (m, 1H), 9.15 (m, 1H) |

TABLE 2-continued

| No. | R² | R⁵ | NMR |
|---|---|---|---|
| 12c | i-Pr | H | (DMSO-d6); 1.18 (d, J = 6.4 Hz, 6H), 1.3-2.4 (m, 9H), 2.45 (t, J = 11.2 Hz, 1H), 2.93 (brd, J = 12.4 Hz, 2H), 3.38 (m, 1H), 3.95 (m, 1H), 4.11 (d, J = 5.2 Hz, 2H), 4.34 (m, 1H), 4.77 (m, 1H), 6.08 (t, J = 8.4 Hz, 1H), 6.36(t, J = 8.4 Hz, 1H), 8.31(s, 2H), 8.35(m, 1H), 8.44 (m, 1H), 8.61(brd, J = 5.2 Hz, 1H), 8.86 (brs, 1H). |
| 12d | i-Pr | H | (DMSO-d6); 0.78 (s, 3H), 0.86 (s, 3H), 0.93 (s, 3H), 1.0-1.6 (m, 14H), 1.65 (brs, 1H), 1.69 (m, 2H), 1.87 (m, 2H), 2.15 (m, 2H), 2.92 (m, 2H), 4.19 (brd, J = 6.0 Hz, 2H), 4.25 (m, 1H), 8.53 (d, J = 8.4 Hz, 1H), 8.65 (m, 1H), 8.94 (m, 1H) |
| 12e | i-Pr | H | (DMSO-d6); 1.17 (d, J = 5.6 Hz, 6H), 1.3-1.7(m, 15H), 1.7-2.1 (m, 4H), 2.13 (m, 1H), 2.89 (brd, J = 10.8 Hz, 2H), 3.98 (brs, 1H), 4.18 (d, J = 4.4 Hz, 2H), 8.59 (d, J = 6.8 Hz, 1H), 8.74 (m, 1H), 9.01 (m, 1H) |
| 12f | i-Pr | H | (DMSO-d6); 1.18 (d, J = 6.4 Hz, 6H), 1.26(q, J = 11.6 Hz, 2H), 1.41 (d, J = 12.4 Hz, 2H), 1.55-1.8 (m, 10H), 1.86 (d, J = 12.4 Hz, 2H), 1.96 (brs, 1H), 2.06 (brs, 2H), 2.60 (t, J = 12.0 Hz, 2H), 3.05 (d, J = 11.6 Hz, 2H), 3.30 (m, J = 6.4 Hz, 1H), 3.73 (brs, 1H), 3.94 (brs, 1H), 4.13 (d, J = 6.4 Hz, 2H), 8.37 (d, J = 6.8 Hz, 1H) |
| 12g | n-Pr | H | (DMSO-d6); 0.81 (s, 3H), 0.84 (s, 3H), 0.91 (t, J = 7.6 Hz, 3H), 0.96 (s, 3H), 1.04 (d, J = 6.0 Hz, 1H), 1.88 (m, 2H), 1.35-1.9 (m, 10H), 2.13 (brs, 2H), 2.80 (m, 2H), 2.88 (m, 2H), 3.30 (m, 2H), 3.92 (m, 1H), 4.18 (d, J = 6.0 Hz, 1H), 7.97 (d, J = 8.4 Hz, 1H), 8.74 (m, 1H), 9.05 (m, 1H) |
| 12h | n-Pr | H | (DMSO-d6); 0.91(t, J = 7.6 Hz, 3H), 1.04 (d, J = 6.4 Hz, 1H), 1.4-2.0 (m, 18 H), 2.13 (brs, 1H), 2.82 (t, J = 6.8 Hz, 2H), 2.90 (m, 2H), 3.28 (d, J = 12.4 Hz, 2H), 3.60 (m, 1H), 3.85 (brs, 1H), 4.18 (d, J = 6.0 Hz, 2H), 8.34 (d, J = 7.2 Hz, 1H), 8.95 (m, 1H), 9.22 (m, 1H) |
| 12i | n-Pr | H | (DMSO-d6); 0.91 (t, J = 7.6 Hz, 3H), 1.20 (m, 2H), 1.3-2.4 (m, 9H), 2.49 (t, J = 12.8 Hz, 1H), 2.81(brt, J = 6.8 Hz, 2H), 2.96 (brd, J = 11.6 Hz, 2H), 3.94 (m, 1H), 4.11 (d, J = 6.0 Hz, 2H), 4.33 (m, 1H), 4.43 (m, 1H), 6.14 (t, J = 8.4 Hz, 1H), 6.41 (t, J = 8.4 Hz, 1H), 8.24 (brd, J = 7.6 Hz, 1H), 8.31(s, 2H), 8.38 (brd, J = 7.2 Hz, 1H), 8.63 (d, J = 6.8 Hz, 2H) |
| 12j | n-Pr | H | Free (DMSO-d6); 0.90 (t, J = 7.6 Hz, 3H), 1.03 (d, J = 6.4 Hz, 1H), 1.17 (m, 2H), 1.35-1.9 (m, 16H), 2.02 (brs, 2H), 2.07 (brs, 2H), 2.45 (m, 1H), 2.79 (t, J = 6.8 Hz, 2H), 2.94(m, 2H), 3.93 (s, 1H), 4.18(d, 2H), 8.31(m, 1H) |

EXAMPLE 3

[Formula 28]

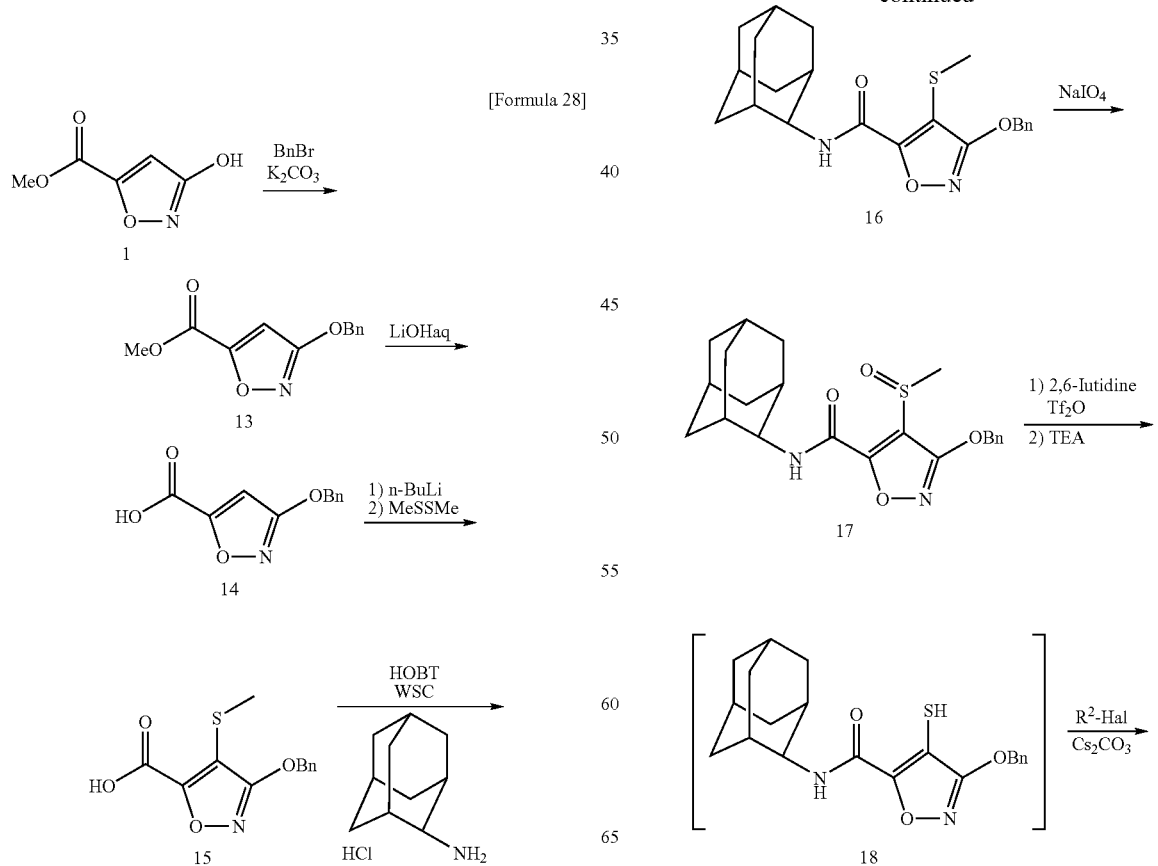

-continued

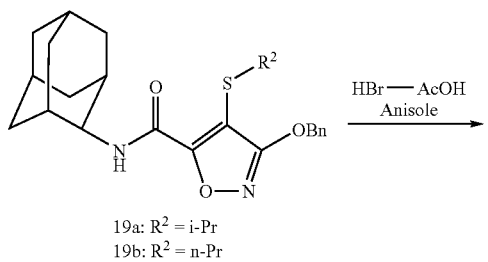

19a: R² = i-Pr
19b: R² = n-Pr

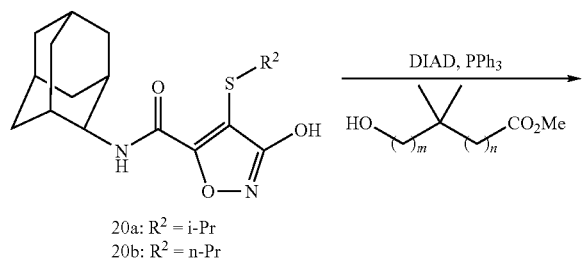

20a: R² = i-Pr
20b: R² = n-Pr

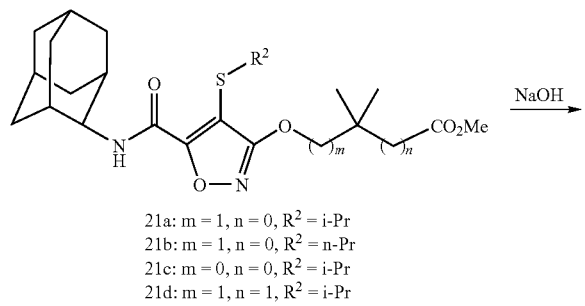

21a: m = 1, n = 0, R² = i-Pr
21b: m = 1, n = 0, R² = n-Pr
21c: m = 0, n = 0, R² = i-Pr
21d: m = 1, n = 1, R² = i-Pr

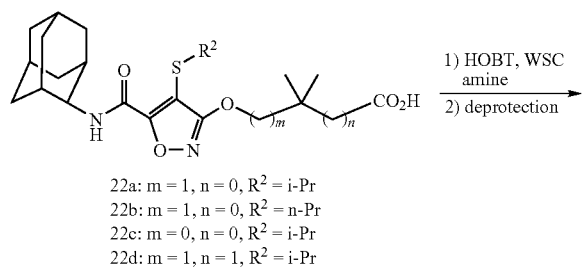

22a: m = 1, n = 0, R² = i-Pr
22b: m = 1, n = 0, R² = n-Pr
22c: m = 0, n = 0, R² = i-Pr
22d: m = 1, n = 1, R² = i-Pr

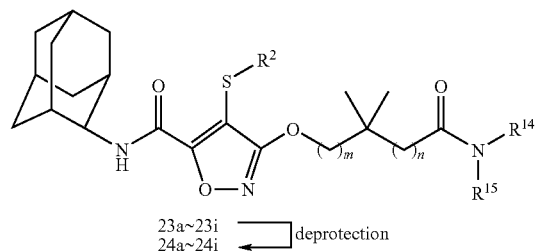

23a~23i
24a~24i  deprotection

-continued

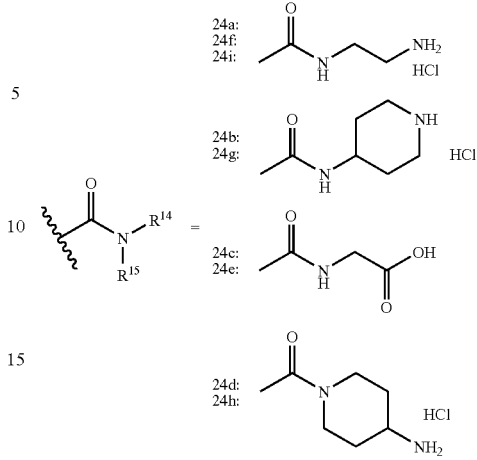

To a solution of Compound 1 (14 g) in dimethylformamide (140 ml) was added potassium carbonate (19 g), then the resulting mixture was stirred at 70° C. for 1 hr. Benzyl bromide (18 ml) was slowly added dropwisely to the reaction mixture at 70° C. and the reaction solution was stirred for 3 hrs. After termination of the reaction, the reaction solution was poured into ice-cold water and extracted with ethyl acetate. The organic layer was washed with brine and dried with magnesium sulfate and concentrated. The residue (13) was dissolved in tetrahydrofuran (100 ml)-methanol (100 ml), and 1N lithium hydroxide aqueous soln. (200 ml) was added to the resulting solution. The solution was stirred at room temperature for 14 hrs. After termination of the reaction, the solution was diluted with $H_2O$ and the aqueous layer was washed with diethylether. The mixture was acidified with 2N HCl aqueous soln., and extracted with ethyl acetate. The organic layer was washed with brine and dried with sodium sulfate and concentrated. The residue was washed with hexane to give Compound 14 (21.9 g).

To a solution of Compound 14 (14 g) in tetrahydrofuran (1.2 L) was slowly added n-butyllithium (1.57M in n-hexane, 100 ml) dropwisely at −78° C. After stirring at room temperature for 1 hr, the resulting solution was cooled again to −78° C. Dimethyl disulfide (8.1 ml) was added to the solution and the reaction solution was stirred at room temperature for 2 hrs. After termination of the reaction, the solution was diluted with $H_2O$ and the mixture was acidified with 2N HCl aqueous soln. The solution was extracted with ethyl acetate and dried with sodium sulfate and concentrated. The residue was washed with diisopropyl ether-hexane to give Compound 15 (11.9 g).

To a solution of Compound 15 (17 g) in dimethylformamide (377 ml) were added 2-adamantanamine hydrochloride (14.4 g), 1-(3-dimethylaminopropyl)-3-ethylcarbodiimide hydrochloride (18.4 g) and 1-hydroxybenzotriazole (1.73 g) under $N_2$ atmosphere, then triethylamine (24.1 ml) was slowly added dropwisely to the solution. The resulting solution was stirred at room temperature for 5 hrs. After termination of the reaction, the solution was poured into 2N HCl aqueous soln. (400 ml) and ice (300 ml), then extracted with ethyl acetate. The extraction was washed with sat. sodium hydrogencarbonate soln. and brine successively, then dried with sodium sulfate and concentrated. The residue was purified by silicagel columnchromatography to give Compound 16 (21.1 g).

Compound 16 (21 g) was dissolved in dioxane (420 ml)-methanol (210 ml)-$H_2O$ (210 ml), and then sodium periodate (47.3 g) was added to the resulting solution. The solution was stirred at 55° C. for 48 hrs. After termination of the reaction, dioxane and methanol were removed. The solution was diluted with H₂O and extracted with chloroform. The organic layer was washed with brine and dried with sodium sulfate and concentrated. The residue was recrystallized from ethyl acetate-hexane to give Compound 17 (16.5 g).

Under N₂ atmosphere, 2,6-lutidine (30 g) was added To Compound 17 (17.6 g) and the resulting mixture was suspended. Trifluoroacetic anhydride (25.8 ml) was added dropwisely to the resulting mixture over 15 min under ice-cooling. The resulting solution was stirred at 60° C. for 1 hr, and the solution was removed. Under N₂ atmosphere, methanol (141 ml) was added to the residue under ice-cooling, and triethylamine (28 ml) was added dropwisely to the resulting solution. The resulting solution was stirred at room temperature for 3 hrs. After termination of the reaction, the solution was poured into 2N NaOH aqueous soln. and ice and washed with diethylether. The aqueous layer was acidified with 2N HCl aqueous soln., and extracted with ethyl acetate. The organic layer was washed with brine and dried with sodium sulfate and concentrated to give Compound 18.

Compound 18 was dissolved in dimethylformamide (54 ml) and acetonitrile (54 ml) under N₂ atmosphere, and cesium carbonate (34.3 g) was added to the resulting solution under ice-cooling. 2-Bromopropane (7.9 ml) was added to the solution and the solution was stirred at room temperature for 24 hrs. After termination of the reaction, the solution was poured into ice-cold water. The resulting mixture was acidified with 2N HCl aqueous soln., and extracted with ethyl acetate. The organic layer was washed with brine and dried with sodium sulfate and concentrated to give Compound 19a (12.0 g).

Anisole (30.5 ml) was added to Compound 19a (12.0 g). 25% HBr/AcOH (120 ml) was added to the resulting mixture. The solution was stirred at room temperature for 4 hrs.

After termination of the reaction, the reaction solution was poured into ice water, and extracted with ethyl acetate. The solution was washed with brine, and dried with sodium sulfate and concentrated. Hexane was added to the residue, and the resulting crystal was collected by filtration to give Compound 20a (8.8 g).

To a solution of Compound 20a (8.8 g) in tetrahydrofuran (180 ml) were added triphenylphosphine (11 g) and hydroxypivalic acid methyl ester (5.5 g) under N₂ atmosphere. Azodicarboxylic acid diisopropyl (8.3 ml) was added dropwisely to the solution, then the whole mixture was stirred at room temperature for 3 hrs. After termination of the reaction, the solvent was removed. Diethylether was added to the residue and the obtained triphenylphosphine oxide was removed. Diethylether was removed and the residue was purified by silicagel columnchromatography to give Compound 21a (9.55 g).

Compound 21a (11.1 g) was dissolved in tetrahydrofuran (84 ml)-methanol (42 ml), and 2N lithium hydroxide aqueous soln. (24.7 ml) was added to the resulting solution. The solution was stirred at room temperature for 8 hrs and at 50° C. for 2 hrs. After termination of the reaction, tetrahydrofuran and methanol were removed. The solution was diluted with H₂O and the aqueous layer was washed with diethylether. The mixture was acidified with 2N HCl aqueous soln., and extracted with ethyl acetate. The organic layer was washed with brine and dried with sodium sulfate and concentrated to give Compound 22a (10.6 g). Compounds 22b, 22c and 22d were synthesized in accordance with the method shown in the above examples.

22a: (DMSO-d6); 1.17 (d, J=6.8 Hz, 6H), 1.23 (s, 6H), 1.57-1.99 (m, 14H), 4.03-4.05 (m, 1H), 4.27 (s, 2H), 8.40 (d, J=7.2 Hz, 1H), 12.14-12.81 (brs, 1H)

22b: (DMSO-d6); 0.89 (t, J=7.2 Hz, 3H), 1.22 (s, 6H), 1.40-1.98 (m, 16H), 2.78 (t, J=7.2 Hz, 2H), 4.01-4.08 (m, 1H), 4.27 (s, 2H), 8.36 (d, J=8.0 Hz, 1H)

22c: (DMSO-d6); 1.20 (d, J=6.8 Hz, 6H), 1.57-2.00 (m, 20H), 3.35-3.40 (m, 1H), 4.30 (br, 1H), 8.44 (d, J=6.8 Hz, 1H), 13.09 (s, 3H)

22d: (DMSO-d6); 1.09 (s, 6H), 1.20 (d, J=6.4 Hz, 6H), 1.59 (d, J=12.4 Hz, 2H), 1.72 (s, 2H), 1.82 (br, 6H), 1.94-2.00 (m, 4H), 2.31 (s, 2H), 3.30 (br, 1H), 4.04 (br, 1H), 4.13 (s, 2H), 8.42 (d, J=6.8 Hz, 1H), 12.11 (s, 1H)

To a solution of Compound 22a (10.6 g) in dimethylformamide (210 ml) were added tert-butyl-2-aminoethylcarbamate (4.66 g), 1-(3-dimethylaminopropyl)-3-ethylcarbodiimide hydrochloride (7.0 g) and 1-hydroxybenzotriazole (1.64 g) under N₂ atmosphere, then the resulting solution was stirred at room temperature for 10 hrs. After termination of the reaction, the solution was poured into ice-cold water and extracted with ethyl acetate. The organic layer was washed with sat. sodium hydrogencarbonate soln. and brine successively, and dried with sodium sulfate. The residue was recrystallized from ethyl acetate-hexane to give Compound 23a (13.3 g).

4N HCl/AcOEt (133 ml) was added to Compound 23a (13.3 g). The resulting solution was stirred at room temperature for 2 hrs. After termination of the reaction, the solution was diluted with diisopropyl ether to give crystal. The obtained crystal was collected by filtration and washed with diisopropylether, then dried to give Compound 24a (11.5 g).

The above-mentioned examples are concerning Compound 22a and 24a. Compounds 22b~22d and 24b~24i were synthesized in accordance with the method shown in the above examples.

TABLE 3

| No. | $R^2$ | m | n | NMR |
|---|---|---|---|---|
| 24a | i-Pr | 1 | 0 | (DMSO-d6); 1.17 (d, J = 6.8 Hz, 6H), 1.22 (s, 6H), 1.58-1.98 (m, 14H), 2.70-2.76 (m, 2H), 3.20-3.80 (m, 4H), 4.03-4.08 (m, 1H), 4.27 (s, 2H), 7.86-7.89 (m, 1H), 8.40 (d, J = 7.2 Hz, 1H) |
| 24b | i-Pr | 1 | 0 | (DMSO-d6); 1.17 (d, J = 6.8 Hz, 6H), 1.221(s, 6H), 1.58-1.98 (m, 18H), 2.87-2.93 (m, 2H), 3.22-3.81 (m, 5H), 4.02-4.05 (m, 1H), 4.30 (s, 2H), 7.69 (d, J = 7.2 Hz, 1H), 8.39 (d, J = 7.6 Hz, 1H) |
| 24c | i-Pr | 1 | 0 | (DMSO-d6); 1.16 (d, J = 6.8 Hz, 6H), 1.23 (s, 6H), 1.58-1.98 (m, 14H), 3.71 (d, J = 5.6 Hz, 2H), 4.03-4.05 (m, 1H), 4.28 (s, 2H), 7.98-8.06 (m, 1H), 8.39 (d, J = 7.2 Hz, 1H) |
| 24d | i-Pr | 1 | 0 | (DMSO-d6); 1.17 (d, J = 6.8 Hz, 6H), 1.26-1.34 (m, 8H), 1.58-1.96 (m, 16H), 2.84-4.04 (m, 8H), 4.22-4.29 (m, 3H), 8.40 (d, J = 7.2 Hz, 1H) |

TABLE 3-continued
| No. | $R^2$ | m | n | NMR |
|---|---|---|---|---|
| 24e | n-Pr | 1 | 0 | (DMSO-d6); 0.88 (t, J = 7.2 Hz, 3H), 1.23 (s, 6H), 1.39-1.98 (m, 16H), 2.77 (t, J = 7.2 Hz, 2H), 3.72(d, J = 5.6 Hz, 2H), 4.01-4.03 (m, 1H), 4.27 (s, 2H), 8.04 (m, 1H), 8.33 (d, J = 6.8 Hz, 1H) |
| 24f | n-Pr | 1 | 0 | (DMSO-d6); 0.88 (t, J = 7.2 Hz, 3H), 1.22 (s, 6H), 1.44-1.97 (m, 16H), 2.75-2.79 (m, 2H), 3.22-4.01 (m, 7H), 4.26 (s, 2H), 7.84-7.86 (m, 1H), 8.34 (d, J = 7.6 Hz, 1H) |
| 24g | n-Pr | 1 | 0 | (DMSO-d6); 0.89 (t, J = 7.2 Hz, 3H), 1.21 (s, 6H), 1.42-2.00 (m, 20H), 2.76-3.81 (m, 8H), 4.03 (d, J = 6.8 Hz, 1H), 4.30 (s, 2H), 7.66 (d, J = 7.2 Hz, 1H), 8.35 (d, J = 6.8 Hz, 1H) |
| 24h | n-Pr | 1 | 0 | (DMSO-d6); 0.89 (t, J = 7.2 Hz, 3H), 1.34-2.00 (m, 29H), 2.77-2.92 (m, 3H), 4.01-4.03 (m, 1H), 4.28-4.31 (m, 3H), 8.15 (brs, 2H), 8.37 (d, J = 7.2 Hz, 1H) |
| 24i | i-Pr | 0 | 0 | (DMSO-d6); 1.21 (d, J = 6.8 Hz, 6H), 1.58-1.99 (m, 20H), 2.57 (br, 2H), 3.06-3.10 (m, 2H), 3.40-3.46 (m, 1H), 4.04 (br, 1H), 7.75 (br, 1H), 8.43 (d, J = 7.6 Hz, 1H) |
EXAMPLE 4
[Formula 29]
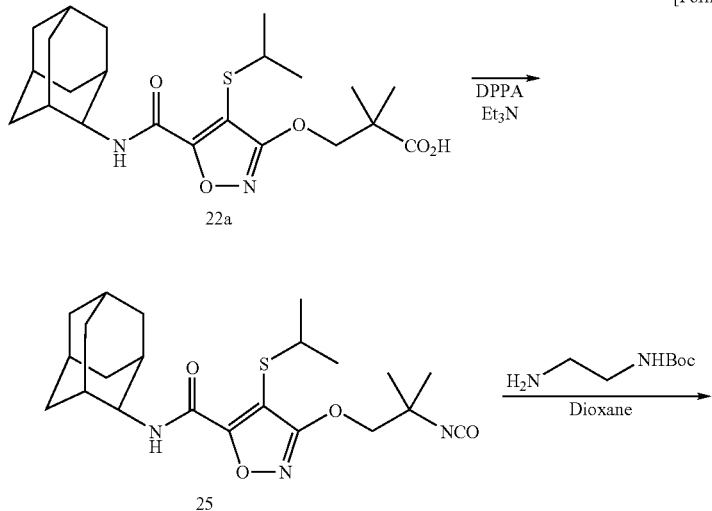
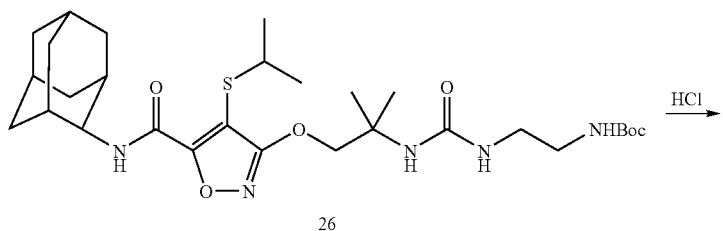
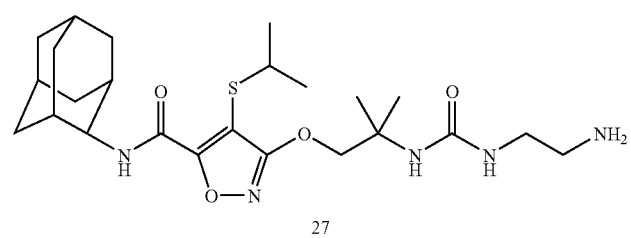

-continued

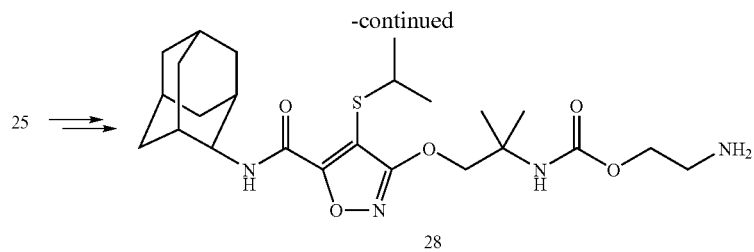
28

Compound 22a (200 mg) was dissolved in toluene (2 ml) and dioxane (1 ml), and then diphenylphosphoryl azide (103 μl) was added to the resulting solution. The solution was stirred at 120° C. for 5 hrs. After termination of the reaction, the solution was diluted with ethyl acetate. The resulting mixture was washed with 1N HCl aqueous soln., sat. sodium hydrogencarbonate soln. and brine successively, and dried with sodium sulfate and concentrated to give Compound 25 (140 mg).

To a solution of Compound 25 (60 mg) in dioxane (0.6 ml) was added tert-butyl-2-aminoethylcarbamate (45 mg), then the resulting solution was stirred at room temperature for 2 hrs. After termination of the reaction, 2N HCl aqueous soln. was added to the solution, then extracted with ethyl acetate. The organic layer was washed with sat. sodium hydrogencarbonate soln. and brine successively, and dried with sodium sulfate and concentrated. Diethylether was added to the residue, and the resulting powder was collected by filtration and dried to give Compound 26 (81 mg).

4N HCl/dioxane (0.8 ml) was added to Compound 26 (79 mg), then the resulting solution was stirred at room temperature for 1.5 hrs. After termination of the reaction, the solution was diluted with H₂O and washed with diethylether. The aqueous layer was alkalified with 2N NaOH aqueous soln., and extracted with ethyl acetate. The organic layer was washed with brine and dried with magnesium sulfate and concentrated. The residue was purified by silicagel columnchromatography to give Compound 27 (46 mg).

Compound 28 was synthesized by using Compound 25 and tert-butyl-2-hydroxyethylcarbamate in accordance with the method shown in the above Examples.

TABLE 4

| No. | NMR |
|---|---|
| 27 | (CDCl3); 1.29 (d, J = 6.8 Hz, 6H), 1.42 (s, 6H), 1.70-2.04 (m, 14H), 2.84 (br, 2H), 3.22 (br, 2H), 3.38-3.44 (m, 1H), 4.25 (br, 1H), 4.43 (s, 2H), 5.43 (s, 1H), 5.48 (br, 1H), 8.13 (d, J = 8.0 Hz, 1H) |
| 28 | (DMSO-d6); 1.19 (d, J = 6.8 Hz, 6H), 1.29 (s, 6H), 1.59 (d, J = 12.4 Hz, 2H), 1.72 (s, 2H), 1.82 (br, 6H), 1.93-1.99 (m, 4H), 2.67 (t, J = 6.0 Hz, 2H), 3.33-3.38 (m, 1H), 3.82 (t, J = 6.0 Hz, 2H), 4.03 (br, 1H), 4.33 (s, 2H), 7.11 (s, 1H), 8.41 (d, J = 7.6 Hz, 2H) |

EXAMPLE 5

[Formula 30]

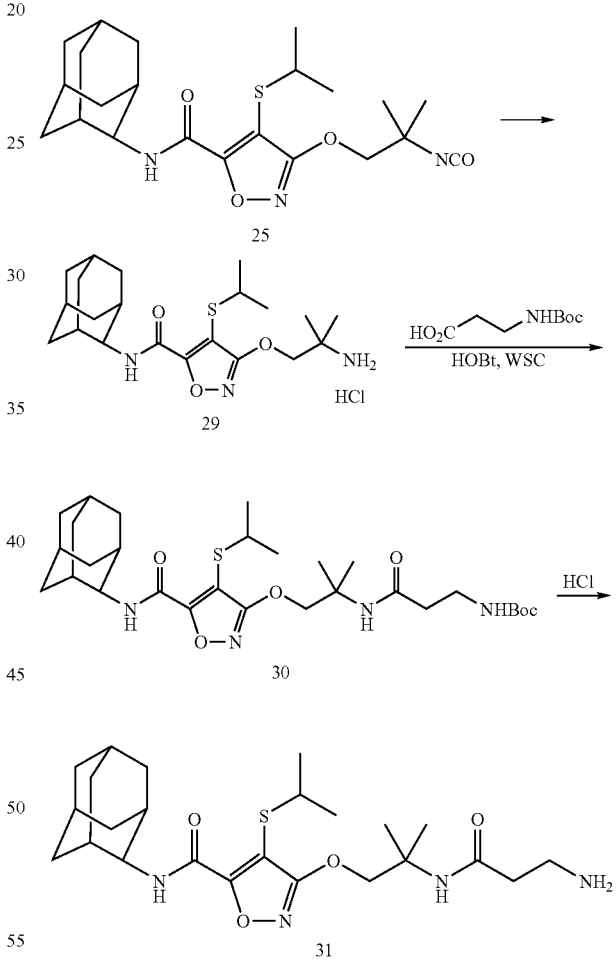

4N HCl/dioxane (4.2 ml) was added to Compound 25 (210 mg), then the resulting solution was stirred at room temperature for 7 hrs. After termination of the reaction, diethylether was added to the solution, and the obtained white precipitate was collected by filtration and washed with diethylether, then dried to give Compound 29 (135 mg).

To a solution of Compound 29 (50 mg) in dimethylformamide (1 ml) were added N-Boc-β-alanine (26 mg), 1-(3-dimethylaminopropyl)-3-ethylcarbodiimide hydrochloride (33 mg) and 1-hydroxybenzotriazole (8 mg), then triethylamine (43 μl) was added dropwisely to the solution. The resulting solution was stirred at room temperature for 9 hrs. After termination of the reaction, 2N HCl aqueous soln. (400 ml) was added to the solution, then extracted with ethyl acetate. The extraction was washed with sat. sodium hydrogencarbonate soln. and brine successively, then dried with sodium sulfate and concentrated. The residue was purified by silicagel columnchromatography to give Compound 30 (62 mg).

4N HCl/dioxane (1.2 ml) was added to Compound 30 (62 mg), then the resulting solution was stirred at room temperature for 2 hrs. After termination of the reaction, the solution was diluted with H₂O and washed with diisopropylether. The aqueous layer was alkalified with 2N NaOH aqueous soln., and extracted with ethyl acetate. The organic layer was washed with brine and dried with sodium sulfate and concentrated. The residue was purified by silicagel columnchromatography to give Compound 31 (35 mg).

TABLE 5

| No. | NMR |
|---|---|
| 29 | (DMSO-d6); 1.20 (d, J = 6.8 Hz, 6H), 1.39 (s, 6H), 1.60 (d, J = 11.6 Hz, 2H), 1.72 (s, 2H), 1.83 (br, 6H), 1.94-2.00 (m, 4H), 3.41-3.49 (m, 1H), 4.04 (br, 1H), 4.35 (s, 2H), 8.46 (d, J = 7.2 Hz, 1H), 8.56 (brs, 3H) |
| 31 | (DMSO-d6); 1.20 (d, J = 5.6 Hz, 6H), 1.32 (s, 6H), 1.59 (d, J = 12.4 Hz, 2H), 1.72 (s, 2H), 1.82 (br, 6H), 1.93-1.99 (m, 4H), 2.13 (br, 2H), 2.70 (br, 2H), 3.31-3.40 (m, 1H), 4.03 (br, 1H), 4.41 (s, 2H), 7.81 (s, 1H), 8.40 (m, 1H) |

The following compounds were synthesized as well as the above-mentioned execution example 1~5.

Liquid chromatography mass spectrometry (LC-MS) made of Waters was used for the measurement of molecular weight. The column made of Phenomenex Luna 5 μC18 (2)100 A (50 mm×4.60 mmΦ) was used for the measurement. The elution was a straight line inclination of MeCN density (10%~100%/3 min) at flow velocity 3.0 mL/min.

TABLE 6

| No. | Structure | NMR | retention time | MS |
|---|---|---|---|---|
| II-1 | 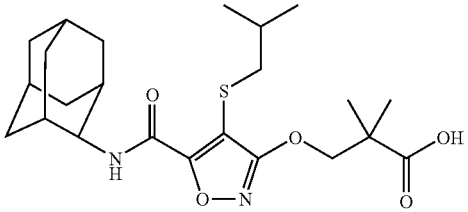 | (DMSO-d6); 0.91 (d, J = 6.4 Hz, 6H), 1.24 (s, 6H), 1.55-2.02 (m, 15H), 2.71 (d, J = 6.8 Hz, 2H), 4.02 (brs, 1H), 4.28 (s, 2H), 8.37 (d, J = 7.2 Hz, 1H), 12.53 (s, 1H) | | |
| II-2 | 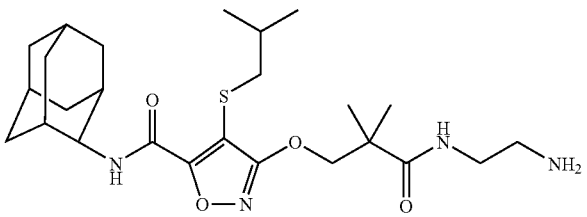 | (DMSO-d6); 0.91 (d, J = 6.0 Hz, 6H), 1.21 (s, 6H), 1.55-2.01 (m, 15H), 2.57 (brs, 2H), 2.71 (d, J = 6.0 Hz, 2H), 3.07 (brs, 2H), 4.02 (brs, 1H), 4.27 (s, 2H), 7.66 (brs, 1H), 8.35 (d, J = 5.6 Hz, 1H) | | |
| II-3 | 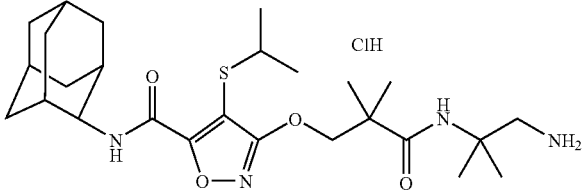 | (DMSO-d6); 1.19 (d, J = 6.4 Hz, 6H), 1.24 (s, 6H), 1.30 (s, 6H), 1.58-1.99 (m, 14H), 3.07 (brs, 2H), 3.30-3.40 (m, 1H), 4.03 (brs, 1H), 4.31 (s, 2H), 7.10 (s, 1H), 8.09 (brs, 3H), 8.41 (d, J = 6.4 Hz, 1H) | | |
| II-4 | 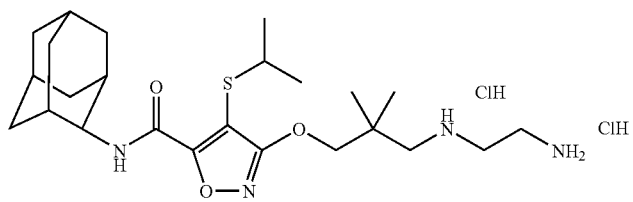 | (DMSO-d6); 1.13 (s, 6H), 1.22 (d, J = 6.4 Hz, 6H), 1.59-1.99 (m, 14H), 2.89 (brs, 2H), , 3.13 (brs, 2H), 3.18 (brs, 2H), 3.30-3.40 (m, 1H), 4.04 (brs, 1H), 4.17 (s, 2H), 8.43 (d, J = 8.4 Hz, 1H) | | |
| II-5 | 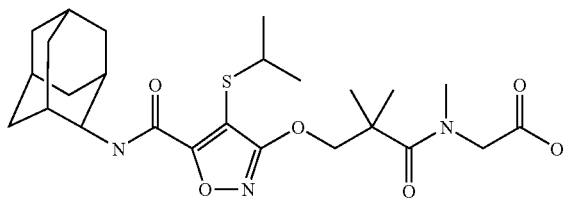 | | 2.43 | 507.9 |

TABLE 6-continued

| No. | Structure | NMR | retention time | MS |
|---|---|---|---|---|
| II-6 | 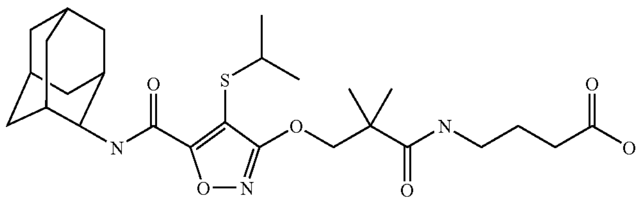 | | 2.26 | 522.4 |
| II-7 | Chiral | | 2.35 | 508.4 |

TABLE 7

| No. | Structure | NMR | retention time | MS |
|---|---|---|---|---|
| II-8 | 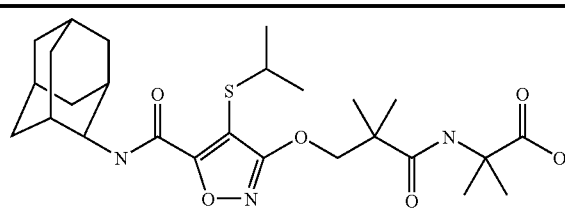 | | 2.45 | 523.1 |
| II-9 | 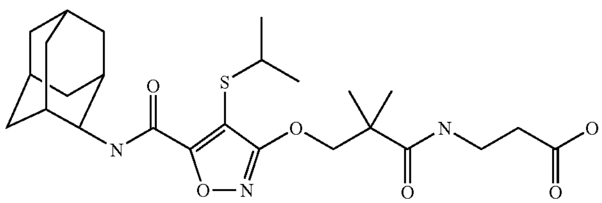 | | 2.25 | 508.4 |
| II-10 | 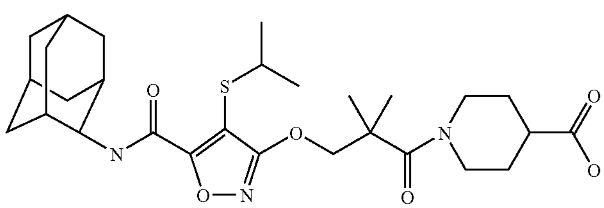 | | 2.46 | 547.9 |
| II-11 | Chiral | | 2.53 | 548.4 |

TABLE 7-continued

| No. | Structure | NMR | retention time | MS |
|---|---|---|---|---|
| II-12 | 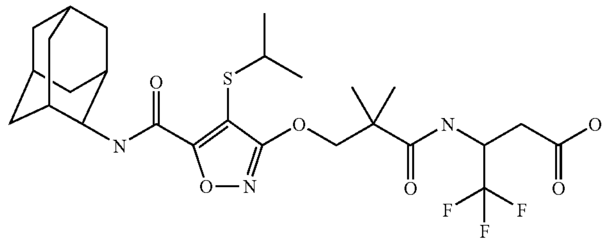 | | 2.57 | 576.4 |
| II-13 | 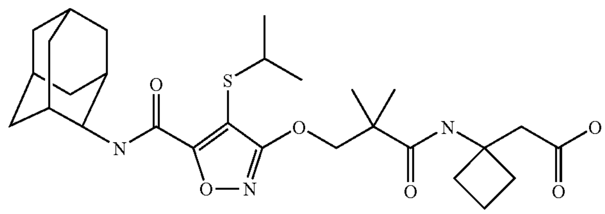 | | 2.540 | 547.9 |
| II-14 | 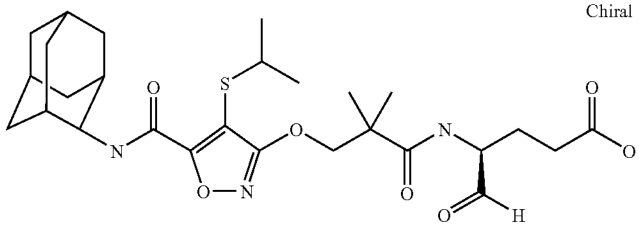 | Chiral | 2.03 | 564.9 |

TABLE 8

| No. | Structure | NMR | retention time | MS |
|---|---|---|---|---|
| II-15 | 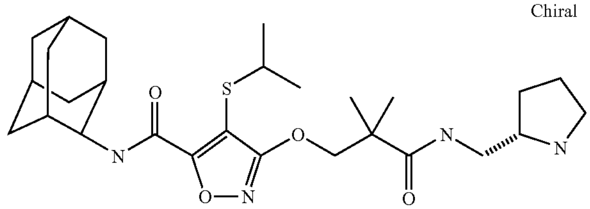 | Chiral | 1.54 | 520.5 |
| II-16 | 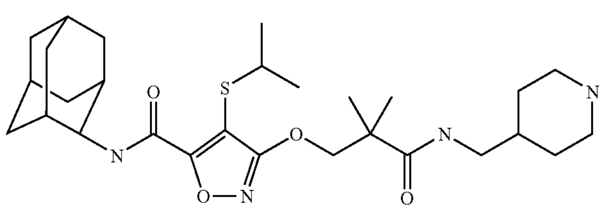 | | 1.52 | 534.5 |
| II-17 | 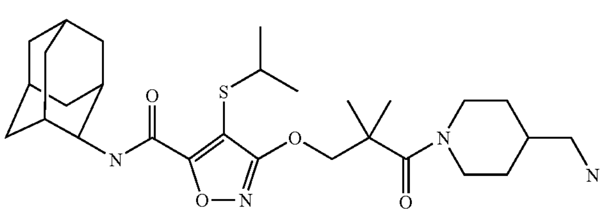 | | 1.52 | 534.3 |

TABLE 8-continued

| No. | Structure | NMR | retention time | MS |
|---|---|---|---|---|
| II-18 | 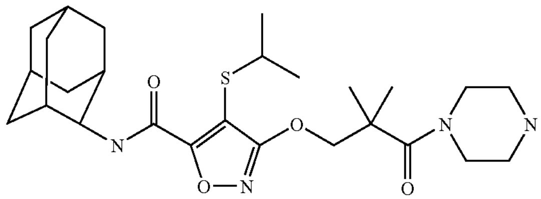 | | 1.49 | 505.6 |
| II-19 | 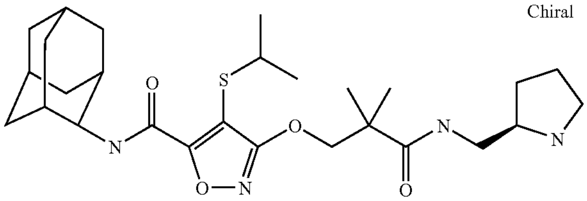 | Chiral | 1.50 | 520.5 |
| II-20 | 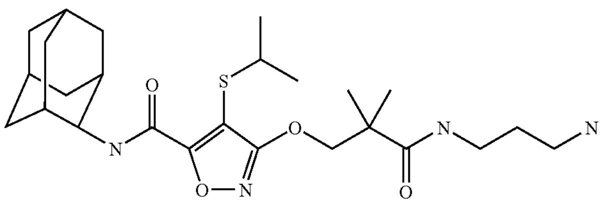 | | 1.46 | 494.3 |
| II-21 | 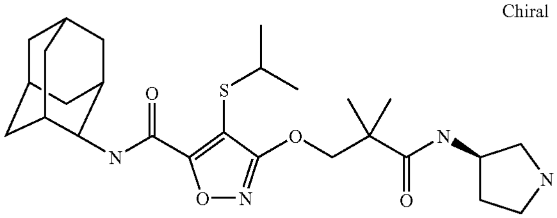 | Chiral | 1.48 | 506.5 |

TABLE 9

| No. | Structure | NMR | retention time | MS |
|---|---|---|---|---|
| II-22 | 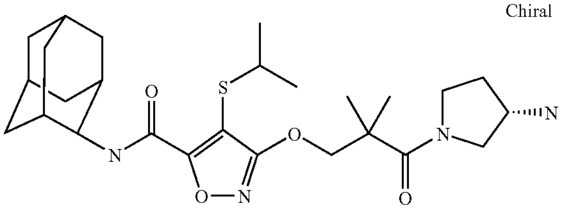 | Chiral | 1.49 | 506.3 |
| II-23 | 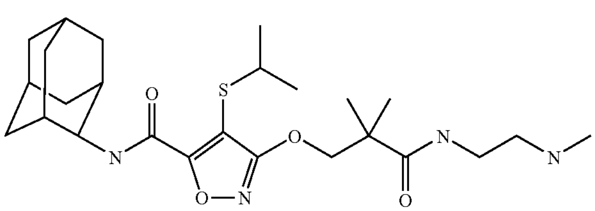 | | 1.48 | 494.5 |

TABLE 9-continued

| No. | Structure | NMR | retention time | MS |
|---|---|---|---|---|
| II-24 | 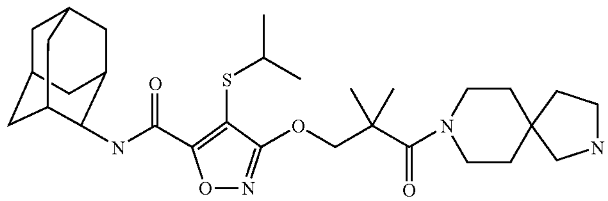 | | 1.56 | 560.2 |
| II-25 | 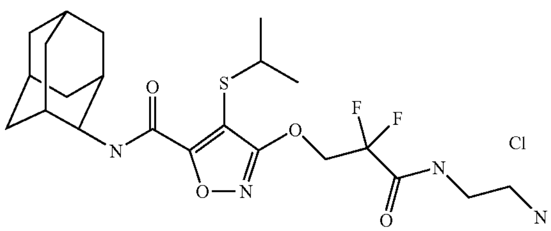 | (DMSO-d6); 1.19(d, J = 6.4 Hz, 6H), 1.53-2.02(m, 14H), 2.88-2.98(m, 2H), 3.25-3.37(m, 1H), 3.40-3.50(m, 2H), 4.00-4.08(m, 1H), 4.89(t, J = 13.6 Hz, 2H), 8.14-8.24(br, 2H), 8.47(d, J = 7.2 Hz, 1H), 9.25-9.31(br, 1H) | | |
| II-26 | 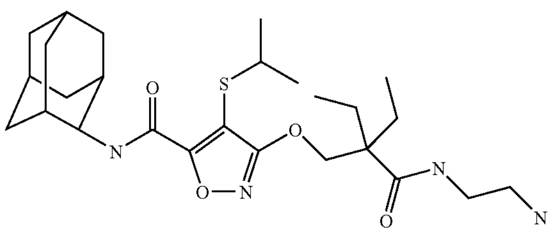 | (DMSO-d6); 0.76(t, J = 6.4 Hz, 6H), 1.17(d, J = 6.4 Hz, 6H), 1.49-2.03(m, 18H), 2.52-2.63(m, 2H), 2.91-3.52(m, 3H), 3.97-4.07(m, 1H), 4.33(s, 2H), 7.65-7.72(br, 1H), 8.41 (d, J = 6.4 Hz, 1H) | | |
| II-27 | 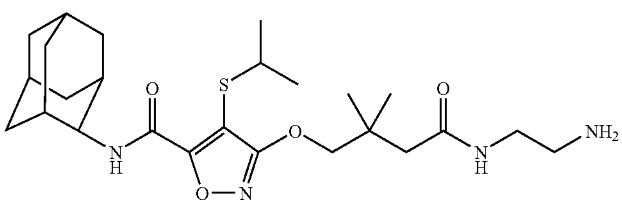 | hydrochloride (DMSO-d6); 1.06 (s, 6H), 1.20 (d, J = 6.4 Hz, 6H), 1.58-2.00 (m, 14H), 2.20 (s, 2H), 2.83 (brs, 2H), 3.27-3.40 (m, 3H), 4.04 (brs, 1H), 4.15 (s, 2H), 8.09 (brs, 3H), 8.31 (brs, 1H), 8.44 (d, J = 7.2 Hz, 1H) | | |
| II-28 | 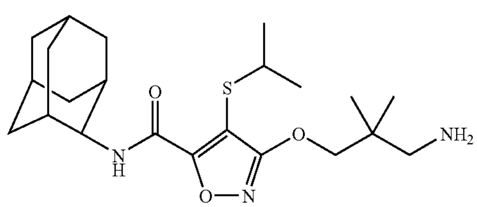 | (DMSO-d6); 0.92 (s, 6H), 1.20 (d, J = 6.4 Hz, 6H), 1.58-1.99 (m, 14H), 2.48 (s, 2H), 3.32-3.36 (, m, 1H), 4.05 (brs, 3H), 8.40 (d, J = 6.8 Hz, 1H) | | |

TABLE 10

| No. | Structure | NMR | retention time | MS |
|---|---|---|---|---|
| II-29 | Chiral | (DMSO-d6) 1.16-1.22(m, 14H), 1.58-1.99(m, 14H), 3.33-3.42(m, 1H), 4.01-4.07(m, 1H), 4.27(s, 2H), 4.50-4.55(m, 1H), 6.89(brs, 1H), 7.35(brs, 1H), 7.88(d, J = 6.8 Hz, 1H), 8.39(d, J = 5.6 Hz, 1H) | | |

TABLE 10-continued

| No. | Structure | NMR | retention time | MS |
|---|---|---|---|---|
| II-30 | Chiral | (DMSO-d6) 1.09-1.23(m, 14H), 1.58-2.13(m, 16H), 3.33-3.42(m, 1H), 4.00-4.05(m, 1H), 4.13-4.20(m, 1H), 4.29(s, 2H), 6.80(brs, 1H), 7.23(brs, 1H), 7.93-7.94(m, 1H), 8.37-8.40(m, 1H) | | |
| II-31 | 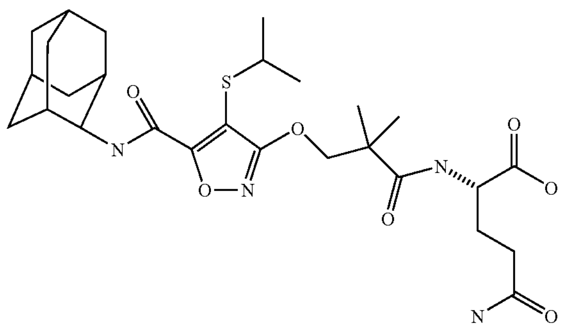 | (DMSO-d6) 1.09-1.24(m, 14H), 1.58-2.13(m, 16H), 3.33-3.42(m, 1H), 4.02-4.05(m, 1H), 4.13-4.20(m, 1H), 4.29(s, 2H), 6.80(brs, 1H), 7.29(brs, 1H), 7.93-7.95(m, 1H), 8.36-8.41(m, 1H) | | |
| II-32 | 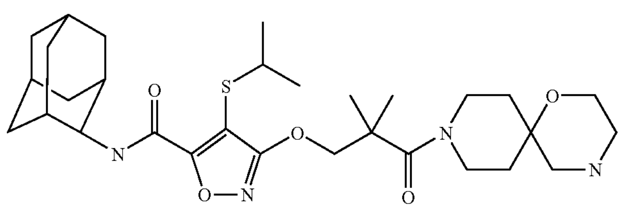 | | 1.53 | 576.4 |
| II-33 | Chiral | | 2.43 | 548.6 |
| II-34 | 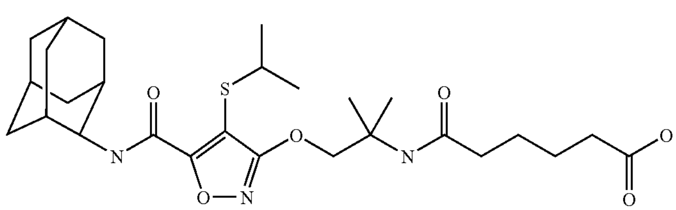 | | 2.38 | 536 |
| II-35 | Chiral | | 2.41 | 522 |

TABLE 11

| No. | Structure | NMR | retention time | MS |
|---|---|---|---|---|
| II-36 | 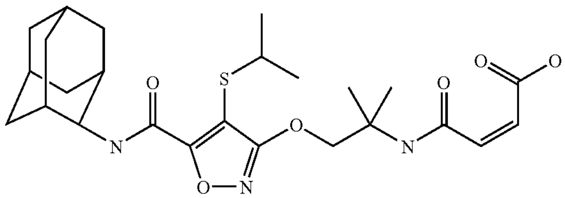 | | 2.37 | 505.9 |
| II-37 | 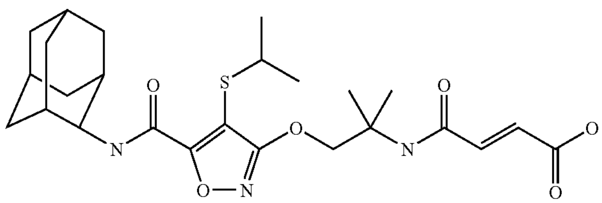 | | 2.37 | 505.9 |
| II-38 | 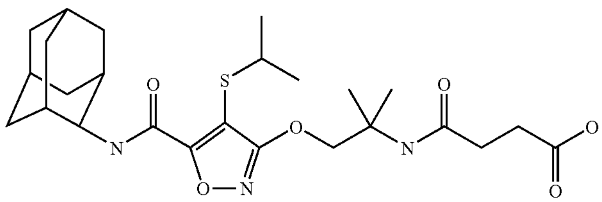 | | 2.34 | 508 |
| II-39 | 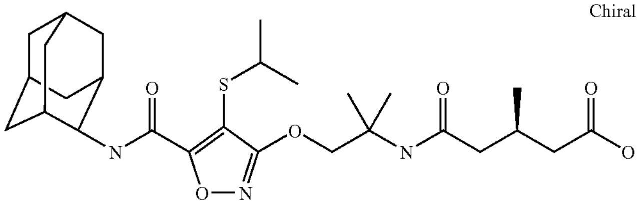 | Chiral | 2.41 | 536 |
| II-40 | 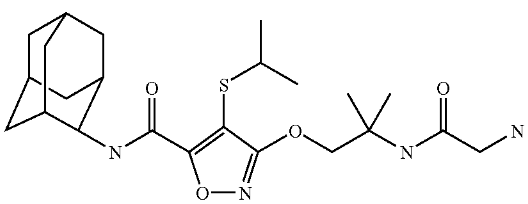 | | 1.49 | 466.2 |
| II-41 | 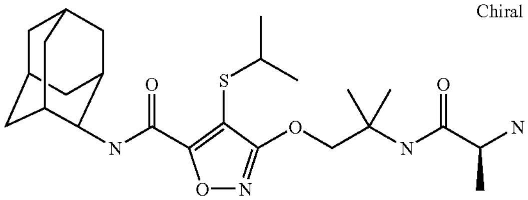 | Chiral | 1.45 | 480.3 |
| II-42 | 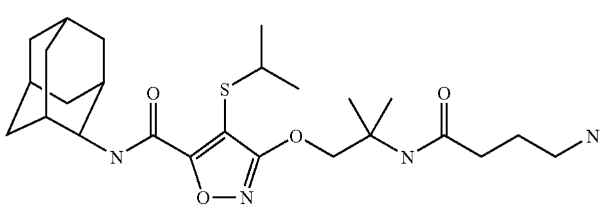 | | 1.46 | 494.3 |

TABLE 12

| No. | Structure | NMR | retention time | MS |
|---|---|---|---|---|
| II-43 | 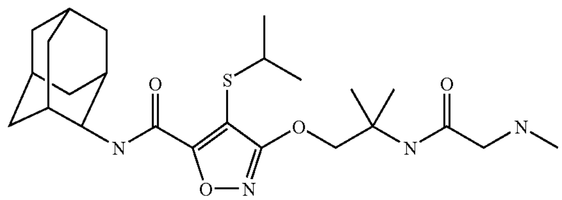 | | 1.52 | 480.4 |
| II-44 | Chiral | | 1.48 | 537 |
| II-45 | Chiral | | 1.65 | 556.5 |
| II-46 | Chiral | | 1.67 | 594.6 |
| II-47 | Chiral | | 1.56 | 508.4 |
| II-48 | 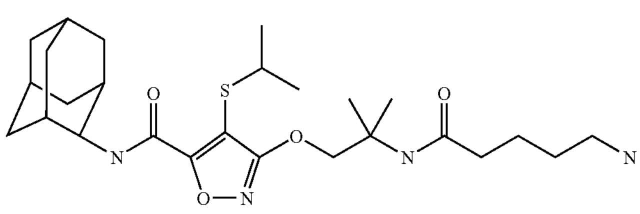 | | 1.54 | 507 |

TABLE 12-continued

| No. | Structure | NMR | retention time | MS |
|---|---|---|---|---|
| II-49 | 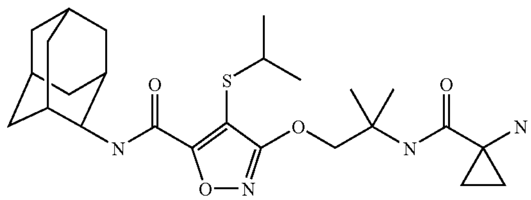 | | 1.56 | 491 |

TABLE 13

| No. | Structure | NMR | retention time | MS |
|---|---|---|---|---|
| II-50 | 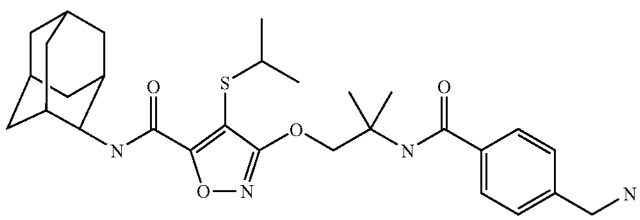 | | 1.54 | 541.6 |
| II-51 | 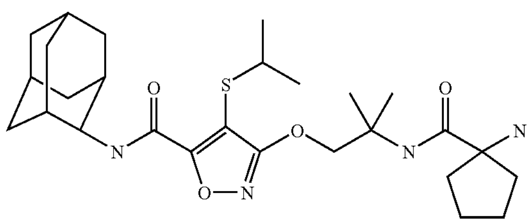 | | 1.54 | 519.1 |
| II-52 | 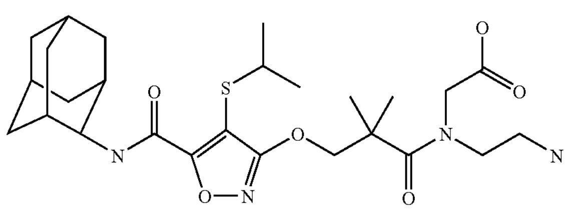 | (CD3OD); 1.28 (d, J = 6.8 Hz, 6H), 1.42 (s, 6H), 1.74-2.01 (m, 14H), 3.17 (brs, 2H), 3.38-3.44 (m, 1H), 3.62 (brs, 2H), 4.14 (s, 2H), 4.20 (, s, 1H), 4.39 (s, 2H), 8.46 (d, J = 5.6 Hz, 1H) | | |
| II-53 | 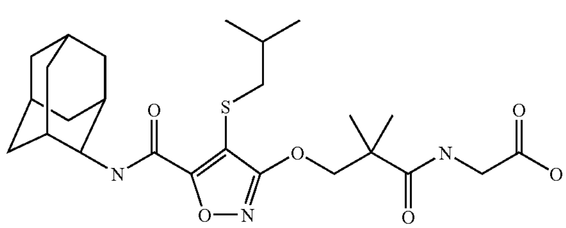 | (DMSO-d6); 0.90 (d, J = 6.4 Hz, 6H), 1.25 (s, 6H), 1.56-2.05 (m, 15H), 2.70 (d, J = 6.8 Hz, 2H), 3.73 (d, J = 5.6 Hz, 2H), 4.03 (d, J = 6.4 Hz, 1H), 4.28 (s, 2H), 8.05 (brs, 1H), 8.35 (d, J = 7.2 Hz, 1H) | | |
| II-54 | 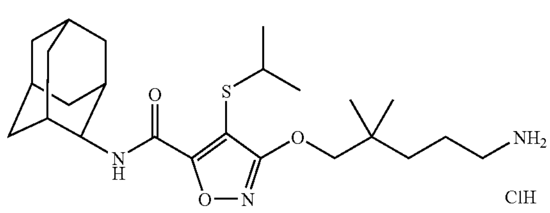 | (DMSO-d6); 0.99 (s, 6H), 1.21 (d, J = 6.4 Hz, 6H), 1.36 (brs, 2H), 1.50-1.99 (m, 16H), 2.74 (brs, 2H), 3.30-3.36 (, m, 1H), 4.00 (s, 2H), 4.04 (brs, 1H), 7.83 (brs, 3H), 8.42 (d, J = 7.2 Hz, 1H) | | |

TABLE 13-continued

| No. | Structure | NMR | retention time | MS |
|---|---|---|---|---|
| II-55 | Cl | (DMSO-d6) 1.16-1.24(m, 10H), 1.59-2.21(m, 14H), 2.90-2.92(m, 1H), 3.32-3.44(m, 4H), 4.03-4.05(m, 1H), 4.39(s, 2H), 7.36(brs, 1H), 7.60(brs, 1H), 8.39-8.41(m, 1H), 8.56-8.62(m, 1H) | | |
| II-56 | Chiral | (DMSO-d6) 1.17-1.20(m, 12H), 1.31-2.06(m, 13H), 3.33-3.42(m, 1H), 3.89-3.93(m, 1H), 4.25(s, 2H), 4.47(s, 1H), 6.97(brs, 1H), 7.23(brs, 1H), 8.34-8.36(m, 1H) | | |

TABLE 14

| No. | Structure | NMR | retention time | MS |
|---|---|---|---|---|
| II-57 | Chiral | (DMSO-d6) 1.17(d, J = 6.8 Hz, 6H), 1.33(s, 6H), 1.40-2.10(m, 13H), 3.33-3.42(m, 1H), 3.52-3.58(m, 8H), 3.90-4.03(m, 1H), 4.32(s, 2H), 4.47(s, 1H), 8.36(d, J = 7.2 Hz, 1H) | | |
| II-58 | Chiral | (DMSO-d6) 1.01-1.22(m, 12H), 1.39-2.04(m, 13H), 2.70-2.77(m, 2H), 3.33-3.42(m, 4H), 3.87-3.94(m, 1H), 4.27(s, 2H), 4.44-4.50(m, 1H), 7.86-7.91(m, 1H), 8.30-8.38(m, 1H) | | |
| II-59 | ClH | (DMSO-d6); 1.03(s, 3H), 1.05(s, 3H), 1.20(d, J = 6.9 Hz, 6H), 1.58-2.00(m, 14H), 3.10-3.23(m, 2H)3.35-3.44(m, 2H), 3.54-3.64(m, 1H), 4.03-4.05(m, 1H), 4.23(s, 2H), 7.57(s, 1H), 8.13(bs, 2H), 8.44(d, J = 7.2 Hz, 1H) | | |

TABLE 14-continued

| No. | Structure | NMR | retention time | MS |
|---|---|---|---|---|
| II-60 | Chiral | (DMSO-d6); 1.17-2.00 (m, 30H), 2.71 (brs, 1H), 2.97 (brs, 1H), 3.33-3.41 (, m, 1H), 3.57-3.70 (brm, 2H), 4.03 (brs, 1H), 4.21 (brs, 1H), 4.31 (d, J = 10 Hz, 1H), 4.38 (d, J = 10 Hz, 1H), 8.14 (brs, 3H), 8.41 (d, J = 6.4 Hz, 1H) | | |
| II-61 | Chiral | (DMSO-d6) 1.17(d, J = 6.8 Hz, 6H), 1.40-2.22(m, 17H), 3.33-3.42(m, 1H), 3.44(t, J = 6.8 Hz, 2H), 3.60-3.63(m, 2H), 3.94-3.98(m, 1H), 4.38-4.42(m, 2H), 4.47(s, 1H), 8.36(d, J = 7.6 Hz, 1H) | | |
| II-62 | Chiral | (DMSO-d6) 0.81-1.76(m, 23H), 2.80-2.85(m, 2H), 3.33-3.42(m, 3H), 3.88-3.94(m, 1H), 4.23(s, 1H), 7.72-8.05(m, 4H) | | |
| II-63 | Chiral | (DMSO-d6) 1.19(d, J = 6.4 Hz, 6H), 1.40-2.07(m, 13H), 2.93-3.37(m, 5H), 3.94-3.98(m, 1H), 4.23(s, 1H), 8.37(d, J = 7.2 Hz, 1H) | | |

TABLE 15

| No. | Structure | NMR | retention time | MS |
|---|---|---|---|---|
| II-64 | 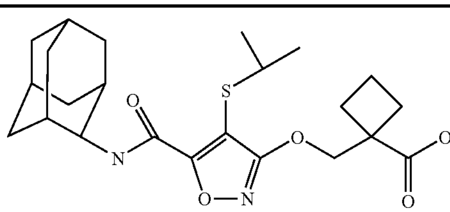 | (DMSO-d6) 1.16(d, J = 6.4 Hz, 6H), 1.57-2.44(m, 20H), 3.28-3.33(m, 1H), 4.01-4.06(m, 1H), 4.52(s, 2H), 8.39(d, J = 6.8 Hz, 1H), 12.55(brs, 1H) | | |
| II-65 | Chiral | (DMSO-d6) 1.18(d, J = 6.8 Hz, 6H), 1.40-1.2.07(m, 13H), 2.96(s, 3H), 3.37-3.44(m, 3H), 3.93-3.97(m, 1H), 4.31-4.36(m, 2H), 4.47(s, 1H), 7.29-7.35(m, 1H), 8.38(d, J = 6.8 Hz, 1H) | | |

TABLE 15-continued

| No. | Structure | NMR | retention time | MS |
|---|---|---|---|---|
| II-66 | 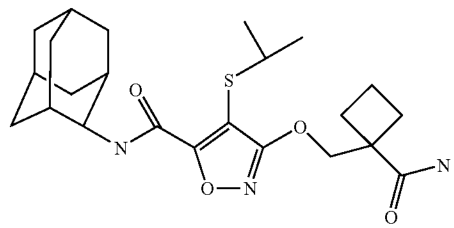 | (DMSO-d6) 1.17(d, J = 6.4 Hz, 6H), 1.58-2.39(m, 20H), 3.28-3.33(m, 1H), 4.01-4.06(m, 1H), 4.51(s, 2H), 7.01(brs, 1H), 7.28(brs, 1H), 8.39(d, J = 7.2 Hz, 1H) | | |
| II-67 | 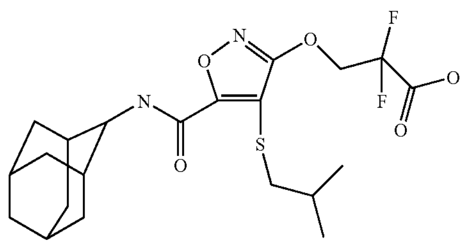 | (DMSO-d6); 0.9(d, J = 6.9 Hz, 6H), 1.51-2.06(m, 14H), 2.70(d, J = 6.9 Hz, 2H), 2.81-2.89(m, 2H), 4.03(m, 1H), 4.88(t, J = 12.9 Hz, 2H), 8.46(m, 1H) | | |

TABLE 16

| No. | Structure | NMR |
|---|---|---|
| II-68 | 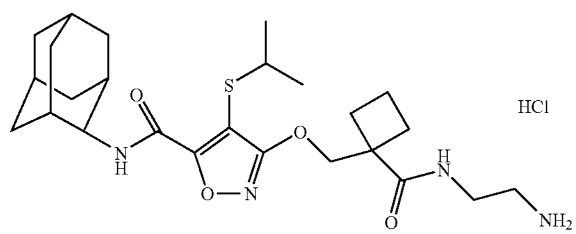 | (DMSO-d6); 1.16(d, J = 6.6 Hz, 6H), 1.57-2.06(m. 18H), 2.34-2.48(m, 2H), 2.81-2.89(m, 2H), 3.25-3.38(m, 2H), 4.00-4.07(m, 1H), 4.53(s, 2H), 8.01 (br.s, 2H), 8.12(m, 1H), 8.42(d, J = 7.2 Hz, 1H) |
| II-69 | 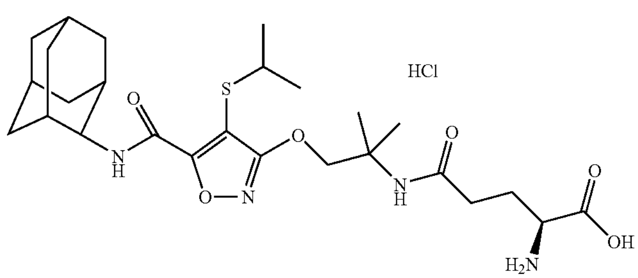 | (DMSO-d6); 1.20(d, J = 6.0 Hz, 6H), 1.33(s, 6H), 1.53-2.04(m, 16H), 2.16-2.42(m, 2H), 3.30-3.43(m, 1H), 3.78-3.88(m, 1H), 3.99-4.07(m, 1H), 4.41(s, 2H), 7.91-7.96(br, 1H), 8.41(d, J = 6.4 Hz, 1H), 8.46-8.55(br, 2H) |
| II-70 | 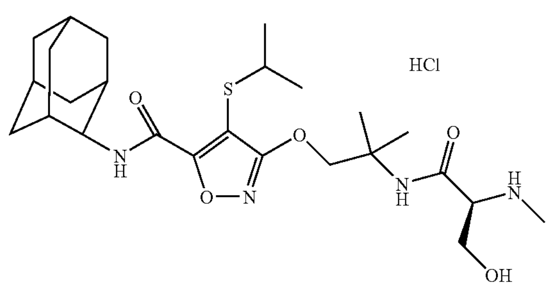 | (DMSO-d6); 1.21(d, J = 6.0 Hz, 6H), 1.37(s, 6H), 1.53-2.03(m, 17H), 3.31-3.46(m, 1H), 3.69-3.88(m, 3H), 3.99-4.08(m, 1H), 4.34-4.50(m, 2H), 5.41-5.66(br, 1H), 8.41(d, J = 6.8 Hz, 1H), 8.60-8.66(br, 1H), 8.77-8.91(br, 1H), 9.20-9.32(br, 1H) |

TABLE 16-continued

| No. | Structure | NMR |
|---|---|---|
| II-71 | 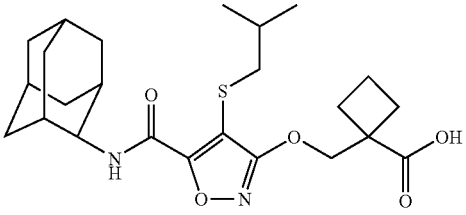 | (DMSO-d6); 0.90 (d, J = 6.4 Hz, 6H), 1.55-2.10 (m, 19H), 2.38 (brs, 2H), 2.69 (d, J = 6.4 Hz, 2H), 4.02 (brs, 1H), 4.52 (s, 2H), 8.36 (d, J = 6.4 Hz, 1H), 12.55 (brs, 1H) |
| II-72 | 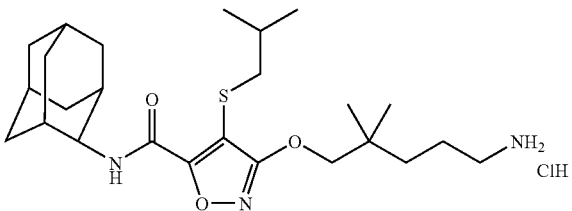 | (DMSO-d6): 0.93 (d, J = 4.4 Hz, 6H), 0.99 (s, 6H), 1.36 (brs, 2H), 1.55-2.01 (m, 17H), 2.75 (brs, 4H), 3.97-4.04 (brm, 3H), 8.03 (brs, 3H), 8.38 (d, J = 4.8 Hz, 1H) |
| II-73 | 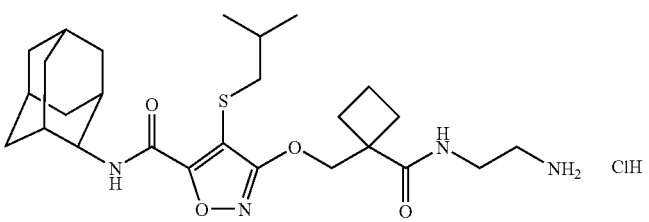 | (DMSO-d6); 0.90 (d, J = 6.0 Hz, 6H), 1.55-2.05 (m, 19H), 2.43 (brs, 2H), 2.70 (d, J = 6.4 Hz, 2H), 2.85 (brs, 2H), 3.35 (brs, 2H), 4.02 (brs, 1H), 4.54 (s, 2H), 8.16 (brs, 3H), 8.35 (d, J = 6.8 Hz, 1H) |
| II-74 | 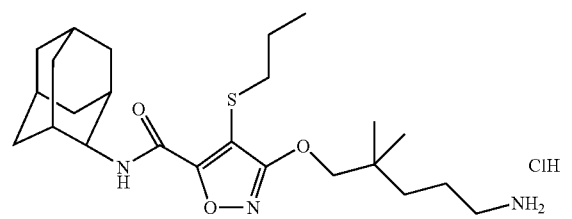 | (DMSO-d6); 0.90(t, J = 7.2 Hz, 3H), 0.97(s,, 6H), 1.34-1.99(m, 20H), 2.68-2.80(m, 2H)2,82(t, J = 7.2 Hz, 2H)3.99(s, 2H), 3.99-4.03(m, 1H)7.80(bs, 2H), 8.37(d, J = 7.2 Hz, 1H) |

TABLE 17

| No. | Structure | NMR |
|---|---|---|
| II-75 | 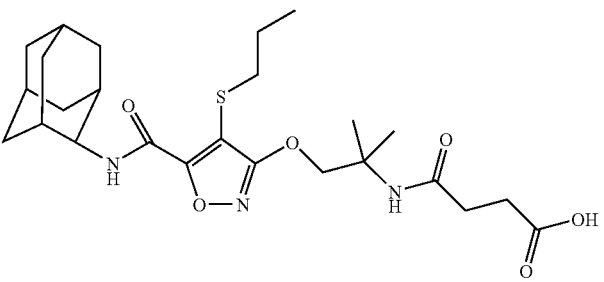 | (CDCl3); 0.99(t, J= 7.2 Hz, 3H), 1.13(d, J = 7.2 Hz, 2H), 1.46(s,, 6H), 1.53-2.08(m, 20H), 2.40-2.49(m, 2H), 2.58-2.66(m, 2H), 2.85(t, J = 7.2 Hz, 2H), 3.63-3.67(m, 1H), 4.24-4.27(m, 1H), 4.44(s, 2H), 6.15(s, 1H), 7.95(d, J = 8.4 Hz, 1H) |
| II-76 | 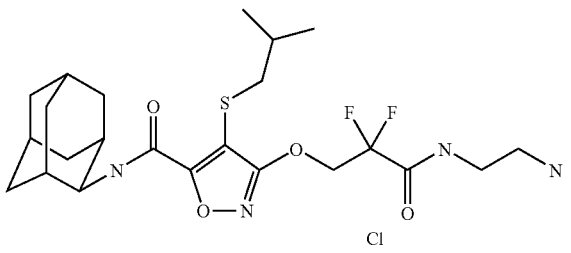 | (DMSO-d6); 0.9(d, J = 6.9 Hz, 6H), 1.54-2.03(m. 14H), 2.71(t, J = 3.3 Hz, 2H), 2.89-2.94(m, 2H), 4.90(t, J = 13.5 Hz, 2H), 8.14(br-s, 1H), 8.46(m, 1H), 8.46(d, J = 7.2 Hz, 1H), 9.28(s, 1H) |

TABLE 17-continued

| No. | Structure | NMR |
|---|---|---|
| II-77 | 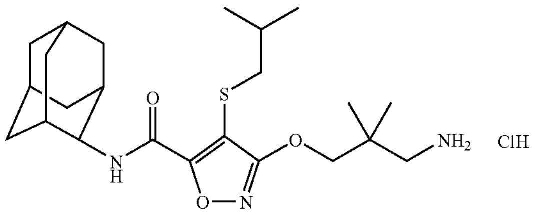 | (DMSO-d6); 0.93 (d, J = 6.4 Hz, 6H), 1.09 (s, 6H), 1.56-2.02 (m, 15H), 2.75 (d, J = 6.8 Hz, 2H), 2.83 (brs, 2H), 4.03 (brs, 1H), 4.14 (s, 2H), 8.22 (brs, 3H), 8.40 (d, J = 7.2 Hz, 1H) |
| II-78 | 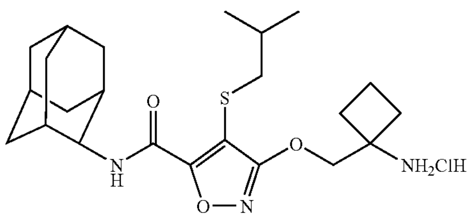 | (DMSO-d6): 0.93 (d, J = 6.4 Hz, 6H), 1.57-2.07 (m, 17H), 2.21 (brs, 2H), 2.33-2.42 (m, 2H), 2.79 (d, J = 6.8 Hz, 2H), 4.04 (brs, 1H), 4.52 (s, 2H), 2.79 (d, J = 6.4 Hz, 1H), 8.67 (brs, 3H) |
| II-79 | 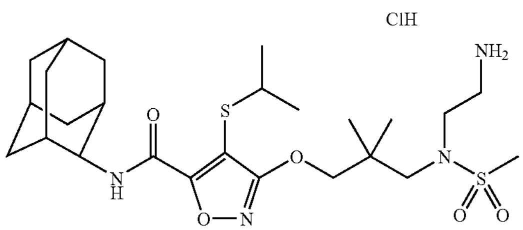 | (DMSO-d6); 1.04 (s, 6H), 1.21 (d, J = 6.4 Hz, 6H), 1.58-1.99 (m, 14H), 3.00 (s, 3H),, 3.09 (brs, 2H), 3.17 (s, 2H), 3.37-3.47 (,m, 3H), 4.06 (brs, 3H), 8.19 (brs, 3H), 8.41 (d, J = 7.2 Hz, 1H) |
| II-80 | 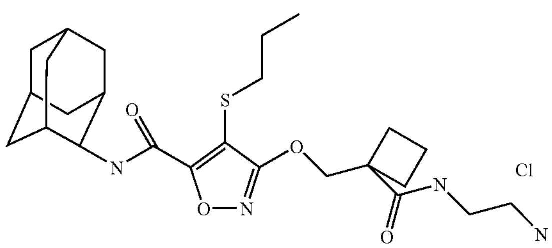 | (DMSO-d6) 0.99-1.99(m, 25H), 2.71-2.77(m, 2H), 3.28-3.33(m, 1H), 3.52-3.60(m, 2H), 4.01-4.06(m, 7.72-7.87(m, 3H), 8.41-8.44(m, 1H) |
| II-81 | 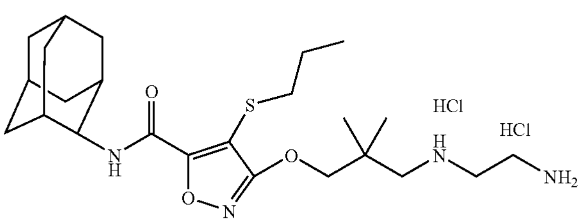 | (DMSO-d6) 0.92(t, J = 7.4 Hz, 3H), 1.16(s, 6H), 1.40-2.05(m, 16H), 2.83(t, J = 7.2 Hz, 2H), 2.95-3.05(m, 2H), 3.20-3.30(m, 4H), 4.02(m, 1H), 4.18(s, 2H), 8.32(m, 2H), 8.41(d, J = 7.2 Hz, 1H), 9.06(m, 1H) |

TABLE 18

| No. | Structure | NMR |
|---|---|---|
| II-82 | 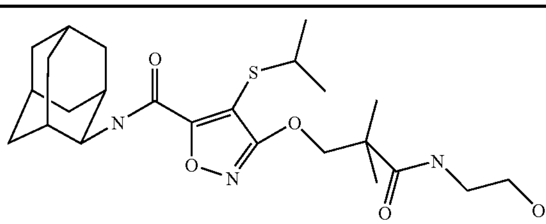 | (DMSO-d6); 1.15-1.19(m, 12H), 1.56-1.99(m, 14H), 3.09-3.15(m, 2H), 3.28-3.33(m, 3H), 4.26(s, 1H), 4.83(t, J = 5.4 Hz, 1H), 7.65(m, 1H), 8.41(d, J = 7.5 Hz, 1H) |

TABLE 18-continued

| No. | Structure | NMR |
|---|---|---|
| II-83 | 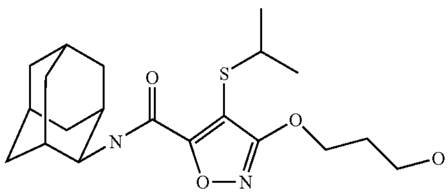 | (DMSO-d6); 1.19(d, J = 7.5 Hz, 6H), 1.54-2.03(m, 16H), 3.3-3.33(m, 1H), 3.51-3.57(m, 2H), 4.04(m, 1H), 4.35(t, J = 6.6 Hz, 2H), 4.61(m, 1H), 8.44(d, J = 7.2 Hz, 1H) |
| II-84 | 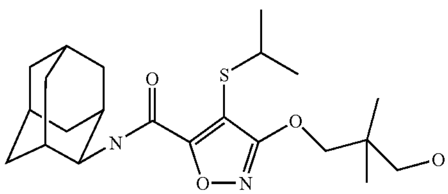 | (DMSO-d6); 1.02(s, 6H), 1.20(d, J = 6.6 Hz, 6H), 1.62-2.01(m, 14H), 3.4(m, 1H), 3.47(s, 2H), 4.19(s, 2H), 4.30(m, 1H), 8.09(m, 1H) |
| II-85 | 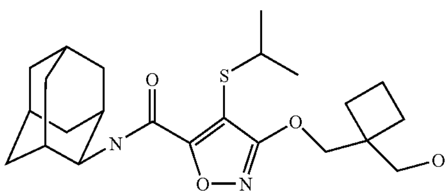 | (DMSO-d6); 1.29(d, J = 6.6 Hz, 6H), 1.69-2.02(m, 20H), 3.37(q, J = 6.9 Hz, 1H), 3.69(s, 2H), 4.29(m, 1H), 4.44(s, 1H), 8.10(m, 1H) |
| II-86 | 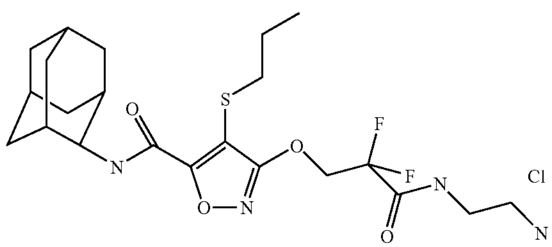 | (DMSO-d6) 0.87-2.01(m, 19H), 2.76-2.80(m, 2H), 3.40-4.10(m, 5H), 4.81-4.93(m, 2H), 8.06-8.31(m, 3H), 8.43(d, J = 6.8 Hz, 1H) |
| II-87 | 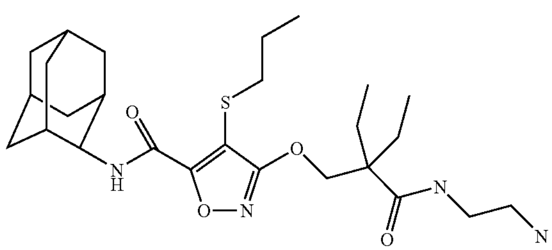 | (DMSO-d6) 0.75-2.01(m, 29H), 2.76-2.79(m, 2H), 3.11-3.53(m, 3H), 4.02-4.08(m, 1H), 4.34(s, 2H), 7.72-7.79(m, 3H), 8.37-8.38(m, 1H) |
| II-88 | 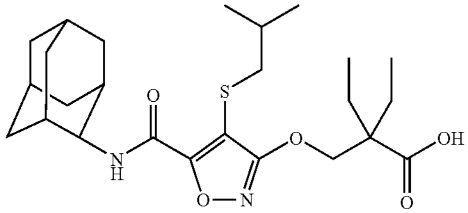 | (DMSO-d6); 0.83 (t, J = 7.2 Hz, 6H), 0.91 (d, J = 6.4 Hz, 6H), 1.55-2.02 (m, 19H), 2.70 (d, J = 6.8 Hz, 2H), 4.03 (d, J = 6.8 Hz, 1H), 4.34 (s, 2H), 8.38 (d, J = 6.8 Hz, 1H), 12.68 (s, 1H) |

TABLE 19

| No. | Structure | NMR |
|---|---|---|
| II-89 | 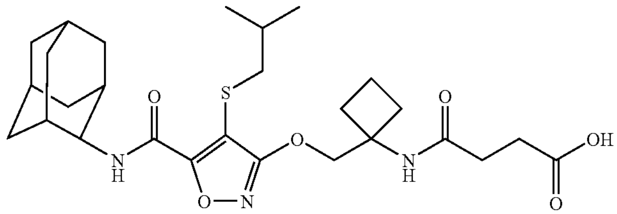 | (DMSO-d6); 0.92 (d, J = 6.4 Hz, 6H), 1.55-2.20 (m, 21H), 2.29-2.33 (m, 2H), 2.37-2.40 (m, 2H), 2.75 (d, J = 6.8 Hz, 2H), 4.03 (brd, J = 6.8 Hz, 1H), 4.45 (s, 2H), 8.16 (s, 1H), 8.37 (d, J = 7.2 Hz, 1H), 12.02 (s, 1H) |
| II-90 | 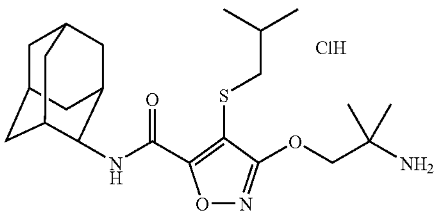 | (DMSO-d6); 0.93 (d, J = 6.8 Hz, 6H), 1.39 (s, 6H), 1.56-2.02 (m, 15H), 2.79 (d, J = 6.4 Hz, 2H), 4.03 (brs, 1H), 4.35 (s, 2H), 8.43 (d, J = 6.8 Hz, 1H), 8.57 (brs, 3H) |
| II-91 | 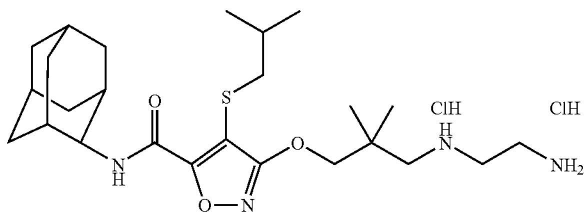 | (DMSO-d6); 0.94 (d, J = 6.8 Hz, 6H), 1.18 (s, 6H), 1.56-2.02 (m, 15H), 2.77 (d, J = 6.8 Hz, 2H), 3.01 (brs, 2H), 3.24-3.33 (brm, 4H), 4.03 (brs, 1H), 4.20 (s, 2H), 8.40 (d, J = 7.2 Hz, 1H), 8.49 (brs, 3H), 9.31 (brs, 2H) |
| II-92 | 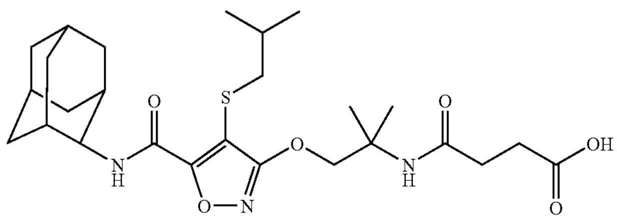 | (DMSO-d6); 0.89-0.96 (brm, 6H), 1.32 (s, 6H), 1.55-2.03 (m, 15H), 2.27-2.40 (brm, 4H), 2.75 (brs, 2H), 4.03 (brs, 1H), 4.38 (s, 2H), 7.72 (s, 1H), 8.39 (brs, 1H), 12.02 (s, 1H) |
| II-93 | 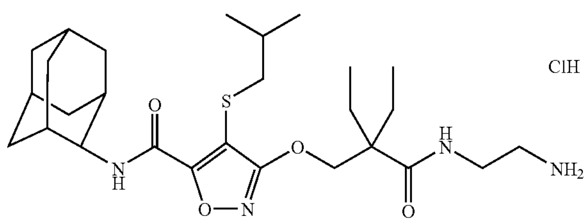 | (DMSO-d6); 0.77 (t, J = 6.0 Hz, 6H), 0.91 (d, J = 6.4 Hz, 6H), 1.55-2.02 (m, 19H), 2.70 (d, J = 6.8 Hz, 2H), 2.84 (brs, 2H), 4.02 (brs, 1H), 4.36 (s, 2H), 8.14 (brs, 3H), 8.21 (brs, 1H), 8.40 (d, J = 6.8 Hz, 1H) |
| II-94 | 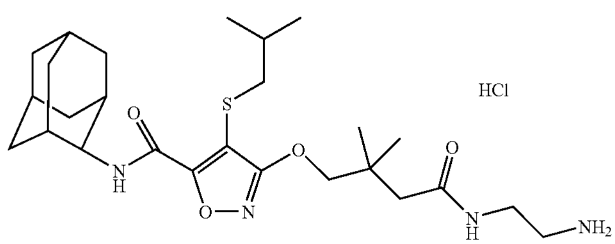 | (DMSO-d6); 0.74(d, J = 6.9 Hz, 6H), 0.89(s, 6H), 1.38-1.85(m, 15H), 2.02(s, 2H), 2.58(d, J = 6.6 Hz, 2H), 2.66(t, J = 6.6 Hz, 2H), 3.08-3.14(m, 2H), 3.82-3.89(m, 1H), 3.98(s, 2H), 7.77(br.s, 2H), 8.06(t, J = 5.7 Hz, 1H), 8.23(d, J = 6.9 Hz, 1H) |
| II-95 | 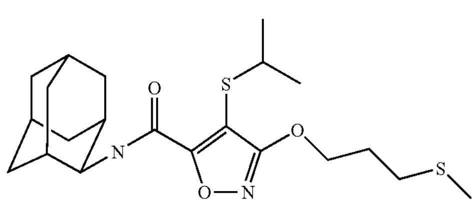 | (DMSO-d6); 1.19(d, J = 7.5 Hz, 6H), 1.54-2.03(m, 16H), 2.04(s, 3H), 3.3-3.33(m, 1H), 3.51-3.57(m, 2H), 4.04(m, 1H), 4.35(t, J = 6.6 Hz, 2H), 4.61 (m, 1H), 8.44(d, J = 7.2 Hz, 1H) |

TABLE 20

| No. | Structure | NMR |
|---|---|---|
| II-96 | 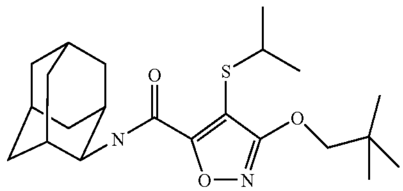 | (DMSO-d6); 1.05(s, 9H), 1.31 (d, J = 6.9 Hz, 6H), 1.74-2.02(m, 14H), 3.43(q, J = 6.9 Hz, 1H), 4.0(s, 2H), 4.31(m, 1H), 8.12(m, 1H) |
| II-97 | 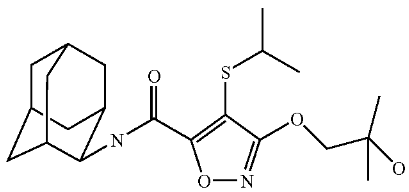 | (DMSO-d6); 1.23-1.35(m, 12H), 1.70-2.05(m, 14H), 3.41 (q, J = 6.6 Hz, 1H), 4.21 (s, 2H), 4.28(m, 1H), 8.11(m, 1H) |
| II-98 | 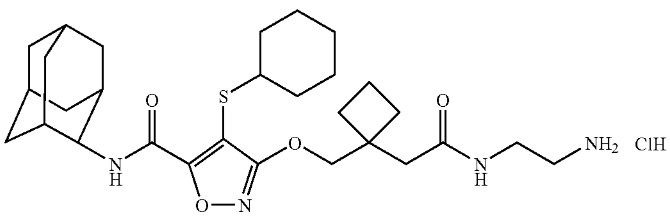 | (DMSO-d6); 1.18-2.02 (m, 30H), 2.45 (s, 2H), 2.83 (t, J = 6.6 Hz, 2H), 3.14 (brs, 1H), 3.24-3.32 (m, 2H), 4.04 (brs, 1H), 4.34 (s, 2H), 7.89 (brs, 3H), 8.22 (t, J = 6.0 Hz, 1H), 8.42 (d, J = 7.2 Hz, 1H) |
| II-99 | 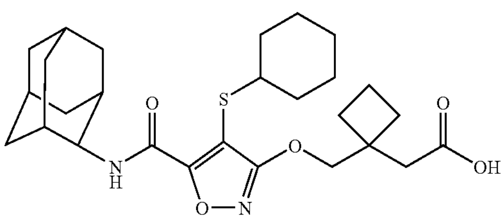 | (DMSO-d6); 1.10-2.02 (m, 30H), 2.57 (s, 2H), 3.11 (brs, 1H), 4.04 (brs, 1H), 4.34 (s, 2H), 8.42 (d, J = 7.2 Hz, 1H), 12.18 (s, 1H) |
| II-100 | 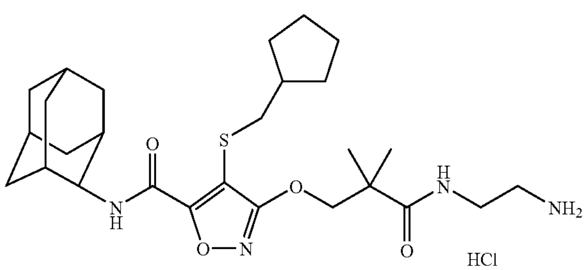 | (CDCl3); 1.17-1.30 (m, 2H), 1.35 (s, 6H), 1.43-2.05 (m, 21H), 2.88 (d, J = 7.2 Hz, 2H), 3.23 (br, 2H), 3.66 (br, 2H), 4.21-4.24 (m, 1H), 4.43 (s, 2H), 7.86 (br, 1H), 8.07-8.10 (m, 1H), 8.23 (br, 2H) |
| II-101 | 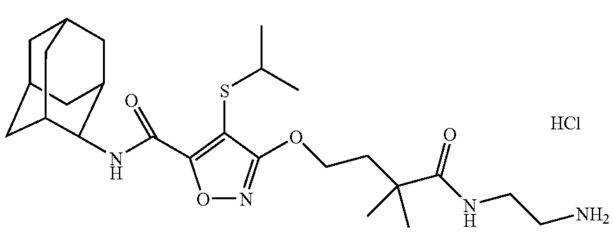 | (DMSO-d6); 1.17-1.19(m, 12H), 1.54-2.03(m, 17H), 2.80-2.92(m, 2H), 3.25-3.35(m, 2H), 4.01-4.06(m, 1H), 4.26(t, J = 7.2 Hz, 2H), 7.89(t, J = 5.7 Hz, 1H), 7.97(br.s, 2H), 8.43(d, J = 7.2 Hz, 1H) |

TABLE 20-continued

| No. | Structure | NMR |
|---|---|---|
| II-102 | 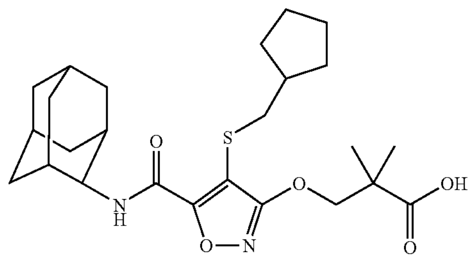 | (CDCl3); 0.93-1.10 (m, 3H), 1.15 (s, 6H), 1.28-1.82 (m, 20H), 2.65 (d, J = 7.2 Hz, 2H), 4.05-4.08 (m, 1H), 4.16 (s, 2H), 7.70-7.73 (m, 1H) |

TABLE 21

| No. | Structure | NMR |
|---|---|---|
| II-103 | 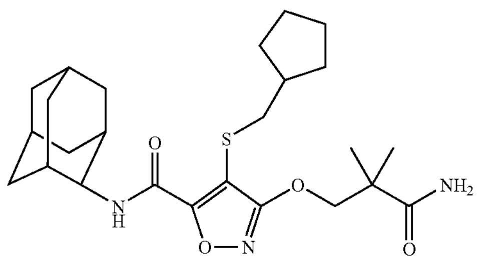 | (CDCl3); 0.92-1.10 (m, 3H), 1.13 (s, 6H), 1.28-1.84 (m, 20H), 2.67 (d, J = 7.5 Hz, 2H), 4.04-4.08 (m, 1H), 4.14 (s, 2H), 5.32 (br, 1H), 5.74 (br, 1H), 7.64-7.68 (m, 1H) |
| II-104 | 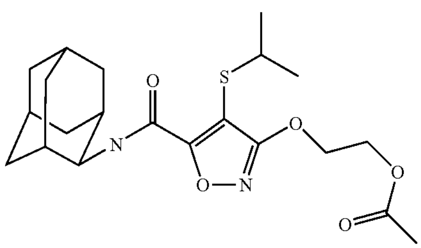 | (DMSO-d6); 1.30(d, J = 6.6 Hz, 6H), 1.74-2.02(m, 14H), 2.09(s, 3H), 3.41 (q, J = 6.6 Hz, 1H), 4.28(m, 1H), 4.45-4.48(m, 2H), 4.54-4.58(m, 2H), 8.11 (m, 1H) |
| II-105 | 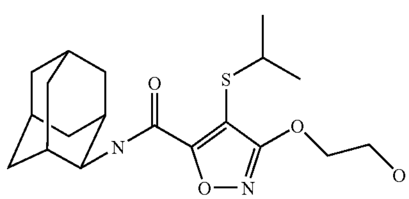 | (DMSO-d6); 1.26-1.31(m, 6H), 1.71-2.02(m, 14H), 3.42(q, J = 6.6 Hz, 1H), 3.99-4.03(m, 2H), 4.29(m, 1H), 4.49(m, 2H), 8.11(m, 1H) |
| II-106 Chiral | | (DMSO-d6); 1.03(s, 6H), 1.31 (d, J = 6.6 Hz, 6H), 1.58-2.02(m, 10H), 2.20-2.29(m, 2H), 3.41 (q, J = 6.6 Hz, 1H), 3.47(s, 2H), 4.19(s, 2H), 4.26(m, 1H), 7.99(m, 1H) |
| II-107 | 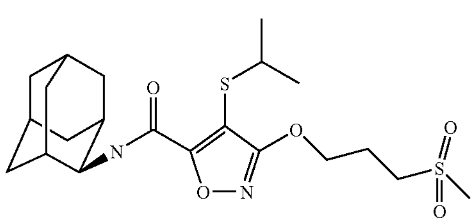 | (DMSO-d6); 1.19(d, J = 7.5 Hz, 6H), 1.54-2.03(m, 16H), 3.12(s, 3H), 3.3-3.33(m, 1H), 3.51-3.57(m, 2H), 4.04(m, 1H), 4.35(t, J = 6.6 Hz, 2H), 4.61 (m, 1H), 8.44(d, J = 7.2 Hz, 1H) |

TABLE 21-continued

| No. | Structure | NMR |
|---|---|---|
| II-108 | 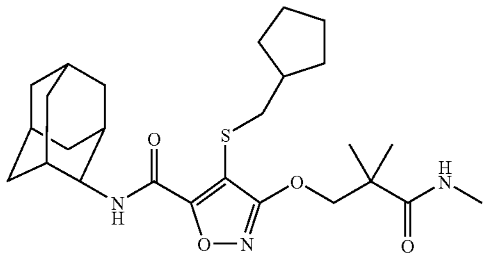 | (CDCl3); 1.17-1.27 (m, 2H), 1.32 (s, 6H), 1.50-2.05 (m, 21H), 2.82-2.88 (m, 5H), 4.26-4.29 (m, 1H), 4.34 (s, 2H), 6.00-6.03 (m, 1H), 7.85-7.89 (m, 1H) |
| II-109 | 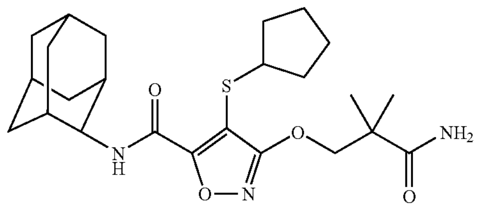 | (CDCl3); 1.35 (s, 6H), 1.51-2.10 (m, 22H), 3.58 (m, 1H), 4.26-4.29 (m, 1H), 4.35 (s, 2H), 5.59 (br, 1H), 6.02 (br, 1H), 8.03-8.08 (m, 1H) |

TABLE 22

| No. | Structure | NMR |
|---|---|---|
| II-110 | 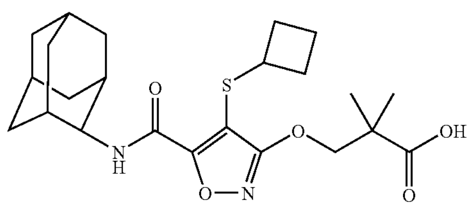 | (CDCl3); 1.36 (s, 6H), 1.68-1.77 (m, 4H), 1.83-2.05 (m, 14H), 2.21-2.31 (m, 2H), 3.75 (quintet, J = 9.0 Hz, 1H), 4.26-4.30 (m, 1H), 4.36 (s, 2H), 8.06-8.10 (m, 1H) |
| II-111 | 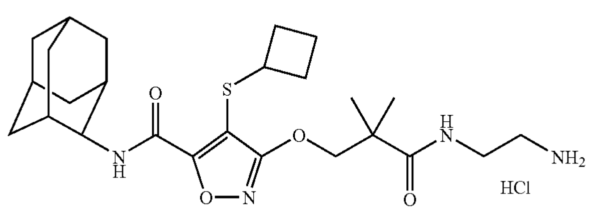 | (DMSO-d6); 1.22 (s, 6H), 1.55-1.59 (m, 2H), 1.69-1.98 (m, 16H), 2.14-2.21 (m, 2H), 2.80-2.84 (m, 2H), 3.28-3.33 (m, 2H), 3.75 (quintet, J = 9.0 Hz, 1H), 3 99-4.04 (m, 1H), 4.26 (s, 2H), 8.02-8.11 (m, 3H), 8.39-8.41(m, 1H) |
| II-112 | 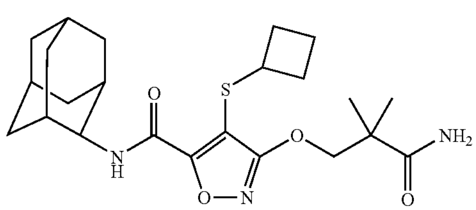 | (CDCl3); 1.35 (s, 6H), 1.68-1.78 (m, 4H), 1.84-2.05 (m, 14H), 2.23-2.34 (m, 2H), 3.76 (quintet, J = 9.0 Hz, 1H), 4.26-4.30 (m, 1H), 4.35 (s, 2H), 5.61 (br, 1H), 6.02 (br, 1H), 8.03-8.05 (m, 1H) |
| II-113 | 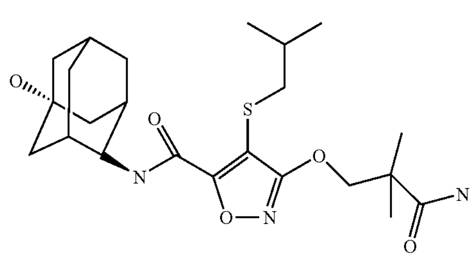 | (DMSO-d6) 0.89(d, J = 6.8 Hz, 6H), 1.24-2.07(m, 20H), 2.68(d, J = 6.8 Hz, 2H), 3.90-3.98(m, 1H), 4.34(s, 2H), 4.47(s, 1H), 6.90-6.96(m, 2H), 8.33(d, J = 7.2 Hzm, 1H) |

TABLE 22-continued

| No. | Structure | NMR |
|---|---|---|
| II-114 | 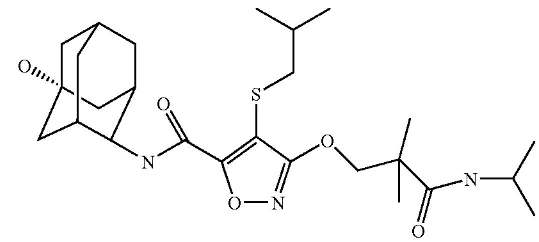 | (DMSO-d6) 0.90(d, J = 6.8 Hz, 6H), 1.05(d, J = 6.4 Hz, 6H), 1.19-2.07(m, 20H), 2.70(d, J = 6.4 Hz, 2H), 3.83-3.96(m, 2H), 4.27(s, 2H), 4.49(s, 1H), 7.38(d, J = 7.6 Hz, 1H), 8.32-8.34(m, 1H) |
| II-115 | 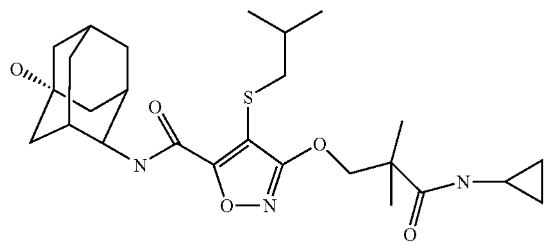 | (DMSO-d6) 0.40-0.62(m, 4H), 0.91(d, J = 6.4 Hz, 6H), 1.18(s, 6H), 1.19-2.07(m, 14H), 2.59-2.73(m, 3H), 3.83-3.96(m, 1H), 4.25(s, 2H), 4.49(s, 1H), 7.63-7.67(m, 1H), 8.31-8.34(m, 1H) |
| II-116 | Chiral | (DMSO-d6) 0.90(d, J = 6.8 Hz, 6H), 1.00(t, J = 7.2 Hz, 3H), 1.20(s, 6H), 1.24-2.07(m, 14H), 2.70(d, J = 6.8 Hz, 2H), 3.06-3.12(m, 2H), 3.92-3.96(m, 1H), 4.26(s, 2H), 4.49(s, 1H), 7.69(t, J = 7.2 Hz, 1H), 8.33(d, J = 7.2 Hz, 1H) |

TABLE 23

| No. | Structure | NMR |
|---|---|---|
| II-117 | 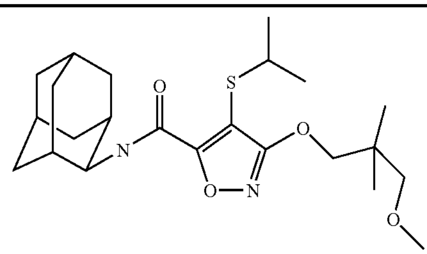 | (DMSO-d6); 1.03(s, 6H), 1.30(d, J = 6.9 Hz, 6H), 1.61-2.02(m, 14H), 3.23(s, 2H), 3.31(s, 3H), 3.41(q, J = 6.6 Hz, 1H), 4.12(s, 2H), 4.28(m, 1H), 8.10(m, 1H) |
| II-118 | Chiral | (DMSO-d6); 1.3-1.35(m, 12H), 1.60-1.92(m, 10H), 2.20-2.29(m, 3H), 3.41 (q, J = 6.6 Hz, 1H), 4.20(s, 2H), 4.25(m, 1H), 8.00(m, 1H) |
| II-119 | 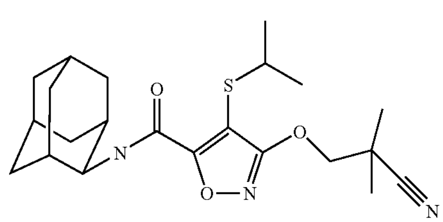 | (DMSO-d6); 1.2(d, J = 6.6 Hz, 6H), 1.43(s, 6H), 1.56-2.01(m, 14H), 3.37(q, J = 6.6 Hz, 1H), 4.04(m, 1H), 4.35(s, 2H), 8.10(m, 1H) |

TABLE 23-continued
| No. | Structure | NMR |
|---|---|---|
| II-120 | Chiral 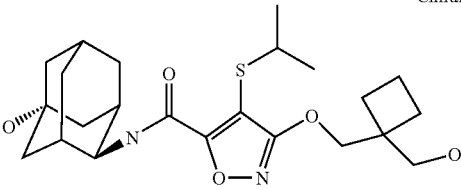 | (DMSO-d6); 1.29(d, J = 6.9 Hz, 6H), 1.57-2.01 (m, 16H), 2.05-2.14(m, 3H), 3.38(q, J = 6.6 Hz, 1H), 3.69(s, 2H), 4.24(m, 1H), 4.43(s, 2H), 7.97(m, 1H) |
| II-121 | 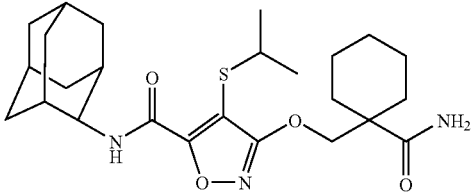 | (DMSO-d6) 1.17(d, J = 6.4 Hz, 6H), 1.23-1.99(m, 24H), 3.28-3.33(m, 1H), 4.03(d, J = 5.6 Hz, 1H), 4.27(s, 2H), 7.00(brs, 1H), 7.25(brs, 1H), 8.38(d, J = 7.2 Hz, 1H) |
| II-122 | 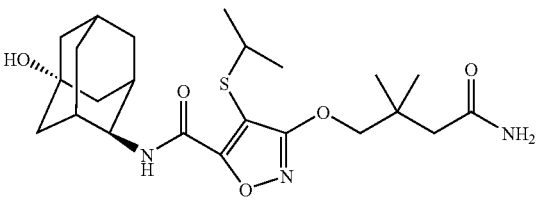 | (CDCl3); 1.18 (s, 6H), 1.31 (d, J = 6.0 Hz, 6H), 1.44-1.46 (m, 2H), 1.56-2.25 (m, 11H), 2.31 (s, 2H), 3.39-3.45 (m, 1H), 3.65 (br, 1H), 4.20 (s, 2H), 4.22-4.26 (m, 1H), 5.66-5.70 (m, 2H), 7.95-7.97 (m, 1H) |
| II-123 | 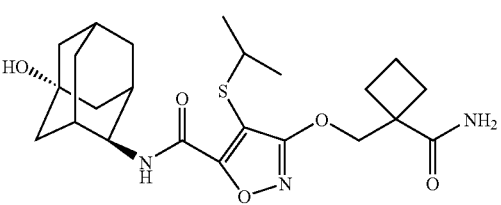 | (CDCl3); 1.28 (d, J = 6.0 Hz, 6H), 1.58-1.62 (m, 2H), 1.77-2.12 (m, 12H), 2.21-2.23 (m, 3H), 2.48-2.57 (m, 2H), 3.33-3.42 (m, 1H), 4.24-4.26 (m, 1H), 4.59 (s, 2H), 5.46 (br, 1H), 5.89 (br, 1H), 7.90-7.93 (m, 1H) |
TABLE 24
| No. | Structure | NMR |
|---|---|---|
| II-124 | Chiral 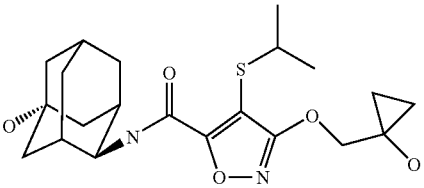 | (DMSO-d6); 0.77(t, J = 6.9 Hz, 2H), 0.97(t, J = 6.9 Hz, 2H), 1.32(d, J = 6.6 Hz, 6H), 1.57-1.95(m, 10H), 2.0-2.26(m, 3H), 3.44(q, J = 6.6 Hz, 1H), 4.24(m, 1H), 4.43(s, 2H), 7.98(m, 1H) |
| II-125 | 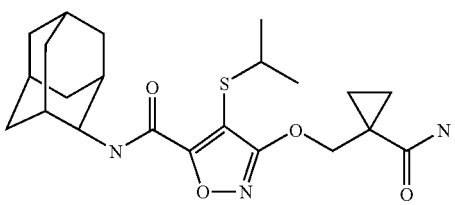 | (DMSO-d6) 0.88-0.92(m, 2H), 1.11-1.19(m, 8H), 1.59-1.99(m, 14H), 3.30-3.45(m, 1H), 4.04(d, J = 5.2 Hz, 1H), 4.40(s, 2H), 7.01 (brs, 1H), 7.16(brs, 1H), 8.40(d, J = 7.2 Hz, 1H) |

TABLE 24-continued

| No. | Structure | NMR |
|---|---|---|
| II-126 | Chiral | (DMSO-d6) 1.14-2.08(m, 25H), 3.30-3.45(m, 1H), 3.94-3.97(m, 1H), 4.10-4.26(m, 3H), 4.49(s, 1H), 7.76(d, J = 6.4 Hz, 1H), 8.31-8.35(m, 1H) |
| II-127 | Chiral | (DMSO-d6) 1.16-2.08(m, 34H), 3.30-3.45(m, 1H), 3.90-3.97(m, 1H), 4.27(s, 2H), 4.49(s, 1H), 6.77(s, 1H), 8.34(d, J = 7.2 Hz, 1H) |
| II-128 | 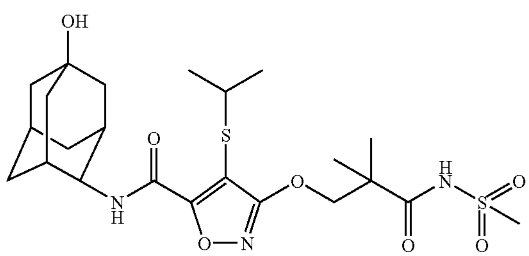 | (DMSO-d6) 1.14-2.06(m, 25H), 3.30-3.45(m, 4H), 3.90-3.97(m, 1H), 4.33-4.50(m, 3H), 6.86-6.88(m, 1H), 8.33-8.36(m, 1H) |
| II-129 | 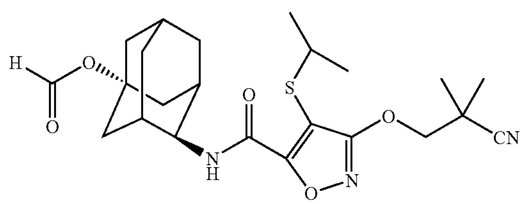 | (CDCl3); 1.33 (d, J = 6.0 Hz, 6H), 1.51 (s, 6H), 1.62-1.87 (m, 8H), 2.24-2.28 (m, 5H), 3.44-3.53 (m, 1H), 4.28 (s, 2H), 4.30-4.33 (m, 1H), 8.01 (s, 1H), 8.04-8.07 (m, 1H) |
| II-130 | 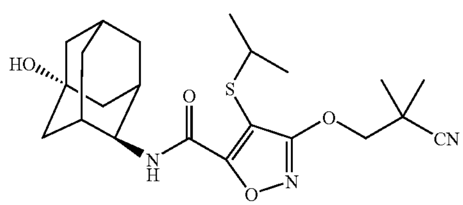 | (CDCl3); 1.33 (d, J = 6.0 Hz, 6H), 1.34 (s, 3H), 1.51 (s, 6H), 1.62-1.63 (m, 2H), 1.77-1.85 (m, 6H), 1.91-1.97 (m, 2H), 2.53 (br, 3H), 3.44-3.53 (m, 1H), 4.24-4.27 (m, 1H), 4.28 (s, 2H), 8.04-8.06 (m, 1H) |

TABLE 25

| No. | Structure | NMR |
|---|---|---|
| II-131 | 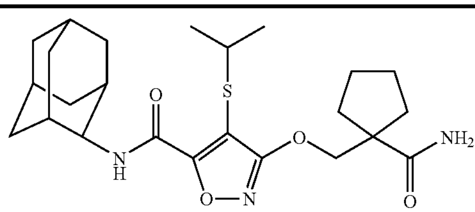 | (DMSO-d6) 1.17(d, J = 6.4 Hz, 6H), 1.57-2.03(m, 22H), 3.30-3.45(m, 1H), 4.00-4.08(m, 1H), 4.35(s, 2H), 6.94(brs, 1H), 7.25(brs, 1H), 8.38(d, J = 8.0 Hz, 1H) |

TABLE 25-continued

| No. | Structure | NMR |
|---|---|---|
| II-132 | Chiral | (DMSO-d6) 1.17(d, J = 6.0 Hz, 6H), 1.28(s, 6H), 1.39-2.06(m, 13H), 3.30-3.57(m, 4H), 3.90-4.00(m, 1H), 4.33(s, 2H), 4.49(s, 1H), 7.10-7.18(m, 1H), 8.27-8.39(m, 1H) |
| II-133 | 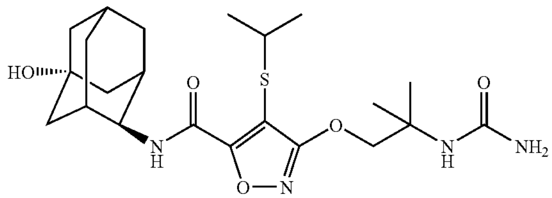 | (DMSO-d6) 1.19(d, J = 6.8 Hz, 6H), 1.28(s, 6H), 1.39-2.07(m, 13H), 3.30-3.50(m, 1H), 3.90-4.00(m, 1H), 4.37(s, 2H), 4.49(s, 1H), 5.32(s, 2H), 5.95(s, 1H), 8.36(d, J = 6.4 Hz, 1H) |
| II-134 | Chiral | (DMSO-d6) 1.39-2.39(m, 27H), 3.56-3.60(m, 1H), 3.90-4.00(m, 1H), 4.47(s, 1H), 4.52(s, 2H), 7.00(s, 1H), 7.29(s, 1H), 8.32(d, J = 7.2 Hz, 1H) |
| II-135 | Chiral | (DMSO-d6) 1.20(s, 6H), 1.34-2.06(m, 21H), 3.57-3.60(m, 1H), 3.90-3.98(m, 1H), 4.26(s, 2H), 4.46(s, 1H), 6.97(s, 1H), 7.23(s, 1H), 8.33(d, J = 6.8 Hz, 1H) |
| II-136 | 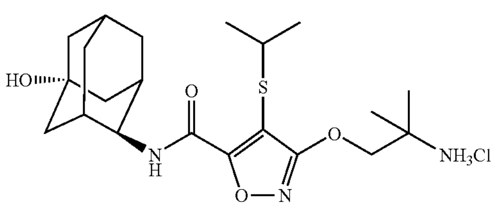 | (DMSO-d6) 1.20(d, J = 6.8 Hz, 6H), 1.36(s, 6H), 1.41-2.07(m, 13H), 3.30-3.50(m, 1H), 3.90-3.98(m, 1H), 4.33(s, 2H), 4.49(s, 1H), 8.14-8.30(m, 2H), 8.41(d, J = 6.8 Hz, 1H) |
| II-137 | 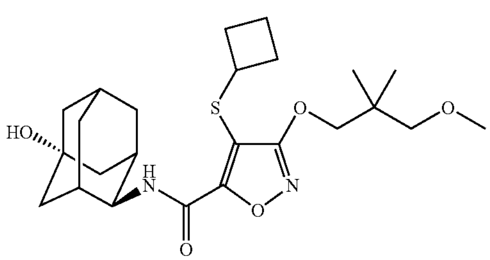 | (DMSO-d6); 0.97 (s, 6H), 1.38-1.42 (m, 2H), 1.62-1.93 (m, 12H), 2.05 (br, 3H), 2.18-2.25 (m, 2H), 3.20 (s, 2H), 3.25 (s, 3H), 3.79 (quintet, J = 9.0 Hz, 1H), 3.93-3.96 (m, 1H), 4.03 (s, 2H), 4.52 (s, 1H), 8.37-8.40(m, 1H) |

TABLE 26
| No. | Structure | NMR |
|---|---|---|
| II-138 | 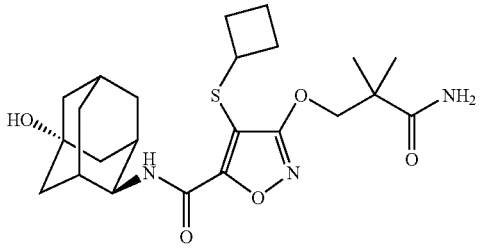 | (DMSO-d6); 1.19 (s, 6H), 1.37-1.43 (m, 2H), 1.62-1.89 (m, 12H), 2.05 (br, 3H), 2.18-2.25 (m, 2H), 3.79 (quintet, J = 9.0 Hz, 1H), 3.93-3.95 (m, 1H), 4.24 (s, 2H), 4.49 (s, 1H), 7.01 (s, 1H), 7.26 (s, 1H), 8.35-8.37(m, 1H) |
| II-139 | 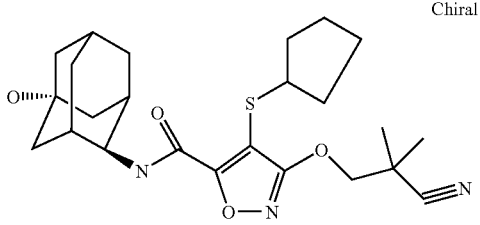 Chiral | (DMSO-d6) 1.24-2.09(m, 21H), 3.59-3.70(m, 1H), 3.90-4.02(m, 1H), 4.30-4.53(m, 3H), 8.35-8.46(m, 1H) |
| II-140 | 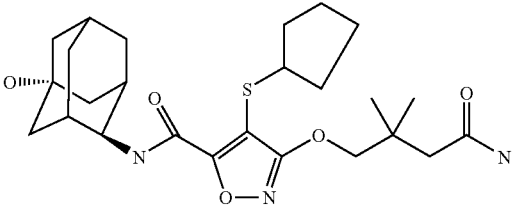 Chiral | (DMSO-d6) 1.06(s, 6H), 1.42-2.13(m, 23H), 3.55-3.62(m, 1H), 3.90-3.98(m, 1H), 4.16(s, 2H), 4.47(s, 1H), 6.77(brs, 1H), 7.29(brs, 1H), 8.36(d, J = 6.4 Hz, 1H) |
| II-141 | 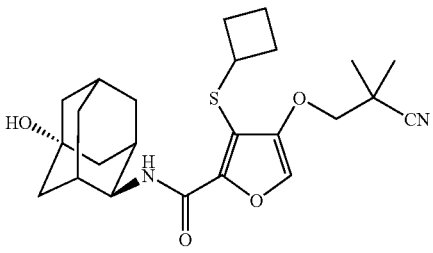 | (DMSO-d6); 1.43 (s, 6H), 1.37-1.45 (m, 2H), 1.62-1.94 (m, 12H), 2.06 (br, 3H), 2.21-2.29 (m, 2H), 3.83 (quintet, J = 9.0 Hz, 1H), 3.94-3.96 (m, 1H), 4.34 (s, 2H), 4.49 (s, 1H), 8.40-8.42(m, 1H) |
| II-142 | 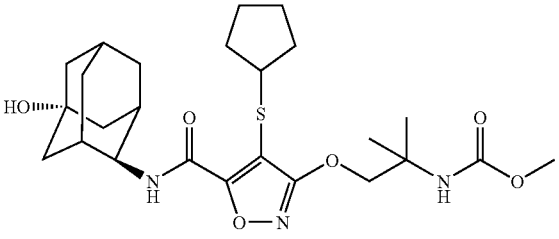 | (DMSO-d6) 1.28-2.06(m, 27H), 3.40-3.69(m, 4H), 3.90-3.98(m, 1H), 4.33(s, 2H), 4.53(s, 1H), 7.09-7.18(m, 1H), 8.34(d, J = 6.4 Hz, 1H) |
| II-143 | 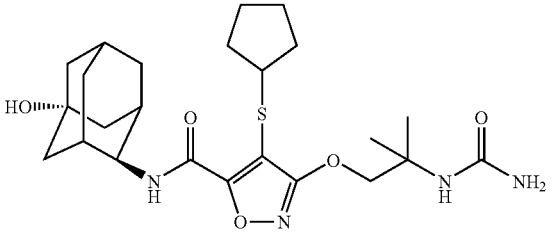 | (DMSO-d6) 1.28(s, 6H), 1.39-2.06(m, 21H), 3.58-3.64(m, 1H), 3.90-3.98(m, 1H), 4.37(s, 2H), 4.51(s, 1H), 5.32(s, 2H), 5.97(s, 1H), 8.34(d, J = 7.2 Hz, 1H) |

TABLE 26-continued

| No. | Structure | NMR |
|---|---|---|
| II-144 | 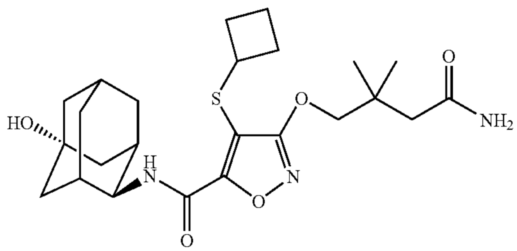 | (DMSO-d6); 1.06 (s, 6H), 1.39-1.42 (m, 2H), 1.62-1.92 (m, 12H), 2.06 (br, 3H), 2.13 (s, 2H), 2.18-2.26 (m, 2H), 3.80 (quintet, J = 9.0 Hz, 1H), 3.93-3.96 (m, 1H), 4.15 (s, 2H), 4.49 (s, 1H), 6.80 (s, 1H), 7.31 (s, 1H), 8.37-8.40(m, 1H) |

TABLE 27

| No. | Structure | NMR |
|---|---|---|
| II-145 | 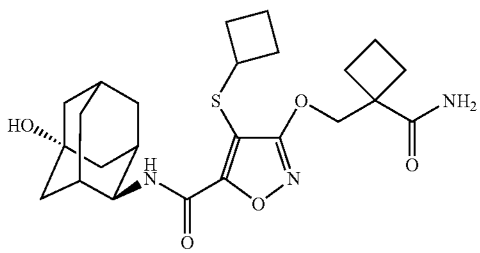 | (DMSO-d6); 1.38-1.42 (m, 2H), 1.62-1.99 (m, 19H), 2.16-2.23 (m, 2H), 2.30-2.38 (m, 2H), 3.79 (quintet, J = 9.0 Hz, 1H), 3.92-3.95 (m, 1H), 4.49 (s, 1H), 4.51 (s, 2H), 7.05 (s, 1H), 7.31 (s, 1H), 8.34-8.37(m, 1H) |
| II-146 | 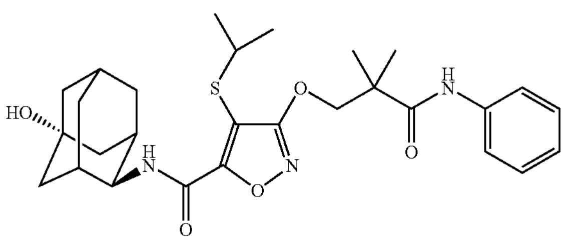 | (DMSO-d6); 1.02 (d, 6H, J = 6.0 Hz), 1.34 (s, 6H), 1.34-1.41 (m, 2H), 1.62-1.73 (m, 6H), 1.82-1.86 (m, 2H), 2.04 (br, 3H), 3.23 (quintet, J = 9.0 Hz, 1H), 3.91-3.94 (m, 1H), 4.43 (s, 2H), 4.49 (s, 1H), 7.04 (t, 1H, J = 9.0 Hz), 7.29 (t, 2H, J = 9.0 Hz), 7.62 (d, 2H, J = 9.0 Hz), 8.33-8.35 (m, 1H), 9.40 (s, 1H) |
| II-147 | 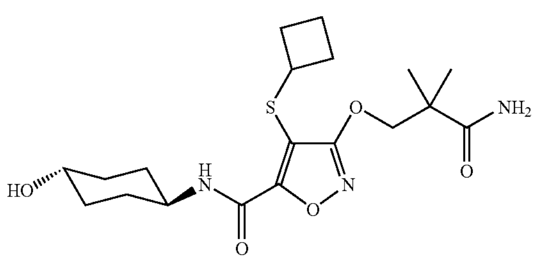 | (DMSO-d6); 1.19 (s, 6H), 1.18-1.41 (m, 4H), 1.75-1.85 (m, 8H), 2.18-2.27 (m, 2H), 3.34-3.42 (m, 1H), 3.60-3.70 (m, 1H), 3.90 (quintet, J = 9.0 Hz, 1H), 4.23 (s, 2H), 4.58 (d, J = 3.0 Hz, 1H), 7.03 (s, 1H), 7.27 (s, 1H), 8.54-8.56 (m, 1H) |
| II-148 | 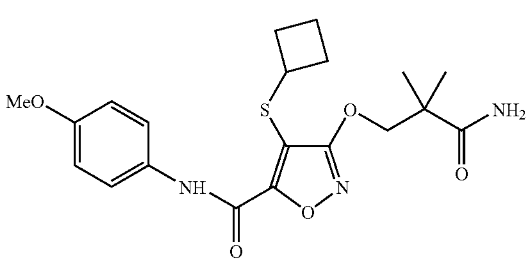 | (DMSO-d6); 1.22 (s, 6H), 1.82-1.92 (m, 4H), 2.24-2.30 (m, 2H), 3.75 (s, 3H), 3.94-4.03 (m, 1H), 4.28 (s, 2H), 6.93 (dd, J = 3.0 Hz, 6.0 Hz, 2H), 7.06 (s, 1H), 7.30 (s, 1H), 7.64 (dd, J = 3.0 Hz, 6.0 Hz, 2H) |

TABLE 27-continued

| No. | Structure | NMR |
|---|---|---|
| II-149 | 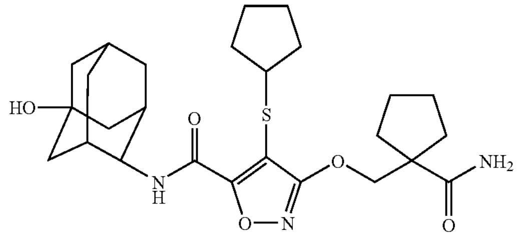 | (DMSO-d6) 1.26-2.06(m, 29H), 3.52-3.60(m, 1H), 3.90-3.98(m, 1H), 4.36(s, 2H), 4.49(s, 1H), 6.95(brs, 1H), 7.26(brs, 1H), 8.31(d, J = 6.8 Hz, 1H) |
| II-150 | 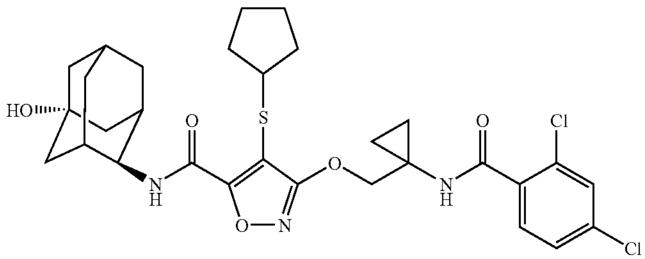 | (DMSO-d6) 0.84-2.06(m, 25H), 3.62-3.69(m, 1H), 3.90-3.98(m, 1H), 4.42(s, 1H), 4.45(s, 2H), 7.34-7.65(m, 4H), 8.32-8.37(m, 1H) |
| II-151 | 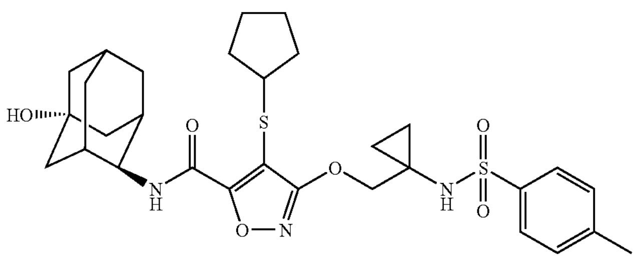 | (DMSO-d6) 0.66-2.13(m, 25H), 2.33(s, 3H), 3.70-3.73(m, 1H), 3.94-3.98(m, 1H), 4.15(s, 2H), 4.47(s, 1H), 7.25-7.37(m, 3H), 7.67(d, J = 8.4 Hz, 2H), 8.32-8.37(m, 1H) |

TABLE 28

| No. | Structure | NMR |
|---|---|---|
| II-152 | 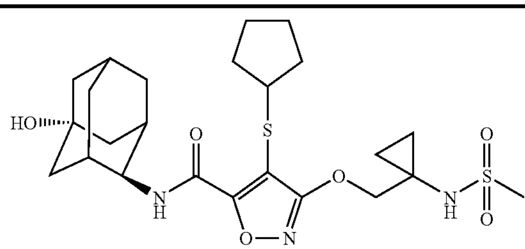 | (DMSO-d6) 0.90-2.07(m, 25H), 2.97(s, 3H), 3.69-3.72(m, 1H), 3.90-3.98(m, 1H), 4.31(s, 2H), 4.46(s, 1H), 7.77(s, 1H), 8.35(d, J = 5.6 Hz, 1H) |
| II-153 | 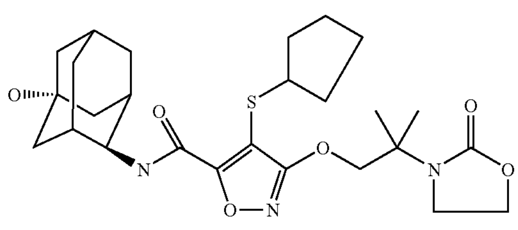 | (DMSO-d6) 1.25-2.15(m, 27H), 3.48-3.60(m, 1H), 3.63-3.77(m, 2H), 3.90-3.98(m, 1H), 4.11-4.22(m, 2H), 4.40-4.63(m, 3H), 8.32-8.50(m, 1H) |
| II-154 | Chiral | (DMSO-d6) 1.25-2.17(m, 29H), 3.20(t, J = 7.2 Hz, 2H), 3.42(t, J = 6.8 Hz, 2H), 3.60-3.65(m, 1H), 3.92-3.98(m, 1H), 4.35(s, 2H), 4.46(s, 1H), 8.36(d, J = 7.6 Hz, 1H) |

TABLE 28-continued

| No. | Structure | NMR |
|---|---|---|
| II-155 | Chiral | (DMSO-d6) 0.88-2.07(m, 25H), 3.65-3.62(m, 1H), 3.90-3.98(m, 1H), 4.35(s, 2H), 4.47(brs, 1H), 7.00-7.50(brs, 2H), 8.37(d, J = 6.8 Hz, 1H) |

The following compounds as the present compound can be synthesized as well as the above Example. The abbreviations used in the tables are as follows.

| Et | ethyl |
|---|---|
| Pro | n-propyl |
| i-Pro | isopropyl |
| Bu | n-butyl |
| i-Bu | isobutyl |

The abbreviations used for $R^3$ are as follows.

[Formula 31]

A-1

A-2

A-3

A-4

A-5

A-6

A-7

A-8

A-9

A-10

A-11

A-12

A-13

A-14

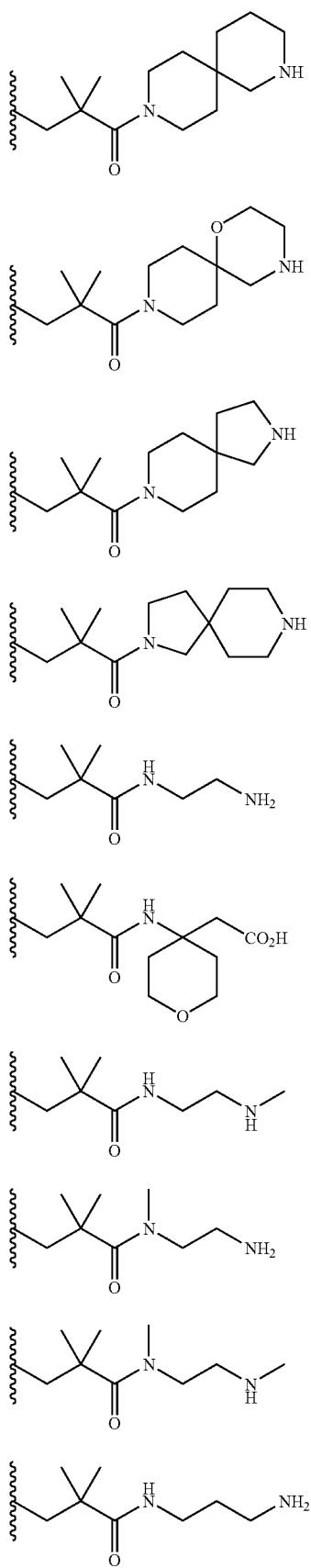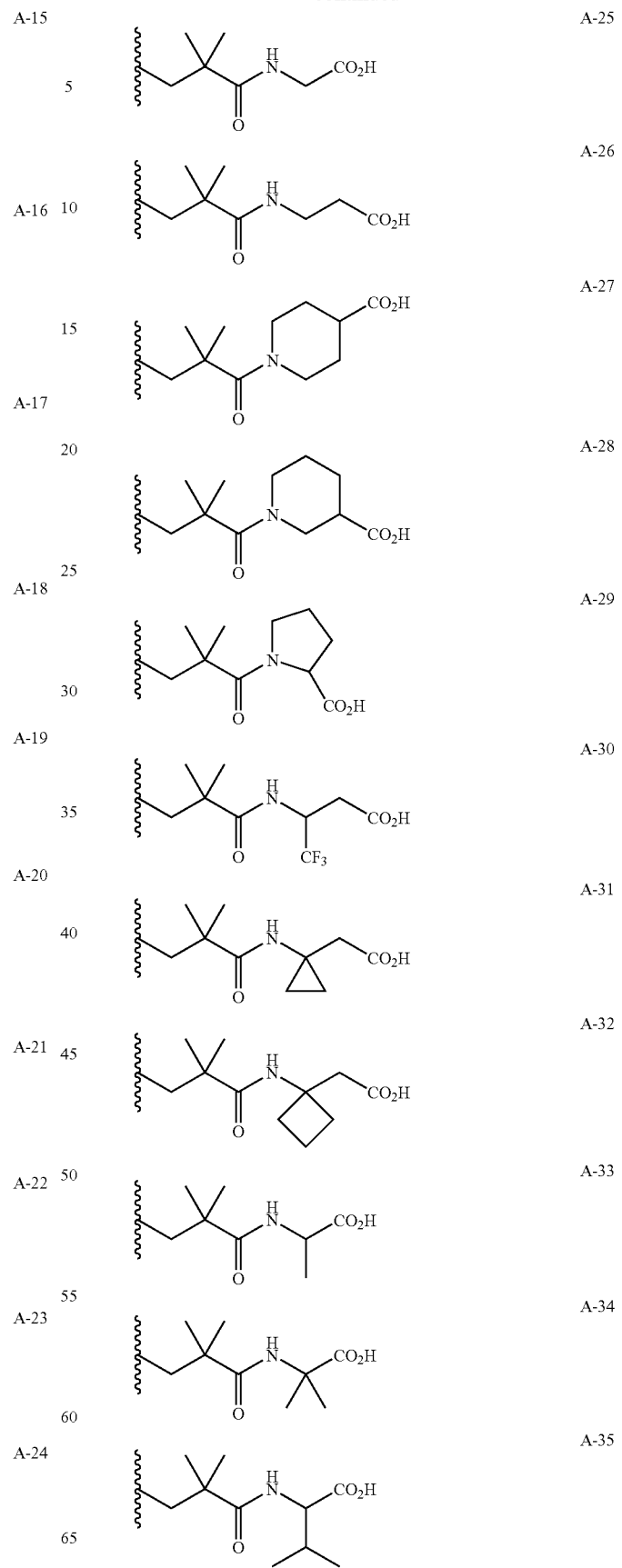

A-36 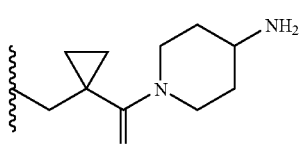
B-8
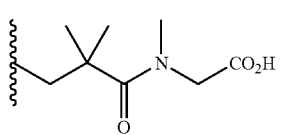
A-37 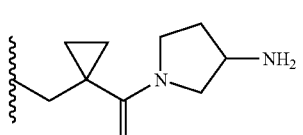
B-9
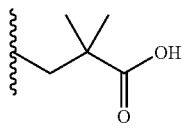
A-38 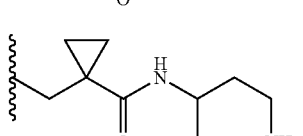
B-10
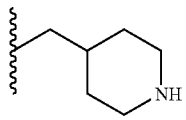
A-39 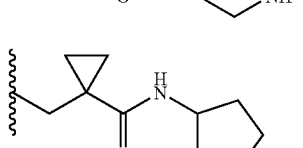
B-11
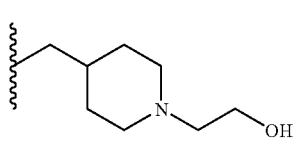
[Formula 32]
B-1 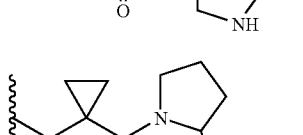
B-12
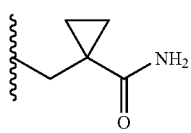
B-2 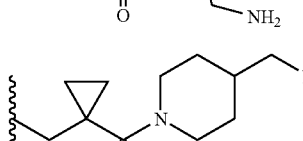
B-13
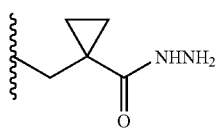
B-3 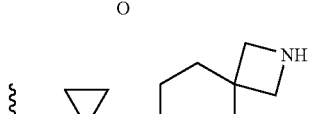
B-14
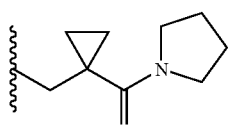
B-4 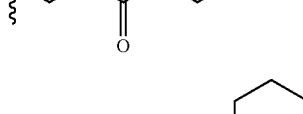
B-15
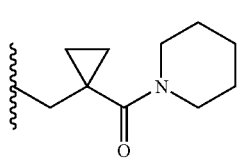
B-5 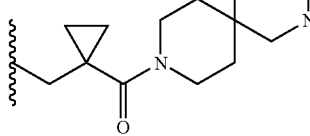
B-16
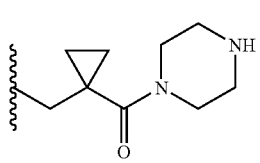
B-6 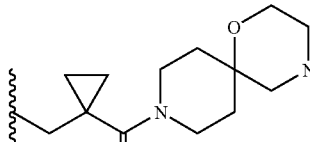
B-17
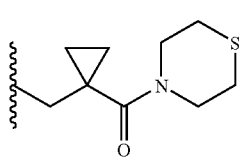
B-7
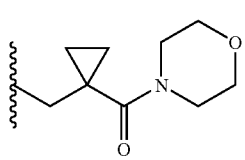
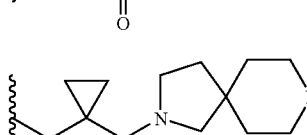

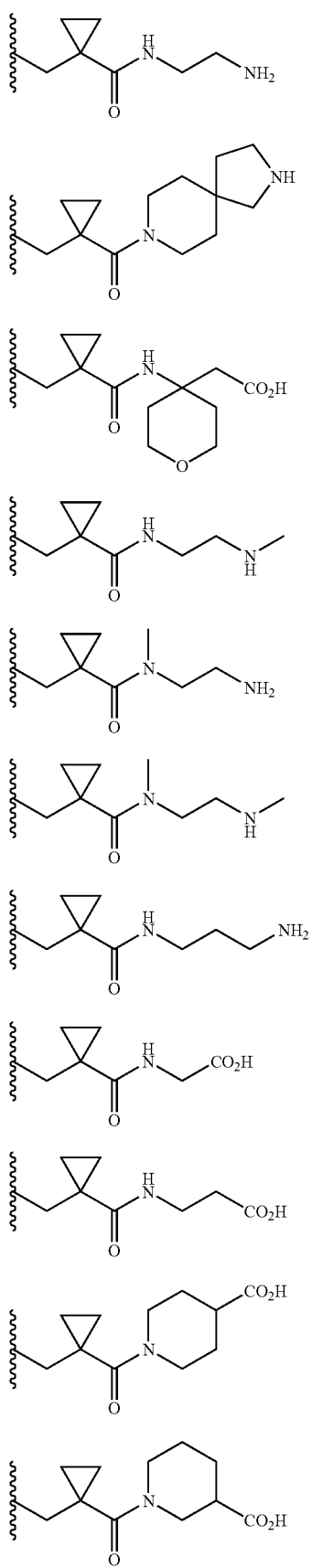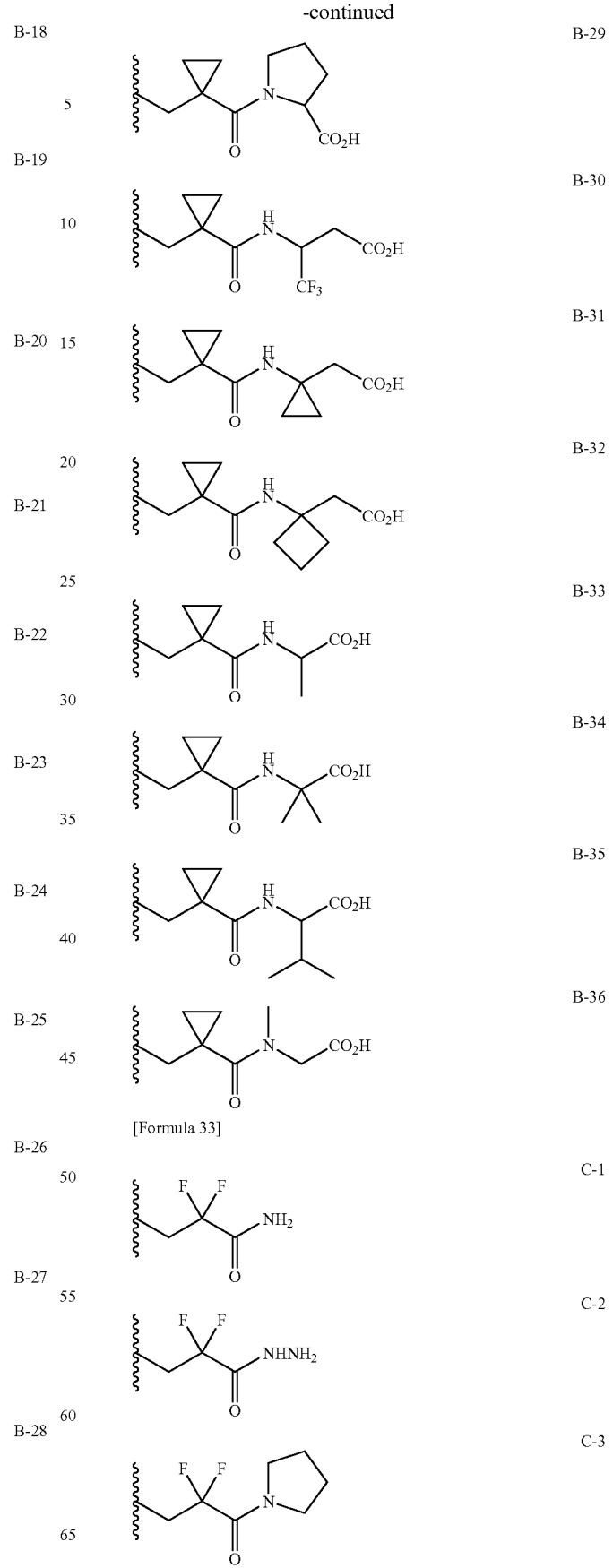

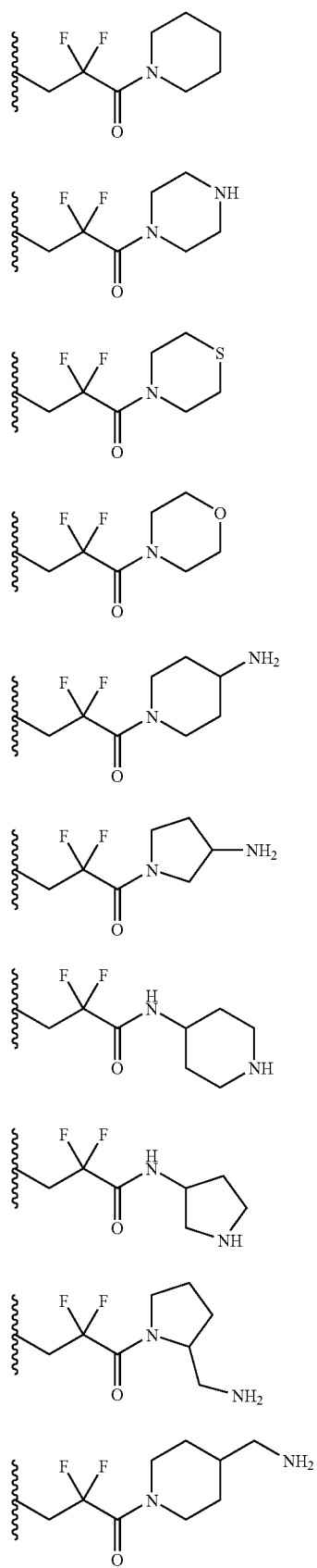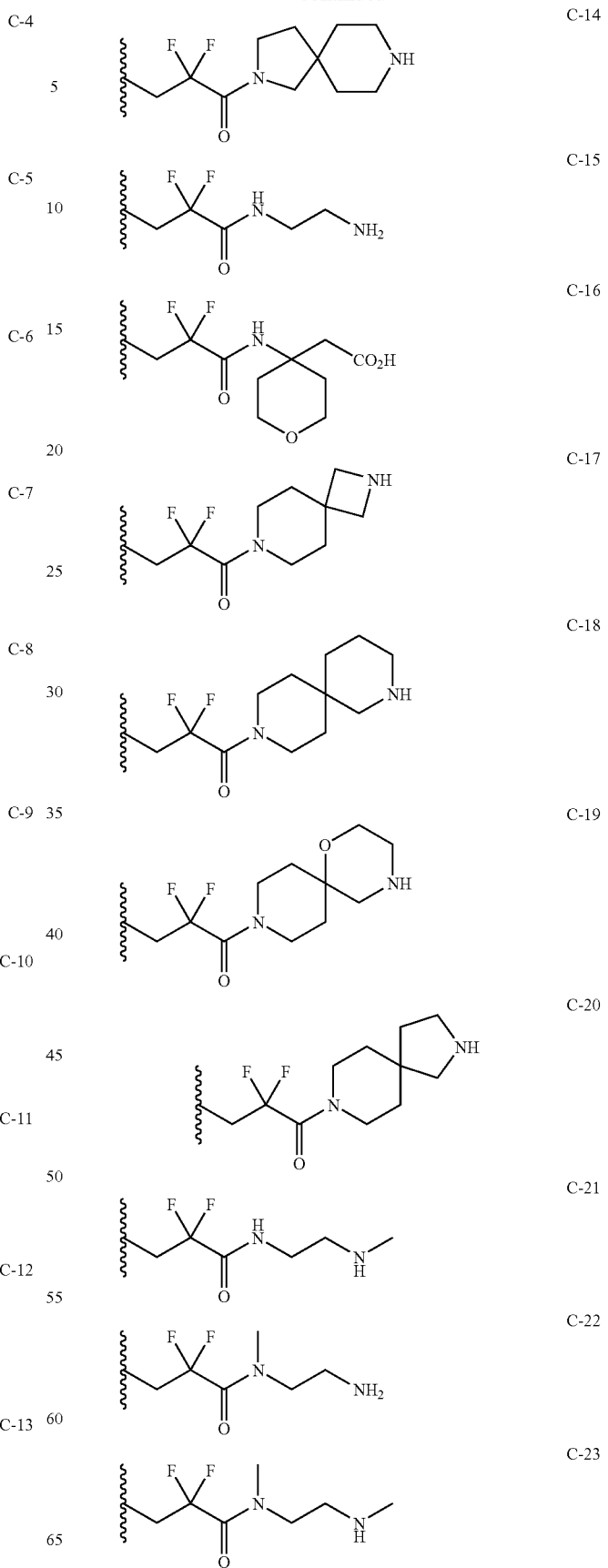

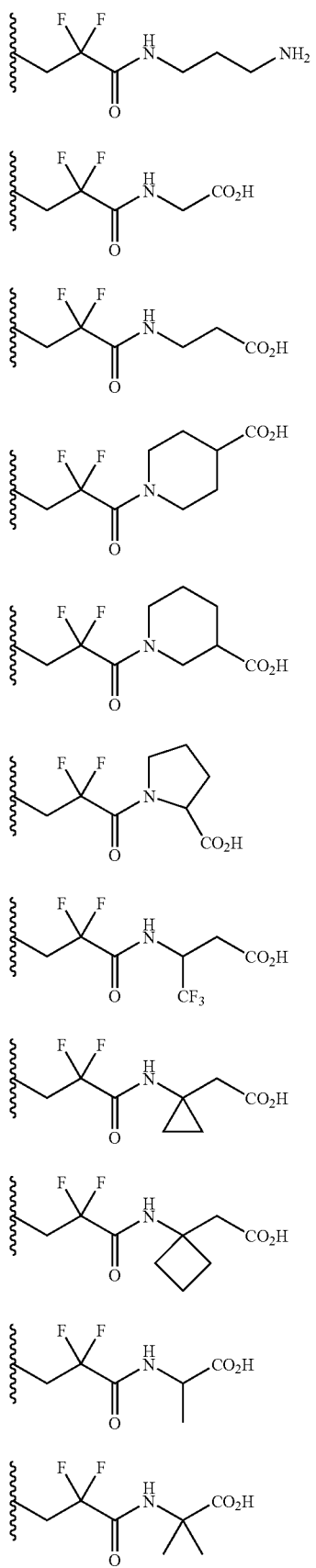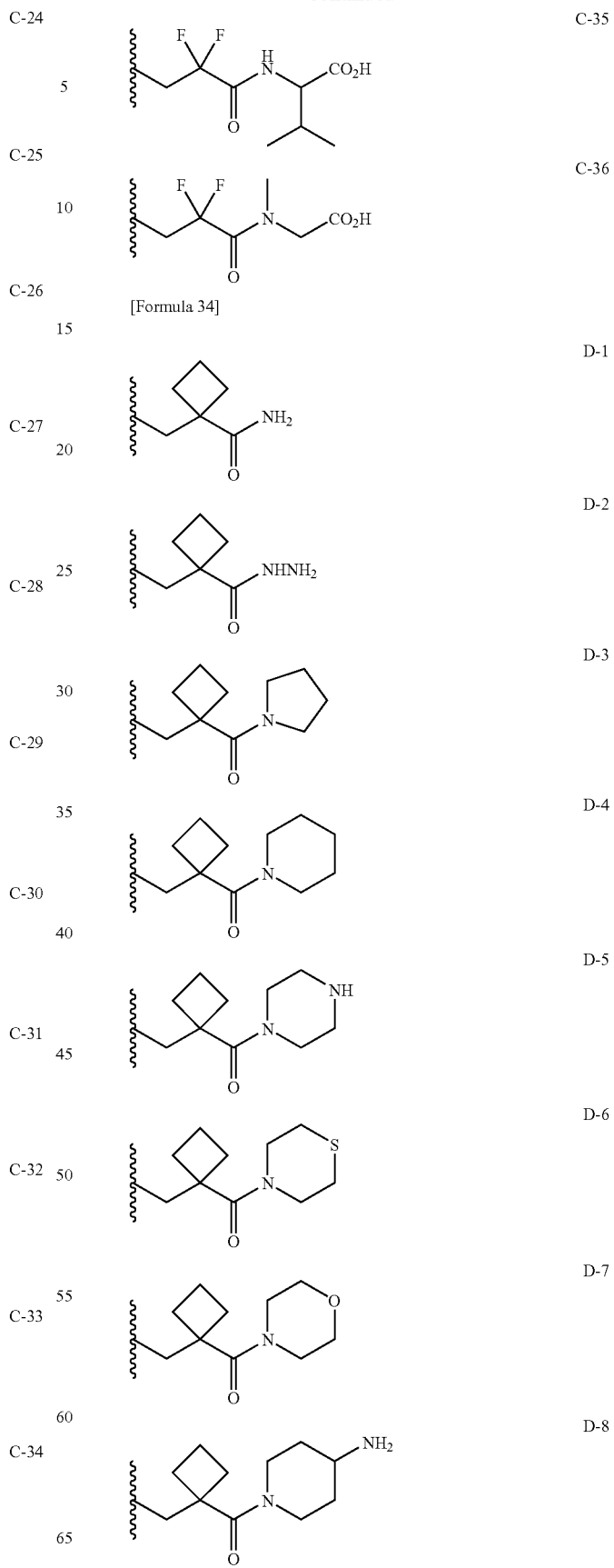

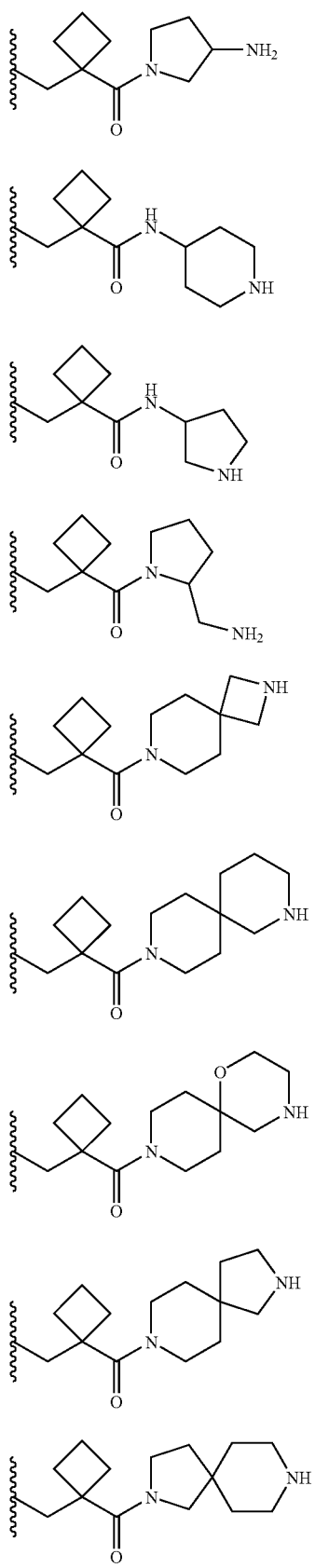
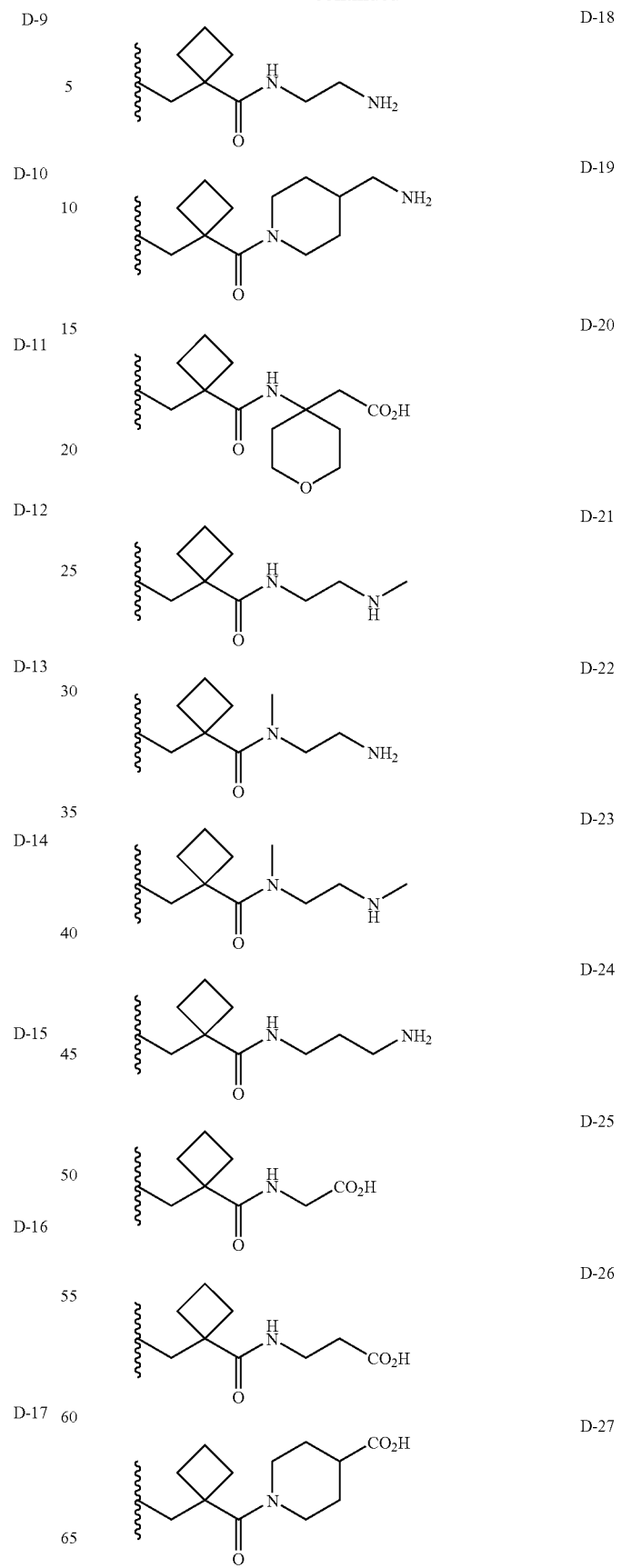

-continued
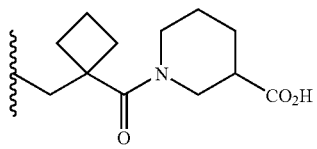 D-28
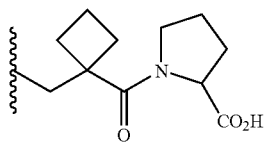 D-29
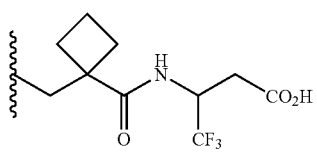 D-30
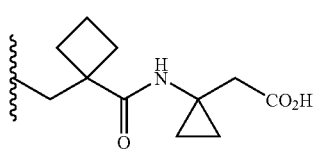 D-31
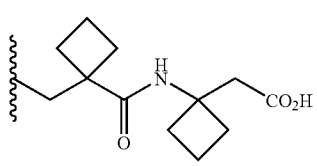 D-32
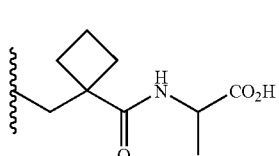 D-33
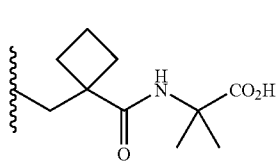 D-34
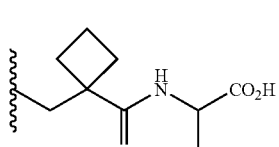 D-35
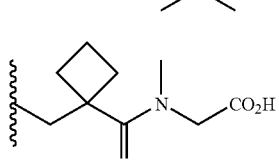 D-36
[Formula 36]
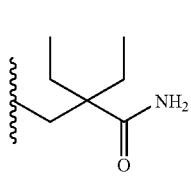 E-1
-continued
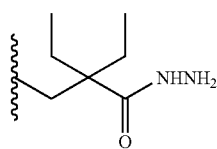 E-2
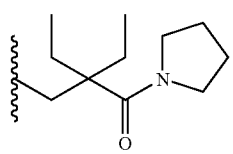 E-3
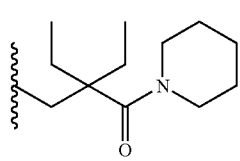 E-4
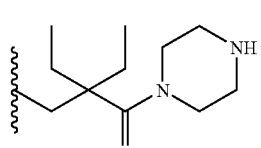 E-5
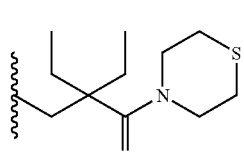 E-6
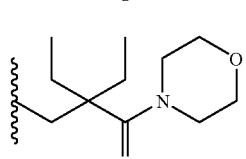 E-7
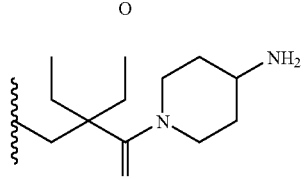 E-8
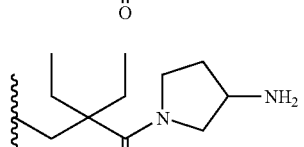 E-9
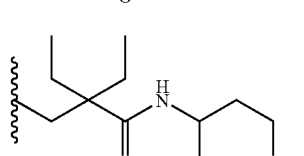 E-10
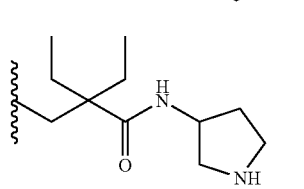 E-11

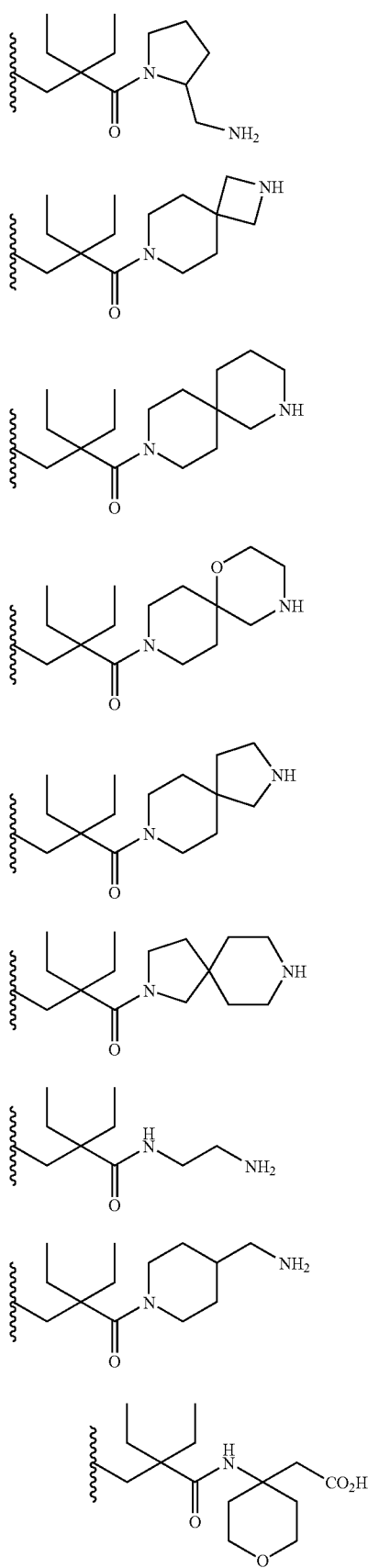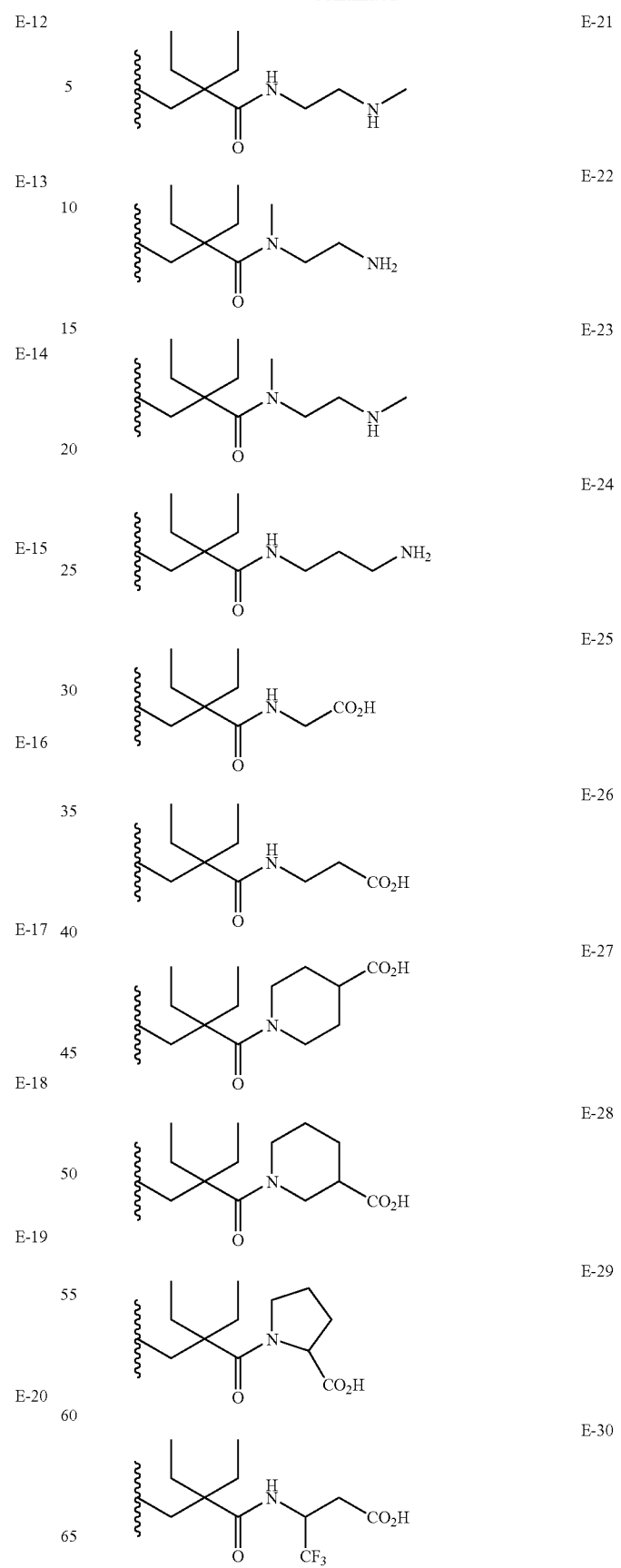

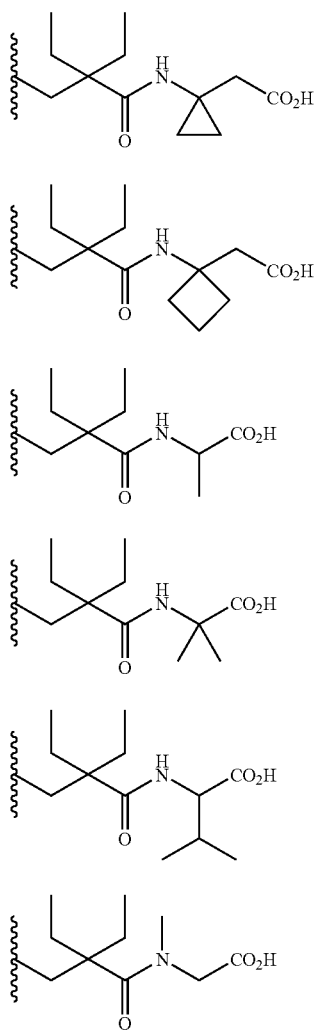
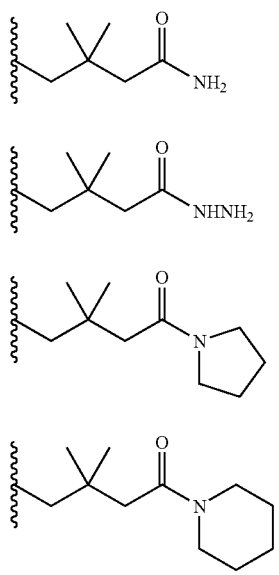
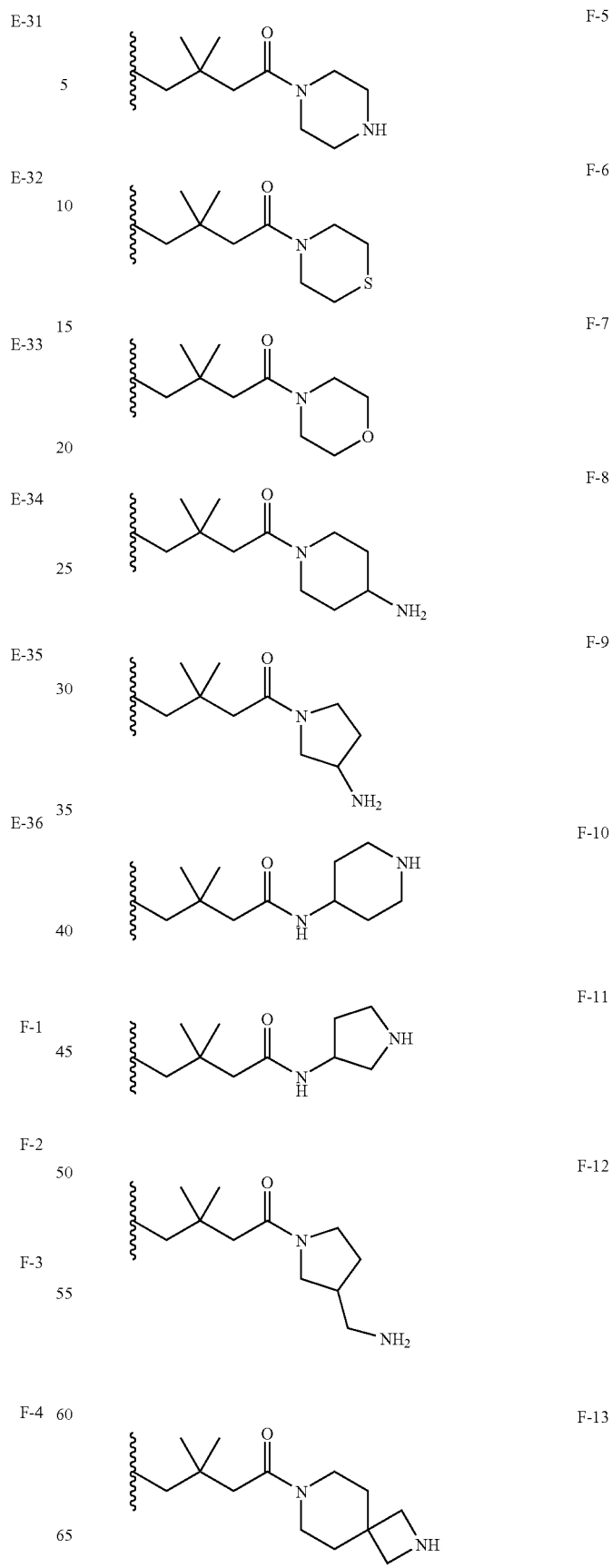

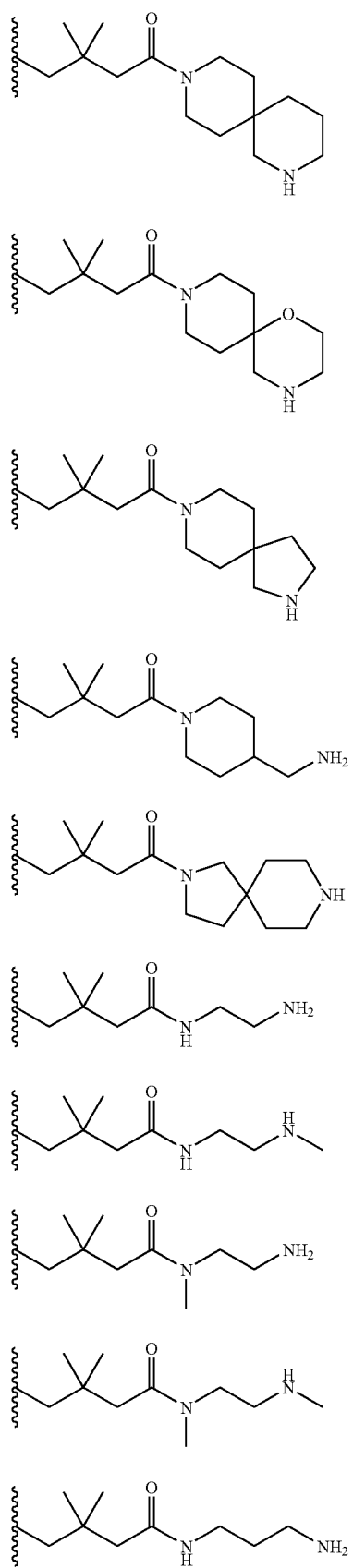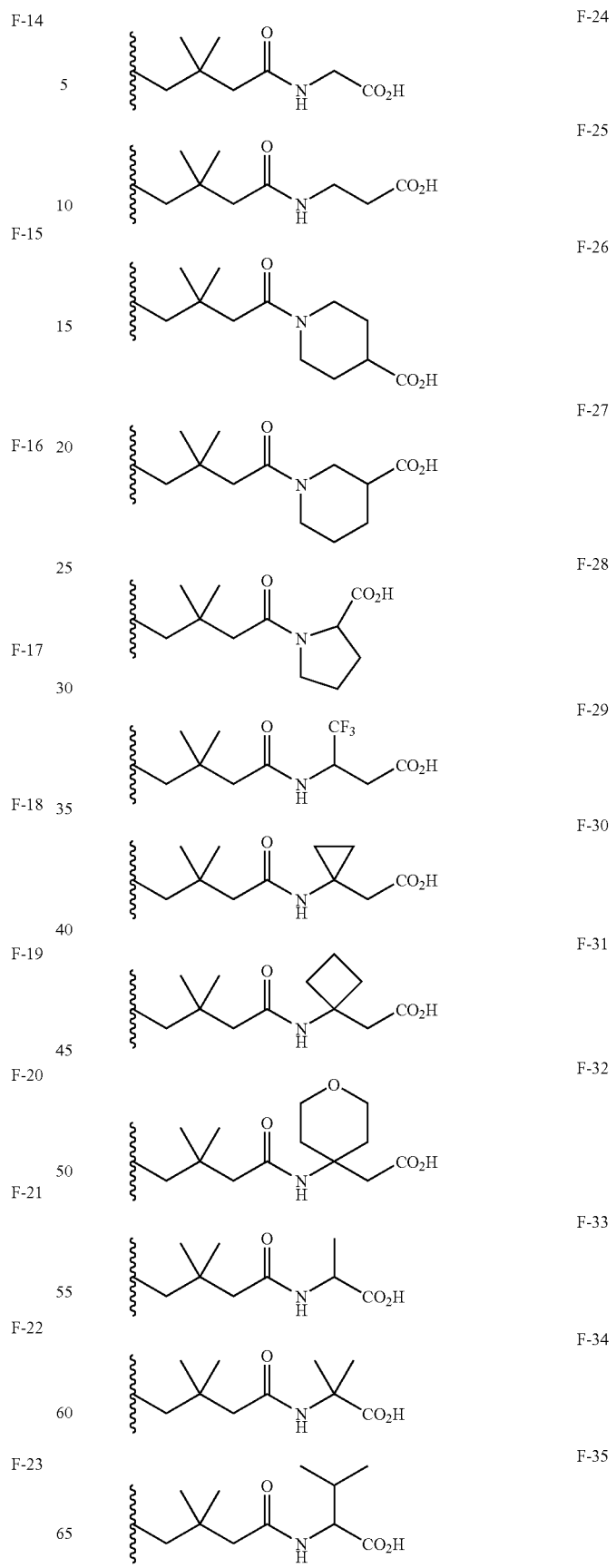

[Formula 37]
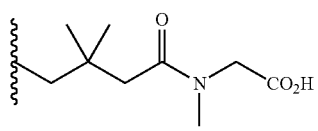
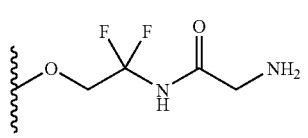 F-36
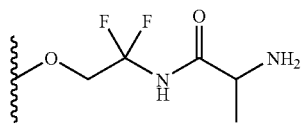 G-1
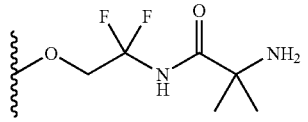 G-2
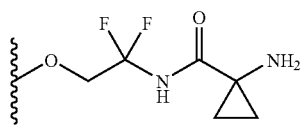 G-3
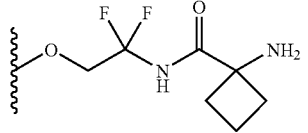 G-4
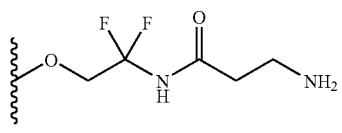 G-5
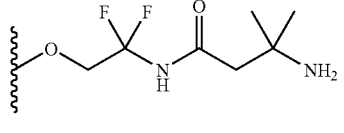 G-6
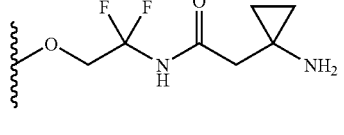 G-7
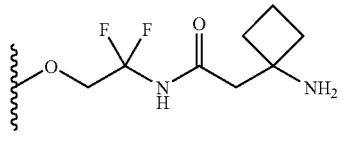 G-8
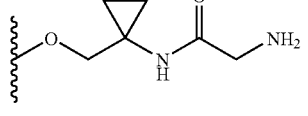 G-9
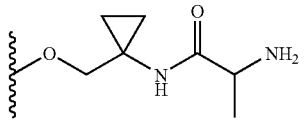 H-1
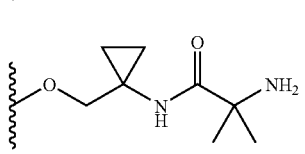 H-2
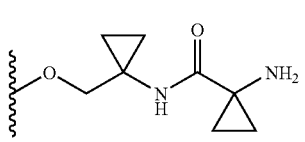 H-3
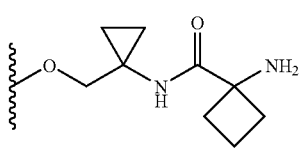 H-4
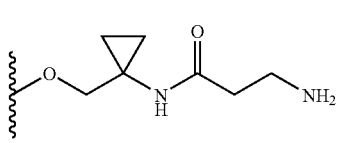 H-5
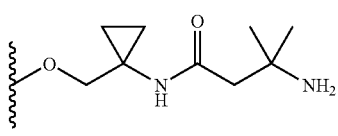 H-6
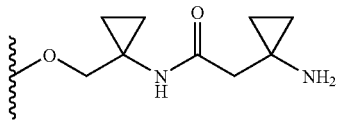 H-7
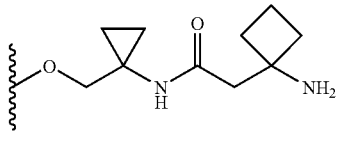 H-8
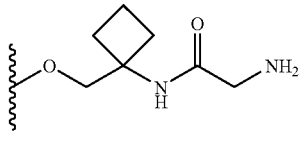 H-9
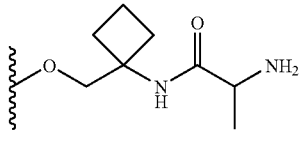 I-1
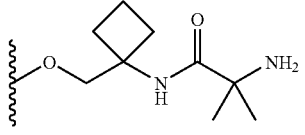 I-2
I-3

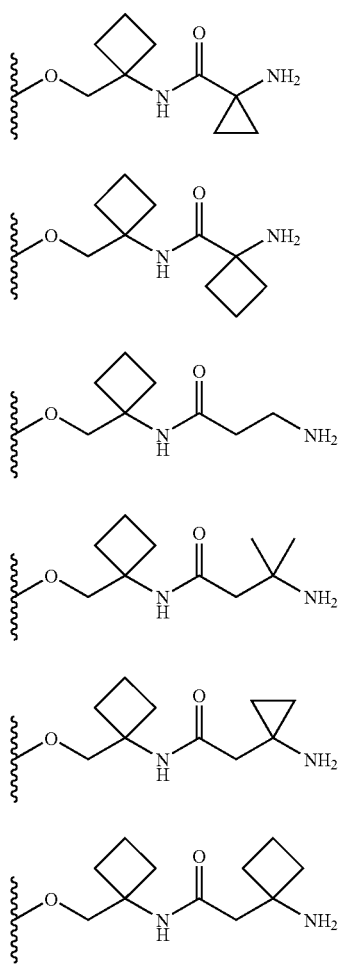
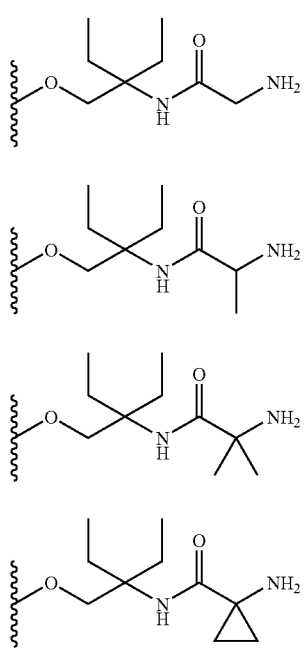
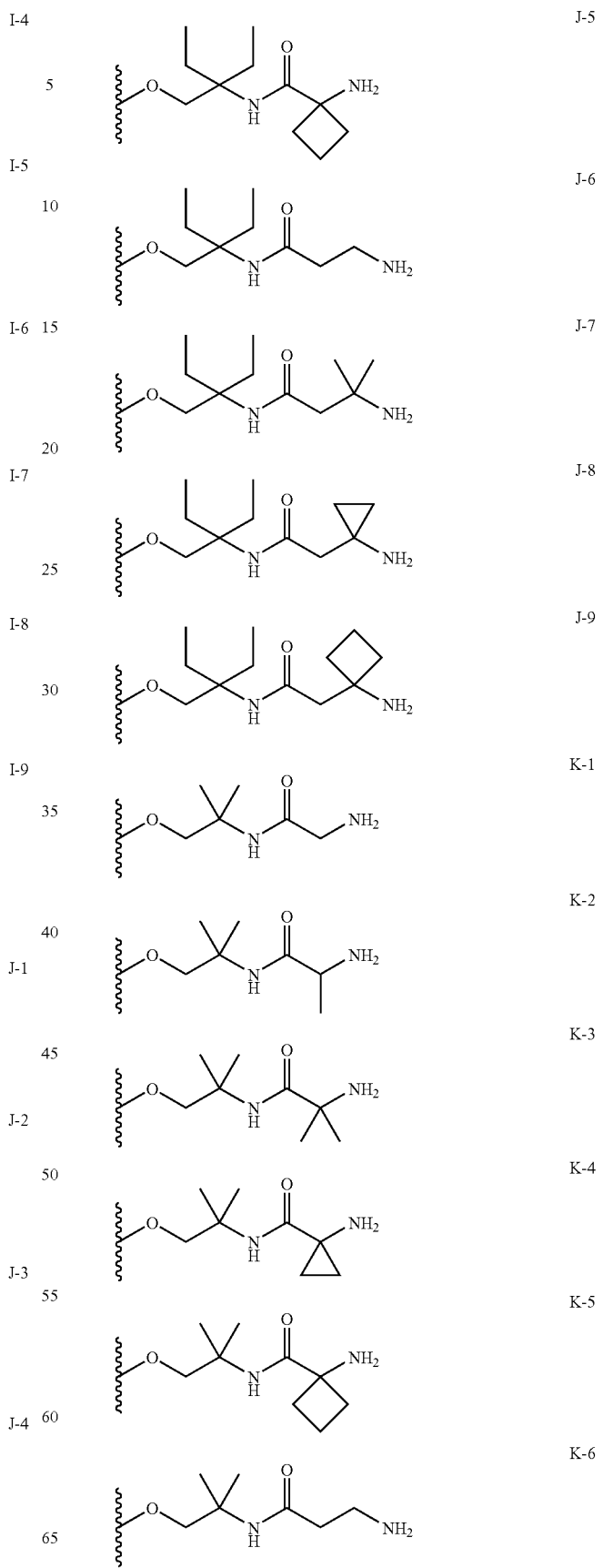

-continued

K-7
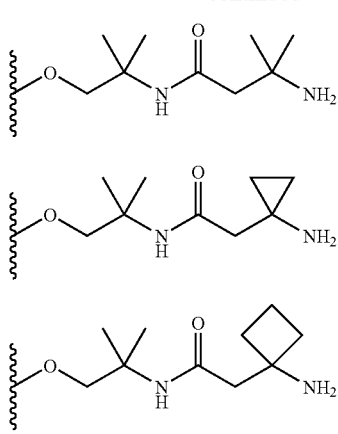

K-8

K-9

The abbreviations used for R⁴ are as follows.
5-OH-2-Adm encompasses syn and anti. Preferred is anti.

[Formula 39]

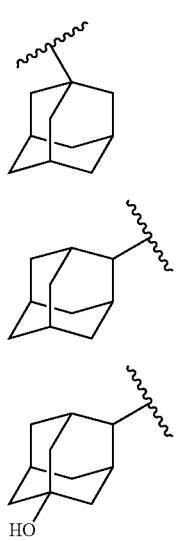

1-Adm

2-Adm

5-OH-2-Adm

Concretely, the defined compound is shown by using the formula (V).

[Formula 40]

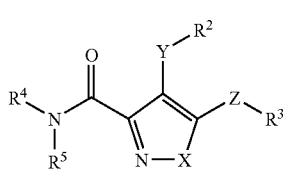

(V)

(Compound No., R², R³, X, Y, Z, R⁴, R⁵)=(1-1,i-Bu,A-1,S,S,O,1-Adm,H),(1-2,i-Bu,A-2,S,S,O,1-Adm,H),(1-3,i-Bu,A-3,S,S,O,1-Adm,H),(1-4,i-Bu,A-4,S,S,O,1-Adm,H),(1-5,i-Bu,A-5,S,S,O,1-Adm,H),(1-6,i-Bu,A-6,S,S,O,1-Adm,H),(1-7,i-Bu,A-7,S,S,O,1-Adm,H),(1-8,i-Bu,A-8,S,S,O,1-Adm,H),(1-9,i-Bu,A-9,S,S,O,1-Adm,H),(1-10,i-Bu,A-10,S,S,O,1-Adm,H),(1-11,i-Bu,A-11,S,S,O,1-Adm,H),(1-12,i-Bu,A-12,S,S,O,1-Adm,H),(1-13,i-Bu,A-13,S,S,O,1-Adm,H),(1-14,i-Bu,A-14,S,S,O,1-Adm,H),(1-15,i-Bu,A-15,S,S,O,1-Adm,H),(1-16,i-Bu,A-16,S,S,O,1-Adm,H),(1-17,i-Bu,A-17,S,S,O,1-Adm,H),(1-18,i-Bu,A-18,S,S,O,1-Adm,H),(1-19,i-Bu,A-19,S,S,O,1-Adm,H),(1-20,i-Bu,A-20,S,S,O,1-Adm,H),(1-21,i-Bu,A-21,S,S,O,1-Adm,H),(1-22,i-Bu,A-22,S,S,O,1-Adm,H),(1-23,i-Bu,A-23,S,S,O,1-Adm,H),(1-24,i-Bu,A-24,S,S,O,1-Adm,H),(1-25,i-Bu,A-25,S,S,O,1-Adm,H),(1-26,i-Bu,A-26,S,S,O,1-Adm,H),(1-27,i-Bu,A-27,S,S,O,1-Adm,H),(1-28,i-Bu,A-28,S,S,O,1-Adm,H),(1-29,i-Bu,A-29,S,S,O,1-Adm,H),(1-30,i-Bu,A-30,S,S,O,1-Adm,H),(1-31,i-Bu,A-31,S,S,O,1-Adm,H),(1-32,i-Bu,A-32,S,S,O,1-Adm,H),(1-33,i-Bu,A-33,S,S,O,1-Adm,H),(1-34,i-Bu,A-34,S,S,O,1-Adm,H),(1-35,i-Bu,A-35,S,S,O,1-Adm,H),(1-36,i-Bu,A-36,S,S,O,1-Adm,H),(1-37,i-Bu,A-1,S,S,O,2-Adm,H),(1-38,i-Bu,A-2,S,S,O,2-Adm,H),(1-39,i-Bu,A-3,S,S,O,2-Adm,H),(1-40,i-Bu,A-4,S,S,O,2-Adm,H),(1-41,i-Bu,A-5,S,S,O,2-Adm,H),(1-42,i-Bu,A-6,S,S,O,2-Adm,H),(1-43,i-Bu,A-7,S,S,O,2-Adm,H),(1-44,i-Bu,A-8,S,S,O,2-Adm,H),(1-45,i-Bu,A-9,S,S,O,2-Adm,H),(1-46,i-Bu,A-10,S,S,O,2-Adm,H),(1-47,i-Bu,A-1,S,S,O,2-Adm,H),(1-48,i-Bu,A-12,S,S,O,2-Adm,H),(1-49,i-Bu,A-13,S,S,O,2-Adm,H),(1-50,i-Bu,A-14,S,S,O,2-Adm,H),(1-51,i-Bu,A-15,S,S,O,2-Adm,H),(1-52,i-Bu,A-16,S,S,O,2-Adm,H),(1-53,i-Bu,A-17,S,S,O,2-Adm,H),(1-54,i-Bu,A-18,S,S,O,2-Adm,H),(1-55,i-Bu,A-19,S,S,O,2-Adm,H),(1-56,i-Bu,A-20,S,S,O,2-Adm,H),(1-57,i-Bu,A-21,S,S,O,2-Adm,H),(1-58,i-Bu,A-22,S,S,O,2-Adm,H),(1-59,i-Bu,A-23,S,S,O,2-Adm,H),(1-60,i-Bu,A-24,S,S,O,2-Adm,H),(1-61,i-Bu,A-25,S,S,O,2-Adm,H),(1-62,i-Bu,A-26,S,S,O,2-Adm,H),(1-63,i-Bu,A-27,S,S,O,2-Adm,H),(1-64,i-Bu,A-28,S,S,O,2-Adm,H),(1-65,i-Bu,A-29,S,S,O,2-Adm,H),(1-66,i-Bu,A-30,S,S,O,2-Adm,H),(1-67,i-Bu,A-31,S,S,O,2-Adm,H),(1-68,i-Bu,A-32,S,S,O,2-Adm,H),(1-69,i-Bu,A-33,S,S,O,2-Adm,H),(1-70,i-Bu,A-34,S,S,O,2-Adm,H),(1-71,i-Bu,A-35,S,S,O,2-Adm,H),(1-72,i-Bu,A-36,S,S,O,2-Adm,H),(1-73,i-Bu,A-1,S,S,O,5-OH-2-Adm,H),(1-74,i-Bu,A-2,S,S,O,5-OH-2-Adm,H),(1-75,i-Bu,A-3,S,S,O,5-OH-2-Adm,H),(1-76,i-Bu,A-4,S,S,O,5-OH-2-Adm,H),(1-77,i-Bu,A-5,S,S,O,5-OH-2-Adm,H),(1-78,i-Bu,A-6,S,S,O,5-OH-2-Adm,H),(1-79,i-Bu,A-7,S,S,O,5-OH-2-Adm,H),(1-80,i-Bu,A-8,S,S,O,5-OH-2-Adm,H),(1-81,i-Bu,A-9,S,S,O,5-OH-2-Adm,H),(1-82,i-Bu,A-10,S,S,O,5-OH-2-Adm,H),(1-83,i-Bu,A-11,S,S,O,5-OH-2-Adm,H),(1-84,i-Bu,A-12,S,S,O,5-OH-2-Adm,H),(1-85,i-Bu,A-13,S,S,O,5-OH-2-Adm,H),(1-86,i-Bu,A-14,S,S,O,5-OH-2-Adm,H),(1-87,i-Bu,A-15,S,S,O,5-OH-2-Adm,H),(1-88,i-Bu,A-16,S,S,O,5-OH-2-Adm,H),(1-89,i-Bu,A-17,S,S,O,5-OH-2-Adm,H),(1-90,i-Bu,A-18,S,S,O,5-OH-2-Adm,H),(1-91,i-Bu,A-19,S,S,O,5-OH-2-Adm,H),(1-92,i-Bu,A-20,S,S,O,5-OH-2-Adm,H),(1-93,i-Bu,A-21,S,S,O,5-OH-2-Adm,H),(1-94,i-Bu,A-22,S,S,O,5-OH-2-Adm,H),(1-95,i-Bu,A-23,S,S,O,5-OH-2-Adm,H),(1-96,i-Bu,A-24,S,S,O,5-OH-2-Adm,H),(1-97,i-Bu,A-25,S,S,O,5-OH-2-Adm,H),(1-98,i-Bu,A-26,S,S,O,5-OH-2-Adm,H),(1-99,i-Bu,A-27,S,S,O,5-OH-2-Adm,H),(1-100,i-Bu,A-28,S,S,O,5-OH-2-Adm,H),(1-101,i-Bu,A-29,S,S,O,5-OH-2-Adm,H),(1-102,i-Bu,A-30,S,S,O,5-OH-2-Adm,H),(1-103,i-Bu,A-31,S,S,O,5-OH-2-Adm,H),(1-104,i-Bu,A-32,S,S,O,5-OH-2-Adm,H),(1-105,i-Bu,A-33,S,S,O,5-OH-2-Adm,H),(1-106,i-Bu,A-34,S,S,O,5-OH-2-Adm,H),(1-107,i-Bu,A-35,S,S,O,5-OH-2-Adm,H),(1-108,i-Bu,A-36,S,S,O,5-OH-2-Adm,H),(1-109,i-Bu,B-1,S,S,O,1-Adm,H),(1-110,i-Bu,B-2,S,S,O,1-Adm,H),(1-111,i-Bu,B-3,S,S,O,1-Adm,H),(1-112,i-Bu,B-4,S,S,O,1-Adm,H),(1-113,i-Bu,B-5,S,S,O,1-Adm,H),(1-114,i-Bu,B-6,S,S,O,1-Adm,H),(1-115,i-Bu,B-7,S,S,O,1-Adm,H),(1-116,i-Bu,B-8,S,S,O,1-Adm,H),(1-117,i-Bu, B-9,S,S,O,1-Adm,H),(1-118,i-Bu,B-10,S,S,O,1-Adm,H),
(1-119,i-Bu,B-11,S,S,O,1-Adm,H),(1-120,i-Bu,B-12,S,S,O,
1-Adm,H),(1-121,i-Bu,B-13,S,S,O,1-Adm,H),(1-122,i-Bu,
B-14,S,S,O,1-Adm,H),(1-123,i-Bu,B-15,S,S,O,1-Adm,H),
(1-124,i-Bu,B-16,S,S,O,1-Adm,H),(1-125,i-Bu,B-17,S,S,O,
1-Adm,H),(1-126,i-Bu,B-18,S,S,O,1-Adm,H),(1-127,i-Bu,
B-19,S,S,O,1-Adm,H),(1-128,i-Bu,B-20,S,S,O,1-Adm,H),
(1-129,i-Bu,B-21,S,S,O,1-Adm,H),(1-130,i-Bu,B-22,S,S,O,
1-Adm,H),(1-131,i-Bu,B-23,S,S,O,1-Adm,H),(1-132,i-Bu,
B-24,S,S,O,1-Adm,H),(1-133,i-Bu,B-25,S,S,O,1-Adm,H),
(1-134,i-Bu,B-26,S,S,O,1-Adm,H),(1-135,i-Bu,B-27,S,S,O,
1-Adm,H),(1-136,i-Bu,B-28,S,S,O,1-Adm,H),(1-137,i-Bu,
B-29,S,S,O,1-Adm,H),(1-138,i-Bu,B-30,S,S,O,1-Adm,H),
(1-139,i-Bu,B-31,S,S,O,1-Adm,H),(1-140,i-Bu,B-32,S,S,O,
1-Adm,H),(1-141,i-Bu,B-33,S,S,O,1-Adm,H),(1-142,i-Bu,
B-34,S,S,O,1-Adm,H),(1-143,i-Bu,B-35,S,S,O,1-Adm,H),
(1-144,i-Bu,B-36,S,S,O,1-Adm,H),(1-145,i-Bu,B-1,S,S,O,
2-Adm,H),(1-146,i-Bu,B-2,S,S,O,2-Adm,H),(1-147,i-Bu,B-
3,S,S,O,2-Adm,H),(1-148,i-Bu,B-4,S,S,O,2-Adm,H),(1-
149,i-Bu,B-5,S,S,O,2-Adm,H),(1-150,i-Bu,B-6,S,S,O,2-
Adm,H),(1-151,i-Bu,B-7,S,S,O,2-Adm,H),(1-152,i-Bu,B-8,
S,S,O,2-Adm,H),(1-153,i-Bu,B-9,S,S,O,2-Adm,H),(1-154,
i-Bu,B-10,S,S,O,2-Adm,H),(1-155,i-Bu,B-11,S,S,O,2-
Adm,H),(1-156,i-Bu,B-12,S,S,O,2-Adm,H),(1-157,i-Bu,B-
13,S,S,O,2-Adm,H),(1-158,i-Bu,B-14,S,S,O,2-Adm,H),(1-
159,i-Bu,B-15,S,S,O,2-Adm,H),(1-160,i-Bu,B-16,S,S,O,2-
Adm,H),(1-161,i-Bu,B-17,S,S,O,2-Adm,H),(1-162,i-Bu,B-
18,S,S,O,2-Adm,H),(1-163,i-Bu,B-19,S,S,O,2-Adm,H),(1-
164,i-Bu,B-20,S,S,O,2-Adm,H),(1-165,i-Bu,B-21,S,S,O,2-
Adm,H),(1-166,i-Bu,B-22,S,S,O,2-Adm,H),(1-167,i-Bu,B-
23,S,S,O,2-Adm,H),(1-168,i-Bu,B-24,S,S,O,2-Adm,H),(1-
169,i-Bu,B-25,S,S,O,2-Adm,H),(1-170,i-Bu,B-26,S,S,O,2-
Adm,H),(1-171,i-Bu,B-27,S,S,O,2-Adm,H),(1-172,i-Bu,B-
28,S,S,O,2-Adm,H),(1-173,i-Bu,B-29,S,S,O,2-Adm,H),(1-
174,i-Bu,B-30,S,S,O,2-Adm,H),(1-175,i-Bu,B-31,S,S,O,2-
Adm,H),(1-176,i-Bu,B-32,S,S,O,2-Adm,H),(1-177,i-Bu,B-
33,S,S,O,2-Adm,H),(1-178,i-Bu,B-34,S,S,O,2-Adm,H),(1-
179,i-Bu,B-35,S,S,O,2-Adm,H),(1-180,i-Bu,B-36,S,S,O,2-
Adm,H),(1-181,i-Bu,B-1,S,S,O,5-OH-2-Adm,H),(1-182,i-
Bu,B-2,S,S,O,5-OH-2-Adm,H),(1-183,i-Bu,B-3,S,S,O,5-
OH-2-Adm,H),(1-184,i-Bu,B-4,S,S,O,5-OH-2-Adm,H),(1-
185,i-Bu,B-5,S,S,O,5-OH-2-Adm,H),(1-186,i-Bu,B-6,S,S,
O,5-OH-2-Adm,H),(1-187,i-Bu,B-7,S,S,O,5-OH-2-Adm,
H),(1-188,i-Bu,B-8,S,S,O,5-OH-2-Adm,H),(1-189,i-Bu,B-
9,S,S,O,5-OH-2-Adm,H),(1-190,i-Bu,B-10,S,S,O,5-OH-2-
Adm,H),(1-191,i-Bu,B-11,S,S,O,5-OH-2-Adm,H),(1-192,i-
Bu,B-12,S,S,O,5-OH-2-Adm,H),(1-193,i-Bu,B-13,S,S,O,5-
OH-2-Adm,H),(1-194,i-Bu,B-14,S,S,O,5-OH-2-Adm,H),
(1-195,i-Bu,B-15,S,S,O,5-OH-2-Adm,H),(1-196,i-Bu,B-16,
S,S,O,5-OH-2-Adm,H),(1-197,i-Bu,B-17,S,S,O,5-OH-2-
Adm,H),(1-198,i-Bu,B-18,S,S,O,5-OH-2-Adm,H),(1-199,i-
Bu,B-19,S,S,O,5-OH-2-Adm,H),(1-200,i-Bu,B-20,S,S,O,5-
OH-2-Adm,H),(1-201,i-Bu,B-21,S,S,O,5-OH-2-Adm,H),
(1-202,i-Bu,B-22,S,S,O,5-OH-2-Adm,H),(1-203,i-Bu,B-23,
S,S,O,5-OH-2-Adm,H),(1-204,i-Bu,B-24,S,S,O,5-OH-2-
Adm,H),(1-205,i-Bu,B-25,S,S,O,5-OH-2-Adm,H),(1-206,i-
Bu,B-26,S,S,O,5-OH-2-Adm,H),(1-207,i-Bu,B-27,S,S,O,5-
OH-2-Adm,H),(1-208,i-Bu,B-28,S,S,O,5-OH-2-Adm,H),
(1-209,i-Bu,B-29,S,S,O,5-OH-2-Adm,H),(1-210,i-Bu,B-30,
S,S,O,5-OH-2-Adm,H),(1-211,i-Bu,B-31,S,S,O,5-OH-2-
Adm,H),(1-212,i-Bu,B-32,S,S,O,5-OH-2-Adm,H),(1-213,i-
Bu,B-33,S,S,O,5-OH-2-Adm,H),(1-214,i-Bu,B-34,S,S,O,5-
OH-2-Adm,H),(1-215,i-Bu,B-35,S,S,O,5-OH-2-Adm,H),
(1-216,i-Bu,B-36,S,S,O,5-OH-2-Adm,H),(1-217,i-Bu,C-1,
S,S,O,1-Adm,H),(1-218,i-Bu,C-2,S,S,O,1-Adm,H),(1-219,
i-Bu,C-3,S,S,O,1-Adm,H),(1-220,i-Bu,C-4,S,S,O,1-Adm,
H),(1-221,i-Bu,C-5,S,S,O,1-Adm,H),(1-222,i-Bu,C-6,S,S,
O,1-Adm,H),(1-223,i-Bu,C-7,S,S,O,1-Adm,H),(1-224,i-Bu,
C-8,S,S,O,1-Adm,H),(1-225,i-Bu,C-9,S,S,O,1-Adm,H),(1-
226,i-Bu,C-10,S,S,O,1-Adm,H),(1-227,i-Bu,C-11,S,S,O,1-
Adm,H),(1-228,i-Bu,C-12,S,S,O,1-Adm,H),(1-229,i-Bu,C-
13,S,S,O,1-Adm,H),(1-230,i-Bu,C-14,S,S,O,1-Adm,H),(1-
231,i-Bu,C-15,S,S,O,1-Adm,H),(1-232,i-Bu,C-16,S,S,O,1-
Adm,H),(1-233,i-Bu,C-17,S,S,O,1-Adm,H),(1-234,i-Bu,C-
18,S,S,O,1-Adm,H),(1-235,i-Bu,C-19,S,S,O,1-Adm,H),(1-
236,i-Bu,C-20,S,S,O,1-Adm,H),(1-237,i-Bu,C-21,S,S,O,1-
Adm,H),(1-238,i-Bu,C-22,S,S,O,1-Adm,H),(1-239,i-Bu,C-
23,S,S,O,1-Adm,H),(1-240,i-Bu,C-24,S,S,O,1-Adm,H),(1-
241,i-Bu,C-25,S,S,O,1-Adm,H),(1-242,i-Bu,C-26,S,S,O,1-
Adm,H),(1-243,i-Bu,C-27,S,S,O,1-Adm,H),(1-244,i-Bu,C-
28,S,S,O,1-Adm,H),(1-245,i-Bu,C-29,S,S,O,1-Adm,H),(1-
246,i-Bu,C-30,S,S,O,1-Adm,H),(1-247,i-Bu,C-31,S,S,O,1-
Adm,H),(1-248,i-Bu,C-32,S,S,O,1-Adm,H),(1-249,i-Bu,C-
33,S,S,O,1-Adm,H),(1-250,i-Bu,C-34,S,S,O,1-Adm,H),(1-
251,i-Bu,C-35,S,S,O,1-Adm,H),(1-252,i-Bu,C-36,S,S,O,1-
Adm,H),(1-253,i-Bu,C-1,S,S,O,2-Adm,H),(1-254,i-Bu,C-2,
S,S,O,2-Adm,H),(1-255,i-Bu,C-3,S,S,O,2-Adm,H),(1-256,
i-Bu,C-4,S,S,O,2-Adm,H),(1-257,i-Bu,C-5,S,S,O,2-Adm,
H),(1-258,i-Bu,C-6,S,S,O,2-Adm,H),(1-259,i-Bu,C-7,S,S,
O,2-Adm,H),(1-260,i-Bu,C-8,S,S,O,2-Adm,H),(1-261,i-Bu,
C-9,S,S,O,2-Adm,H),(1-262,i-Bu,C-10,S,S,O,2-Adm,H),
(1-263,i-Bu,C-11,S,S,O,2-Adm,H),(1-264,i-Bu,C-12,S,S,O,
2-Adm,H),(1-265,i-Bu,C-13,S,S,O,2-Adm,H),(1-266,i-Bu,
C-14,S,S,O,2-Adm,H),(1-267,i-Bu,C-15,S,S,O,2-Adm,H),
(1-268,i-Bu,C-16,S,S,O,2-Adm,H),(1-269,i-Bu,C-17,S,S,O,
2-Adm,H),(1-270,i-Bu,C-18,S,S,O,2-Adm,H),(1-271,i-Bu,
C-19,S,S,O,2-Adm,H),(1-272,i-Bu,C-20,S,S,O,2-Adm,H),
(1-273,i-Bu,C-21,S,S,O,2-Adm,H),(1-274,i-Bu,C-22,S,S,O,
2-Adm,H),(1-275,i-Bu,C-23,S,S,O,2-Adm,H),(1-276,i-Bu,
C-24,S,S,O,2-Adm,H),(1-277,i-Bu,C-25,S,S,O,2-Adm,H),
(1-278,i-Bu,C-26,S,S,O,2-Adm,H),(1-279,i-Bu,C-27,S,S,O,
2-Adm,H),(1-280,i-Bu,C-28,S,S,O,2-Adm,H),(1-281,i-Bu,
C-29,S,S,O,2-Adm,H),(1-282,i-Bu,C-30,S,S,O,2-Adm,H),
(1-283,i-Bu,C-31,S,S,O,2-Adm,H),(1-284,i-Bu,C-32,S,S,O,
2-Adm,H),(1-285,i-Bu,C-33,S,S,O,2-Adm,H),(1-286,i-Bu,
C-34,S,S,O,2-Adm,H),(1-287,i-Bu,C-35,S,S,O,2-Adm,H),
(1-288,i-Bu,C-36,S,S,O,2-Adm,H),(1-289,i-Bu,C-1,S,S,O,
5-OH-2-Adm,H),(1-290,i-Bu,C-2,S,S,O,5-OH-2-Adm,H),
(1-291,i-Bu,C-3,S,S,O,5-OH-2-Adm,H),(1-292,i-Bu,C-4,S,
S,O,5-OH-2-Adm,H),(1-293,i-Bu,C-5,S,S,O,5-OH-2-Adm,
H),(1-294,i-Bu,C-6,S,S,O,5-OH-2-Adm,H),(1-295,i-Bu,C-
7,S,S,O,5-OH-2-Adm,H),(1-296,i-Bu,C-8,S,S,O,5-OH-2-
Adm,H),(1-297,i-Bu,C-9,S,S,O,5-OH-2-Adm,H),(1-298,i-
Bu,C-10,S,S,O,5-OH-2-Adm,H),(1-299,i-Bu,C-11,S,S,O,5-
OH-2-Adm,H),(1-300,i-Bu,C-12,S,S,O,5-OH-2-Adm,H),
(1-301,i-Bu,C-13,S,S,O,5-OH-2-Adm,H),(1-302,i-Bu,C-14,
S,S,O,5-OH-2-Adm,H),(1-303,i-Bu,C-15,S,S,O,5-OH-2-
Adm,H),(1-304,i-Bu,C-16,S,S,O,5-OH-2-Adm,H),(1-305,i-
Bu,C-17,S,S,O,5-OH-2-Adm,H),(1-306,i-Bu,C-18,S,S,O,5-
OH-2-Adm,H),(1-307,i-Bu,C-19,S,S,O,5-OH-2-Adm,H),
(1-308,i-Bu,C-20,S,S,O,5-OH-2-Adm,H),(1-309,i-Bu,C-21,
S,S,O,5-OH-2-Adm,H),(1-310,i-Bu,C-22,S,S,O,5-OH-2-
Adm,H),(1-311,i-Bu,C-23,S,S,O,5-OH-2-Adm,H),(1-312,i-
Bu,C-24,S,S,O,5-OH-2-Adm,H),(1-313,i-Bu,C-25,S,S,O,5-
OH-2-Adm,H),(1-314,i-Bu,C-26,S,S,O,5-OH-2-Adm,H),
(1-315,i-Bu,C-27,S,S,O,5-OH-2-Adm,H),(1-316,i-Bu,C-28,
S,S,O,5-OH-2-Adm,H),(1-317,i-Bu,C-29,S,S,O,5-OH-2-
Adm,H),(1-318,i-Bu,C-30,S,S,O,5-OH-2-Adm,H),(1-319,i-
Bu,C-31,S,S,O,5-OH-2-Adm,H),(1-320,i-Bu,C-32,S,S,O,5-
OH-2-Adm,H),(1-321,i-Bu,C-33,S,S,O,5-OH-2-Adm,H),
(1-322,i-Bu,C-34,S,S,O,5-OH-2-Adm,H),(1-323,i-Bu,C-35, S,S,O,5-OH-2-Adm,H),(1-324,i-Bu,C-36,S,S,O,5-OH-2-Adm,H),(1-325,i-Bu,D-1,S,S,O,1-Adm,H),(1-326,i-Bu,D-2,S,S,O,1-Adm,H),(1-327,i-Bu,D-3,S,S,O,1-Adm,H),(1-328,i-Bu,D-4,S,S,O,1-Adm,H),(1-329,i-Bu,D-5,S,S,O,1-Adm,H),(1-330,i-Bu,D-6,S,S,O,1-Adm,H),(1-331,i-Bu,D-7,S,S,O,1-Adm,H),(1-332,i-Bu,D-8,S,S,O,1-Adm,H),(1-333,i-Bu,D-9,S,S,O,1-Adm,H),(1-334,i-Bu,D-10,S,S,O,1-Adm,H),(1-335,i-Bu,D-11,S,S,O,1-Adm,H),(1-336,i-Bu,D-12,S,S,O,1-Adm,H),(1-337,i-Bu,D-13,S,S,O,1-Adm,H),(1-338,i-Bu,D-14,S,S,O,1-Adm,H),(1-339,i-Bu,D-15,S,S,O,1-Adm,H),(1-340,i-Bu,D-16,S,S,O,1-Adm,H),(1-341,i-Bu,D-17,S,S,O,1-Adm,H),(1-342,i-Bu,D-18,S,S,O,1-Adm,H),(1-343,i-Bu,D-19,S,S,O,1-Adm,H),(1-344,i-Bu,D-20,S,S,O,1-Adm,H),(1-345,i-Bu,D-21,S,S,O,1-Adm,H),(1-346,i-Bu,D-22,S,S,O,1-Adm,H),(1-347,i-Bu,D-23,S,S,O,1-Adm,H),(1-348,i-Bu,D-24,S,S,O,1-Adm,H),(1-349,i-Bu,D-25,S,S,O,1-Adm,H),(1-350,i-Bu,D-26,S,S,O,1-Adm,H),(1-351,i-Bu,D-27,S,S,O,1-Adm,H),(1-352,i-Bu,D-28,S,S,O,1-Adm,H),(1-353,i-Bu,D-29,S,S,O,1-Adm,H),(1-354,i-Bu,D-30,S,S,O,1-Adm,H),(1-355,i-Bu,D-31,S,S,O,1-Adm,H),(1-356,i-Bu,D-32,S,S,O,1-Adm,H),(1-357,i-Bu,D-33,S,S,O,1-Adm,H),(1-358,i-Bu,D-34,S,S,O,1-Adm,H),(1-359,i-Bu,D-35,S,S,O,1-Adm,H),(1-360,i-Bu,D-36,S,S,O,1-Adm,H),(1-361,i-Bu,D-1,S,S,O,2-Adm,H),(1-362,i-Bu,D-2,S,S,O,2-Adm,H),(1-363,i-Bu,D-3,S,S,O,2-Adm,H),(1-364,i-Bu,D-4,S,S,O,2-Adm,H),(1-365,i-Bu,D-5,S,S,O,2-Adm,H),(1-366,i-Bu,D-6,S,S,O,2-Adm,H),(1-367,i-Bu,D-7,S,S,O,2-Adm,H),(1-368,i-Bu,D-8,S,S,O,2-Adm,H),(1-369,i-Bu,D-9,S,S,O,2-Adm,H),(1-370,i-Bu,D-10,S,S,O,2-Adm,H),(1-371,i-Bu,D-11,S,S,O,2-Adm,H),(1-372,i-Bu,D-12,S,S,O,2-Adm,H),(1-373,i-Bu,D-13,S,S,O,2-Adm,H),(1-374,i-Bu,D-14,S,S,O,2-Adm,H),(1-375,i-Bu,D-15,S,S,O,2-Adm,H),(1-376,i-Bu,D-16,S,S,O,2-Adm,H),(1-377,i-Bu,D-17,S,S,O,2-Adm,H),(1-378,i-Bu,D-18,S,S,O,2-Adm,H),(1-379,i-Bu,D-19,S,S,O,2-Adm,H),(1-380,i-Bu,D-20,S,S,O,2-Adm,H),(1-381,i-Bu,D-21,S,S,O,2-Adm,H),(1-382,i-Bu,D-22,S,S,O,2-Adm,H),(1-383,i-Bu,D-23,S,S,O,2-Adm,H),(1-384,i-Bu,D-24,S,S,O,2-Adm,H),(1-385,i-Bu,D-25,S,S,O,2-Adm,H),(1-386,i-Bu,D-26,S,S,O,2-Adm,H),(1-387,i-Bu,D-27,S,S,O,2-Adm,H),(1-388,i-Bu,D-28,S,S,O,2-Adm,H),(1-389,i-Bu,D-29,S,S,O,2-Adm,H),(1-390,i-Bu,D-30,S,S,O,2-Adm,H),(1-391,i-Bu,D-31,S,S,O,2-Adm,H),(1-392,i-Bu,D-32,S,S,O,2-Adm,H),(1-393,i-Bu,D-33,S,S,O,2-Adm,H),(1-394,i-Bu,D-34,S,S,O,2-Adm,H),(1-395,i-Bu,D-35,S,S,O,2-Adm,H),(1-396,i-Bu,D-36,S,S,O,2-Adm,H),(1-397,i-Bu,D-1,S,S,O,5-OH-2-Adm,H),(1-398,i-Bu,D-2,S,S,O,5-OH-2-Adm,H),(1-399,i-Bu,D-3,S,S,O,5-OH-2-Adm,H),(1-400,i-Bu,D-4,S,S,O,5-OH-2-Adm,H),(1-401,i-Bu,D-5,S,S,O,5-OH-2-Adm,H),(1-402,i-Bu,D-6,S,S,O,5-OH-2-Adm,H),(1-403,i-Bu,D-7,S,S,O,5-OH-2-Adm,H),(1-404,i-Bu,D-8,S,S,O,5-OH-2-Adm,H),(1-405,i-Bu,D-9,S,S,O,5-OH-2-Adm,H),(1-406,i-Bu,D-10,S,S,O,5-OH-2-Adm,H),(1-407,i-Bu,D-11,S,S,O,5-OH-2-Adm,H),(1-408,i-Bu,D-12,S,S,O,5-OH-2-Adm,H),(1-409,i-Bu,D-13,S,S,O,5-OH-2-Adm,H),(1-410,i-Bu,D-14,S,S,O,5-OH-2-Adm,H),(1-411,i-Bu,D-15,S,S,O,5-OH-2-Adm,H),(1-412,i-Bu,D-16,S,S,O,5-OH-2-Adm,H),(1-413,i-Bu,D-17,S,S,O,5-OH-2-Adm,H),(1-414,i-Bu,D-18,S,S,O,5-OH-2-Adm,H),(1-415,i-Bu,D-19,S,S,O,5-OH-2-Adm,H),(1-416,i-Bu,D-20,S,S,O,5-OH-2-Adm,H),(1-417,i-Bu,D-21,S,S,O,5-OH-2-Adm,H),(1-418,i-Bu,D-22,S,S,O,5-OH-2-Adm,H),(1-419,i-Bu,D-23,S,S,O,5-OH-2-Adm,H),(1-420,i-Bu,D-24,S,S,O,5-OH-2-Adm,H),(1-421,i-Bu,D-25,S,S,O,5-OH-2-Adm,H),(1-422,i-Bu,D-26,S,S,O,5-OH-2-Adm,H),(1-423,i-Bu,D-27,S,S,O,5-OH-2-Adm,H),(1-424,i-Bu,D-28,S,S,O,5-OH-2-Adm,H),(1-425,i-Bu,D-29,S,S,O,5-OH-2-Adm,H),(1-426,i-Bu,D-30,S,S,O,5-OH-2-Adm,H),(1-427,i-Bu,D-31,S,S,O,5-OH-2-Adm,H),(1-428,i-Bu,D-32,S,S,O,5-OH-2-Adm,H),(1-429,i-Bu,D-33,S,S,O,5-OH-2-Adm,H),(1-430,i-Bu,D-34,S,S,O,5-OH-2-Adm,H),(1-431,i-Bu,D-35,S,S,O,5-OH-2-Adm,H),(1-432,i-Bu,D-36,S,S,O,5-OH-2-Adm,H),(1-433,i-Bu,E-1,S,S,O,1-Adm,H),(1-434,i-Bu,E-2,S,S,O,1-Adm,H),(1-435,i-Bu,E-3,S,S,O,1-Adm,H),(1-436,i-Bu,E-4,S,S,O,1-Adm,H),(1-437,i-Bu,E-5,S,S,O,1-Adm,H),(1-438,i-Bu,E-6,S,S,O,1-Adm,H),(1-439,i-Bu,E-7,S,S,O,1-Adm,H),(1-440,i-Bu,E-8,S,S,O,1-Adm,H),(1-441,i-Bu,E-9,S,S,O,1-Adm,H),(1-442,i-Bu,E-10,S,S,O,1-Adm,H),(1-443,i-Bu,E-11,S,S,O,1-Adm,H),(1-444,i-Bu,E-12,S,S,O,1-Adm,H),(1-445,i-Bu,E-13,S,S,O,1-Adm,H),(1-446,i-Bu,E-14,S,S,O,1-Adm,H),(1-447,i-Bu,E-15,S,S,O,1-Adm,H),(1-448,i-Bu,E-16,S,S,O,1-Adm,H),(1-449,i-Bu,E-17,S,S,O,1-Adm,H),(1-450,i-Bu,E-18,S,S,O,1-Adm,H),(1-451,i-Bu,E-19,S,S,O,1-Adm,H),(1-452,i-Bu,E-20,S,S,O,1-Adm,H),(1-453,i-Bu,E-21,S,S,O,1-Adm,H),(1-454,i-Bu,E-22,S,S,O,1-Adm,H),(1-455,i-Bu,E-23,S,S,O,1-Adm,H),(1-456,i-Bu,E-24,S,S,O,1-Adm,H),(1-457,i-Bu,E-25,S,S,O,1-Adm,H),(1-458,i-Bu,E-26,S,S,O,1-Adm,H),(1-459,i-Bu,E-27,S,S,O,1-Adm,H),(1-460,i-Bu,E-28,S,S,O,1-Adm,H),(1-461,i-Bu,E-29,S,S,O,1-Adm,H),(1-462,i-Bu,E-30,S,S,O,1-Adm,H),(1-463,i-Bu,E-31,S,S,O,1-Adm,H),(1-464,i-Bu,E-32,S,S,O,1-Adm,H),(1-465,i-Bu,E-33,S,S,O,1-Adm,H),(1-466,i-Bu,E-34,S,S,O,1-Adm,H),(1-467,i-Bu,E-35,S,S,O,1-Adm,H),(1-468,i-Bu,E-36,S,S,O,1-Adm,H),(1-469,i-Bu,E-1,S,S,O,2-Adm,H),(1-470,i-Bu,E-2,S,S,O,2-Adm,H),(1-471,i-Bu,E-3,S,S,O,2-Adm,H),(1-472,i-Bu,E-4,S,S,O,2-Adm,H),(1-473,i-Bu,E-5,S,S,O,2-Adm,H),(1-474,i-Bu,E-6,S,S,O,2-Adm,H),(1-475,i-Bu,E-7,S,S,O,2-Adm,H),(1-476,i-Bu,E-8,S,S,O,2-Adm,H),(1-477,i-Bu,E-9,S,S,O,2-Adm,H),(1-478,i-Bu,E-10,S,S,O,2-Adm,H),(1-479,i-Bu,E-11,S,S,O,2-Adm,H),(1-480,i-Bu,E-12,S,S,O,2-Adm,H),(1-481,i-Bu,E-13,S,S,O,2-Adm,H),(1-482,i-Bu,E-14,S,S,O,2-Adm,H),(1-483,i-Bu,E-15,S,S,O,2-Adm,H),(1-484,i-Bu,E-16,S,S,O,2-Adm,H),(1-485,i-Bu,E-17,S,S,O,2-Adm,H),(1-486,i-Bu,E-18,S,S,O,2-Adm,H),(1-487,i-Bu,E-19,S,S,O,2-Adm,H),(1-488,i-Bu,E-20,S,S,O,2-Adm,H),(1-489,i-Bu,E-21,S,S,O,2-Adm,H),(1-490,i-Bu,E-22,S,S,O,2-Adm,H),(1-491,i-Bu,E-23,S,S,O,2-Adm,H),(1-492,i-Bu,E-24,S,S,O,2-Adm,H),(1-493,i-Bu,E-25,S,S,O,2-Adm,H),(1-494,i-Bu,E-26,S,S,O,2-Adm,H),(1-495,i-Bu,E-27,S,S,O,2-Adm,H),(1-496,i-Bu,E-28,S,S,O,2-Adm,H),(1-497,i-Bu,E-29,S,S,O,2-Adm,H),(1-498,i-Bu,E-30,S,S,O,2-Adm,H),(1-499,i-Bu,E-31,S,S,O,2-Adm,H),(1-500,i-Bu,E-32,S,S,O,2-Adm,H),(1-501,i-Bu,E-33,S,S,O,2-Adm,H),(1-502,i-Bu,E-34,S,S,O,2-Adm,H),(1-503,i-Bu,E-35,S,S,O,2-Adm,H),(1-504,i-Bu,E-36,S,S,O,2-Adm,H),(1-505,i-Bu,E-1,S,S,O,5-OH-2-Adm,H),(1-506,i-Bu,E-2,S,S,O,5-OH-2-Adm,H),(1-507,i-Bu,E-3,S,S,O,5-OH-2-Adm,H),(1-508,i-Bu,E-4,S,S,O,5-OH-2-Adm,H),(1-509,i-Bu,E-5,S,S,O,5-OH-2-Adm,H),(1-510,i-Bu,E-6,S,S,O,5-OH-2-Adm,H),(1-511,i-Bu,E-7,S,S,O,5-OH-2-Adm,H),(1-512,i-Bu,E-8,S,S,O,5-OH-2-Adm,H),(1-513,i-Bu,E-9,S,S,O,5-OH-2-Adm,H),(1-514,i-Bu,E-10,S,S,O,5-OH-2-Adm,H),(1-515,i-Bu,E-11,S,S,O,5-OH-2-Adm,H),(1-516,i-Bu,E-12,S,S,O,5-OH-2-Adm,H),(1-517,i-Bu,E-13,S,S,O,5-OH-2-Adm,H),(1-518,i-Bu,E-14,S,S,O,5-OH-2-Adm,H),(1-519,i-Bu,E-15,S,S,O,5-OH-2-Adm,H),(1-520,i-Bu,E-16,S,S,O,5-OH-2-Adm,H),(1-521,i-Bu,E-17,S,S,O,5-OH-2-Adm,H),(1-522,i-Bu,E-18,S,S,O,5-OH-2-Adm,H),(1-523,i-Bu,E-19,S,S,O,5-OH-2-Adm,H),(1-524,i-Bu,E-20,S,S,O,5-OH-2-Adm,H),(1-525,i-Bu,E-21,S,S,O,5-OH-2-Adm,H),(1-526,i-Bu,E-22,S,S,O,5-OH-2-Adm,H),(1-527,i-Bu,E-23,S,S,O,5-OH-2-Adm,H),(1-528,i-Bu,E-24,S,S,O,5-OH-2-Adm,H),(1-529,i-Bu,E-25,S,S,O,5-OH-2-Adm,H),(1-530,i-Bu,E-26,S,S,O,5-OH-2-Adm,H),(1-531,i-Bu,E-27,S,S,O,5-OH-2-Adm,H),(1-532,i-Bu,E-28,S,S,O,5-OH-2-Adm,H),(1-533,i-Bu,E-29,S,S,O,5-OH-2-Adm,H),(1-534,i-Bu,E-30,S,S,O,5-

OH-2-Adm,H),(1-535,i-Bu,E-31,S,S,O,5-OH-2-Adm,H),(1-536,i-Bu,E-32,S,S,O,5-OH-2-Adm,H),(1-537,i-Bu,E-33,S,S,O,5-OH-2-Adm,H),(1-538,i-Bu,E-34,S,S,O,5-OH-2-Adm,H),(1-539,i-Bu,E-35,S,S,O,5-OH-2-Adm,H),(1-540,i-Bu,E-36,S,S,O,5-OH-2-Adm,H),(1-541,i-Bu,F-1,S,S,O,1-Adm,H),(1-542,i-Bu,F-2,S,S,O,1-Adm,H),(1-543,i-Bu,F-3,S,S,O,1-Adm,H),(1-544,i-Bu,F-4,S,S,O,1-Adm,H),(1-545,i-Bu,F-5,S,S,O,1-Adm,H),(1-546,i-Bu,F-6,S,S,O,1-Adm,H),(1-547,i-Bu,F-7,S,S,O,1-Adm,H),(1-548,i-Bu,F-8,S,S,O,1-Adm,H),(1-549,i-Bu,F-9,S,S,O,1-Adm,H),(1-550,i-Bu,F-10,S,S,O,1-Adm,H),(1-551,i-Bu,F-11,S,S,O,1-Adm,H),(1-552,i-Bu,F-12,S,S,O,1-Adm,H),(1-553,i-Bu,F-13,S,S,O,1-Adm,H),(1-554,i-Bu,F-14,S,S,O,1-Adm,H),(1-555,i-Bu,F-15,S,S,O,1-Adm,H),(1-556,i-Bu,F-16,S,S,O,1-Adm,H),(1-557,i-Bu,F-17,S,S,O,1-Adm,H),(1-558,i-Bu,F-18,S,S,O,1-Adm,H),(1-559,i-Bu,F-19,S,S,O,1-Adm,H),(1-560,i-Bu,F-20,S,S,O,1-Adm,H),(1-561,i-Bu,F-21,S,S,O,1-Adm,H),(1-562,i-Bu,F-22,S,S,O,1-Adm,H),(1-563,i-Bu,F-23,S,S,O,1-Adm,H),(1-564,i-Bu,F-24,S,S,O,1-Adm,H),(1-565,i-Bu,F-25,S,S,O,1-Adm,H),(1-566,i-Bu,F-26,S,S,O,1-Adm,H),(1-567,i-Bu,F-27,S,S,O,1-Adm,H),(1-568,i-Bu,F-28,S,S,O,1-Adm,H),(1-569,i-Bu,F-29,S,S,O,1-Adm,H),(1-570,i-Bu,F-30,S,S,O,1-Adm,H),(1-571,i-Bu,F-31,S,S,O,1-Adm,H),(1-572,i-Bu,F-32,S,S,O,1-Adm,H),(1-573,i-Bu,F-33,S,S,O,1-Adm,H),(1-574,i-Bu,F-34,S,S,O,1-Adm,H),(1-575,i-Bu,F-35,S,S,O,1-Adm,H),(1-576,i-Bu,F-36,S,S,O,1-Adm,H),(1-577,i-Bu,F-1,S,S,O,2-Adm,H),(1-578,i-Bu,F-2,S,S,O,2-Adm,H),(1-579,i-Bu,F-3,S,S,O,2-Adm,H),(1-580,i-Bu,F-4,S,S,O,2-Adm,H),(1-581,i-Bu,F-5,S,S,O,2-Adm,H),(1-582,i-Bu,F-6,S,S,O,2-Adm,H),(1-583,i-Bu,F-7,S,S,O,2-Adm,H),(1-584,i-Bu,F-8,S,S,O,2-Adm,H),(1-585,i-Bu,F-9,S,S,O,2-Adm,H),(1-586,i-Bu,F-10,S,S,O,2-Adm,H),(1-587,i-Bu,F-11,S,S,O,2-Adm,H),(1-588,i-Bu,F-12,S,S,O,2-Adm,H),(1-589,i-Bu,F-13,S,S,O,2-Adm,H),(1-590,i-Bu,F-14,S,S,O,2-Adm,H),(1-591,i-Bu,F-15,S,S,O,2-Adm,H),(1-592,i-Bu,F-16,S,S,O,2-Adm,H),(1-593,i-Bu,F-17,S,S,O,2-Adm,H),(1-594,i-Bu,F-18,S,S,O,2-Adm,H),(1-595,i-Bu,F-19,S,S,O,2-Adm,H),(1-596,i-Bu,F-20,S,S,O,2-Adm,H),(1-597,i-Bu,F-21,S,S,O,2-Adm,H),(1-598,i-Bu,F-22,S,S,O,2-Adm,H),(1-599,i-Bu,F-23,S,S,O,2-Adm,H),(1-600,i-Bu,F-24,S,S,O,2-Adm,H),(1-601,i-Bu,F-25,S,S,O,2-Adm,H),(1-602,i-Bu,F-26,S,S,O,2-Adm,H),(1-603,i-Bu,F-27,S,S,O,2-Adm,H),(1-604,i-Bu,F-28,S,S,O,2-Adm,H),(1-605,i-Bu,F-29,S,S,O,2-Adm,H),(1-606,i-Bu,F-30,S,S,O,2-Adm,H),(1-607,i-Bu,F-31,S,S,O,2-Adm,H),(1-608,i-Bu,F-32,S,S,O,2-Adm,H),(1-609,i-Bu,F-33,S,S,O,2-Adm,H),(1-610,i-Bu,F-34,S,S,O,2-Adm,H),(1-611,i-Bu,F-35,S,S,O,2-Adm,H),(1-612,i-Bu,F-36,S,S,O,2-Adm,H),(1-613,i-Bu,F-1,S,S,O,5-OH-2-Adm,H),(1-614,i-Bu,F-2,S,S,O,5-OH-2-Adm,H),(1-615,i-Bu,F-3,S,S,O,5-OH-2-Adm,H),(1-616,i-Bu,F-4,S,S,O,5-OH-2-Adm,H),(1-617,i-Bu,F-5,S,S,O,5-OH-2-Adm,H),(1-618,i-Bu,F-6,S,S,O,5-OH-2-Adm,H),(1-619,i-Bu,F-7,S,S,O,5-OH-2-Adm,H),(1-620,i-Bu,F-8,S,S,O,5-OH-2-Adm,H),(1-621,i-Bu,F-9,S,S,O,5-OH-2-Adm,H),(1-622,i-Bu,F-10,S,S,O,5-OH-2-Adm,H),(1-623,i-Bu,F-11,S,S,O,5-OH-2-Adm,H),(1-624,i-Bu,F-12,S,S,O,5-OH-2-Adm,H),(1-625,i-Bu,F-13,S,S,O,5-OH-2-Adm,H),(1-626,i-Bu,F-14,S,S,O,5-OH-2-Adm,H),(1-627,i-Bu,F-15,S,S,O,5-OH-2-Adm,H),(1-628,i-Bu,F-16,S,S,O,5-OH-2-Adm,H),(1-629,i-Bu,F-17,S,S,O,5-OH-2-Adm,H),(1-630,i-Bu,F-18,S,S,O,5-OH-2-Adm,H),(1-631,i-Bu,F-19,S,S,O,5-OH-2-Adm,H),(1-632,i-Bu,F-20,S,S,O,5-OH-2-Adm,H),(1-633,i-Bu,F-21,S,S,O,5-OH-2-Adm,H),(1-634,i-Bu,F-22,S,S,O,5-OH-2-Adm,H),(1-635,i-Bu,F-23,S,S,O,5-OH-2-Adm,H),(1-636,i-Bu,F-24,S,S,O,5-OH-2-Adm,H),(1-637,i-Bu,F-25,S,S,O,5-OH-2-Adm,H),(1-638,i-Bu,F-26,S,S,O,5-OH-2-Adm,H),(1-639,i-Bu,F-27,S,S,O,5-OH-2-Adm,H),(1-640,i-Bu,F-28,S,S,O,5-OH-2-Adm,H),(1-641,i-Bu,F-29,S,S,O,5-OH-2-Adm,H),(1-642,i-Bu,F-30,S,S,O,5-OH-2-Adm,H),(1-643,i-Bu,F-31,S,S,O,5-OH-2-Adm,H),(1-644,i-Bu,F-32,S,S,O,5-OH-2-Adm,H),(1-645,i-Bu,F-33,S,S,O,5-OH-2-Adm,H),(1-646,i-Bu,F-34,S,S,O,5-OH-2-Adm,H),(1-647,i-Bu,F-35,S,S,O,5-OH-2-Adm,H),(1-648,i-Bu,F-36,S,S,O,5-OH-2-Adm,H),(1-649,i-Bu,G-1,S,S,O,1-Adm,H),(1-650,i-Bu,G-2,S,S,O,1-Adm,H),(1-651,i-Bu,G-3,S,S,O,1-Adm,H),(1-652,i-Bu,G-4,S,S,O,1-Adm,H),(1-653,i-Bu,G-5,S,S,O,1-Adm,H),(1-654,i-Bu,G-6,S,S,O,1-Adm,H),(1-655,i-Bu,G-7,S,S,O,1-Adm,H),(1-656,i-Bu,G-8,S,S,O,1-Adm,H),(1-657,i-Bu,G-9,S,S,O,1-Adm,H),(1-658,i-Bu,G-1,S,S,O,2-Adm,H),(1-659,i-Bu,G-2,S,S,O,2-Adm,H),(1-660,i-Bu,G-3,S,S,O,2-Adm,H),(1-661,i-Bu,G-4,S,S,O,2-Adm,H),(1-662,i-Bu,G-5,S,S,O,2-Adm,H),(1-663,i-Bu,G-6,S,S,O,2-Adm,H),(1-664,i-Bu,G-7,S,S,O,2-Adm,H),(1-665,i-Bu,G-8,S,S,O,2-Adm,H),(1-666,i-Bu,G-9,S,S,O,2-Adm,H),(1-667,i-Bu,G-1,S,S,O,5-OH-2-Adm,H),(1-668,i-Bu,G-2,S,S,O,5-OH-2-Adm,H),(1-669,i-Bu,G-3,S,S,O,5-OH-2-Adm,H),(1-670,i-Bu,G-4,S,S,O,5-OH-2-Adm,H),(1-671,i-Bu,G-5,S,S,O,5-OH-2-Adm,H),(1-672,i-Bu,G-6,S,S,O,5-OH-2-Adm,H),(1-673,i-Bu,G-7,S,S,O,5-OH-2-Adm,H),(1-674,i-Bu,G-8,S,S,O,5-OH-2-Adm,H),(1-675,i-Bu,G-9,S,S,O,5-OH-2-Adm,H),(1-676,i-Bu,H-1,S,S,O,1-Adm,H),(1-677,i-Bu,H-2,S,S,O,1-Adm,H),(1-678,i-Bu,H-3,S,S,O,1-Adm,H),(1-679,i-Bu,H-4,S,S,O,1-Adm,H),(1-680,i-Bu,H-5,S,S,O,1-Adm,H),(1-681,i-Bu,H-6,S,S,O,1-Adm,H),(1-682,i-Bu,H-7,S,S,O,1-Adm,H),(1-683,i-Bu,H-8,S,S,O,1-Adm,H),(1-684,i-Bu,H-9,S,S,O,1-Adm,H),(1-685,i-Bu,H-1,S,S,O,2-Adm,H),(1-686,i-Bu,H-2,S,S,O,2-Adm,H),(1-687,i-Bu,H-3,S,S,O,2-Adm,H),(1-688,i-Bu,H-4,S,S,O,2-Adm,H),(1-689,i-Bu,H-5,S,S,O,2-Adm,H),(1-690,i-Bu,H-6,S,S,O,2-Adm,H),(1-691,i-Bu,H-7,S,S,O,2-Adm,H),(1-692,i-Bu,H-8,S,S,O,2-Adm,H),(1-693,i-Bu,H-9,S,S,O,2-Adm,H),(1-694,i-Bu,H-1,S,S,O,5-OH-2-Adm,H),(1-695,i-Bu,H-2,S,S,O,5-OH-2-Adm,H),(1-696,i-Bu,H-3,S,S,O,5-OH-2-Adm,H),(1-697,i-Bu,H-4,S,S,O,5-OH-2-Adm,H),(1-698,i-Bu,H-5,S,S,O,5-OH-2-Adm,H),(1-699,i-Bu,H-6,S,S,O,5-OH-2-Adm,H),(1-700,i-Bu,H-7,S,S,O,5-OH-2-Adm,H),(1-701,i-Bu,H-8,S,S,O,5-OH-2-Adm,H),(1-702,i-Bu,H-9,S,S,O,5-OH-2-Adm,H),(1-703,i-Bu,I-1,S,S,O,1-Adm,H),(1-704,i-Bu,I-2,S,S,O,1-Adm,H),(1-705,i-Bu,I-3,S,S,O,1-Adm,H),(1-706,i-Bu,I-4,S,S,O,1-Adm,H),(1-707,i-Bu,I-5,S,S,O,1-Adm,H),(1-708,i-Bu,I-6,S,S,O,1-Adm,H),(1-709,i-Bu,I-7,S,S,O,1-Adm,H),(1-710,i-Bu,I-8,S,S,O,1-Adm,H),(1-711,i-Bu,I-9,S,S,O,1-Adm,H),(1-712,i-Bu,I-1,S,S,O,2-Adm,H),(1-713,i-Bu,I-2,S,S,O,2-Adm,H),(1-714,i-Bu,I-3,S,S,O,2-Adm,H),(1-715,i-Bu,I-4,S,S,O,2-Adm,H),(1-716,i-Bu,I-5,S,S,O,2-Adm,H),(1-717,i-Bu,I-6,S,S,O,2-Adm,H),(1-718,i-Bu,I-7,S,S,O,2-Adm,H),(1-719,i-Bu,I-8,S,S,O,2-Adm,H),(1-720,i-Bu,I-9,S,S,O,2-Adm,H),(1-721,i-Bu,I-1,S,S,O,5-OH-2-Adm,H),(1-722,i-Bu,I-2,S,S,O,5-OH-2-Adm,H),(1-723,i-Bu,I-3,S,S,O,5-OH-2-Adm,H),(1-724,i-Bu,I-4,S,S,O,5-OH-2-Adm,H),(1-725,i-Bu,I-5,S,S,O,5-OH-2-Adm,H),(1-726,i-Bu,I-6,S,S,O,5-OH-2-Adm,H),(1-727,i-Bu,I-7,S,S,O,5-OH-2-Adm,H),(1-728,i-Bu,I-8,S,S,O,5-OH-2-Adm,H),(1-729,i-Bu,I-9,S,S,O,5-OH-2-Adm,H),(1-730,i-Bu,J-1,S,S,O,1-Adm,H),(1-731,i-Bu,J-2,S,S,O,1-Adm,H),(1-732,i-Bu,J-3,S,S,O,1-Adm,H),(1-733,i-Bu,J-4,S,S,O,1-Adm,H),(1-734,i-Bu,J-5,S,S,O,1-Adm,H),(1-735,i-Bu,J-6,S,S,O,1-Adm,H),(1-736,i-Bu,J-7,S,S,O,1-Adm,H),(1-737,i-Bu,J-8,S,S,O,1-Adm,H),(1-738,i-Bu,J-9,S,S,O,1-Adm,H),(1-739,i-Bu,J-1,S,S,O,2-Adm,H),(1-740,i-Bu,J-2,S,S,O,2-Adm,H),(1-741,i-Bu,J-3,S,S,O,2-Adm,H),(1-742,i-Bu,J-4,S,S,O,2-Adm,H),(1-743,i-

Bu,J-5,S,S,O,2-Adm,H),(1-744,i-Bu,J-6,S,S,O,2-Adm,H),(1-745,i-Bu,J-7,S,S,O,2-Adm,H),(1-746,i-Bu,J-8,S,S,O,2-Adm,H),(1-747,i-Bu,J-9,S,S,O,2-Adm,H),(1-748,i-Bu,J-1,S,S,O,5-OH-2-Adm,H),(1-749,i-Bu,J-2,S,S,O,5-OH-2-Adm,H),(1-750,i-Bu,J-3,S,S,O,5-OH-2-Adm,H),(1-751,i-Bu,J-4,S,S,O,5-OH-2-Adm,H),(1-752,i-Bu,J-5,S,S,O,5-OH-2-Adm,H),(1-753,i-Bu,J-6,S,S,O,5-OH-2-Adm,H),(1-754,i-Bu,J-7,S,S,O,5-OH-2-Adm,H),(1-755,i-Bu,J-8,S,S,O,5-OH-2-Adm,H),(1-756,i-Bu,J-9,S,S,O,5-OH-2-Adm,H),(1-757,i-Bu,K-1,S,S,O,1-Adm,H),(1-758,i-Bu,K-2,S,S,O,1-Adm,H),(1-759,i-Bu,K-3,S,S,O,1-Adm,H),(1-760,i-Bu,K-4,S,S,O,1-Adm,H),(1-761,i-Bu,K-5,S,S,O,1-Adm,H),(1-762,i-Bu,K-6,S,S,O,1-Adm,H),(1-763,i-Bu,K-7,S,S,O,1-Adm,H),(1-764,i-Bu,K-8,S,S,O,1-Adm,H),(1-765,i-Bu,K-9,S,S,O,1-Adm,H),(1-766,i-Bu,K-1,S,S,O,2-Adm,H),(1-767,i-Bu,K-2,S,S,O,2-Adm,H),(1-768,i-Bu,K-3,S,S,O,2-Adm,H),(1-769,i-Bu,K-4,S,S,O,2-Adm,H),(1-770,i-Bu,K-5,S,S,O,2-Adm,H),(1-771,i-Bu,K-6,S,S,O,2-Adm,H),(1-772,i-Bu,K-7,S,S,O,2-Adm,H),(1-773,i-Bu,K-8,S,S,O,2-Adm,H),(1-774,i-Bu,K-9,S,S,O,2-Adm,H),(1-775,i-Bu,K-1,S,S,O,5-OH-2-Adm,H),(1-776,i-Bu,K-2,S,S,O,5-OH-2-Adm,H),(1-777,i-Bu,K-3,S,S,O,5-OH-2-Adm,H),(1-778,i-Bu,K-4,S,S,O,5-OH-2-Adm,H),(1-779,i-Bu,K-5,S,S,O,5-OH-2-Adm,H),(1-780,i-Bu,K-6,S,S,O,5-OH-2-Adm,H),(1-781,i-Bu,K-7,S,S,O,5-OH-2-Adm,H),(1-782,i-Bu,K-8,S,S,O,5-OH-2-Adm,H),(1-783,i-Bu,K-9,S,S,O,5-OH-2-Adm,H)

(Compound No., $R^2,R^3,X,Y,Z,R^4,R^5$)=(2-1,Pro,A-1,S,S,O,1-Adm,H),(2-2,Pro,A-2,S,S,O,1-Adm,H),(2-3,Pro,A-3,S,S,O,1-Adm,H),(2-4,Pro,A-4,S,S,O,1-Adm,H),(2-5,Pro,A-5,S,S,O,1-Adm,H),(2-6,Pro,A-6,S,S,O,1-Adm,H),(2-7,Pro,A-7,S,S,O,1-Adm,H),(2-8,Pro,A-8,S,S,O,1-Adm,H),(2-9,Pro,A-9,S,S,O,1-Adm,H),(2-10,Pro,A-10,S,S,O,1-Adm,H),(2-11,Pro,A-11,S,S,O,1-Adm,H),(2-12,Pro,A-12,S,S,O,1-Adm,H),(2-13,Pro,A-13,S,S,O,1-Adm,H),(2-14,Pro,A-14,S,S,O,1-Adm,H),(2-15,Pro,A-15,S,S,O,1-Adm,H),(2-16,Pro,A-16,S,S,O,1-Adm,H),(2-17,Pro,A-17,S,S,O,1-Adm,H),(2-18,Pro,A-18,S,S,O,1-Adm,H),(2-19,Pro,A-19,S,S,O,1-Adm,H),(2-20,Pro,A-20,S,S,O,1-Adm,H),(2-21,Pro,A-21,S,S,O,1-Adm,H),(2-22,Pro,A-22,S,S,O,1-Adm,H),(2-23,Pro,A-23,S,S,O,1-Adm,H),(2-24,Pro,A-24,S,S,O,1-Adm,H),(2-25,Pro,A-25,S,S,O,1-Adm,H),(2-26,Pro,A-26,S,S,O,1-Adm,H),(2-27,Pro,A-27,S,S,O,1-Adm,H),(2-28,Pro,A-28,S,S,O,1-Adm,H),(2-29,Pro,A-29,S,S,O,1-Adm,H),(2-30,Pro,A-30,S,S,O,1-Adm,H),(2-31,Pro,A-31,S,S,O,1-Adm,H),(2-32,Pro,A-32,S,S,O,1-Adm,H),(2-33,Pro,A-33,S,S,O,1-Adm,H),(2-34,Pro,A-34,S,S,O,1-Adm,H),(2-35,Pro,A-35,S,S,O,1-Adm,H),(2-36,Pro,A-36,S,S,O,1-Adm,H),(2-37,Pro,A-1,S,S,O,2-Adm,H),(2-38,Pro,A-2,S,S,O,2-Adm,H),(2-39,Pro,A-3,S,S,O,2-Adm,H),(2-40,Pro,A-4,S,S,O,2-Adm,H),(2-41,Pro,A-5,S,S,O,2-Adm,H),(2-42,Pro,A-6,S,S,O,2-Adm,H),(2-43,Pro,A-7,S,S,O,2-Adm,H),(2-44,Pro,A-8,S,S,O,2-Adm,H),(2-45,Pro,A-9,S,S,O,2-Adm,H),(2-46,Pro,A-1,S,S,O,2-Adm,H),(2-47,Pro,A-11,S,S,O,2-Adm,H),(2-48,Pro,A-12,S,S,O,2-Adm,H),(2-49,Pro,A-13,S,S,O,2-Adm,H),(2-50,Pro,A-14,S,S,O,2-Adm,H),(2-51,Pro,A-15,S,S,O,2-Adm,H),(2-52,Pro,A-16,S,S,O,2-Adm,H),(2-53,Pro,A-17,S,S,O,2-Adm,H),(2-54,Pro,A-18,S,S,O,2-Adm,H),(2-55,Pro,A-19,S,S,O,2-Adm,H),(2-56,Pro,A-20,S,S,O,2-Adm,H),(2-57,Pro,A-21,S,S,O,2-Adm,H),(2-58,Pro,A-22,S,S,O,2-Adm,H),(2-59,Pro,A-23,S,S,O,2-Adm,H),(2-60,Pro,A-24,S,S,O,2-Adm,H),(2-61,Pro,A-25,S,S,O,2-Adm,H),(2-62,Pro,A-26,S,S,O,2-Adm,H),(2-63,Pro,A-27,S,S,O,2-Adm,H),(2-64,Pro,A-28,S,S,O,2-Adm,H),(2-65,Pro,A-29,S,S,O,2-Adm,H),(2-66,Pro,A-30,S,S,O,2-Adm,H),(2-67,Pro,A-31,S,S,O,2-Adm,H),(2-68,Pro,A-32,S,S,O,2-Adm,H),(2-69,Pro,A-33,S,S,O,2-Adm,H),(2-70,Pro,A-34,S,S,O,2-Adm,H),(2-71,Pro,A-35,S,S,O,2-Adm,H),(2-72,Pro,A-36,S,S,O,2-Adm,H),(2-73,Pro,A-1,S,S,O,5-OH-2-Adm,H),(2-74,Pro,A-2,S,S,O,5-OH-2-Adm,H),(2-75,Pro,A-3,S,S,O,5-OH-2-Adm,H),(2-76,Pro,A-4,S,S,O,5-OH-2-Adm,H),(2-77,Pro,A-5,S,S,O,5-OH-2-Adm,H),(2-78,Pro,A-6,S,S,O,5-OH-2-Adm,H),(2-79,Pro,A-7,S,S,O,5-OH-2-Adm,H),(2-80,Pro,A-8,S,S,O,5-OH-2-Adm,H),(2-81,Pro,A-9,S,S,O,5-OH-2-Adm,H),(2-82,Pro,A-10,S,S,O,5-OH-2-Adm,H),(2-83,Pro,A-11,S,S,O,5-OH-2-Adm,H),(2-84,Pro,A-12,S,S,O,5-OH-2-Adm,H),(2-85,Pro,A-13,S,S,O,5-OH-2-Adm,H),(2-86,Pro,A-14,S,S,O,5-OH-2-Adm,H),(2-87,Pro,A-15,S,S,O,5-OH-2-Adm,H),(2-88,Pro,A-16,S,S,O,5-OH-2-Adm,H),(2-89,Pro,A-17,S,S,O,5-OH-2-Adm,H),(2-90,Pro,A-18,S,S,O,5-OH-2-Adm,H),(2-91,Pro,A-19,S,S,O,5-OH-2-Adm,H),(2-92,Pro,A-20,S,S,O,5-OH-2-Adm,H),(2-93,Pro,A-21,S,S,O,5-OH-2-Adm,H),(2-94,Pro,A-22,S,S,O,5-OH-2-Adm,H),(2-95,Pro,A-23,S,S,O,5-OH-2-Adm,H),(2-96,Pro,A-24,S,S,O,5-OH-2-Adm,H),(2-97,Pro,A-25,S,S,O,5-OH-2-Adm,H),(2-98,Pro,A-26,S,S,O,5-OH-2-Adm,H),(2-99,Pro,A-27,S,S,O,5-OH-2-Adm,H),(2-100,Pro,A-28,S,S,O,5-OH-2-Adm,H),(2-101,Pro,A-29,S,S,O,5-OH-2-Adm,H),(2-102,Pro,A-30,S,S,O,5-OH-2-Adm,H),(2-103,Pro,A-31,S,S,O,5-OH-2-Adm,H),(2-104,Pro,A-32,S,S,O,5-OH-2-Adm,H),(2-105,Pro,A-33,S,S,O,5-OH-2-Adm,H),(2-106,Pro,A-34,S,S,O,5-OH-2-Adm,H),(2-107,Pro,A-35,S,S,O,5-OH-2-Adm,H),(2-108,Pro,A-36,S,S,O,5-OH-2-Adm,H),(2-109,Pro,B-1,S,S,O,1-Adm,H),(2-110,Pro,B-2,S,S,O,1-Adm,H),(2-111,Pro,B-3,S,S,O,1-Adm,H),(2-112,Pro,B-4,S,S,O,1-Adm,H),(2-113,Pro,B-5,S,S,O,1-Adm,H),(2-114,Pro,B-6,S,S,O,1-Adm,H),(2-115,Pro,B-7,S,S,O,1-Adm,H),(2-116,Pro,B-8,S,S,O,1-Adm,H),(2-117,Pro,B-9,S,S,O,1-Adm,H),(2-118,Pro,B-11,S,S,O,1-Adm,H),(2-119,Pro,B-11,S,S,O,1-Adm,H),(2-120,Pro,B-12,S,S,O,1-Adm,H),(2-121,Pro,B-13,S,S,O,1-Adm,H),(2-122,Pro,B-14,S,S,O,1-Adm,H),(2-123,Pro,B-15,S,S,O,1-Adm,H),(2-124,Pro,B-16,S,S,O,1-Adm,H),(2-125,Pro,B-17,S,S,O,1-Adm,H),(2-126,Pro,B-18,S,S,O,1-Adm,H),(2-127,Pro,B-19,S,S,O,1-Adm,H),(2-128,Pro,B-20,S,S,O,1-Adm,H),(2-129,Pro,B-21,S,S,O,1-Adm,H),(2-130,Pro,B-22,S,S,O,1-Adm,H),(2-131,Pro,B-23,S,S,O,1-Adm,H),(2-132,Pro,B-24,S,S,O,1-Adm,H),(2-133,Pro,B-25,S,S,O,1-Adm,H),(2-134,Pro,B-26,S,S,O,1-Adm,H),(2-135,Pro,B-27,S,S,O,1-Adm,H),(2-136,Pro,B-28,S,S,O,1-Adm,H),(2-137,Pro,B-29,S,S,O,1-Adm,H),(2-138,Pro,B-30,S,S,O,1-Adm,H),(2-139,Pro,B-31,S,S,O,1-Adm,H),(2-140,Pro,B-32,S,S,O,1-Adm,H),(2-141,Pro,B-33,S,S,O,1-Adm,H),(2-142,Pro,B-34,S,S,O,1-Adm,H),(2-143,Pro,B-35,S,S,O,1-Adm,H),(2-144,Pro,B-36,S,S,O,1-Adm,H),(2-145,Pro,B-1,S,S,O,2-Adm,H),(2-146,Pro,B-2,S,S,O,2-Adm,H),(2-147,Pro,B-3,S,S,O,2-Adm,H),(2-148,Pro,B-4,S,S,O,2-Adm,H),(2-149,Pro,B-5,S,S,O,2-Adm,H),(2-150,Pro,B-6,S,S,O,2-Adm,H),(2-151,Pro,B-7,S,S,O,2-Adm,H),(2-152,Pro,B-8,S,S,O,2-Adm,H),(2-153,Pro,B-9,S,S,O,2-Adm,H),(2-154,Pro,B-10,S,S,O,2-Adm,H),(2-155,Pro,B-11,S,S,O,2-Adm,H),(2-156,Pro,B-12,S,S,O,2-Adm,H),(2-157,Pro,B-13,S,S,O,2-Adm,H),(2-158,Pro,B-14,S,S,O,2-Adm,H),(2-159,Pro,B-15,S,S,O,2-Adm,H),(2-160,Pro,B-16,S,S,O,2-Adm,H),(2-161,Pro,B-17,S,S,O,2-Adm,H),(2-162,Pro,B-18,S,S,O,2-Adm,H),(2-163,Pro,B-19,S,S,O,2-Adm,H),(2-164,Pro,B-20,S,S,O,2-Adm,H),(2-165,Pro,B-21,S,S,O,2-Adm,H),(2-166,Pro,B-22,S,S,O,2-Adm,H),(2-167,Pro,B-23,S,S,O,2-Adm,H),(2-168,Pro,B-24,S,S,O,2-Adm,H),(2-169,Pro,B-25,S,S,O,2-Adm,H),(2-170,Pro,B-26,S,S,O,2-Adm,H),(2-171,Pro,B-27,S,S,O,2-Adm,H),(2-172,Pro,B-28,S,S,O,2-Adm,H),(2-173,Pro,B-29,S,S,O,2-Adm,H),(2-174,Pro,B-30,S,S,O,2-Adm,H),(2-175,Pro,B-31,S,S,O,2-Adm,H),(2-176,Pro,B-32,S,S,O,2-Adm,H),(2-177,Pro,B-33,S,S,O,2-Adm,H), (2-178,Pro,B-34,S,S,O,2-

Adm,H),(2-179,Pro,B-35,S,S,O,2-Adm,H),(2-180,Pro,B-36,S,S,O,2-Adm,H),(2-181,Pro,B-1,S,S,O,5-OH-2-Adm,H),(2-182,Pro,B-2,S,S,O,5-OH-2-Adm,H),(2-183,Pro,B-3,S,S,O,5-OH-2-Adm,H),(2-184,Pro,B-4,S,S,O,5-OH-2-Adm,H),(2-185,Pro,B-5,S,S,O,5-OH-2-Adm,H),(2-186,Pro,B-6,S,S,O,5-OH-2-Adm,H),(2-187,Pro,B-7,S,S,O,5-OH-2-Adm,H),(2-188,Pro,B-8,S,S,O,5-OH-2-Adm,H),(2-189,Pro,B-9,S,S,O,5-OH-2-Adm,H),(2-190,Pro,B-10,S,S,O,5-OH-2-Adm,H),(2-191,Pro,B-11,S,S,O,5-OH-2-Adm,H),(2-192,Pro,B-12,S,S,O,5-OH-2-Adm,H),(2-193,Pro,B-13,S,S,O,5-OH-2-Adm,H),(2-194,Pro,B-14,S,S,O,5-OH-2-Adm,H),(2-195,Pro,B-15,S,S,O,5-OH-2-Adm,H),(2-196,Pro,B-16,S,S,O,5-OH-2-Adm,H),(2-197,Pro,B-17,S,S,O,5-OH-2-Adm,H),(2-198,Pro,B-18,S,S,O,5-OH-2-Adm,H),(2-199,Pro,B-19,S,S,O,5-OH-2-Adm,H),(2-200,Pro,B-20,S,S,O,5-OH-2-Adm,H),(2-201,Pro,B-21,S,S,O,5-OH-2-Adm,H),(2-202,Pro,B-22,S,S,O,5-OH-2-Adm,H),(2-203,Pro,B-23,S,S,O,5-OH-2-Adm,H),(2-204,Pro,B-24,S,S,O,5-OH-2-Adm,H),(2-205,Pro,B-25,S,S,O,5-OH-2-Adm,H),(2-206,Pro,B-26,S,S,O,5-OH-2-Adm,H),(2-207,Pro,B-27,S,S,O,5-OH-2-Adm,H),(2-208,Pro,B-28,S,S,O,5-OH-2-Adm,H),(2-209,Pro,B-29,S,S,O,5-OH-2-Adm,H),(2-210,Pro,B-30,S,S,O,5-OH-2-Adm,H),(2-211,Pro,B-31,S,S,O,5-OH-2-Adm,H),(2-212,Pro,B-32,S,S,O,5-OH-2-Adm,H),(2-213,Pro,B-33,S,S,O,5-OH-2-Adm,H),(2-214,Pro,B-34,S,S,O,5-OH-2-Adm,H),(2-215,Pro,B-35,S,S,O,5-OH-2-Adm,H),(2-216,Pro,B-36,S,S,O,5-OH-2-Adm,H),(2-217,Pro,C-1,S,S,O,1-Adm,H),(2-218,Pro,C-2,S,S,O,1-Adm,H),(2-219,Pro,C-3,S,S,O,1-Adm,H),(2-220,Pro,C-4,S,S,O,1-Adm,H),(2-221,Pro,C-5,S,S,O,1-Adm,H),(2-222,Pro,C-6,S,S,O,1-Adm,H),(2-223,Pro,C-7,S,S,O,1-Adm,H),(2-224,Pro,C-8,S,S,O,1-Adm,H),(2-225,Pro,C-9,S,S,O,1-Adm,H),(2-226,Pro,C-10,S,S,O,1-Adm,H),(2-227,Pro,C-11,S,S,O,1-Adm,H),(2-228,Pro,C-12,S,S,O,1-Adm,H),(2-229,Pro,C-13,S,S,O,1-Adm,H),(2-230,Pro,C-14,S,S,O,1-Adm,H),(2-231,Pro,C-15,S,S,O,1-Adm,H),(2-232,Pro,C-16,S,S,O,1-Adm,H),(2-233,Pro,C-17,S,S,O,1-Adm,H),(2-234,Pro,C-18,S,S,O,1-Adm,H),(2-235,Pro,C-19,S,S,O,1-Adm,H),(2-236,Pro,C-20,S,S,O,1-Adm,H),(2-237,Pro,C-21,S,S,O,1-Adm,H),(2-238,Pro,C-22,S,S,O,1-Adm,H),(2-239,Pro,C-23,S,S,O,1-Adm,H),(2-240,Pro,C-24,S,S,O,1-Adm,H),(2-241,Pro,C-25,S,S,O,1-Adm,H),(2-242,Pro,C-26,S,S,O,1-Adm,H),(2-243,Pro,C-27,S,S,O,1-Adm,H),(2-244,Pro,C-28,S,S,O,1-Adm,H),(2-245,Pro,C-29,S,S,O,1-Adm,H),(2-246,Pro,C-30,S,S,O,1-Adm,H),(2-247,Pro,C-31,S,S,O,1-Adm,H),(2-248,Pro,C-32,S,S,O,1-Adm,H),(2-249,Pro,C-33,S,S,O,1-Adm,H),(2-250,Pro,C-34,S,S,O,1-Adm,H),(2-251,Pro,C-35,S,S,O,1-Adm,H),(2-252,Pro,C-36,S,S,O,1-Adm,H),(2-253,Pro,C-1,S,S,O,2-Adm,H),(2-254,Pro,C-2,S,S,O,2-Adm,H),(2-255,Pro,C-3,S,S,O,2-Adm,H),(2-256,Pro,C-4,S,S,O,2-Adm,H),(2-257,Pro,C-5,S,S,O,2-Adm,H),(2-258,Pro,C-6,S,S,O,2-Adm,H),(2-259,Pro,C-7,S,S,O,2-Adm,H),(2-260,Pro,C-8,S,S,O,2-Adm,H),(2-261,Pro,C-9,S,S,O,2-Adm,H),(2-262,Pro,C-11,S,S,O,2-Adm,H),(2-263,Pro,C-11,S,S,O,2-Adm,H),(2-264,Pro,C-12,S,S,O,2-Adm,H),(2-265,Pro,C-13,S,S,O,2-Adm,H),(2-266,Pro,C-14,S,S,O,2-Adm,H),(2-267,Pro,C-15,S,S,O,2-Adm,H),(2-268,Pro,C-16,S,S,O,2-Adm,H),(2-269,Pro,C-17,S,S,O,2-Adm,H),(2-270,Pro,C-18,S,S,O,2-Adm,H),(2-271,Pro,C-19,S,S,O,2-Adm,H),(2-272,Pro,C-20,S,S,O,2-Adm,H),(2-273,Pro,C-21,S,S,O,2-Adm,H),(2-274,Pro,C-22,S,S,O,2-Adm,H),(2-275,Pro,C-23,S,S,O,2-Adm,H),(2-276,Pro,C-24,S,S,O,2-Adm,H),(2-277,Pro,C-25,S,S,O,2-Adm,H),(2-278,Pro,C-26,S,S,O,2-Adm,H),(2-279,Pro,C-27,S,S,O,2-Adm,H),(2-280,Pro,C-28,S,S,O,2-Adm,H),(2-281,Pro,C-29,S,S,O,2-Adm,H),(2-282,Pro,C-30,S,S,O,2-Adm,H),(2-283,Pro,C-31,S,S,O,2-Adm,H),(2-284, Pro,C-32,S,S,O,2-Adm,H),(2-285,Pro,C-33,S,S,O,2-Adm,H),(2-286,Pro,C-34,S,S,O,2-Adm,H),(2-287,Pro,C-35,S,S,O,2-Adm,H),(2-288,Pro,C-36,S,S,O,2-Adm,H),(2-289,Pro,C-1,S,S,O,5-OH-2-Adm,H),(2-290,Pro,C-2,S,S,O,5-OH-2-Adm,H),(2-291,Pro,C-3,S,S,O,5-OH-2-Adm,H),(2-292,Pro,C-4,S,S,O,5-OH-2-Adm,H),(2-293,Pro,C-5,S,S,O,5-OH-2-Adm,H),(2-294,Pro,C-6,S,S,O,5-OH-2-Adm,H),(2-295,Pro,C-7,S,S,O,5-OH-2-Adm,H),(2-296,Pro,C-8,S,S,O,5-OH-2-Adm,H),(2-297,Pro,C-9,S,S,O,5-OH-2-Adm,H),(2-298,Pro,C-10,S,S,O,5-OH-2-Adm,H),(2-299,Pro,C-11,S,S,O,5-OH-2-Adm,H),(2-300,Pro,C-12,S,S,O,5-OH-2-Adm,H),(2-301,Pro,C-13,S,S,O,5-OH-2-Adm,H),(2-302,Pro,C-14,S,S,O,5-OH-2-Adm,H),(2-303,Pro,C-15,S,S,O,5-OH-2-Adm,H),(2-304,Pro,C-16,S,S,O,5-OH-2-Adm,H),(2-305,Pro,C-17,S,S,O,5-OH-2-Adm,H),(2-306,Pro,C-18,S,S,O,5-OH-2-Adm,H),(2-307,Pro,C-19,S,S,O,5-OH-2-Adm,H),(2-308,Pro,C-20,S,S,O,5-OH-2-Adm,H),(2-309,Pro,C-21,S,S,O,5-OH-2-Adm,H),(2-310,Pro,C-22,S,S,O,5-OH-2-Adm,H),(2-311,Pro,C-23,S,S,O,5-OH-2-Adm,H),(2-312,Pro,C-24,S,S,O,5-OH-2-Adm,H),(2-313,Pro,C-25,S,S,O,5-OH-2-Adm,H),(2-314,Pro,C-26,S,S,O,5-OH-2-Adm,H),(2-315,Pro,C-27,S,S,O,5-OH-2-Adm,H),(2-316,Pro,C-28,S,S,O,5-OH-2-Adm,H),(2-317,Pro,C-29,S,S,O,5-OH-2-Adm,H),(2-318,Pro,C-30,S,S,O,5-OH-2-Adm,H),(2-319,Pro,C-31,S,S,O,5-OH-2-Adm,H),(2-320,Pro,C-32,S,S,O,5-OH-2-Adm,H),(2-321,Pro,C-33,S,S,O,5-OH-2-Adm,H),(2-322,Pro,C-34,S,S,O,5-OH-2-Adm,H),(2-323,Pro,C-35,S,S,O,5-OH-2-Adm,H),(2-324,Pro,C-36,S,S,O,5-OH-2-Adm,H),(2-325,Pro,D-1,S,S,O,1-Adm,H),(2-326,Pro,D-2,S,S,O,1-Adm,H),(2-327,Pro,D-3,S,S,O,1-Adm,H),(2-328,Pro,D-4,S,S,O,1-Adm,H),(2-329,Pro,D-5,S,S,O,1-Adm,H),(2-330,Pro,D-6,S,S,O,1-Adm,H),(2-331,Pro,D-7,S,S,O,1-Adm,H),(2-332,Pro,D-8,S,S,O,1-Adm,H),(2-333,Pro,D-9,S,S,O,1-Adm,H),(2-334,Pro,D-110,S,S,O,1-Adm,H),(2-335,Pro,D-111,S,S,O,1-Adm,H),(2-336,Pro,D-12,S,S,O,1-Adm,H),(2-337,Pro,D-13,S,S,O,1-Adm,H),(2-338,Pro,D-14,S,S,O,1-Adm,H),(2-339,Pro,D-15,S,S,O,1-Adm,H),(2-340,Pro,D-16,S,S,O,1-Adm,H),(2-341,Pro,D-17,S,S,O,1-Adm,H),(2-342,Pro,D-18,S,S,O,1-Adm,H),(2-343,Pro,D-19,S,S,O,1-Adm,H),(2-344,Pro,D-20,S,S,O,1-Adm,H),(2-345,Pro,D-21,S,S,O,1-Adm,H),(2-346,Pro,D-22,S,S,O,1-Adm,H),(2-347,Pro,D-23,S,S,O,1-Adm,H),(2-348,Pro,D-24,S,S,O,1-Adm,H),(2-349,Pro,D-25,S,S,O,1-Adm,H),(2-350,Pro,D-26,S,S,O,1-Adm,H),(2-351,Pro,D-27,S,S,O,1-Adm,H),(2-352,Pro,D-28,S,S,O,1-Adm,H),(2-353,Pro,D-29,S,S,O,1-Adm,H),(2-354,Pro,D-30,S,S,O,1-Adm,H),(2-355,Pro,D-31,S,S,O,1-Adm,H),(2-356,Pro,D-32,S,S,O,1-Adm,H),(2-357,Pro,D-33,S,S,O,1-Adm,H),(2-358,Pro,D-34,S,S,O,1-Adm,H),(2-359,Pro,D-35,S,S,O,1-Adm,H),(2-360,Pro,D-36,S,S,O,1-Adm,H),(2-361,Pro,D-1,S,S,O,2-Adm,H),(2-362,Pro,D-2,S,S,O,2-Adm,H),(2-363,Pro,D-3,S,S,O,2-Adm,H),(2-364,Pro,D-4,S,S,O,2-Adm,H),(2-365,Pro,D-5,S,S,O,2-Adm,H),(2-366,Pro,D-6,S,S,O,2-Adm,H),(2-367,Pro,D-7,S,S,O,2-Adm,H),(2-368,Pro,D-8,S,S,O,2-Adm,H),(2-369,Pro,D-9,S,S,O,2-Adm,H),(2-370,Pro,D-110,S,S,O,2-Adm,H),(2-371,Pro,D-111,S,S,O,2-Adm,H),(2-372,Pro,D-12,S,S,O,2-Adm,H),(2-373,Pro,D-13,S,S,O,2-Adm,H),(2-374,Pro,D-14,S,S,O,2-Adm,H),(2-375,Pro,D-15,S,S,O,2-Adm,H),(2-376,Pro,D-16,S,S,O,2-Adm,H),(2-377,Pro,D-17,S,S,O,2-Adm,H),(2-378,Pro,D-18,S,S,O,2-Adm,H),(2-379,Pro,D-19,S,S,O,2-Adm,H),(2-380,Pro,D-20,S,S,O,2-Adm,H),(2-381,Pro,D-21,S,S,O,2-Adm,H),(2-382,Pro,D-22,S,S,O,2-Adm,H),(2-383,Pro,D-23,S,S,O,2-Adm,H),(2-384,Pro,D-24,S,S,O,2-Adm,H),(2-385,Pro,D-25,S,S,O,2-Adm,H),(2-386,Pro,D-26,S,S,O,2-Adm,H),(2-387,Pro,D-27,S,S,O,2-Adm,H),(2-388,Pro,D-28,S,S,O,2-Adm,H),(2-389,Pro,D-29,S,S,O,2-Adm,H),(2-390,Pro,D-30,S,S,O,2-Adm,H),(2-391,Pro,D-31,S,S,O,2- Adm,H),(2-392,Pro,D-32,S,S,O,2-

Adm,H),(2-393,Pro,D-33,S,S,O,2-Adm,H),(2-394,Pro,D-34,S,S,O,2-Adm,H),(2-395,Pro,D-35,S,S,O,2-Adm,H),(2-396,Pro,D-36,S,S,O,2-Adm,H),(2-397,Pro,D-1,S,S,O,5-OH-2-Adm,H),(2-398,Pro,D-2,S,S,O,5-OH-2-Adm,H),(2-399,Pro,D-3,S,S,O,5-OH-2-Adm,H),(2-400,Pro,D-4,S,S,O,5-OH-2-Adm,H),(2-401,Pro,D-5,S,S,O,5-OH-2-Adm,H),(2-402,Pro,D-6,S,S,O,5-OH-2-Adm,H),(2-403,Pro,D-7,S,S,O,5-OH-2-Adm,H),(2-404,Pro,D-8,S,S,O,5-OH-2-Adm,H),(2-405,Pro,D-9,S,S,O,5-OH-2-Adm,H),(2-406,Pro,D-110,S,S,O,5-OH-2-Adm,H),(2-407,Pro,D-111,S,S,O,5-OH-2-Adm,H),(2-408,Pro,D-12,S,S,O,5-OH-2-Adm,H),(2-409,Pro,D-13,S,S,O,5-OH-2-Adm,H),(2-410,Pro,D-14,S,S,O,5-OH-2-Adm,H),(2-411,Pro,D-11,S,S,O,5-OH-2-Adm,H),(2-412,Pro,D-16,S,S,O,5-OH-2-Adm,H),(2-413,Pro,D-17,S,S,O,5-OH-2-Adm,H),(2-414,Pro,D-18,S,S,O,5-OH-2-Adm,H),(2-415,Pro,D-119,S,S,O,5-OH-2-Adm,H),(2-416,Pro,D-20,S,S,O,5-OH-2-Adm,H),(2-417,Pro,D-21,S,S,O,5-OH-2-Adm,H),(2-418,Pro,D-22,S,S,O,5-OH-2-Adm,H),(2-419,Pro,D-23,S,S,O,5-OH-2-Adm,H),(2-420,Pro,D-24,S,S,O,5-OH-2-Adm,H),(2-421,Pro,D-25,S,S,O,5-OH-2-Adm,H),(2-422,Pro,D-26,S,S,O,5-OH-2-Adm,H),(2-423,Pro,D-27,S,S,O,5-OH-2-Adm,H),(2-424,Pro,D-28,S,S,O,5-OH-2-Adm,H),(2-425,Pro,D-29,S,S,O,5-OH-2-Adm,H),(2-426,Pro,D-30,S,S,O,5-OH-2-Adm,H),(2-427,Pro,D-31,S,S,O,5-OH-2-Adm,H),(2-428,Pro,D-32,S,S,O,5-OH-2-Adm,H),(2-429,Pro,D-33,S,S,O,5-OH-2-Adm,H),(2-430,Pro,D-34,S,S,O,5-OH-2-Adm,H),(2-431,Pro,D-35,S,S,O,5-OH-2-Adm,H),(2-432,Pro,D-36,S,S,O,5-OH-2-Adm,H),(2-433,Pro,E-1,S,S,O,1-Adm,H),(2-434,Pro,E-2,S,S,O,1-Adm,H),(2-435,Pro,E-3,S,S,O,1-Adm,H),(2-436,Pro,E-4,S,S,O,1-Adm,H),(2-437,Pro,E-5,S,S,O,1-Adm,H),(2-438,Pro,E-6,S,S,O,1-Adm,H),(2-439,Pro,E-7,S,S,O,1-Adm,H),(2-440,Pro,E-8,S,S,O,1-Adm,H),(2-441,Pro,E-9,S,S,O,1-Adm,H),(2-442,Pro,E-10,S,S,O,1-Adm,H),(2-443,Pro,E-11,S,S,O,1-Adm,H),(2-444,Pro,E-12,S,S,O,1-Adm,H),(2-445,Pro,E-13,S,S,O,1-Adm,H),(2-446,Pro,E-14,S,S,O,1-Adm,H),(2-447,Pro,E-15,S,S,O,1-Adm,H),(2-448,Pro,E-16,S,S,O,1-Adm,H),(2-449,Pro,E-17,S,S,O,1-Adm,H),(2-450,Pro,E-18,S,S,O,1-Adm,H),(2-451,Pro,E-19,S,S,O,1-Adm,H),(2-452,Pro,E-20,S,S,O,1-Adm,H),(2-453,Pro,E-21,S,S,O,1-Adm,H),(2-454,Pro,E-22,S,S,O,1-Adm,H),(2-455,Pro,E-23,S,S,O,1-Adm,H),(2-456,Pro,E-24,S,S,O,1-Adm,H),(2-457,Pro,E-25,S,S,O,1-Adm,H),(2-458,Pro,E-26,S,S,O,1-Adm,H),(2-459,Pro,E-27,S,S,O,1-Adm,H),(2-460,Pro,E-28,S,S,O,1-Adm,H),(2-461,Pro,E-29,S,S,O,1-Adm,H),(2-462,Pro,E-30,S,S,O,1-Adm,H),(2-463,Pro,E-31,S,S,O,1-Adm,H),(2-464,Pro,E-32,S,S,O,1-Adm,H),(2-465,Pro,E-33,S,S,O,1-Adm,H),(2-466,Pro,E-34,S,S,O,1-Adm,H),(2-467,Pro,E-35,S,S,O,1-Adm,H),(2-468,Pro,E-36,S,S,O,1-Adm,H),(2-469,Pro,E-1,S,S,O,2-Adm,H),(2-470,Pro,E-2,S,S,O,2-Adm,H),(2-471,Pro,E-3,S,S,O,2-Adm,H),(2-472,Pro,E-4,S,S,O,2-Adm,H),(2-473,Pro,E-5,S,S,O,2-Adm,H),(2-474,Pro,E-6,S,S,O,2-Adm,H),(2-475,Pro,E-7,S,S,O,2-Adm,H),(2-476,Pro,E-8,S,S,O,2-Adm,H),(2-477,Pro,E-9,S,S,O,2-Adm,H),(2-478,Pro,E-110,S,S,O,2-Adm,H),(2-479,Pro,E-111,S,S,O,2-Adm,H),(2-480,Pro,E-12,S,S,O,2-Adm,H),(2-481,Pro,E-13,S,S,O,2-Adm,H),(2-482,Pro,E-14,S,S,O,2-Adm,H),(2-483,Pro,E-11,S,S,O,2-Adm,H),(2-484,Pro,E-16,S,S,O,2-Adm,H),(2-485,Pro,E-17,S,S,O,2-Adm,H),(2-486,Pro,E-18,S,S,O,2-Adm,H),(2-487,Pro,E-119,S,S,O,2-Adm,H),(2-488,Pro,E-20,S,S,O,2-Adm,H),(2-489,Pro,E-21,S,S,O,2-Adm,H),(2-490,Pro,E-22,S,S,O,2-Adm,H),(2-491,Pro,E-23,S,S,O,2-Adm,H),(2-492,Pro,E-24,S,S,O,2-Adm,H),(2-493,Pro,E-25,S,S,O,2-Adm,H),(2-494,Pro,E-26,S,S,O,2-Adm,H),(2-495,Pro,E-27,S,S,O,2-Adm,H),(2-496,Pro,E-28,S,S,O,2-Adm,H),(2-497,Pro,E-29,S,S,O,2-Adm,H),(2-498,Pro,E-30,S,S,O,2-Adm,H), (2-499,Pro,E-31,S,S,O,2-Adm,H),(2-500,Pro,E-32,S,S,O,2-Adm,H),(2-501,Pro,E-33,S,S,O,2-Adm,H),(2-502,Pro,E-34,S,S,O,2-Adm,H),(2-503,Pro,E-35,S,S,O,2-Adm,H),(2-504,Pro,E-36,S,S,O,2-Adm,H),(2-505,Pro,E-1,S,S,O,5-OH-2-Adm,H),(2-506,Pro,E-2,S,S,O,5-OH-2-Adm,H),(2-507,Pro,E-3,S,S,O,5-OH-2-Adm,H),(2-508,Pro,E-4,S,S,O,5-OH-2-Adm,H),(2-509,Pro,E-5,S,S,O,5-OH-2-Adm,H),(2-510,Pro,E-6,S,S,O,5-OH-2-Adm,H),(2-511,Pro,E-7,S,S,O,5-OH-2-Adm,H),(2-512,Pro,E-8,S,S,O,5-OH-2-Adm,H),(2-513,Pro,E-9,S,S,O,5-OH-2-Adm,H),(2-514,Pro,E-10,S,S,O,5-OH-2-Adm,H),(2-515,Pro,E-11,S,S,O,5-OH-2-Adm,H),(2-516,Pro,E-12,S,S,O,5-OH-2-Adm,H),(2-517,Pro,E-13,S,S,O,5-OH-2-Adm,H),(2-518,Pro,E-14,S,S,O,5-OH-2-Adm,H),(2-519,Pro,E-15,S,S,O,5-OH-2-Adm,H),(2-520,Pro,E-16,S,S,O,5-OH-2-Adm,H),(2-521,Pro,E-17,S,S,O,5-OH-2-Adm,H),(2-522,Pro,E-18,S,S,O,5-OH-2-Adm,H),(2-523,Pro,E-19,S,S,O,5-OH-2-Adm,H),(2-524,Pro,E-20,S,S,O,5-OH-2-Adm,H),(2-525,Pro,E-21,S,S,O,5-OH-2-Adm,H),(2-526,Pro,E-22,S,S,O,5-OH-2-Adm,H),(2-527,Pro,E-23,S,S,O,5-OH-2-Adm,H),(2-528,Pro,E-24,S,S,O,5-OH-2-Adm,H),(2-529,Pro,E-25,S,S,O,5-OH-2-Adm,H),(2-530,Pro,E-26,S,S,O,5-OH-2-Adm,H),(2-531,Pro,E-27,S,S,O,5-OH-2-Adm,H),(2-532,Pro,E-28,S,S,O,5-OH-2-Adm,H),(2-533,Pro,E-29,S,S,O,5-OH-2-Adm,H),(2-534,Pro,E-30,S,S,O,5-OH-2-Adm,H),(2-535,Pro,E-31,S,S,O,5-OH-2-Adm,H),(2-536,Pro,E-32,S,S,O,5-OH-2-Adm,H),(2-537,Pro,E-33,S,S,O,5-OH-2-Adm,H),(2-538,Pro,E-34,S,S,O,5-OH-2-Adm,H),(2-539,Pro,E-35,S,S,O,5-OH-2-Adm,H),(2-540,Pro,E-36,S,S,O,5-OH-2-Adm,H),(2-541,Pro,F-1,S,S,O,1-Adm,H),(2-542,Pro,F-2,S,S,O,1-Adm,H),(2-543,Pro,F-3,S,S,O,1-Adm,H),(2-544,Pro,F-4,S,S,O,1-Adm,H),(2-545,Pro,F-5,S,S,O,1-Adm,H),(2-546,Pro,F-6,S,S,O,1-Adm,H),(2-547,Pro,F-7,S,S,O,1-Adm,H),(2-548,Pro,F-8,S,S,O,1-Adm,H),(2-549,Pro,F-9,S,S,O,1-Adm,H),(2-550,Pro,F-110,S,S,O,1-Adm,H),(2-551,Pro,F-111,S,S,O,1-Adm,H),(2-552,Pro,F-12,S,S,O,1-Adm,H),(2-553,Pro,F-13,S,S,O,1-Adm,H),(2-554,Pro,F-14,S,S,O,1-Adm,H),(2-555,Pro,F-15,S,S,O,1-Adm,H),(2-556,Pro,F-16,S,S,O,1-Adm,H),(2-557,Pro,F-17,S,S,O,1-Adm,H),(2-558,Pro,F-18,S,S,O,1-Adm,H),(2-559,Pro,F-19,S,S,O,1-Adm,H),(2-560,Pro,F-20,S,S,O,1-Adm,H),(2-561,Pro,F-21,S,S,O,1-Adm,H),(2-562,Pro,F-22,S,S,O,1-Adm,H),(2-563,Pro,F-23,S,S,O,1-Adm,H),(2-564,Pro,F-24,S,S,O,1-Adm,H),(2-565,Pro,F-25,S,S,O,1-Adm,H),(2-566,Pro,F-26,S,S,O,1-Adm,H),(2-567,Pro,F-27,S,S,O,1-Adm,H),(2-568,Pro,F-28,S,S,O,11-Adm,H),(2-569,Pro,F-29,S,S,O,1-Adm,H),(2-570,Pro,F-30,S,S,O,1-Adm,H),(2-571,Pro,F-31,S,S,O,1-Adm,H),(2-572,Pro,F-32,S,S,O,1-Adm,H),(2-573,Pro,F-33,S,S,O,1-Adm,H),(2-574,Pro,F-34,S,S,O,1-Adm,H),(2-575,Pro,F-35,S,S,O,11-Adm,H),(2-576,Pro,F-36,S,S,O,1-Adm,H),(2-577,Pro,F-1,S,S,O,2-Adm,H),(2-578,Pro,F-2,S,S,O,2-Adm,H),(2-579,Pro,F-3,S,S,O,2-Adm,H),(2-580,Pro,F-4,S,S,O,2-Adm,H),(2-581,Pro,F-5,S,S,O,2-Adm,H),(2-582,Pro,F-6,S,S,O,2-Adm,H),(2-583,Pro,F-7,S,S,O,2-Adm,H),(2-584,Pro,F-8,S,S,O,2-Adm,H),(2-585,Pro,F-9,S,S,O,2-Adm,H),(2-586,Pro,F-10,S,S,O,2-Adm,H),(2-587,Pro,F-111,S,S,O,2-Adm,H),(2-588,Pro,F-12,S,S,O,2-Adm,H),(2-589,Pro,F-13,S,S,O,2-Adm,H),(2-590,Pro,F-14,S,S,O,2-Adm,H),(2-591,Pro,F-11,S,S,O,2-Adm,H), (2-592,Pro,F-16,S,S,O,2-Adm,H),(2-593,Pro,F-17,S,S,O,2-Adm,H),(2-594,Pro,F-18,S,S,O,2-Adm,H),(2-595,Pro,F-19,S,S,O,2-Adm,H),(2-596,Pro,F-20,S,S,O,2-Adm,H),(2-597,Pro,F-21,S,S,O,2-Adm,H),(2-598,Pro,F-22,S,S,O,2-Adm,H),(2-599,Pro,F-23,S,S,O,2-Adm,H),(2-600,Pro,F-24,S,S,O,2-Adm,H),(2-601,Pro,F-25,S,S,O,2-Adm,H),(2-602,Pro,F-26,S,S,O,2-Adm,H),(2-603,Pro,F-27,S,S,O,2-Adm,H),(2-604,Pro,F-28,S,S,O,2-Adm,H),(2-605,Pro,F-29,S,S,O,2-Adm,H),(2-

606,Pro,F-30,S,S,O,2-Adm,H),(2-607,Pro,F-31,S,S,O,2-Adm,H),(2-608,Pro,F-32,S,S,O,2-Adm,H),(2-609,Pro,F-33,S,S,O,2-Adm,H),(2-610,Pro,F-34,S,S,O,2-Adm,H),(2-611,Pro,F-35,S,S,O,2-Adm,H),(2-612,Pro,F-36,S,S,O,2-Adm,H),(2-613,Pro,F-1,S,S,O,5-OH-2-Adm,H),(2-614,Pro,F-2,S,S,O,5-OH-2-Adm,H),(2-615,Pro,F-3,S,S,O,5-OH-2-Adm,H),(2-616,Pro,F-4,S,S,O,5-OH-2-Adm,H),(2-617,Pro,F-5,S,S,O,5-OH-2-Adm,H),(2-618,Pro,F-6,S,S,O,5-OH-2-Adm,H),(2-619,Pro,F-7,S,S,O,5-OH-2-Adm,H),(2-620,Pro,F-8,S,S,O,5-OH-2-Adm,H),(2-621,Pro,F-9,S,S,O,5-OH-2-Adm,H),(2-622,Pro,F-10,S,S,O,5-OH-2-Adm,H),(2-623,Pro,F-11,S,S,O,5-OH-2-Adm,H),(2-624,Pro,F-12,S,S,O,5-OH-2-Adm,H),(2-625,Pro,F-13,S,S,O,5-OH-2-Adm,H),(2-626,Pro,F-14,S,S,O,5-OH-2-Adm,H),(2-627,Pro,F-15,S,S,O,5-OH-2-Adm,H),(2-628,Pro,F-16,S,S,O,5-OH-2-Adm,H),(2-629,Pro,F-17,S,S,O,5-OH-2-Adm,H),(2-630,Pro,F-18,S,S,O,5-OH-2-Adm,H),(2-631,Pro,F-19,S,S,O,5-OH-2-Adm,H),(2-632,Pro,F-20,S,S,O,5-OH-2-Adm,H),(2-633,Pro,F-21,S,S,O,5-OH-2-Adm,H),(2-634,Pro,F-22,S,S,O,5-OH-2-Adm,H),(2-635,Pro,F-23,S,S,O,5-OH-2-Adm,H),(2-636,Pro,F-24,S,S,O,5-OH-2-Adm,H),(2-637,Pro,F-25,S,S,O,5-OH-2-Adm,H),(2-638,Pro,F-26,S,S,O,5-OH-2-Adm,H),(2-639,Pro,F-27,S,S,O,5-OH-2-Adm,H),(2-640,Pro,F-28,S,S,O,5-OH-2-Adm,H),(2-641,Pro,F-29,S,S,O,5-OH-2-Adm,H),(2-642,Pro,F-30,S,S,O,5-OH-2-Adm,H),(2-643,Pro,F-31,S,S,O,5-OH-2-Adm,H),(2-644,Pro,F-32,S,S,O,5-OH-2-Adm,H),(2-645,Pro,F-33,S,S,O,5-OH-2-Adm,H),(2-646,Pro,F-34,S,S,O,5-OH-2-Adm,H),(2-647,Pro,F-35,S,S,O,5-OH-2-Adm,H),(2-648,Pro,F-36,S,S,O,5-OH-2-Adm,H),(2-649,Pro,G-1,S,S,O,1-Adm,H),(2-650,Pro,G-2,S,S,O,1-Adm,H),(2-651,Pro,G-3,S,S,O,1-Adm,H),(2-652,Pro,G-4,S,S,O,1-Adm,H),(2-653,Pro,G-5,S,S,O,1-Adm,H),(2-654,Pro,G-6,S,S,O,1-Adm,H),(2-655,Pro,G-7,S,S,O,1-Adm,H),(2-656,Pro,G-8,S,S,O,1-Adm,H),(2-657,Pro,G-9,S,S,O,1-Adm,H),(2-658,Pro,G-1,S,S,O,2-Adm,H),(2-659,Pro,G-2,S,S,O,2-Adm,H),(2-660,Pro,G-3,S,S,O,2-Adm,H),(2-661,Pro,G-4,S,S,O,2-Adm,H),(2-662,Pro,G-5,S,S,O,2-Adm,H),(2-663,Pro,G-6,S,S,O,2-Adm,H),(2-664,Pro,G-7,S,S,O,2-Adm,H),(2-665,Pro,G-8,S,S,O,2-Adm,H),(2-666,Pro,G-9,S,S,O,2-Adm,H),(2-667,Pro,G-1,S,S,O,5-OH-2-Adm,H),(2-668,Pro,G-2,S,S,O,5-OH-2-Adm,H),(2-669,Pro,G-3,S,S,O,5-OH-2-Adm,H),(2-670,Pro,G-4,S,S,O,5-OH-2-Adm,H),(2-671,Pro,G-5,S,S,O,5-OH-2-Adm,H),(2-672,Pro,G-6,S,S,O,5-OH-2-Adm,H),(2-673,Pro,G-7,S,S,O,5-OH-2-Adm,H),(2-674,Pro,G-8,S,S,O,5-OH-2-Adm,H),(2-675,Pro,G-9,S,S,O,5-OH-2-Adm,H),(2-676,Pro,H-1,S,S,O,1-Adm,H),(2-677,Pro,H-2,S,S,O,1-Adm,H),(2-678,Pro,H-3,S,S,O,1-Adm,H),(2-679,Pro,H-4,S,S,O,1-Adm,H),(2-680,Pro,H-5,S,S,O,1-Adm,H),(2-681,Pro,H-6,S,S,O,1-Adm,H),(2-682,Pro,H-7,S,S,O,1-Adm,H),(2-683,Pro,H-8,S,S,O,1-Adm,H),(2-684,Pro,H-9,S,S,O,1-Adm,H),(2-685,Pro,H-1,S,S,O,2-Adm,H),(2-686,Pro,H-2,S,S,O,2-Adm,H),(2-687,Pro,H-3,S,S,O,2-Adm,H),(2-688,Pro,H-4,S,S,O,2-Adm,H),(2-689,Pro,H-5,S,S,O,2-Adm,H),(2-690,Pro,H-6,S,S,O,2-Adm,H),(2-691,Pro,H-7,S,S,O,2-Adm,H),(2-692,Pro,H-8,S,S,O,2-Adm,H),(2-693,Pro,H-9,S,S,O,2-Adm,H),(2-694,Pro,H-1,S,S,O,5-OH-2-Adm,H),(2-695,Pro,H-2,S,S,O,5-OH-2-Adm,H),(2-696,Pro,H-3,S,S,O,5-OH-2-Adm,H),(2-697,Pro,H-4,S,S,O,5-OH-2-Adm,H),(2-698,Pro,H-5,S,S,O,5-OH-2-Adm,H),(2-699,Pro,H-6,S,S,O,5-OH-2-Adm,H),(2-700,Pro,H-7,S,S,O,5-OH-2-Adm,H),(2-701,Pro,H-8,S,S,O,5-OH-2-Adm,H),(2-702,Pro,H-9,S,S,O,5-OH-2-Adm,H),(2-703,Pro,I-1,S,S,O,1-Adm,H),(2-704,Pro,I-2,S,S,O,1-Adm,H),(2-705,Pro,I-3,S,S,O,1-Adm,H),(2-706,Pro,I-4,S,S,O,1-Adm,H),(2-707,Pro,I-5,S,S,O,1-Adm,H),(2-708,Pro,I-6,S,S,O,1-Adm,H),(2-709,Pro,I-7,S,S,O,1-Adm,H),(2-710,Pro,I-8,S,S,O,1-Adm,H),(2-711,Pro,I-9,S,S,O,1-Adm,H),(2-712,Pro,I-1,S,S,O,2-Adm,H),(2-713,Pro,I-2,S,S,O,2-Adm,H),(2-714,Pro,I-3,S,S,O,2-Adm,H),(2-715,Pro,I-4,S,S,O,2-Adm,H),(2-716,Pro,I-5,S,S,O,2-Adm,H),(2-717,Pro,I-6,S,S,O,2-Adm,H),(2-718,Pro,I-7,S,S,O,2-Adm,H),(2-719,Pro,I-8,S,S,O,2-Adm,H),(2-720,Pro,I-9,S,S,O,2-Adm,H),(2-721,Pro,I-1,S,S,O,5-OH-2-Adm,H),(2-722,Pro,I-2,S,S,O,5-OH-2-Adm,H),(2-723,Pro,I-3,S,S,O,5-OH-2-Adm,H),(2-724,Pro,I-4,S,S,O,5-OH-2-Adm,H),(2-725,Pro,I-5,S,S,O,5-OH-2-Adm,H),(2-726,Pro,I-6,S,S,O,5-OH-2-Adm,H),(2-727,Pro,I-7,S,S,O,5-OH-2-Adm,H),(2-728,Pro,I-8,S,S,O,5-OH-2-Adm,H),(2-729,Pro,I-9,S,S,O,5-OH-2-Adm,H),(2-730,Pro,J-1,S,S,O,1-Adm,H),(2-731,Pro,J-2,S,S,O,1-Adm,H),(2-732,Pro,J-3,S,S,O,1-Adm,H),(2-733,Pro,J-4,S,S,O,1-Adm,H),(2-734,Pro,J-5,S,S,O,1-Adm,H),(2-735,Pro,J-6,S,S,O,1-Adm,H),(2-736,Pro,J-7,S,S,O,1-Adm,H),(2-737,Pro,J-8,S,S,O,1-Adm,H),(2-738,Pro,J-9,S,S,O,1-Adm,H),(2-739,Pro,J-1,S,S,O,2-Adm,H),(2-740,Pro,J-2,S,S,O,2-Adm,H),(2-741,Pro,J-3,S,S,O,2-Adm,H),(2-742,Pro,J-4,S,S,O,2-Adm,H),(2-743,Pro,J-5,S,S,O,2-Adm,H),(2-744,Pro,J-6,S,S,O,2-Adm,H),(2-745,Pro,J-7,S,S,O,2-Adm,H),(2-746,Pro,J-8,S,S,O,2-Adm,H),(2-747,Pro,J-9,S,S,O,2-Adm,H),(2-748,Pro,J-1,S,S,O,5-OH-2-Adm,H),(2-749,Pro,J-2,S,S,O,5-OH-2-Adm,H),(2-750,Pro,J-3,S,S,O,5-OH-2-Adm,H),(2-751,Pro,J-4,S,S,O,5-OH-2-Adm,H),(2-752,Pro,J-5,S,S,O,5-OH-2-Adm,H),(2-753,Pro,J-6,S,S,O,5-OH-2-Adm,H),(2-754,Pro,J-7,S,S,O,5-OH-2-Adm,H),(2-755,Pro,J-8,S,S,O,5-OH-2-Adm,H),(2-756,Pro,J-9,S,S,O,5-OH-2-Adm,H),(2-757,Pro,K-1,S,S,O,1-Adm,H),(2-758,Pro,K-2,S,S,O,1-Adm,H),(2-759,Pro,K-3,S,S,O,1-Adm,H),(2-760,Pro,K-4,S,S,O,1-Adm,H),(2-761,Pro,K-5,S,S,O,1-Adm,H),(2-762,Pro,K-6,S,S,O,1-Adm,H),(2-763,Pro,K-7,S,S,O,1-Adm,H),(2-764,Pro,K-8,S,S,O,1-Adm,H),(2-765,Pro,K-9,S,S,O,1-Adm,H),(2-766,Pro,K-1,S,S,O,2-Adm,H),(2-767,Pro,K-2,S,S,O,2-Adm,H),(2-768,Pro,K-3,S,S,O,2-Adm,H),(2-769,Pro,K-4,S,S,O,2-Adm,H),(2-770,Pro,K-5,S,S,O,2-Adm,H),(2-771,Pro,K-6,S,S,O,2-Adm,H),(2-772,Pro,K-7,S,S,O,2-Adm,H),(2-773,Pro,K-8,S,S,O,2-Adm,H),(2-774,Pro,K-9,S,S,O,2-Adm,H),(2-775,Pro,K-1,S,S,O,5-OH-2-Adm,H),(2-776,Pro,K-2,S,S,O,5-OH-2-Adm,H),(2-777,Pro,K-3,S,S,O,5-OH-2-Adm,H),(2-778,Pro,K-4,S,S,O,5-OH-2-Adm,H),(2-779,Pro,K-5,S,S,O,5-OH-2-Adm,H),(2-780,Pro,K-6,S,S,O,5-OH-2-Adm,H),(2-781,Pro,K-7,S,S,O,5-OH-2-Adm,H),(2-782,Pro,K-8,S,S,O,5-OH-2-Adm,H),(2-783,Pro,K-9,S,S,O,5-OH-2-Adm,H)

(Compound No., $R^2,R^3,X,Y,Z,R^4,R^5$)=(3-1,i-Pro,A-1,S,S,O,1-Adm,H),(3-2,i-Pro,A-2,S,S,O,1-Adm,H),(3-3,i-Pro,A-3,S,S,O,1-Adm,H),(3-4,i-Pro,A-4,S,S,O,1-Adm,H),(3-5,i-Pro,A-5,S,S,O,1-Adm,H),(3-6,i-Pro,A-6,S,S,O,1-Adm,H),(3-7,i-Pro,A-7,S,S,O,1-Adm,H),(3-8,i-Pro,A-8,S,S,O,1-Adm,H),(3-9,i-Pro,A-9,S,S,O,1-Adm,H),(3-10,i-Pro,A-10,S,S,O,1-Adm,H),(3-11,i-Pro,A-11,S,S,O,1-Adm,H),(3-12,i-Pro,A-12,S,S,O,1-Adm,H),(3-13,i-Pro,A-13,S,S,O,1-Adm,H),(3-14,i-Pro,A-14,S,S,O,1-Adm,H),(3-15,i-Pro,A-15,S,S,O,1-Adm,H),(3-16,i-Pro,A-16,S,S,O,1-Adm,H),(3-17,i-Pro,A-17,S,S,O,1-Adm,H),(3-18,i-Pro,A-18,S,S,O,1-Adm,H),(3-19,i-Pro,A-19,S,S,O,1-Adm,H),(3-20,i-Pro,A-20,S,S,O,1-Adm,H),(3-21,i-Pro,A-21,S,S,O,1-Adm,H),(3-22,i-Pro,A-22,S,S,O,1-Adm,H),(3-23,i-Pro,A-23,S,S,O,1-Adm,H),(3-24,i-Pro,A-24,S,S,O,1-Adm,H),(3-25,i-Pro,A-25,S,S,O,1-Adm,H),(3-26,i-Pro,A-26,S,S,O,1-Adm,H),(3-27,i-Pro,A-27,S,S,O,1-Adm,H),(3-28,i-Pro,A-28,S,S,O,1-Adm,H),(3-29,i-Pro,A-29,S,S,O,1-Adm,H),(3-30,i-Pro,A-30,S,S,O,1-Adm,H),(3-31,i-Pro,A-31,S,S,O,1-Adm,H),(3-32,i-Pro,A-32,S,S,O,1-Adm,H),(3-33,i-Pro,A-33,S,S,O,1-Adm,H),(3-34,i-Pro,A-34,S,S,O,1-Adm,H),(3-35,i-Pro,A-35,S,S,O,1-Adm,H),(3-36,i-Pro,A-36,S,S,O,1-Adm,H),(3-37,i-Pro,A-1,S,S,O,2-Adm,H),(3-38,i-Pro,A-2,S,S,O,2-Adm,H),(3-39,i-Pro,A-3,S,S,O,2-Adm,H), (3-40,i-Pro,A-4,S,S,O,2-

Adm,H),(3-41,i-Pro,A-5,S,S,O,2-Adm,H),(3-42,i-Pro,A-6, S,S,O,2-Adm,H),(3-43,i-Pro,A-7,S,S,O,2-Adm,H),(3-44,i-Pro,A-8,S,S,O,2-Adm,H),(3-45,i-Pro,A-9,S,S,O,2-Adm,H), (3-46,i-Pro,A-110,S,S,O,2-Adm,H),(3-47,i-Pro,A-111,S,S, O,2-Adm,H),(3-48,i-Pro,A-12,S,S,O,2-Adm,H),(3-49,i-Pro, A-13,S,S,O,2-Adm,H),(3-50,i-Pro,A-14,S,S,O,2-Adm,H), (3-51,i-Pro,A-15,S,S,O,2-Adm,H),(3-52,i-Pro,A-16,S,S,O, 2-Adm,H),(3-53,i-Pro,A-17,S,S,O,2-Adm,H),(3-54,i-Pro, A-18,S,S,O,2-Adm,H),(3-55,i-Pro,A-119,S,S,O,2-Adm,H), (3-56,i-Pro,A-20,S,S,O,2-Adm,H),(3-57,i-Pro,A-21,S,S,O, 2-Adm,H),(3-58,i-Pro,A-22,S,S,O,2-Adm,H),(3-59,i-Pro, A-23,S,S,O,2-Adm,H),(3-60,i-Pro,A-24,S,S,O,2-Adm,H), (3-61,i-Pro,A-25,S,S,O,2-Adm,H),(3-62,i-Pro,A-26,S,S,O, 2-Adm,H),(3-63,i-Pro,A-27,S,S,O,2-Adm,H),(3-64,i-Pro, A-28,S,S,O,2-Adm,H),(3-65,i-Pro,A-29,S,S,O,2-Adm,H), (3-66,i-Pro,A-30,S,S,O,2-Adm,H),(3-67,i-Pro,A-31,S,S,O, 2-Adm,H),(3-68,i-Pro,A-32,S,S,O,2-Adm,H),(3-69,i-Pro, A-33,S,S,O,2-Adm,H),(3-70,i-Pro,A-34,S,S,O,2-Adm,H), (3-71,i-Pro,A-35,S,S,O,2-Adm,H),(3-72,i-Pro,A-36,S,S,O, 2-Adm,H),(3-73,i-Pro,A-1,S,S,O,5-OH-2-Adm,H),(3-74,i-Pro,A-2,S,S,O,5-OH-2-Adm,H),(3-75,i-Pro,A-3,S,S,O,5-OH-2-Adm,H),(3-76,i-Pro,A-4,S,S,O,5-OH-2-Adm,H),(3-77,i-Pro,A-5,S,S,O,5-OH-2-Adm,H),(3-78,i-Pro,A-6,S,S,O, 5-OH-2-Adm,H),(3-79,i-Pro,A-7,S,S,O,5-OH-2-Adm,H), (3-80,i-Pro,A-8,S,S,O,5-OH-2-Adm,H),(3-81,i-Pro,A-9,S, S,O,5-OH-2-Adm,H),(3-82,i-Pro,A-11,S,S,O,5-OH-2-Adm,H),(3-83,i-Pro,A-11,S,S,O,5-OH-2-Adm,H),(3-84,i-Pro,A-12,S,S,O,5-OH-2-Adm,H),(3-85,i-Pro,A-13,S,S,O,5-OH-2-Adm,H),(3-86,i-Pro,A-14,S,S,O,5-OH-2-Adm,H),(3-87,i-Pro,A-15,S,S,O,5-OH-2-Adm,H),(3-88,i-Pro,A-16,S,S, O,5-OH-2-Adm,H),(3-89,i-Pro,A-17,S,S,O,5-OH-2-Adm, H),(3-90,i-Pro,A-18,S,S,O,5-OH-2-Adm,H),(3-91,i-Pro,A-19,S,S,O,5-OH-2-Adm,H),(3-92,i-Pro,A-20,S,S,O,5-OH-2-Adm,H),(3-93,i-Pro,A-21,S,S,O,5-OH-2-Adm,H),(3-94,i-Pro,A-22,S,S,O,5-OH-2-Adm,H),(3-95,i-Pro,A-23,S,S,O,5-OH-2-Adm,H),(3-96,i-Pro,A-24,S,S,O,5-OH-2-Adm,H),(3-97,i-Pro,A-25,S,S,O,5-OH-2-Adm,H),(3-98,i-Pro,A-26,S,S, O,5-OH-2-Adm,H),(3-99,i-Pro,A-27,S,S,O,5-OH-2-Adm, H),(3-110,i-Pro,A-28,S,S,O,5-OH-2-Adm,H),(3-101,i-Pro, A-29,S,S,O,5-OH-2-Adm,H),(3-102,i-Pro,A-30,S,S,O,5-OH-2-Adm,H),(3-103,i-Pro,A-31,S,S,O,5-OH-2-Adm,H), (3-104,i-Pro,A-32,S,S,O,5-OH-2-Adm,H),(3-105,i-Pro,A-33,S,S,O,5-OH-2-Adm,H),(3-106,i-Pro,A-34,S,S,O,5-OH-2-Adm,H),(3-107,i-Pro,A-35,S,S,O,5-OH-2-Adm,H),(3-108,i-Pro,A-36,S,S,O,5-OH-2-Adm,H),(3-119,i-Pro,B-1,S, S,O,1-Adm,H),(3-111,i-Pro,B-2,S,S,O,1-Adm,H),(3-11,i-Pro,B-3,S,S,O,1-Adm,H),(3-112,i-Pro,B-4,S,S,O,1-Adm, H),(3-113,i-Pro,B-5,S,S,O,1-Adm,H),(3-114,i-Pro,B-6,S,S, O,1-Adm,H),(3-115,i-Pro,B-7,S,S,O,1-Adm,H),(3-116,i-Pro,B-8,S,S,O,1-Adm,H),(3-117,i-Pro,B-9,S,S,O,1-Adm, H),(3-118,i-Pro,B-10,S,S,O,1-Adm,H),(3-119,i-Pro,B-11,S, S,O,1-Adm,H),(3-120,i-Pro,B-12,S,S,O,1-Adm,H),(3-121, i-Pro,B-13,S,S,O,1-Adm,H),(3-122,i-Pro,B-14,S,S,O,1-Adm,H),(3-123,i-Pro,B-15,S,S,O,1-Adm,H),(3-124,i-Pro, B-16,S,S,O,1-Adm,H),(3-125,i-Pro,B-17,S,S,O,1-Adm,H), (3-126,i-Pro,B-18,S,S,O,1-Adm,H),(3-127,i-Pro,B-119,S,S, O,1-Adm,H),(3-128,i-Pro,B-20,S,S,O,1-Adm,H),(3-129,i-Pro,B-21,S,S,O,1-Adm,H),(3-130,i-Pro,B-22,S,S,O,1-Adm, H),(3-131,i-Pro,B-23,S,S,O,1-Adm,H),(3-132,i-Pro,B-24,S, S,O,1-Adm,H),(3-133,i-Pro,B-25,S,S,O,1-Adm,H),(3-134, i-Pro,B-26,S,S,O,1-Adm,H),(3-135,i-Pro,B-27,S,S,O,1-Adm,H),(3-136,i-Pro,B-28,S,S,O,1-Adm,H),(3-137,i-Pro, B-29,S,S,O,1-Adm,H),(3-138,i-Pro,B-30,S,S,O,1-Adm,H), (3-139,i-Pro,B-31,S,S,O,1-Adm,H),(3-140,i-Pro,B-32,S,S, O,1-Adm,H),(3-141,i-Pro,B-33,S,S,O,1-Adm,H),(3-142,i-Pro,B-34,S,S,O,1-Adm,H),(3-143,i-Pro,B-35,S,S,O,11-Adm,H),(3-144,i-Pro,B-36,S,S,O,1-Adm,H),(3-145,i-Pro, B-1,S,S,O,2-Adm,H), (3-146,i-Pro,B-2,S,S,O,2-Adm,H),(3-147,i-Pro,B-3,S,S,O,2-Adm,H),(3-148,i-Pro,B-4,S,S,O,2-Adm,H),(3-149,i-Pro,B-5,S,S,O,2-Adm,H),(3-150,i-Pro,B-6,S,S,O,2-Adm,H),(3-151,i-Pro,B-7,S,S,O,2-Adm,H),(3-152,i-Pro,B-8,S,S,O,2-Adm,H),(3-153,i-Pro,B-9,S,S,O,2-Adm,H),(3-154,i-Pro,B-110,S,S,O,2-Adm,H),(3-155,i-Pro, B-111,S,S,O,2-Adm,H),(3-156,i-Pro,B-12,S,S,O,2-Adm, H),(3-157,i-Pro,B-13,S,S,O,2-Adm,H),(3-158,i-Pro,B-14,S, S,O,2-Adm,H),(3-159,i-Pro,B-15,S,S,O,2-Adm,H),(3-160, i-Pro,B-16,S,S,O,2-Adm,H),(3-161,i-Pro,B-17,S,S,O,2-Adm,H),(3-162,i-Pro,B-18,S,S,O,2-Adm,H),(3-163,i-Pro, B-119,S,S,O,2-Adm,H),(3-164,i-Pro,B-20,S,S,O,2-Adm, H),(3-165,i-Pro,B-21,S,S,O,2-Adm,H),(3-166,i-Pro,B-22,S, S,O,2-Adm,H),(3-167,i-Pro,B-23,S,S,O,2-Adm,H),(3-168, i-Pro,B-24,S,S,O,2-Adm,H),(3-169,i-Pro,B-25,S,S,O,2-Adm,H),(3-170,i-Pro,B-26,S,S,O,2-Adm,H),(3-171,i-Pro, B-27,S,S,O,2-Adm,H),(3-172,i-Pro,B-28,S,S,O,2-Adm,H), (3-173,i-Pro,B-29,S,S,O,2-Adm,H),(3-174,i-Pro,B-30,S,S, O,2-Adm,H),(3-175,i-Pro,B-31,S,S,O,2-Adm,H),(3-176,i-Pro,B-32,S,S,O,2-Adm,H),(3-177,i-Pro,B-33,S,S,O,2-Adm, H),(3-178,i-Pro,B-34,S,S,O,2-Adm,H),(3-179,i-Pro,B-35,S, S,O,2-Adm,H),(3-180,i-Pro,B-36,S,S,O,2-Adm,H),(3-181, i-Pro,B-1,S,S,O,5-OH-2-Adm,H),(3-182,i-Pro,B-2,S,S,O,5-OH-2-Adm,H),(3-183,i-Pro,B-3,S,S,O,5-OH-2-Adm,H),(3-184,i-Pro,B-4,S,S,O,5-OH-2-Adm,H),(3-185,i-Pro,B-5,S,S, O,5-OH-2-Adm,H),(3-186,i-Pro,B-6,S,S,O,5-OH-2-Adm, H),(3-187,i-Pro,B-7,S,S,O,5-OH-2-Adm,H),(3-188,i-Pro,B-8,S,S,O,5-OH-2-Adm,H),(3-189,i-Pro,B-9,S,S,O,5-OH-2-Adm,H),(3-190,i-Pro,B-10,S,S,O,5-OH-2-Adm,H),(3-191, i-Pro,B-11,S,S,O,5-OH-2-Adm,H),(3-192,i-Pro,B-12,S,S, O,5-OH-2-Adm,H),(3-193,i-Pro,B-13,S,S,O,5-OH-2-Adm, H),(3-194,i-Pro,B-14,S,S,O,5-OH-2-Adm,H),(3-195,i-Pro, B-15,S,S,O,5-OH-2-Adm,H),(3-196,i-Pro,B-16,S,S,O,5-OH-2-Adm,H),(3-197,i-Pro,B-17,S,S,O,5-OH-2-Adm,H), (3-198,i-Pro,B-18,S,S,O,5-OH-2-Adm,H),(3-199,i-Pro,B-19,S,S,O,5-OH-2-Adm,H),(3-200,i-Pro,B-20,S,S,O,5-OH-2-Adm,H),(3-201,i-Pro,B-21,S,S,O,5-OH-2-Adm,H),(3-202,i-Pro,B-22,S,S,O,5-OH-2-Adm,H),(3-203,i-Pro,B-23, S,S,O,5-OH-2-Adm,H),(3-204,i-Pro,B-24,S,S,O,5-OH-2-Adm,H),(3-205,i-Pro,B-25,S,S,O,5-OH-2-Adm,H),(3-206, i-Pro,B-26,S,S,O,5-OH-2-Adm,H),(3-207,i-Pro,B-27,S,S, O,5-OH-2-Adm,H),(3-208,i-Pro,B-28,S,S,O,5-OH-2-Adm, H),(3-209,i-Pro,B-29,S,S,O,5-OH-2-Adm,H),(3-210,i-Pro, B-30,S,S,O,5-OH-2-Adm,H),(3-211,i-Pro,B-31,S,S,O,5-OH-2-Adm,H),(3-212,i-Pro,B-32,S,S,O,5-OH-2-Adm,H), (3-213,i-Pro,B-33,S,S,O,5-OH-2-Adm,H),(3-214,i-Pro,B-34,S,S,O,5-OH-2-Adm,H),(3-215,i-Pro,B-35,S,S,O,5-OH-2-Adm,H),(3-216,i-Pro,B-36,S,S,O,5-OH-2-Adm,H),(3-217,i-Pro,C-1,S,S,O,1-Adm,H),(3-218,i-Pro,C-2,S,S,O,1-Adm,H),(3-219,i-Pro,C-3,S,S,O,1-Adm,H),(3-220,i-Pro,C-4,S,S,O,1-Adm,H),(3-221,i-Pro,C-5,S,S,O,1-Adm,H),(3-222,i-Pro,C-6,S,S,O,1-Adm,H),(3-223,i-Pro,C-7,S,S,O,1-Adm,H),(3-224,i-Pro,C-8,S,S,O,1-Adm,H),(3-225,i-Pro,C-9,S,S,O,1-Adm,H),(3-226,i-Pro,C-11,S,S,O,1-Adm,H),(3-227,i-Pro,C-11,S,S,O,1-Adm,H),(3-228,i-Pro,C-12,S,S,O, 1-Adm,H),(3-229,i-Pro,C-13,S,S,O,1-Adm,H),(3-230,i-Pro, C-14,S,S,O,1-Adm,H),(3-231,i-Pro,C-15,S,S,O,1-Adm,H), (3-232,i-Pro,C-16,S,S,O,1-Adm,H),(3-233,i-Pro,C-17,S,S, O,1-Adm,H),(3-234,i-Pro,C-18,S,S,O,1-Adm,H),(3-235,i-Pro,C-19,S,S,O,1-Adm,H),(3-236,i-Pro,C-20,S,S,O,1-Adm, H),(3-237,i-Pro,C-21,S,S,O,1-Adm,H),(3-238,i-Pro,C-22,S, S,O,1-Adm,H),(3-239,i-Pro,C-23,S,S,O,1-Adm,H),(3-240, i-Pro,C-24,S,S,O,1-Adm,H),(3-241,i-Pro,C-2,S,S,O,1-Adm,H),(3-242,i-Pro,C-26,S,S,O,1-Adm,H),(3-243,i-Pro, C-27,S,S,O,1-Adm,H),(3-244,i-Pro,C-28,S,S,O,1-Adm,H), (3-245,i-Pro,C-29,S,S,O,1-Adm,H),(3-246,i-Pro,C-30,S,S, O,1-Adm,H),(3-247,i-Pro, C-31,S,S,O,1-Adm,H),(3-248,i-

Pro,C-32,S,S,O,1-Adm,H),(3-249,i-Pro,C-33,S,S,O,1-Adm, H),(3-250,i-Pro,C-34,S,S,O,1-Adm,H),(3-251,i-Pro,C-35,S, S,O,1-Adm,H),(3-252,i-Pro,C-36,S,S,O,1-Adm,H),(3-253, i-Pro,C-1,S,S,O,2-Adm,H),(3-254,i-Pro,C-2,S,S,O,2-Adm, H),(3-255,i-Pro,C-3,S,S,O,2-Adm,H),(3-256,i-Pro,C-4,S,S, O,2-Adm,H),(3-257,i-Pro,C-5,S,S,O,2-Adm,H),(3-258,i-Pro,C-6,S,S,O,2-Adm,H),(3-259,i-Pro,C-7,S,S,O,2-Adm, H),(3-260,i-Pro,C-8,S,S,O,2-Adm,H),(3-261,i-Pro,C-9,S,S, O,2-Adm,H),(3-262,i-Pro,C-11,S,S,O,2-Adm,H),(3-263,i-Pro,C-11,S,S,O,2-Adm,H),(3-264,i-Pro,C-12,S,S,O,2-Adm, H),(3-265,i-Pro,C-13,S,S,O,2-Adm,H),(3-266,i-Pro,C-14,S, S,O,2-Adm,H),(3-267,i-Pro,C-15,S,S,O,2-Adm,H),(3-268, i-Pro,C-16,S,S,O,2-Adm,H),(3-269,i-Pro,C-17,S,S,O,2-Adm,H),(3-270,i-Pro,C-18,S,S,O,2-Adm,H),(3-271,i-Pro, C-19,S,S,O,2-Adm,H),(3-272,i-Pro,C-20,S,S,O,2-Adm,H), (3-273,i-Pro,C-21,S,S,O,2-Adm,H),(3-274,i-Pro,C-22,S,S, O,2-Adm,H),(3-275,i-Pro,C-23,S,S,O,2-Adm,H),(3-276,i-Pro,C-24,S,S,O,2-Adm,H),(3-277,i-Pro,C-25,S,S,O,2-Adm, H),(3-278,i-Pro,C-26,S,S,O,2-Adm,H),(3-279,i-Pro,C-27,S, S,O,2-Adm,H),(3-280,i-Pro,C-28,S,S,O,2-Adm,H),(3-281, i-Pro,C-29,S,S,O,2-Adm,H),(3-282,i-Pro,C-30,S,S,O,2-Adm,H),(3-283,i-Pro,C-31,S,S,O,2-Adm,H),(3-284,i-Pro, C-32,S,S,O,2-Adm,H),(3-285,i-Pro,C-33,S,S,O,2-Adm,H), (3-286,i-Pro,C-34,S,S,O,2-Adm,H),(3-287,i-Pro,C-35,S, O,2-Adm,H),(3-288,i-Pro,C-36,S,S,O,2-Adm,H),(3-289,i-Pro,C-1,S,S,O,5-OH-2-Adm,H),(3-290,i-Pro,C-2,S,S,O,5-OH-2-Adm,H),(3-291,i-Pro,C-3,S,S,O,5-OH-2-Adm,H),(3-292,i-Pro,C-4,S,S,O,5-OH-2-Adm,H),(3-293,i-Pro,C-5,S,S, O,5-OH-2-Adm,H),(3-294,i-Pro,C-6,S,S,O,5-OH-2-Adm, H),(3-295,i-Pro,C-7,S,S,O,5-OH-2-Adm,H),(3-296,i-Pro,C-8,S,S,O,5-OH-2-Adm,H),(3-297,i-Pro,C-9,S,S,O,5-OH-2-Adm,H),(3-298,i-Pro,C-10,S,S,O,5-OH-2-Adm,H),(3-299, i-Pro,C-11,S,S,O,5-OH-2-Adm,H),(3-300,i-Pro,C-12,S,S, O,5-OH-2-Adm,H),(3-301,i-Pro,C-13,S,S,O,5-OH-2-Adm, H),(3-302,i-Pro,C-14,S,S,O,5-OH-2-Adm,H),(3-303,i-Pro, C-15,S,S,O,5-OH-2-Adm,H),(3-304,i-Pro,C-16,S,S,O,5-OH-2-Adm,H),(3-305,i-Pro,C-17,S,S,O,5-OH-2-Adm,H), (3-306,i-Pro,C-18,S,S,O,5-OH-2-Adm,H),(3-307,i-Pro,C-19,S,S,O,5-OH-2-Adm,H),(3-308,i-Pro,C-20,S,S,O,5-OH-2-Adm,H),(3-309,i-Pro,C-21,S,S,O,5-OH-2-Adm,H),(3-310,i-Pro,C-22,S,S,O,5-OH-2-Adm,H),(3-311,i-Pro,C-23, S,S,O,5-OH-2-Adm,H),(3-312,i-Pro,C-24,S,S,O,5-OH-2-Adm,H),(3-313,i-Pro,C-25,S,S,O,5-OH-2-Adm,H),(3-314, i-Pro,C-26,S,S,O,5-OH-2-Adm,H),(3-315,i-Pro,C-27,S,S, O,5-OH-2-Adm,H),(3-316,i-Pro,C-28,S,S,O,5-OH-2-Adm, H),(3-317,i-Pro,C-29,S,S,O,5-OH-2-Adm,H),(3-318,i-Pro, C-30,S,S,O,5-OH-2-Adm,H),(3-319,i-Pro,C-31,S,S,O,5-OH-2-Adm,H),(3-320,i-Pro,C-32,S,S,O,5-OH-2-Adm,H), (3-321,i-Pro,C-33,S,S,O,5-OH-2-Adm,H),(3-322,i-Pro,C-34,S,S,O,5-OH-2-Adm,H),(3-323,i-Pro,C-35,S,S,O,5-OH-2-Adm,H),(3-324,i-Pro,C-36,S,S,O,5-OH-2-Adm,H),(3-325,i-Pro,D-1,S,S,O,1-Adm,H),(3-326,i-Pro,D-2,S,S,O,1-Adm,H),(3-327,i-Pro,D-3,S,S,O,1-Adm,H),(3-328,i-Pro,D-4,S,S,O,1-Adm,H),(3-329,i-Pro,D-5,S,S,O,1-Adm,H),(3-330,i-Pro,D-6,S,S,O,1-Adm,H),(3-331,i-Pro,D-7,S,S,O,1-Adm,H),(3-332,i-Pro,D-8,S,S,O,1-Adm,H),(3-333,i-Pro,D-9,S,S,O,1-Adm,H),(3-334,i-Pro,D-11,S,S,O,1-Adm,H),(3-335,i-Pro,D-11,S,S,O,1-Adm,H),(3-336,i-Pro,D-12,S,S,O, 1-Adm,H),(3-337,i-Pro,D-13,S,S,O,1-Adm,H),(3-338,i-Pro, D-14,S,S,O,1-Adm,H),(3-339,i-Pro,D-15,S,S,O,1-Adm,H), (3-340,i-Pro,D-16,S,S,O,1-Adm,H),(3-341,i-Pro,D-17,S,S, O,1-Adm,H),(3-342,i-Pro,D-18,S,S,O,1-Adm,H),(3-343,i-Pro,D-19,S,S,O,1-Adm,H),(3-344,i-Pro,D-20,S,S,O,1-Adm,H),(3-345,i-Pro,D-21,S,S,O,1-Adm,H),(3-346,i-Pro, D-22,S,S,O,1-Adm,H),(3-347,i-Pro,D-23,S,S,O,1-Adm,H), (3-348,i-Pro,D-24,S,S,O,1-Adm,H),(3-349,i-Pro,D-25,S,S, O,1-Adm,H),(3-350,i-Pro,D- 26,S,S,O,1-Adm,H),(3-351,i-Pro,D-27,S,S,O,1-Adm,H),(3-352,i-Pro,D-28,S,S,O,1-Adm,H),(3-353,i-Pro,D-29,S,S,O,1-Adm,H),(3-354,i-Pro, D-30,S,S,O,1-Adm,H),(3-355,i-Pro,D-31,S,S,O,1-Adm,H), (3-356,i-Pro,D-32,S,S,O,1-Adm,H),(3-357,i-Pro,D-33,S,S, O,1-Adm,H),(3-358,i-Pro,D-34,S,S,O,1-Adm,H),(3-359,i-Pro,D-35,S,S,O,1-Adm,H),(3-360,i-Pro,D-36,S,S,O,1-Adm,H),(3-361,i-Pro,D-1,S,S,O,2-Adm,H),(3-362,i-Pro,D-2,S,S,O,2-Adm,H),(3-363,i-Pro,D-3,S,S,O,2-Adm,H),(3-364,i-Pro,D-4,S,S,O,2-Adm,H),(3-365,i-Pro,D-5,S,S,O,2-Adm,H),(3-366,i-Pro,D-6,S,S,O,2-Adm,H),(3-367,i-Pro,D-7,S,S,O,2-Adm,H),(3-368,i-Pro,D-8,S,S,O,2-Adm,H),(3-369,i-Pro,D-9,S,S,O,2-Adm,H),(3-370,i-Pro,D-01,S,S,O,2-Adm,H),(3-371,i-Pro,D-11,S,S,O,2-Adm,H),(3-372,i-Pro, D-12,S,S,O,2-Adm,H),(3-373,i-Pro,D-13,S,S,O,2-Adm,H), (3-374,i-Pro,D-14,S,S,O,2-Adm,H),(3-375,i-Pro,D-11,S,S, O,2-Adm,H),(3-376,i-Pro,D-16,S,S,O,2-Adm,H),(3-377,i-Pro,D-17,S,S,O,2-Adm,H),(3-378,i-Pro,D-18,S,S,O,2-Adm,H),(3-379,i-Pro,D-19,S,S,O,2-Adm,H),(3-380,i-Pro, D-20,S,S,O,2-Adm,H),(3-381,i-Pro,D-21,S,S,O,2-Adm,H), (3-382,i-Pro,D-22,S,S,O,2-Adm,H),(3-383,i-Pro,D-23,S,S, O,2-Adm,H),(3-384,i-Pro,D-24,S,S,O,2-Adm,H),(3-385,i-Pro,D-25,S,S,O,2-Adm,H),(3-386,i-Pro,D-26,S,S,O,2-Adm,H),(3-387,i-Pro,D-27,S,S,O,2-Adm,H),(3-388,i-Pro, D-28,S,S,O,2-Adm,H),(3-389,i-Pro,D-29,S,S,O,2-Adm,H), (3-390,i-Pro,D-30,S,S,O,2-Adm,H),(3-391,i-Pro,D-31,S,S, O,2-Adm,H),(3-392,i-Pro,D-32,S,S,O,2-Adm,H),(3-393,i-Pro,D-33,S,S,O,2-Adm,H),(3-394,i-Pro,D-34,S,S,O,2-Adm,H),(3-395,i-Pro,D-35,S,S,O,2-Adm,H),(3-396,i-Pro, D-36,S,S,O,2-Adm,H),(3-397,i-Pro,D-1,S,S,O,5-OH-2-Adm,H),(3-398,i-Pro,D-2,S,S,O,5-OH-2-Adm,H),(3-399,i-Pro,D-3,S,S,O,5-OH-2-Adm,H),(3-400,i-Pro,D-4,S,S,O,5-OH-2-Adm,H),(3-401,i-Pro,D-5,S,S,O,5-OH-2-Adm,H),(3-402,i-Pro,D-6,S,S,O,5-OH-2-Adm,H),(3-403,i-Pro,D-7,S,S, O,5-OH-2-Adm,H),(3-404,i-Pro,D-8,S,S,O,5-OH-2-Adm, H),(3-405,i-Pro,D-9,S,S,O,5-OH-2-Adm,H),(3-406,i-Pro, D-10,S,S,O,5-OH-2-Adm,H),(3-407,i-Pro,D-11,S,S,O,5-OH-2-Adm,H),(3-408,i-Pro,D-12,S,S,O,5-OH-2-Adm,H), (3-409,i-Pro,D-13,S,S,O,5-OH-2-Adm,H),(3-410,i-Pro,D-14,S,S,O,5-OH-2-Adm,H),(3-411,i-Pro,D-15,S,S,O,5-OH-2-Adm,H),(3-412,i-Pro,D-16,S,S,O,5-OH-2-Adm,H),(3-413,i-Pro,D-17,S,S,O,5-OH-2-Adm,H),(3-414,i-Pro,D-18, S,S,O,5-OH-2-Adm,H),(3-415,i-Pro,D-19,S,S,O,5-OH-2-Adm,H),(3-416,i-Pro,D-20,S,S,O,5-OH-2-Adm,H),(3-417, i-Pro,D-21,S,S,O,5-OH-2-Adm,H),(3-418,i-Pro,D-22,S,S, O,5-OH-2-Adm,H),(3-419,i-Pro,D-23,S,S,O,5-OH-2-Adm, H),(3-420,i-Pro,D-24,S,S,O,5-OH-2-Adm,H),(3-421,i-Pro, D-25,S,S,O,5-OH-2-Adm,H),(3-422,i-Pro,D-26,S,S,O,5-OH-2-Adm,H),(3-423,i-Pro,D-27,S,S,O,5-OH-2-Adm,H), (3-424,i-Pro,D-28,S,S,O,5-OH-2-Adm,H),(3-425,i-Pro,D-29,S,S,O,5-OH-2-Adm,H),(3-426,i-Pro,D-30,S,S,O,5-OH-2-Adm,H),(3-427,i-Pro,D-31,S,S,O,5-OH-2-Adm,H),(3-428,i-Pro,D-32,S,S,O,5-OH-2-Adm,H),(3-429,i-Pro,D-33, S,S,O,5-OH-2-Adm,H),(3-430,i-Pro,D-34,S,S,O,5-OH-2-Adm,H),(3-431,i-Pro,D-35,S,S,O,5-OH-2-Adm,H),(3-432, i-Pro,D-36,S,S,O,5-OH-2-Adm,H),(3-433,i-Pro,E-1,S,S,O, 1-Adm,H),(3-434,i-Pro,E-2,S,S,O,1-Adm,H),(3-435,i-Pro, E-3,S,S,O,1-Adm,H),(3-436,i-Pro,E-4,S,S,O,1-Adm,H),(3-437,i-Pro,E-5,S,S,O,1-Adm,H),(3-438,i-Pro,E-6,S,S,O,1-Adm,H),(3-439,i-Pro,E-7,S,S,O,1-Adm,H),(3-440,i-Pro,E-8,S,S,O,1-Adm,H),(3-441,i-Pro,E-9,S,S,O,1-Adm,H),(3-442,i-Pro,E-11,S,S,O,1-Adm,H),(3-443,i-Pro,E-11,S,S,O,1-Adm,H),(3-444,i-Pro,E-12,S,S,O,1-Adm,H),(3-445,i-Pro,E-13,S,S,O,1-Adm,H),(3-446,i-Pro,E-14,S,S,O,1-Adm,H),(3-447,i-Pro,E-15,S,S,O,1-Adm,H),(3-448,i-Pro,E-16,S,S,O,1-Adm,H),(3-449,i-Pro,E-17,S,S,O,1-Adm,H),(3-450,i-Pro,E-18,S,S,O,1-Adm,H),(3-451,i-Pro,E-19,S,S,O,1-Adm,H),(3-452,i-Pro,E-20,S,S,O,1-Adm,H),(3-453,i-Pro,E-21,S,S,O,1-

Adm,H),(3-454,i-Pro,E-22,S,S,O,1-Adm,H),(3-455,i-Pro,E-23,S,S,O,1-Adm,H),(3-456,i-Pro,E-24,S,S,O,1-Adm,H),(3-457,i-Pro,E-25,S,S,O,1-Adm,H),(3-458,i-Pro,E-26,S,S,O,1-Adm,H),(3-459,i-Pro,E-27,S,S,O,1-Adm,H),(3-460,i-Pro,E-28,S,S,O,1-Adm,H),(3-461,i-Pro,E-29,S,S,O,1-Adm,H),(3-462,i-Pro,E-30,S,S,O,1-Adm,H),(3-463,i-Pro,E-31,S,S,O,1-Adm,H),(3-464,i-Pro,E-32,S,S,O,1-Adm,H),(3-465,i-Pro,E-33,S,S,O,1-Adm,H),(3-466,i-Pro,E-34,S,S,O,1-Adm,H),(3-467,i-Pro,E-35,S,S,O,1-Adm,H),(3-468,i-Pro,E-36,S,S,O,1-Adm,H),(3-469,i-Pro,E-1,S,S,O,2-Adm,H),(3-470,i-Pro,E-2,S,S,O,2-Adm,H),(3-471,i-Pro,E-3,S,S,O,2-Adm,H),(3-472,i-Pro,E-4,S,S,O,2-Adm,H),(3-473,i-Pro,E-5,S,S,O,2-Adm,H),(3-474,i-Pro,E-6,S,S,O,2-Adm,H),(3-475,i-Pro,E-7,S,S,O,2-Adm,H),(3-476,i-Pro,E-8,S,S,O,2-Adm,H),(3-477,i-Pro,E-9,S,S,O,2-Adm,H),(3-478,i-Pro,E-11,S,S,O,2-Adm,H),(3-479,i-Pro,E-11,S,S,O,2-Adm,H),(3-480,i-Pro,E-12,S,S,O,2-Adm,H),(3-481,i-Pro,E-13,S,S,O,2-Adm,H),(3-482,i-Pro,E-14,S,S,O,2-Adm,H),(3-483,i-Pro,E-15,S,S,O,2-Adm,H),(3-484,i-Pro,E-16,S,S,O,2-Adm,H),(3-485,i-Pro,E-17,S,S,O,2-Adm,H),(3-486,i-Pro,E-18,S,S,O,2-Adm,H),(3-487,i-Pro,E-19,S,S,O,2-Adm,H),(3-488,i-Pro,E-20,S,S,O,2-Adm,H),(3-489,i-Pro,E-21,S,S,O,2-Adm,H),(3-490,i-Pro,E-22,S,S,O,2-Adm,H),(3-491,i-Pro,E-23,S,S,O,2-Adm,H),(3-492,i-Pro,E-24,S,S,O,2-Adm,H),(3-493,i-Pro,E-25,S,S,O,2-Adm,H),(3-494,i-Pro,E-26,S,S,O,2-Adm,H),(3-495,i-Pro,E-27,S,S,O,2-Adm,H),(3-496,i-Pro,E-28,S,S,O,2-Adm,H),(3-497,i-Pro,E-29,S,S,O,2-Adm,H),(3-498,i-Pro,E-30,S,S,O,2-Adm,H),(3-499,i-Pro,E-31,S,S,O,2-Adm,H),(3-500,i-Pro,E-32,S,S,O,2-Adm,H),(3-501,i-Pro,E-33,S,S,O,2-Adm,H),(3-502,i-Pro,E-34,S,S,O,2-Adm,H),(3-503,i-Pro,E-35,S,S,O,2-Adm,H),(3-504,i-Pro,E-36,S,S,O,2-Adm,H),(3-505,i-Pro,E-1,S,S,O,5-OH-2-Adm,H),(3-506,i-Pro,E-2,S,S,O,5-OH-2-Adm,H),(3-507,i-Pro,E-3,S,S,O,5-OH-2-Adm,H),(3-508,i-Pro,E-4,S,S,O,5-OH-2-Adm,H),(3-509,i-Pro,E-5,S,S,O,5-OH-2-Adm,H),(3-510,i-Pro,E-6,S,S,O,5-OH-2-Adm,H),(3-511,i-Pro,E-7,S,S,O,5-OH-2-Adm,H),(3-512,i-Pro,E-8,S,S,O,5-OH-2-Adm,H),(3-513,i-Pro,E-9,S,S,O,5-OH-2-Adm,H),(3-514,i-Pro,E-10,S,S,O,5-OH-2-Adm,H),(3-515,i-Pro,E-11,S,S,O,5-OH-2-Adm,H),(3-516,i-Pro,E-12,S,S,O,5-OH-2-Adm,H),(3-517,i-Pro,E-13,S,S,O,5-OH-2-Adm,H),(3-518,i-Pro,E-14,S,S,O,5-OH-2-Adm,H),(3-519,i-Pro,E-15,S,S,O,5-OH-2-Adm,H),(3-520,i-Pro,E-16,S,S,O,5-OH-2-Adm,H),(3-521,i-Pro,E-17,S,S,O,5-OH-2-Adm,H),(3-522,i-Pro,E-18,S,S,O,5-OH-2-Adm,H),(3-523,i-Pro,E-119,S,S,O,5-OH-2-Adm,H),(3-524,i-Pro,E-20,S,S,O,5-OH-2-Adm,H),(3-525,i-Pro,E-21,S,S,O,5-OH-2-Adm,H),(3-526,i-Pro,E-22,S,S,O,5-OH-2-Adm,H),(3-527,i-Pro,E-23,S,S,O,5-OH-2-Adm,H),(3-528,i-Pro,E-24,S,S,O,5-OH-2-Adm,H),(3-529,i-Pro,E-25,S,S,O,5-OH-2-Adm,H),(3-530,i-Pro,E-26,S,S,O,5-OH-2-Adm,H),(3-531,i-Pro,E-27,S,S,O,5-OH-2-Adm,H),(3-532,i-Pro,E-28,S,S,O,5-OH-2-Adm,H),(3-533,i-Pro,E-29,S,S,O,5-OH-2-Adm,H),(3-534,i-Pro,E-30,S,S,O,5-OH-2-Adm,H),(3-535,i-Pro,E-31,S,S,O,5-OH-2-Adm,H),(3-536,i-Pro,E-32,S,S,O,5-OH-2-Adm,H),(3-537,i-Pro,E-33,S,S,O,5-OH-2-Adm,H),(3-538,i-Pro,E-34,S,S,O,5-OH-2-Adm,H),(3-539,i-Pro,E-35,S,S,O,5-OH-2-Adm,H),(3-540,i-Pro,E-36,S,S,O,5-OH-2-Adm,H),(3-541,i-Pro,F-1,S,S,O,1-Adm,H),(3-542,i-Pro,F-2,S,S,O,1-Adm,H),(3-543,i-Pro,F-3,S,S,O,1-Adm,H),(3-544,i-Pro,F-4,S,S,O,1-Adm,H),(3-545,i-Pro,F-5,S,S,O,1-Adm,H),(3-546,i-Pro,F-6,S,S,O,1-Adm,H),(3-547,i-Pro,F-7,S,S,O,1-Adm,H),(3-548,i-Pro,F-8,S,S,O,1-Adm,H),(3-549,i-Pro,F-9,S,S,O,1-Adm,H),(3-550,i-Pro,F-11,S,S,O,1-Adm,H),(3-551,i-Pro,F-11,S,S,O,1-Adm,H),(3-552,i-Pro,F-12,S,S,O,1-Adm,H),(3-553,i-Pro,F-13,S,S,O,1-Adm,H),(3-554,i-Pro,F-14,S,S,O,1-Adm,H),(3-555,i-Pro,F-15,S,S,O,1-Adm,H),(3-556,i-Pro,F-16,S,S,O,1-Adm,H),(3-557,i-Pro,F-17,S,S,O,1-Adm,H),(3-558,i-Pro,F-18,S,S,O,1-Adm,H),(3-559,i-Pro,F-19,S,S,O,1-Adm,H),(3-560,i-Pro,F-20,S,S,O,1-Adm,H),(3-561,i-Pro,F-21,S,S,O,1-Adm,H),(3-562,i-Pro,F-22,S,S,O,1-Adm,H),(3-563,i-Pro,F-23,S,S,O,1-Adm,H),(3-564,i-Pro,F-24,S,S,O,1-Adm,H),(3-565,i-Pro,F-25,S,S,O,1-Adm,H),(3-566,i-Pro,F-26,S,S,O,1-Adm,H),(3-567,i-Pro,F-27,S,S,O,1-Adm,H),(3-568,i-Pro,F-28,S,S,O,1-Adm,H),(3-569,i-Pro,F-29,S,S,O,1-Adm,H),(3-570,i-Pro,F-30,S,S,O,1-Adm,H),(3-571,i-Pro,F-31,S,S,O,1-Adm,H),(3-572,i-Pro,F-32,S,S,O,1-Adm,H),(3-573,i-Pro,F-33,S,S,O,1-Adm,H),(3-574,i-Pro,F-34,S,S,O,1-Adm,H),(3-575,i-Pro,F-35,S,S,O,1-Adm,H),(3-576,i-Pro,F-36,S,S,O,1-Adm,H),(3-577,i-Pro,F-1,S,S,O,2-Adm,H),(3-578,i-Pro,F-2,S,S,O,2-Adm,H),(3-579,i-Pro,F-3,S,S,O,2-Adm,H),(3-580,i-Pro,F-4,S,S,O,2-Adm,H),(3-581,i-Pro,F-5,S,S,O,2-Adm,H),(3-582,i-Pro,F-6,S,S,O,2-Adm,H),(3-583,i-Pro,F-7,S,S,O,2-Adm,H),(3-584,i-Pro,F-8,S,S,O,2-Adm,H),(3-585,i-Pro,F-9,S,S,O,2-Adm,H),(3-586,i-Pro,F-10,S,S,O,2-Adm,H),(3-587,i-Pro,F-11,S,S,O,2-Adm,H),(3-588,i-Pro,F-12,S,S,O,2-Adm,H),(3-589,i-Pro,F-13,S,S,O,2-Adm,H),(3-590,i-Pro,F-14,S,S,O,2-Adm,H),(3-591,i-Pro,F-15,S,S,O,2-Adm,H),(3-592,i-Pro,F-16,S,S,O,2-Adm,H),(3-593,i-Pro,F-17,S,S,O,2-Adm,H),(3-594,i-Pro,F-18,S,S,O,2-Adm,H),(3-595,i-Pro,F-19,S,S,O,2-Adm,H),(3-596,i-Pro,F-20,S,S,O,2-Adm,H),(3-597,i-Pro,F-21,S,S,O,2-Adm,H),(3-598,i-Pro,F-22,S,S,O,2-Adm,H),(3-599,i-Pro,F-23,S,S,O,2-Adm,H),(3-600,i-Pro,F-24,S,S,O,2-Adm,H),(3-601,i-Pro,F-25,S,S,O,2-Adm,H),(3-602,i-Pro,F-26,S,S,O,2-Adm,H),(3-603,i-Pro,F-27,S,S,O,2-Adm,H),(3-604,i-Pro,F-28,S,S,O,2-Adm,H),(3-605,i-Pro,F-29,S,S,O,2-Adm,H),(3-606,i-Pro,F-30,S,S,O,2-Adm,H),(3-607,i-Pro,F-31,S,S,O,2-Adm,H),(3-608,i-Pro,F-32,S,S,O,2-Adm,H),(3-609,i-Pro,F-33,S,S,O,2-Adm,H),(3-610,i-Pro,F-34,S,S,O,2-Adm,H),(3-611,i-Pro,F-35,S,S,O,2-Adm,H),(3-612,i-Pro,F-36,S,S,O,2-Adm,H),(3-613,i-Pro,F-1,S,S,O,5-OH-2-Adm,H),(3-614,i-Pro,F-2,S,S,O,5-OH-2-Adm,H),(3-615,i-Pro,F-3,S,S,O,5-OH-2-Adm,H),(3-616,i-Pro,F-4,S,S,O,5-OH-2-Adm,H),(3-617,i-Pro,F-5,S,S,O,5-OH-2-Adm,H),(3-618,i-Pro,F-6,S,S,O,5-OH-2-Adm,H),(3-619,i-Pro,F-7,S,S,O,5-OH-2-Adm,H),(3-620,i-Pro,F-8,S,S,O,5-OH-2-Adm,H),(3-621,i-Pro,F-9,S,S,O,5-OH-2-Adm,H),(3-622,i-Pro,F-10,S,S,O,5-OH-2-Adm,H),(3-623,i-Pro,F-11,S,S,O,5-OH-2-Adm,H),(3-624,i-Pro,F-12,S,S,O,5-OH-2-Adm,H),(3-625,i-Pro,F-13,S,S,O,5-OH-2-Adm,H),(3-626,i-Pro,F-14,S,S,O,5-OH-2-Adm,H),(3-627,i-Pro,F-15,S,S,O,5-OH-2-Adm,H),(3-628,i-Pro,F-16,S,S,O,5-OH-2-Adm,H),(3-629,i-Pro,F-17,S,S,O,5-OH-2-Adm,H),(3-630,i-Pro,F-18,S,S,O,5-OH-2-Adm,H),(3-631,i-Pro,F-19,S,S,O,5-OH-2-Adm,H),(3-632,i-Pro,F-20,S,S,O,5-OH-2-Adm,H),(3-633,i-Pro,F-21,S,S,O,5-OH-2-Adm,H),(3-634,i-Pro,F-22,S,S,O,5-OH-2-Adm,H),(3-635,i-Pro,F-23,S,S,O,5-OH-2-Adm,H),(3-636,i-Pro,F-24,S,S,O,5-OH-2-Adm,H),(3-637,i-Pro,F-25,S,S,O,5-OH-2-Adm,H),(3-638,i-Pro,F-26,S,S,O,5-OH-2-Adm,H),(3-639,i-Pro,F-27,S,S,O,5-OH-2-Adm,H),(3-640,i-Pro,F-28,S,S,O,5-OH-2-Adm,H),(3-641,i-Pro,F-29,S,S,O,5-OH-2-Adm,H),(3-642,i-Pro,F-30,S,S,O,5-OH-2-Adm,H),(3-643,i-Pro,F-31,S,S,O,5-OH-2-Adm,H),(3-644,i-Pro,F-32,S,S,O,5-OH-2-Adm,H),(3-645,i-Pro,F-33,S,S,O,5-OH-2-Adm,H),(3-646,i-Pro,F-34,S,S,O,5-OH-2-Adm,H),(3-647,i-Pro,F-35,S,S,O,5-OH-2-Adm,H),(3-648,i-Pro,F-36,S,S,O,5-OH-2-Adm,H),(3-649,i-Pro,G-1,S,S,O,1-Adm,H),(3-650,i-Pro,G-2,S,S,O,1-Adm,H),(3-651,i-Pro,G-3,S,S,O,1-Adm,H),(3-652,i-Pro,G-4,S,S,O,1-Adm,H),(3-653,i-Pro,G-5,S,S,O,1-Adm,H),(3-654,i-Pro,G-6,S,S,O,1-Adm,H),(3-655,i-Pro,G-7,S,S,O,1-Adm,H),(3-656,i-Pro,G-8,S,S,O,1-Adm,H),(3-657,i-Pro,G-9,S,S,O,1-Adm,H),(3-658,i-Pro,G-1,S,S,O,2-Adm,H),(3-659,i-Pro,G-2,S,S,O,2-Adm,H),(3-660,i-Pro,G-3,S,S,O,2-Adm,H),(3-661,i-Pro,G-4,S,S,O,2-Adm,H),(3-662,i-Pro,G-5,S,S,O,2-Adm,H),(3-663,i-Pro,G-6,S,S,O,2-Adm,H),(3-664,i-Pro,G-7,S,S,

O,2-Adm,H),(3-665,i-Pro,G-8,S,S,O,2-Adm,H),(3-666,i-Pro,G-9,S,S,O,2-Adm,H),(3-667,i-Pro,G-1,S,S,O,5-OH-2-Adm,H),(3-668,i-Pro,G-2,S,S,O,5-OH-2-Adm,H),(3-669,i-Pro,G-3,S,S,O,5-OH-2-Adm,H),(3-670,i-Pro,G-4,S,S,O,5-OH-2-Adm,H),(3-671,i-Pro,G-5,S,S,O,5-OH-2-Adm,H),(3-672,i-Pro,G-6,S,S,O,5-OH-2-Adm,H),(3-673,i-Pro,G-7,S,S,O,5-OH-2-Adm,H),(3-674,i-Pro,G-8,S,S,O,5-OH-2-Adm,H),(3-675,i-Pro,G-9,S,S,O,5-OH-2-Adm,H),(3-676,i-Pro,H-1,S,S,O,1-Adm,H),(3-677,i-Pro,H-2,S,S,O,1-Adm,H),(3-678,i-Pro,H-3,S,S,O,1-Adm,H),(3-679,i-Pro,H-4,S,S,O,1-Adm,H),(3-680,i-Pro,H-5,S,S,O,1-Adm,H),(3-681,i-Pro,H-6,S,S,O,1-Adm,H),(3-682,i-Pro,H-7,S,S,O,1-Adm,H),(3-683,i-Pro,H-8,S,S,O,1-Adm,H),(3-684,i-Pro,H-9,S,S,O,1-Adm,H),(3-685,i-Pro,H-1,S,S,O,2-Adm,H),(3-686,i-Pro,H-2,S,S,O,2-Adm,H),(3-687,i-Pro,H-3,S,S,O,2-Adm,H),(3-688,i-Pro,H-4,S,S,O,2-Adm,H),(3-689,i-Pro,H-5,S,S,O,2-Adm,H),(3-690,i-Pro,H-6,S,S,O,2-Adm,H),(3-691,i-Pro,H-7,S,S,O,2-Adm,H),(3-692,i-Pro,H-8,S,S,O,2-Adm,H),(3-693,i-Pro,H-9,S,S,O,2-Adm,H),(3-694,i-Pro,H-1,S,S,O,5-OH-2-Adm,H),(3-695,i-Pro,H-2,S,S,O,5-OH-2-Adm,H),(3-696,i-Pro,H-3,S,S,O,5-OH-2-Adm,H),(3-697,i-Pro,H-4,S,S,O,5-OH-2-Adm,H),(3-698,i-Pro,H-5,S,S,O,5-OH-2-Adm,H),(3-699,i-Pro,H-6,S,S,O,5-OH-2-Adm,H),(3-700,i-Pro,H-7,S,S,O,5-OH-2-Adm,H),(3-701,i-Pro,H-8,S,S,O,5-OH-2-Adm,H),(3-702,i-Pro,H-9,S,S,O,5-OH-2-Adm,H),(3-703,i-Pro,I-1,S,S,O,1-Adm,H),(3-704,i-Pro,I-2,S,S,O,1-Adm,H),(3-705,i-Pro,I-3,S,S,O,1-Adm,H),(3-706,i-Pro,I-4,S,S,O,1-Adm,H),(3-707,i-Pro,I-5,S,S,O,1-Adm,H),(3-708,i-Pro,I-6,S,S,O,1-Adm,H),(3-709,i-Pro,I-7,S,S,O,1-Adm,H),(3-710,i-Pro,I-8,S,S,O,1-Adm,H),(3-711,i-Pro,I-9,S,S,O,1-Adm,H),(3-712,i-Pro,I-1,S,S,O,2-Adm,H),(3-713,i-Pro,I-2,S,S,O,2-Adm,H),(3-714,i-Pro,I-3,S,S,O,2-Adm,H),(3-715,i-Pro,I-4,S,S,O,2-Adm,H),(3-716,i-Pro,I-5,S,S,O,2-Adm,H),(3-717,i-Pro,I-6,S,S,O,2-Adm,H),(3-718,i-Pro,I-7,S,S,O,2-Adm,H),(3-719,i-Pro,I-8,S,S,O,2-Adm,H),(3-720,i-Pro,I-9,S,S,O,2-Adm,H),(3-721,i-Pro,I-1,S,S,O,5-OH-2-Adm,H),(3-722,i-Pro,I-2,S,S,O,5-OH-2-Adm,H),(3-723,i-Pro,I-3,S,S,O,5-OH-2-Adm,H),(3-724,i-Pro,I-4,S,S,O,5-OH-2-Adm,H),(3-725,i-Pro,I-5,S,S,O,5-OH-2-Adm,H),(3-726,i-Pro,I-6,S,S,O,5-OH-2-Adm,H),(3-727,i-Pro,I-7,S,S,O,5-OH-2-Adm,H),(3-728,i-Pro,I-8,S,S,O,5-OH-2-Adm,H),(3-729,i-Pro,I-9,S,S,O,5-OH-2-Adm,H),(3-730,i-Pro,J-1,S,S,O,1-Adm,H),(3-731,i-Pro,J-2,S,S,O,1-Adm,H),(3-732,i-Pro,J-3,S,S,O,1-Adm,H),(3-733,i-Pro,J-4,S,S,O,1-Adm,H),(3-734,i-Pro,J-5,S,S,O,1-Adm,H),(3-735,i-Pro,J-6,S,S,O,1-Adm,H),(3-736,i-Pro,J-7,S,S,O,1-Adm,H),(3-737,i-Pro,J-8,S,S,O,1-Adm,H),(3-738,i-Pro,J-9,S,S,O,1-Adm,H),(3-739,i-Pro,J-1,S,S,O,2-Adm,H),(3-740,i-Pro,J-2,S,S,O,2-Adm,H),(3-741,i-Pro,J-3,S,S,O,2-Adm,H),(3-742,i-Pro,J-4,S,S,O,2-Adm,H),(3-743,i-Pro,J-5,S,S,O,2-Adm,H),(3-744,i-Pro,J-6,S,S,O,2-Adm,H),(3-745,i-Pro,J-7,S,S,O,2-Adm,H),(3-746,i-Pro,J-8,S,S,O,2-Adm,H),(3-747,i-Pro,J-9,S,S,O,2-Adm,H),(3-748,i-Pro,J-1,S,S,O,5-OH-2-Adm,H),(3-749,i-Pro,J-2,S,S,O,5-OH-2-Adm,H),(3-750,i-Pro,J-3,S,S,O,5-OH-2-Adm,H),(3-751,i-Pro,J-4,S,S,O,5-OH-2-Adm,H),(3-752,i-Pro,J-5,S,S,O,5-OH-2-Adm,H),(3-753,i-Pro,J-6,S,S,O,5-OH-2-Adm,H),(3-754,i-Pro,J-7,S,S,O,5-OH-2-Adm,H),(3-755,i-Pro,J-8,S,S,O,5-OH-2-Adm,H),(3-756,i-Pro,J-9,S,S,O,5-OH-2-Adm,H),(3-757,i-Pro,K-1,S,S,O,1-Adm,H),(3-758,i-Pro,K-2,S,S,O,1-Adm,H),(3-759,i-Pro,K-3,S,S,O,1-Adm,H),(3-760,i-Pro,K-4,S,S,O,1-Adm,H),(3-761,i-Pro,K-5,S,S,O,1-Adm,H),(3-762,i-Pro,K-6,S,S,O,1-Adm,H),(3-763,i-Pro,K-7,S,S,O,1-Adm,H),(3-764,i-Pro,K-8,S,S,O,1-Adm,H),(3-765,i-Pro,K-9,S,S,O,1-Adm,H),(3-766,i-Pro,K-1,S,S,O,2-Adm,H),(3-767,i-Pro,K-2,S,S,O,2-Adm,H),(3-768,i-Pro,K-3,S,S,O,2-Adm,H),(3-769,i-Pro,K-4,S,S,O,2-Adm,H),(3-770,i-Pro,K-5,S,S,O,2-Adm,H),(3-771,i-Pro,K-6,S,S,O,2-Adm,H),(3-772,i-Pro,K-7,S,S,O,2-Adm,H),(3-773,i-Pro,K-8,S,S,O,2-Adm,H),(3-774,i-Pro,K-9,S,S,O,2-Adm,H),(3-775,i-Pro,K-1,S,S,O,5-OH-2-Adm,H),(3-776,i-Pro,K-2,S,S,O,5-OH-2-Adm,H),(3-777,i-Pro,K-3,S,S,O,5-OH-2-Adm,H),(3-778,i-Pro,K-4,S,S,O,5-OH-2-Adm,H),(3-779,i-Pro,K-5,S,S,O,5-OH-2-Adm,H),(3-780,i-Pro,K-6,S,S,O,5-OH-2-Adm,H),(3-781,i-Pro,K-7,S,S,O,5-OH-2-Adm,H),(3-782,i-Pro,K-8,S,S,O,5-OH-2-Adm,H),(3-783,i-Pro,K-9,S,S,O,5-OH-2-Adm,H)

(Compound No., $R^2,R^3,X,Y,Z,R^4,R^5$)=(4-1,i-Bu,A-1,O,S,O,1-Adm,H),(4-2,i-Bu,A-2,O,S,O,1-Adm,H),(4-3,i-Bu,A-3,O,S,O,1-Adm,H),(4-4,i-Bu,A-4,O,S,O,1-Adm,H),(4-5,i-Bu,A-5,O,S,O,1-Adm,H),(4-6,i-Bu,A-6,O,S,O,1-Adm,H),(4-7,i-Bu,A-7,O,S,O,1-Adm,H),(4-8,i-Bu,A-8,O,S,O,1-Adm,H),(4-9,i-Bu,A-9,O,S,O,1-Adm,H),(4-10,i-Bu,A-10,O,S,O,1-Adm,H),(4-11,i-Bu,A-11,O,S,O,1-Adm,H),(4-12,i-Bu,A-12,O,S,O,1-Adm,H),(4-13,i-Bu,A-13,O,S,O,1-Adm,H),(4-14,i-Bu,A-14,O,S,O,1-Adm,H),(4-15,i-Bu,A-15,O,S,O,1-Adm,H),(4-16,i-Bu,A-16,O,S,O,1-Adm,H),(4-17,i-Bu,A-17,O,S,O,1-Adm,H),(4-18,i-Bu,A-18,O,S,O,1-Adm,H),(4-19,i-Bu,A-19,O,S,O,1-Adm,H),(4-20,i-Bu,A-20,O,S,O,1-Adm,H),(4-21,i-Bu,A-21,O,S,O,1-Adm,H),(4-22,i-Bu,A-22,O,S,O,1-Adm,H),(4-23,i-Bu,A-23,O,S,O,1-Adm,H),(4-24,i-Bu,A-24,O,S,O,1-Adm,H),(4-25,i-Bu,A-25,O,S,O,1-Adm,H),(4-26,i-Bu,A-26,O,S,O,1-Adm,H),(4-27,i-Bu,A-27,O,S,O,1-Adm,H),(4-28,i-Bu,A-28,O,S,O,1-Adm,H),(4-29,i-Bu,A-29,O,S,O,1-Adm,H),(4-30,i-Bu,A-30,O,S,O,1-Adm,H),(4-31,i-Bu,A-31,O,S,O,1-Adm,H),(4-32,i-Bu,A-32,O,S,O,1-Adm,H),(4-33,i-Bu,A-33,O,S,O,1-Adm,H),(4-34,i-Bu,A-34,O,S,O,1-Adm,H),(4-35,i-Bu,A-35,O,S,O,1-Adm,H),(4-36,i-Bu,A-36,O,S,O,1-Adm,H),(4-37,i-Bu,A-1,O,S,O,2-Adm,H),(4-38,i-Bu,A-2,O,S,O,2-Adm,H),(4-39,i-Bu,A-3,O,S,O,2-Adm,H),(4-40,i-Bu,A-4,O,S,O,2-Adm,H),(4-41,i-Bu,A-5,O,S,O,2-Adm,H),(4-42,i-Bu,A-6,O,S,O,2-Adm,H),(4-43,i-Bu,A-7,O,S,O,2-Adm,H),(4-44,i-Bu,A-8,O,S,O,2-Adm,H),(4-45,i-Bu,A-9,O,S,O,2-Adm,H),(4-46,i-Bu,A-10,O,S,O,2-Adm,H),(4-47,i-Bu,A-11,O,S,O,2-Adm,H),(4-48,i-Bu,A-12,O,S,O,2-Adm,H),(4-49,i-Bu,A-13,O,S,O,2-Adm,H),(4-50,i-Bu,A-14,O,S,O,2-Adm,H),(4-51,i-Bu,A-15,O,S,O,2-Adm,H),(4-52,i-Bu,A-16,O,S,O,2-Adm,H),(4-53,i-Bu,A-17,O,S,O,2-Adm,H),(4-54,i-Bu,A-18,O,S,O,2-Adm,H),(4-55,i-Bu,A-19,O,S,O,2-Adm,H),(4-56,i-Bu,A-20,O,S,O,2-Adm,H),(4-57,i-Bu,A-21,O,S,O,2-Adm,H),(4-58,i-Bu,A-22,O,S,O,2-Adm,H),(4-59,i-Bu,A-23,O,S,O,2-Adm,H),(4-60,i-Bu,A-24,O,S,O,2-Adm,H),(4-61,i-Bu,A-25,O,S,O,2-Adm,H),(4-62,i-Bu,A-26,O,S,O,2-Adm,H),(4-63,i-Bu,A-27,O,S,O,2-Adm,H),(4-64,i-Bu,A-28,O,S,O,2-Adm,H),(4-65,i-Bu,A-29,O,S,O,2-Adm,H),(4-66,i-Bu,A-30,O,S,O,2-Adm,H),(4-67,i-Bu,A-31,O,S,O,2-Adm,H),(4-68,i-Bu,A-32,O,S,O,2-Adm,H),(4-69,i-Bu,A-33,O,S,O,2-Adm,H),(4-70,i-Bu,A-34,O,S,O,2-Adm,H),(4-71,i-Bu,A-35,O,S,O,2-Adm,H),(4-72,i-Bu,A-36,O,S,O,2-Adm,H),(4-73,i-Bu,A-1,O,S,O,5-OH-2-Adm,H),(4-74,i-Bu,A-2,O,S,O,5-OH-2-Adm,H),(4-75,i-Bu,A-3,O,S,O,5-OH-2-Adm,H),(4-76,i-Bu,A-4,O,S,O,5-OH-2-Adm,H),(4-77,i-Bu,A-5,O,S,O,5-OH-2-Adm,H),(4-78,i-Bu,A-6,O,S,O,5-OH-2-Adm,H),(4-79,i-Bu,A-7,O,S,O,5-OH-2-Adm,H),(4-80,i-Bu,A-8,O,S,O,5-OH-2-Adm,H),(4-81,i-Bu,A-9,O,S,O,5-OH-2-Adm,H),(4-82,i-Bu,A-10,O,S,O,5-OH-2-Adm,H),(4-83,i-Bu,A-11,O,S,O,5-OH-2-Adm,H),(4-84,i-Bu,A-12,O,S,O,5-OH-2-Adm,H),(4-85,i-Bu,A-13,O,S,O,5-OH-2-Adm,H),(4-86,i-Bu,A-14,O,S,O,5-OH-2-Adm,H),(4-87,i-Bu,A-15,O,S,O,5-OH-2-Adm,H),(4-88,i-Bu,A-16,O,S,O,5-OH-2-Adm,H),(4-89,i-Bu,A-17,O,S,O,5-OH-2-Adm,H),(4-90,i-Bu,A-18,O,S,O,5-OH-2-Adm,H),(4-91,i-Bu,A-19,O,S,O,5-OH-2-

Adm,H),(4-92,i-Bu,A-20,O,S,O,5-OH-2-Adm,H),(4-93,i-Bu,A-21,O,S,O,5-OH-2-Adm,H),(4-94,i-Bu,A-22,O,S,O,5-OH-2-Adm,H),(4-95,i-Bu,A-23,O,S,O,5-OH-2-Adm,H),(4-96,i-Bu,A-24,O,S,O,5-OH-2-Adm,H),(4-97,i-Bu,A-25,O,S,O,5-OH-2-Adm,H),(4-98,i-Bu,A-26,O,S,O,5-OH-2-Adm,H),(4-99,i-Bu,A-27,O,S,O,5-OH-2-Adm,H),(4-100,i-Bu,A-28,O,S,O,5-OH-2-Adm,H),(4-101,i-Bu,A-29,O,S,O,5-OH-2-Adm,H),(4-102,i-Bu,A-30,O,S,O,5-OH-2-Adm,H),(4-103,i-Bu,A-31,O,S,O,5-OH-2-Adm,H),(4-104,i-Bu,A-32,O,S,O,5-OH-2-Adm,H),(4-105,i-Bu,A-33,O,S,O,5-OH-2-Adm,H),(4-106,i-Bu,A-34,O,S,O,5-OH-2-Adm,H),(4-107,i-Bu,A-35,O,S,O,5-OH-2-Adm,H),(4-108,i-Bu,A-36,O,S,O,5-OH-2-Adm,H),(4-109,i-Bu,B-1,O,S,O,1-Adm,H),(4-110,i-Bu,B-2,O,S,O,1-Adm,H),(4-111,i-Bu,B-3,O,S,O,1-Adm,H),(4-112,i-Bu,B-4,O,S,O,1-Adm,H),(4-113,i-Bu,B-5,O,S,O,1-Adm,H),(4-114,i-Bu,B-6,O,S,O,1-Adm,H),(4-115,i-Bu,B-7,O,S,O,1-Adm,H),(4-116,i-Bu,B-8,O,S,O,1-Adm,H),(4-117,i-Bu,B-9,O,S,O,1-Adm,H),(4-118,i-Bu,B-10,O,S,O,1-Adm,H),(4-119,i-Bu,B-1,O,S,O,1-Adm,H),(4-120,i-Bu,B-12,O,S,O,1-Adm,H),(4-121,i-Bu,B-13,O,S,O,1-Adm,H),(4-122,i-Bu,B-14,O,S,O,1-Adm,H),(4-123,i-Bu,B-15,O,S,O,1-Adm,H),(4-124,i-Bu,B-16,O,S,O,1-Adm,H),(4-125,i-Bu,B-17,O,S,O,1-Adm,H),(4-126,i-Bu,B-18,O,S,O,1-Adm,H),(4-127,i-Bu,B-19,O,S,O,1-Adm,H),(4-128,i-Bu,B-20,O,S,O,1-Adm,H),(4-129,i-Bu,B-21,O,S,O,1-Adm,H),(4-130,i-Bu,B-22,O,S,O,1-Adm,H),(4-131,i-Bu,B-23,O,S,O,1-Adm,H),(4-132,i-Bu,B-24,O,S,O,1-Adm,H),(4-133,i-Bu,B-25,O,S,O,1-Adm,H),(4-134,i-Bu,B-26,O,S,O,1-Adm,H),(4-135,i-Bu,B-27,O,S,O,1-Adm,H),(4-136,i-Bu,B-28,O,S,O,1-Adm,H),(4-137,i-Bu,B-29,O,S,O,1-Adm,H),(4-138,i-Bu,B-30,O,S,O,1-Adm,H),(4-139,i-Bu,B-31,O,S,O,1-Adm,H),(4-140,i-Bu,B-32,O,S,O,1-Adm,H),(4-141,i-Bu,B-33,O,S,O,1-Adm,H),(4-142,i-Bu,B-34,O,S,O,1-Adm,H),(4-143,i-Bu,B-35,O,S,O,1-Adm,H),(4-144,i-Bu,B-36,O,S,O,1-Adm,H),(4-145,i-Bu,B-1,O,S,O,2-Adm,H),(4-146,i-Bu,B-2,O,S,O,2-Adm,H),(4-147,i-Bu,B-3,O,S,O,2-Adm,H),(4-148,i-Bu,B-4,O,S,O,2-Adm,H),(4-149,i-Bu,B-5,O,S,O,2-Adm,H),(4-150,i-Bu,B-6,O,S,O,2-Adm,H),(4-151,i-Bu,B-7,O,S,O,2-Adm,H),(4-152,i-Bu,B-8,O,S,O,2-Adm,H),(4-153,i-Bu,B-9,O,S,O,2-Adm,H),(4-154,i-Bu,B-10,O,S,O,2-Adm,H),(4-155,i-Bu,B-11,O,S,O,2-Adm,H),(4-156,i-Bu,B-12,O,S,O,2-Adm,H),(4-157,i-Bu,B-13,O,S,O,2-Adm,H),(4-158,i-Bu,B-14,O,S,O,2-Adm,H),(4-159,i-Bu,B-15,O,S,O,2-Adm,H),(4-160,i-Bu,B-16,O,S,O,2-Adm,H),(4-161,i-Bu,B-17,O,S,O,2-Adm,H),(4-162,i-Bu,B-18,O,S,O,2-Adm,H),(4-163,i-Bu,B-19,O,S,O,2-Adm,H),(4-164,i-Bu,B-20,O,S,O,2-Adm,H),(4-165,i-Bu,B-21,O,S,O,2-Adm,H),(4-166,i-Bu,B-22,O,S,O,2-Adm,H),(4-167,i-Bu,B-23,O,S,O,2-Adm,H),(4-168,i-Bu,B-24,O,S,O,2-Adm,H),(4-169,i-Bu,B-25,O,S,O,2-Adm,H),(4-170,i-Bu,B-26,O,S,O,2-Adm,H),(4-171,i-Bu,B-27,O,S,O,2-Adm,H),(4-172,i-Bu,B-28,O,S,O,2-Adm,H),(4-173,i-Bu,B-29,O,S,O,2-Adm,H),(4-174,i-Bu,B-30,O,S,O,2-Adm,H),(4-175,i-Bu,B-31,O,S,O,2-Adm,H),(4-176,i-Bu,B-32,O,S,O,2-Adm,H),(4-177,i-Bu,B-33,O,S,O,2-Adm,H),(4-178,i-Bu,B-34,O,S,O,2-Adm,H),(4-179,i-Bu,B-35,O,S,O,2-Adm,H),(4-180,i-Bu,B-36,O,S,O,2-Adm,H),(4-181,i-Bu,B-1,O,S,O,5-OH-2-Adm,H),(4-182,i-Bu,B-2,O,S,O,5-OH-2-Adm,H),(4-183,i-Bu,B-3,O,S,O,5-OH-2-Adm,H),(4-184,i-Bu,B-4,O,S,O,5-OH-2-Adm,H),(4-185,i-Bu,B-5,O,S,O,5-OH-2-Adm,H),(4-186,i-Bu,B-6,O,S,O,5-OH-2-Adm,H),(4-187,i-Bu,B-7,O,S,O,5-OH-2-Adm,H),(4-188,i-Bu,B-8,O,S,O,5-OH-2-Adm,H),(4-189,i-Bu,B-9,O,S,O,5-OH-2-Adm,H),(4-190,i-Bu,B-10,O,S,O,5-OH-2-Adm,H),(4-191,i-Bu,B-11,O,S,O,5-OH-2-Adm,H),(4-192,i-Bu,B-12,O,S,O,5-OH-2-Adm,H),(4-193,i-Bu,B-13,O,S,O,5-OH-2-Adm,H),(4-194,i-Bu,B-14,O,S,O,5-OH-2-Adm,H),(4-195,i-Bu,B-15,O,S,O,5-OH-2-Adm,H),(4-196,i-Bu,B-16,O,S,O,5-OH-2-Adm,H),(4-197,i-Bu,B-17,O,S,O,5-OH-2-Adm,H),(4-198,i-Bu,B-18,O,S,O,5-OH-2-Adm,H),(4-199,i-Bu,B-19,O,S,O,5-OH-2-Adm,H),(4-200,i-Bu,B-20,O,S,O,5-OH-2-Adm,H),(4-201,i-Bu,B-21,O,S,O,5-OH-2-Adm,H),(4-202,i-Bu,B-22,O,S,O,5-OH-2-Adm,H),(4-203,i-Bu,B-23,O,S,O,5-OH-2-Adm,H),(4-204,i-Bu,B-24,O,S,O,5-OH-2-Adm,H),(4-205,i-Bu,B-25,O,S,O,5-OH-2-Adm,H),(4-206,i-Bu,B-26,O,S,O,5-OH-2-Adm,H),(4-207,i-Bu,B-27,O,S,O,5-OH-2-Adm,H),(4-208,i-Bu,B-28,O,S,O,5-OH-2-Adm,H),(4-209,i-Bu,B-29,O,S,O,5-OH-2-Adm,H),(4-210,i-Bu,B-30,O,S,O,5-OH-2-Adm,H),(4-211,i-Bu,B-31,O,S,O,5-OH-2-Adm,H),(4-212,i-Bu,B-32,O,S,O,5-OH-2-Adm,H),(4-213,i-Bu,B-33,O,S,O,5-OH-2-Adm,H),(4-214,i-Bu,B-34,O,S,O,5-OH-2-Adm,H),(4-215,i-Bu,B-35,O,S,O,5-OH-2-Adm,H),(4-216,i-Bu,B-36,O,S,O,5-OH-2-Adm,H),(4-217,i-Bu,C-1,O,S,O,1-Adm,H),(4-218,i-Bu,C-2,O,S,O,1-Adm,H),(4-219,i-Bu,C-3,O,S,O,1-Adm,H),(4-220,i-Bu,C-4,O,S,O,1-Adm,H),(4-221,i-Bu,C-5,O,S,O,1-Adm,H),(4-222,i-Bu,C-6,O,S,O,1-Adm,H),(4-223,i-Bu,C-7,O,S,O,1-Adm,H),(4-224,i-Bu,C-8,O,S,O,1-Adm,H),(4-225,i-Bu,C-9,O,S,O,1-Adm,H),(4-226,i-Bu,C-10,O,S,O,1-Adm,H),(4-227,i-Bu,C-11,O,S,O,1-Adm,H),(4-228,i-Bu,C-12,O,S,O,1-Adm,H),(4-229,i-Bu,C-13,O,S,O,1-Adm,H),(4-230,i-Bu,C-14,O,S,O,1-Adm,H),(4-231,i-Bu,C-15,O,S,O,1-Adm,H),(4-232,i-Bu,C-16,O,S,O,1-Adm,H),(4-233,i-Bu,C-17,O,S,O,1-Adm,H),(4-234,i-Bu,C-18,O,S,O,1-Adm,H),(4-235,i-Bu,C-19,O,S,O,1-Adm,H),(4-236,i-Bu,C-20,O,S,O,1-Adm,H),(4-237,i-Bu,C-21,O,S,O,1-Adm,H),(4-238,i-Bu,C-22,O,S,O,1-Adm,H),(4-239,i-Bu,C-23,O,S,O,1-Adm,H),(4-240,i-Bu,C-24,O,S,O,1-Adm,H),(4-241,i-Bu,C-25,O,S,O,1-Adm,H),(4-242,i-Bu,C-26,O,S,O,1-Adm,H),(4-243,i-Bu,C-27,O,S,O,1-Adm,H),(4-244,i-Bu,C-28,O,S,O,1-Adm,H),(4-245,i-Bu,C-29,O,S,O,1-Adm,H),(4-246,i-Bu,C-30,O,S,O,1-Adm,H),(4-247,i-Bu,C-31,O,S,O,1-Adm,H),(4-248,i-Bu,C-32,O,S,O,1-Adm,H),(4-249,i-Bu,C-33,O,S,O,1-Adm,H),(4-250,i-Bu,C-34,O,S,O,1-Adm,H),(4-251,i-Bu,C-35,O,S,O,1-Adm,H),(4-252,i-Bu,C-36,O,S,O,1-Adm,H),(4-253,i-Bu,C-1,O,S,O,2-Adm,H),(4-254,i-Bu,C-2,O,S,O,2-Adm,H),(4-255,i-Bu,C-3,O,S,O,2-Adm,H),(4-256,i-Bu,C-4,O,S,O,2-Adm,H),(4-257,i-Bu,C-5,O,S,O,2-Adm,H),(4-258,i-Bu,C-6,O,S,O,2-Adm,H),(4-259,i-Bu,C-7,O,S,O,2-Adm,H),(4-260,i-Bu,C-8,O,S,O,2-Adm,H),(4-261,i-Bu,C-9,O,S,O,2-Adm,H),(4-262,i-Bu,C-10,O,S,O,2-Adm,H),(4-263,i-Bu,C-11,O,S,O,2-Adm,H),(4-264,i-Bu,C-12,O,S,O,2-Adm,H),(4-265,i-Bu,C-13,O,S,O,2-Adm,H),(4-266,i-Bu,C-14,O,S,O,2-Adm,H),(4-267,i-Bu,C-15,O,S,O,2-Adm,H),(4-268,i-Bu,C-16,O,S,O,2-Adm,H),(4-269,i-Bu,C-17,O,S,O,2-Adm,H),(4-270,i-Bu,C-18,O,S,O,2-Adm,H),(4-271,i-Bu,C-19,O,S,O,2-Adm,H),(4-272,i-Bu,C-20,O,S,O,2-Adm,H),(4-273,i-Bu,C-21,O,S,O,2-Adm,H),(4-274,i-Bu,C-22,O,S,O,2-Adm,H),(4-275,i-Bu,C-23,O,S,O,2-Adm,H),(4-276,i-Bu,C-24,O,S,O,2-Adm,H),(4-277,i-Bu,C-25,O,S,O,2-Adm,H),(4-278,i-Bu,C-26,O,S,O,2-Adm,H),(4-279,i-Bu,C-27,O,S,O,2-Adm,H),(4-280,i-Bu,C-28,O,S,O,2-Adm,H),(4-281,i-Bu,C-29,O,S,O,2-Adm,H),(4-282,i-Bu,C-30,O,S,O,2-Adm,H),(4-283,i-Bu,C-31,O,S,O,2-Adm,H),(4-284,i-Bu,C-32,O,S,O,2-Adm,H),(4-285,i-Bu,C-33,O,S,O,2-Adm,H),(4-286,i-Bu,C-34,O,S,O,2-Adm,H),(4-287,i-Bu,C-35,O,S,O,2-Adm,H),(4-288,i-Bu,C-36,O,S,O,2-Adm,H),(4-289,i-Bu,C-1,O,S,O,5-OH-2-Adm,H),(4-290,i-Bu,C-2,O,S,O,5-OH-2-Adm,H),(4-291,i-Bu,C-3,O,S,O,5-OH-2-Adm,H),(4-292,i-Bu,C-4,O,S,O,5-OH-2-Adm,H),(4-293,i-Bu,C-5,O,S,O,5-OH-2-Adm,H),(4-294,i-Bu,C-6,O,S,O,5-OH-2-Adm,H),(4-295,i-Bu,C-7,O,S,O,5-OH-2-Adm,H),(4-296,i-Bu,C-8,O,S,O,5-OH-2-Adm,H),(4-297,i-Bu,C-9,O,S,O,5-OH-2-Adm,H),(4-298,i-Bu,C-10,O,S,O,5-OH-2-Adm,H),(4-299,i-Bu,C-11,O,S,O,5-OH-2-Adm,H),(4-300,i-Bu,C-12,O,S,O,5-OH-2-Adm,H),(4-301,i-Bu,C-13,O,S,O,5-OH-2-Adm,H),(4-302,i-Bu,C-14,O,S,O,5-OH-2-Adm,H),(4-303,i-Bu,C-15,O,S,O,5-OH-2-Adm,H),(4-304,i-Bu,C-16,O,S,O,5-OH-2-Adm,H),(4-305,i-Bu,C-17,O,S,O,5-OH-2-Adm,H),(4-306,i-Bu,C-18,O,S,O,5-OH-2-Adm,H),(4-307,i-Bu,C-19,O,

S,O,5-OH-2-Adm,H),(4-308,i-Bu,C-20,O,S,O,5-OH-2-Adm,H),(4-309,i-Bu,C-21,O,S,O,5-OH-2-Adm,H),(4-310,i-Bu,C-22,O,S,O,5-OH-2-Adm,H),(4-311,i-Bu,C-23,O,S,O,5-OH-2-Adm,H),(4-312,i-Bu,C-24,O,S,O,5-OH-2-Adm,H),(4-313,i-Bu,C-25,O,S,O,5-OH-2-Adm,H),(4-314,i-Bu,C-26,O,S,O,5-OH-2-Adm,H),(4-315,i-Bu,C-27,O,S,O,5-OH-2-Adm,H),(4-316,i-Bu,C-28,O,S,O,5-OH-2-Adm,H),(4-317,i-Bu,C-29,O,S,O,5-OH-2-Adm,H),(4-318,i-Bu,C-30,O,S,O,5-OH-2-Adm,H),(4-319,i-Bu,C-31,O,S,O,5-OH-2-Adm,H),(4-320,i-Bu,C-32,O,S,O,5-OH-2-Adm,H),(4-321,i-Bu,C-33,O,S,O,5-OH-2-Adm,H),(4-322,i-Bu,C-34,O,S,O,5-OH-2-Adm,H),(4-323,i-Bu,C-35,O,S,O,5-OH-2-Adm,H),(4-324,i-Bu,C-36,O,S,O,5-OH-2-Adm,H),(4-325,i-Bu,D-1,O,S,O,1-Adm,H),(4-326,i-Bu,D-2,O,S,O,1-Adm,H),(4-327,i-Bu,D-3,O,S,O,1-Adm,H),(4-328,i-Bu,D-4,O,S,O,1-Adm,H),(4-329,i-Bu,D-5,O,S,O,1-Adm,H),(4-330,i-Bu,D-6,O,S,O,1-Adm,H),(4-331,i-Bu,D-7,O,S,O,1-Adm,H),(4-332,i-Bu,D-8,O,S,O,1-Adm,H),(4-333,i-Bu,D-9,O,S,O,1-Adm,H),(4-334,i-Bu,D-10,O,S,O,1-Adm,H),(4-335,i-Bu,D-11,O,S,O,1-Adm,H),(4-336,i-Bu,D-12,O,S,O,1-Adm,H),(4-337,i-Bu,D-13,O,S,O,1-Adm,H),(4-338,i-Bu,D-14,O,S,O,1-Adm,H),(4-339,i-Bu,D-15,O,S,O,1-Adm,H),(4-340,i-Bu,D-16,O,S,O,1-Adm,H),(4-341,i-Bu,D-17,O,S,O,1-Adm,H),(4-342,i-Bu,D-18,O,S,O,1-Adm,H),(4-343,i-Bu,D-19,O,S,O,1-Adm,H),(4-344,i-Bu,D-20,O,S,O,1-Adm,H),(4-345,i-Bu,D-21,O,S,O,1-Adm,H),(4-346,i-Bu,D-22,O,S,O,1-Adm,H),(4-347,i-Bu,D-23,O,S,O,1-Adm,H),(4-348,i-Bu,D-24,O,S,O,1-Adm,H),(4-349,i-Bu,D-25,O,S,O,1-Adm,H),(4-350,i-Bu,D-26,O,S,O,1-Adm,H),(4-351,i-Bu,D-27,O,S,O,1-Adm,H),(4-352,i-Bu,D-28,O,S,O,1-Adm,H),(4-353,i-Bu,D-29,O,S,O,1-Adm,H),(4-354,i-Bu,D-30,O,S,O,1-Adm,H),(4-355,i-Bu,D-31,O,S,O,1-Adm,H),(4-356,i-Bu,D-32,O,S,O,1-Adm,H),(4-357,i-Bu,D-33,O,S,O,1-Adm,H),(4-358,i-Bu,D-34,O,S,O,1-Adm,H),(4-359,i-Bu,D-35,O,S,O,1-Adm,H),(4-360,i-Bu,D-36,O,S,O,1-Adm,H),(4-361,i-Bu,D-1,O,S,O,2-Adm,H),(4-362,i-Bu,D-2,O,S,O,2-Adm,H),(4-363,i-Bu,D-3,O,S,O,2-Adm,H),(4-364,i-Bu,D-4,O,S,O,2-Adm,H),(4-365,i-Bu,D-5,O,S,O,2-Adm,H),(4-366,i-Bu,D-6,O,S,O,2-Adm,H),(4-367,i-Bu,D-7,O,S,O,2-Adm,H),(4-368,i-Bu,D-8,O,S,O,2-Adm,H),(4-369,i-Bu,D-9,O,S,O,2-Adm,H),(4-370,i-Bu,D-10,O,S,O,2-Adm,H),(4-371,i-Bu,D-11,O,S,O,2-Adm,H),(4-372,i-Bu,D-12,O,S,O,2-Adm,H),(4-373,i-Bu,D-13,O,S,O,2-Adm,H),(4-374,i-Bu,D-14,O,S,O,2-Adm,H),(4-375,i-Bu,D-15,O,S,O,2-Adm,H),(4-376,i-Bu,D-16,O,S,O,2-Adm,H),(4-377,i-Bu,D-17,O,S,O,2-Adm,H),(4-378,i-Bu,D-18,O,S,O,2-Adm,H),(4-379,i-Bu,D-19,O,S,O,2-Adm,H),(4-380,i-Bu,D-20,O,S,O,2-Adm,H),(4-381,i-Bu,D-21,O,S,O,2-Adm,H),(4-382,i-Bu,D-22,O,S,O,2-Adm,H),(4-383,i-Bu,D-23,O,S,O,2-Adm,H),(4-384,i-Bu,D-24,O,S,O,2-Adm,H),(4-385,i-Bu,D-25,O,S,O,2-Adm,H),(4-386,i-Bu,D-26,O,S,O,2-Adm,H),(4-387,i-Bu,D-27,O,S,O,2-Adm,H),(4-388,i-Bu,D-28,O,S,O,2-Adm,H),(4-389,i-Bu,D-29,O,S,O,2-Adm,H),(4-390,i-Bu,D-30,O,S,O,2-Adm,H),(4-391,i-Bu,D-31,O,S,O,2-Adm,H),(4-392,i-Bu,D-32,O,S,O,2-Adm,H),(4-393,i-Bu,D-33,O,S,O,2-Adm,H),(4-394,i-Bu,D-34,O,S,O,2-Adm,H),(4-395,i-Bu,D-35,O,S,O,2-Adm,H),(4-396,i-Bu,D-36,O,S,O,2-Adm,H),(4-397,i-Bu,D-1,O,S,O,5-OH-2-Adm,H),(4-398,i-Bu,D-2,O,S,O,5-OH-2-Adm,H),(4-399,i-Bu,D-3,O,S,O,5-OH-2-Adm,H),(4-400,i-Bu,D-4,O,S,O,5-OH-2-Adm,H),(4-401,i-Bu,D-5,O,S,O,5-OH-2-Adm,H),(4-402,i-Bu,D-6,O,S,O,5-OH-2-Adm,H),(4-403,i-Bu,D-7,O,S,O,5-OH-2-Adm,H),(4-404,i-Bu,D-8,O,S,O,5-OH-2-Adm,H),(4-405,i-Bu,D-9,O,S,O,5-OH-2-Adm,H),(4-406,i-Bu,D-10,O,S,O,5-OH-2-Adm,H),(4-407,i-Bu,D-11,O,S,O,5-OH-2-Adm,H),(4-408,i-Bu,D-12,O,S,O,5-OH-2-Adm,H),(4-409,i-Bu,D-13,O,S,O,5-OH-2-Adm,H),(4-410,i-Bu,D-14,O,S,O,5-OH-2-Adm,H), (4-411,i-Bu,D-15,O,S,O,5-OH-2-Adm,H),(4-412,i-Bu,D-16,O,S,O,5-OH-2-Adm,H),(4-413,i-Bu,D-17,O,S,O,5-OH-2-Adm,H),(4-414,i-Bu,D-18,O,S,O,5-OH-2-Adm,H),(4-415,i-Bu,D-19,O,S,O,5-OH-2-Adm,H),(4-416,i-Bu,D-20,O,S,O,5-OH-2-Adm,H),(4-417,i-Bu,D-21,O,S,O,5-OH-2-Adm,H),(4-418,i-Bu,D-22,O,S,O,5-OH-2-Adm,H),(4-419,i-Bu,D-23,O,S,O,5-OH-2-Adm,H),(4-420,i-Bu,D-24,O,S,O,5-OH-2-Adm,H),(4-421,i-Bu,D-25,O,S,O,5-OH-2-Adm,H),(4-422,i-Bu,D-26,O,S,O,5-OH-2-Adm,H),(4-423,i-Bu,D-27,O,S,O,5-OH-2-Adm,H),(4-424,i-Bu,D-28,O,S,O,5-OH-2-Adm,H),(4-425,i-Bu,D-29,O,S,O,5-OH-2-Adm,H),(4-426,i-Bu,D-30,O,S,O,5-OH-2-Adm,H),(4-427,i-Bu,D-31,O,S,O,5-OH-2-Adm,H),(4-428,i-Bu,D-32,O,S,O,5-OH-2-Adm,H),(4-429,i-Bu,D-33,O,S,O,5-OH-2-Adm,H),(4-430,i-Bu,D-34,O,S,O,5-OH-2-Adm,H),(4-431,i-Bu,D-35,O,S,O,5-OH-2-Adm,H),(4-432,i-Bu,D-36,O,S,O,5-OH-2-Adm,H),(4-433,i-Bu,E-1,O,S,O,1-Adm,H),(4-434,i-Bu,E-2,O,S,O,1-Adm,H),(4-435,i-Bu,E-3,O,S,O,1-Adm,H),(4-436,i-Bu,E-4,O,S,O,1-Adm,H),(4-437,i-Bu,E-5,O,S,O,1-Adm,H),(4-438,i-Bu,E-6,O,S,O,1-Adm,H),(4-439,i-Bu,E-7,O,S,O,1-Adm,H),(4-440,i-Bu,E-8,O,S,O,1-Adm,H),(4-441,i-Bu,E-9,O,S,O,1-Adm,H),(4-442,i-Bu,E-10,O,S,O,1-Adm,H),(4-443,i-Bu,E-11,O,S,O,1-Adm,H),(4-444,i-Bu,E-12,O,S,O,1-Adm,H),(4-445,i-Bu,E-13,O,S,O,1-Adm,H),(4-446,i-Bu,E-14,O,S,O,1-Adm,H),(4-447,i-Bu,E-15,O,S,O,1-Adm,H),(4-448,i-Bu,E-16,O,S,O,1-Adm,H),(4-449,i-Bu,E-17,O,S,O,1-Adm,H),(4-450,i-Bu,E-18,O,S,O,1-Adm,H),(4-451,i-Bu,E-19,O,S,O,1-Adm,H),(4-452,i-Bu,E-20,O,S,O,1-Adm,H),(4-453,i-Bu,E-21,O,S,O,1-Adm,H),(4-454,i-Bu,E-22,O,S,O,1-Adm,H),(4-455,i-Bu,E-23,O,S,O,1-Adm,H),(4-456,i-Bu,E-24,O,S,O,1-Adm,H),(4-457,i-Bu,E-25,O,S,O,1-Adm,H),(4-458,i-Bu,E-26,O,S,O,1-Adm,H),(4-459,i-Bu,E-27,O,S,O,1-Adm,H),(4-460,i-Bu,E-28,O,S,O,1-Adm,H),(4-461,i-Bu,E-29,O,S,O,1-Adm,H),(4-462,i-Bu,E-30,O,S,O,1-Adm,H),(4-463,i-Bu,E-31,O,S,O,1-Adm,H),(4-464,i-Bu,E-32,O,S,O,1-Adm,H),(4-465,i-Bu,E-33,O,S,O,1-Adm,H),(4-466,i-Bu,E-34,O,S,O,1-Adm,H),(4-467,i-Bu,E-35,O,S,O,1-Adm,H),(4-468,i-Bu,E-36,O,S,O,1-Adm,H),(4-469,i-Bu,E-1,O,S,O,2-Adm,H),(4-470,i-Bu,E-2,O,S,O,2-Adm,H),(4-471,i-Bu,E-3,O,S,O,2-Adm,H),(4-472,i-Bu,E-4,O,S,O,2-Adm,H),(4-473,i-Bu,E-5,O,S,O,2-Adm,H),(4-474,i-Bu,E-6,O,S,O,2-Adm,H),(4-475,i-Bu,E-7,O,S,O,2-Adm,H),(4-476,i-Bu,E-8,O,S,O,2-Adm,H),(4-477,i-Bu,E-9,O,S,O,2-Adm,H),(4-478,i-Bu,E-10,O,S,O,2-Adm,H),(4-479,i-Bu,E-11,O,S,O,2-Adm,H),(4-480,i-Bu,E-12,O,S,O,2-Adm,H),(4-481,i-Bu,E-13,O,S,O,2-Adm,H),(4-482,i-Bu,E-14,O,S,O,2-Adm,H),(4-483,i-Bu,E-15,O,S,O,2-Adm,H),(4-484,i-Bu,E-16,O,S,O,2-Adm,H),(4-485,i-Bu,E-17,O,S,O,2-Adm,H),(4-486,i-Bu,E-18,O,S,O,2-Adm,H),(4-487,i-Bu,E-19,O,S,O,2-Adm,H),(4-488,i-Bu,E-20,O,S,O,2-Adm,H),(4-489,i-Bu,E-21,O,S,O,2-Adm,H),(4-490,i-Bu,E-22,O,S,O,2-Adm,H),(4-491,i-Bu,E-23,O,S,O,2-Adm,H),(4-492,i-Bu,E-24,O,S,O,2-Adm,H),(4-493,i-Bu,E-25,O,S,O,2-Adm,H),(4-494,i-Bu,E-26,O,S,O,2-Adm,H),(4-495,i-Bu,E-27,O,S,O,2-Adm,H),(4-496,i-Bu,E-28,O,S,O,2-Adm,H),(4-497,i-Bu,E-29,O,S,O,2-Adm,H),(4-498,i-Bu,E-30,O,S,O,2-Adm,H),(4-499,i-Bu,E-31,O,S,O,2-Adm,H),(4-500,i-Bu,E-32,O,S,O,2-Adm,H),(4-501,i-Bu,E-33,O,S,O,2-Adm,H),(4-502,i-Bu,E-34,O,S,O,2-Adm,H),(4-503,i-Bu,E-35,O,S,O,2-Adm,H),(4-504,i-Bu,E-36,O,S,O,2-Adm,H),(4-505,i-Bu,E-1,O,S,O,5-OH-2-Adm,H),(4-506,i-Bu,E-2,O,S,O,5-OH-2-Adm,H),(4-507,i-Bu,E-3,O,S,O,5-OH-2-Adm,H),(4-508,i-Bu,E-4,O,S,O,5-OH-2-Adm,H),(4-509,i-Bu,E-5,O,S,O,5-OH-2-Adm,H),(4-510,i-Bu,E-6,O,S,O,5-OH-2-Adm,H),(4-511,i-Bu,E-7,O,S,O,5-OH-2-Adm,H),(4-512,i-Bu,E-8,O,S,O,5-OH-2-Adm,H),(4-513,i-Bu,E-9,O,S,O,5-OH-2-Adm,H),(4-514,i-Bu,E-10,O,S,O,5-OH-2-Adm,H),(4-515,i-Bu,E-11,O,

S,O,5-OH-2-Adm,H),(4-516,i-Bu,E-12,O,S,O,5-OH-2-Adm,H),(4-517,i-Bu,E-13,O,S,O,5-OH-2-Adm,H),(4-518,i-Bu,E-14,O,S,O,5-OH-2-Adm,H),(4-519,i-Bu,E-15,O,S,O,5-OH-2-Adm,H),(4-520,i-Bu,E-16,O,S,O,5-OH-2-Adm,H),(4-521,i-Bu,E-17,O,S,O,5-OH-2-Adm,H),(4-522,i-Bu,E-18,O,S,O,5-OH-2-Adm,H),(4-523,i-Bu,E-19,O,S,O,5-OH-2-Adm,H),(4-524,i-Bu,E-20,O,S,O,5-OH-2-Adm,H),(4-525,i-Bu,E-21,O,S,O,5-OH-2-Adm,H),(4-526,i-Bu,E-22,O,S,O,5-OH-2-Adm,H),(4-527,i-Bu,E-23,O,S,O,5-OH-2-Adm,H),(4-528,i-Bu,E-24,O,S,O,5-OH-2-Adm,H),(4-529,i-Bu,E-25,O,S,O,5-OH-2-Adm,H),(4-530,i-Bu,E-26,O,S,O,5-OH-2-Adm,H),(4-531,i-Bu,E-27,O,S,O,5-OH-2-Adm,H),(4-532,i-Bu,E-28,O,S,O,5-OH-2-Adm,H),(4-533,i-Bu,E-29,O,S,O,5-OH-2-Adm,H),(4-534,i-Bu,E-30,O,S,O,5-OH-2-Adm,H),(4-535,i-Bu,E-31,O,S,O,5-OH-2-Adm,H),(4-536,i-Bu,E-32,O,S,O,5-OH-2-Adm,H),(4-537,i-Bu,E-33,O,S,O,5-OH-2-Adm,H),(4-538,i-Bu,E-34,O,S,O,5-OH-2-Adm,H),(4-539,i-Bu,E-35,O,S,O,5-OH-2-Adm,H),(4-540,i-Bu,E-36,O,S,O,5-OH-2-Adm,H),(4-541,i-Bu,F-1,O,S,O,1-Adm,H),(4-542,i-Bu,F-2,O,S,O,1-Adm,H),(4-543,i-Bu,F-3,O,S,O,1-Adm,H),(4-544,i-Bu,F-4,O,S,O,1-Adm,H),(4-545,i-Bu,F-5,O,S,O,1-Adm,H),(4-546,i-Bu,F-6,O,S,O,1-Adm,H),(4-547,i-Bu,F-7,O,S,O,1-Adm,H),(4-548,i-Bu,F-8,O,S,O,1-Adm,H),(4-549,i-Bu,F-9,O,S,O,1-Adm,H),(4-550,i-Bu,F-10,O,S,O,1-Adm,H),(4-551,i-Bu,F-11,O,S,O,1-Adm,H),(4-552,i-Bu,F-12,O,S,O,1-Adm,H),(4-553,i-Bu,F-13,O,S,O,1-Adm,H),(4-554,i-Bu,F-14,O,S,O,1-Adm,H),(4-555,i-Bu,F-15,O,S,O,1-Adm,H),(4-556,i-Bu,F-16,O,S,O,1-Adm,H),(4-557,i-Bu,F-17,O,S,O,1-Adm,H),(4-558,i-Bu,F-18,O,S,O,1-Adm,H),(4-559,i-Bu,F-19,O,S,O,1-Adm,H),(4-560,i-Bu,F-20,O,S,O,1-Adm,H),(4-561,i-Bu,F-21,O,S,O,1-Adm,H),(4-562,i-Bu,F-22,O,S,O,1-Adm,H),(4-563,i-Bu,F-23,O,S,O,1-Adm,H),(4-564,i-Bu,F-24,O,S,O,1-Adm,H),(4-565,i-Bu,F-25,O,S,O,1-Adm,H),(4-566,i-Bu,F-26,O,S,O,1-Adm,H),(4-567,i-Bu,F-27,O,S,O,1-Adm,H),(4-568,i-Bu,F-28,O,S,O,1-Adm,H),(4-569,i-Bu,F-29,O,S,O,1-Adm,H),(4-570,i-Bu,F-30,O,S,O,1-Adm,H),(4-571,i-Bu,F-31,O,S,O,1-Adm,H),(4-572,i-Bu,F-32,O,S,O,1-Adm,H),(4-573,i-Bu,F-33,O,S,O,1-Adm,H),(4-574,i-Bu,F-34,O,S,O,1-Adm,H),(4-575,i-Bu,F-35,O,S,O,1-Adm,H),(4-576,i-Bu,F-36,O,S,O,1-Adm,H),(4-577,i-Bu,F-1,O,S,O,2-Adm,H),(4-578,i-Bu,F-2,O,S,O,2-Adm,H),(4-579,i-Bu,F-3,O,S,O,2-Adm,H),(4-580,i-Bu,F-4,O,S,O,2-Adm,H),(4-581,i-Bu,F-5,O,S,O,2-Adm,H),(4-582,i-Bu,F-6,O,S,O,2-Adm,H),(4-583,i-Bu,F-7,O,S,O,2-Adm,H),(4-584,i-Bu,F-8,O,S,O,2-Adm,H),(4-585,i-Bu,F-9,O,S,O,2-Adm,H),(4-586,i-Bu,F-10,O,S,O,2-Adm,H),(4-587,i-Bu,F-11,O,S,O,2-Adm,H),(4-588,i-Bu,F-12,O,S,O,2-Adm,H),(4-589,i-Bu,F-13,O,S,O,2-Adm,H),(4-590,i-Bu,F-14,O,S,O,2-Adm,H),(4-591,i-Bu,F-15,O,S,O,2-Adm,H),(4-592,i-Bu,F-16,O,S,O,2-Adm,H),(4-593,i-Bu,F-17,O,S,O,2-Adm,H),(4-594,i-Bu,F-18,O,S,O,2-Adm,H),(4-595,i-Bu,F-19,O,S,O,2-Adm,H),(4-596,i-Bu,F-20,O,S,O,2-Adm,H),(4-597,i-Bu,F-21,O,S,O,2-Adm,H),(4-598,i-Bu,F-22,O,S,O,2-Adm,H),(4-599,i-Bu,F-23,O,S,O,2-Adm,H),(4-600,i-Bu,F-24,O,S,O,2-Adm,H),(4-601,i-Bu,F-25,O,S,O,2-Adm,H),(4-602,i-Bu,F-26,O,S,O,2-Adm,H),(4-603,i-Bu,F-27,O,S,O,2-Adm,H),(4-604,i-Bu,F-28,O,S,O,2-Adm,H),(4-605,i-Bu,F-29,O,S,O,2-Adm,H),(4-606,i-Bu,F-30,O,S,O,2-Adm,H),(4-607,i-Bu,F-31,O,S,O,2-Adm,H),(4-608,i-Bu,F-32,O,S,O,2-Adm,H),(4-609,i-Bu,F-33,O,S,O,2-Adm,H),(4-610,i-Bu,F-34,O,S,O,2-Adm,H),(4-611,i-Bu,F-35,O,S,O,2-Adm,H),(4-612,i-Bu,F-36,O,S,O,2-Adm,H),(4-613,i-Bu,F-1,O,S,O,5-OH-2-Adm,H),(4-614,i-Bu,F-2,O,S,O,5-OH-2-Adm,H),(4-615,i-Bu,F-3,O,S,O,5-OH-2-Adm,H),(4-616,i-Bu,F-4,O,S,O,5-OH-2-Adm,H),(4-617,i-Bu,F-5,O,S,O,5-OH-2-Adm,H),(4-618,i-Bu,F-6,O,S,O,5-OH-2-Adm,H),(4-619,i-Bu,F-7,O,S,O,5-OH-2-Adm,H),(4-620,i-Bu,F-8,O,S,O,5-OH-2-Adm,H),(4-621,i-Bu,F-9,O,S, O,5-OH-2-Adm,H),(4-622,i-Bu,F-10,O,S,O,5-OH-2-Adm,H),(4-623,i-Bu,F-11,O,S,O,5-OH-2-Adm,H),(4-624,i-Bu,F-12,O,S,O,5-OH-2-Adm,H),(4-625,i-Bu,F-13,O,S,O,5-OH-2-Adm,H),(4-626,i-Bu,F-14,O,S,O,5-OH-2-Adm,H),(4-627,i-Bu,F-15,O,S,O,5-OH-2-Adm,H),(4-628,i-Bu,F-16,O,S,O,5-OH-2-Adm,H),(4-629,i-Bu,F-17,O,S,O,5-OH-2-Adm,H),(4-630,i-Bu,F-18,O,S,O,5-OH-2-Adm,H),(4-631,i-Bu,F-19,O,S,O,5-OH-2-Adm,H),(4-632,i-Bu,F-20,O,S,O,5-OH-2-Adm,H),(4-633,i-Bu,F-21,O,S,O,5-OH-2-Adm,H),(4-634,i-Bu,F-22,O,S,O,5-OH-2-Adm,H),(4-635,i-Bu,F-23,O,S,O,5-OH-2-Adm,H),(4-636,i-Bu,F-24,O,S,O,5-OH-2-Adm,H),(4-637,i-Bu,F-25,O,S,O,5-OH-2-Adm,H),(4-638,i-Bu,F-26,O,S,O,5-OH-2-Adm,H),(4-639,i-Bu,F-27,O,S,O,5-OH-2-Adm,H),(4-640,i-Bu,F-28,O,S,O,5-OH-2-Adm,H),(4-641,i-Bu,F-29,O,S,O,5-OH-2-Adm,H),(4-642,i-Bu,F-30,O,S,O,5-OH-2-Adm,H),(4-643,i-Bu,F-31,O,S,O,5-OH-2-Adm,H),(4-644,i-Bu,F-32,O,S,O,5-OH-2-Adm,H),(4-645,i-Bu,F-33,O,S,O,5-OH-2-Adm,H),(4-646,i-Bu,F-34,O,S,O,5-OH-2-Adm,H),(4-647,i-Bu,F-35,O,S,O,5-OH-2-Adm,H),(4-648,i-Bu,F-36,O,S,O,5-OH-2-Adm,H),(4-649,i-Bu,G-1,O,S,O,1-Adm,H),(4-650,i-Bu,G-2,O,S,O,1-Adm,H),(4-651,i-Bu,G-3,O,S,O,1-Adm,H),(4-652,i-Bu,G-4,O,S,O,1-Adm,H),(4-653,i-Bu,G-5,O,S,O,1-Adm,H),(4-654,i-Bu,G-6,O,S,O,1-Adm,H),(4-655,i-Bu,G-7,O,S,O,1-Adm,H),(4-656,i-Bu,G-8,O,S,O,1-Adm,H),(4-657,i-Bu,G-9,O,S,O,1-Adm,H),(4-658,i-Bu,G-1,O,S,O,2-Adm,H),(4-659,i-Bu,G-2,O,S,O,2-Adm,H),(4-660,i-Bu,G-3,O,S,O,2-Adm,H),(4-661,i-Bu,G-4,O,S,O,2-Adm,H),(4-662,i-Bu,G-5,O,S,O,2-Adm,H),(4-663,i-Bu,G-6,O,S,O,2-Adm,H),(4-664,i-Bu,G-7,O,S,O,2-Adm,H),(4-665,i-Bu,G-8,O,S,O,2-Adm,H),(4-666,i-Bu,G-9,O,S,O,2-Adm,H),(4-667,i-Bu,G-1,O,S,O,5-OH-2-Adm,H),(4-668,i-Bu,G-2,O,S,O,5-OH-2-Adm,H),(4-669,i-Bu,G-3,O,S,O,5-OH-2-Adm,H),(4-670,i-Bu,G-4,O,S,O,5-OH-2-Adm,H),(4-671,i-Bu,G-5,O,S,O,5-OH-2-Adm,H),(4-672,i-Bu,G-6,O,S,O,5-OH-2-Adm,H),(4-673,i-Bu,G-7,O,S,O,5-OH-2-Adm,H),(4-674,i-Bu,G-8,O,S,O,5-OH-2-Adm,H),(4-675,i-Bu,G-9,O,S,O,5-OH-2-Adm,H),(4-676,i-Bu,H-1,O,S,O,1-Adm,H),(4-677,i-Bu,H-2,O,S,O,1-Adm,H),(4-678,i-Bu,H-3,O,S,O,1-Adm,H),(4-679,i-Bu,H-4,O,S,O,1-Adm,H),(4-680,i-Bu,H-5,O,S,O,1-Adm,H),(4-681,i-Bu,H-6,O,S,O,1-Adm,H),(4-682,i-Bu,H-7,O,S,O,1-Adm,H),(4-683,i-Bu,H-8,O,S,O,1-Adm,H),(4-684,i-Bu,H-9,O,S,O,1-Adm,H),(4-685,i-Bu,H-1,O,S,O,2-Adm,H),(4-686,i-Bu,H-2,O,S,O,2-Adm,H),(4-687,i-Bu,H-3,O,S,O,2-Adm,H),(4-688,i-Bu,H-4,O,S,O,2-Adm,H),(4-689,i-Bu,H-5,O,S,O,2-Adm,H),(4-690,i-Bu,H-6,O,S,O,2-Adm,H),(4-691,i-Bu,H-7,O,S,O,2-Adm,H),(4-692,i-Bu,H-8,O,S,O,2-Adm,H),(4-693,i-Bu,H-9,O,S,O,2-Adm,H),(4-694,i-Bu,H-1,O,S,O,5-OH-2-Adm,H),(4-695,i-Bu,H-2,O,S,O,5-OH-2-Adm,H),(4-696,i-Bu,H-3,O,S,O,5-OH-2-Adm,H),(4-697,i-Bu,H-4,O,S,O,5-OH-2-Adm,H),(4-698,i-Bu,H-5,O,S,O,5-OH-2-Adm,H),(4-699,i-Bu,H-6,O,S,O,5-OH-2-Adm,H),(4-700,i-Bu,H-7,O,S,O,5-OH-2-Adm,H),(4-701,i-Bu,H-8,O,S,O,5-OH-2-Adm,H),(4-702,i-Bu,H-9,O,S,O,5-OH-2-Adm,H),(4-703,i-Bu,I-1,O,S,O,1-Adm,H),(4-704,i-Bu,I-2,O,S,O,1-Adm,H),(4-705,i-Bu,I-3,O,S,O,1-Adm,H),(4-706,i-Bu,I-4,O,S,O,1-Adm,H),(4-707,i-Bu,I-5,O,S,O,1-Adm,H),(4-708,i-Bu,I-6,O,S,O,1-Adm,H),(4-709,i-Bu,I-7,O,S,O,1-Adm,H),(4-710,i-Bu,I-8,O,S,O,1-Adm,H),(4-711,i-Bu,I-9,O,S,O,1-Adm,H),(4-712,i-Bu,I-1,O,S,O,2-Adm,H),(4-713,i-Bu,I-2,O,S,O,2-Adm,H),(4-714,i-Bu,I-3,O,S,O,2-Adm,H),(4-715,i-Bu,I-4,O,S,O,2-Adm,H),(4-716,i-Bu,I-5,O,S,O,2-Adm,H),(4-717,i-Bu,I-6,O,S,O,2-Adm,H),(4-718,i-Bu,I-7,O,S,O,2-Adm,H),(4-719,i-Bu,I-8,O,S,O,2-Adm,H),(4-720,i-Bu,I-9,O,S,O,2-Adm,H),(4-721,i-Bu,I-1,O,S,O,5-OH-2-Adm,H),(4-722,i-Bu,I-2,O,S,O,5-OH-2-Adm,H),(4-723,i-Bu,I-3,O,S,O,5-OH-2-Adm,H),(4-724,i-Bu,I-4,O,S,O,5-OH-2-Adm,H), (4-725,i-Bu,I-5,O,S,

O,5-OH-2-Adm,H),(4-726,i-Bu,I-6,O,S,O,5-OH-2-Adm, H),(4-727,i-Bu,I-7,O,S,O,5-OH-2-Adm,H),(4-728,i-Bu,I-8, O,S,O,5-OH-2-Adm,H),(4-729,i-Bu,I-9,O,S,O,5-OH-2-Adm,H),(4-730,i-Bu,J-1,O,S,O,1-Adm,H),(4-731,i-Bu,J-2, O,S,O,1-Adm,H),(4-732,i-Bu,J-3,O,S,O,1-Adm,H),(4-733, i-Bu,J-4,O,S,O,1-Adm,H),(4-734,i-Bu,J-5,O,S,O,1-Adm, H),(4-735,i-Bu,J-6,O,S,O,1-Adm,H),(4-736,i-Bu,J-7,O,S, O,1-Adm,H),(4-737,i-Bu,J-8,O,S,O,1-Adm,H),(4-738,i-Bu, J-9,O,S,O,1-Adm,H),(4-739,i-Bu,J-1,O,S,O,2-Adm,H),(4-740,i-Bu,J-2,O,S,O,2-Adm,H),(4-741,i-Bu,J-3,O,S,O,2-Adm,H),(4-742,i-Bu,J-4,O,S,O,2-Adm,H),(4-743,i-Bu,J-5, O,S,O,2-Adm,H),(4-744,i-Bu,J-6,O,S,O,2-Adm,H),(4-745, i-Bu,J-7,O,S,O,2-Adm,H),(4-746,i-Bu,J-8,O,S,O,2-Adm, H),(4-747,i-Bu,J-9,O,S,O,2-Adm,H),(4-748,i-Bu,J-1,O,S, O,5-OH-2-Adm,H),(4-749,i-Bu,J-2,O,S,O,5-OH-2-Adm, H),(4-750,i-Bu,J-3,O,S,O,5-OH-2-Adm,H),(4-751,i-Bu,J-4, O,S,O,5-OH-2-Adm,H),(4-752,i-Bu,J-5,O,S,O,5-OH-2-Adm,H),(4-753,i-Bu,J-6,O,S,O,5-OH-2-Adm,H),(4-754,i-Bu,J-7,O,S,O,5-OH-2-Adm,H),(4-755,i-Bu,J-8,O,S,O,5-OH-2-Adm,H),(4-756,i-Bu,J-9,O,S,O,5-OH-2-Adm,H),(4-757,i-Bu,K-1,O,S,O,1-Adm,H),(4-758,i-Bu,K-2,O,S,O,1-Adm,H),(4-759,i-Bu,K-3,O,S,O,1-Adm,H),(4-760,i-Bu,K-4,O,S,O,1-Adm,H),(4-761,i-Bu,K-5,O,S,O,1-Adm,H),(4-762,i-Bu,K-6,O,S,O,1-Adm,H),(4-763,i-Bu,K-7,O,S,O,1-Adm,H),(4-764,i-Bu,K-8,O,S,O,1-Adm,H),(4-765,i-Bu,K-9,O,S,O,1-Adm,H),(4-766,i-Bu,K-1,O,S,O,2-Adm,H),(4-767,i-Bu,K-2,O,S,O,2-Adm,H),(4-768,i-Bu,K-3,O,S,O,2-Adm,H),(4-769,i-Bu,K-4,O,S,O,2-Adm,H),(4-770,i-Bu,K-5,O,S,O,2-Adm,H),(4-771,i-Bu,K-6,O,S,O,2-Adm,H),(4-772,i-Bu,K-7,O,S,O,2-Adm,H),(4-773,i-Bu,K-8,O,S,O,2-Adm,H),(4-774,i-Bu,K-9,O,S,O,2-Adm,H),(4-775,i-Bu,K-1,O,S,O,5-OH-2-Adm,H),(4-776,i-Bu,K-2,O,S,O,5-OH-2-Adm,H),(4-777,i-Bu,K-3,O,S,O,5-OH-2-Adm,H),(4-778,i-Bu,K-4,O,S,O,5-OH-2-Adm,H),(4-779,i-Bu,K-5,O,S,O,5-OH-2-Adm,H),(4-780,i-Bu,K-6,O,S,O,5-OH-2-Adm,H),(4-781,i-Bu,K-7,O,S,O,5-OH-2-Adm,H),(4-782,i-Bu,K-8,O,S, O,5-OH-2-Adm,H),(4-783,i-Bu,K-9,O,S,O,5-OH-2-Adm, H)

(Compound No., $R^2,R^3,X,Y,Z,R^4,R^5$)=(5-1,i-Pro,A-1,O, S,O,1-Adm,H),(5-2,i-Pro,A-2,O,S,O,1-Adm,H),(5-3,i-Pro, A-3,O,S,O,1-Adm,H),(5-4,i-Pro,A-4,O,S,O,1-Adm,H),(5-5, i-Pro,A-5,O,S,O,1-Adm,H),(5-6,i-Pro,A-6,O,S,O,1-Adm, H),(5-7,i-Pro,A-7,O,S,O,1-Adm,H),(5-8,i-Pro,A-8,O,S,O,1-Adm,H),(5-9,i-Pro,A-9,O,S,O,1-Adm,H),(5-10,i-Pro,A-10, O,S,O,1-Adm,H),(5-11,i-Pro,A-13,O,S,O,1-Adm,H),(5-12, i-Pro,A-12,O,S,O,1-Adm,H),(5-13,i-Pro,A-13,O,S,O,1-Adm,H),(5-14,i-Pro,A-14,O,S,O,1-Adm,H),(5-15,i-Pro,A-15,O,S,O,1-Adm,H),(5-16,i-Pro,A-16,O,S,O,1-Adm,H),(5-17,i-Pro,A-17,O,S,O,1-Adm,H),(5-18,i-Pro,A-18,O,S,O,1-Adm,H),(5-19,i-Pro,A-19,O,S,O,1-Adm,H),(5-20,i-Pro,A-20,O,S,O,1-Adm,H),(5-21,i-Pro,A-21,O,S,O,1-Adm,H),(5-22,i-Pro,A-22,O,S,O,1-Adm,H),(5-23,i-Pro,A-23,O,S,O,1-Adm,H),(5-24,i-Pro,A-24,O,S,O,1-Adm,H),(5-25,i-Pro,A-25,O,S,O,1-Adm,H),(5-26,i-Pro,A-26,O,S,O,1-Adm,H),(5-27,i-Pro,A-27,O,S,O,1-Adm,H),(5-28,i-Pro,A-28,O,S,O,1-Adm,H),(5-29,i-Pro,A-29,O,S,O,1-Adm,H),(5-30,i-Pro,A-30,O,S,O,1-Adm,H),(5-31,i-Pro,A-31,O,S,O,1-Adm,H),(5-32,i-Pro,A-32,O,S,O,1-Adm,H),(5-33,i-Pro,A-33,O,S,O,1-Adm,H),(5-34,i-Pro,A-34,O,S,O,1-Adm,H),(5-35,i-Pro,A-35,O,S,O,1-Adm,H),(5-36,i-Pro,A-36,O,S,O,1-Adm,H),(5-37,i-Pro,A-1,O,S,O,2-Adm,H),(5-38,i-Pro,A-2,O,S,O,2-Adm,H),(5-39,i-Pro,A-3,O,S,O,2-Adm,H),(5-40,i-Pro,A-4, O,S,O,2-Adm,H),(5-41,i-Pro,A-5,O,S,O,2-Adm,H),(5-42,i-Pro,A-6,O,S,O,2-Adm,H),(5-43,i-Pro,A-7,O,S,O,2-Adm, H),(5-44,i-Pro,A-8,O,S,O,2-Adm,H),(5-45,i-Pro,A-9,O,S, O,2-Adm,H),(5-46,i-Pro,A-10,O,S,O,2-Adm,H),(5-47,i-Pro,A-11,O,S,O,2-Adm,H),(5-48,i-Pro,A-12,O,S,O,2-Adm, H),(5-49,i-Pro,A-13,O,S,O,2-Adm,H),(5-50,i-Pro,A-14,O, S,O,2-Adm,H),(5-51,i-Pro,A-15,O,S,O,2-Adm,H),(5-52,i-Pro,A-16,O,S,O,2-Adm,H),(5-53,i-Pro,A-17,O,S,O,2-Adm, H),(5-54,i-Pro,A-18,O,S,O,2-Adm,H),(5-55,i-Pro,A-19,O, S,O,2-Adm,H),(5-56,i-Pro,A-20,O,S,O,2-Adm,H),(5-57,i-Pro,A-21,O,S,O,2-Adm,H),(5-58,i-Pro,A-22,O,S,O,2-Adm, H),(5-59,i-Pro,A-23,O,S,O,2-Adm,H),(5-60,i-Pro,A-24,O, S,O,2-Adm,H),(5-61,i-Pro,A-25,O,S,O,2-Adm,H),(5-62,i-Pro,A-26,O,S,O,2-Adm,H),(5-63,i-Pro,A-27,O,S,O,2-Adm, H),(5-64,i-Pro,A-28,O,S,O,2-Adm,H),(5-65,i-Pro,A-29,O, S,O,2-Adm,H),(5-66,i-Pro,A-30,O,S,O,2-Adm,H),(5-67,i-Pro,A-31,O,S,O,2-Adm,H),(5-68,i-Pro,A-32,O,S,O,2-Adm, H),(5-69,i-Pro,A-33,O,S,O,2-Adm,H),(5-70,i-Pro,A-34,O, S,O,2-Adm,H),(5-71,i-Pro,A-35,O,S,O,2-Adm,H),(5-72,i-Pro,A-36,O,S,O,2-Adm,H),(5-73,i-Pro,A-1,O,S,O,5-OH-2-Adm,H),(5-74,i-Pro,A-2,O,S,O,5-OH-2-Adm,H),(5-75,i-Pro,A-3,O,S,O,5-OH-2-Adm,H),(5-76,i-Pro,A-4,O,S,O,5-OH-2-Adm,H),(5-77,i-Pro,A-5,O,S,O,5-OH-2-Adm,H),(5-78,i-Pro,A-6,O,S,O,5-OH-2-Adm,H),(5-79,i-Pro,A-7,O,S, O,5-OH-2-Adm,H),(5-80,i-Pro,A-8,O,S,O,5-OH-2-Adm, H),(5-81,i-Pro,A-9,O,S,O,5-OH-2-Adm,H),(5-82,i-Pro,A-10,O,S,O,5-OH-2-Adm,H),(5-83,i-Pro,A-11,O,S,O,5-OH-2-Adm,H),(5-84,i-Pro,A-12,O,S,O,5-OH-2-Adm,H),(5-85, i-Pro,A-13,O,S,O,5-OH-2-Adm,H),(5-86,i-Pro,A-14,O,S, O,5-OH-2-Adm,H),(5-87,i-Pro,A-15,O,S,O,5-OH-2-Adm, H),(5-88,i-Pro,A-16,O,S,O,5-OH-2-Adm,H),(5-89,i-Pro,A-17,O,S,O,5-OH-2-Adm,H),(5-90,i-Pro,A-18,O,S,O,5-OH-2-Adm,H),(5-91,i-Pro,A-19,O,S,O,5-OH-2-Adm,H),(5-92, i-Pro,A-20,O,S,O,5-OH-2-Adm,H),(5-93,i-Pro,A-21,O,S, O,5-OH-2-Adm,H),(5-94,i-Pro,A-22,O,S,O,5-OH-2-Adm, H),(5-95,i-Pro,A-23,O,S,O,5-OH-2-Adm,H),(5-96,i-Pro,A-24,O,S,O,5-OH-2-Adm,H),(5-97,i-Pro,A-25,O,S,O,5-OH-2-Adm,H),(5-98,i-Pro,A-26,O,S,O,5-OH-2-Adm,H),(5-99, i-Pro,A-27,O,S,O,5-OH-2-Adm,H),(5-100,i-Pro,A-28,O,S, O,5-OH-2-Adm,H),(5-101,i-Pro,A-29,O,S,O,5-OH-2-Adm, H),(5-102,i-Pro,A-30,O,S,O,5-OH-2-Adm,H),(5-103,i-Pro, A-31,O,S,O,5-OH-2-Adm,H),(5-104,i-Pro,A-32,O,S,O,5-OH-2-Adm,H),(5-105,i-Pro,A-33,O,S,O,5-OH-2-Adm,H), (5-106,i-Pro,A-34,O,S,O,5-OH-2-Adm,H),(5-107,i-Pro,A-35,O,S,O,5-OH-2-Adm,H),(5-108,i-Pro,A-36,O,S,O,5-OH-2-Adm,H),(5-119,i-Pro,B-1,O,S,O,1-Adm,H),(5-110,i-Pro, B-2,O,S,O,1-Adm,H),(5-111,i-Pro,B-3,O,S,O,1-Adm,H), (5-112,i-Pro,B-4,O,S,O,1-Adm,H),(5-113,i-Pro,B-5,O,S, O,1-Adm,H),(5-114,i-Pro,B-6,O,S,O,1-Adm,H),(5-115,i-Pro, B-7,O,S,O,1-Adm,H),(5-116,i-Pro,B-8,O,S,O,1-Adm,H), (5-117,i-Pro,B-9,O,S,O,1-Adm,H),(5-118,i-Pro,B-11,O,S, O,1-Adm,H),(5-119,i-Pro,B-11,O,S,O,1-Adm,H),(5-120,i-Pro,B-12,O,S,O,1-Adm,H),(5-121,i-Pro,B-13,O,S,O,1-Adm,H),(5-122,i-Pro,B-14,O,S,O,1-Adm,H),(5-123,i-Pro, B-15,O,S,O,1-Adm,H),(5-124,i-Pro,B-16,O,S,O,1-Adm,H), (5-125,i-Pro,B-17,O,S,O,1-Adm,H),(5-126,i-Pro,B-18,O,S, O,1-Adm,H),(5-127,i-Pro,B-19,O,S,O,1-Adm,H),(5-128,i-Pro,B-20,O,S,O,1-Adm,H),(5-129,i-Pro,B-21,O,S,O,1-Adm,H),(5-130,i-Pro,B-22,O,S,O,1-Adm,H),(5-131,i-Pro, B-23,O,S,O,1-Adm,H),(5-132,i-Pro,B-24,O,S,O,1-Adm,H), (5-133,i-Pro,B-25,O,S,O,1-Adm,H),(5-134,i-Pro,B-26,O,S, O,1-Adm,H),(5-13,i-Pro,B-27,O,S,O,1-Adm,H),(5-136,i-Pro,B-28,O,S,O,1-Adm,H),(5-137,i-Pro,B-29,O,S,O,1-Adm,H),(5-138,i-Pro,B-30,O,S,O,1-Adm,H),(5-139,i-Pro, B-31,O,S,O,1-Adm,H),(5-140,i-Pro,B-32,O,S,O,1-Adm,H), (5-141,i-Pro,B-33,O,S,O,1-Adm,H),(5-142,i-Pro,B-34,O,S, O,1-Adm,H),(5-143,i-Pro,B-35,O,S,O,1-Adm,H),(5-144,i-Pro,B-36,O,S,O,1-Adm,H),(5-145,i-Pro,B-1,O,S,O,2-Adm, H),(5-146,i-Pro,B-2,O,S,O,2-Adm,H),(5-147,i-Pro,B-3,O, S,O,2-Adm,H),(5-148,i-Pro,B-4,O,S,O,2-Adm,H),(5-149,i-Pro,B-5,O,S,O,2-Adm,H),(5-150,i-Pro,B-6,O,S,O,2-Adm, H),(5-151,i-Pro,B-7,O,S,O,2-Adm,H), (5-152,i-Pro,B-8,O, S,O,2-Adm,H),(5-153,i-Pro,B-9,O,S,O,2-Adm,H),(5-154,i-Pro,B-10,O,S,O,2-Adm,H),(5-155,i-Pro,B-11,O,S,O,2-Adm,H),(5-156,i-Pro,B-12,O,S,O,2-Adm,H),(5-157,i-Pro,B-13,O,S,O,2-Adm,H),(5-158,i-Pro,B-14,O,S,O,2-Adm,H),(5-159,i-Pro,B-15,O,S,O,2-Adm,H),(5-160,i-Pro,B-16,O,S,O,2-Adm,H),(5-161,i-Pro,B-17,O,S,O,2-Adm,H),(5-162,i-Pro,B-18,O,S,O,2-Adm,H),(5-163,i-Pro,B-119,O,S,O,2-Adm,H),(5-164,i-Pro,B-20,O,S,O,2-Adm,H),(5-165,i-Pro,B-21,O,S,O,2-Adm,H),(5-166,i-Pro,B-22,O,S,O,2-Adm,H),(5-167,i-Pro,B-23,O,S,O,2-Adm,H),(5-168,i-Pro,B-24,O,S,O,2-Adm,H),(5-169,i-Pro,B-25,O,S,O,2-Adm,H),(5-170,i-Pro,B-26,O,S,O,2-Adm,H),(5-171,i-Pro,B-27,O,S,O,2-Adm,H),(5-172,i-Pro,B-28,O,S,O,2-Adm,H),(5-173,i-Pro,B-29,O,S,O,2-Adm,H),(5-174,i-Pro,B-30,O,S,O,2-Adm,H),(5-175,i-Pro,B-31,O,S,O,2-Adm,H),(5-176,i-Pro,B-32,O,S,O,2-Adm,H),(5-177,i-Pro,B-33,O,S,O,2-Adm,H),(5-178,i-Pro,B-34,O,S,O,2-Adm,H),(5-179,i-Pro,B-35,O,S,O,2-Adm,H),(5-180,i-Pro,B-36,O,S,O,2-Adm,H),(5-181,i-Pro,B-11,O,S,O,5-OH-2-Adm,H),(5-182,i-Pro,B-2,O,S,O,5-OH-2-Adm,H),(5-183,i-Pro,B-3,O,S,O,5-OH-2-Adm,H),(5-184,i-Pro,B-4,O,S,O,5-OH-2-Adm,H),(5-185,i-Pro,B-5,O,S,O,5-OH-2-Adm,H),(5-186,i-Pro,B-6,O,S,O,5-OH-2-Adm,H),(5-187,i-Pro,B-7,O,S,O,5-OH-2-Adm,H),(5-188,i-Pro,B-8,O,S,O,5-OH-2-Adm,H),(5-189,i-Pro,B-9,O,S,O,5-OH-2-Adm,H),(5-190,i-Pro,B-10,O,S,O,5-OH-2-Adm,H),(5-191,i-Pro,B-11,O,S,O,5-OH-2-Adm,H),(5-192,i-Pro,B-12,O,S,O,5-OH-2-Adm,H),(5-193,i-Pro,B-13,O,S,O,5-OH-2-Adm,H),(5-194,i-Pro,B-14,O,S,O,5-OH-2-Adm,H),(5-195,i-Pro,B-15,O,S,O,5-OH-2-Adm,H),(5-196,i-Pro,B-16,O,S,O,5-OH-2-Adm,H),(5-197,i-Pro,B-17,O,S,O,5-OH-2-Adm,H),(5-198,i-Pro,B-18,O,S,O,5-OH-2-Adm,H),(5-1199,i-Pro,B-119,O,S,O,5-OH-2-Adm,H),(5-200,i-Pro,B-20,O,S,O,5-OH-2-Adm,H),(5-201,i-Pro,B-21,O,S,O,5-OH-2-Adm,H),(5-202,i-Pro,B-22,O,S,O,5-OH-2-Adm,H),(5-203,i-Pro,B-23,O,S,O,5-OH-2-Adm,H),(5-204,i-Pro,B-24,O,S,O,5-OH-2-Adm,H),(5-205,i-Pro,B-25,O,S,O,5-OH-2-Adm,H),(5-206,i-Pro,B-26,O,S,O,5-OH-2-Adm,H),(5-207,i-Pro,B-27,O,S,O,5-OH-2-Adm,H),(5-208,i-Pro,B-28,O,S,O,5-OH-2-Adm,H),(5-209,i-Pro,B-29,O,S,O,5-OH-2-Adm,H),(5-210,i-Pro,B-30,O,S,O,5-OH-2-Adm,H),(5-211,i-Pro,B-31,O,S,O,5-OH-2-Adm,H),(5-212,i-Pro,B-32,O,S,O,5-OH-2-Adm,H),(5-213,i-Pro,B-33,O,S,O,5-OH-2-Adm,H),(5-214,i-Pro,B-34,O,S,O,5-OH-2-Adm,H),(5-215,i-Pro,B-35,O,S,O,5-OH-2-Adm,H),(5-216,i-Pro,B-36,O,S,O,5-OH-2-Adm,H),(5-217,i-Pro,C-1,O,S,O,1-Adm,H),(5-218,i-Pro,C-2,O,S,O,1-Adm,H),(5-219,i-Pro,C-3,O,S,O,1-Adm,H),(5-220,i-Pro,C-4,O,S,O,1-Adm,H),(5-221,i-Pro,C-5,O,S,O,1-Adm,H),(5-222,i-Pro,C-6,O,S,O,1-Adm,H),(5-223,i-Pro,C-7,O,S,O,1-Adm,H),(5-224,i-Pro,C-8,O,S,O,1-Adm,H),(5-225,i-Pro,C-9,O,S,O,1-Adm,H),(5-226,i-Pro,C-11,O,S,O,1-Adm,H),(5-227,i-Pro,C-11,O,S,O,1-Adm,H),(5-228,i-Pro,C-12,O,S,O,1-Adm,H),(5-229,i-Pro,C-13,O,S,O,1-Adm,H),(5-230,i-Pro,C-14,O,S,O,1-Adm,H),(5-231,i-Pro,C-15,O,S,O,1-Adm,H),(5-232,i-Pro,C-16,O,S,O,1-Adm,H),(5-233,i-Pro,C-17,O,S,O,1-Adm,H),(5-234,i-Pro,C-18,O,S,O,1-Adm,H),(5-235,i-Pro,C-19,O,S,O,1-Adm,H),(5-236,i-Pro,C-20,O,S,O,1-Adm,H),(5-237,i-Pro,C-21,O,S,O,1-Adm,H),(5-238,i-Pro,C-22,O,S,O,1-Adm,H),(5-239,i-Pro,C-23,O,S,O,1-Adm,H),(5-240,i-Pro,C-24,O,S,O,1-Adm,H),(5-241,i-Pro,C-25,O,S,O,1-Adm,H),(5-242,i-Pro,C-26,O,S,O,1-Adm,H),(5-243,i-Pro,C-27,O,S,O,1-Adm,H),(5-244,i-Pro,C-28,O,S,O,1-Adm,H),(5-245,i-Pro,C-29,O,S,O,1-Adm,H),(5-246,i-Pro,C-30,O,S,O,1-Adm,H),(5-247,i-Pro,C-31,O,S,O,1-Adm,H),(5-248,i-Pro,C-32,O,S,O,1-Adm,H),(5-249,i-Pro,C-33,O,S,O,1-Adm,H),(5-250,i-Pro,C-34,O,S,O,1-Adm,H),(5-251,i-Pro,C-35,O,S,O,1-Adm,H),(5-252,i-Pro,C-36,O,S,O,1-Adm,H), (5-253,i-Pro,C-1,O,S,O,2-Adm,H),(5-254,i-Pro,C-2,O,S,O,2-Adm,H),(5-255,i-Pro,C-3,O,S,O,2-Adm,H),(5-256,i-Pro,C-4,O,S,O,2-Adm,H),(5-257,i-Pro,C-5,O,S,O,2-Adm,H),(5-258,i-Pro,C-6,O,S,O,2-Adm,H),(5-259,i-Pro,C-7,O,S,O,2-Adm,H),(5-260,i-Pro,C-8,O,S,O,2-Adm,H),(5-261,i-Pro,C-9,O,S,O,2-Adm,H),(5-262,i-Pro,C-10,O,S,O,2-Adm,H),(5-263,i-Pro,C-11,O,S,O,2-Adm,H),(5-264,i-Pro,C-12,O,S,O,2-Adm,H),(5-265,i-Pro,C-13,O,S,O,2-Adm,H),(5-266,i-Pro,C-14,O,S,O,2-Adm,H),(5-267,i-Pro,C-15,O,S,O,2-Adm,H),(5-268,i-Pro,C-16,O,S,O,2-Adm,H),(5-269,i-Pro,C-17,O,S,O,2-Adm,H),(5-270,i-Pro,C-18,O,S,O,2-Adm,H),(5-271,i-Pro,C-19,O,S,O,2-Adm,H),(5-272,i-Pro,C-20,O,S,O,2-Adm,H),(5-273,i-Pro,C-21,O,S,O,2-Adm,H),(5-274,i-Pro,C-22,O,S,O,2-Adm,H),(5-275,i-Pro,C-23,O,S,O,2-Adm,H),(5-276,i-Pro,C-24,O,S,O,2-Adm,H),(5-277,i-Pro,C-25,O,S,O,2-Adm,H),(5-278,i-Pro,C-26,O,S,O,2-Adm,H),(5-279,i-Pro,C-27,O,S,O,2-Adm,H),(5-280,i-Pro,C-28,O,S,O,2-Adm,H),(5-281,i-Pro,C-29,O,S,O,2-Adm,H),(5-282,i-Pro,C-30,O,S,O,2-Adm,H),(5-283,i-Pro,C-31,O,S,O,2-Adm,H),(5-284,i-Pro,C-32,O,S,O,2-Adm,H),(5-285,i-Pro,C-33,O,S,O,2-Adm,H),(5-286,i-Pro,C-34,O,S,O,2-Adm,H),(5-287,i-Pro,C-35,O,S,O,2-Adm,H),(5-288,i-Pro,C-36,O,S,O,2-Adm,H),(5-289,i-Pro,C-1,O,S,O,5-OH-2-Adm,H),(5-290,i-Pro,C-2,O,S,O,5-OH-2-Adm,H),(5-291,i-Pro,C-3,O,S,O,5-OH-2-Adm,H),(5-292,i-Pro,C-4,O,S,O,5-OH-2-Adm,H),(5-293,i-Pro,C-5,O,S,O,5-OH-2-Adm,H),(5-294,i-Pro,C-6,O,S,O,5-OH-2-Adm,H),(5-295,i-Pro,C-7,O,S,O,5-OH-2-Adm,H),(5-296,i-Pro,C-8,O,S,O,5-OH-2-Adm,H),(5-297,i-Pro,C-9,O,S,O,5-OH-2-Adm,H),(5-298,i-Pro,C-10,O,S,O,5-OH-2-Adm,H),(5-299,i-Pro,C-11,O,S,O,5-OH-2-Adm,H),(5-300,i-Pro,C-12,O,S,O,5-OH-2-Adm,H),(5-301,i-Pro,C-13,O,S,O,5-OH-2-Adm,H),(5-302,i-Pro,C-14,O,S,O,5-OH-2-Adm,H),(5-303,i-Pro,C-15,O,S,O,5-OH-2-Adm,H),(5-304,i-Pro,C-16,O,S,O,5-OH-2-Adm,H),(5-305,i-Pro,C-17,O,S,O,5-OH-2-Adm,H),(5-306,i-Pro,C-18,O,S,O,5-OH-2-Adm,H),(5-307,i-Pro,C-19,O,S,O,5-OH-2-Adm,H),(5-308,i-Pro,C-20,O,S,O,5-OH-2-Adm,H),(5-309,i-Pro,C-21,O,S,O,5-OH-2-Adm,H),(5-310,i-Pro,C-22,O,S,O,5-OH-2-Adm,H),(5-311,i-Pro,C-23,O,S,O,5-OH-2-Adm,H),(5-312,i-Pro,C-24,O,S,O,5-OH-2-Adm,H),(5-313,i-Pro,C-25,O,S,O,5-OH-2-Adm,H),(5-314,i-Pro,C-26,O,S,O,5-OH-2-Adm,H),(5-315,i-Pro,C-27,O,S,O,5-OH-2-Adm,H),(5-316,i-Pro,C-28,O,S,O,5-OH-2-Adm,H),(5-317,i-Pro,C-29,O,S,O,5-OH-2-Adm,H),(5-318,i-Pro,C-30,O,S,O,5-OH-2-Adm,H),(5-319,i-Pro,C-31,O,S,O,5-OH-2-Adm,H),(5-320,i-Pro,C-32,O,S,O,5-OH-2-Adm,H),(5-321,i-Pro,C-33,O,S,O,5-OH-2-Adm,H),(5-322,i-Pro,C-34,O,S,O,5-OH-2-Adm,H),(5-323,i-Pro,C-35,O,S,O,5-OH-2-Adm,H),(5-324,i-Pro,C-36,O,S,O,5-OH-2-Adm,H),(5-325,i-Pro,D-1,O,S,O,1-Adm,H),(5-326,i-Pro,D-2,O,S,O,1-Adm,H),(5-327,i-Pro,D-3,O,S,O,1-Adm,H),(5-328,i-Pro,D-4,O,S,O,1-Adm,H),(5-329,i-Pro,D-5,O,S,O,1-Adm,H),(5-330,i-Pro,D-6,O,S,O,1-Adm,H),(5-331,i-Pro,D-7,O,S,O,1-Adm,H),(5-332,i-Pro,D-8,O,S,O,1-Adm,H),(5-333,i-Pro,D-9,O,S,O,1-Adm,H),(5-334,i-Pro,D-10,O,S,O,1-Adm,H),(5-335,i-Pro,D-11,O,S,O,1-Adm,H),(5-336,i-Pro,D-12,O,S,O,1-Adm,H),(5-337,i-Pro,D-13,O,S,O,1-Adm,H),(5-338,i-Pro,D-14,O,S,O,1-Adm,H),(5-339,i-Pro,D-15,O,S,O,1-Adm,H),(5-340,i-Pro,D-16,O,S,O,1-Adm,H),(5-341,i-Pro,D-17,O,S,O,1-Adm,H),(5-342,i-Pro,D-18,O,S,O,1-Adm,H),(5-343,i-Pro,D-19,O,S,O,1-Adm,H),(5-344,i-Pro,D-20,O,S,O,1-Adm,H),(5-345,i-Pro,D-21,O,S,O,1-Adm,H),(5-346,i-Pro,D-22,O,S,O,1-Adm,H),(5-347,i-Pro,D-23,O,S,O,1-Adm,H),(5-348,i-Pro,D-24,O,S,O,1-Adm,H),(5-349,i-Pro,D-25,O,S,O,1-Adm,H),(5-350,i-Pro,D-26,O,S,O,1-Adm,H),(5-351,i-Pro,D-27,O,S,O,1-Adm,H),(5-352,i-Pro,D-28,O,S,O,1-Adm,H),(5-353,i-Pro,D-29,O,S,O,1-Adm,H),(5-354,i-Pro,D-30,O,S,O,1-Adm,H), (5-355,i-Pro,D-31, O,S,O,1-Adm,H),(5-356,i-Pro,D-32,O,S,O,1-Adm,H),(5-357,i-Pro,D-33,O,S,O,1-Adm,H),(5-358,i-Pro,D-34,O,S,O,1-Adm,H),(5-359,i-Pro,D-35,O,S,O,1-Adm,H),(5-360,i-Pro,D-36,O,S,O,1-Adm,H),(5-361,i-Pro,D-1,O,S,O,2-Adm,H),(5-362,i-Pro,D-2,O,S,O,2-Adm,H),(5-363,i-Pro,D-3,O,S,O,2-Adm,H),(5-364,i-Pro,D-4,O,S,O,2-Adm,H),(5-365,i-Pro,D-5,O,S,O,2-Adm,H),(5-366,i-Pro,D-6,O,S,O,2-Adm,H),(5-367,i-Pro,D-7,O,S,O,2-Adm,H),(5-368,i-Pro,D-8,O,S,O,2-Adm,H),(5-369,i-Pro,D-9,O,S,O,2-Adm,H),(5-370,i-Pro,D-10,O,S,O,2-Adm,H),(5-371,i-Pro,D-11,O,S,O,2-Adm,H),(5-372,i-Pro,D-12,O,S,O,2-Adm,H),(5-373,i-Pro,D-13,O,S,O,2-Adm,H),(5-374,i-Pro,D-14,O,S,O,2-Adm,H),(5-375,i-Pro,D-15,O,S,O,2-Adm,H),(5-376,i-Pro,D-16,O,S,O,2-Adm,H),(5-377,i-Pro,D-17,O,S,O,2-Adm,H),(5-378,i-Pro,D-18,O,S,O,2-Adm,H),(5-379,i-Pro,D-19,O,S,O,2-Adm,H),(5-380,i-Pro,D-20,O,S,O,2-Adm,H),(5-381,i-Pro,D-21,O,S,O,2-Adm,H),(5-382,i-Pro,D-22,O,S,O,2-Adm,H),(5-383,i-Pro,D-23,O,S,O,2-Adm,H),(5-384,i-Pro,D-24,O,S,O,2-Adm,H),(5-385,i-Pro,D-25,O,S,O,2-Adm,H),(5-386,i-Pro,D-26,O,S,O,2-Adm,H),(5-387,i-Pro,D-27,O,S,O,2-Adm,H),(5-388,i-Pro,D-28,O,S,O,2-Adm,H),(5-389,i-Pro,D-29,O,S,O,2-Adm,H),(5-390,i-Pro,D-30,O,S,O,2-Adm,H),(5-391,i-Pro,D-31,O,S,O,2-Adm,H),(5-392,i-Pro,D-32,O,S,O,2-Adm,H),(5-393,i-Pro,D-33,O,S,O,2-Adm,H),(5-394,i-Pro,D-34,O,S,O,2-Adm,H),(5-395,i-Pro,D-35,O,S,O,2-Adm,H),(5-396,i-Pro,D-36,O,S,O,2-Adm,H),(5-397,i-Pro,D-1,O,S,O,5-OH-2-Adm,H),(5-398,i-Pro,D-2,O,S,O,5-OH-2-Adm,H),(5-399,i-Pro,D-3,O,S,O,5-OH-2-Adm,H),(5-400,i-Pro,D-4,O,S,O,5-OH-2-Adm,H),(5-401,i-Pro,D-5,O,S,O,5-OH-2-Adm,H),(5-402,i-Pro,D-6,O,S,O,5-OH-2-Adm,H),(5-403,i-Pro,D-7,O,S,O,5-OH-2-Adm,H),(5-404,i-Pro,D-8,O,S,O,5-OH-2-Adm,H),(5-405,i-Pro,D-9,O,S,O,5-OH-2-Adm,H),(5-406,i-Pro,D-10,O,S,O,5-OH-2-Adm,H),(5-407,i-Pro,D-11,O,S,O,5-OH-2-Adm,H),(5-408,i-Pro,D-12,O,S,O,5-OH-2-Adm,H),(5-409,i-Pro,D-13,O,S,O,5-OH-2-Adm,H),(5-410,i-Pro,D-14,O,S,O,5-OH-2-Adm,H),(5-411,i-Pro,D-15,O,S,O,5-OH-2-Adm,H),(5-412,i-Pro,D-16,O,S,O,5-OH-2-Adm,H),(5-413,i-Pro,D-17,O,S,O,5-OH-2-Adm,H),(5-414,i-Pro,D-18,O,S,O,5-OH-2-Adm,H),(5-415,i-Pro,D-19,O,S,O,5-OH-2-Adm,H),(5-416,i-Pro,D-20,O,S,O,5-OH-2-Adm,H),(5-417,i-Pro,D-21,O,S,O,5-OH-2-Adm,H),(5-418,i-Pro,D-22,O,S,O,5-OH-2-Adm,H),(5-419,i-Pro,D-23,O,S,O,5-OH-2-Adm,H),(5-420,i-Pro,D-24,O,S,O,5-OH-2-Adm,H),(5-421,i-Pro,D-25,O,S,O,5-OH-2-Adm,H),(5-422,i-Pro,D-26,O,S,O,5-OH-2-Adm,H),(5-423,i-Pro,D-27,O,S,O,5-OH-2-Adm,H),(5-424,i-Pro,D-28,O,S,O,5-OH-2-Adm,H),(5-425,i-Pro,D-29,O,S,O,5-OH-2-Adm,H),(5-426,i-Pro,D-30,O,S,O,5-OH-2-Adm,H),(5-427,i-Pro,D-31,O,S,O,5-OH-2-Adm,H),(5-428,i-Pro,D-32,O,S,O,5-OH-2-Adm,H),(5-429,i-Pro,D-33,O,S,O,5-OH-2-Adm,H),(5-430,i-Pro,D-34,O,S,O,5-OH-2-Adm,H),(5-431,i-Pro,D-35,O,S,O,5-OH-2-Adm,H),(5-432,i-Pro,D-36,O,S,O,5-OH-2-Adm,H),(5-433,i-Pro,E-11,O,S,O,1-Adm,H),(5-434,i-Pro,E-2,O,S,O,1-Adm,H),(5-435,i-Pro,E-3,O,S,O,1-Adm,H),(5-436,i-Pro,E-4,O,S,O,1-Adm,H),(5-437,i-Pro,E-5,O,S,O,1-Adm,H),(5-438,i-Pro,E-6,O,S,O,1-Adm,H),(5-439,i-Pro,E-7,O,S,O,1-Adm,H),(5-440,i-Pro,E-8,O,S,O,1-Adm,H),(5-441,i-Pro,E-9,O,S,O,1-Adm,H),(5-442,i-Pro,E-110,O,S,O,1-Adm,H),(5-443,i-Pro,E-111,O,S,O,1-Adm,H),(5-444,i-Pro,E-12,O,S,O,1-Adm,H),(5-445,i-Pro,E-13,O,S,O,1-Adm,H),(5-446,i-Pro,E-14,O,S,O,1-Adm,H),(5-447,i-Pro,E-15,O,S,O,1-Adm,H),(5-448,i-Pro,E-16,O,S,O,1-Adm,H),(5-449,i-Pro,E-17,O,S,O,1-Adm,H),(5-450,i-Pro,E-18,O,S,O,1-Adm,H),(5-451,i-Pro,E-19,O,S,O,1-Adm,H),(5-452,i-Pro,E-20,O,S,O,1-Adm,H),(5-453,i-Pro,E-21,O,S,O,1-Adm,H),(5-454,i-Pro,E-22,O,S,O,1-Adm,H),(5-455,i-Pro,E-23,O,S,O,1-Adm,H), (5-456,i-Pro,E-24,O,S,O,1-Adm,H),(5-457,i-Pro,E-25,O,S,O,1-Adm,H),(5-458,i-Pro,E-26,O,S,O,1-Adm,H),(5-459,i-Pro,E-27,O,S,O,1-Adm,H),(5-460,i-Pro,E-28,O,S,O,1-Adm,H),(5-461,i-Pro,E-29,O,S,O,1-Adm,H),(5-462,i-Pro,E-30,O,S,O,1-Adm,H),(5-463,i-Pro,E-31,O,S,O,1-Adm,H),(5-464,i-Pro,E-32,O,S,O,1-Adm,H),(5-465,i-Pro,E-33,O,S,O,1-Adm,H),(5-466,i-Pro,E-34,O,S,O,1-Adm,H),(5-467,i-Pro,E-35,O,S,O,1-Adm,H),(5-468,i-Pro,E-36,O,S,O,1-Adm,H),(5-469,i-Pro,E-1,O,S,O,2-Adm,H),(5-470,i-Pro,E-2,O,S,O,2-Adm,H),(5-471,i-Pro,E-3,O,S,O,2-Adm,H),(5-472,i-Pro,E-4,O,S,O,2-Adm,H),(5-473,i-Pro,E-5,O,S,O,2-Adm,H),(5-474,i-Pro,E-6,O,S,O,2-Adm,H),(5-475,i-Pro,E-7,O,S,O,2-Adm,H),(5-476,i-Pro,E-8,O,S,O,2-Adm,H),(5-477,i-Pro,E-9,O,S,O,2-Adm,H),(5-478,i-Pro,E-10,O,S,O,2-Adm,H),(5-479,i-Pro,E-11,O,S,O,2-Adm,H),(5-480,i-Pro,E-12,O,S,O,2-Adm,H),(5-481,i-Pro,E-13,O,S,O,2-Adm,H),(5-482,i-Pro,E-14,O,S,O,2-Adm,H),(5-483,i-Pro,E-15,O,S,O,2-Adm,H),(5-484,i-Pro,E-16,O,S,O,2-Adm,H),(5-485,i-Pro,E-17,O,S,O,2-Adm,H),(5-486,i-Pro,E-18,O,S,O,2-Adm,H),(5-487,i-Pro,E-19,O,S,O,2-Adm,H),(5-488,i-Pro,E-20,O,S,O,2-Adm,H),(5-489,i-Pro,E-21,O,S,O,2-Adm,H),(5-490,i-Pro,E-22,O,S,O,2-Adm,H),(5-491,i-Pro,E-23,O,S,O,2-Adm,H),(5-492,i-Pro,E-24,O,S,O,2-Adm,H),(5-493,i-Pro,E-25,O,S,O,2-Adm,H),(5-494,i-Pro,E-26,O,S,O,2-Adm,H),(5-495,i-Pro,E-27,O,S,O,2-Adm,H),(5-496,i-Pro,E-28,O,S,O,2-Adm,H),(5-497,i-Pro,E-29,O,S,O,2-Adm,H),(5-498,i-Pro,E-30,O,S,O,2-Adm,H),(5-499,i-Pro,E-31,O,S,O,2-Adm,H),(5-500,i-Pro,E-32,O,S,O,2-Adm,H),(5-501,i-Pro,E-33,O,S,O,2-Adm,H),(5-502,i-Pro,E-34,O,S,O,2-Adm,H),(5-503,i-Pro,E-35,O,S,O,2-Adm,H),(5-504,i-Pro,E-36,O,S,O,2-Adm,H),(5-505,i-Pro,E-1,O,S,O,5-OH-2-Adm,H),(5-506,i-Pro,E-2,O,S,O,5-OH-2-Adm,H),(5-507,i-Pro,E-3,O,S,O,5-OH-2-Adm,H),(5-508,i-Pro,E-4,O,S,O,5-OH-2-Adm,H),(5-509,i-Pro,E-5,O,S,O,5-OH-2-Adm,H),(5-510,i-Pro,E-6,O,S,O,5-OH-2-Adm,H),(5-511,i-Pro,E-7,O,S,O,5-OH-2-Adm,H),(5-512,i-Pro,E-8,O,S,O,5-OH-2-Adm,H),(5-513,i-Pro,E-9,O,S,O,5-OH-2-Adm,H),(5-514,i-Pro,E-10,O,S,O,5-OH-2-Adm,H),(5-515,i-Pro,E-11,O,S,O,5-OH-2-Adm,H),(5-516,i-Pro,E-12,O,S,O,5-OH-2-Adm,H),(5-517,i-Pro,E-13,O,S,O,5-OH-2-Adm,H),(5-518,i-Pro,E-14,O,S,O,5-OH-2-Adm,H),(5-519,i-Pro,E-15,O,S,O,5-OH-2-Adm,H),(5-520,i-Pro,E-16,O,S,O,5-OH-2-Adm,H),(5-521,i-Pro,E-17,O,S,O,5-OH-2-Adm,H),(5-522,i-Pro,E-18,O,S,O,5-OH-2-Adm,H),(5-523,i-Pro,E-19,O,S,O,5-OH-2-Adm,H),(5-524,i-Pro,E-20,O,S,O,5-OH-2-Adm,H),(5-525,i-Pro,E-21,O,S,O,5-OH-2-Adm,H),(5-526,i-Pro,E-22,O,S,O,5-OH-2-Adm,H),(5-527,i-Pro,E-23,O,S,O,5-OH-2-Adm,H),(5-528,i-Pro,E-24,O,S,O,5-OH-2-Adm,H),(5-529,i-Pro,E-25,O,S,O,5-OH-2-Adm,H),(5-530,i-Pro,E-26,O,S,O,5-OH-2-Adm,H),(5-531,i-Pro,E-27,O,S,O,5-OH-2-Adm,H),(5-532,i-Pro,E-28,O,S,O,5-OH-2-Adm,H),(5-533,i-Pro,E-29,O,S,O,5-OH-2-Adm,H),(5-534,i-Pro,E-30,O,S,O,5-OH-2-Adm,H),(5-535,i-Pro,E-31,O,S,O,5-OH-2-Adm,H),(5-536,i-Pro,E-32,O,S,O,5-OH-2-Adm,H),(5-537,i-Pro,E-33,O,S,O,5-OH-2-Adm,H),(5-538,i-Pro,E-34,O,S,O,5-OH-2-Adm,H),(5-539,i-Pro,E-35,O,S,O,5-OH-2-Adm,H),(5-540,i-Pro,E-36,O,S,O,5-OH-2-Adm,H),(5-541,i-Pro,F-1,O,S,O,1-Adm,H),(5-542,i-Pro,F-2,O,S,O,1-Adm,H),(5-543,i-Pro,F-3,O,S,O,1-Adm,H),(5-544,i-Pro,F-4,O,S,O,1-Adm,H),(5-545,i-Pro,F-5,O,S,O,1-Adm,H),(5-546,i-Pro,F-6,O,S,O,1-Adm,H),(5-547,i-Pro,F-7,O,S,O,1-Adm,H),(5-548,i-Pro,F-8,O,S,O,1-Adm,H),(5-549,i-Pro,F-9,O,S,O,1-Adm,H),(5-550,i-Pro,F-11,O,S,O,1-Adm,H),(5-551,i-Pro,F-11,O,S,O,1-Adm,H),(5-552,i-Pro,F-12,O,S,O,1-Adm,H),(5-553,i-Pro,F-13,O,S,O,1-Adm,H),(5-554,i-Pro,F-14,O,S,O,1-Adm,H),(5-555,i-Pro,F-15,O,S,O,1-Adm,H),(5-556,i-Pro,F-16,O,S,O,1-Adm,H),(5-557,i-Pro,F-17,O,S,O,1-Adm,H), (5-558,i-Pro,F-18,O,S,O,1-

Adm,H),(5-559,i-Pro,F-19,O,S,O,1-Adm,H),(5-560,i-Pro,F-20,O,S,O,1-Adm,H),(5-561,i-Pro,F-21,O,S,O,1-Adm,H),(5-562,i-Pro,F-22,O,S,O,1-Adm,H),(5-563,i-Pro,F-23,O,S,O,1-Adm,H),(5-564,i-Pro,F-24,O,S,O,1-Adm,H),(5-565,i-Pro,F-25,O,S,O,1-Adm,H),(5-566,i-Pro,F-26,O,S,O,1-Adm,H),(5-567,i-Pro,F-27,O,S,O,1-Adm,H),(5-568,i-Pro,F-28,O,S,O,1-Adm,H),(5-569,i-Pro,F-29,O,S,O,1-Adm,H),(5-570,i-Pro,F-30,O,S,O,1-Adm,H),(5-571,i-Pro,F-31,O,S,O,1-Adm,H),(5-572,i-Pro,F-32,O,S,O,1-Adm,H),(5-573,i-Pro,F-33,O,S,O,1-Adm,H),(5-574,i-Pro,F-34,O,S,O,1-Adm,H),(5-575,i-Pro,F-35,O,S,O,1-Adm,H),(5-576,i-Pro,F-36,O,S,O,1-Adm,H),(5-577,i-Pro,F-1,O,S,O,2-Adm,H),(5-578,i-Pro,F-2,O,S,O,2-Adm,H),(5-579,i-Pro,F-3,O,S,O,2-Adm,H),(5-580,i-Pro,F-4,O,S,O,2-Adm,H),(5-581,i-Pro,F-5,O,S,O,2-Adm,H),(5-582,i-Pro,F-6,O,S,O,2-Adm,H),(5-583,i-Pro,F-7,O,S,O,2-Adm,H),(5-584,i-Pro,F-8,O,S,O,2-Adm,H),(5-585,i-Pro,F-9,O,S,O,2-Adm,H),(5-586,i-Pro,F-10,O,S,O,2-Adm,H),(5-587,i-Pro,F-11,O,S,O,2-Adm,H),(5-588,i-Pro,F-12,O,S,O,2-Adm,H),(5-589,i-Pro,F-13,O,S,O,2-Adm,H),(5-590,i-Pro,F-14,O,S,O,2-Adm,H),(5-591,i-Pro,F-15,O,S,O,2-Adm,H),(5-592,i-Pro,F-16,O,S,O,2-Adm,H),(5-593,i-Pro,F-17,O,S,O,2-Adm,H),(5-594,i-Pro,F-18,O,S,O,2-Adm,H),(5-595,i-Pro,F-19,O,S,O,2-Adm,H),(5-596,i-Pro,F-20,O,S,O,2-Adm,H),(5-597,i-Pro,F-21,O,S,O,2-Adm,H),(5-598,i-Pro,F-22,O,S,O,2-Adm,H),(5-599,i-Pro,F-23,O,S,O,2-Adm,H),(5-600,i-Pro,F-24,O,S,O,2-Adm,H),(5-601,i-Pro,F-25,O,S,O,2-Adm,H),(5-602,i-Pro,F-26,O,S,O,2-Adm,H),(5-603,i-Pro,F-27,O,S,O,2-Adm,H),(5-604,i-Pro,F-28,O,S,O,2-Adm,H),(5-605,i-Pro,F-29,O,S,O,2-Adm,H),(5-606,i-Pro,F-30,O,S,O,2-Adm,H),(5-607,i-Pro,F-31,O,S,O,2-Adm,H),(5-608,i-Pro,F-32,O,S,O,2-Adm,H),(5-609,i-Pro,F-33,O,S,O,2-Adm,H),(5-610,i-Pro,F-34,O,S,O,2-Adm,H),(5-611,i-Pro,F-35,O,S,O,2-Adm,H),(5-612,i-Pro,F-36,O,S,O,2-Adm,H),(5-613,i-Pro,F-1,O,S,O,5-OH-2-Adm,H),(5-614,i-Pro,F-2,O,S,O,5-OH-2-Adm,H),(5-615,i-Pro,F-3,O,S,O,5-OH-2-Adm,H),(5-616,i-Pro,F-4,O,S,O,5-OH-2-Adm,H),(5-617,i-Pro,F-5,O,S,O,5-OH-2-Adm,H),(5-618,i-Pro,F-6,O,S,O,5-OH-2-Adm,H),(5-619,i-Pro,F-7,O,S,O,5-OH-2-Adm,H),(5-620,i-Pro,F-8,O,S,O,5-OH-2-Adm,H),(5-621,i-Pro,F-9,O,S,O,5-OH-2-Adm,H),(5-622,i-Pro,F-10,O,S,O,5-OH-2-Adm,H),(5-623,i-Pro,F-11,O,S,O,5-OH-2-Adm,H),(5-624,i-Pro,F-12,O,S,O,5-OH-2-Adm,H),(5-625,i-Pro,F-13,O,S,O,5-OH-2-Adm,H),(5-626,i-Pro,F-14,O,S,O,5-OH-2-Adm,H),(5-627,i-Pro,F-15,O,S,O,5-OH-2-Adm,H),(5-628,i-Pro,F-16,O,S,O,5-OH-2-Adm,H),(5-629,i-Pro,F-17,O,S,O,5-OH-2-Adm,H),(5-630,i-Pro,F-18,O,S,O,5-OH-2-Adm,H),(5-631,i-Pro,F-19,O,S,O,5-OH-2-Adm,H),(5-632,i-Pro,F-20,O,S,O,5-OH-2-Adm,H),(5-633,i-Pro,F-21,O,S,O,5-OH-2-Adm,H),(5-634,i-Pro,F-22,O,S,O,5-OH-2-Adm,H),(5-635,i-Pro,F-23,O,S,O,5-OH-2-Adm,H),(5-636,i-Pro,F-24,O,S,O,5-OH-2-Adm,H),(5-637,i-Pro,F-25,O,S,O,5-OH-2-Adm,H),(5-638,i-Pro,F-26,O,S,O,5-OH-2-Adm,H),(5-639,i-Pro,F-27,O,S,O,5-OH-2-Adm,H),(5-640,i-Pro,F-28,O,S,O,5-OH-2-Adm,H),(5-641,i-Pro,F-29,O,S,O,5-OH-2-Adm,H),(5-642,i-Pro,F-30,O,S,O,5-OH-2-Adm,H),(5-643,i-Pro,F-31,O,S,O,5-OH-2-Adm,H),(5-644,i-Pro,F-32,O,S,O,5-OH-2-Adm,H),(5-645,i-Pro,F-33,O,S,O,5-OH-2-Adm,H),(5-646,i-Pro,F-34,O,S,O,5-OH-2-Adm,H),(5-647,i-Pro,F-35,O,S,O,5-OH-2-Adm,H),(5-648,i-Pro,F-36,O,S,O,5-OH-2-Adm,H),(5-649,i-Pro,G-1,O,S,O,1-Adm,H),(5-650,i-Pro,G-2,O,S,O,1-Adm,H),(5-651,i-Pro,G-3,O,S,O,1-Adm,H),(5-652,i-Pro,G-4,O,S,O,1-Adm,H),(5-653,i-Pro,G-5,O,S,O,1-Adm,H),(5-654,i-Pro,G-6,O,S,O,1-Adm,H),(5-655,i-Pro,G-7,O,S,O,1-Adm,H),(5-656,i-Pro,G-8,O,S,O,1-Adm,H),(5-657,i-Pro,G-9,O,S,O,1-Adm,H),(5-658,i-Pro,G-1,O,S,O,2-Adm,H),(5-659,i-Pro,G-2,O,S,O,2-Adm,H),(5-660,i-Pro,G-3,O,S,O,2-Adm,H),(5-661,i-Pro,G-4,O,S,O,2-Adm,H),(5-662,i-Pro,G-5,O,S,O,2-Adm,H),(5-663,i-Pro,G-6,O,S,O,2-Adm,H),(5-664,i-Pro,G-7,O,S,O,2-Adm,H),(5-665,i-Pro,G-8,O,S,O,2-Adm,H),(5-666,i-Pro,G-9,O,S,O,2-Adm,H),(5-667,i-Pro,G-1,O,S,O,5-OH-2-Adm,H),(5-668,i-Pro,G-2,O,S,O,5-OH-2-Adm,H),(5-669,i-Pro,G-3,O,S,O,5-OH-2-Adm,H),(5-670,i-Pro,G-4,O,S,O,5-OH-2-Adm,H),(5-671,i-Pro,G-5,O,S,O,5-OH-2-Adm,H),(5-672,i-Pro,G-6,O,S,O,5-OH-2-Adm,H),(5-673,i-Pro,G-7,O,S,O,5-OH-2-Adm,H),(5-674,i-Pro,G-8,O,S,O,5-OH-2-Adm,H),(5-675,i-Pro,G-9,O,S,O,5-OH-2-Adm,H),(5-676,i-Pro,H-1,O,S,O,1-Adm,H),(5-677,i-Pro,H-2,O,S,O,1-Adm,H),(5-678,i-Pro,H-3,O,S,O,1-Adm,H),(5-679,i-Pro,H-4,O,S,O,1-Adm,H),(5-680,i-Pro,H-5,O,S,O,1-Adm,H),(5-681,i-Pro,H-6,O,S,O,1-Adm,H),(5-682,i-Pro,H-7,O,S,O,1-Adm,H),(5-683,i-Pro,H-8,O,S,O,1-Adm,H),(5-684,i-Pro,H-9,O,S,O,1-Adm,H),(5-685,i-Pro,H-1,O,S,O,2-Adm,H),(5-686,i-Pro,H-2,O,S,O,2-Adm,H),(5-687,i-Pro,H-3,O,S,O,2-Adm,H),(5-688,i-Pro,H-4,O,S,O,2-Adm,H),(5-689,i-Pro,H-5,O,S,O,2-Adm,H),(5-690,i-Pro,H-6,O,S,O,2-Adm,H),(5-691,i-Pro,H-7,O,S,O,2-Adm,H),(5-692,i-Pro,H-8,O,S,O,2-Adm,H),(5-693,i-Pro,H-9,O,S,O,2-Adm,H),(5-694,i-Pro,H-1,O,S,O,5-OH-2-Adm,H),(5-695,i-Pro,H-2,O,S,O,5-OH-2-Adm,H),(5-696,i-Pro,H-3,O,S,O,5-OH-2-Adm,H),(5-697,i-Pro,H-4,O,S,O,5-OH-2-Adm,H),(5-698,i-Pro,H-5,O,S,O,5-OH-2-Adm,H),(5-699,i-Pro,H-6,O,S,O,5-OH-2-Adm,H),(5-700,i-Pro,H-7,O,S,O,5-OH-2-Adm,H),(5-701,i-Pro,H-8,O,S,O,5-OH-2-Adm,H),(5-702,i-Pro,H-9,O,S,O,5-OH-2-Adm,H),(5-703,i-Pro,I-1,O,S,O,1-Adm,H),(5-704,i-Pro,I-2,O,S,O,1-Adm,H),(5-705,i-Pro,I-3,O,S,O,1-Adm,H),(5-706,i-Pro,I-4,O,S,O,1-Adm,H),(5-707,i-Pro,I-5,O,S,O,1-Adm,H),(5-708,i-Pro,I-6,O,S,O,1-Adm,H),(5-709,i-Pro,I-7,O,S,O,1-Adm,H),(5-710,i-Pro,I-8,O,S,O,1-Adm,H),(5-711,i-Pro,I-9,O,S,O,1-Adm,H),(5-712,i-Pro,I-1,O,S,O,2-Adm,H),(5-713,i-Pro,I-2,O,S,O,2-Adm,H),(5-714,i-Pro,I-3,O,S,O,2-Adm,H),(5-715,i-Pro,I-4,O,S,O,2-Adm,H),(5-716,i-Pro,I-5,O,S,O,2-Adm,H),(5-717,i-Pro,I-6,O,S,O,2-Adm,H),(5-718,i-Pro,I-7,O,S,O,2-Adm,H),(5-719,i-Pro,I-8,O,S,O,2-Adm,H),(5-720,i-Pro,I-9,O,S,O,2-Adm,H),(5-721,i-Pro,I-1,O,S,O,5-OH-2-Adm,H),(5-722,i-Pro,I-2,O,S,O,5-OH-2-Adm,H),(5-723,i-Pro,I-3,O,S,O,5-OH-2-Adm,H),(5-724,i-Pro,I-4,O,S,O,5-OH-2-Adm,H),(5-725,i-Pro,I-5,O,S,O,5-OH-2-Adm,H),(5-726,i-Pro,I-6,O,S,O,5-OH-2-Adm,H),(5-727,i-Pro,I-7,O,S,O,5-OH-2-Adm,H),(5-728,i-Pro,I-8,O,S,O,5-OH-2-Adm,H),(5-729,i-Pro,I-9,O,S,O,5-OH-2-Adm,H),(5-730,i-Pro,J-1,O,S,O,1-Adm,H),(5-731,i-Pro,J-2,O,S,O,1-Adm,H),(5-732,i-Pro,J-3,O,S,O,1-Adm,H),(5-733,i-Pro,J-4,O,S,O,1-Adm,H),(5-734,i-Pro,J-5,O,S,O,1-Adm,H),(5-735,i-Pro,J-6,O,S,O,1-Adm,H),(5-736,i-Pro,J-7,O,S,O,1-Adm,H),(5-737,i-Pro,J-8,O,S,O,1-Adm,H),(5-738,i-Pro,J-9,O,S,O,1-Adm,H),(5-739,i-Pro,J-1,O,S,O,2-Adm,H),(5-740,i-Pro,J-2,O,S,O,2-Adm,H),(5-741,i-Pro,J-3,O,S,O,2-Adm,H),(5-742,i-Pro,J-4,O,S,O,2-Adm,H),(5-743,i-Pro,J-5,O,S,O,2-Adm,H),(5-744,i-Pro,J-6,O,S,O,2-Adm,H),(5-745,i-Pro,J-7,O,S,O,2-Adm,H),(5-746,i-Pro,J-8,O,S,O,2-Adm,H),(5-747,i-Pro,J-9,O,S,O,2-Adm,H),(5-748,i-Pro,J-1,O,S,O,5-OH-2-Adm,H),(5-749,i-Pro,J-2,O,S,O,5-OH-2-Adm,H),(5-750,i-Pro,J-3,O,S,O,5-OH-2-Adm,H),(5-751,i-Pro,J-4,O,S,O,5-OH-2-Adm,H),(5-752,i-Pro,J-5,O,S,O,5-OH-2-Adm,H),(5-753,i-Pro,J-6,O,S,O,5-OH-2-Adm,H),(5-754,i-Pro,J-7,O,S,O,5-OH-2-Adm,H),(5-755,i-Pro,J-8,O,S,O,5-OH-2-Adm,H),(5-756,i-Pro,J-9,O,S,O,5-OH-2-Adm,H),(5-757,i-Pro,K-1,O,S,O,1-Adm,H),(5-758,i-Pro,K-2,O,S,O,1-Adm,H),(5-759,i-Pro,K-3,O,S,O,1-Adm,H),(5-760,i-Pro,K-4,O,S,O,1-Adm,H),(5-761,i-Pro,K-5,O,S,O,1-Adm,H),(5-762,i-Pro,K-6,O,S,O,1-Adm,H),(5-763,i-Pro,K-7,O,S,O,1-Adm,H),(5-764,i-Pro,K-8,O,S,O,1-Adm,H),(5-765,i-Pro,K-9,O,S,O,1-Adm,H), (5-766,i-Pro,K-1,O,S,O,2-Adm,H),(5-

767,i-Pro,K-2,O,S,O,2-Adm,H),(5-768,i-Pro,K-3,O,S,O,2-Adm,H),(5-769,i-Pro,K-4,O,S,O,2-Adm,H),(5-770,i-Pro,K-5,O,S,O,2-Adm,H),(5-771,i-Pro,K-6,O,S,O,2-Adm,H),(5-772,i-Pro,K-7,O,S,O,2-Adm,H),(5-773,i-Pro,K-8,O,S,O,2-Adm,H),(5-774,i-Pro,K-9,O,S,O,2-Adm,H),(5-775,i-Pro,K-1,O,S,O,5-OH-2-Adm,H),(5-776,i-Pro,K-2,O,S,O,5-OH-2-Adm,H),(5-777,i-Pro,K-3,O,S,O,5-OH-2-Adm,H),(5-778,i-Pro,K-4,O,S,O,5-OH-2-Adm,H),(5-779,i-Pro,K-5,O,S,O,5-OH-2-Adm,H),(5-780,i-Pro,K-6,O,S,O,5-OH-2-Adm,H),(5-781,i-Pro,K-7,O,S,O,5-OH-2-Adm,H),(5-782,i-Pro,K-8,O,S,O,5-OH-2-Adm,H),(5-783,i-Pro,K-9,O,S,O,5-OH-2-Adm,H)

(Compound No., $R^2,R^3,X,Y,Z,R^4,R^5$)=(6-1,Pro,A-1,O,S,O,1-Adm,H),(6-2,Pro,A-2,O,S,O,1-Adm,H),(6-3,Pro,A-3,O,S,O,1-Adm,H),(6-4,Pro,A-4,O,S,O,1-Adm,H),(6-5,Pro,A-5,O,S,O,1-Adm,H),(6-6,Pro,A-6,O,S,O,1-Adm,H),(6-7,Pro,A-7,O,S,O,1-Adm,H),(6-8,Pro,A-8,O,S,O,1-Adm,H),(6-9,Pro,A-9,O,S,O,1-Adm,H),(6-10,Pro,A-10,O,S,O,1-Adm,H),(6-11,Pro,A-11,O,S,O,1-Adm,H),(6-12,Pro,A-12,O,S,O,1-Adm,H),(6-13,Pro,A-13,O,S,O,1-Adm,H),(6-14,Pro,A-14,O,S,O,1-Adm,H),(6-15,Pro,A-15,O,S,O,1-Adm,H),(6-16,Pro,A-16,O,S,O,1-Adm,H),(6-17,Pro,A-17,O,S,O,1-Adm,H),(6-18,Pro,A-18,O,S,O,1-Adm,H),(6-19,Pro,A-19,O,S,O,1-Adm,H),(6-20,Pro,A-20,O,S,O,1-Adm,H),(6-21,Pro,A-21,O,S,O,1-Adm,H),(6-22,Pro,A-22,O,S,O,1-Adm,H),(6-23,Pro,A-23,O,S,O,1-Adm,H),(6-24,Pro,A-24,O,S,O,1-Adm,H),(6-25,Pro,A-25,O,S,O,1-Adm,H),(6-26,Pro,A-26,O,S,O,1-Adm,H),(6-27,Pro,A-27,O,S,O,1-Adm,H),(6-28,Pro,A-28,O,S,O,1-Adm,H),(6-29,Pro,A-29,O,S,O,1-Adm,H),(6-30,Pro,A-30,O,S,O,1-Adm,H),(6-31,Pro,A-31,O,S,O,1-Adm,H),(6-32,Pro,A-32,O,S,O,1-Adm,H),(6-33,Pro,A-33,O,S,O,1-Adm,H),(6-34,Pro,A-34,O,S,O,1-Adm,H),(6-35,Pro,A-35,O,S,O,1-Adm,H),(6-36,Pro,A-36,O,S,O,1-Adm,H),(6-37,Pro,A-1,O,S,O,2-Adm,H),(6-38,Pro,A-2,O,S,O,2-Adm,H),(6-39,Pro,A-3,O,S,O,2-Adm,H),(6-40,Pro,A-4,O,S,O,2-Adm,H),(6-41,Pro,A-5,O,S,O,2-Adm,H),(6-42,Pro,A-6,O,S,O,2-Adm,H),(6-43,Pro,A-7,O,S,O,2-Adm,H),(6-44,Pro,A-8,O,S,O,2-Adm,H),(6-45,Pro,A-9,O,S,O,2-Adm,H),(6-46,Pro,A-11,O,S,O,2-Adm,H),(6-47,Pro,A-11,O,S,O,2-Adm,H),(6-48,Pro,A-12,O,S,O,2-Adm,H),(6-49,Pro,A-13,O,S,O,2-Adm,H),(6-50,Pro,A-14,O,S,O,2-Adm,H),(6-51,Pro,A-15,O,S,O,2-Adm,H),(6-52,Pro,A-16,O,S,O,2-Adm,H),(6-53,Pro,A-17,O,S,O,2-Adm,H),(6-54,Pro,A-18,O,S,O,2-Adm,H),(6-55,Pro,A-19,O,S,O,2-Adm,H),(6-56,Pro,A-20,O,S,O,2-Adm,H),(6-57,Pro,A-21,O,S,O,2-Adm,H),(6-58,Pro,A-22,O,S,O,2-Adm,H),(6-59,Pro,A-23,O,S,O,2-Adm,H),(6-60,Pro,A-24,O,S,O,2-Adm,H),(6-61,Pro,A-25,O,S,O,2-Adm,H),(6-62,Pro,A-26,O,S,O,2-Adm,H),(6-63,Pro,A-27,O,S,O,2-Adm,H),(6-64,Pro,A-28,O,S,O,2-Adm,H),(6-65,Pro,A-29,O,S,O,2-Adm,H),(6-66,Pro,A-30,O,S,O,2-Adm,H),(6-67,Pro,A-31,O,S,O,2-Adm,H),(6-68,Pro,A-32,O,S,O,2-Adm,H),(6-69,Pro,A-33,O,S,O,2-Adm,H),(6-70,Pro,A-34,O,S,O,2-Adm,H),(6-71,Pro,A-35,O,S,O,2-Adm,H),(6-72,Pro,A-36,O,S,O,2-Adm,H),(6-73,Pro,A-1,O,S,O,5-OH-2-Adm,H),(6-74,Pro,A-2,O,S,O,5-OH-2-Adm,H),(6-75,Pro,A-3,O,S,O,5-OH-2-Adm,H),(6-76,Pro,A-4,O,S,O,5-OH-2-Adm,H),(6-77,Pro,A-5,O,S,O,5-OH-2-Adm,H),(6-78,Pro,A-6,O,S,O,5-OH-2-Adm,H),(6-79,Pro,A-7,O,S,O,5-OH-2-Adm,H),(6-80,Pro,A-8,O,S,O,5-OH-2-Adm,H),(6-81,Pro,A-9,O,S,O,5-OH-2-Adm,H),(6-82,Pro,A-10,O,S,O,5-OH-2-Adm,H),(6-83,Pro,A-11,O,S,O,5-OH-2-Adm,H),(6-84,Pro,A-12,O,S,O,5-OH-2-Adm,H),(6-85,Pro,A-13,O,S,O,5-OH-2-Adm,H),(6-86,Pro,A-14,O,S,O,5-OH-2-Adm,H),(6-87,Pro,A-15,O,S,O,5-OH-2-Adm,H),(6-88,Pro,A-16,O,S,O,5-OH-2-Adm,H),(6-89,Pro,A-17,O,S,O,5-OH-2-Adm,H),(6-90,Pro,A-18,O,S,O,5-OH-2-Adm,H),(6-91, Pro,A-19,O,S,O,5-OH-2-Adm,H),(6-92,Pro,A-20,O,S,O,5-OH-2-Adm,H),(6-93,Pro,A-21,O,S,O,5-OH-2-Adm,H),(6-94,Pro,A-22,O,S,O,5-OH-2-Adm,H),(6-95,Pro,A-23,O,S,O,5-OH-2-Adm,H),(6-96,Pro,A-24,O,S,O,5-OH-2-Adm,H),(6-97,Pro,A-25,O,S,O,5-OH-2-Adm,H),(6-98,Pro,A-26,O,S,O,5-OH-2-Adm,H),(6-99,Pro,A-27,O,S,O,5-OH-2-Adm,H),(6-100,Pro,A-28,O,S,O,5-OH-2-Adm,H),(6-101,Pro,A-29,O,S,O,5-OH-2-Adm,H),(6-102,Pro,A-30,O,S,O,5-OH-2-Adm,H),(6-103,Pro,A-31,O,S,O,5-OH-2-Adm,H),(6-104,Pro,A-32,O,S,O,5-OH-2-Adm,H),(6-105,Pro,A-33,O,S,O,5-OH-2-Adm,H),(6-106,Pro,A-34,O,S,O,5-OH-2-Adm,H),(6-107,Pro,A-35,O,S,O,5-OH-2-Adm,H),(6-108,Pro,A-36,O,S,O,5-OH-2-Adm,H),(6-109,Pro,B-1,O,S,O,1-Adm,H),(6-110,Pro,B-2,O,S,O,1-Adm,H),(6-111,Pro,B-3,O,S,O,1-Adm,H),(6-112,Pro,B-4,O,S,O,1-Adm,H),(6-113,Pro,B-5,O,S,O,1-Adm,H),(6-114,Pro,B-6,O,S,O,1-Adm,H),(6-115,Pro,B-7,O,S,O,1-Adm,H),(6-116,Pro,B-8,O,S,O,1-Adm,H),(6-117,Pro,B-9,O,S,O,1-Adm,H),(6-118,Pro,B-10,O,S,O,1-Adm,H),(6-119,Pro,B-11,O,S,O,1-Adm,H),(6-120,Pro,B-12,O,S,O,1-Adm,H),(6-121,Pro,B-13,O,S,O,1-Adm,H),(6-122,Pro,B-14,O,S,O,1-Adm,H),(6-123,Pro,B-15,O,S,O,1-Adm,H),(6-124,Pro,B-16,O,S,O,1-Adm,H),(6-125,Pro,B-17,O,S,O,1-Adm,H),(6-126,Pro,B-18,O,S,O,1-Adm,H),(6-127,Pro,B-19,O,S,O,1-Adm,H),(6-128,Pro,B-20,O,S,O,1-Adm,H),(6-129,Pro,B-21,O,S,O,1-Adm,H),(6-130,Pro,B-22,O,S,O,1-Adm,H),(6-131,Pro,B-23,O,S,O,1-Adm,H),(6-132,Pro,B-24,O,S,O,1-Adm,H),(6-133,Pro,B-25,O,S,O,1-Adm,H),(6-134,Pro,B-26,O,S,O,1-Adm,H),(6-135,Pro,B-27,O,S,O,1-Adm,H),(6-136,Pro,B-28,O,S,O,1-Adm,H),(6-137,Pro,B-29,O,S,O,1-Adm,H),(6-138,Pro,B-30,O,S,O,1-Adm,H),(6-139,Pro,B-31,O,S,O,1-Adm,H),(6-140,Pro,B-32,O,S,O,1-Adm,H),(6-141,Pro,B-33,O,S,O,1-Adm,H),(6-142,Pro,B-34,O,S,O,1-Adm,H),(6-143,Pro,B-35,O,S,O,1-Adm,H),(6-144,Pro,B-36,O,S,O,1-Adm,H),(6-145,Pro,B-1,O,S,O,2-Adm,H),(6-146,Pro,B-2,O,S,O,2-Adm,H),(6-147,Pro,B-3,O,S,O,2-Adm,H),(6-148,Pro,B-4,O,S,O,2-Adm,H),(6-149,Pro,B-5,O,S,O,2-Adm,H),(6-1500,Pro,B-6,O,S,O,2-Adm,H),(6-1511,Pro,B-7,O,S,O,2-Adm,H),(6-152,Pro,B-8,O,S,O,2-Adm,H),(6-153,Pro,B-9,O,S,O,2-Adm,H),(6-154,Pro,B-10,O,S,O,2-Adm,H),(6-155,Pro,B-11,O,S,O,2-Adm,H),(6-156,Pro,B-12,O,S,O,2-Adm,H),(6-157,Pro,B-13,O,S,O,2-Adm,H),(6-158,Pro,B-14,O,S,O,2-Adm,H),(6-159,Pro,B-15,O,S,O,2-Adm,H),(6-160,Pro,B-16,O,S,O,2-Adm,H),(6-161,Pro,B-17,O,S,O,2-Adm,H),(6-162,Pro,B-18,O,S,O,2-Adm,H),(6-163,Pro,B-19,O,S,O,2-Adm,H),(6-164,Pro,B-20,O,S,O,2-Adm,H),(6-165,Pro,B-21,O,S,O,2-Adm,H),(6-166,Pro,B-22,O,S,O,2-Adm,H),(6-167,Pro,B-23,O,S,O,2-Adm,H),(6-168,Pro,B-24,O,S,O,2-Adm,H),(6-169,Pro,B-25,O,S,O,2-Adm,H),(6-170,Pro,B-26,O,S,O,2-Adm,H),(6-171,Pro,B-27,O,S,O,2-Adm,H),(6-172,Pro,B-28,O,S,O,2-Adm,H),(6-173,Pro,B-29,O,S,O,2-Adm,H),(6-174,Pro,B-30,O,S,O,2-Adm,H),(6-175,Pro,B-31,O,S,O,2-Adm,H),(6-176,Pro,B-32,O,S,O,2-Adm,H),(6-177,Pro,B-33,O,S,O,2-Adm,H),(6-178,Pro,B-34,O,S,O,2-Adm,H),(6-179,Pro,B-35,O,S,O,2-Adm,H),(6-180,Pro,B-36,O,S,O,2-Adm,H),(6-181,Pro,B-1,O,S,O,5-OH-2-Adm,H),(6-182,Pro,B-2,O,S,O,5-OH-2-Adm,H),(6-183,Pro,B-3,O,S,O,5-OH-2-Adm,H),(6-184,Pro,B-4,O,S,O,5-OH-2-Adm,H),(6-185,Pro,B-5,O,S,O,5-OH-2-Adm,H),(6-186,Pro,B-6,O,S,O,5-OH-2-Adm,H),(6-187,Pro,B-7,O,S,O,5-OH-2-Adm,H),(6-188,Pro,B-8,O,S,O,5-OH-2-Adm,H),(6-189,Pro,B-9,O,S,O,5-OH-2-Adm,H),(6-190,Pro,B-10,O,S,O,5-OH-2-Adm,H),(6-191,Pro,B-11,O,S,O,5-OH-2-Adm,H),(6-192,Pro,B-12,O,S,O,5-OH-2-Adm,H),(6-193,Pro,B-13,O,S,O,5-OH-2-Adm,H),(6-194,Pro,B-14,O,S,O,5-OH-2-Adm,H),(6-195,Pro,B-15,O,S,O,5-OH-2-Adm,H),(6-196,Pro,B-16,O,S,O,5-OH-2-Adm,H),(6-197,Pro,B-17,O,S,O,5-OH-2-Adm,H), (6-198,Pro,B-18, O,S,O,5-OH-2-Adm,H),(6-199,Pro,B-19,O,S,O,5-OH-2-Adm,H),(6-200,Pro,B-20,O,S,O,5-OH-2-Adm,H),(6-201,Pro,B-21,O,S,O,5-OH-2-Adm,H),(6-202,Pro,B-22,O,S,O,5-OH-2-Adm,H),(6-203,Pro,B-23,O,S,O,5-OH-2-Adm,H),(6-204,Pro,B-24,O,S,O,5-OH-2-Adm,H),(6-205,Pro,B-25,O,S,O,5-OH-2-Adm,H),(6-206,Pro,B-26,O,S,O,5-OH-2-Adm,H),(6-207,Pro,B-27,O,S,O,5-OH-2-Adm,H),(6-208,Pro,B-28,O,S,O,5-OH-2-Adm,H),(6-209,Pro,B-29,O,S,O,5-OH-2-Adm,H),(6-210,Pro,B-30,O,S,O,5-OH-2-Adm,H),(6-211,Pro,B-31,O,S,O,5-OH-2-Adm,H),(6-212,Pro,B-32,O,S,O,5-OH-2-Adm,H),(6-213,Pro,B-33,O,S,O,5-OH-2-Adm,H),(6-214,Pro,B-34,O,S,O,5-OH-2-Adm,H),(6-215,Pro,B-35,O,S,O,5-OH-2-Adm,H),(6-216,Pro,B-36,O,S,O,5-OH-2-Adm,H),(6-217,Pro,C-1,O,S,O,1-Adm,H),(6-218,Pro,C-2,O,S,O,1-Adm,H),(6-219,Pro,C-3,O,S,O,1-Adm,H),(6-220,Pro,C-4,O,S,O,1-Adm,H),(6-221,Pro,C-5,O,S,O,1-Adm,H),(6-222,Pro,C-6,O,S,O,1-Adm,H),(6-223,Pro,C-7,O,S,O,1-Adm,H),(6-224,Pro,C-8,O,S,O,1-Adm,H),(6-225,Pro,C-9,O,S,O,1-Adm,H),(6-226,Pro,C-1,O,S,O,1-Adm,H),(6-227,Pro,C-11,O,S,O,1-Adm,H),(6-228,Pro,C-12,O,S,O,1-Adm,H),(6-229,Pro,C-13,O,S,O,1-Adm,H),(6-230,Pro,C-14,O,S,O,1-Adm,H),(6-231,Pro,C-15,O,S,O,1-Adm,H),(6-232,Pro,C-16,O,S,O,1-Adm,H),(6-233,Pro,C-17,O,S,O,1-Adm,H),(6-234,Pro,C-18,O,S,O,1-Adm,H),(6-235,Pro,C-19,O,S,O,1-Adm,H),(6-236,Pro,C-20,O,S,O,1-Adm,H),(6-237,Pro,C-21,O,S,O,1-Adm,H),(6-238,Pro,C-22,O,S,O,1-Adm,H),(6-239,Pro,C-23,O,S,O,1-Adm,H),(6-240,Pro,C-24,O,S,O,1-Adm,H),(6-241,Pro,C-25,O,S,O,1-Adm,H),(6-242,Pro,C-26,O,S,O,1-Adm,H),(6-243,Pro,C-27,O,S,O,1-Adm,H),(6-244,Pro,C-28,O,S,O,1-Adm,H),(6-245,Pro,C-29,O,S,O,1-Adm,H),(6-246,Pro,C-30,O,S,O,1-Adm,H),(6-247,Pro,C-31,O,S,O,1-Adm,H),(6-248,Pro,C-32,O,S,O,1-Adm,H),(6-249,Pro,C-33,O,S,O,1-Adm,H),(6-250,Pro,C-34,O,S,O,1-Adm,H),(6-251,Pro,C-35,O,S,O,1-Adm,H),(6-252,Pro,C-36,O,S,O,1-Adm,H),(6-253,Pro,C-1,O,S,O,2-Adm,H),(6-254,Pro,C-2,O,S,O,2-Adm,H),(6-255,Pro,C-3,O,S,O,2-Adm,H),(6-256,Pro,C-4,O,S,O,2-Adm,H),(6-257,Pro,C-5,O,S,O,2-Adm,H),(6-258,Pro,C-6,O,S,O,2-Adm,H),(6-259,Pro,C-7,O,S,O,2-Adm,H),(6-260,Pro,C-8,O,S,O,2-Adm,H),(6-261,Pro,C-9,O,S,O,2-Adm,H),(6-262,Pro,C-10,O,S,O,2-Adm,H),(6-263,Pro,C-11,O,S,O,2-Adm,H),(6-264,Pro,C-12,O,S,O,2-Adm,H),(6-265,Pro,C-13,O,S,O,2-Adm,H),(6-266,Pro,C-14,O,S,O,2-Adm,H),(6-267,Pro,C-15,O,S,O,2-Adm,H),(6-268,Pro,C-16,O,S,O,2-Adm,H),(6-269,Pro,C-17,O,S,O,2-Adm,H),(6-270,Pro,C-18,O,S,O,2-Adm,H),(6-271,Pro,C-19,O,S,O,2-Adm,H),(6-272,Pro,C-20,O,S,O,2-Adm,H),(6-273,Pro,C-21,O,S,O,2-Adm,H),(6-274,Pro,C-22,O,S,O,2-Adm,H),(6-275,Pro,C-23,O,S,O,2-Adm,H),(6-276,Pro,C-24,O,S,O,2-Adm,H),(6-277,Pro,C-25,O,S,O,2-Adm,H),(6-278,Pro,C-26,O,S,O,2-Adm,H),(6-279,Pro,C-27,O,S,O,2-Adm,H),(6-280,Pro,C-28,O,S,O,2-Adm,H),(6-281,Pro,C-29,O,S,O,2-Adm,H),(6-282,Pro,C-30,O,S,O,2-Adm,H),(6-283,Pro,C-31,O,S,O,2-Adm,H),(6-284,Pro,C-32,O,S,O,2-Adm,H),(6-285,Pro,C-33,O,S,O,2-Adm,H),(6-286,Pro,C-34,O,S,O,2-Adm,H),(6-287,Pro,C-35,O,S,O,2-Adm,H),(6-288,Pro,C-36,O,S,O,2-Adm,H),(6-289,Pro,C-1,O,S,O,5-OH-2-Adm,H),(6-290,Pro,C-2,O,S,O,5-OH-2-Adm,H),(6-291,Pro,C-3,O,S,O,5-OH-2-Adm,H),(6-292,Pro,C-4,O,S,O,5-OH-2-Adm,H),(6-293,Pro,C-5,O,S,O,5-OH-2-Adm,H),(6-294,Pro,C-6,O,S,O,5-OH-2-Adm,H),(6-295,Pro,C-7,O,S,O,5-OH-2-Adm,H),(6-296,Pro,C-8,O,S,O,5-OH-2-Adm,H),(6-297,Pro,C-9,O,S,O,5-OH-2-Adm,H),(6-298,Pro,C-10,O,S,O,5-OH-2-Adm,H),(6-299,Pro,C-11,O,S,O,5-OH-2-Adm,H),(6-300,Pro,C-12,O,S,O,5-OH-2-Adm,H),(6-301,Pro,C-13,O,S,O,5-OH-2-Adm,H),(6-302,Pro,C-14,O,S,O,5-OH-2-Adm,H),(6-303,Pro,C-15,O,S,O,5-OH-2-Adm,H), (6-304,Pro,C-16,O,S,O,5-OH-2-Adm,H), (6-305,Pro,C-17,O,S,O,5-OH-2-Adm,H),(6-306,Pro,C-18,O,S,O,5-OH-2-Adm,H),(6-307,Pro,C-19,O,S,O,5-OH-2-Adm,H),(6-308,Pro,C-20,O,S,O,5-OH-2-Adm,H),(6-309,Pro,C-21,O,S,O,5-OH-2-Adm,H),(6-310,Pro,C-22,O,S,O,5-OH-2-Adm,H),(6-311,Pro,C-23,O,S,O,5-OH-2-Adm,H),(6-312,Pro,C-24,O,S,O,5-OH-2-Adm,H),(6-313,Pro,C-25,O,S,O,5-OH-2-Adm,H),(6-314,Pro,C-26,O,S,O,5-OH-2-Adm,H),(6-315,Pro,C-27,O,S,O,5-OH-2-Adm,H),(6-316,Pro,C-28,O,S,O,5-OH-2-Adm,H),(6-317,Pro,C-29,O,S,O,5-OH-2-Adm,H),(6-318,Pro,C-30,O,S,O,5-OH-2-Adm,H),(6-319,Pro,C-31,O,S,O,5-OH-2-Adm,H),(6-320,Pro,C-32,O,S,O,5-OH-2-Adm,H),(6-321,Pro,C-33,O,S,O,5-OH-2-Adm,H),(6-322,Pro,C-34,O,S,O,5-OH-2-Adm,H),(6-323,Pro,C-35,O,S,O,5-OH-2-Adm,H),(6-324,Pro,C-36,O,S,O,5-OH-2-Adm,H),(6-325,Pro,D-1,O,S,O,1-Adm,H),(6-326,Pro,D-2,O,S,O,1-Adm,H),(6-327,Pro,D-3,O,S,O,1-Adm,H),(6-328,Pro,D-4,O,S,O,1-Adm,H),(6-329,Pro,D-5,O,S,O,1-Adm,H),(6-330,Pro,D-6,O,S,O,1-Adm,H),(6-331,Pro,D-7,O,S,O,1-Adm,H),(6-332,Pro,D-8,O,S,O,1-Adm,H),(6-333,Pro,D-9,O,S,O,1-Adm,H),(6-334,Pro,D-10,O,S,O,1-Adm,H),(6-335,Pro,D-11,O,S,O,1-Adm,H),(6-336,Pro,D-12,O,S,O,1-Adm,H),(6-337,Pro,D-13,O,S,O,1-Adm,H),(6-338,Pro,D-14,O,S,O,1-Adm,H),(6-339,Pro,D-15,O,S,O,1-Adm,H),(6-340,Pro,D-16,O,S,O,1-Adm,H),(6-341,Pro,D-17,O,S,O,1-Adm,H),(6-342,Pro,D-18,O,S,O,1-Adm,H),(6-343,Pro,D-19,O,S,O,1-Adm,H),(6-344,Pro,D-20,O,S,O,1-Adm,H),(6-345,Pro,D-21,O,S,O,1-Adm,H),(6-346,Pro,D-22,O,S,O,1-Adm,H),(6-347,Pro,D-23,O,S,O,1-Adm,H),(6-348,Pro,D-24,O,S,O,1-Adm,H),(6-349,Pro,D-25,O,S,O,1-Adm,H),(6-350,Pro,D-26,O,S,O,1-Adm,H),(6-351,Pro,D-27,O,S,O,1-Adm,H),(6-352,Pro,D-28,O,S,O,1-Adm,H),(6-353,Pro,D-29,O,S,O,1-Adm,H),(6-354,Pro,D-30,O,S,O,1-Adm,H),(6-355,Pro,D-31,O,S,O,1-Adm,H),(6-356,Pro,D-32,O,S,O,1-Adm,H),(6-357,Pro,D-33,O,S,O,1-Adm,H),(6-358,Pro,D-34,O,S,O,1-Adm,H),(6-359,Pro,D-35,O,S,O,1-Adm,H),(6-360,Pro,D-36,O,S,O,1-Adm,H),(6-361,Pro,D-1,O,S,O,2-Adm,H),(6-362,Pro,D-2,O,S,O,2-Adm,H),(6-363,Pro,D-3,O,S,O,2-Adm,H),(6-364,Pro,D-4,O,S,O,2-Adm,H),(6-365,Pro,D-5,O,S,O,2-Adm,H),(6-366,Pro,D-6,O,S,O,2-Adm,H),(6-367,Pro,D-7,O,S,O,2-Adm,H),(6-368,Pro,D-8,O,S,O,2-Adm,H),(6-369,Pro,D-9,O,S,O,2-Adm,H),(6-370,Pro,D-10,O,S,O,2-Adm,H),(6-371,Pro,D-11,O,S,O,2-Adm,H),(6-372,Pro,D-12,O,S,O,2-Adm,H),(6-373,Pro,D-13,O,S,O,2-Adm,H),(6-374,Pro,D-14,O,S,O,2-Adm,H),(6-375,Pro,D-15,O,S,O,2-Adm,H),(6-376,Pro,D-16,O,S,O,2-Adm,H),(6-377,Pro,D-17,O,S,O,2-Adm,H),(6-378,Pro,D-18,O,S,O,2-Adm,H),(6-379,Pro,D-19,O,S,O,2-Adm,H),(6-380,Pro,D-20,O,S,O,2-Adm,H),(6-381,Pro,D-21,O,S,O,2-Adm,H),(6-382,Pro,D-22,O,S,O,2-Adm,H),(6-383,Pro,D-23,O,S,O,2-Adm,H),(6-384,Pro,D-24,O,S,O,2-Adm,H),(6-385,Pro,D-25,O,S,O,2-Adm,H),(6-386,Pro,D-26,O,S,O,2-Adm,H),(6-387,Pro,D-27,O,S,O,2-Adm,H),(6-388,Pro,D-28,O,S,O,2-Adm,H),(6-389,Pro,D-29,O,S,O,2-Adm,H),(6-390,Pro,D-30,O,S,O,2-Adm,H),(6-391,Pro,D-31,O,S,O,2-Adm,H),(6-392,Pro,D-32,O,S,O,2-Adm,H),(6-393,Pro,D-33,O,S,O,2-Adm,H),(6-394,Pro,D-34,O,S,O,2-Adm,H),(6-395,Pro,D-35,O,S,O,2-Adm,H),(6-396,Pro,D-36,O,S,O,2-Adm,H),(6-397,Pro,D-1,O,S,O,5-OH-2-Adm,H),(6-398,Pro,D-2,O,S,O,5-OH-2-Adm,H),(6-399,Pro,D-3,O,S,O,5-OH-2-Adm,H),(6-400,Pro,D-4,O,S,O,5-OH-2-Adm,H),(6-401,Pro,D-5,O,S,O,5-OH-2-Adm,H),(6-402,Pro,D-6,O,S,O,5-OH-2-Adm,H),(6-403,Pro,D-7,O,S,O,5-OH-2-Adm,H),(6-404,Pro,D-8,O,S,O,5-OH-2-Adm,H),(6-405,Pro,D-9,O,S,O,5-OH-2-Adm,H),(6-406,Pro,D-10,O,S,O,5-OH-2-Adm,H),(6-407,Pro,D-11,O,S,O,5-OH-2-Adm,H),(6-408,Pro,D-12,O,S,O,5-OH-2-Adm,H),(6-409,Pro,D-13,O,S,O,5-OH-2-Adm,H), (6-410,Pro,D-14,O,S,O,5-OH-2-Adm,H), (6-411,Pro,D-15,O,S,O,5-OH-2-Adm,H),(6-412,Pro,D-16,O,S,O,5-OH-2-Adm,H),(6-413,Pro,D-17,O,S,O,5-OH-2-Adm,H),(6-414,Pro,D-18,O,S,O,5-OH-2-Adm,H),(6-415,Pro,D-19,O,S,O,5-OH-2-Adm,H),(6-416,Pro,D-20,O,S,O,5-OH-2-Adm,H),(6-417,Pro,D-21,O,S,O,5-OH-2-Adm,H),(6-418,Pro,D-22,O,S,O,5-OH-2-Adm,H),(6-419,Pro,D-23,O,S,O,5-OH-2-Adm,H),(6-420,Pro,D-24,O,S,O,5-OH-2-Adm,H),(6-421,Pro,D-25,O,S,O,5-OH-2-Adm,H),(6-422,Pro,D-26,O,S,O,5-OH-2-Adm,H),(6-423,Pro,D-27,O,S,O,5-OH-2-Adm,H),(6-424,Pro,D-28,O,S,O,5-OH-2-Adm,H),(6-425,Pro,D-29,O,S,O,5-OH-2-Adm,H),(6-426,Pro,D-30,O,S,O,5-OH-2-Adm,H),(6-427,Pro,D-31,O,S,O,5-OH-2-Adm,H),(6-428,Pro,D-32,O,S,O,5-OH-2-Adm,H),(6-429,Pro,D-33,O,S,O,5-OH-2-Adm,H),(6-430,Pro,D-34,O,S,O,5-OH-2-Adm,H),(6-431,Pro,D-35,O,S,O,5-OH-2-Adm,H),(6-432,Pro,D-36,O,S,O,5-OH-2-Adm,H),(6-433,Pro,E-1,O,S,O,1-Adm,H),(6-434,Pro,E-2,O,S,O,1-Adm,H),(6-435,Pro,E-3,O,S,O,1-Adm,H),(6-436,Pro,E-4,O,S,O,1-Adm,H),(6-437,Pro,E-5,O,S,O,1-Adm,H),(6-438,Pro,E-6,O,S,O,1-Adm,H),(6-439,Pro,E-7,O,S,O,1-Adm,H),(6-440,Pro,E-8,O,S,O,1-Adm,H),(6-441,Pro,E-9,O,S,O,1-Adm,H),(6-442,Pro,E-10,O,S,O,1-Adm,H),(6-443,Pro,E-11,O,S,O,1-Adm,H),(6-444,Pro,E-12,O,S,O,1-Adm,H),(6-445,Pro,E-13,O,S,O,1-Adm,H),(6-446,Pro,E-14,O,S,O,1-Adm,H),(6-447,Pro,E-15,O,S,O,1-Adm,H),(6-448,Pro,E-16,O,S,O,1-Adm,H),(6-449,Pro,E-17,O,S,O,1-Adm,H),(6-450,Pro,E-18,O,S,O,1-Adm,H),(6-451,Pro,E-19,O,S,O,1-Adm,H),(6-452,Pro,E-20,O,S,O,1-Adm,H),(6-453,Pro,E-21,O,S,O,1-Adm,H),(6-454,Pro,E-22,O,S,O,1-Adm,H),(6-455,Pro,E-23,O,S,O,1-Adm,H),(6-456,Pro,E-24,O,S,O,1-Adm,H),(6-457,Pro,E-25,O,S,O,1-Adm,H),(6-458,Pro,E-26,O,S,O,1-Adm,H),(6-459,Pro,E-27,O,S,O,1-Adm,H),(6-460,Pro,E-28,O,S,O,1-Adm,H),(6-461,Pro,E-29,O,S,O,1-Adm,H),(6-462,Pro,E-30,O,S,O,1-Adm,H),(6-463,Pro,E-31,O,S,O,1-Adm,H),(6-464,Pro,E-32,O,S,O,1-Adm,H),(6-465,Pro,E-33,O,S,O,1-Adm,H),(6-466,Pro,E-34,O,S,O,1-Adm,H),(6-467,Pro,E-35,O,S,O,1-Adm,H),(6-468,Pro,E-36,O,S,O,1-Adm,H),(6-469,Pro,E-1,O,S,O,2-Adm,H),(6-470,Pro,E-2,O,S,O,2-Adm,H),(6-471,Pro,E-3,O,S,O,2-Adm,H),(6-472,Pro,E-4,O,S,O,2-Adm,H),(6-473,Pro,E-5,O,S,O,2-Adm,H),(6-474,Pro,E-6,O,S,O,2-Adm,H),(6-475,Pro,E-7,O,S,O,2-Adm,H),(6-476,Pro,E-8,O,S,O,2-Adm,H),(6-477,Pro,E-9,O,S,O,2-Adm,H),(6-478,Pro,E-10,O,S,O,2-Adm,H),(6-479,Pro,E-11,O,S,O,2-Adm,H),(6-480,Pro,E-12,O,S,O,2-Adm,H),(6-481,Pro,E-13,O,S,O,2-Adm,H),(6-482,Pro,E-14,O,S,O,2-Adm,H),(6-483,Pro,E-15,O,S,O,2-Adm,H),(6-484,Pro,E-16,O,S,O,2-Adm,H),(6-485,Pro,E-17,O,S,O,2-Adm,H),(6-486,Pro,E-18,O,S,O,2-Adm,H),(6-487,Pro,E-19,O,S,O,2-Adm,H),(6-488,Pro,E-20,O,S,O,2-Adm,H),(6-489,Pro,E-21,O,S,O,2-Adm,H),(6-490,Pro,E-22,O,S,O,2-Adm,H),(6-491,Pro,E-23,O,S,O,2-Adm,H),(6-492,Pro,E-24,O,S,O,2-Adm,H),(6-493,Pro,E-25,O,S,O,2-Adm,H),(6-494,Pro,E-26,O,S,O,2-Adm,H),(6-495,Pro,E-27,O,S,O,2-Adm,H),(6-496,Pro,E-28,O,S,O,2-Adm,H),(6-497,Pro,E-29,O,S,O,2-Adm,H),(6-498,Pro,E-30,O,S,O,2-Adm,H),(6-499,Pro,E-31,O,S,O,2-Adm,H),(6-500,Pro,E-32,O,S,O,2-Adm,H),(6-501,Pro,E-33,O,S,O,2-Adm,H),(6-502,Pro,E-34,O,S,O,2-Adm,H),(6-503,Pro,E-35,O,S,O,2-Adm,H),(6-504,Pro,E-36,O,S,O,2-Adm,H),(6-505,Pro,E-1,O,S,O,5-OH-2-Adm,H),(6-506,Pro,E-2,O,S,O,5-OH-2-Adm,H),(6-507,Pro,E-3,O,S,O,5-OH-2-Adm,H),(6-508,Pro,E-4,O,S,O,5-OH-2-Adm,H),(6-509,Pro,E-5,O,S,O,5-OH-2-Adm,H),(6-510,Pro,E-6,O,S,O,5-OH-2-Adm,H),(6-511,Pro,E-7,O,S,O,5-OH-2-Adm,H),(6-512,Pro,E-8,O,S,O,5-OH-2-Adm,H),(6-513,Pro,E-9,O,S,O,5-OH-2-Adm,H),(6-514,Pro,E-10,O,S,O,5-OH-2-Adm,H),(6-515,Pro,E-11,O,S,O,5-OH-2-Adm,H),(6-516,Pro, E-12,O,S,O,5-OH-2-Adm,H),(6-517,Pro,E-13,O,S,O,5-OH-2-Adm,H),(6-518,Pro,E-14,O,S,O,5-OH-2-Adm,H),(6-519,Pro,E-15,O,S,O,5-OH-2-Adm,H),(6-520,Pro,E-16,O,S,O,5-OH-2-Adm,H),(6-521,Pro,E-17,O,S,O,5-OH-2-Adm,H),(6-522,Pro,E-18,O,S,O,5-OH-2-Adm,H),(6-523,Pro,E-19,O,S,O,5-OH-2-Adm,H),(6-524,Pro,E-20,O,S,O,5-OH-2-Adm,H),(6-525,Pro,E-21,O,S,O,5-OH-2-Adm,H),(6-526,Pro,E-22,O,S,O,5-OH-2-Adm,H),(6-527,Pro,E-23,O,S,O,5-OH-2-Adm,H),(6-528,Pro,E-24,O,S,O,5-OH-2-Adm,H),(6-529,Pro,E-25,O,S,O,5-OH-2-Adm,H),(6-530,Pro,E-26,O,S,O,5-OH-2-Adm,H),(6-531,Pro,E-27,O,S,O,5-OH-2-Adm,H),(6-532,Pro,E-28,O,S,O,5-OH-2-Adm,H),(6-533,Pro,E-29,O,S,O,5-OH-2-Adm,H),(6-534,Pro,E-30,O,S,O,5-OH-2-Adm,H),(6-535,Pro,E-31,O,S,O,5-OH-2-Adm,H),(6-536,Pro,E-32,O,S,O,5-OH-2-Adm,H),(6-537,Pro,E-33,O,S,O,5-OH-2-Adm,H),(6-538,Pro,E-34,O,S,O,5-OH-2-Adm,H),(6-539,Pro,E-35,O,S,O,5-OH-2-Adm,H),(6-540,Pro,E-36,O,S,O,5-OH-2-Adm,H),(6-541,Pro,F-1,O,S,O,1-Adm,H),(6-542,Pro,F-2,O,S,O,1-Adm,H),(6-543,Pro,F-3,O,S,O,1-Adm,H),(6-544,Pro,F-4,O,S,O,1-Adm,H),(6-545,Pro,F-5,O,S,O,1-Adm,H),(6-546,Pro,F-6,O,S,O,1-Adm,H),(6-547,Pro,F-7,O,S,O,1-Adm,H),(6-548,Pro,F-8,O,S,O,1-Adm,H),(6-549,Pro,F-9,O,S,O,1-Adm,H),(6-550,Pro,F-10,O,S,O,1-Adm,H),(6-551,Pro,F-11,O,S,O,1-Adm,H),(6-552,Pro,F-12,O,S,O,1-Adm,H),(6-553,Pro,F-13,O,S,O,1-Adm,H),(6-554,Pro,F-14,O,S,O,1-Adm,H),(6-555,Pro,F-15,O,S,O,1-Adm,H),(6-556,Pro,F-16,O,S,O,1-Adm,H),(6-557,Pro,F-17,O,S,O,1-Adm,H),(6-558,Pro,F-18,O,S,O,1-Adm,H),(6-559,Pro,F-19,O,S,O,1-Adm,H),(6-560,Pro,F-20,O,S,O,1-Adm,H),(6-561,Pro,F-21,O,S,O,1-Adm,H),(6-562,Pro,F-22,O,S,O,1-Adm,H),(6-563,Pro,F-23,O,S,O,1-Adm,H),(6-564,Pro,F-24,O,S,O,1-Adm,H),(6-565,Pro,F-25,O,S,O,1-Adm,H),(6-566,Pro,F-26,O,S,O,1-Adm,H),(6-567,Pro,F-27,O,S,O,1-Adm,H),(6-568,Pro,F-28,O,S,O,1-Adm,H),(6-569,Pro,F-29,O,S,O,1-Adm,H),(6-570,Pro,F-30,O,S,O,1-Adm,H),(6-571,Pro,F-31,O,S,O,1-Adm,H),(6-572,Pro,F-32,O,S,O,1-Adm,H),(6-573,Pro,F-33,O,S,O,1-Adm,H),(6-574,Pro,F-34,O,S,O,1-Adm,H),(6-575,Pro,F-35,O,S,O,1-Adm,H),(6-576,Pro,F-36,O,S,O,1-Adm,H),(6-577,Pro,F-1,O,S,O,2-Adm,H),(6-578,Pro,F-2,O,S,O,2-Adm,H),(6-579,Pro,F-3,O,S,O,2-Adm,H),(6-580,Pro,F-4,O,S,O,2-Adm,H),(6-581,Pro,F-5,O,S,O,2-Adm,H),(6-582,Pro,F-6,O,S,O,2-Adm,H),(6-583,Pro,F-7,O,S,O,2-Adm,H),(6-584,Pro,F-8,O,S,O,2-Adm,H),(6-585,Pro,F-9,O,S,O,2-Adm,H),(6-586,Pro,F-10,O,S,O,2-Adm,H),(6-587,Pro,F-11,O,S,O,2-Adm,H),(6-588,Pro,F-12,O,S,O,2-Adm,H),(6-589,Pro,F-13,O,S,O,2-Adm,H),(6-590,Pro,F-14,O,S,O,2-Adm,H),(6-591,Pro,F-15,O,S,O,2-Adm,H),(6-592,Pro,F-16,O,S,O,2-Adm,H),(6-593,Pro,F-17,O,S,O,2-Adm,H),(6-594,Pro,F-18,O,S,O,2-Adm,H),(6-595,Pro,F-19,O,S,O,2-Adm,H),(6-596,Pro,F-20,O,S,O,2-Adm,H),(6-597,Pro,F-21,O,S,O,2-Adm,H),(6-598,Pro,F-22,O,S,O,2-Adm,H),(6-599,Pro,F-23,O,S,O,2-Adm,H),(6-600,Pro,F-24,O,S,O,2-Adm,H),(6-601,Pro,F-25,O,S,O,2-Adm,H),(6-602,Pro,F-26,O,S,O,2-Adm,H),(6-603,Pro,F-27,O,S,O,2-Adm,H),(6-604,Pro,F-28,O,S,O,2-Adm,H),(6-605,Pro,F-29,O,S,O,2-Adm,H),(6-606,Pro,F-30,O,S,O,2-Adm,H),(6-607,Pro,F-31,O,S,O,2-Adm,H),(6-608,Pro,F-32,O,S,O,2-Adm,H),(6-609,Pro,F-33,O,S,O,2-Adm,H),(6-610,Pro,F-34,O,S,O,2-Adm,H),(6-611,Pro,F-35,O,S,O,2-Adm,H),(6-612,Pro,F-36,O,S,O,2-Adm,H),(6-613,Pro,F-1,O,S,O,5-OH-2-Adm,H),(6-614,Pro,F-2,O,S,O,5-OH-2-Adm,H),(6-615,Pro,F-3,O,S,O,5-OH-2-Adm,H),(6-616,Pro,F-4,O,S,O,5-OH-2-Adm,H),(6-617,Pro,F-5,O,S,O,5-OH-2-Adm,H),(6-618,Pro,F-6,O,S,O,5-OH-2-Adm,H),(6-619,Pro,F-7,O,S,O,5-OH-2-Adm,H),(6-620,Pro,F-8,O,S,O,5-OH-2-Adm,H),(6-621,Pro,F-9,O,S,O,5-OH-2-Adm,H),(6-622,Pro,F-10,O,S,O,5-OH-2-Adm,H),(6-623,Pro,F-11,O,S,O,5-OH-2-Adm,H), (6-624,Pro,F-12,O,S,O,5-OH-2-

Adm,H),(6-625,Pro,F-13,O,S,O,5-OH-2-Adm,H),(6-626, Pro,F-14,O,S,O,5-OH-2-Adm,H),(6-627,Pro,F-15,O,S,O,5-OH-2-Adm,H),(6-628,Pro,F-16,O,S,O,5-OH-2-Adm,H),(6-629,Pro,F-17,O,S,O,5-OH-2-Adm,H),(6-630,Pro,F-18,O,S,O,5-OH-2-Adm,H),(6-631,Pro,F-19,O,S,O,5-OH-2-Adm,H),(6-632,Pro,F-20,O,S,O,5-OH-2-Adm,H),(6-633,Pro,F-21,O,S,O,5-OH-2-Adm,H),(6-634,Pro,F-22,O,S,O,5-OH-2-Adm,H),(6-635,Pro,F-23,O,S,O,5-OH-2-Adm,H),(6-636, Pro,F-24,O,S,O,5-OH-2-Adm,H),(6-637,Pro,F-25,O,S,O,5-OH-2-Adm,H),(6-638,Pro,F-26,O,S,O,5-OH-2-Adm,H),(6-639,Pro,F-27,O,S,O,5-OH-2-Adm,H),(6-640,Pro,F-28,O,S,O,5-OH-2-Adm,H),(6-641,Pro,F-29,O,S,O,5-OH-2-Adm, H),(6-642,Pro,F-30,O,S,O,5-OH-2-Adm,H),(6-643,Pro,F-31,O,S,O,5-OH-2-Adm,H),(6-644,Pro,F-32,O,S,O,5-OH-2-Adm,H),(6-645,Pro,F-33,O,S,O,5-OH-2-Adm,H),(6-646, Pro,F-34,O,S,O,5-OH-2-Adm,H),(6-647,Pro,F-35,O,S,O,5-OH-2-Adm,H),(6-648,Pro,F-36,O,S,O,5-OH-2-Adm,H),(6-649,Pro,G-1,O,S,O,1-Adm,H),(6-650,Pro,G-2,O,S,O,1-Adm,H),(6-651,Pro,G-3,O,S,O,1-Adm,H),(6-652,Pro,G-4, O,S,O,1-Adm,H),(6-653,Pro,G-5,O,S,O,1-Adm,H),(6-654, Pro,G-6,O,S,O,1-Adm,H),(6-655,Pro,G-7,O,S,O,1-Adm, H),(6-656,Pro,G-8,O,S,O,1-Adm,H),(6-657,Pro,G-9,O,S,O,1-Adm,H),(6-658,Pro,G-1,O,S,O,2-Adm,H),(6-659,Pro,G-2,O,S,O,2-Adm,H),(6-660,Pro,G-3,O,S,O,2-Adm,H),(6-661,Pro,G-4,O,S,O,2-Adm,H),(6-662,Pro,G-5,O,S,O,2-Adm,H),(6-663,Pro,G-6,O,S,O,2-Adm,H),(6-664,Pro,G-7, O,S,O,2-Adm,H),(6-665,Pro,G-8,O,S,O,2-Adm,H),(6-666, Pro,G-9,O,S,O,2-Adm,H),(6-667,Pro,G-1,O,S,O,5-OH-2-Adm,H),(6-668,Pro,G-2,O,S,O,5-OH-2-Adm,H),(6-669, Pro,G-3,O,S,O,5-OH-2-Adm,H),(6-670,Pro,G-4,O,S,O,5-OH-2-Adm,H),(6-671,Pro,G-5,O,S,O,5-OH-2-Adm,H),(6-672,Pro,G-6,O,S,O,5-OH-2-Adm,H),(6-673,Pro,G-7,O,S, O,5-OH-2-Adm,H),(6-674,Pro,G-8,O,S,O,5-OH-2-Adm, H),(6-675,Pro,G-9,O,S,O,5-OH-2-Adm,H),(6-676,Pro,H-1, O,S,O,1-Adm,H),(6-677,Pro,H-2,O,S,O,1-Adm,H),(6-678, Pro,H-3,O,S,O,1-Adm,H),(6-679,Pro,H-4,O,S,O,1-Adm, H),(6-680,Pro,H-5,O,S,O,1-Adm,H),(6-681,Pro,H-6,O,S,O,1-Adm,H),(6-682,Pro,H-7,O,S,O,1-Adm,H),(6-683,Pro,H-8,O,S,O,1-Adm,H),(6-684,Pro,H-9,O,S,O,1-Adm,H),(6-685,Pro,H-1,O,S,O,2-Adm,H),(6-686,Pro,H-2,O,S,O,2-Adm,H),(6-687,Pro,H-3,O,S,O,2-Adm,H),(6-688,Pro,H-4, O,S,O,2-Adm,H),(6-689,Pro,H-5,O,S,O,2-Adm,H),(6-690, Pro,H-6,O,S,O,2-Adm,H),(6-691,Pro,H-7,O,S,O,2-Adm, H),(6-692,Pro,H-8,O,S,O,2-Adm,H),(6-693,Pro,H-9,O,S,O,2-Adm,H),(6-694,Pro,H-1,O,S,O,5-OH-2-Adm,H),(6-695, Pro,H-2,O,S,O,5-OH-2-Adm,H),(6-696,Pro,H-3,O,S,O,5-OH-2-Adm,H),(6-697,Pro,H-4,O,S,O,5-OH-2-Adm,H),(6-698,Pro,H-5,O,S,O,5-OH-2-Adm,H),(6-699,Pro,H-6,O,S, O,5-OH-2-Adm,H),(6-700,Pro,H-7,O,S,O,5-OH-2-Adm, H),(6-701,Pro,H-8,O,S,O,5-OH-2-Adm,H),(6-702,Pro,H-9, O,S,O,5-OH-2-Adm,H),(6-703,Pro,I-1,O,S,O,1-Adm,H), (6-704,Pro,I-2,O,S,O,1-Adm,H),(6-705,Pro,I-3,O,S,O,1-Adm,H),(6-706,Pro,I-4,O,S,O,1-Adm,H),(6-707,Pro,I-5,O, S,O,1-Adm,H),(6-708,Pro,I-6,O,S,O,1-Adm,H),(6-709,Pro, I-7,O,S,O,1-Adm,H),(6-710,Pro,I-8,O,S,O,1-Adm,H),(6-711,Pro,I-9,O,S,O,1-Adm,H),(6-712,Pro,I-1,O,S,O,2-Adm, H),(6-713,Pro,I-2,O,S,O,2-Adm,H),(6-714,Pro,I-3,O,S,O,2-Adm,H),(6-715,Pro,I-4,O,S,O,2-Adm,H),(6-716,Pro,I-5,O, S,O,2-Adm,H),(6-717,Pro,I-6,O,S,O,2-Adm,H),(6-718,Pro, I-7,O,S,O,2-Adm,H),(6-719,Pro,I-8,O,S,O,2-Adm,H),(6-720,Pro,I-9,O,S,O,2-Adm,H),(6-721,Pro,I-1,O,S,O,5-OH-2-Adm,H),(6-722,Pro,I-2,O,S,O,5-OH-2-Adm,H),(6-723, Pro,I-3,O,S,O,5-OH-2-Adm,H),(6-724,Pro,I-4,O,S,O,5-OH-2-Adm,H),(6-725,Pro,I-5,O,S,O,5-OH-2-Adm,H),(6-726,Pro,I-6,O,S,O,5-OH-2-Adm,H),(6-727,Pro,I-7,O,S,O, 5-OH-2-Adm,H),(6-728,Pro,I-8,O,S,O,5-OH-2-Adm,H),(6-729,Pro,I-9,O,S,O,5-OH-2-Adm,H), (6-730,Pro,J-1,O,S,O, 1-Adm,H),(6-731,Pro,J-2,O,S,O,1-Adm,H),(6-732,Pro,J-3, O,S,O,1-Adm,H),(6-733,Pro,J-4,O,S,O,1-Adm,H),(6-734, Pro,J-5,O,S,O,1-Adm,H),(6-735,Pro,J-6,O,S,O,1-Adm,H), (6-736,Pro,J-7,O,S,O,1-Adm,H),(6-737,Pro,J-8,O,S,O,1-Adm,H),(6-738,Pro,J-9,O,S,O,1-Adm,H),(6-739,Pro,J-1,O, S,O,2-Adm,H),(6-740,Pro,J-2,O,S,O,2-Adm,H),(6-741,Pro, J-3,O,S,O,2-Adm,H),(6-742,Pro,J-4,O,S,O,2-Adm,H),(6-743,Pro,J-5,O,S,O,2-Adm,H),(6-744,Pro,J-6,O,S,O,2-Adm, H),(6-745,Pro,J-7,O,S,O,2-Adm,H),(6-746,Pro,J-8,O,S,O, 2-Adm,H),(6-747,Pro,J-9,O,S,O,2-Adm,H),(6-748,Pro,J-1, O,S,O,5-OH-2-Adm,H),(6-749,Pro,J-2,O,S,O,5-OH-2-Adm,H),(6-750,Pro,J-3,O,S,O,5-OH-2-Adm,H),(6-751,Pro, J-4,O,S,O,5-OH-2-Adm,H),(6-752,Pro,J-5,O,S,O,5-OH-2-Adm,H),(6-753,Pro,J-6,O,S,O,5-OH-2-Adm,H),(6-754,Pro, J-7,O,S,O,5-OH-2-Adm,H),(6-755,Pro,J-8,O,S,O,5-OH-2-Adm,H),(6-756,Pro,J-9,O,S,O,5-OH-2-Adm,H),(6-757,Pro, K-1,O,S,O,1-Adm,H),(6-758,Pro,K-2,O,S,O,1-Adm,H),(6-759,Pro,K-3,O,S,O,1-Adm,H),(6-760,Pro,K-4,O,S,O,1-Adm,H),(6-761,Pro,K-5,O,S,O,1-Adm,H),(6-762,Pro,K-6, O,S,O,1-Adm,H),(6-763,Pro,K-7,O,S,O,1-Adm,H),(6-764, Pro,K-8,O,S,O,1-Adm,H),(6-765,Pro,K-9,O,S,O,1-Adm, H),(6-766,Pro,K-1,O,S,O,2-Adm,H),(6-767,Pro,K-2,O,S,O, 2-Adm,H),(6-768,Pro,K-3,O,S,O,2-Adm,H),(6-769,Pro,K-4,O,S,O,2-Adm,H),(6-770,Pro,K-5,O,S,O,2-Adm,H),(6-771,Pro,K-6,O,S,O,2-Adm,H),(6-772,Pro,K-7,O,S,O,2-Adm,H),(6-773,Pro,K-8,O,S,O,2-Adm,H),(6-774,Pro,K-9, O,S,O,2-Adm,H),(6-775,Pro,K-1,O,S,O,5-OH-2-Adm,H), (6-776,Pro,K-2,O,S,O,5-OH-2-Adm,H),(6-777,Pro,K-3,O, S,O,5-OH-2-Adm,H),(6-778,Pro,K-4,O,S,O,5-OH-2-Adm, H),(6-779,Pro,K-5,O,S,O,5-OH-2-Adm,H),(6-780,Pro,K-6, O,S,O,5-OH-2-Adm,H),(6-781,Pro,K-7,O,S,O,5-OH-2-Adm,H),(6-782,Pro,K-8,O,S,O,5-OH-2-Adm,H),(6-783, Pro,K-9,O,S,O,5-OH-2-Adm,H)

Concretely, the defined compound is shown by using the formula (VI).

[Formula 41]

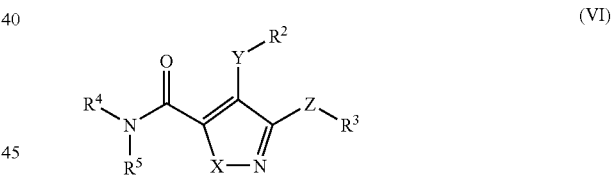

(VI)

(Compound No., $R^2,R^3,X,Y,Z,R^4,R^5$)=(7-1,i-Bu,A-1,S,S, O,1-Adm,H),(7-2,i-Bu,A-2,S,S,O,1-Adm,H),(7-3,i-Bu,A-3, S,S,O,1-Adm,H),(7-4,i-Bu,A-4,S,S,O,1-Adm,H),(7-5,i-Bu, A-5,S,S,O,1-Adm,H),(7-6,i-Bu,A-6,S,S,O,1-Adm,H),(7-7, i-Bu,A-7,S,S,O,1-Adm,H),(7-8,i-Bu,A-8,S,S,O,1-Adm,H), (7-9,i-Bu,A-9,S,S,O,1-Adm,H),(7-10,i-Bu,A-10,S,S,O,1-Adm,H),(7-11,i-Bu,A-11,S,S,O,1-Adm,H),(7-12,i-Bu,A-12,S,S,O,1-Adm,H),(7-13,i-Bu,A-13,S,S,O,1-Adm,H),(7-14,i-Bu,A-14,S,S,O,1-Adm,H),(7-15,i-Bu,A-15,S,S,O,1-Adm,H),(7-16,i-Bu,A-16,S,S,O,1-Adm,H),(7-17,i-Bu,A-17,S,S,O,1-Adm,H),(7-18,i-Bu,A-18,S,S,O,1-Adm,H),(7-19,i-Bu,A-19,S,S,O,1-Adm,H),(7-20,i-Bu,A-20,S,S,O,1-Adm,H),(7-21,i-Bu,A-21,S,S,O,1-Adm,H),(7-22,i-Bu,A-22,S,S,O,1-Adm,H),(7-23,i-Bu,A-23,S,S,O,1-Adm,H),(7-24,i-Bu,A-24,S,S,O,1-Adm,H),(7-25,i-Bu,A-25,S,S,O,1-Adm,H),(7-26,i-Bu,A-26,S,S,O,1-Adm,H),(7-27,i-Bu,A-27,S,S,O,1-Adm,H),(7-28,i-Bu,A-28,S,S,O,1-Adm,H),(7-29,i-Bu,A-29,S,S,O,1-Adm,H),(7-30,i-Bu,A-30,S,S,O,1-Adm,H),(7-31,i-Bu,A-31,S,S,O,1-Adm,H),(7-32,i-Bu,A-32,S,S,O,1-Adm,H),(7-33,i-Bu,A-33,S,S,O, 1-Adm,H),(7-

34,i-Bu,A-34,S,S,O,1-Adm,H),(7-35,i-Bu,A-35,S,S,O,1-Adm,H),(7-36,i-Bu,A-36,S,S,O,1-Adm,H),(7-37,i-Bu,A-1,S,S,O,2-Adm,H),(7-38,i-Bu,A-2,S,S,O,2-Adm,H),(7-39,i-Bu,A-3,S,S,O,2-Adm,H),(7-40,i-Bu,A-4,S,S,O,2-Adm,H),(7-41,i-Bu,A-5,S,S,O,2-Adm,H),(7-42,i-Bu,A-6,S,S,O,2-Adm,H),(7-43,i-Bu,A-7,S,S,O,2-Adm,H),(7-44,i-Bu,A-8,S,S,O,2-Adm,H),(7-45,i-Bu,A-9,S,S,O,2-Adm,H),(7-46,i-Bu,A-10,S,S,O,2-Adm,H),(7-47,i-Bu,A-11,S,S,O,2-Adm,H),(7-48,i-Bu,A-12,S,S,O,2-Adm,H),(7-49,i-Bu,A-13,S,S,O,2-Adm,H),(7-50,i-Bu,A-14,S,S,O,2-Adm,H),(7-51,i-Bu,A-15,S,S,O,2-Adm,H),(7-52,i-Bu,A-16,S,S,O,2-Adm,H),(7-53,i-Bu,A-17,S,S,O,2-Adm,H),(7-54,i-Bu,A-18,S,S,O,2-Adm,H),(7-55,i-Bu,A-19,S,S,O,2-Adm,H),(7-56,i-Bu,A-20,S,S,O,2-Adm,H),(7-57,i-Bu,A-21,S,S,O,2-Adm,H),(7-58,i-Bu,A-22,S,S,O,2-Adm,H),(7-59,i-Bu,A-23,S,S,O,2-Adm,H),(7-60,i-Bu,A-24,S,S,O,2-Adm,H),(7-61,i-Bu,A-25,S,S,O,2-Adm,H),(7-62,i-Bu,A-26,S,S,O,2-Adm,H),(7-63,i-Bu,A-27,S,S,O,2-Adm,H),(7-64,i-Bu,A-28,S,S,O,2-Adm,H),(7-65,i-Bu,A-29,S,S,O,2-Adm,H),(7-66,i-Bu,A-30,S,S,O,2-Adm,H),(7-67,i-Bu,A-31,S,S,O,2-Adm,H),(7-68,i-Bu,A-32,S,S,O,2-Adm,H),(7-69,i-Bu,A-33,S,S,O,2-Adm,H),(7-70,i-Bu,A-34,S,S,O,2-Adm,H),(7-71,i-Bu,A-35,S,S,O,2-Adm,H),(7-72,i-Bu,A-36,S,S,O,2-Adm,H),(7-73,i-Bu,A-1,S,S,O,5-OH-2-Adm,H),(7-74,i-Bu,A-2,S,S,O,5-OH-2-Adm,H),(7-75,i-Bu,A-3,S,S,O,5-OH-2-Adm,H),(7-76,i-Bu,A-4,S,S,O,5-OH-2-Adm,H),(7-77,i-Bu,A-5,S,S,O,5-OH-2-Adm,H),(7-78,i-Bu,A-6,S,S,O,5-OH-2-Adm,H),(7-79,i-Bu,A-7,S,S,O,5-OH-2-Adm,H),(7-80,i-Bu,A-8,S,S,O,5-OH-2-Adm,H),(7-81,i-Bu,A-9,S,S,O,5-OH-2-Adm,H),(7-82,i-Bu,A-10,S,S,O,5-OH-2-Adm,H),(7-83,i-Bu,A-11,S,S,O,5-OH-2-Adm,H),(7-84,i-Bu,A-12,S,S,O,5-OH-2-Adm,H),(7-85,i-Bu,A-13,S,S,O,5-OH-2-Adm,H),(7-86,i-Bu,A-14,S,S,O,5-OH-2-Adm,H),(7-87,i-Bu,A-15,S,S,O,5-OH-2-Adm,H),(7-88,i-Bu,A-16,S,S,O,5-OH-2-Adm,H),(7-89,i-Bu,A-17,S,S,O,5-OH-2-Adm,H),(7-90,i-Bu,A-18,S,S,O,5-OH-2-Adm,H),(7-91,i-Bu,A-19,S,S,O,5-OH-2-Adm,H),(7-92,i-Bu,A-20,S,S,O,5-OH-2-Adm,H),(7-93,i-Bu,A-21,S,S,O,5-OH-2-Adm,H),(7-94,i-Bu,A-22,S,S,O,5-OH-2-Adm,H),(7-95,i-Bu,A-23,S,S,O,5-OH-2-Adm,H),(7-96,i-Bu,A-24,S,S,O,5-OH-2-Adm,H),(7-97,i-Bu,A-25,S,S,O,5-OH-2-Adm,H),(7-98,i-Bu,A-26,S,S,O,5-OH-2-Adm,H),(7-99,i-Bu,A-27,S,S,O,5-OH-2-Adm,H),(7-100,i-Bu,A-28,S,S,O,5-OH-2-Adm,H),(7-101,i-Bu,A-29,S,S,O,5-OH-2-Adm,H),(7-102,i-Bu,A-30,S,S,O,5-OH-2-Adm,H),(7-103,i-Bu,A-31,S,S,O,5-OH-2-Adm,H),(7-104,i-Bu,A-32,S,S,O,5-OH-2-Adm,H),(7-105,i-Bu,A-33,S,S,O,5-OH-2-Adm,H),(7-106,i-Bu,A-34,S,S,O,5-OH-2-Adm,H),(7-107,i-Bu,A-35,S,S,O,5-OH-2-Adm,H),(7-108,i-Bu,A-36,S,S,O,5-OH-2-Adm,H),(7-109,i-Bu,B-1,S,S,O,1-Adm,H),(7-110,i-Bu,B-2,S,S,O,1-Adm,H),(7-111,i-Bu,B-3,S,S,O,1-Adm,H),(7-112,i-Bu,B-4,S,S,O,1-Adm,H),(7-113,i-Bu,B-5,S,S,O,1-Adm,H),(7-114,i-Bu,B-6,S,S,O,1-Adm,H),(7-115,i-Bu,B-7,S,S,O,1-Adm,H),(7-116,i-Bu,B-8,S,S,O,1-Adm,H),(7-117,i-Bu,B-9,S,S,O,1-Adm,H),(7-118,i-Bu,B-10,S,S,O,1-Adm,H),(7-119,i-Bu,B-11,S,S,O,1-Adm,H),(7-120,i-Bu,B-12,S,S,O,1-Adm,H),(7-121,i-Bu,B-13,S,S,O,1-Adm,H),(7-122,i-Bu,B-14,S,S,O,1-Adm,H),(7-123,i-Bu,B-15,S,S,O,1-Adm,H),(7-124,i-Bu,B-16,S,S,O,1-Adm,H),(7-125,i-Bu,B-17,S,S,O,1-Adm,H),(7-126,i-Bu,B-18,S,S,O,1-Adm,H),(7-127,i-Bu,B-19,S,S,O,1-Adm,H),(7-128,i-Bu,B-20,S,S,O,1-Adm,H),(7-129,i-Bu,B-21,S,S,O,1-Adm,H),(7-130,i-Bu,B-22,S,S,O,1-Adm,H),(7-131,i-Bu,B-23,S,S,O,1-Adm,H),(7-132,i-Bu,B-24,S,S,O,1-Adm,H),(7-133,i-Bu,B-25,S,S,O,1-Adm,H),(7-134,i-Bu,B-26,S,S,O,1-Adm,H),(7-135,i-Bu,B-27,S,S,O,1-Adm,H),(7-136,i-Bu,B-28,S,S,O,1-Adm,H),(7-137,i-Bu,B-29,S,S,O,1-Adm,H),(7-138,i-Bu,B-30,S,S,O,1-Adm,H),(7-139,i-Bu,B-31,S,S,O,1-Adm,H),(7-140,i-Bu,B-32,S,S,O,1-Adm,H),(7-141,i-Bu,B-33,S,S,O,1-Adm,H),(7-142,i-Bu,B-34,S,S,O,1-Adm,H),(7-143,i-Bu,B-35,S,S,O,1-Adm,H),(7-144,i-Bu,B-36,S,S,O,1-Adm,H),(7-145,i-Bu,B-1,S,S,O,2-Adm,H),(7-146,i-Bu,B-2,S,S,O,2-Adm,H),(7-147,i-Bu,B-3,S,S,O,2-Adm,H),(7-148,i-Bu,B-4,S,S,O,2-Adm,H),(7-149,i-Bu,B-5,S,S,O,2-Adm,H),(7-150,i-Bu,B-6,S,S,O,2-Adm,H),(7-151,i-Bu,B-7,S,S,O,2-Adm,H),(7-152,i-Bu,B-8,S,S,O,2-Adm,H),(7-153,i-Bu,B-9,S,S,O,2-Adm,H),(7-154,i-Bu,B-10,S,S,O,2-Adm,H),(7-155,i-Bu,B-11,S,S,O,2-Adm,H),(7-156,i-Bu,B-12,S,S,O,2-Adm,H),(7-157,i-Bu,B-13,S,S,O,2-Adm,H),(7-158,i-Bu,B-14,S,S,O,2-Adm,H),(7-159,i-Bu,B-15,S,S,O,2-Adm,H),(7-160,i-Bu,B-16,S,S,O,2-Adm,H),(7-161,i-Bu,B-17,S,S,O,2-Adm,H),(7-162,i-Bu,B-18,S,S,O,2-Adm,H),(7-163,i-Bu,B-19,S,S,O,2-Adm,H),(7-164,i-Bu,B-20,S,S,O,2-Adm,H),(7-165,i-Bu,B-21,S,S,O,2-Adm,H),(7-166,i-Bu,B-22,S,S,O,2-Adm,H),(7-167,i-Bu,B-23,S,S,O,2-Adm,H),(7-168,i-Bu,B-24,S,S,O,2-Adm,H),(7-169,i-Bu,B-25,S,S,O,2-Adm,H),(7-170,i-Bu,B-26,S,S,O,2-Adm,H),(7-171,i-Bu,B-27,S,S,O,2-Adm,H),(7-172,i-Bu,B-28,S,S,O,2-Adm,H),(7-173,i-Bu,B-29,S,S,O,2-Adm,H),(7-174,i-Bu,B-30,S,S,O,2-Adm,H),(7-175,i-Bu,B-31,S,S,O,2-Adm,H),(7-176,i-Bu,B-32,S,S,O,2-Adm,H),(7-177,i-Bu,B-33,S,S,O,2-Adm,H),(7-178,i-Bu,B-34,S,S,O,2-Adm,H),(7-179,i-Bu,B-35,S,S,O,2-Adm,H),(7-180,i-Bu,B-36,S,S,O,2-Adm,H),(7-181,i-Bu,B-1,S,S,O,5-OH-2-Adm,H),(7-182,i-Bu,B-2,S,S,O,5-OH-2-Adm,H),(7-183,i-Bu,B-3,S,S,O,5-OH-2-Adm,H),(7-184,i-Bu,B-4,S,S,O,5-OH-2-Adm,H),(7-185,i-Bu,B-5,S,S,O,5-OH-2-Adm,H),(7-186,i-Bu,B-6,S,S,O,5-OH-2-Adm,H),(7-187,i-Bu,B-7,S,S,O,5-OH-2-Adm,H),(7-188,i-Bu,B-8,S,S,O,5-OH-2-Adm,H),(7-189,i-Bu,B-9,S,S,O,5-OH-2-Adm,H),(7-190,i-Bu,B-10,S,S,O,5-OH-2-Adm,H),(7-191,i-Bu,B-11,S,S,O,5-OH-2-Adm,H),(7-192,i-Bu,B-12,S,S,O,5-OH-2-Adm,H),(7-193,i-Bu,B-13,S,S,O,5-OH-2-Adm,H),(7-194,i-Bu,B-14,S,S,O,5-OH-2-Adm,H),(7-195,i-Bu,B-15,S,S,O,5-OH-2-Adm,H),(7-196,i-Bu,B-16,S,S,O,5-OH-2-Adm,H),(7-197,i-Bu,B-17,S,S,O,5-OH-2-Adm,H),(7-198,i-Bu,B-18,S,S,O,5-OH-2-Adm,H),(7-199,i-Bu,B-19,S,S,O,5-OH-2-Adm,H),(7-200,i-Bu,B-20,S,S,O,5-OH-2-Adm,H),(7-201,i-Bu,B-21,S,S,O,5-OH-2-Adm,H),(7-202,i-Bu,B-22,S,S,O,5-OH-2-Adm,H),(7-203,i-Bu,B-23,S,S,O,5-OH-2-Adm,H),(7-204,i-Bu,B-24,S,S,O,5-OH-2-Adm,H),(7-205,i-Bu,B-25,S,S,O,5-OH-2-Adm,H),(7-206,i-Bu,B-26,S,S,O,5-OH-2-Adm,H),(7-207,i-Bu,B-27,S,S,O,5-OH-2-Adm,H),(7-208,i-Bu,B-28,S,S,O,5-OH-2-Adm,H),(7-209,i-Bu,B-29,S,S,O,5-OH-2-Adm,H),(7-210,i-Bu,B-30,S,S,O,5-OH-2-Adm,H),(7-211,i-Bu,B-31,S,S,O,5-OH-2-Adm,H),(7-212,i-Bu,B-32,S,S,O,5-OH-2-Adm,H),(7-213,i-Bu,B-33,S,S,O,5-OH-2-Adm,H),(7-214,i-Bu,B-34,S,S,O,5-OH-2-Adm,H),(7-215,i-Bu,B-35,S,S,O,5-OH-2-Adm,H),(7-216,i-Bu,B-36,S,S,O,5-OH-2-Adm,H),(7-217,i-Bu,C-1,S,S,O,1-Adm,H),(7-218,i-Bu,C-2,S,S,O,1-Adm,H),(7-219,i-Bu,C-3,S,S,O,1-Adm,H),(7-220,i-Bu,C-4,S,S,O,1-Adm,H),(7-221,i-Bu,C-5,S,S,O,1-Adm,H),(7-222,i-Bu,C-6,S,S,O,1-Adm,H),(7-223,i-Bu,C-7,S,S,O,1-Adm,H),(7-224,i-Bu,C-8,S,S,O,1-Adm,H),(7-225,i-Bu,C-9,S,S,O,1-Adm,H),(7-226,i-Bu,C-10,S,S,O,1-Adm,H),(7-227,i-Bu,C-11,S,S,O,1-Adm,H),(7-228,i-Bu,C-12,S,S,O,1-Adm,H),(7-229,i-Bu,C-13,S,S,O,1-Adm,H),(7-230,i-Bu,C-14,S,S,O,1-Adm,H),(7-231,i-Bu,C-15,S,S,O,1-Adm,H),(7-232,i-Bu,C-16,S,S,O,1-Adm,H),(7-233,i-Bu,C-17,S,S,O,1-Adm,H),(7-234,i-Bu,C-18,S,S,O,1-Adm,H),(7-235,i-Bu,C-19,S,S,O,1-Adm,H),(7-236,i-Bu,C-20,S,S,O,1-Adm,H),(7-237,i-Bu,C-21,S,S,O,1-Adm,H),(7-238,i-Bu,C-22,S,S,O,1-Adm,H),(7-239,i-Bu,C-23,S,S,O,1-Adm,H),(7-240,i-Bu,C-24,S,S,O,1-Adm,H),(7-241,i-Bu,C-25,S,S,O,1-Adm,H),(7-242,i-Bu,C-26,S,S,O,1-Adm,H),(7-243,i-Bu,C-27,S,S,O,1-Adm,H),(7-244,i-Bu,C-28,S,S,O,1-Adm,H), (7-245,i-Bu,C-29,S,S,O,1-Adm,H),(7-

246,i-Bu,C-30,S,S,O,1-Adm,H),(7-247,i-Bu,C-31,S,S,O,1-Adm,H),(7-248,i-Bu,C-32,S,S,O,1-Adm,H),(7-249,i-Bu,C-33,S,S,O,1-Adm,H),(7-250,i-Bu,C-34,S,S,O,1-Adm,H),(7-251,i-Bu,C-35,S,S,O,1-Adm,H),(7-252,i-Bu,C-36,S,S,O,1-Adm,H),(7-253,i-Bu,C-1,S,S,O,2-Adm,H),(7-254,i-Bu,C-2,S,S,O,2-Adm,H),(7-255,i-Bu,C-3,S,S,O,2-Adm,H),(7-256,i-Bu,C-4,S,S,O,2-Adm,H),(7-257,i-Bu,C-5,S,S,O,2-Adm,H),(7-258,i-Bu,C-6,S,S,O,2-Adm,H),(7-259,i-Bu,C-7,S,S,O,2-Adm,H),(7-260,i-Bu,C-8,S,S,O,2-Adm,H),(7-261,i-Bu,C-9,S,S,O,2-Adm,H),(7-262,i-Bu,C-10,S,S,O,2-Adm,H),(7-263,i-Bu,C-11,S,S,O,2-Adm,H),(7-264,i-Bu,C-12,S,S,O,2-Adm,H),(7-265,i-Bu,C-13,S,S,O,2-Adm,H),(7-266,i-Bu,C-14,S,S,O,2-Adm,H),(7-267,i-Bu,C-15,S,S,O,2-Adm,H),(7-268,i-Bu,C-16,S,S,O,2-Adm,H),(7-269,i-Bu,C-17,S,S,O,2-Adm,H),(7-270,i-Bu,C-18,S,S,O,2-Adm,H),(7-271,i-Bu,C-19,S,S,O,2-Adm,H),(7-272,i-Bu,C-20,S,S,O,2-Adm,H),(7-273,i-Bu,C-21,S,S,O,2-Adm,H),(7-274,i-Bu,C-22,S,S,O,2-Adm,H),(7-275,i-Bu,C-23,S,S,O,2-Adm,H),(7-276,i-Bu,C-24,S,S,O,2-Adm,H),(7-277,i-Bu,C-25,S,S,O,2-Adm,H),(7-278,i-Bu,C-26,S,S,O,2-Adm,H),(7-279,i-Bu,C-27,S,S,O,2-Adm,H),(7-280,i-Bu,C-28,S,S,O,2-Adm,H),(7-281,i-Bu,C-29,S,S,O,2-Adm,H),(7-282,i-Bu,C-30,S,S,O,2-Adm,H),(7-283,i-Bu,C-31,S,S,O,2-Adm,H),(7-284,i-Bu,C-32,S,S,O,2-Adm,H),(7-285,i-Bu,C-33,S,S,O,2-Adm,H),(7-286,i-Bu,C-34,S,S,O,2-Adm,H),(7-287,i-Bu,C-35,S,S,O,2-Adm,H),(7-288,i-Bu,C-36,S,S,O,2-Adm,H),(7-289,i-Bu,C-1,S,S,O,5-OH-2-Adm,H),(7-290,i-Bu,C-2,S,S,O,5-OH-2-Adm,H),(7-291,i-Bu,C-3,S,S,O,5-OH-2-Adm,H),(7-292,i-Bu,C-4,S,S,O,5-OH-2-Adm,H),(7-293,i-Bu,C-5,S,S,O,5-OH-2-Adm,H),(7-294,i-Bu,C-6,S,S,O,5-OH-2-Adm,H),(7-295,i-Bu,C-7,S,S,O,5-OH-2-Adm,H),(7-296,i-Bu,C-8,S,S,O,5-OH-2-Adm,H),(7-297,i-Bu,C-9,S,S,O,5-OH-2-Adm,H),(7-298,i-Bu,C-10,S,S,O,5-OH-2-Adm,H),(7-299,i-Bu,C-11,S,S,O,5-OH-2-Adm,H),(7-300,i-Bu,C-12,S,S,O,5-OH-2-Adm,H),(7-301,i-Bu,C-13,S,S,O,5-OH-2-Adm,H),(7-302,i-Bu,C-14,S,S,O,5-OH-2-Adm,H),(7-303,i-Bu,C-15,S,S,O,5-OH-2-Adm,H),(7-304,i-Bu,C-16,S,S,O,5-OH-2-Adm,H),(7-305,i-Bu,C-17,S,S,O,5-OH-2-Adm,H),(7-306,i-Bu,C-18,S,S,O,5-OH-2-Adm,H),(7-307,i-Bu,C-19,S,S,O,5-OH-2-Adm,H),(7-308,i-Bu,C-20,S,S,O,5-OH-2-Adm,H),(7-309,i-Bu,C-21,S,S,O,5-OH-2-Adm,H),(7-310,i-Bu,C-22,S,S,O,5-OH-2-Adm,H),(7-311,i-Bu,C-23,S,S,O,5-OH-2-Adm,H),(7-312,i-Bu,C-24,S,S,O,5-OH-2-Adm,H),(7-313,i-Bu,C-25,S,S,O,5-OH-2-Adm,H),(7-314,i-Bu,C-26,S,S,O,5-OH-2-Adm,H),(7-315,i-Bu,C-27,S,S,O,5-OH-2-Adm,H),(7-316,i-Bu,C-28,S,S,O,5-OH-2-Adm,H),(7-317,i-Bu,C-29,S,S,O,5-OH-2-Adm,H),(7-318,i-Bu,C-30,S,S,O,5-OH-2-Adm,H),(7-319,i-Bu,C-31,S,S,O,5-OH-2-Adm,H),(7-320,i-Bu,C-32,S,S,O,5-OH-2-Adm,H),(7-321,i-Bu,C-33,S,S,O,5-OH-2-Adm,H),(7-322,i-Bu,C-34,S,S,O,5-OH-2-Adm,H),(7-323,i-Bu,C-35,S,S,O,5-OH-2-Adm,H),(7-324,i-Bu,C-36,S,S,O,5-OH-2-Adm,H),(7-325,i-Bu,D-1,S,S,O,1-Adm,H),(7-326,i-Bu,D-2,S,S,O,1-Adm,H),(7-327,i-Bu,D-3,S,S,O,1-Adm,H),(7-328,i-Bu,D-4,S,S,O,1-Adm,H),(7-329,i-Bu,D-5,S,S,O,1-Adm,H),(7-330,i-Bu,D-6,S,S,O,1-Adm,H),(7-331,i-Bu,D-7,S,S,O,1-Adm,H),(7-332,i-Bu,D-8,S,S,O,1-Adm,H),(7-333,i-Bu,D-9,S,S,O,1-Adm,H),(7-334,i-Bu,D-10,S,S,O,1-Adm,H),(7-335,i-Bu,D-11,S,S,O,1-Adm,H),(7-336,i-Bu,D-12,S,S,O,1-Adm,H),(7-337,i-Bu,D-13,S,S,O,1-Adm,H),(7-338,i-Bu,D-14,S,S,O,1-Adm,H),(7-339,i-Bu,D-15,S,S,O,1-Adm,H),(7-340,i-Bu,D-16,S,S,O,1-Adm,H),(7-341,i-Bu,D-17,S,S,O,1-Adm,H),(7-342,i-Bu,D-18,S,S,O,1-Adm,H),(7-343,i-Bu,D-19,S,S,O,1-Adm,H),(7-344,i-Bu,D-20,S,S,O,1-Adm,H),(7-345,i-Bu,D-21,S,S,O,1-Adm,H),(7-346,i-Bu,D-22,S,S,O,1-Adm,H),(7-347,i-Bu,D-23,S,S,O,1-Adm,H),(7-348,i-Bu,D-24,S,S,O,1-Adm,H),(7-349,i-Bu,D-25,S,S,O,1-Adm,H),(7-350,i-Bu, D-26,S,S,O,1-Adm,H),(7-351,i-Bu,D-27,S,S,O,1-Adm,H),(7-352,i-Bu,D-28,S,S,O,1-Adm,H),(7-353,i-Bu,D-29,S,S,O,1-Adm,H),(7-354,i-Bu,D-30,S,S,O,1-Adm,H),(7-355,i-Bu,D-31,S,S,O,1-Adm,H),(7-356,i-Bu,D-32,S,S,O,1-Adm,H),(7-357,i-Bu,D-33,S,S,O,1-Adm,H),(7-358,i-Bu,D-34,S,S,O,1-Adm,H),(7-359,i-Bu,D-35,S,S,O,1-Adm,H),(7-360,i-Bu,D-36,S,S,O,1-Adm,H),(7-361,i-Bu,D-1,S,S,O,2-Adm,H),(7-362,i-Bu,D-2,S,S,O,2-Adm,H),(7-363,i-Bu,D-3,S,S,O,2-Adm,H),(7-364,i-Bu,D-4,S,S,O,2-Adm,H),(7-365,i-Bu,D-5,S,S,O,2-Adm,H),(7-366,i-Bu,D-6,S,S,O,2-Adm,H),(7-367,i-Bu,D-7,S,S,O,2-Adm,H),(7-368,i-Bu,D-8,S,S,O,2-Adm,H),(7-369,i-Bu,D-9,S,S,O,2-Adm,H),(7-370,i-Bu,D-10,S,S,O,2-Adm,H),(7-371,i-Bu,D-11,S,S,O,2-Adm,H),(7-372,i-Bu,D-12,S,S,O,2-Adm,H),(7-373,i-Bu,D-13,S,S,O,2-Adm,H),(7-374,i-Bu,D-14,S,S,O,2-Adm,H),(7-375,i-Bu,D-15,S,S,O,2-Adm,H),(7-376,i-Bu,D-16,S,S,O,2-Adm,H),(7-377,i-Bu,D-17,S,S,O,2-Adm,H),(7-378,i-Bu,D-18,S,S,O,2-Adm,H),(7-379,i-Bu,D-19,S,S,O,2-Adm,H),(7-380,i-Bu,D-20,S,S,O,2-Adm,H),(7-381,i-Bu,D-21,S,S,O,2-Adm,H),(7-382,i-Bu,D-22,S,S,O,2-Adm,H),(7-383,i-Bu,D-23,S,S,O,2-Adm,H),(7-384,i-Bu,D-24,S,S,O,2-Adm,H),(7-385,i-Bu,D-25,S,S,O,2-Adm,H),(7-386,i-Bu,D-26,S,S,O,2-Adm,H),(7-387,i-Bu,D-27,S,S,O,2-Adm,H),(7-388,i-Bu,D-28,S,S,O,2-Adm,H),(7-389,i-Bu,D-29,S,S,O,2-Adm,H),(7-390,i-Bu,D-30,S,S,O,2-Adm,H),(7-391,i-Bu,D-31,S,S,O,2-Adm,H),(7-392,i-Bu,D-32,S,S,O,2-Adm,H),(7-393,i-Bu,D-33,S,S,O,2-Adm,H),(7-394,i-Bu,D-34,S,S,O,2-Adm,H),(7-395,i-Bu,D-35,S,S,O,2-Adm,H),(7-396,i-Bu,D-36,S,S,O,2-Adm,H),(7-397,i-Bu,D-1,S,S,O,5-OH-2-Adm,H),(7-398,i-Bu,D-2,S,S,O,5-OH-2-Adm,H),(7-399,i-Bu,D-3,S,S,O,5-OH-2-Adm,H),(7-400,i-Bu,D-4,S,S,O,5-OH-2-Adm,H),(7-401,i-Bu,D-5,S,S,O,5-OH-2-Adm,H),(7-402,i-Bu,D-6,S,S,O,5-OH-2-Adm,H),(7-403,i-Bu,D-7,S,S,O,5-OH-2-Adm,H),(7-404,i-Bu,D-8,S,S,O,5-OH-2-Adm,H),(7-405,i-Bu,D-9,S,S,O,5-OH-2-Adm,H),(7-406,i-Bu,D-10,S,S,O,5-OH-2-Adm,H),(7-407,i-Bu,D-11,S,S,O,5-OH-2-Adm,H),(7-408,i-Bu,D-12,S,S,O,5-OH-2-Adm,H),(7-409,i-Bu,D-13,S,S,O,5-OH-2-Adm,H),(7-410,i-Bu,D-14,S,S,O,5-OH-2-Adm,H),(7-411,i-Bu,D-15,S,S,O,5-OH-2-Adm,H),(7-412,i-Bu,D-16,S,S,O,5-OH-2-Adm,H),(7-413,i-Bu,D-17,S,S,O,5-OH-2-Adm,H),(7-414,i-Bu,D-18,S,S,O,5-OH-2-Adm,H),(7-415,i-Bu,D-19,S,S,O,5-OH-2-Adm,H),(7-416,i-Bu,D-20,S,S,O,5-OH-2-Adm,H),(7-417,i-Bu,D-21,S,S,O,5-OH-2-Adm,H),(7-418,i-Bu,D-22,S,S,O,5-OH-2-Adm,H),(7-419,i-Bu,D-23,S,S,O,5-OH-2-Adm,H),(7-420,i-Bu,D-24,S,S,O,5-OH-2-Adm,H),(7-421,i-Bu,D-25,S,S,O,5-OH-2-Adm,H),(7-422,i-Bu,D-26,S,S,O,5-OH-2-Adm,H),(7-423,i-Bu,D-27,S,S,O,5-OH-2-Adm,H),(7-424,i-Bu,D-28,S,S,O,5-OH-2-Adm,H),(7-425,i-Bu,D-29,S,S,O,5-OH-2-Adm,H),(7-426,i-Bu,D-30,S,S,O,5-OH-2-Adm,H),(7-427,i-Bu,D-31,S,S,O,5-OH-2-Adm,H),(7-428,i-Bu,D-32,S,S,O,5-OH-2-Adm,H),(7-429,i-Bu,D-33,S,S,O,5-OH-2-Adm,H),(7-430,i-Bu,D-34,S,S,O,5-OH-2-Adm,H),(7-431,i-Bu,D-35,S,S,O,5-OH-2-Adm,H),(7-432,i-Bu,D-36,S,S,O,5-OH-2-Adm,H),(7-433,i-Bu,E-1,S,S,O,1-Adm,H),(7-434,i-Bu,E-2,S,S,O,1-Adm,H),(7-435,i-Bu,E-3,S,S,O,1-Adm,H),(7-436,i-Bu,E-4,S,S,O,1-Adm,H),(7-437,i-Bu,E-5,S,S,O,1-Adm,H),(7-438,i-Bu,E-6,S,S,O,1-Adm,H),(7-439,i-Bu,E-7,S,S,O,1-Adm,H),(7-440,i-Bu,E-8,S,S,O,1-Adm,H),(7-441,i-Bu,E-9,S,S,O,1-Adm,H),(7-442,i-Bu,E-10,S,S,O,1-Adm,H),(7-443,i-Bu,E-11,S,S,O,1-Adm,H),(7-444,i-Bu,E-12,S,S,O,1-Adm,H),(7-445,i-Bu,E-13,S,S,O,1-Adm,H),(7-446,i-Bu,E-14,S,S,O,1-Adm,H),(7-447,i-Bu,E-15,S,S,O,1-Adm,H),(7-448,i-Bu,E-16,S,S,O,1-Adm,H),(7-449,i-Bu,E-17,S,S,O,1-Adm,H),(7-450,i-Bu,E-18,S,S,O,1-Adm,H),(7-451,i-Bu,E-19,S,S,O,1-Adm,H),(7-452,i-Bu,E-20,S,S,O,1-Adm,H),(7-453,i-Bu,E-21,S,S,O,1-Adm,H),(7-454,i-Bu,E-22,S,S,O,1-Adm,H),(7-455,i-Bu,E-23,S,S,O,1-Adm,H),(7-456,i-

Bu,E-24,S,S,O,1-Adm,H),(7-457,i-Bu,E-25,S,S,O,1-Adm, H),(7-458,i-Bu,E-26,S,S,O,1-Adm,H),(7-459,i-Bu,E-27,S, S,O,1-Adm,H),(7-460,i-Bu,E-28,S,S,O,1-Adm,H),(7-461,i-Bu,E-29,S,S,O,1-Adm,H),(7-462,i-Bu,E-30,S,S,O,1-Adm, H),(7-463,i-Bu,E-31,S,S,O,1-Adm,H),(7-464,i-Bu,E-32,S, S,O,1-Adm,H),(7-465,i-Bu,E-33,S,S,O,1-Adm,H),(7-466,i-Bu,E-34,S,S,O,1-Adm,H),(7-467,i-Bu,E-35,S,S,O,1-Adm, H),(7-468,i-Bu,E-36,S,S,O,1-Adm,H),(7-469,i-Bu,E-1,S,S, O,2-Adm,H),(7-470,i-Bu,E-2,S,S,O,2-Adm,H),(7-471,i-Bu, E-3,S,S,O,2-Adm,H),(7-472,i-Bu,E-4,S,S,O,2-Adm,H),(7-473,i-Bu,E-5,S,S,O,2-Adm,H),(7-474,i-Bu,E-6,S,S,O,2-Adm,H),(7-475,i-Bu,E-7,S,S,O,2-Adm,H),(7-476,i-Bu,E-8, S,S,O,2-Adm,H),(7-477,i-Bu,E-9,S,S,O,2-Adm,H),(7-478, i-Bu,E-10,S,S,O,2-Adm,H),(7-479,i-Bu,E-11,S,S,O,2-Adm, H),(7-480,i-Bu,E-12,S,S,O,2-Adm,H),(7-481,i-Bu,E-13,S, S,O,2-Adm,H),(7-482,i-Bu,E-14,S,S,O,2-Adm,H),(7-483,i-Bu,E-15,S,S,O,2-Adm,H),(7-484,i-Bu,E-16,S,S,O,2-Adm, H),(7-485,i-Bu,E-17,S,S,O,2-Adm,H),(7-486,i-Bu,E-18,S, S,O,2-Adm,H),(7-487,i-Bu,E-19,S,S,O,2-Adm,H),(7-488,i-Bu,E-20,S,S,O,2-Adm,H),(7-489,i-Bu,E-21,S,S,O,2-Adm, H),(7-490,i-Bu,E-22,S,S,O,2-Adm,H),(7-491,i-Bu,E-23,S, S,O,2-Adm,H),(7-492,i-Bu,E-24,S,S,O,2-Adm,H),(7-493,i-Bu,E-25,S,S,O,2-Adm,H),(7-494,i-Bu,E-26,S,S,O,2-Adm, H),(7-495,i-Bu,E-27,S,S,O,2-Adm,H),(7-496,i-Bu,E-28,S, S,O,2-Adm,H),(7-497,i-Bu,E-29,S,S,O,2-Adm,H),(7-498,i-Bu,E-30,S,S,O,2-Adm,H),(7-499,i-Bu,E-31,S,S,O,2-Adm, H),(7-500,i-Bu,E-32,S,S,O,2-Adm,H),(7-501,i-Bu,E-33,S, S,O,2-Adm,H),(7-502,i-Bu,E-34,S,S,O,2-Adm,H),(7-503,i-Bu,E-35,S,S,O,2-Adm,H),(7-504,i-Bu,E-36,S,S,O,2-Adm, H),(7-505,i-Bu,E-1,S,S,O,5-OH-2-Adm,H),(7-506,i-Bu,E-2,S,S,O,5-OH-2-Adm,H),(7-507,i-Bu,E-3,S,S,O,5-OH-2-Adm,H),(7-508,i-Bu,E-4,S,S,O,5-OH-2-Adm,H),(7-509,i-Bu,E-5,S,S,O,5-OH-2-Adm,H),(7-510,i-Bu,E-6,S,S,O,5-OH-2-Adm,H),(7-511,i-Bu,E-7,S,S,O,5-OH-2-Adm,H),(7-512,i-Bu,E-8,S,S,O,5-OH-2-Adm,H),(7-513,i-Bu,E-9,S,S, O,5-OH-2-Adm,H),(7-514,i-Bu,E-10,S,S,O,5-OH-2-Adm, H),(7-515,i-Bu,E-11,S,S,O,5-OH-2-Adm,H),(7-516,i-Bu,E-12,S,S,O,5-OH-2-Adm,H),(7-517,i-Bu,E-13,S,S,O,5-OH-2-Adm,H),(7-518,i-Bu,E-14,S,S,O,5-OH-2-Adm,H),(7-519,i-Bu,E-15,S,S,O,5-OH-2-Adm,H),(7-520,i-Bu,E-16,S,S,O,5-OH-2-Adm,H),(7-521,i-Bu,E-17,S,S,O,5-OH-2-Adm,H), (7-522,i-Bu,E-18,S,S,O,5-OH-2-Adm,H),(7-523,i-Bu,E-19, S,S,O,5-OH-2-Adm,H),(7-524,i-Bu,E-20,S,S,O,5-OH-2-Adm,H),(7-525,i-Bu,E-21,S,S,O,5-OH-2-Adm,H),(7-526,i-Bu,E-22,S,S,O,5-OH-2-Adm,H),(7-527,i-Bu,E-23,S,S,O,5-OH-2-Adm,H),(7-528,i-Bu,E-24,S,S,O,5-OH-2-Adm,H), (7-529,i-Bu,E-25,S,S,O,5-OH-2-Adm,H),(7-530,i-Bu,E-26, S,S,O,5-OH-2-Adm,H),(7-531,i-Bu,E-27,S,S,O,5-OH-2-Adm,H),(7-532,i-Bu,E-28,S,S,O,5-OH-2-Adm,H),(7-533,i-Bu,E-29,S,S,O,5-OH-2-Adm,H),(7-534,i-Bu,E-30,S,S,O,5-OH-2-Adm,H),(7-535,i-Bu,E-31,S,S,O,5-OH-2-Adm,H), (7-536,i-Bu,E-32,S,S,O,5-OH-2-Adm,H),(7-537,i-Bu,E-33, S,S,O,5-OH-2-Adm,H),(7-538,i-Bu,E-34,S,S,O,5-OH-2-Adm,H),(7-539,i-Bu,E-35,S,S,O,5-OH-2-Adm,H),(7-540,i-Bu,E-36,S,S,O,5-OH-2-Adm,H),(7-541,i-Bu,F-1,S,S,O,1-Adm,H),(7-542,i-Bu,F-2,S,S,O,1-Adm,H),(7-543,i-Bu,F-3, S,S,O,1-Adm,H),(7-544,i-Bu,F-4,S,S,O,1-Adm,H),(7-545, i-Bu,F-5,S,S,O,1-Adm,H),(7-546,i-Bu,F-6,S,S,O,1-Adm, H),(7-547,i-Bu,F-7,S,S,O,1-Adm,H),(7-548,i-Bu,F-8,S,S, O,1-Adm,H),(7-549,i-Bu,F-9,S,S,O,1-Adm,H),(7-550,i-Bu, F-10,S,S,O,1-Adm,H),(7-551,i-Bu,F-11,S,S,O,1-Adm,H), (7-552,i-Bu,F-12,S,S,O,1-Adm,H),(7-553,i-Bu,F-13,S,S,O, 1-Adm,H),(7-554,i-Bu,F-14,S,S,O,1-Adm,H),(7-555,i-Bu, F-15,S,S,O,1-Adm,H),(7-556,i-Bu,F-16,S,S,O,1-Adm,H), (7-557,i-Bu,F-17,S,S,O,1-Adm,H),(7-558,i-Bu,F-18,S,S,O, 1-Adm,H),(7-559,i-Bu,F-19,S,S,O,1-Adm,H),(7-560,i-Bu, F-20,S,S,O,1-Adm,H), (7-561,i-Bu,F-21,S,S,O,1-Adm,H), (7-562,i-Bu,F-22,S,S,O,1-Adm,H),(7-563,i-Bu,F-23,S,S,O, 1-Adm,H),(7-564,i-Bu,F-24,S,S,O,1-Adm,H),(7-565,i-Bu, F-25,S,S,O,1-Adm,H),(7-566,i-Bu,F-26,S,S,O,1-Adm,H), (7-567,i-Bu,F-27,S,S,O,1-Adm,H),(7-568,i-Bu,F-28,S,S,O, 1-Adm,H),(7-569,i-Bu,F-29,S,S,O,1-Adm,H),(7-570,i-Bu, F-30,S,S,O,1-Adm,H),(7-571,i-Bu,F-31,S,S,O,1-Adm,H), (7-572,i-Bu,F-32,S,S,O,1-Adm,H),(7-573,i-Bu,F-33,S,S,O, 1-Adm,H),(7-574,i-Bu,F-34,S,S,O,1-Adm,H),(7-575,i-Bu, F-35,S,S,O,1-Adm,H),(7-576,i-Bu,F-36,S,S,O,1-Adm,H), (7-577,i-Bu,F-1,S,S,O,2-Adm,H),(7-578,i-Bu,F-2,S,S,O,2-Adm,H),(7-579,i-Bu,F-3,S,S,O,2-Adm,H),(7-580,i-Bu,F-4, S,S,O,2-Adm,H),(7-581,i-Bu,F-5,S,S,O,2-Adm,H),(7-582, i-Bu,F-6,S,S,O,2-Adm,H),(7-583,i-Bu,F-7,S,S,O,2-Adm, H),(7-584,i-Bu,F-8,S,S,O,2-Adm,H),(7-585,i-Bu,F-9,S,S, O,2-Adm,H),(7-586,i-Bu,F-10,S,S,O,2-Adm,H),(7-587,i-Bu,F-11,S,S,O,2-Adm,H),(7-588,i-Bu,F-12,S,S,O,2-Adm, H),(7-589,i-Bu,F-13,S,S,O,2-Adm,H),(7-590,i-Bu,F-14,S, S,O,2-Adm,H),(7-591,i-Bu,F-15,S,S,O,2-Adm,H),(7-592,i-Bu,F-16,S,S,O,2-Adm,H),(7-593,i-Bu,F-17,S,S,O,2-Adm, H),(7-594,i-Bu,F-18,S,S,O,2-Adm,H),(7-595,i-Bu,F-19,S, S,O,2-Adm,H),(7-596,i-Bu,F-20,S,S,O,2-Adm,H),(7-597,i-Bu,F-21,S,S,O,2-Adm,H),(7-598,i-Bu,F-22,S,S,O,2-Adm, H),(7-599,i-Bu,F-23,S,S,O,2-Adm,H),(7-600,i-Bu,F-24,S, S,O,2-Adm,H),(7-601,i-Bu,F-25,S,S,O,2-Adm,H),(7-602,i-Bu,F-26,S,S,O,2-Adm,H),(7-603,i-Bu,F-27,S,S,O,2-Adm, H),(7-604,i-Bu,F-28,S,S,O,2-Adm,H),(7-605,i-Bu,F-29,S, S,O,2-Adm,H),(7-606,i-Bu,F-30,S,S,O,2-Adm,H),(7-607,i-Bu,F-31,S,S,O,2-Adm,H),(7-608,i-Bu,F-32,S,S,O,2-Adm, H),(7-609,i-Bu,F-33,S,S,O,2-Adm,H),(7-610,i-Bu,F-34,S, S,O,2-Adm,H),(7-611,i-Bu,F-35,S,S,O,2-Adm,H),(7-612,i-Bu,F-36,S,S,O,2-Adm,H),(7-613,i-Bu,F-1,S,S,O,5-OH-2-Adm,H),(7-614,i-Bu,F-2,S,S,O,5-OH-2-Adm,H),(7-615,i-Bu,F-3,S,S,O,5-OH-2-Adm,H),(7-616,i-Bu,F-4,S,S,O,5-OH-2-Adm,H),(7-617,i-Bu,F-5,S,S,O,5-OH-2-Adm,H),(7-618,i-Bu,F-6,S,S,O,5-OH-2-Adm,H),(7-619,i-Bu,F-7,S,S, O,5-OH-2-Adm,H),(7-620,i-Bu,F-8,S,S,O,5-OH-2-Adm, H),(7-621,i-Bu,F-9,S,S,O,5-OH-2-Adm,H),(7-622,i-Bu,F-10,S,S,O,5-OH-2-Adm,H),(7-623,i-Bu,F-11,S,S,O,5-OH-2-Adm,H),(7-624,i-Bu,F-12,S,S,O,5-OH-2-Adm,H),(7-625,i-Bu,F-13,S,S,O,5-OH-2-Adm,H),(7-626,i-Bu,F-14,S,S,O,5-OH-2-Adm,H),(7-627,i-Bu,F-15,S,S,O,5-OH-2-Adm,H),(7-628,i-Bu,F-16,S,S,O,5-OH-2-Adm,H),(7-629,i-Bu,F-17,S, S,O,5-OH-2-Adm,H),(7-630,i-Bu,F-18,S,S,O,5-OH-2-Adm,H),(7-631,i-Bu,F-19,S,S,O,5-OH-2-Adm,H),(7-632,i-Bu,F-20,S,S,O,5-OH-2-Adm,H),(7-633,i-Bu,F-21,S,S,O,5-OH-2-Adm,H),(7-634,i-Bu,F-22,S,S,O,5-OH-2-Adm,H),(7-635,i-Bu,F-23,S,S,O,5-OH-2-Adm,H),(7-636,i-Bu,F-24,S, S,O,5-OH-2-Adm,H),(7-637,i-Bu,F-25,S,S,O,5-OH-2-Adm,H),(7-638,i-Bu,F-26,S,S,O,5-OH-2-Adm,H),(7-639,i-Bu,F-27,S,S,O,5-OH-2-Adm,H),(7-640,i-Bu,F-28,S,S,O,5-OH-2-Adm,H),(7-641,i-Bu,F-29,S,S,O,5-OH-2-Adm,H),(7-642,i-Bu,F-30,S,S,O,5-OH-2-Adm,H),(7-643,i-Bu,F-31,S, S,O,5-OH-2-Adm,H),(7-644,i-Bu,F-32,S,S,O,5-OH-2-Adm,H),(7-645,i-Bu,F-33,S,S,O,5-OH-2-Adm,H),(7-646,i-Bu,F-34,S,S,O,5-OH-2-Adm,H),(7-647,i-Bu,F-35,S,S,O,5-OH-2-Adm,H),(7-648,i-Bu,F-36,S,S,O,5-OH-2-Adm,H),(7-649,i-Bu,G-1,S,S,O,1-Adm,H),(7-650,i-Bu,G-2,S,S,O,1-Adm,H),(7-651,i-Bu,G-3,S,S,O,1-Adm,H),(7-652,i-Bu,G-4,S,S,O,1-Adm,H),(7-653,i-Bu,G-5,S,S,O,1-Adm,H),(7-654,i-Bu,G-6,S,S,O,1-Adm,H),(7-655,i-Bu,G-7,S,S,O,1-Adm,H),(7-656,i-Bu,G-8,S,S,O,1-Adm,H),(7-657,i-Bu,G-9,S,S,O,1-Adm,H),(7-658,i-Bu,G-1,S,S,O,2-Adm,H),(7-659,i-Bu,G-2,S,S,O,2-Adm,H),(7-660,i-Bu,G-3,S,S,O,2-Adm,H),(7-661,i-Bu,G-4,S,S,O,2-Adm,H),(7-662,i-Bu,G-5,S,S,O,2-Adm,H),(7-663,i-Bu,G-6,S,S,O,2-Adm,H),(7-664,i-Bu,G-7,S,S,O,2-Adm,H),(7-665,i-Bu,G-8,S,S,O,2-Adm,H),(7-666,i-Bu, G-9,S,S,O,2-Adm,H),(7-667,i-Bu,G-

1,S,S,O,5-OH-2-Adm,H),(7-668,i-Bu,G-2,S,S,O,5-OH-2-Adm,H),(7-669,i-Bu,G-3,S,S,O,5-OH-2-Adm,H),(7-670,i-Bu,G-4,S,S,O,5-OH-2-Adm,H),(7-671,i-Bu,G-5,S,S,O,5-OH-2-Adm,H),(7-672,i-Bu,G-6,S,S,O,5-OH-2-Adm,H),(7-673,i-Bu,G-7,S,S,O,5-OH-2-Adm,H),(7-674,i-Bu,G-8,S,S,O,5-OH-2-Adm,H),(7-675,i-Bu,G-9,S,S,O,5-OH-2-Adm,H),(7-676,i-Bu,H-1,S,S,O,1-Adm,H),(7-677,i-Bu,H-2,S,S,O,1-Adm,H),(7-678,i-Bu,H-3,S,S,O,1-Adm,H),(7-679,i-Bu,H-4,S,S,O,1-Adm,H),(7-680,i-Bu,H-5,S,S,O,1-Adm,H),(7-681,i-Bu,H-6,S,S,O,1-Adm,H),(7-682,i-Bu,H-7,S,S,O,1-Adm,H),(7-683,i-Bu,H-8,S,S,O,1-Adm,H),(7-684,i-Bu,H-9,S,S,O,1-Adm,H),(7-685,i-Bu,H-1,S,S,O,2-Adm,H),(7-686,i-Bu,H-2,S,S,O,2-Adm,H),(7-687,i-Bu,H-3,S,S,O,2-Adm,H),(7-688,i-Bu,H-4,S,S,O,2-Adm,H),(7-689,i-Bu,H-5,S,S,O,2-Adm,H),(7-690,i-Bu,H-6,S,S,O,2-Adm,H),(7-691,i-Bu,H-7,S,S,O,2-Adm,H),(7-692,i-Bu,H-8,S,S,O,2-Adm,H),(7-693,i-Bu,H-9,S,S,O,2-Adm,H),(7-694,i-Bu,H-1,S,S,O,5-OH-2-Adm,H),(7-695,i-Bu,H-2,S,S,O,5-OH-2-Adm,H),(7-696,i-Bu,H-3,S,S,O,5-OH-2-Adm,H),(7-697,i-Bu,H-4,S,S,O,5-OH-2-Adm,H),(7-698,i-Bu,H-5,S,S,O,5-OH-2-Adm,H),(7-699,i-Bu,H-6,S,S,O,5-OH-2-Adm,H),(7-700,i-Bu,H-7,S,S,O,5-OH-2-Adm,H),(7-701,i-Bu,H-8,S,S,O,5-OH-2-Adm,H),(7-702,i-Bu,H-9,S,S,O,5-OH-2-Adm,H),(7-703,i-Bu,I-1,S,S,O,1-Adm,H),(7-704,i-Bu,I-2,S,S,O,1-Adm,H),(7-705,i-Bu,I-3,S,S,O,1-Adm,H),(7-706,i-Bu,I-4,S,S,O,1-Adm,H),(7-707,i-Bu,I-5,S,S,O,1-Adm,H),(7-708,i-Bu,I-6,S,S,O,1-Adm,H),(7-709,i-Bu,I-7,S,S,O,1-Adm,H),(7-710,i-Bu,I-8,S,S,O,1-Adm,H),(7-711,i-Bu,I-9,S,S,O,1-Adm,H),(7-712,i-Bu,I-1,S,S,O,2-Adm,H),(7-713,i-Bu,I-2,S,S,O,2-Adm,H),(7-714,i-Bu,I-3,S,S,O,2-Adm,H),(7-715,i-Bu,I-4,S,S,O,2-Adm,H),(7-716,i-Bu,I-5,S,S,O,2-Adm,H),(7-717,i-Bu,I-6,S,S,O,2-Adm,H),(7-718,i-Bu,I-7,S,S,O,2-Adm,H),(7-719,i-Bu,I-8,S,S,O,2-Adm,H),(7-720,i-Bu,I-9,S,S,O,2-Adm,H),(7-721,i-Bu,I-1,S,S,O,5-OH-2-Adm,H),(7-722,i-Bu,I-2,S,S,O,5-OH-2-Adm,H),(7-723,i-Bu,I-3,S,S,O,5-OH-2-Adm,H),(7-724,i-Bu,I-4,S,S,O,5-OH-2-Adm,H),(7-725,i-Bu,I-5,S,S,O,5-OH-2-Adm,H),(7-726,i-Bu,I-6,S,S,O,5-OH-2-Adm,H),(7-727,i-Bu,I-7,S,S,O,5-OH-2-Adm,H),(7-728,i-Bu,I-8,S,S,O,5-OH-2-Adm,H),(7-729,i-Bu,I-9,S,S,O,5-OH-2-Adm,H),(7-730,i-Bu,J-1,S,S,O,1-Adm,H),(7-731,i-Bu,J-2,S,S,O,1-Adm,H),(7-732,i-Bu,J-3,S,S,O,1-Adm,H),(7-733,i-Bu,J-4,S,S,O,1-Adm,H),(7-734,i-Bu,J-5,S,S,O,1-Adm,H),(7-735,i-Bu,J-6,S,S,O,1-Adm,H),(7-736,i-Bu,J-7,S,S,O,1-Adm,H),(7-737,i-Bu,J-8,S,S,O,1-Adm,H),(7-738,i-Bu,J-9,S,S,O,1-Adm,H),(7-739,i-Bu,J-1,S,S,O,2-Adm,H),(7-740,i-Bu,J-2,S,S,O,2-Adm,H),(7-741,i-Bu,J-3,S,S,O,2-Adm,H),(7-742,i-Bu,J-4,S,S,O,2-Adm,H),(7-743,i-Bu,J-5,S,S,O,2-Adm,H),(7-744,i-Bu,J-6,S,S,O,2-Adm,H),(7-745,i-Bu,J-7,S,S,O,2-Adm,H),(7-746,i-Bu,J-8,S,S,O,2-Adm,H),(7-747,i-Bu,J-9,S,S,O,2-Adm,H),(7-748,i-Bu,J-1,S,S,O,5-OH-2-Adm,H),(7-749,i-Bu,J-2,S,S,O,5-OH-2-Adm,H),(7-750,i-Bu,J-3,S,S,O,5-OH-2-Adm,H),(7-751,i-Bu,J-4,S,S,O,5-OH-2-Adm,H),(7-752,i-Bu,J-5,S,S,O,5-OH-2-Adm,H),(7-753,i-Bu,J-6,S,S,O,5-OH-2-Adm,H),(7-754,i-Bu,J-7,S,S,O,5-OH-2-Adm,H),(7-755,i-Bu,J-8,S,S,O,5-OH-2-Adm,H),(7-756,i-Bu,J-9,S,S,O,5-OH-2-Adm,H),(7-757,i-Bu,K-1,S,S,O,1-Adm,H),(7-758,i-Bu,K-2,S,S,O,1-Adm,H),(7-759,i-Bu,K-3,S,S,O,1-Adm,H),(7-760,i-Bu,K-4,S,S,O,1-Adm,H),(7-761,i-Bu,K-5,S,S,O,1-Adm,H),(7-762,i-Bu,K-6,S,S,O,1-Adm,H),(7-763,i-Bu,K-7,S,S,O,1-Adm,H),(7-764,i-Bu,K-8,S,S,O,1-Adm,H),(7-765,i-Bu,K-9,S,S,O,1-Adm,H),(7-766,i-Bu,K-1,S,S,O,2-Adm,H),(7-767,i-Bu,K-2,S,S,O,2-Adm,H),(7-768,i-Bu,K-3,S,S,O,2-Adm,H),(7-769,i-Bu,K-4,S,S,O,2-Adm,H),(7-770,i-Bu,K-5,S,S,O,2-Adm,H),(7-771,i-Bu,K-6,S,S,O,2-Adm,H),(7-772,i-Bu,K-7,S,S,O,2-Adm,H),(7-773,i-Bu,K-8,S,S,O,2-Adm,H), (7-774,i-Bu,K-9,S,S,O,2-Adm,H),(7-775,i-Bu,K-1,S,S,O,5-OH-2-Adm,H),(7-776,i-Bu,K-2,S,S,O,5-OH-2-Adm,H),(7-777,i-Bu,K-3,S,S,O,5-OH-2-Adm,H),(7-778,i-Bu,K-4,S,S,O,5-OH-2-Adm,H),(7-779,i-Bu,K-5,S,S,O,5-OH-2-Adm,H),(7-780,i-Bu,K-6,S,S,O,5-OH-2-Adm,H),(7-781,i-Bu,K-7,S,S,O,5-OH-2-Adm,H),(7-782,i-Bu,K-8,S,S,O,5-OH-2-Adm,H),(7-783,i-Bu,K-9,S,S,O,5-OH-2-Adm,H)

(Compound No., $R^2,R^3,X,Y,Z,R^4,R^5$)=(8-1,Pro,A-1,S,S,O,1-Adm,H),(8-2,Pro,A-2,S,S,O,1-Adm,H),(8-3,Pro,A-3,S,S,O,1-Adm,H),(8-4,Pro,A-4,S,S,O,1-Adm,H),(8-5,Pro,A-5,S,S,O,1-Adm,H),(8-6,Pro,A-6,S,S,O,1-Adm,H),(8-7,Pro,A-7,S,S,O,1-Adm,H),(8-8,Pro,A-8,S,S,O,1-Adm,H),(8-9,Pro,A-9,S,S,O,1-Adm,H),(8-10,Pro,A-10,S,S,O,1-Adm,H),(8-11,Pro,A-11,S,S,O,1-Adm,H),(8-12,Pro,A-12,S,S,O,1-Adm,H),(8-13,Pro,A-13,S,S,O,1-Adm,H),(8-14,Pro,A-14,S,S,O,1-Adm,H),(8-15,Pro,A-15,S,S,O,1-Adm,H),(8-16,Pro,A-16,S,S,O,1-Adm,H),(8-17,Pro,A-17,S,S,O,1-Adm,H),(8-18,Pro,A-18,S,S,O,1-Adm,H),(8-19,Pro,A-19,S,S,O,1-Adm,H),(8-20,Pro,A-20,S,S,O,1-Adm,H),(8-21,Pro,A-21,S,S,O,1-Adm,H),(8-22,Pro,A-22,S,S,O,1-Adm,H),(8-23,Pro,A-23,S,S,O,1-Adm,H),(8-24,Pro,A-24,S,S,O,1-Adm,H),(8-25,Pro,A-25,S,S,O,1-Adm,H),(8-26,Pro,A-26,S,S,O,1-Adm,H),(8-27,Pro,A-27,S,S,O,1-Adm,H),(8-28,Pro,A-28,S,S,O,1-Adm,H),(8-29,Pro,A-29,S,S,O,1-Adm,H),(8-30,Pro,A-30,S,S,O,1-Adm,H),(8-31,Pro,A-31,S,S,O,1-Adm,H),(8-32,Pro,A-32,S,S,O,1-Adm,H),(8-33,Pro,A-33,S,S,O,1-Adm,H),(8-34,Pro,A-34,S,S,O,1-Adm,H),(8-35,Pro,A-35,S,S,O,1-Adm,H),(8-36,Pro,A-36,S,S,O,1-Adm,H),(8-37,Pro,A-1,S,S,O,2-Adm,H),(8-38,Pro,A-2,S,S,O,2-Adm,H),(8-39,Pro,A-3,S,S,O,2-Adm,H),(8-40,Pro,A-4,S,S,O,2-Adm,H),(8-41,Pro,A-5,S,S,O,2-Adm,H),(8-42,Pro,A-6,S,S,O,2-Adm,H),(8-43,Pro,A-7,S,S,O,2-Adm,H),(8-44,Pro,A-9,S,S,O,2-Adm,H),(8-45,Pro,A-11,S,S,O,2-Adm,H),(8-46,Pro,A-12,S,S,O,2-Adm,H),(8-47,Pro,A-13,S,S,O,2-Adm,H),(8-48,Pro,A-14,S,S,O,2-Adm,H),(8-49,Pro,A-15,S,S,O,2-Adm,H),(8-50,Pro,A-16,S,S,O,2-Adm,H),(8-51,Pro,A-17,S,S,O,2-Adm,H),(8-52,Pro,A-18,S,S,O,2-Adm,H),(8-53,Pro,A-20,S,S,O,2-Adm,H),(8-54,Pro,A-21,S,S,O,2-Adm,H),(8-55,Pro,A-22,S,S,O,2-Adm,H),(8-56,Pro,A-23,S,S,O,2-Adm,H),(8-57,Pro,A-24,S,S,O,2-Adm,H),(8-58,Pro,A-26,S,S,O,2-Adm,H),(8-59,Pro,A-27,S,S,O,2-Adm,H),(8-60,Pro,A-28,S,S,O,2-Adm,H),(8-61,Pro,A-29,S,S,O,2-Adm,H),(8-62,Pro,A-30,S,S,O,2-Adm,H),(8-63,Pro,A-31,S,S,O,2-Adm,H),(8-64,Pro,A-32,S,S,O,2-Adm,H),(8-65,Pro,A-33,S,S,O,2-Adm,H),(8-66,Pro,A-34,S,S,O,2-Adm,H),(8-67,Pro,A-35,S,S,O,2-Adm,H),(8-68,Pro,A-36,S,S,O,2-Adm,H),(8-69,Pro,A-1,S,S,O,5-OH-2-Adm,H),(8-70,Pro,A-2,S,S,O,5-OH-2-Adm,H),(8-71,Pro,A-3,S,S,O,5-OH-2-Adm,H),(8-72,Pro,A-4,S,S,O,5-OH-2-Adm,H),(8-73,Pro,A-5,S,S,O,5-OH-2-Adm,H),(8-74,Pro,A-6,S,S,O,5-OH-2-Adm,H),(8-75,Pro,A-7,S,S,O,5-OH-2-Adm,H),(8-76,Pro,A-8,S,S,O,5-OH-2-Adm,H),(8-77,Pro,A-9,S,S,O,5-OH-2-Adm,H),(8-78,Pro,A-10,S,S,O,5-OH-2-Adm,H),(8-79,Pro,A-11,S,S,O,5-OH-2-Adm,H),(8-80,Pro,A-12,S,S,O,5-OH-2-Adm,H),(8-81,Pro,A-13,S,S,O,5-OH-2-Adm,H),(8-82,Pro,A-14,S,S,O,5-OH-2-Adm,H),(8-83,Pro,A-15,S,S,O,5-OH-2-Adm,H),(8-84,Pro,A-16,S,S,O,5-OH-2-Adm,H),(8-85,Pro,A-17,S,S,O,5-OH-2-Adm,H),(8-86,Pro,A-18,S,S,O,5-OH-2-Adm,H),(8-87,Pro,A-19,S,S,O,5-OH-2-Adm,H),(8-88,Pro,A-20,S,S,O,5-OH-2-Adm,H),(8-89,Pro,A-21,S,S,O,5-OH-2-Adm,H),(8-90,Pro,A-22,S,S,O,5-OH-2-Adm,H),(8-91,Pro,A-23,S,S,O,5-OH-2-Adm,H),(8-92,Pro,A-24,S,S,O,5-OH-2-Adm,H),(8-93,Pro,A-25,S,S,O,5-OH-2-Adm,H),(8-94,Pro,A-26,S,S,O,5-OH-2-Adm,H),(8-95,Pro,A-27,S,S,O,5-OH-2-Adm,H),(8-96,Pro,A-28,S,S,O,5-OH-2-Adm,H),(8-97,Pro,A-29,S,S,O,5-OH-2-Adm,H),(8-98,Pro,A-30,S,S,O,5-OH-2-Adm,H),(8-99,Pro,A-31,S,S,O,5-OH-2-Adm,H), (8-100,Pro,A-32,S,S,O,5-OH-2-Adm,H),(8-101,Pro,A-33, S,S,O,5-OH-2-Adm,H),(8-102,Pro,A-34,S,S,O,5-OH-2- Adm,H),(8-103,Pro,A-35,S,S,O,5-OH-2-Adm,H),(8-104, Pro,A-36,S,S,O,5-OH-2-Adm,H),(8-105,Pro,B-1,S,S,O,1- Adm,H),(8-106,Pro,B-2,S,S,O,1-Adm,H),(8-107,Pro,B-3,S, S,O,1-Adm,H),(8-108,Pro,B-4,S,S,O,1-Adm,H),(8-109,Pro, B-5,S,S,O,1-Adm,H),(8-110,Pro,B-6,S,S,O,1-Adm,H),(8- 11,Pro,B-7,S,S,O,1-Adm,H),(8-112,Pro,B-8,S,S,O,1-Adm, H),(8-113,Pro,B-9,S,S,O,1-Adm,H),(8-114,Pro,B-10,S,S,O, 1-Adm,H),(8-115,Pro,B-1,S,S,O,1-Adm,H),(8-116,Pro,B- 12,S,S,O,1-Adm,H),(8-117,Pro,B-13,S,S,O,1-Adm,H),(8- 118,Pro,B-14,S,S,O,1-Adm,H),(8-119,Pro,B-15,S,S,O,1- Adm,H),(8-120,Pro,B-16,S,S,O,1-Adm,H),(8-121,Pro,B- 17,S,S,O,1-Adm,H),(8-122,Pro,B-18,S,S,O,1-Adm,H),(8- 123,Pro,B-19,S,S,O,1-Adm,H),(8-124,Pro,B-20,S,S,O,1- Adm,H),(8-125,Pro,B-21,S,S,O,1-Adm,H),(8-126,Pro,B- 22,S,S,O,1-Adm,H),(8-127,Pro,B-23,S,S,O,1-Adm,H),(8- 128,Pro,B-24,S,S,O,1-Adm,H),(8-129,Pro,B-25,S,S,O,1- Adm,H),(8-130,Pro,B-26,S,S,O,1-Adm,H),(8-131,Pro,B- 27,S,S,O,1-Adm,H),(8-132,Pro,B-28,S,S,O,1-Adm,H),(8- 133,Pro,B-29,S,S,O,1-Adm,H),(8-134,Pro,B-30,S,S,O,1- Adm,H),(8-135,Pro,B-31,S,S,O,1-Adm,H),(8-136,Pro,B- 32,S,S,O,1-Adm,H),(8-137,Pro,B-33,S,S,O,1-Adm,H),(8- 138,Pro,B-34,S,S,O,1-Adm,H),(8-139,Pro,B-35,S,S,O,1- Adm,H),(8-140,Pro,B-36,S,S,O,1-Adm,H),(8-141,Pro,B-1, S,S,O,2-Adm,H),(8-142,Pro,B-2,S,S,O,2-Adm,H),(8-143, Pro,B-3,S,S,O,2-Adm,H),(8-144,Pro,B-4,S,S,O,2-Adm,H), (8-145,Pro,B-5,S,S,O,2-Adm,H),(8-146,Pro,B-6,S,S,O,2- Adm,H),(8-147,Pro,B-7,S,S,O,2-Adm,H),(8-148,Pro,B-8,S, S,O,2-Adm,H),(8-149,Pro,B-9,S,S,O,2-Adm,H),(8-150,Pro, B-10,S,S,O,2-Adm,H),(8-151,Pro,B-11,S,S,O,2-Adm,H), (8-152,Pro,B-12,S,S,O,2-Adm,H),(8-153,Pro,B-13,S,S,O,2- Adm,H),(8-154,Pro,B-14,S,S,O,2-Adm,H),(8-155,Pro,B- 15,S,S,O,2-Adm,H),(8-156,Pro,B-16,S,S,O,2-Adm,H),(8- 157,Pro,B-17,S,S,O,2-Adm,H),(8-158,Pro,B-18,S,S,O,2- Adm,H),(8-159,Pro,B-19,S,S,O,2-Adm,H),(8-160,Pro,B- 20,S,S,O,2-Adm,H),(8-161,Pro,B-21,S,S,O,2-Adm,H),(8- 162,Pro,B-22,S,S,O,2-Adm,H),(8-163,Pro,B-23,S,S,O,2- Adm,H),(8-164,Pro,B-24,S,S,O,2-Adm,H),(8-165,Pro,B- 25,S,S,O,2-Adm,H),(8-166,Pro,B-26,S,S,O,2-Adm,H),(8- 167,Pro,B-27,S,S,O,2-Adm,H),(8-168,Pro,B-28,S,S,O,2- Adm,H),(8-169,Pro,B-29,S,S,O,2-Adm,H),(8-170,Pro,B- 30,S,S,O,2-Adm,H),(8-171,Pro,B-31,S,S,O,2-Adm,H),(8- 172,Pro,B-32,S,S,O,2-Adm,H),(8-173,Pro,B-33,S,S,O,2- Adm,H),(8-174,Pro,B-34,S,S,O,2-Adm,H),(8-175,Pro,B- 35,S,S,O,2-Adm,H),(8-176,Pro,B-36,S,S,O,2-Adm,H),(8- 177,Pro,B-1,S,S,O,5-OH-2-Adm,H),(8-178,Pro,B-2,S,S,O, 5-OH-2-Adm,H),(8-179,Pro,B-3,S,S,O,5-OH-2-Adm,H), (8-180,Pro,B-4,S,S,O,5-OH-2-Adm,H),(8-181,Pro,B-5,S,S, O,5-OH-2-Adm,H),(8-182,Pro,B-6,S,S,O,5-OH-2-Adm,H), (8-183,Pro,B-7,S,S,O,5-OH-2-Adm,H),(8-184,Pro,B-8,S,S, O,5-OH-2-Adm,H),(8-185,Pro,B-9,S,S,O,5-OH-2-Adm,H), (8-186,Pro,B-10,S,S,O,5-OH-2-Adm,H),(8-187,Pro,B-11,S, S,O,5-OH-2-Adm,H),(8-188,Pro,B-12,S,S,O,5-OH-2-Adm, H),(8-189,Pro,B-13,S,S,O,5-OH-2-Adm,H),(8-190,Pro,B- 14,S,S,O,5-OH-2-Adm,H),(8-191,Pro,B-15,S,S,O,5-OH-2- Adm,H),(8-192,Pro,B-16,S,S,O,5-OH-2-Adm,H),(8-193, Pro,B-17,S,S,O,5-OH-2-Adm,H),(8-194,Pro,B-18,S,S,O,5- OH-2-Adm,H),(8-195,Pro,B-19,S,S,O,5-OH-2-Adm,H),(8- 196,Pro,B-20,S,S,O,5-OH-2-Adm,H),(8-197,Pro,B-21,S,S, O,5-OH-2-Adm,H),(8-198,Pro,B-22,S,S,O,5-OH-2-Adm, H),(8-199,Pro,B-23,S,S,O,5-OH-2-Adm,H),(8-200,Pro,B- 24,S,S,O,5-OH-2-Adm,H),(8-201,Pro,B-25,S,S,O,5-OH-2- Adm,H),(8-202,Pro,B-26,S,S,O,5-OH-2-Adm,H),(8-203, Pro,B-27,S,S,O,5-OH-2-Adm,H),(8-204,Pro,B-28,S,S,O,5- OH-2-Adm,H),(8-205,Pro,B-29,S,S,O,5-OH-2-Adm,H),(8- 206,Pro,B-30,S,S,O,5-OH-2-Adm,H), (8-207,Pro,B-31,S,S, O,5-OH-2-Adm,H),(8-208,Pro,B-32,S,S,O,5-OH-2-Adm, H),(8-209,Pro,B-33,S,S,O,5-OH-2-Adm,H),(8-210,Pro,B- 34,S,S,O,5-OH-2-Adm,H),(8-211,Pro,B-35,S,S,O,5-OH-2- Adm,H),(8-212,Pro,B-36,S,S,O,5-OH-2-Adm,H),(8-213, Pro,C-1,S,S,O,1-Adm,H),(8-214,Pro,C-2,S,S,O,1-Adm,H), (8-215,Pro,C-3,S,S,O,1-Adm,H),(8-216,Pro,C-4,S,S,O,1- Adm,H),(8-217,Pro,C-5,S,S,O,1-Adm,H),(8-218,Pro,C-6,S, S,O,1-Adm,H),(8-219,Pro,C-7,S,S,O,1-Adm,H),(8-220,Pro, C-8,S,S,O,1-Adm,H),(8-221,Pro,C-9,S,S,O,1-Adm,H),(8- 222,Pro,C-10,S,S,O,1-Adm,H),(8-223,Pro,C-11,S,S,O,1- Adm,H),(8-224,Pro,C-12,S,S,O,1-Adm,H),(8-225,Pro,C- 13,S,S,O,1-Adm,H),(8-226,Pro,C-14,S,S,O,1-Adm,H),(8- 227,Pro,C-15,S,S,O,1-Adm,H),(8-228,Pro,C-16,S,S,O,1- Adm,H),(8-229,Pro,C-17,S,S,O,1-Adm,H),(8-230,Pro,C- 18,S,S,O,1-Adm,H),(8-231,Pro,C-19,S,S,O,1-Adm,H),(8- 232,Pro,C-20,S,S,O,1-Adm,H),(8-233,Pro,C-21,S,S,O,1- Adm,H),(8-234,Pro,C-22,S,S,O,1-Adm,H),(8-235,Pro,C- 23,S,S,O,1-Adm,H),(8-236,Pro,C-24,S,S,O,1-Adm,H),(8- 237,Pro,C-25,S,S,O,1-Adm,H),(8-238,Pro,C-26,S,S,O,1- Adm,H),(8-239,Pro,C-27,S,S,O,1-Adm,H),(8-240,Pro,C- 28,S,S,O,1-Adm,H),(8-241,Pro,C-29,S,S,O,1-Adm,H),(8- 242,Pro,C-30,S,S,O,1-Adm,H),(8-243,Pro,C-31,S,S,O,1- Adm,H),(8-244,Pro,C-32,S,S,O,1-Adm,H),(8-245,Pro,C- 33,S,S,O,1-Adm,H),(8-246,Pro,C-34,S,S,O,1-Adm,H),(8- 247,Pro,C-35,S,S,O,1-Adm,H),(8-248,Pro,C-36,S,S,O,1- Adm,H),(8-249,Pro,C-1,S,S,O,2-Adm,H),(8-250,Pro,C-2,S, S,O,2-Adm,H),(8-251,Pro,C-3,S,S,O,2-Adm,H),(8-252,Pro, C-4,S,S,O,2-Adm,H),(8-253,Pro,C-5,S,S,O,2-Adm,H),(8- 254,Pro,C-6,S,S,O,2-Adm,H),(8-255,Pro,C-7,S,S,O,2- Adm,H),(8-256,Pro,C-8,S,S,O,2-Adm,H),(8-257,Pro,C-9,S, S,O,2-Adm,H),(8-258,Pro,C-10,S,S,O,2-Adm,H),(8-259, Pro,C-11,S,S,O,2-Adm,H),(8-260,Pro,C-12,S,S,O,2-Adm, H),(8-261,Pro,C-13,S,S,O,2-Adm,H),(8-262,Pro,C-14,S,S, O,2-Adm,H),(8-263,Pro,C-11,S,S,O,2-Adm,H),(8-264,Pro, C-16,S,S,O,2-Adm,H),(8-265,Pro,C-17,S,S,O,2-Adm,H), (8-266,Pro,C-18,S,S,O,2-Adm,H),(8-267,Pro,C-19,S,S,O,2- Adm,H),(8-268,Pro,C-20,S,S,O,2-Adm,H),(8-269,Pro,C- 21,S,S,O,2-Adm,H),(8-270,Pro,C-22,S,S,O,2-Adm,H),(8- 271,Pro,C-23,S,S,O,2-Adm,H),(8-272,Pro,C-24,S,S,O,2- Adm,H),(8-273,Pro,C-25,S,S,O,2-Adm,H),(8-274,Pro,C- 26,S,S,O,2-Adm,H),(8-275,Pro,C-27,S,S,O,2-Adm,H),(8- 276,Pro,C-28,S,S,O,2-Adm,H),(8-277,Pro,C-29,S,S,O,2- Adm,H),(8-278,Pro,C-30,S,S,O,2-Adm,H),(8-279,Pro,C- 31,S,S,O,2-Adm,H),(8-280,Pro,C-32,S,S,O,2-Adm,H),(8- 281,Pro,C-33,S,S,O,2-Adm,H),(8-282,Pro,C-34,S,S,O,2- Adm,H),(8-283,Pro,C-35,S,S,O,2-Adm,H),(8-284,Pro,C- 36,S,S,O,2-Adm,H),(8-285,Pro,C-1,S,S,O,5-OH-2-Adm, H),(8-286,Pro,C-2,S,S,O,5-OH-2-Adm,H),(8-287,Pro,C-3, S,S,O,5-OH-2-Adm,H),(8-288,Pro,C-4,S,S,O,5-OH-2- Adm,H),(8-289,Pro,C-5,S,S,O,5-OH-2-Adm,H),(8-290,Pro, C-6,S,S,O,5-OH-2-Adm,H),(8-291,Pro,C-7,S,S,O,5-OH-2- Adm,H),(8-292,Pro,C-8,S,S,O,5-OH-2-Adm,H),(8-293,Pro, C-9,S,S,O,5-OH-2-Adm,H),(8-294,Pro,C-110,S,S,O,5-OH- 2-Adm,H),(8-295,Pro,C-111,S,S,O,5-OH-2-Adm,H),(8- 296,Pro,C-12,S,S,O,5-OH-2-Adm,H),(8-297,Pro,C-13,S,S, O,5-OH-2-Adm,H),(8-298,Pro,C-14,S,S,O,5-OH-2-Adm, H),(8-299,Pro,C-15,S,S,O,5-OH-2-Adm,H),(8-300,Pro,C- 16,S,S,O,5-OH-2-Adm,H),(8-301,Pro,C-17,S,S,O,5-OH-2- Adm,H),(8-302,Pro,C-18,S,S,O,5-OH-2-Adm,H),(8-303, Pro,C-19,S,S,O,5-OH-2-Adm,H),(8-304,Pro,C-20,S,S,O,5- OH-2-Adm,H),(8-305,Pro,C-21,S,S,O,5-OH-2-Adm,H),(8- 306,Pro,C-22,S,S,O,5-OH-2-Adm,H),(8-307,Pro,C-23,S,S, O,5-OH-2-Adm,H),(8-308,Pro,C-24,S,S,O,5-OH-2-Adm, H),(8-309,Pro,C-25,S,S,O,5-OH-2-Adm,H),(8-310,Pro,C- 26,S,S,O,5-OH-2-Adm,H),(8-311,Pro,C-27,S,S,O,5-OH-2- Adm,H),(8-312,Pro,C-28,S,S,O,5-OH-2-Adm,H),(8-313, Pro,C-29,S,S,O,5-OH-2-Adm,H), (8-314,Pro,C-30,S,S,O,5-

OH-2-Adm,H),(8-315,Pro,C-31,S,S,O,5-OH-2-Adm,H),(8-316,Pro,C-32,S,S,O,5-OH-2-Adm,H),(8-317,Pro,C-33,S,S,O,5-OH-2-Adm,H),(8-318,Pro,C-34,S,S,O,5-OH-2-Adm,H),(8-319,Pro,C-35,S,S,O,5-OH-2-Adm,H),(8-320,Pro,C-36,S,S,O,5-OH-2-Adm,H),(8-321,Pro,D-1,S,S,O,1-Adm,H),(8-322,Pro,D-2,S,S,O,1-Adm,H),(8-323,Pro,D-3,S,S,O,1-Adm,H),(8-324,Pro,D-4,S,S,O,1-Adm,H),(8-325,Pro,D-5,S,S,O,1-Adm,H),(8-326,Pro,D-6,S,S,O,1-Adm,H),(8-327,Pro,D-7,S,S,O,1-Adm,H),(8-328,Pro,D-8,S,S,O,1-Adm,H),(8-329,Pro,D-9,S,S,O,1-Adm,H),(8-330,Pro,D-110,S,S,O,1-Adm,H),(8-331,Pro,D-111,S,S,O,1-Adm,H),(8-332,Pro,D-12,S,S,O,1-Adm,H),(8-333,Pro,D-13,S,S,O,1-Adm,H),(8-334,Pro,D-14,S,S,O,1-Adm,H),(8-335,Pro,D-15,S,S,O,1-Adm,H),(8-336,Pro,D-16,S,S,O,1-Adm,H),(8-337,Pro,D-17,S,S,O,1-Adm,H),(8-338,Pro,D-18,S,S,O,1-Adm,H),(8-339,Pro,D-119,S,S,O,1-Adm,H),(8-340,Pro,D-20,S,S,O,1-Adm,H),(8-341,Pro,D-21,S,S,O,1-Adm,H),(8-342,Pro,D-22,S,S,O,1-Adm,H),(8-343,Pro,D-23,S,S,O,1-Adm,H),(8-344,Pro,D-24,S,S,O,1-Adm,H),(8-345,Pro,D-25,S,S,O,1-Adm,H),(8-346,Pro,D-26,S,S,O,1-Adm,H),(8-347,Pro,D-27,S,S,O,1-Adm,H),(8-348,Pro,D-28,S,S,O,1-Adm,H),(8-349,Pro,D-29,S,S,O,1-Adm,H),(8-350,Pro,D-30,S,S,O,1-Adm,H),(8-351,Pro,D-31,S,S,O,1-Adm,H),(8-352,Pro,D-32,S,S,O,1-Adm,H),(8-353,Pro,D-33,S,S,O,1-Adm,H),(8-354,Pro,D-34,S,S,O,1-Adm,H),(8-355,Pro,D-35,S,S,O,1-Adm,H),(8-356,Pro,D-36,S,S,O,1-Adm,H),(8-357,Pro,D-1,S,S,O,2-Adm,H),(8-358,Pro,D-2,S,S,O,2-Adm,H),(8-359,Pro,D-3,S,S,O,2-Adm,H),(8-360,Pro,D-4,S,S,O,2-Adm,H),(8-361,Pro,D-5,S,S,O,2-Adm,H),(8-362,Pro,D-6,S,S,O,2-Adm,H),(8-363,Pro,D-7,S,S,O,2-Adm,H),(8-364,Pro,D-8,S,S,O,2-Adm,H),(8-365,Pro,D-9,S,S,O,2-Adm,H),(8-366,Pro,D-10,S,S,O,2-Adm,H),(8-367,Pro,D-11,S,S,O,2-Adm,H),(8-368,Pro,D-12,S,S,O,2-Adm,H),(8-369,Pro,D-13,S,S,O,2-Adm,H),(8-370,Pro,D-14,S,S,O,2-Adm,H),(8-371,Pro,D-15,S,S,O,2-Adm,H),(8-372,Pro,D-16,S,S,O,2-Adm,H),(8-373,Pro,D-17,S,S,O,2-Adm,H),(8-374,Pro,D-18,S,S,O,2-Adm,H),(8-375,Pro,D-19,S,S,O,2-Adm,H),(8-376,Pro,D-20,S,S,O,2-Adm,H),(8-377,Pro,D-21,S,S,O,2-Adm,H),(8-378,Pro,D-22,S,S,O,2-Adm,H),(8-379,Pro,D-23,S,S,O,2-Adm,H),(8-380,Pro,D-24,S,S,O,2-Adm,H),(8-381,Pro,D-25,S,S,O,2-Adm,H),(8-382,Pro,D-26,S,S,O,2-Adm,H),(8-383,Pro,D-27,S,S,O,2-Adm,H),(8-384,Pro,D-28,S,S,O,2-Adm,H),(8-385,Pro,D-29,S,S,O,2-Adm,H),(8-386,Pro,D-30,S,S,O,2-Adm,H),(8-387,Pro,D-31,S,S,O,2-Adm,H),(8-388,Pro,D-32,S,S,O,2-Adm,H),(8-389,Pro,D-33,S,S,O,2-Adm,H),(8-390,Pro,D-34,S,S,O,2-Adm,H),(8-391,Pro,D-35,S,S,O,2-Adm,H),(8-392,Pro,D-36,S,S,O,2-Adm,H),(8-393,Pro,D-1,S,S,O,5-OH-2-Adm,H),(8-394,Pro,D-2,S,S,O,5-OH-2-Adm,H),(8-395,Pro,D-3,S,S,O,5-OH-2-Adm,H),(8-396,Pro,D-4,S,S,O,5-OH-2-Adm,H),(8-397,Pro,D-5,S,S,O,5-OH-2-Adm,H),(8-398,Pro,D-6,S,S,O,5-OH-2-Adm,H),(8-399,Pro,D-7,S,S,O,5-OH-2-Adm,H),(8-400,Pro,D-8,S,S,O,5-OH-2-Adm,H),(8-401,Pro,D-9,S,S,O,5-OH-2-Adm,H),(8-402,Pro,D-10,S,S,O,5-OH-2-Adm,H),(8-403,Pro,D-11,S,S,O,5-OH-2-Adm,H),(8-404,Pro,D-12,S,S,O,5-OH-2-Adm,H),(8-405,Pro,D-13,S,S,O,5-OH-2-Adm,H),(8-406,Pro,D-14,S,S,O,5-OH-2-Adm,H),(8-407,Pro,D-15,S,S,O,5-OH-2-Adm,H),(8-408,Pro,D-16,S,S,O,5-OH-2-Adm,H),(8-409,Pro,D-17,S,S,O,5-OH-2-Adm,H),(8-410,Pro,D-18,S,S,O,5-OH-2-Adm,H),(8-411,Pro,D-19,S,S,O,5-OH-2-Adm,H),(8-412,Pro,D-20,S,S,O,5-OH-2-Adm,H),(8-413,Pro,D-21,S,S,O,5-OH-2-Adm,H),(8-414,Pro,D-22,S,S,O,5-OH-2-Adm,H),(8-415,Pro,D-23,S,S,O,5-OH-2-Adm,H),(8-416,Pro,D-24,S,S,O,5-OH-2-Adm,H),(8-417,Pro,D-25,S,S,O,5-OH-2-Adm,H),(8-418,Pro,D-26,S,S,O,5-OH-2-Adm,H),(8-419,Pro,D-27,S,S,O,5-OH-2-Adm,H),(8-420,Pro,D-28,S,S,O,5-OH-2-Adm,H), (8-421,Pro,D-29,S,S,O,5-OH-2-Adm,H),(8-422,Pro,D-30,S,S,O,5-OH-2-Adm,H),(8-423,Pro,D-31,S,S,O,5-OH-2-Adm,H),(8-424,Pro,D-32,S,S,O,5-OH-2-Adm,H),(8-425,Pro,D-33,S,S,O,5-OH-2-Adm,H),(8-426,Pro,D-34,S,S,O,5-OH-2-Adm,H),(8-427,Pro,D-35,S,S,O,5-OH-2-Adm,H),(8-428,Pro,D-36,S,S,O,5-OH-2-Adm,H),(8-429,Pro,E-1,S,S,O,1-Adm,H),(8-430,Pro,E-2,S,S,O,1-Adm,H),(8-431,Pro,E-3,S,S,O,1-Adm,H),(8-432,Pro,E-4,S,S,O,1-Adm,H),(8-433,Pro,E-5,S,S,O,1-Adm,H),(8-434,Pro,E-6,S,S,O,1-Adm,H),(8-435,Pro,E-7,S,S,O,1-Adm,H),(8-436,Pro,E-8,S,S,O,1-Adm,H),(8-437,Pro,E-9,S,S,O,1-Adm,H),(8-438,Pro,E-10,S,S,O,1-Adm,H),(8-439,Pro,E-11,S,S,O,1-Adm,H),(8-440,Pro,E-12,S,S,O,1-Adm,H),(8-441,Pro,E-13,S,S,O,1-Adm,H),(8-442,Pro,E-14,S,S,O,1-Adm,H),(8-443,Pro,E-15,S,S,O,1-Adm,H),(8-444,Pro,E-16,S,S,O,1-Adm,H),(8-445,Pro,E-17,S,S,O,1-Adm,H),(8-446,Pro,E-18,S,S,O,1-Adm,H),(8-447,Pro,E-19,S,S,O,1-Adm,H),(8-448,Pro,E-20,S,S,O,1-Adm,H),(8-449,Pro,E-21,S,S,O,1-Adm,H),(8-450,Pro,E-22,S,S,O,1-Adm,H),(8-451,Pro,E-23,S,S,O,1-Adm,H),(8-452,Pro,E-24,S,S,O,1-Adm,H),(8-453,Pro,E-25,S,S,O,1-Adm,H),(8-454,Pro,E-26,S,S,O,1-Adm,H),(8-455,Pro,E-27,S,S,O,1-Adm,H),(8-456,Pro,E-28,S,S,O,1-Adm,H),(8-457,Pro,E-29,S,S,O,1-Adm,H),(8-458,Pro,E-30,S,S,O,1-Adm,H),(8-459,Pro,E-31,S,S,O,1-Adm,H),(8-460,Pro,E-32,S,S,O,1-Adm,H),(8-461,Pro,E-33,S,S,O,1-Adm,H),(8-462,Pro,E-34,S,S,O,1-Adm,H),(8-463,Pro,E-35,S,S,O,1-Adm,H),(8-464,Pro,E-36,S,S,O,1-Adm,H),(8-465,Pro,E-1,S,S,O,2-Adm,H),(8-466,Pro,E-2,S,S,O,2-Adm,H),(8-467,Pro,E-3,S,S,O,2-Adm,H),(8-468,Pro,E-4,S,S,O,2-Adm,H),(8-469,Pro,E-5,S,S,O,2-Adm,H),(8-470,Pro,E-6,S,S,O,2-Adm,H),(8-471,Pro,E-7,S,S,O,2-Adm,H),(8-472,Pro,E-8,S,S,O,2-Adm,H),(8-473,Pro,E-9,S,S,O,2-Adm,H),(8-474,Pro,E-10,S,S,O,2-Adm,H),(8-475,Pro,E-11,S,S,O,2-Adm,H),(8-476,Pro,E-12,S,S,O,2-Adm,H),(8-477,Pro,E-13,S,S,O,2-Adm,H),(8-478,Pro,E-14,S,S,O,2-Adm,H),(8-479,Pro,E-15,S,S,O,2-Adm,H),(8-480,Pro,E-16,S,S,O,2-Adm,H),(8-481,Pro,E-17,S,S,O,2-Adm,H),(8-482,Pro,E-18,S,S,O,2-Adm,H),(8-483,Pro,E-19,S,S,O,2-Adm,H),(8-484,Pro,E-20,S,S,O,2-Adm,H),(8-485,Pro,E-21,S,S,O,2-Adm,H),(8-486,Pro,E-22,S,S,O,2-Adm,H),(8-487,Pro,E-23,S,S,O,2-Adm,H),(8-488,Pro,E-24,S,S,O,2-Adm,H),(8-489,Pro,E-25,S,S,O,2-Adm,H),(8-490,Pro,E-26,S,S,O,2-Adm,H),(8-491,Pro,E-27,S,S,O,2-Adm,H),(8-492,Pro,E-28,S,S,O,2-Adm,H),(8-493,Pro,E-29,S,S,O,2-Adm,H),(8-494,Pro,E-30,S,S,O,2-Adm,H),(8-495,Pro,E-31,S,S,O,2-Adm,H),(8-496,Pro,E-32,S,S,O,2-Adm,H),(8-497,Pro,E-33,S,S,O,2-Adm,H),(8-498,Pro,E-34,S,S,O,2-Adm,H),(8-499,Pro,E-35,S,S,O,2-Adm,H),(8-500,Pro,E-36,S,S,O,2-Adm,H),(8-501,Pro,E-1,S,S,O,5-OH-2-Adm,H),(8-502,Pro,E-2,S,S,O,5-OH-2-Adm,H),(8-503,Pro,E-3,S,S,O,5-OH-2-Adm,H),(8-504,Pro,E-4,S,S,O,5-OH-2-Adm,H),(8-505,Pro,E-5,S,S,O,5-OH-2-Adm,H),(8-506,Pro,E-6,S,S,O,5-OH-2-Adm,H),(8-507,Pro,E-7,S,S,O,5-OH-2-Adm,H),(8-508,Pro,E-8,S,S,O,5-OH-2-Adm,H),(8-509,Pro,E-9,S,S,O,5-OH-2-Adm,H),(8-510,Pro,E-10,S,S,O,5-OH-2-Adm,H),(8-511,Pro,E-11,S,S,O,5-OH-2-Adm,H),(8-512,Pro,E-12,S,S,O,5-OH-2-Adm,H),(8-513,Pro,E-13,S,S,O,5-OH-2-Adm,H),(8-514,Pro,E-14,S,S,O,5-OH-2-Adm,H),(8-515,Pro,E-15,S,S,O,5-OH-2-Adm,H),(8-516,Pro,E-16,S,S,O,5-OH-2-Adm,H),(8-517,Pro,E-17,S,S,O,5-OH-2-Adm,H),(8-518,Pro,E-18,S,S,O,5-OH-2-Adm,H),(8-519,Pro,E-19,S,S,O,5-OH-2-Adm,H),(8-520,Pro,E-20,S,S,O,5-OH-2-Adm,H),(8-521,Pro,E-21,S,S,O,5-OH-2-Adm,H),(8-522,Pro,E-22,S,S,O,5-OH-2-Adm,H),(8-523,Pro,E-23,S,S,O,5-OH-2-Adm,H),(8-524,Pro,E-24,S,S,O,5-OH-2-Adm,H),(8-525,Pro,E-25,S,S,O,5-OH-2-Adm,H),(8-526,Pro,E-26,S,S,O,5-OH-2-Adm,H),(8-527,Pro,E-27,S,S,O,5-OH-2-Adm,H), (8-528,Pro,E-28,S,S,O,5-OH-2-Adm,H),(8-529,Pro,E-

29,S,S,O,5-OH-2-Adm,H),(8-530,Pro,E-30,S,S,O,5-OH-2-Adm,H),(8-531,Pro,E-31,S,S,O,5-OH-2-Adm,H),(8-532,Pro,E-32,S,S,O,5-OH-2-Adm,H),(8-533,Pro,E-33,S,S,O,5-OH-2-Adm,H),(8-534,Pro,E-34,S,S,O,5-OH-2-Adm,H),(8-535,Pro,E-35,S,S,O,5-OH-2-Adm,H),(8-536,Pro,E-36,S,S,O,5-OH-2-Adm,H),(8-537,Pro,F-1,S,S,O,1-Adm,H),(8-538,Pro,F-2,S,S,O,1-Adm,H),(8-539,Pro,F-3,S,S,O,1-Adm,H),(8-540,Pro,F-4,S,S,O,1-Adm,H),(8-541,Pro,F-5,S,S,O,1-Adm,H),(8-542,Pro,F-6,S,S,O,1-Adm,H),(8-543,Pro,F-7,S,S,O,1-Adm,H),(8-544,Pro,F-8,S,S,O,1-Adm,H),(8-545,Pro,F-9,S,S,O,1-Adm,H),(8-546,Pro,F-10,S,S,O,1-Adm,H),(8-547,Pro,F-11,S,S,O,1-Adm,H),(8-548,Pro,F-12,S,S,O,1-Adm,H),(8-549,Pro,F-13,S,S,O,1-Adm,H),(8-550,Pro,F-14,S,S,O,1-Adm,H),(8-551,Pro,F-15,S,S,O,1-Adm,H),(8-552,Pro,F-16,S,S,O,1-Adm,H),(8-553,Pro,F-17,S,S,O,1-Adm,H),(8-554,Pro,F-18,S,S,O,1-Adm,H),(8-555,Pro,F-19,S,S,O,1-Adm,H),(8-556,Pro,F-20,S,S,O,1-Adm,H),(8-557,Pro,F-21,S,S,O,1-Adm,H),(8-558,Pro,F-22,S,S,O,1-Adm,H),(8-559,Pro,F-23,S,S,O,1-Adm,H),(8-560,Pro,F-24,S,S,O,1-Adm,H),(8-561,Pro,F-25,S,S,O,1-Adm,H),(8-562,Pro,F-26,S,S,O,1-Adm,H),(8-563,Pro,F-27,S,S,O,1-Adm,H),(8-564,Pro,F-28,S,S,O,1-Adm,H),(8-565,Pro,F-29,S,S,O,1-Adm,H),(8-566,Pro,F-30,S,S,O,1-Adm,H),(8-567,Pro,F-31,S,S,O,1-Adm,H),(8-568,Pro,F-32,S,S,O,1-Adm,H),(8-569,Pro,F-33,S,S,O,1-Adm,H),(8-570,Pro,F-34,S,S,O,1-Adm,H),(8-571,Pro,F-35,S,S,O,1-Adm,H),(8-572,Pro,F-36,S,S,O,1-Adm,H),(8-573,Pro,F-1,S,S,O,2-Adm,H),(8-574,Pro,F-2,S,S,O,2-Adm,H),(8-575,Pro,F-3,S,S,O,2-Adm,H),(8-576,Pro,F-4,S,S,O,2-Adm,H),(8-577,Pro,F-5,S,S,O,2-Adm,H),(8-578,Pro,F-6,S,S,O,2-Adm,H),(8-579,Pro,F-7,S,S,O,2-Adm,H),(8-580,Pro,F-8,S,S,O,2-Adm,H),(8-581,Pro,F-9,S,S,O,2-Adm,H),(8-582,Pro,F-10,S,S,O,2-Adm,H),(8-583,Pro,F-11,S,S,O,2-Adm,H),(8-584,Pro,F-12,S,S,O,2-Adm,H),(8-585,Pro,F-13,S,S,O,2-Adm,H),(8-586,Pro,F-14,S,S,O,2-Adm,H),(8-587,Pro,F-15,S,S,O,2-Adm,H),(8-588,Pro,F-16,S,S,O,2-Adm,H),(8-589,Pro,F-17,S,S,O,2-Adm,H),(8-590,Pro,F-18,S,S,O,2-Adm,H),(8-591,Pro,F-19,S,S,O,2-Adm,H),(8-592,Pro,F-20,S,S,O,2-Adm,H),(8-593,Pro,F-21,S,S,O,2-Adm,H),(8-594,Pro,F-22,S,S,O,2-Adm,H),(8-595,Pro,F-23,S,S,O,2-Adm,H),(8-596,Pro,F-24,S,S,O,2-Adm,H),(8-597,Pro,F-25,S,S,O,2-Adm,H),(8-598,Pro,F-26,S,S,O,2-Adm,H),(8-599,Pro,F-27,S,S,O,2-Adm,H),(8-600,Pro,F-28,S,S,O,2-Adm,H),(8-601,Pro,F-29,S,S,O,2-Adm,H),(8-602,Pro,F-30,S,S,O,2-Adm,H),(8-603,Pro,F-31,S,S,O,2-Adm,H),(8-604,Pro,F-32,S,S,O,2-Adm,H),(8-605,Pro,F-33,S,S,O,2-Adm,H),(8-606,Pro,F-34,S,S,O,2-Adm,H),(8-607,Pro,F-35,S,S,O,2-Adm,H),(8-608,Pro,F-36,S,S,O,2-Adm,H),(8-609,Pro,F-1,S,S,O,5-OH-2-Adm,H),(8-610,Pro,F-2,S,S,O,5-OH-2-Adm,H),(8-611,Pro,F-3,S,S,O,5-OH-2-Adm,H),(8-612,Pro,F-4,S,S,O,5-OH-2-Adm,H),(8-613,Pro,F-5,S,S,O,5-OH-2-Adm,H),(8-614,Pro,F-6,S,S,O,5-OH-2-Adm,H),(8-615,Pro,F-7,S,S,O,5-OH-2-Adm,H),(8-616,Pro,F-8,S,S,O,5-OH-2-Adm,H),(8-617,Pro,F-9,S,S,O,5-OH-2-Adm,H),(8-618,Pro,F-10,S,S,O,5-OH-2-Adm,H),(8-619,Pro,F-11,S,S,O,5-OH-2-Adm,H),(8-620,Pro,F-12,S,S,O,5-OH-2-Adm,H),(8-621,Pro,F-13,S,S,O,5-OH-2-Adm,H),(8-622,Pro,F-14,S,S,O,5-OH-2-Adm,H),(8-623,Pro,F-15,S,S,O,5-OH-2-Adm,H),(8-624,Pro,F-16,S,S,O,5-OH-2-Adm,H),(8-625,Pro,F-17,S,S,O,5-OH-2-Adm,H),(8-626,Pro,F-18,S,S,O,5-OH-2-Adm,H),(8-627,Pro,F-19,S,S,O,5-OH-2-Adm,H),(8-628,Pro,F-20,S,S,O,5-OH-2-Adm,H),(8-629,Pro,F-21,S,S,O,5-OH-2-Adm,H),(8-630,Pro,F-22,S,S,O,5-OH-2-Adm,H),(8-631,Pro,F-23,S,S,O,5-OH-2-Adm,H),(8-632,Pro,F-24,S,S,O,5-OH-2-Adm,H),(8-633,Pro,F-25,S,S,O,5-OH-2-Adm,H),(8-634,Pro,F-26,S,S,O,5-OH-2-Adm,H),(8-635,Pro,F-27,S,S,O,5-OH-2-Adm,H),(8-636,Pro,F-28,S,S,O,5-OH-2-Adm,H), (8-637,Pro,F-29,S,S,O,5-OH-2-Adm,H),(8-638,Pro,F-30,S,S,O,5-OH-2-Adm,H),(8-639,Pro,F-31,S,S,O,5-OH-2-Adm,H),(8-640,Pro,F-32,S,S,O,5-OH-2-Adm,H),(8-641,Pro,F-33,S,S,O,5-OH-2-Adm,H),(8-642,Pro,F-34,S,S,O,5-OH-2-Adm,H),(8-643,Pro,F-35,S,S,O,5-OH-2-Adm,H),(8-644,Pro,F-36,S,S,O,5-OH-2-Adm,H),(8-645,Pro,G-1,S,S,O,1-Adm,H),(8-646,Pro,G-2,S,S,O,1-Adm,H),(8-647,Pro,G-3,S,S,O,1-Adm,H),(8-648,Pro,G-4,S,S,O,1-Adm,H),(8-649,Pro,G-5,S,S,O,1-Adm,H),(8-650,Pro,G-6,S,S,O,1-Adm,H),(8-651,Pro,G-7,S,S,O,1-Adm,H),(8-652,Pro,G-8,S,S,O,1-Adm,H),(8-653,Pro,G-9,S,S,O,1-Adm,H),(8-654,Pro,G-1,S,S,O,2-Adm,H),(8-655,Pro,G-2,S,S,O,2-Adm,H),(8-656,Pro,G-3,S,S,O,2-Adm,H),(8-657,Pro,G-4,S,S,O,2-Adm,H),(8-658,Pro,G-5,S,S,O,2-Adm,H),(8-659,Pro,G-6,S,S,O,2-Adm,H),(8-660,Pro,G-7,S,S,O,2-Adm,H),(8-661,Pro,G-8,S,S,O,2-Adm,H),(8-662,Pro,G-9,S,S,O,2-Adm,H),(8-663,Pro,G-1,S,S,O,5-OH-2-Adm,H),(8-664,Pro,G-2,S,S,O,5-OH-2-Adm,H),(8-665,Pro,G-3,S,S,O,5-OH-2-Adm,H),(8-666,Pro,G-4,S,S,O,5-OH-2-Adm,H),(8-667,Pro,G-5,S,S,O,5-OH-2-Adm,H),(8-668,Pro,G-6,S,S,O,5-OH-2-Adm,H),(8-669,Pro,G-7,S,S,O,5-OH-2-Adm,H),(8-670,Pro,G-8,S,S,O,5-OH-2-Adm,H),(8-671,Pro,G-9,S,S,O,5-OH-2-Adm,H),(8-672,Pro,H-1,S,S,O,1-Adm,H),(8-673,Pro,H-2,S,S,O,1-Adm,H),(8-674,Pro,H-3,S,S,O,1-Adm,H),(8-675,Pro,H-4,S,S,O,1-Adm,H),(8-676,Pro,H-5,S,S,O,1-Adm,H),(8-677,Pro,H-6,S,S,O,1-Adm,H),(8-678,Pro,H-7,S,S,O,1-Adm,H),(8-679,Pro,H-8,S,S,O,1-Adm,H),(8-680,Pro,H-9,S,S,O,1-Adm,H),(8-681,Pro,H-1,S,S,O,2-Adm,H),(8-682,Pro,H-2,S,S,O,2-Adm,H),(8-683,Pro,H-3,S,S,O,2-Adm,H),(8-684,Pro,H-4,S,S,O,2-Adm,H),(8-685,Pro,H-5,S,S,O,2-Adm,H),(8-686,Pro,H-6,S,S,O,2-Adm,H),(8-687,Pro,H-7,S,S,O,2-Adm,H),(8-688,Pro,H-8,S,S,O,2-Adm,H),(8-689,Pro,H-9,S,S,O,2-Adm,H),(8-690,Pro,H-1,S,S,O,5-OH-2-Adm,H),(8-691,Pro,H-2,S,S,O,5-OH-2-Adm,H),(8-692,Pro,H-3,S,S,O,5-OH-2-Adm,H),(8-693,Pro,H-4,S,S,O,5-OH-2-Adm,H),(8-694,Pro,H-5,S,S,O,5-OH-2-Adm,H),(8-695,Pro,H-6,S,S,O,5-OH-2-Adm,H),(8-696,Pro,H-7,S,S,O,5-OH-2-Adm,H),(8-697,Pro,H-8,S,S,O,5-OH-2-Adm,H),(8-698,Pro,H-9,S,S,O,5-OH-2-Adm,H),(8-699,Pro,I-1,S,S,O,1-Adm,H),(8-700,Pro,I-2,S,S,O,1-Adm,H),(8-701,Pro,I-3,S,S,O,1-Adm,H),(8-702,Pro,I-4,S,S,O,1-Adm,H),(8-703,Pro,I-5,S,S,O,1-Adm,H),(8-704,Pro,I-6,S,S,O,1-Adm,H),(8-705,Pro,I-7,S,S,O,1-Adm,H),(8-706,Pro,I-8,S,S,O,1-Adm,H),(8-707,Pro,I-9,S,S,O,1-Adm,H),(8-708,Pro,I-1,S,S,O,2-Adm,H),(8-709,Pro,I-2,S,S,O,2-Adm,H),(8-710,Pro,I-3,S,S,O,2-Adm,H),(8-711,Pro,I-4,S,S,O,2-Adm,H),(8-712,Pro,I-5,S,S,O,2-Adm,H),(8-713,Pro,I-6,S,S,O,2-Adm,H),(8-714,Pro,I-7,S,S,O,2-Adm,H),(8-715,Pro,I-8,S,S,O,2-Adm,H),(8-716,Pro,I-9,S,S,O,2-Adm,H),(8-717,Pro,I-1,S,S,O,5-OH-2-Adm,H),(8-718,Pro,I-2,S,S,O,5-OH-2-Adm,H),(8-719,Pro,I-3,S,S,O,5-OH-2-Adm,H),(8-720,Pro,I-4,S,S,O,5-OH-2-Adm,H),(8-721,Pro,I-5,S,S,O,5-OH-2-Adm,H),(8-722,Pro,I-6,S,S,O,5-OH-2-Adm,H),(8-723,Pro,I-7,S,S,O,5-OH-2-Adm,H),(8-724,Pro,I-8,S,S,O,5-OH-2-Adm,H),(8-725,Pro,I-9,S,S,O,5-OH-2-Adm,H),(8-726,Pro,J-1,S,S,O,1-Adm,H),(8-727,Pro,J-2,S,S,O,1-Adm,H),(8-728,Pro,J-3,S,S,O,1-Adm,H),(8-729,Pro,J-4,S,S,O,1-Adm,H),(8-730,Pro,J-5,S,S,O,1-Adm,H),(8-731,Pro,J-6,S,S,O,1-Adm,H),(8-732,Pro,J-7,S,S,O,1-Adm,H),(8-733,Pro,J-8,S,S,O,1-Adm,H),(8-734,Pro,J-9,S,S,O,1-Adm,H),(8-735,Pro,J-1,S,S,O,2-Adm,H),(8-736,Pro,J-2,S,S,O,2-Adm,H),(8-737,Pro,J-3,S,S,O,2-Adm,H),(8-738,Pro,J-4,S,S,O,2-Adm,H),(8-739,Pro,J-5,S,S,O,2-Adm,H),(8-740,Pro,J-6,S,S,O,2-Adm,H),(8-741,Pro,J-7,S,S,O,2-Adm,H),(8-742,Pro,J-8,S,S,O,2-Adm,H),(8-743,Pro,J-9,S,S,O,2-Adm,H),(8-744,Pro,J-1,S,S,O,5-OH-2-Adm,H),(8-745,Pro,J-2,S,S,O,5-OH-2-Adm,H),(8-746,Pro,J-3,S,S,O,5-OH-2-Adm,H),(8-747,Pro,J-4,S,S,O,5-OH-2-Adm,H), (8-748,Pro,J-5,S,

S,O,5-OH-2-Adm,H),(8-749,Pro,J-6,S,S,O,5-OH-2-Adm,H),(8-750,Pro,J-7,S,S,O,5-OH-2-Adm,H),(8-751,Pro,J-8,S,S,O,5-OH-2-Adm,H),(8-752,Pro,J-9,S,S,O,5-OH-2-Adm,H),(8-753,Pro,K-1,S,S,O,1-Adm,H),(8-754,Pro,K-2,S,S,O,1-Adm,H),(8-755,Pro,K-3,S,S,O,1-Adm,H),(8-756,Pro,K-4,S,S,O,1-Adm,H),(8-757,Pro,K-5,S,S,O,1-Adm,H),(8-758,Pro,K-6,S,S,O,1-Adm,H),(8-759,Pro,K-7,S,S,O,1-Adm,H),(8-760,Pro,K-8,S,S,O,1-Adm,H),(8-761,Pro,K-9,S,S,O,1-Adm,H),(8-762,Pro,K-1,S,S,O,2-Adm,H),(8-763,Pro,K-2,S,S,O,2-Adm,H),(8-764,Pro,K-3,S,S,O,2-Adm,H),(8-765,Pro,K-4,S,S,O,2-Adm,H),(8-766,Pro,K-5,S,S,O,2-Adm,H),(8-767,Pro,K-6,S,S,O,2-Adm,H),(8-768,Pro,K-7,S,S,O,2-Adm,H),(8-769,Pro,K-8,S,S,O,2-Adm,H),(8-770,Pro,K-9,S,S,O,2-Adm,H),(8-771,Pro,K-1,S,S,O,5-OH-2-Adm,H),(8-772,Pro,K-2,S,S,O,5-OH-2-Adm,H),(8-773,Pro,K-3,S,S,O,5-OH-2-Adm,H),(8-774,Pro,K-4,S,S,O,5-OH-2-Adm,H),(8-775,Pro,K-5,S,S,O,5-OH-2-Adm,H),(8-776,Pro,K-6,S,S,O,5-OH-2-Adm,H),(8-777,Pro,K-7,S,S,O,5-OH-2-Adm,H),(8-778,Pro,K-8,S,S,O,5-OH-2-Adm,H),(8-779,Pro,K-9,S,S,O,5-OH-2-Adm,H)

(Compound No., $R^2,R^3,X,Y,Z,R^4,R^5$)=(9-1,i-Pro,A-1,S,S,O,1-Adm,H),(9-2,i-Pro,A-2,S,S,O,1-Adm,H),(9-3,i-Pro,A-3,S,S,O,1-Adm,H),(9-4,i-Pro,A-4,S,S,O,1-Adm,H),(9-5,i-Pro,A-5,S,S,O,1-Adm,H),(9-6,i-Pro,A-6,S,S,O,1-Adm,H),(9-7,i-Pro,A-7,S,S,O,1-Adm,H),(9-8,i-Pro,A-8,S,S,O,1-Adm,H),(9-9,i-Pro,A-9,S,S,O,1-Adm,H),(9-10,i-Pro,A-10,S,S,O,1-Adm,H),(9-11,i-Pro,A-11,S,S,O,1-Adm,H),(9-12,i-Pro,A-12,S,S,O,1-Adm,H),(9-13,i-Pro,A-13,S,S,O,1-Adm,H),(9-14,i-Pro,A-14,S,S,O,1-Adm,H),(9-15,i-Pro,A-15,S,S,O,1-Adm,H),(9-16,i-Pro,A-16,S,S,O,1-Adm,H),(9-17,i-Pro,A-17,S,S,O,1-Adm,H),(9-18,i-Pro,A-18,S,S,O,1-Adm,H),(9-19,i-Pro,A-19,S,S,O,1-Adm,H),(9-20,i-Pro,A-20,S,S,O,1-Adm,H),(9-21,i-Pro,A-21,S,S,O,1-Adm,H),(9-22,i-Pro,A-22,S,S,O,1-Adm,H),(9-23,i-Pro,A-23,S,S,O,1-Adm,H),(9-24,i-Pro,A-24,S,S,O,1-Adm,H),(9-25,i-Pro,A-25,S,S,O,1-Adm,H),(9-26,i-Pro,A-26,S,S,O,1-Adm,H),(9-27,i-Pro,A-27,S,S,O,1-Adm,H),(9-28,i-Pro,A-28,S,S,O,1-Adm,H),(9-29,i-Pro,A-29,S,S,O,1-Adm,H),(9-30,i-Pro,A-30,S,S,O,1-Adm,H),(9-31,i-Pro,A-31,S,S,O,1-Adm,H),(9-32,i-Pro,A-32,S,S,O,1-Adm,H),(9-33,i-Pro,A-33,S,S,O,1-Adm,H),(9-34,i-Pro,A-34,S,S,O,1-Adm,H),(9-35,i-Pro,A-35,S,S,O,1-Adm,H),(9-36,i-Pro,A-36,S,S,O,1-Adm,H),(9-37,i-Pro,A-1,S,S,O,2-Adm,H),(9-38,i-Pro,A-2,S,S,O,2-Adm,H),(9-39,i-Pro,A-3,S,S,O,2-Adm,H),(9-40,i-Pro,A-4,S,S,O,2-Adm,H),(9-41,i-Pro,A-5,S,S,O,2-Adm,H),(9-42,i-Pro,A-6,S,S,O,2-Adm,H),(9-43,i-Pro,A-7,S,S,O,2-Adm,H),(9-44,i-Pro,A-9,S,S,O,2-Adm,H),(9-45,i-Pro,A-11,S,S,O,2-Adm,H),(9-46,i-Pro,A-12,S,S,O,2-Adm,H),(9-47,i-Pro,A-13,S,S,O,2-Adm,H),(9-48,i-Pro,A-14,S,S,O,2-Adm,H),(9-49,i-Pro,A-15,S,S,O,2-Adm,H),(9-50,i-Pro,A-16,S,S,O,2-Adm,H),(9-51,i-Pro,A-17,S,S,O,2-Adm,H),(9-52,i-Pro,A-18,S,S,O,2-Adm,H),(9-53,i-Pro,A-20,S,S,O,2-Adm,H),(9-54,i-Pro,A-21,S,S,O,2-Adm,H),(9-55,i-Pro,A-22,S,S,O,2-Adm,H),(9-56,i-Pro,A-23,S,S,O,2-Adm,H),(9-57,i-Pro,A-24,S,S,O,2-Adm,H),(9-58,i-Pro,A-26,S,S,O,2-Adm,H),(9-59,i-Pro,A-27,S,S,O,2-Adm,H),(9-60,i-Pro,A-28,S,S,O,2-Adm,H),(9-61,i-Pro,A-29,S,S,O,2-Adm,H),(9-62,i-Pro,A-30,S,S,O,2-Adm,H),(9-63,i-Pro,A-31,S,S,O,2-Adm,H),(9-64,i-Pro,A-32,S,S,O,2-Adm,H),(9-65,i-Pro,A-33,S,S,O,2-Adm,H),(9-66,i-Pro,A-34,S,S,O,2-Adm,H),(9-67,i-Pro,A-35,S,S,O,2-Adm,H),(9-68,i-Pro,A-36,S,S,O,2-Adm,H),(9-69,i-Pro,A-1,S,S,O,5-OH-2-Adm,H),(9-70,i-Pro,A-2,S,S,O,5-OH-2-Adm,H),(9-71,i-Pro,A-3,S,S,O,5-OH-2-Adm,H),(9-72,i-Pro,A-4,S,S,O,5-OH-2-Adm,H),(9-73,i-Pro,A-5,S,S,O,5-OH-2-Adm,H),(9-74,i-Pro,A-6,S,S,O,5-OH-2-Adm,H),(9-75,i-Pro,A-7,S,S,O,5-OH-2-Adm,H),(9-76,i-Pro,A-8,S,S,O,5-OH-2-Adm,H),(9-77,i-Pro,A-9,S,S,O,5-OH-2-Adm,H),(9-78,i-Pro,A-10,S,S,O,5-OH-2-Adm,H),(9-79,i-Pro,A-11,S,S,O,5-OH-2-Adm,H),(9-80,i-Pro,A-12,S,S,O,5-OH-2-Adm,H),(9-81,i-Pro,A-13,S,S,O,5-OH-2-Adm,H),(9-82,i-Pro,A-14,S,S,O,5-OH-2-Adm,H),(9-83,i-Pro,A-15,S,S,O,5-OH-2-Adm,H),(9-84,i-Pro,A-16,S,S,O,5-OH-2-Adm,H),(9-85,i-Pro,A-17,S,S,O,5-OH-2-Adm,H),(9-86,i-Pro,A-18,S,S,O,5-OH-2-Adm,H),(9-87,i-Pro,A-19,S,S,O,5-OH-2-Adm,H),(9-88,i-Pro,A-20,S,S,O,5-OH-2-Adm,H),(9-89,i-Pro,A-21,S,S,O,5-OH-2-Adm,H),(9-90,i-Pro,A-22,S,S,O,5-OH-2-Adm,H),(9-91,i-Pro,A-23,S,S,O,5-OH-2-Adm,H),(9-92,i-Pro,A-24,S,S,O,5-OH-2-Adm,H),(9-93,i-Pro,A-25,S,S,O,5-OH-2-Adm,H),(9-94,i-Pro,A-26,S,S,O,5-OH-2-Adm,H),(9-95,i-Pro,A-27,S,S,O,5-OH-2-Adm,H),(9-96,i-Pro,A-28,S,S,O,5-OH-2-Adm,H),(9-97,i-Pro,A-29,S,S,O,5-OH-2-Adm,H),(9-98,i-Pro,A-30,S,S,O,5-OH-2-Adm,H),(9-99,i-Pro,A-31,S,S,O,5-OH-2-Adm,H),(9-100,i-Pro,A-32,S,S,O,5-OH-2-Adm,H),(9-101,i-Pro,A-33,S,S,O,5-OH-2-Adm,H),(9-102,i-Pro,A-34,S,S,O,5-OH-2-Adm,H),(9-103,i-Pro,A-35,S,S,O,5-OH-2-Adm,H),(9-104,i-Pro,A-36,S,S,O,5-OH-2-Adm,H),(9-105,i-Pro,B-1,S,S,O,1-Adm,H),(9-106,i-Pro,B-2,S,S,O,1-Adm,H),(9-107,i-Pro,B-3,S,S,O,1-Adm,H),(9-108,i-Pro,B-4,S,S,O,1-Adm,H),(9-109,i-Pro,B-5,S,S,O,1-Adm,H),(9-110,i-Pro,B-6,S,S,O,1-Adm,H),(9-111,i-Pro,B-7,S,S,O,1-Adm,H),(9-112,i-Pro,B-8,S,S,O,1-Adm,H),(9-113,i-Pro,B-9,S,S,O,1-Adm,H),(9-114,i-Pro,B-10,S,S,O,1-Adm,H),(9-115,i-Pro,B-11,S,S,O,1-Adm,H),(9-116,i-Pro,B-12,S,S,O,1-Adm,H),(9-117,i-Pro,B-13,S,S,O,1-Adm,H),(9-118,i-Pro,B-14,S,S,O,1-Adm,H),(9-119,i-Pro,B-15,S,S,O,1-Adm,H),(9-120,i-Pro,B-16,S,S,O,1-Adm,H),(9-121,i-Pro,B-17,S,S,O,1-Adm,H),(9-122,i-Pro,B-18,S,S,O,1-Adm,H),(9-123,i-Pro,B-19,S,S,O,1-Adm,H),(9-124,i-Pro,B-20,S,S,O,1-Adm,H),(9-125,i-Pro,B-21,S,S,O,1-Adm,H),(9-126,i-Pro,B-22,S,S,O,1-Adm,H),(9-127,i-Pro,B-23,S,S,O,1-Adm,H),(9-128,i-Pro,B-24,S,S,O,1-Adm,H),(9-129,i-Pro,B-25,S,S,O,1-Adm,H),(9-130,i-Pro,B-26,S,S,O,1-Adm,H),(9-131,i-Pro,B-27,S,S,O,1-Adm,H),(9-132,i-Pro,B-28,S,S,O,1-Adm,H),(9-133,i-Pro,B-29,S,S,O,1-Adm,H),(9-134,i-Pro,B-30,S,S,O,1-Adm,H),(9-135,i-Pro,B-31,S,S,O,1-Adm,H),(9-136,i-Pro,B-32,S,S,O,1-Adm,H),(9-137,i-Pro,B-33,S,S,O,1-Adm,H),(9-138,i-Pro,B-34,S,S,O,1-Adm,H),(9-139,i-Pro,B-35,S,S,O,1-Adm,H),(9-140,i-Pro,B-36,S,S,O,1-Adm,H),(9-141,i-Pro,B-1,S,S,O,2-Adm,H),(9-142,i-Pro,B-2,S,S,O,2-Adm,H),(9-143,i-Pro,B-3,S,S,O,2-Adm,H),(9-144,i-Pro,B-4,S,S,O,2-Adm,H),(9-145,i-Pro,B-5,S,S,O,2-Adm,H),(9-146,i-Pro,B-6,S,S,O,2-Adm,H),(9-147,i-Pro,B-7,S,S,O,2-Adm,H),(9-148,i-Pro,B-8,S,S,O,2-Adm,H),(9-149,i-Pro,B-9,S,S,O,2-Adm,H),(9-150,i-Pro,B-110,S,S,O,2-Adm,H),(9-151,i-Pro,B-11,S,S,O,2-Adm,H),(9-152,i-Pro,B-12,S,S,O,2-Adm,H),(9-153,i-Pro,B-13,S,S,O,2-Adm,H),(9-154,i-Pro,B-14,S,S,O,2-Adm,H),(9-155,i-Pro,B-15,S,S,O,2-Adm,H),(9-156,i-Pro,B-16,S,S,O,2-Adm,H),(9-157,i-Pro,B-17,S,S,O,2-Adm,H),(9-158,i-Pro,B-18,S,S,O,2-Adm,H),(9-159,i-Pro,B-19,S,S,O,2-Adm,H),(9-160,i-Pro,B-20,S,S,O,2-Adm,H),(9-161,i-Pro,B-21,S,S,O,2-Adm,H),(9-162,i-Pro,B-22,S,S,O,2-Adm,H),(9-163,i-Pro,B-23,S,S,O,2-Adm,H),(9-164,i-Pro,B-24,S,S,O,2-Adm,H),(9-165,i-Pro,B-25,S,S,O,2-Adm,H),(9-166,i-Pro,B-26,S,S,O,2-Adm,H),(9-167,i-Pro,B-27,S,S,O,2-Adm,H),(9-168,i-Pro,B-28,S,S,O,2-Adm,H),(9-169,i-Pro,B-29,S,S,O,2-Adm,H),(9-170,i-Pro,B-30,S,S,O,2-Adm,H),(9-171,i-Pro,B-31,S,S,O,2-Adm,H),(9-172,i-Pro,B-32,S,S,O,2-Adm,H),(9-173,i-Pro,B-33,S,S,O,2-Adm,H),(9-174,i-Pro,B-34,S,S,O,2-Adm,H),(9-175,i-Pro,B-35,S,S,O,2-Adm,H),(9-176,i-Pro,B-36,S,S,O,2-Adm,H),(9-177,i-Pro,B-1,S,S,O,5-OH-2-Adm,H),(9-178,i-Pro,B-2,S,S,O,5-OH-2-Adm,H),(9-179,i-Pro,B-3,S,S,O,5-OH-2-Adm,H),(9-180,i-Pro,B-4,S,S,O,5-OH-2-Adm,H),(9-181,i-Pro,B-5,S,S,O,5-OH-2-Adm,H),(9-182,i-Pro,B-6,S,S, O,5-OH-2-Adm,H),(9-183,i-Pro,B-7,S,S,O,5-OH-2-Adm,H),(9-184,i-Pro,B-8,S,S,O,5-OH-2-Adm,H),(9-185,i-Pro,B-9,S,S,O,5-OH-2-Adm,H),(9-186,i-Pro,B-10,S,S,O,5-OH-2-Adm,H),(9-187,i-Pro,B-11,S,S,O,5-OH-2-Adm,H),(9-188,i-Pro,B-12,S,S,O,5-OH-2-Adm,H),(9-189,i-Pro,B-13,S,S,O,5-OH-2-Adm,H),(9-190,i-Pro,B-14,S,S,O,5-OH-2-Adm,H),(9-191,i-Pro,B-15,S,S,O,5-OH-2-Adm,H),(9-192,i-Pro,B-16,S,S,O,5-OH-2-Adm,H),(9-193,i-Pro,B-17,S,S,O,5-OH-2-Adm,H),(9-194,i-Pro,B-18,S,S,O,5-OH-2-Adm,H),(9-195,i-Pro,B-19,S,S,O,5-OH-2-Adm,H),(9-196,i-Pro,B-20,S,S,O,5-OH-2-Adm,H),(9-197,i-Pro,B-21,S,S,O,5-OH-2-Adm,H),(9-198,i-Pro,B-22,S,S,O,5-OH-2-Adm,H),(9-199,i-Pro,B-23,S,S,O,5-OH-2-Adm,H),(9-200,i-Pro,B-24,S,S,O,5-OH-2-Adm,H),(9-201,i-Pro,B-25,S,S,O,5-OH-2-Adm,H),(9-202,i-Pro,B-26,S,S,O,5-OH-2-Adm,H),(9-203,i-Pro,B-27,S,S,O,5-OH-2-Adm,H),(9-204,i-Pro,B-28,S,S,O,5-OH-2-Adm,H),(9-205,i-Pro,B-29,S,S,O,5-OH-2-Adm,H),(9-206,i-Pro,B-30,S,S,O,5-OH-2-Adm,H),(9-207,i-Pro,B-31,S,S,O,5-OH-2-Adm,H),(9-208,i-Pro,B-32,S,S,O,5-OH-2-Adm,H),(9-209,i-Pro,B-33,S,S,O,5-OH-2-Adm,H),(9-210,i-Pro,B-34,S,S,O,5-OH-2-Adm,H),(9-211,i-Pro,B-35,S,S,O,5-OH-2-Adm,H),(9-212,i-Pro,B-36,S,S,O,5-OH-2-Adm,H),(9-213,i-Pro,C-1,S,S,O,1-Adm,H),(9-214,i-Pro,C-2,S,S,O,1-Adm,H),(9-215,i-Pro,C-3,S,S,O,1-Adm,H),(9-216,i-Pro,C-4,S,S,O,1-Adm,H),(9-217,i-Pro,C-5,S,S,O,1-Adm,H),(9-218,i-Pro,C-6,S,S,O,1-Adm,H),(9-219,i-Pro,C-7,S,S,O,1-Adm,H),(9-220,i-Pro,C-8,S,S,O,1-Adm,H),(9-221,i-Pro,C-9,S,S,O,1-Adm,H),(9-222,i-Pro,C-11,S,S,O,1-Adm,H),(9-223,i-Pro,C-11,S,S,O,1-Adm,H),(9-224,i-Pro,C-12,S,S,O,1-Adm,H),(9-225,i-Pro,C-13,S,S,O,1-Adm,H),(9-226,i-Pro,C-14,S,S,O,1-Adm,H),(9-227,i-Pro,C-15,S,S,O,1-Adm,H),(9-228,i-Pro,C-16,S,S,O,1-Adm,H),(9-229,i-Pro,C-17,S,S,O,1-Adm,H),(9-230,i-Pro,C-18,S,S,O,1-Adm,H),(9-231,i-Pro,C-19,S,S,O,1-Adm,H),(9-232,i-Pro,C-20,S,S,O,1-Adm,H),(9-233,i-Pro,C-21,S,S,O,1-Adm,H),(9-234,i-Pro,C-22,S,S,O,1-Adm,H),(9-235,i-Pro,C-23,S,S,O,1-Adm,H),(9-236,i-Pro,C-24,S,S,O,1-Adm,H),(9-237,i-Pro,C-25,S,S,O,1-Adm,H),(9-238,i-Pro,C-26,S,S,O,1-Adm,H),(9-239,i-Pro,C-27,S,S,O,1-Adm,H),(9-240,i-Pro,C-28,S,S,O,1-Adm,H),(9-241,i-Pro,C-29,S,S,O,1-Adm,H),(9-242,i-Pro,C-30,S,S,O,1-Adm,H),(9-243,i-Pro,C-31,S,S,O,1-Adm,H),(9-244,i-Pro,C-32,S,S,O,1-Adm,H),(9-245,i-Pro,C-33,S,S,O,1-Adm,H),(9-246,i-Pro,C-34,S,S,O,1-Adm,H),(9-247,i-Pro,C-35,S,S,O,1-Adm,H),(9-248,i-Pro,C-36,S,S,O,1-Adm,H),(9-249,i-Pro,C-1,S,S,O,2-Adm,H),(9-250,i-Pro,C-2,S,S,O,2-Adm,H),(9-251,i-Pro,C-3,S,S,O,2-Adm,H),(9-252,i-Pro,C-4,S,S,O,2-Adm,H),(9-253,i-Pro,C-5,S,S,O,2-Adm,H),(9-254,i-Pro,C-6,S,S,O,2-Adm,H),(9-255,i-Pro,C-7,S,S,O,2-Adm,H),(9-256,i-Pro,C-8,S,S,O,2-Adm,H),(9-257,i-Pro,C-9,S,S,O,2-Adm,H),(9-258,i-Pro,C-100,S,S,O,2-Adm,H),(9-259,i-Pro,C-11,S,S,O,2-Adm,H),(9-260,i-Pro,C-12,S,S,O,2-Adm,H),(9-261,i-Pro,C-13,S,S,O,2-Adm,H),(9-262,i-Pro,C-14,S,S,O,2-Adm,H),(9-263,i-Pro,C-15,S,S,O,2-Adm,H),(9-264,i-Pro,C-16,S,S,O,2-Adm,H),(9-265,i-Pro,C-17,S,S,O,2-Adm,H),(9-266,i-Pro,C-18,S,S,O,2-Adm,H),(9-267,i-Pro,C-19,S,S,O,2-Adm,H),(9-268,i-Pro,C-20,S,S,O,2-Adm,H),(9-269,i-Pro,C-21,S,S,O,2-Adm,H),(9-270,i-Pro,C-22,S,S,O,2-Adm,H),(9-271,i-Pro,C-23,S,S,O,2-Adm,H),(9-272,i-Pro, C-24,S,S,O,2-Adm,H),(9-273,i-Pro,C-25,S,S,O,2-Adm,H),(9-274,i-Pro,C-26,S,S,O,2-Adm,H),(9-275,i-Pro,C-27,S,S,O,2-Adm,H),(9-276,i-Pro,C-28,S,S,O,2-Adm,H),(9-277,i-Pro,C-29,S,S,O,2-Adm,H),(9-278,i-Pro,C-30,S,S,O,2-Adm,H),(9-279,i-Pro,C-31,S,S,O,2-Adm,H),(9-280,i-Pro,C-32,S,S,O,2-Adm,H),(9-281,i-Pro,C-33,S,S,O,2-Adm,H),(9-282,i-Pro,C-34,S,S,O,2-Adm,H),(9-283,i-Pro,C-35,S,S,O,2-Adm,H),(9-284,i-Pro,C-36,S,S,O,2-Adm,H), (9-285,i-Pro,C-1,S,S,O,5-OH-2-Adm,H),(9-286,i-Pro,C-2,S,S,O,5-OH-2-Adm,H),(9-287,i-Pro,C-3,S,S,O,5-OH-2-Adm,H),(9-288,i-Pro,C-4,S,S,O,5-OH-2-Adm,H),(9-289,i-Pro,C-5,S,S,O,5-OH-2-Adm,H),(9-290,i-Pro,C-6,S,S,O,5-OH-2-Adm,H),(9-291,i-Pro,C-7,S,S,O,5-OH-2-Adm,H),(9-292,i-Pro,C-8,S,S,O,5-OH-2-Adm,H),(9-293,i-Pro,C-9,S,S,O,5-OH-2-Adm,H),(9-294,i-Pro,C-11,S,S,O,5-OH-2-Adm,H),(9-295,i-Pro,C-11,S,S,O,5-OH-2-Adm,H),(9-296,i-Pro,C-12,S,S,O,5-OH-2-Adm,H),(9-297,i-Pro,C-13,S,S,O,5-OH-2-Adm,H),(9-298,i-Pro,C-14,S,S,O,5-OH-2-Adm,H),(9-299,i-Pro,C-15,S,S,O,5-OH-2-Adm,H),(9-300,i-Pro,C-16,S,S,O,5-OH-2-Adm,H),(9-301,i-Pro,C-17,S,S,O,5-OH-2-Adm,H),(9-302,i-Pro,C-18,S,S,O,5-OH-2-Adm,H),(9-303,i-Pro,C-19,S,S,O,5-OH-2-Adm,H),(9-304,i-Pro,C-20,S,S,O,5-OH-2-Adm,H),(9-305,i-Pro,C-21,S,S,O,5-OH-2-Adm,H),(9-306,i-Pro,C-22,S,S,O,5-OH-2-Adm,H),(9-307,i-Pro,C-23,S,S,O,5-OH-2-Adm,H),(9-308,i-Pro,C-24,S,S,O,5-OH-2-Adm,H),(9-309,i-Pro,C-25,S,S,O,5-OH-2-Adm,H),(9-310,i-Pro,C-26,S,S,O,5-OH-2-Adm,H),(9-311,i-Pro,C-27,S,S,O,5-OH-2-Adm,H),(9-312,i-Pro,C-28,S,S,O,5-OH-2-Adm,H),(9-313,i-Pro,C-29,S,S,O,5-OH-2-Adm,H),(9-314,i-Pro,C-30,S,S,O,5-OH-2-Adm,H),(9-315,i-Pro,C-31,S,S,O,5-OH-2-Adm,H),(9-316,i-Pro,C-32,S,S,O,5-OH-2-Adm,H),(9-317,i-Pro,C-33,S,S,O,5-OH-2-Adm,H),(9-318,i-Pro,C-34,S,S,O,5-OH-2-Adm,H),(9-319,i-Pro,C-35,S,S,O,5-OH-2-Adm,H),(9-320,i-Pro,C-36,S,S,O,5-OH-2-Adm,H),(9-321,i-Pro,D-1,S,S,O,1-Adm,H),(9-322,i-Pro,D-2,S,S,O,1-Adm,H),(9-323,i-Pro,D-3,S,S,O,1-Adm,H),(9-324,i-Pro,D-4,S,S,O,1-Adm,H),(9-325,i-Pro,D-5,S,S,O,1-Adm,H),(9-326,i-Pro,D-6,S,S,O,1-Adm,H),(9-327,i-Pro,D-7,S,S,O,1-Adm,H),(9-328,i-Pro,D-8,S,S,O,1-Adm,H),(9-329,i-Pro,D-9,S,S,O,1-Adm,H),(9-330,i-Pro,D-10,S,S,O,1-Adm,H),(9-331,i-Pro,D-11,S,S,O,1-Adm,H),(9-332,i-Pro,D-12,S,S,O,1-Adm,H),(9-333,i-Pro,D-13,S,S,O,1-Adm,H),(9-334,i-Pro,D-14,S,S,O,1-Adm,H),(9-335,i-Pro,D-15,S,S,O,1-Adm,H),(9-336,i-Pro,D-16,S,S,O,1-Adm,H),(9-337,i-Pro,D-17,S,S,O,1-Adm,H),(9-338,i-Pro,D-18,S,S,O,1-Adm,H),(9-339,i-Pro,D-19,S,S,O,1-Adm,H),(9-340,i-Pro,D-20,S,S,O,1-Adm,H),(9-341,i-Pro,D-21,S,S,O,1-Adm,H),(9-342,i-Pro,D-22,S,S,O,1-Adm,H),(9-343,i-Pro,D-23,S,S,O,1-Adm,H),(9-344,i-Pro,D-24,S,S,O,1-Adm,H),(9-345,i-Pro,D-25,S,S,O,1-Adm,H),(9-346,i-Pro,D-26,S,S,O,1-Adm,H),(9-347,i-Pro,D-27,S,S,O,1-Adm,H),(9-348,i-Pro,D-28,S,S,O,1-Adm,H),(9-349,i-Pro,D-29,S,S,O,1-Adm,H),(9-350,i-Pro,D-30,S,S,O,1-Adm,H),(9-351,i-Pro,D-31,S,S,O,1-Adm,H),(9-352,i-Pro,D-32,S,S,O,1-Adm,H),(9-353,i-Pro,D-33,S,S,O,1-Adm,H),(9-354,i-Pro,D-34,S,S,O,1-Adm,H),(9-355,i-Pro,D-35,S,S,O,1-Adm,H),(9-356,i-Pro,D-36,S,S,O,1-Adm,H),(9-357,i-Pro,D-1,S,S,O,2-Adm,H),(9-358,i-Pro,D-2,S,S,O,2-Adm,H),(9-359,i-Pro,D-3,S,S,O,2-Adm,H),(9-360,i-Pro,D-4,S,S,O,2-Adm,H),(9-361,i-Pro,D-5,S,S,O,2-Adm,H),(9-362,i-Pro,D-6,S,S,O,2-Adm,H),(9-363,i-Pro,D-7,S,S,O,2-Adm,H),(9-364,i-Pro,D-8,S,S,O,2-Adm,H),(9-365,i-Pro,D-9,S,S,O,2-Adm,H),(9-366,i-Pro,D-10,S,S,O,2-Adm,H),(9-367,i-Pro,D-11,S,S,O,2-Adm,H),(9-368,i-Pro,D-12,S,S,O,2-Adm,H),(9-369,i-Pro,D-13,S,S,O,2-Adm,H),(9-370,i-Pro,D-14,S,S,O,2-Adm,H),(9-371,i-Pro,D-15,S,S,O,2-Adm,H),(9-372,i-Pro,D-16,S,S,O,2-Adm,H),(9-373,i-Pro,D-17,S,S,O,2-Adm,H),(9-374,i-Pro,D-18,S,S,O,2-Adm,H),(9-375,i-Pro,D-19,S,S,O,2-Adm,H),(9-376,i-Pro,D-20,S,S,O,2-Adm,H),(9-377,i-Pro,D-21,S,S,O,2-Adm,H),(9-378,i-Pro,D-22,S,S,O,2-Adm,H),(9-379,i-Pro,D-23,S,S,O,2-Adm,H),(9-380,i-Pro,D-24,S,S,O,2-Adm,H),(9-381,i-Pro,D-25,S,S,O,2-Adm,H),(9-382,i-Pro,D-26,S,S,O,2-Adm,H),(9-383,i-Pro,D-27,S,S,O,2-Adm,H),(9-384,i-Pro,D-28,S,S,O,2-Adm,H),(9-385,i-Pro,D-29,S,S,O,2-Adm,H),(9-386,i-Pro,D-30,S,S,O,2-Adm,H),(9-387,i-Pro,D-31,S,S,O,2-Adm,H), (9-388,i-Pro,D-32,S,S,O,2-Adm,H), (9-389,i-Pro,D-33,S,S,O,2-Adm,H),(9-390,i-Pro,D-34,S,S,O,2-Adm,H),(9-391,i-Pro,D-35,S,S,O,2-Adm,H),(9-392,i-Pro,D-36,S,S,O,2-Adm,H),(9-393,i-Pro,D-1,S,S,O,5-OH-2-Adm,H),(9-394,i-Pro,D-2,S,S,O,5-OH-2-Adm,H),(9-395,i-Pro,D-3,S,S,O,5-OH-2-Adm,H),(9-396,i-Pro,D-4,S,S,O,5-OH-2-Adm,H),(9-397,i-Pro,D-5,S,S,O,5-OH-2-Adm,H),(9-398,i-Pro,D-6,S,S,O,5-OH-2-Adm,H),(9-399,i-Pro,D-7,S,S,O,5-OH-2-Adm,H),(9-400,i-Pro,D-8,S,S,O,5-OH-2-Adm,H),(9-401,i-Pro,D-9,S,S,O,5-OH-2-Adm,H),(9-402,i-Pro,D-10,S,S,O,5-OH-2-Adm,H),(9-403,i-Pro,D-11,S,S,O,5-OH-2-Adm,H),(9-404,i-Pro,D-12,S,S,O,5-OH-2-Adm,H),(9-405,i-Pro,D-13,S,S,O,5-OH-2-Adm,H),(9-406,i-Pro,D-14,S,S,O,5-OH-2-Adm,H),(9-407,i-Pro,D-15,S,S,O,5-OH-2-Adm,H),(9-408,i-Pro,D-16,S,S,O,5-OH-2-Adm,H),(9-409,i-Pro,D-17,S,S,O,5-OH-2-Adm,H),(9-410,i-Pro,D-18,S,S,O,5-OH-2-Adm,H),(9-411,i-Pro,D-19,S,S,O,5-OH-2-Adm,H),(9-412,i-Pro,D-20,S,S,O,5-OH-2-Adm,H),(9-413,i-Pro,D-21,S,S,O,5-OH-2-Adm,H),(9-414,i-Pro,D-22,S,S,O,5-OH-2-Adm,H),(9-415,i-Pro,D-23,S,S,O,5-OH-2-Adm,H),(9-416,i-Pro,D-24,S,S,O,5-OH-2-Adm,H),(9-417,i-Pro,D-25,S,S,O,5-OH-2-Adm,H),(9-418,i-Pro,D-26,S,S,O,5-OH-2-Adm,H),(9-419,i-Pro,D-27,S,S,O,5-OH-2-Adm,H),(9-420,i-Pro,D-28,S,S,O,5-OH-2-Adm,H),(9-421,i-Pro,D-29,S,S,O,5-OH-2-Adm,H),(9-422,i-Pro,D-30,S,S,O,5-OH-2-Adm,H),(9-423,i-Pro,D-31,S,S,O,5-OH-2-Adm,H),(9-424,i-Pro,D-32,S,S,O,5-OH-2-Adm,H),(9-425,i-Pro,D-33,S,S,O,5-OH-2-Adm,H),(9-426,i-Pro,D-34,S,S,O,5-OH-2-Adm,H),(9-427,i-Pro,D-35,S,S,O,5-OH-2-Adm,H),(9-428,i-Pro,D-36,S,S,O,5-OH-2-Adm,H),(9-429,i-Pro,E-1,S,S,O,1-Adm,H),(9-430,i-Pro,E-2,S,S,O,1-Adm,H),(9-431,i-Pro,E-3,S,S,O,1-Adm,H),(9-432,i-Pro,E-4,S,S,O,1-Adm,H),(9-433,i-Pro,E-5,S,S,O,1-Adm,H),(9-434,i-Pro,E-6,S,S,O,1-Adm,H),(9-435,i-Pro,E-7,S,S,O,1-Adm,H),(9-436,i-Pro,E-8,S,S,O,1-Adm,H),(9-437,i-Pro,E-9,S,S,O,1-Adm,H),(9-438,i-Pro,E-10,S,S,O,1-Adm,H),(9-439,i-Pro,E-11,S,S,O,1-Adm,H),(9-440,i-Pro,E-12,S,S,O,1-Adm,H),(9-441,i-Pro,E-13,S,S,O,1-Adm,H),(9-442,i-Pro,E-14,S,S,O,1-Adm,H),(9-443,i-Pro,E-15,S,S,O,1-Adm,H),(9-444,i-Pro,E-16,S,S,O,1-Adm,H),(9-445,i-Pro,E-17,S,S,O,1-Adm,H),(9-446,i-Pro,E-18,S,S,O,1-Adm,H),(9-447,i-Pro,E-19,S,S,O,1-Adm,H),(9-448,i-Pro,E-20,S,S,O,1-Adm,H),(9-449,i-Pro,E-21,S,S,O,1-Adm,H),(9-450,i-Pro,E-22,S,S,O,1-Adm,H),(9-451,i-Pro,E-23,S,S,O,1-Adm,H),(9-452,i-Pro,E-24,S,S,O,1-Adm,H),(9-453,i-Pro,E-25,S,S,O,1-Adm,H),(9-454,i-Pro,E-26,S,S,O,1-Adm,H),(9-455,i-Pro,E-27,S,S,O,1-Adm,H),(9-456,i-Pro,E-28,S,S,O,1-Adm,H),(9-457,i-Pro,E-29,S,S,O,1-Adm,H),(9-458,i-Pro,E-30,S,S,O,1-Adm,H),(9-459,i-Pro,E-31,S,S,O,1-Adm,H),(9-460,i-Pro,E-32,S,S,O,1-Adm,H),(9-461,i-Pro,E-33,S,S,O,1-Adm,H),(9-462,i-Pro,E-34,S,S,O,1-Adm,H),(9-463,i-Pro,E-35,S,S,O,1-Adm,H),(9-464,i-Pro,E-36,S,S,O,1-Adm,H),(9-465,i-Pro,E-1,S,S,O,2-Adm,H),(9-466,i-Pro,E-2,S,S,O,2-Adm,H),(9-467,i-Pro,E-3,S,S,O,2-Adm,H),(9-468,i-Pro,E-4,S,S,O,2-Adm,H),(9-469,i-Pro,E-5,S,S,O,2-Adm,H),(9-470,i-Pro,E-6,S,S,O,2-Adm,H),(9-471,i-Pro,E-7,S,S,O,2-Adm,H),(9-472,i-Pro,E-8,S,S,O,2-Adm,H),(9-473,i-Pro,E-9,S,S,O,2-Adm,H),(9-474,i-Pro,E-10,S,S,O,2-Adm,H),(9-475,i-Pro,E-11,S,S,O,2-Adm,H),(9-476,i-Pro,E-12,S,S,O,2-Adm,H),(9-477,i-Pro,E-13,S,S,O,2-Adm,H),(9-478,i-Pro,E-14,S,S,O,2-Adm,H),(9-479,i-Pro,E-15,S,S,O,2-Adm,H),(9-480,i-Pro,E-16,S,S,O,2-Adm,H),(9-481,i-Pro,E-17,S,S,O,2-Adm,H),(9-482,i-Pro,E-18,S,S,O,2-Adm,H),(9-483,i-Pro,E-19,S,S,O,2-Adm,H),(9-484,i-Pro,E-20,S,S,O,2-Adm,H),(9-485,i-Pro,E-21,S,S,O,2-Adm,H),(9-486,i-Pro,E-22,S,S,O,2-Adm,H),(9-487,i-Pro,E-23,S,S,O,2-Adm,H),(9-488,i-Pro,E-24,S,S,O,2-Adm,H),(9-489,i-Pro,E-25,S,S,O,2-Adm,H),(9-490,i-Pro,E-26,S,S,O,2-Adm,H),(9-491,i-Pro,E-27,S,S,O,2-Adm,H), (9-492,i-Pro,E-28,S,S,O,2-Adm,H),(9-493,i-Pro,E-29,S,S,O,2-Adm,H),(9-494,i-Pro,E-30,S,S,O,2-Adm,H),(9-495,i-Pro,E-31,S,S,O,2-Adm,H),(9-496,i-Pro,E-32,S,S,O,2-Adm,H),(9-497,i-Pro,E-33,S,S,O,2-Adm,H),(9-498,i-Pro,E-34,S,S,O,2-Adm,H),(9-499,i-Pro,E-35,S,S,O,2-Adm,H),(9-500,i-Pro,E-36,S,S,O,2-Adm,H),(9-501,i-Pro,E-1,S,S,O,5-OH-2-Adm,H),(9-502,i-Pro,E-2,S,S,O,5-OH-2-Adm,H),(9-503,i-Pro,E-3,S,S,O,5-OH-2-Adm,H),(9-504,i-Pro,E-4,S,S,O,5-OH-2-Adm,H),(9-505,i-Pro,E-5,S,S,O,5-OH-2-Adm,H),(9-506,i-Pro,E-6,S,S,O,5-OH-2-Adm,H),(9-507,i-Pro,E-7,S,S,O,5-OH-2-Adm,H),(9-508,i-Pro,E-8,S,S,O,5-OH-2-Adm,H),(9-509,i-Pro,E-9,S,S,O,5-OH-2-Adm,H),(9-510,i-Pro,E-10,S,S,O,5-OH-2-Adm,H),(9-511,i-Pro,E-11,S,S,O,5-OH-2-Adm,H),(9-512,i-Pro,E-12,S,S,O,5-OH-2-Adm,H),(9-513,i-Pro,E-13,S,S,O,5-OH-2-Adm,H),(9-514,i-Pro,E-14,S,S,O,5-OH-2-Adm,H),(9-515,i-Pro,E-15,S,S,O,5-OH-2-Adm,H),(9-516,i-Pro,E-16,S,S,O,5-OH-2-Adm,H),(9-517,i-Pro,E-17,S,S,O,5-OH-2-Adm,H),(9-518,i-Pro,E-18,S,S,O,5-OH-2-Adm,H),(9-519,i-Pro,E-19,S,S,O,5-OH-2-Adm,H),(9-520,i-Pro,E-20,S,S,O,5-OH-2-Adm,H),(9-521,i-Pro,E-21,S,S,O,5-OH-2-Adm,H),(9-522,i-Pro,E-22,S,S,O,5-OH-2-Adm,H),(9-523,i-Pro,E-23,S,S,O,5-OH-2-Adm,H),(9-524,i-Pro,E-24,S,S,O,5-OH-2-Adm,H),(9-525,i-Pro,E-25,S,S,O,5-OH-2-Adm,H),(9-526,i-Pro,E-26,S,S,O,5-OH-2-Adm,H),(9-527,i-Pro,E-27,S,S,O,5-OH-2-Adm,H),(9-528,i-Pro,E-28,S,S,O,5-OH-2-Adm,H),(9-529,i-Pro,E-29,S,S,O,5-OH-2-Adm,H),(9-530,i-Pro,E-30,S,S,O,5-OH-2-Adm,H),(9-531,i-Pro,E-31,S,S,O,5-OH-2-Adm,H),(9-532,i-Pro,E-32,S,S,O,5-OH-2-Adm,H),(9-533,i-Pro,E-33,S,S,O,5-OH-2-Adm,H),(9-534,i-Pro,E-34,S,S,O,5-OH-2-Adm,H),(9-535,i-Pro,E-35,S,S,O,5-OH-2-Adm,H),(9-536,i-Pro,E-36,S,S,O,5-OH-2-Adm,H),(9-537,i-Pro,F-1,S,S,O,1-Adm,H),(9-538,i-Pro,F-2,S,S,O,1-Adm,H),(9-539,i-Pro,F-3,S,S,O,1-Adm,H),(9-540,i-Pro,F-4,S,S,O,1-Adm,H),(9-541,i-Pro,F-5,S,S,O,1-Adm,H),(9-542,i-Pro,F-6,S,S,O,1-Adm,H),(9-543,i-Pro,F-7,S,S,O,1-Adm,H),(9-544,i-Pro,F-8,S,S,O,1-Adm,H),(9-545,i-Pro,F-9,S,S,O,1-Adm,H),(9-546,i-Pro,F-11,S,S,O,1-Adm,H),(9-547,i-Pro,F-11,S,S,O,1-Adm,H),(9-548,i-Pro,F-12,S,S,O,1-Adm,H),(9-549,i-Pro,F-13,S,S,O,1-Adm,H),(9-550,i-Pro,F-14,S,S,O,1-Adm,H),(9-551,i-Pro,F-15,S,S,O,1-Adm,H),(9-552,i-Pro,F-16,S,S,O,1-Adm,H),(9-553,i-Pro,F-17,S,S,O,1-Adm,H),(9-554,i-Pro,F-18,S,S,O,1-Adm,H),(9-555,i-Pro,F-19,S,S,O,1-Adm,H),(9-556,i-Pro,F-20,S,S,O,1-Adm,H),(9-557,i-Pro,F-21,S,S,O,1-Adm,H),(9-558,i-Pro,F-22,S,S,O,1-Adm,H),(9-559,i-Pro,F-23,S,S,O,1-Adm,H),(9-560,i-Pro,F-24,S,S,O,1-Adm,H),(9-561,i-Pro,F-25,S,S,O,1-Adm,H),(9-562,i-Pro,F-26,S,S,O,1-Adm,H),(9-563,i-Pro,F-27,S,S,O,1-Adm,H),(9-564,i-Pro,F-28,S,S,O,1-Adm,H),(9-565,i-Pro,F-29,S,S,O,1-Adm,H),(9-566,i-Pro,F-30,S,S,O,1-Adm,H),(9-567,i-Pro,F-31,S,S,O,1-Adm,H),(9-568,i-Pro,F-32,S,S,O,1-Adm,H),(9-569,i-Pro,F-33,S,S,O,1-Adm,H),(9-570,i-Pro,F-34,S,S,O,1-Adm,H),(9-571,i-Pro,F-35,S,S,O,1-Adm,H),(9-572,i-Pro,F-36,S,S,O,1-Adm,H),(9-573,i-Pro,F-1,S,S,O,2-Adm,H),(9-574,i-Pro,F-2,S,S,O,2-Adm,H),(9-575,i-Pro,F-3,S,S,O,2-Adm,H),(9-576,i-Pro,F-4,S,S,O,2-Adm,H),(9-577,i-Pro,F-5,S,S,O,2-Adm,H),(9-578,i-Pro,F-6,S,S,O,2-Adm,H),(9-579,i-Pro,F-7,S,S,O,2-Adm,H),(9-580,i-Pro,F-8,S,S,O,2-Adm,H),(9-581,i-Pro,F-9,S,S,O,2-Adm,H),(9-582,i-Pro,F-10,S,S,O,2-Adm,H),(9-583,i-Pro,F-11,S,S,O,2-Adm,H),(9-584,i-Pro,F-12,S,S,O,2-Adm,H),(9-585,i-Pro,F-13,S,S,O,2-Adm,H),(9-586,i-Pro,F-14,S,S,O,2-Adm,H),(9-587,i-Pro,F-15,S,S,O,2-Adm,H),(9-588,i-Pro,F-16,S,S,O,2-Adm,H),(9-589,i-Pro,F-17,S,S,O,2-Adm,H),(9-590,i-Pro,F-18,S,S,O,2-Adm,H),(9-591,i-Pro,F-19,S,S,O,2-Adm,H),(9-592,i-Pro,F-20,S,S,O,2-Adm,H),(9-593,i-Pro,F-21,S,S,O,2-Adm,H),(9-594,i-Pro,F-22,S,S,O,2-Adm,H),(9-595,i-Pro,F-23,S,S,O,2-Adm,H),(9-596,i-Pro,F-24,S,S,O,2-Adm,H), (9-597,i-Pro,F-25,S, S,O,2-Adm,H),(9-598,i-Pro,F-26,S,S,O,2-Adm,H),(9-599,i-Pro,F-27,S,S,O,2-Adm,H),(9-600,i-Pro,F-28,S,S,O,2-Adm,H),(9-601,i-Pro,F-29,S,S,O,2-Adm,H),(9-602,i-Pro,F-30,S,S,O,2-Adm,H),(9-603,i-Pro,F-31,S,S,O,2-Adm,H),(9-604,i-Pro,F-32,S,S,O,2-Adm,H),(9-605,i-Pro,F-33,S,S,O,2-Adm,H),(9-606,i-Pro,F-34,S,S,O,2-Adm,H),(9-607,i-Pro,F-35,S,S,O,2-Adm,H),(9-608,i-Pro,F-36,S,S,O,2-Adm,H),(9-609,i-Pro,F-1,S,S,O,5-OH-2-Adm,H),(9-610,i-Pro,F-2,S,S,O,5-OH-2-Adm,H),(9-611,i-Pro,F-3,S,S,O,5-OH-2-Adm,H),(9-612,i-Pro,F-4,S,S,O,5-OH-2-Adm,H),(9-613,i-Pro,F-5,S,S,O,5-OH-2-Adm,H),(9-614,i-Pro,F-6,S,S,O,5-OH-2-Adm,H),(9-615,i-Pro,F-7,S,S,O,5-OH-2-Adm,H),(9-616,i-Pro,F-8,S,S,O,5-OH-2-Adm,H),(9-617,i-Pro,F-9,S,S,O,5-OH-2-Adm,H),(9-618,i-Pro,F-10,S,S,O,5-OH-2-Adm,H),(9-619,i-Pro,F-11,S,S,O,5-OH-2-Adm,H),(9-620,i-Pro,F-12,S,S,O,5-OH-2-Adm,H),(9-621,i-Pro,F-13,S,S,O,5-OH-2-Adm,H),(9-622,i-Pro,F-14,S,S,O,5-OH-2-Adm,H),(9-623,i-Pro,F-15,S,S,O,5-OH-2-Adm,H),(9-624,i-Pro,F-16,S,S,O,5-OH-2-Adm,H),(9-625,i-Pro,F-17,S,S,O,5-OH-2-Adm,H),(9-626,i-Pro,F-18,S,S,O,5-OH-2-Adm,H),(9-627,i-Pro,F-19,S,S,O,5-OH-2-Adm,H),(9-628,i-Pro,F-20,S,S,O,5-OH-2-Adm,H),(9-629,i-Pro,F-21,S,S,O,5-OH-2-Adm,H),(9-630,i-Pro,F-22,S,S,O,5-OH-2-Adm,H),(9-631,i-Pro,F-23,S,S,O,5-OH-2-Adm,H),(9-632,i-Pro,F-24,S,S,O,5-OH-2-Adm,H),(9-633,i-Pro,F-25,S,S,O,5-OH-2-Adm,H),(9-634,i-Pro,F-26,S,S,O,5-OH-2-Adm,H),(9-635,i-Pro,F-27,S,S,O,5-OH-2-Adm,H),(9-636,i-Pro,F-28,S,S,O,5-OH-2-Adm,H),(9-637,i-Pro,F-29,S,S,O,5-OH-2-Adm,H),(9-638,i-Pro,F-30,S,S,O,5-OH-2-Adm,H),(9-639,i-Pro,F-31,S,S,O,5-OH-2-Adm,H),(9-640,i-Pro,F-32,S,S,O,5-OH-2-Adm,H),(9-641,i-Pro,F-33,S,S,O,5-OH-2-Adm,H),(9-642,i-Pro,F-34,S,S,O,5-OH-2-Adm,H),(9-643,i-Pro,F-35,S,S,O,5-OH-2-Adm,H),(9-644,i-Pro,F-36,S,S,O,5-OH-2-Adm,H),(9-645,i-Pro,G-1,S,S,O,1-Adm,H),(9-646,i-Pro,G-2,S,S,O,1-Adm,H),(9-647,i-Pro,G-3,S,S,O,1-Adm,H),(9-648,i-Pro,G-4,S,S,O,1-Adm,H),(9-649,i-Pro,G-5,S,S,O,1-Adm,H),(9-650,i-Pro,G-6,S,S,O,1-Adm,H),(9-651,i-Pro,G-7,S,S,O,1-Adm,H),(9-652,i-Pro,G-8,S,S,O,1-Adm,H),(9-653,i-Pro,G-9,S,S,O,1-Adm,H),(9-654,i-Pro,G-1,S,S,O,2-Adm,H),(9-655,i-Pro,G-2,S,S,O,2-Adm,H),(9-656,i-Pro,G-3,S,S,O,2-Adm,H),(9-657,i-Pro,G-4,S,S,O,2-Adm,H),(9-658,i-Pro,G-5,S,S,O,2-Adm,H),(9-659,i-Pro,G-6,S,S,O,2-Adm,H),(9-660,i-Pro,G-7,S,S,O,2-Adm,H),(9-661,i-Pro,G-8,S,S,O,2-Adm,H),(9-662,i-Pro,G-9,S,S,O,2-Adm,H),(9-663,i-Pro,G-1,S,S,O,5-OH-2-Adm,H),(9-664,i-Pro,G-2,S,S,O,5-OH-2-Adm,H),(9-665,i-Pro,G-3,S,S,O,5-OH-2-Adm,H),(9-666,i-Pro,G-4,S,S,O,5-OH-2-Adm,H),(9-667,i-Pro,G-5,S,S,O,5-OH-2-Adm,H),(9-668,i-Pro,G-6,S,S,O,5-OH-2-Adm,H),(9-669,i-Pro,G-7,S,S,O,5-OH-2-Adm,H),(9-670,i-Pro,G-8,S,S,O,5-OH-2-Adm,H),(9-671,i-Pro,G-9,S,S,O,5-OH-2-Adm,H),(9-672,i-Pro,H-1,S,S,O,1-Adm,H),(9-673,i-Pro,H-2,S,S,O,1-Adm,H),(9-674,i-Pro,H-3,S,S,O,1-Adm,H),(9-675,i-Pro,H-4,S,S,O,1-Adm,H),(9-676,i-Pro,H-5,S,S,O,1-Adm,H),(9-677,i-Pro,H-6,S,S,O,1-Adm,H),(9-678,i-Pro,H-7,S,S,O,1-Adm,H),(9-679,i-Pro,H-8,S,S,O,1-Adm,H),(9-680,i-Pro,H-9,S,S,O,1-Adm,H),(9-681,i-Pro,H-1,S,S,O,2-Adm,H),(9-682,i-Pro,H-2,S,S,O,2-Adm,H),(9-683,i-Pro,H-3,S,S,O,2-Adm,H),(9-684,i-Pro,H-4,S,S,O,2-Adm,H),(9-685,i-Pro,H-5,S,S,O,2-Adm,H),(9-686,i-Pro,H-6,S,S,O,2-Adm,H),(9-687,i-Pro,H-7,S,S,O,2-Adm,H),(9-688,i-Pro,H-8,S,S,O,2-Adm,H),(9-689,i-Pro,H-9,S,S,O,2-Adm,H),(9-690,i-Pro,H-1,S,S,O,5-OH-2-Adm,H),(9-691,i-Pro,H-2,S,S,O,5-OH-2-Adm,H),(9-692,i-Pro,H-3,S,S,O,5-OH-2-Adm,H),(9-693,i-Pro,H-4,S,S,O,5-OH-2-Adm,H),(9-694,i-Pro,H-5,S,S,O,5-OH-2-Adm,H),(9-695,i-Pro,H-6,S,S,O,5-OH-2-Adm,H),(9-696,i-Pro,H-7,S,S,O,5-OH-2-Adm,H),(9-697,i-Pro,H-8,S,S,O,5-OH-2-Adm,H),(9-698,i-Pro, H-9,S,S,O,5-OH-2-Adm,H),(9-699,i-Pro,I-1,S,S,O,1-Adm,H),(9-700,i-Pro,I-2,S,S,O,1-Adm,H),(9-701,i-Pro,I-3,S,S,O,1-Adm,H),(9-702,i-Pro,I-4,S,S,O,1-Adm,H),(9-703,i-Pro,I-5,S,S,O,1-Adm,H),(9-704,i-Pro,I-6,S,S,O,1-Adm,H),(9-705,i-Pro,I-7,S,S,O,1-Adm,H),(9-706,i-Pro,I-8,S,S,O,1-Adm,H),(9-707,i-Pro,I-9,S,S,O,1-Adm,H),(9-708,i-Pro,I-1,S,S,O,2-Adm,H),(9-709,i-Pro,I-2,S,S,O,2-Adm,H),(9-710,i-Pro,I-3,S,S,O,2-Adm,H),(9-711,i-Pro,I-4,S,S,O,2-Adm,H),(9-712,i-Pro,I-5,S,S,O,2-Adm,H),(9-713,i-Pro,I-6,S,S,O,2-Adm,H),(9-714,i-Pro,I-7,S,S,O,2-Adm,H),(9-715,i-Pro,I-8,S,S,O,2-Adm,H),(9-716,i-Pro,I-9,S,S,O,2-Adm,H),(9-717,i-Pro,I-1,S,S,O,5-OH-2-Adm,H),(9-718,i-Pro,I-2,S,S,O,5-OH-2-Adm,H),(9-719,i-Pro,I-3,S,S,O,5-OH-2-Adm,H),(9-720,i-Pro,I-4,S,S,O,5-OH-2-Adm,H),(9-721,i-Pro,I-5,S,S,O,5-OH-2-Adm,H),(9-722,i-Pro,I-6,S,S,O,5-OH-2-Adm,H),(9-723,i-Pro,I-7,S,S,O,5-OH-2-Adm,H),(9-724,i-Pro,I-8,S,S,O,5-OH-2-Adm,H),(9-725,i-Pro,I-9,S,S,O,5-OH-2-Adm,H),(9-726,i-Pro,J-1,S,S,O,1-Adm,H),(9-727,i-Pro,J-2,S,S,O,1-Adm,H),(9-728,i-Pro,J-3,S,S,O,1-Adm,H),(9-729,i-Pro,J-4,S,S,O,1-Adm,H),(9-730,i-Pro,J-5,S,S,O,1-Adm,H),(9-731,i-Pro,J-6,S,S,O,1-Adm,H),(9-732,i-Pro,J-7,S,S,O,1-Adm,H),(9-733,i-Pro,J-8,S,S,O,1-Adm,H),(9-734,i-Pro,J-9,S,S,O,1-Adm,H),(9-735,i-Pro,J-1,S,S,O,2-Adm,H),(9-736,i-Pro,J-2,S,S,O,2-Adm,H),(9-737,i-Pro,J-3,S,S,O,2-Adm,H),(9-738,i-Pro,J-4,S,S,O,2-Adm,H),(9-739,i-Pro,J-5,S,S,O,2-Adm,H),(9-740,i-Pro,J-6,S,S,O,2-Adm,H),(9-741,i-Pro,J-7,S,S,O,2-Adm,H),(9-742,i-Pro,J-8,S,S,O,2-Adm,H),(9-743,i-Pro,J-9,S,S,O,2-Adm,H),(9-744,i-Pro,J-1,S,S,O,5-OH-2-Adm,H),(9-745,i-Pro,J-2,S,S,O,5-OH-2-Adm,H),(9-746,i-Pro,J-3,S,S,O,5-OH-2-Adm,H),(9-747,i-Pro,J-4,S,S,O,5-OH-2-Adm,H),(9-748,i-Pro,J-5,S,S,O,5-OH-2-Adm,H),(9-749,i-Pro,J-6,S,S,O,5-OH-2-Adm,H),(9-750,i-Pro,J-7,S,S,O,5-OH-2-Adm,H),(9-751,i-Pro,J-8,S,S,O,5-OH-2-Adm,H),(9-752,i-Pro,J-9,S,S,O,5-OH-2-Adm,H),(9-753,i-Pro,K-1,S,S,O,1-Adm,H),(9-754,i-Pro,K-2,S,S,O,1-Adm,H),(9-755,i-Pro,K-3,S,S,O,1-Adm,H),(9-756,i-Pro,K-4,S,S,O,1-Adm,H),(9-757,i-Pro,K-5,S,S,O,1-Adm,H),(9-758,i-Pro,K-6,S,S,O,1-Adm,H),(9-759,i-Pro,K-7,S,S,O,1-Adm,H),(9-760,i-Pro,K-8,S,S,O,1-Adm,H),(9-761,i-Pro,K-9,S,S,O,1-Adm,H),(9-762,i-Pro,K-1,S,S,O,2-Adm,H),(9-763,i-Pro,K-2,S,S,O,2-Adm,H),(9-764,i-Pro,K-3,S,S,O,2-Adm,H),(9-765,i-Pro,K-4,S,S,O,2-Adm,H),(9-766,i-Pro,K-5,S,S,O,2-Adm,H),(9-767,i-Pro,K-6,S,S,O,2-Adm,H),(9-768,i-Pro,K-7,S,S,O,2-Adm,H),(9-769,i-Pro,K-8,S,S,O,2-Adm,H),(9-770,i-Pro,K-9,S,S,O,2-Adm,H),(9-771,i-Pro,K-1,S,S,O,5-OH-2-Adm,H),(9-772,i-Pro,K-2,S,S,O,5-OH-2-Adm,H),(9-773,i-Pro,K-3,S,S,O,5-OH-2-Adm,H),(9-774,i-Pro,K-4,S,S,O,5-OH-2-Adm,H),(9-775,i-Pro,K-5,S,S,O,5-OH-2-Adm,H),(9-776,i-Pro,K-6,S,S,O,5-OH-2-Adm,H),(9-777,i-Pro,K-7,S,S,O,5-OH-2-Adm,H),(9-778,i-Pro,K-8,S,S,O,5-OH-2-Adm,H),(9-779,i-Pro,K-9,S,S,O,5-OH-2-Adm,H)

(Compound No., $R^2$,$R^3$,X,Y,Z,$R^4$,$R^5$)=(10-1,i-Bu,A-1,O,S,O,1-Adm,H),(10-2,i-Bu,A-2,O,S,O,1-Adm,H),(10-3,i-Bu,A-3,O,S,O,1-Adm,H),(10-4,i-Bu,A-4,O,S,O,1-Adm,H),(10-5,i-Bu,A-5,O,S,O,1-Adm,H),(10-6,i-Bu,A-6,O,S,O,1-Adm,H),(10-7,i-Bu,A-7,O,S,O,1-Adm,H),(10-8,i-Bu,A-8,O,S,O,1-Adm,H),(10-9,i-Bu,A-9,O,S,O,1-Adm,H),(10-10,i-Bu,A-10,O,S,O,1-Adm,H),(10-11,i-Bu,A-11,O,S,O,1-Adm,H),(10-12,i-Bu,A-12,O,S,O,1-Adm,H),(10-13,i-Bu,A-13,O,S,O,1-Adm,H),(10-14,i-Bu,A-14,O,S,O,1-Adm,H),(10-15,i-Bu,A-15,O,S,O,1-Adm,H),(10-16,i-Bu,A-16,O,S,O,1-Adm,H),(10-17,i-Bu,A-17,O,S,O,1-Adm,H),(10-18,i-Bu,A-18,O,S,O,1-Adm,H),(10-19,i-Bu,A-19,O,S,O,1-Adm,H),(10-20,i-Bu,A-20,O,S,O,1-Adm,H),(10-21,i-Bu,A-21,O,S,O,1-Adm,H),(10-22,i-Bu,A-22,O,S,O,1-Adm,H),(10-23,i-Bu,A-23,O,S,O,1-Adm,H),(10-24,i-Bu,A-24,O,S,O,1-Adm,H),(10-25,i-Bu,A-25,O,S,O,1-Adm,H), (10-26,i-Bu,A-26,O,S, O,1-Adm,H),(10-27,i-Bu,A-27,O,S,O,1-Adm,H),(10-28,i-Bu,A-28,O,S,O,1-Adm,H),(10-29,i-Bu,A-29,O,S,O,1-Adm,H),(10-30,i-Bu,A-30,O,S,O,1-Adm,H),(10-31,i-Bu,A-31,O,S,O,1-Adm,H),(10-32,i-Bu,A-32,O,S,O,1-Adm,H),(10-33,i-Bu,A-33,O,S,O,1-Adm,H),(10-34,i-Bu,A-34,O,S,O,1-Adm,H),(10-35,i-Bu,A-35,O,S,O,1-Adm,H),(10-36,i-Bu,A-36,O,S,O,1-Adm,H),(10-37,i-Bu,A-1,O,S,O,2-Adm,H),(10-38,i-Bu,A-2,O,S,O,2-Adm,H),(10-39,i-Bu,A-3,O,S,O,2-Adm,H),(10-40,i-Bu,A-4,O,S,O,2-Adm,H),(10-41,i-Bu,A-5,O,S,O,2-Adm,H),(10-42,i-Bu,A-6,O,S,O,2-Adm,H),(10-43,i-Bu,A-7,O,S,O,2-Adm,H),(10-44,i-Bu,A-8,O,S,O,2-Adm,H),(10-45,i-Bu,A-9,O,S,O,2-Adm,H),(10-46,i-Bu,A-10,O,S,O,2-Adm,H),(10-47,i-Bu,A-11,O,S,O,2-Adm,H),(10-48,i-Bu,A-12,O,S,O,2-Adm,H),(10-49,i-Bu,A-13,O,S,O,2-Adm,H),(10-50,i-Bu,A-14,O,S,O,2-Adm,H),(10-51,i-Bu,A-15,O,S,O,2-Adm,H),(10-52,i-Bu,A-16,O,S,O,2-Adm,H),(10-53,i-Bu,A-17,O,S,O,2-Adm,H),(10-54,i-Bu,A-18,O,S,O,2-Adm,H),(10-55,i-Bu,A-19,O,S,O,2-Adm,H),(10-56,i-Bu,A-20,O,S,O,2-Adm,H),(10-57,i-Bu,A-21,O,S,O,2-Adm,H),(10-58,i-Bu,A-22,O,S,O,2-Adm,H),(10-59,i-Bu,A-23,O,S,O,2-Adm,H),(10-60,i-Bu,A-24,O,S,O,2-Adm,H),(10-61,i-Bu,A-25,O,S,O,2-Adm,H),(10-62,i-Bu,A-26,O,S,O,2-Adm,H),(10-63,i-Bu,A-27,O,S,O,2-Adm,H),(10-64,i-Bu,A-28,O,S,O,2-Adm,H),(10-65,i-Bu,A-29,O,S,O,2-Adm,H),(10-66,i-Bu,A-30,O,S,O,2-Adm,H),(10-67,i-Bu,A-31,O,S,O,2-Adm,H),(10-68,i-Bu,A-32,O,S,O,2-Adm,H),(10-69,i-Bu,A-33,O,S,O,2-Adm,H),(10-70,i-Bu,A-34,O,S,O,2-Adm,H),(10-71,i-Bu,A-35,O,S,O,2-Adm,H),(10-72,i-Bu,A-36,O,S,O,2-Adm,H),(10-73,i-Bu,A-1,O,S,O,5-OH-2-Adm,H),(10-74,i-Bu,A-2,O,S,O,5-OH-2-Adm,H),(10-75,i-Bu,A-3,O,S,O,5-OH-2-Adm,H),(10-76,i-Bu,A-4,O,S,O,5-OH-2-Adm,H),(10-77,i-Bu,A-5,O,S,O,5-OH-2-Adm,H),(10-78,i-Bu,A-6,O,S,O,5-OH-2-Adm,H),(10-79,i-Bu,A-7,O,S,O,5-OH-2-Adm,H),(10-80,i-Bu,A-8,O,S,O,5-OH-2-Adm,H),(10-81,i-Bu,A-9,O,S,O,5-OH-2-Adm,H),(10-82,i-Bu,A-10,O,S,O,5-OH-2-Adm,H),(10-83,i-Bu,A-11,O,S,O,5-OH-2-Adm,H),(10-84,i-Bu,A-12,O,S,O,5-OH-2-Adm,H),(10-85,i-Bu,A-13,O,S,O,5-OH-2-Adm,H),(10-86,i-Bu,A-14,O,S,O,5-OH-2-Adm,H),(10-87,i-Bu,A-15,O,S,O,5-OH-2-Adm,H),(10-88,i-Bu,A-16,O,S,O,5-OH-2-Adm,H),(10-89,i-Bu,A-17,O,S,O,5-OH-2-Adm,H),(10-90,i-Bu,A-18,O,S,O,5-OH-2-Adm,H),(10-91,i-Bu,A-19,O,S,O,5-OH-2-Adm,H),(10-92,i-Bu,A-20,O,S,O,5-OH-2-Adm,H),(10-93,i-Bu,A-21,O,S,O,5-OH-2-Adm,H),(10-94,i-Bu,A-22,O,S,O,5-OH-2-Adm,H),(10-95,i-Bu,A-23,O,S,O,5-OH-2-Adm,H),(10-96,i-Bu,A-24,O,S,O,5-OH-2-Adm,H),(10-97,i-Bu,A-25,O,S,O,5-OH-2-Adm,H),(10-98,i-Bu,A-26,O,S,O,5-OH-2-Adm,H),(10-99,i-Bu,A-27,O,S,O,5-OH-2-Adm,H),(10-100,i-Bu,A-28,O,S,O,5-OH-2-Adm,H),(10-101,i-Bu,A-29,O,S,O,5-OH-2-Adm,H),(10-102,i-Bu,A-30,O,S,O,5-OH-2-Adm,H),(10-103,i-Bu,A-31,O,S,O,5-OH-2-Adm,H),(10-104,i-Bu,A-32,O,S,O,5-OH-2-Adm,H),(10-105,i-Bu,A-33,O,S,O,5-OH-2-Adm,H),(10-106,i-Bu,A-34,O,S,O,5-OH-2-Adm,H),(10-107,i-Bu,A-35,O,S,O,5-OH-2-Adm,H),(10-108,i-Bu,A-36,O,S,O,5-OH-2-Adm,H),(10-109,i-Bu,B-1,O,S,O,1-Adm,H),(10-110,i-Bu,B-2,O,S,O,1-Adm,H),(10-111,i-Bu,B-3,O,S,O,1-Adm,H),(10-112,i-Bu,B-4,O,S,O,1-Adm,H),(10-113,i-Bu,B-5,O,S,O,1-Adm,H),(10-114,i-Bu,B-6,O,S,O,1-Adm,H),(10-115,i-Bu,B-7,O,S,O,1-Adm,H),(10-116,i-Bu,B-8,O,S,O,1-Adm,H),(10-117,i-Bu,B-9,O,S,O,1-Adm,H),(10-118,i-Bu,B-10,O,S,O,1-Adm,H),(10-119,i-Bu,B-11,O,S,O,1-Adm,H),(10-120,i-Bu,B-12,O,S,O,1-Adm,H),(10-121,i-Bu,B-13,O,S,O,1-Adm,H),(10-122,i-Bu,B-14,O,S,O,1-Adm,H),(10-123,i-Bu,B-15,O,S,O,1-Adm,H),(10-124,i-Bu,B-16,O,S,O,1-Adm,H),(10-125,i-Bu,B-17,O,S,O,1-Adm,H),(10-126,i-Bu,B-18,O,S,O,1-Adm,H),(10-127,i-Bu,B-19,O,S,O,1-Adm,H), (10-128,i-Bu,B-20,O,S,O,1-Adm,H),(10-129,i-Bu,B-21,O,S,O,1-Adm,H),(10-130,i-Bu,B-22,O,S,O,1-Adm,H),(10-131,i-Bu,B-23,O,S,O,1-Adm,H),(10-132,i-Bu,B-24,O,S,O,1-Adm,H),(10-133,i-Bu,B-25,O,S,O,1-Adm,H),(10-134,i-Bu,B-26,O,S,O,1-Adm,H),(10-135,i-Bu,B-27,O,S,O,1-Adm,H),(10-136,i-Bu,B-28,O,S,O,1-Adm,H),(10-137,i-Bu,B-29,O,S,O,1-Adm,H),(10-138,i-Bu,B-30,O,S,O,1-Adm,H),(10-139,i-Bu,B-31,O,S,O,1-Adm,H),(10-140,i-Bu,B-32,O,S,O,1-Adm,H),(10-141,i-Bu,B-33,O,S,O,1-Adm,H),(10-142,i-Bu,B-34,O,S,O,1-Adm,H),(10-143,i-Bu,B-35,O,S,O,1-Adm,H),(10-144,i-Bu,B-36,O,S,O,1-Adm,H),(10-145,i-Bu,B-1,O,S,O,2-Adm,H),(10-146,i-Bu,B-2,O,S,O,2-Adm,H),(10-147,i-Bu,B-3,O,S,O,2-Adm,H),(10-148,i-Bu,B-4,O,S,O,2-Adm,H),(10-149,i-Bu,B-5,O,S,O,2-Adm,H),(10-150,i-Bu,B-6,O,S,O,2-Adm,H),(10-151,i-Bu,B-7,O,S,O,2-Adm,H),(10-152,i-Bu,B-8,O,S,O,2-Adm,H),(10-153,i-Bu,B-9,O,S,O,2-Adm,H),(10-154,i-Bu,B-10,O,S,O,2-Adm,H),(10-155,i-Bu,B-11,O,S,O,2-Adm,H),(10-156,i-Bu,B-12,O,S,O,2-Adm,H),(10-157,i-Bu,B-13,O,S,O,2-Adm,H),(10-158,i-Bu,B-14,O,S,O,2-Adm,H),(10-159,i-Bu,B-15,O,S,O,2-Adm,H),(10-160,i-Bu,B-16,O,S,O,2-Adm,H),(10-161,i-Bu,B-17,O,S,O,2-Adm,H),(10-162,i-Bu,B-18,O,S,O,2-Adm,H),(10-163,i-Bu,B-19,O,S,O,2-Adm,H),(10-164,i-Bu,B-20,O,S,O,2-Adm,H),(10-165,i-Bu,B-21,O,S,O,2-Adm,H),(10-166,i-Bu,B-22,O,S,O,2-Adm,H),(10-167,i-Bu,B-23,O,S,O,2-Adm,H),(10-168,i-Bu,B-24,O,S,O,2-Adm,H),(10-169,i-Bu,B-25,O,S,O,2-Adm,H),(10-170,i-Bu,B-26,O,S,O,2-Adm,H),(10-171,i-Bu,B-27,O,S,O,2-Adm,H),(10-172,i-Bu,B-28,O,S,O,2-Adm,H),(10-173,i-Bu,B-29,O,S,O,2-Adm,H),(10-174,i-Bu,B-30,O,S,O,2-Adm,H),(10-175,i-Bu,B-31,O,S,O,2-Adm,H),(10-176,i-Bu,B-32,O,S,O,2-Adm,H),(10-177,i-Bu,B-33,O,S,O,2-Adm,H),(10-178,i-Bu,B-34,O,S,O,2-Adm,H),(10-179,i-Bu,B-35,O,S,O,2-Adm,H),(10-180,i-Bu,B-36,O,S,O,2-Adm,H),(10-181,i-Bu,B-1,O,S,O,5-OH-2-Adm,H),(10-182,i-Bu,B-2,O,S,O,5-OH-2-Adm,H),(10-183,i-Bu,B-3,O,S,O,5-OH-2-Adm,H),(10-184,i-Bu,B-4,O,S,O,5-OH-2-Adm,H),(10-185,i-Bu,B-5,O,S,O,5-OH-2-Adm,H),(10-186,i-Bu,B-6,O,S,O,5-OH-2-Adm,H),(10-187,i-Bu,B-7,O,S,O,5-OH-2-Adm,H),(10-188,i-Bu,B-8,O,S,O,5-OH-2-Adm,H),(10-189,i-Bu,B-9,O,S,O,5-OH-2-Adm,H),(10-190,i-Bu,B-10,O,S,O,5-OH-2-Adm,H),(10-191,i-Bu,B-11,O,S,O,5-OH-2-Adm,H),(10-192,i-Bu,B-12,O,S,O,5-OH-2-Adm,H),(10-193,i-Bu,B-13,O,S,O,5-OH-2-Adm,H),(10-194,i-Bu,B-14,O,S,O,5-OH-2-Adm,H),(10-195,i-Bu,B-15,O,S,O,5-OH-2-Adm,H),(10-196,i-Bu,B-16,O,S,O,5-OH-2-Adm,H),(10-197,i-Bu,B-17,O,S,O,5-OH-2-Adm,H),(10-198,i-Bu,B-18,O,S,O,5-OH-2-Adm,H),(10-199,i-Bu,B-19,O,S,O,5-OH-2-Adm,H),(10-200,i-Bu,B-20,O,S,O,5-OH-2-Adm,H),(10-201,i-Bu,B-21,O,S,O,5-OH-2-Adm,H),(10-202,i-Bu,B-22,O,S,O,5-OH-2-Adm,H),(10-203,i-Bu,B-23,O,S,O,5-OH-2-Adm,H),(10-204,i-Bu,B-24,O,S,O,5-OH-2-Adm,H),(10-205,i-Bu,B-25,O,S,O,5-OH-2-Adm,H),(10-206,i-Bu,B-26,O,S,O,5-OH-2-Adm,H),(10-207,i-Bu,B-27,O,S,O,5-OH-2-Adm,H),(10-208,i-Bu,B-28,O,S,O,5-OH-2-Adm,H),(10-209,i-Bu,B-29,O,S,O,5-OH-2-Adm,H),(10-210,i-Bu,B-30,O,S,O,5-OH-2-Adm,H),(10-211,i-Bu,B-31,O,S,O,5-OH-2-Adm,H),(10-212,i-Bu,B-32,O,S,O,5-OH-2-Adm,H),(10-213,i-Bu,B-33,O,S,O,5-OH-2-Adm,H),(10-214,i-Bu,B-34,O,S,O,5-OH-2-Adm,H),(10-215,i-Bu,B-35,O,S,O,5-OH-2-Adm,H),(10-216,i-Bu,B-36,O,S,O,5-OH-2-Adm,H),(10-217,i-Bu,C-1,O,S,O,1-Adm,H),(10-218,i-Bu,C-2,O,S,O,1-Adm,H),(10-219,i-Bu,C-3,O,S,O,1-Adm,H),(10-220,i-Bu,C-4,O,S,O,1-Adm,H),(10-221,i-Bu,C-5,O,S,O,1-Adm,H),(10-222,i-Bu,C-6,O,S,O,1-Adm,H),(10-223,i-Bu,C-7,O,S,O,1-Adm,H),(10-224,i-Bu,C-8,O,S,O,1-Adm,H),(10-225,i-Bu,C-9,O,S,O,1-Adm,H),(10-226,i-Bu,C-10,O,S,O,1-Adm,H),(10-227,i-Bu,C-11,O,S,O,1-Adm,H), (10-228,i-Bu,C-12,O,S,O,1-Adm,H),(10-

229,i-Bu,C-13,O,S,O,1-Adm,H),(10-230,i-Bu,C-14,O,S,O,1-Adm,H),(10-231,i-Bu,C-15,O,S,O,1-Adm,H),(10-232,i-Bu,C-16,O,S,O,1-Adm,H),(10-233,i-Bu,C-17,O,S,O,1-Adm,H),(10-234,i-Bu,C-18,O,S,O,1-Adm,H),(10-235,i-Bu,C-19,O,S,O,1-Adm,H),(10-236,i-Bu,C-20,O,S,O,1-Adm,H),(10-237,i-Bu,C-21,O,S,O,1-Adm,H),(10-238,i-Bu,C-22,O,S,O,1-Adm,H),(10-239,i-Bu,C-23,O,S,O,1-Adm,H),(10-240,i-Bu,C-24,O,S,O,1-Adm,H),(10-241,i-Bu,C-25,O,S,O,1-Adm,H),(10-242,i-Bu,C-26,O,S,O,1-Adm,H),(10-243,i-Bu,C-27,O,S,O,1-Adm,H),(10-244,i-Bu,C-28,O,S,O,1-Adm,H),(10-245,i-Bu,C-29,O,S,O,1-Adm,H),(10-246,i-Bu,C-30,O,S,O,1-Adm,H),(10-247,i-Bu,C-31,O,S,O,1-Adm,H),(10-248,i-Bu,C-32,O,S,O,1-Adm,H),(10-249,i-Bu,C-33,O,S,O,1-Adm,H),(10-250,i-Bu,C-34,O,S,O,1-Adm,H),(10-251,i-Bu,C-35,O,S,O,1-Adm,H),(10-252,i-Bu,C-36,O,S,O,1-Adm,H),(10-253,i-Bu,C-1,O,S,O,2-Adm,H),(10-254,i-Bu,C-2,O,S,O,2-Adm,H),(10-255,i-Bu,C-3,O,S,O,2-Adm,H),(10-256,i-Bu,C-4,O,S,O,2-Adm,H),(10-257,i-Bu,C-5,O,S,O,2-Adm,H),(10-258,i-Bu,C-6,O,S,O,2-Adm,H),(10-259,i-Bu,C-7,O,S,O,2-Adm,H),(10-260,i-Bu,C-8,O,S,O,2-Adm,H),(10-261,i-Bu,C-9,O,S,O,2-Adm,H),(10-262,i-Bu,C-10,O,S,O,2-Adm,H),(10-263,i-Bu,C-11,O,S,O,2-Adm,H),(10-264,i-Bu,C-12,O,S,O,2-Adm,H),(10-265,i-Bu,C-13,O,S,O,2-Adm,H),(10-266,i-Bu,C-14,O,S,O,2-Adm,H),(10-267,i-Bu,C-15,O,S,O,2-Adm,H),(10-268,i-Bu,C-16,O,S,O,2-Adm,H),(10-269,i-Bu,C-17,O,S,O,2-Adm,H),(10-270,i-Bu,C-18,O,S,O,2-Adm,H),(10-271,i-Bu,C-19,O,S,O,2-Adm,H),(10-272,i-Bu,C-20,O,S,O,2-Adm,H),(10-273,i-Bu,C-21,O,S,O,2-Adm,H),(10-274,i-Bu,C-22,O,S,O,2-Adm,H),(10-275,i-Bu,C-23,O,S,O,2-Adm,H),(10-276,i-Bu,C-24,O,S,O,2-Adm,H),(10-277,i-Bu,C-25,O,S,O,2-Adm,H),(10-278,i-Bu,C-26,O,S,O,2-Adm,H),(10-279,i-Bu,C-27,O,S,O,2-Adm,H),(10-280,i-Bu,C-28,O,S,O,2-Adm,H),(10-281,i-Bu,C-29,O,S,O,2-Adm,H),(10-282,i-Bu,C-30,O,S,O,2-Adm,H),(10-283,i-Bu,C-31,O,S,O,2-Adm,H),(10-284,i-Bu,C-32,O,S,O,2-Adm,H),(10-285,i-Bu,C-33,O,S,O,2-Adm,H),(10-286,i-Bu,C-34,O,S,O,2-Adm,H),(10-287,i-Bu,C-35,O,S,O,2-Adm,H),(10-288,i-Bu,C-36,O,S,O,2-Adm,H),(10-289,i-Bu,C-1,O,S,O,5-OH-2-Adm,H),(10-290,i-Bu,C-2,O,S,O,5-OH-2-Adm,H),(10-291,i-Bu,C-3,O,S,O,5-OH-2-Adm,H),(10-292,i-Bu,C-4,O,S,O,5-OH-2-Adm,H),(10-293,i-Bu,C-5,O,S,O,5-OH-2-Adm,H),(10-294,i-Bu,C-6,O,S,O,5-OH-2-Adm,H),(10-295,i-Bu,C-7,O,S,O,5-OH-2-Adm,H),(10-296,i-Bu,C-8,O,S,O,5-OH-2-Adm,H),(10-297,i-Bu,C-9,O,S,O,5-OH-2-Adm,H),(10-298,i-Bu,C-10,O,S,O,5-OH-2-Adm,H),(10-299,i-Bu,C-11,O,S,O,5-OH-2-Adm,H),(10-300,i-Bu,C-12,O,S,O,5-OH-2-Adm,H),(10-301,i-Bu,C-13,O,S,O,5-OH-2-Adm,H),(10-302,i-Bu,C-14,O,S,O,5-OH-2-Adm,H),(10-303,i-Bu,C-15,O,S,O,5-OH-2-Adm,H),(10-304,i-Bu,C-16,O,S,O,5-OH-2-Adm,H),(10-305,i-Bu,C-17,O,S,O,5-OH-2-Adm,H),(10-306,i-Bu,C-18,O,S,O,5-OH-2-Adm,H),(10-307,i-Bu,C-19,O,S,O,5-OH-2-Adm,H),(10-308,i-Bu,C-20,O,S,O,5-OH-2-Adm,H),(10-309,i-Bu,C-21,O,S,O,5-OH-2-Adm,H),(10-310,i-Bu,C-22,O,S,O,5-OH-2-Adm,H),(10-311,i-Bu,C-23,O,S,O,5-OH-2-Adm,H),(10-312,i-Bu,C-24,O,S,O,5-OH-2-Adm,H),(10-313,i-Bu,C-25,O,S,O,5-OH-2-Adm,H),(10-314,i-Bu,C-26,O,S,O,5-OH-2-Adm,H),(10-315,i-Bu,C-27,O,S,O,5-OH-2-Adm,H),(10-316,i-Bu,C-28,O,S,O,5-OH-2-Adm,H),(10-317,i-Bu,C-29,O,S,O,5-OH-2-Adm,H),(10-318,i-Bu,C-30,O,S,O,5-OH-2-Adm,H),(10-319,i-Bu,C-31,O,S,O,5-OH-2-Adm,H),(10-320,i-Bu,C-32,O,S,O,5-OH-2-Adm,H),(10-321,i-Bu,C-33,O,S,O,5-OH-2-Adm,H),(10-322,i-Bu,C-34,O,S,O,5-OH-2-Adm,H),(10-323,i-Bu,C-35,O,S,O,5-OH-2-Adm,H),(10-324,i-Bu,C-36,O,S,O,5-OH-2-Adm,H),(10-325,i-Bu,D-1,O,S,O,1-Adm,H),(10-326,i-Bu,D-2,O,S,O,1-Adm,H),(10-327,i-Bu,D-3,O,S,O,1-Adm,H), (10-328,i-Bu,D-4,O,S,O,1-Adm,H),(10-329,i-Bu,D-5,O,S,O,1-Adm,H),(10-330,i-Bu,D-6,O,S,O,1-Adm,H),(10-331,i-Bu,D-7,O,S,O,1-Adm,H),(10-332,i-Bu,D-8,O,S,O,1-Adm,H),(10-333,i-Bu,D-9,O,S,O,1-Adm,H),(10-334,i-Bu,D-10,O,S,O,1-Adm,H),(10-335,i-Bu,D-11,O,S,O,1-Adm,H),(10-336,i-Bu,D-12,O,S,O,1-Adm,H),(10-337,i-Bu,D-13,O,S,O,1-Adm,H),(10-338,i-Bu,D-14,O,S,O,1-Adm,H),(10-339,i-Bu,D-15,O,S,O,1-Adm,H),(10-340,i-Bu,D-16,O,S,O,1-Adm,H),(10-341,i-Bu,D-17,O,S,O,1-Adm,H),(10-342,i-Bu,D-18,O,S,O,1-Adm,H),(10-343,i-Bu,D-19,O,S,O,1-Adm,H),(10-344,i-Bu,D-20,O,S,O,1-Adm,H),(10-345,i-Bu,D-21,O,S,O,1-Adm,H),(10-346,i-Bu,D-22,O,S,O,1-Adm,H),(10-347,i-Bu,D-23,O,S,O,1-Adm,H),(10-348,i-Bu,D-24,O,S,O,1-Adm,H),(10-349,i-Bu,D-25,O,S,O,1-Adm,H),(10-350,i-Bu,D-26,O,S,O,1-Adm,H),(10-351,i-Bu,D-27,O,S,O,1-Adm,H),(10-352,i-Bu,D-28,O,S,O,1-Adm,H),(10-353,i-Bu,D-29,O,S,O,1-Adm,H),(10-354,i-Bu,D-30,O,S,O,1-Adm,H),(10-355,i-Bu,D-31,O,S,O,1-Adm,H),(10-356,i-Bu,D-32,O,S,O,1-Adm,H),(10-357,i-Bu,D-33,O,S,O,1-Adm,H),(10-358,i-Bu,D-34,O,S,O,1-Adm,H),(10-359,i-Bu,D-35,O,S,O,1-Adm,H),(10-360,i-Bu,D-36,O,S,O,1-Adm,H),(10-361,i-Bu,D-1,O,S,O,2-Adm,H),(10-362,i-Bu,D-2,O,S,O,2-Adm,H),(10-363,i-Bu,D-3,O,S,O,2-Adm,H),(10-364,i-Bu,D-4,O,S,O,2-Adm,H),(10-365,i-Bu,D-5,O,S,O,2-Adm,H),(10-366,i-Bu,D-6,O,S,O,2-Adm,H), (10-367,i-Bu,D-7,O,S,O,2-Adm,H),(10-368,i-Bu,D-8,O,S,O,2-Adm,H),(10-369,i-Bu,D-9,O,S,O,2-Adm,H),(10-370,i-Bu,D-10,O,S,O,2-Adm,H),(10-371,i-Bu,D-11,O,S,O,2-Adm,H),(10-372,i-Bu,D-12,O,S,O,2-Adm,H),(10-373,i-Bu,D-13,O,S,O,2-Adm,H),(10-374,i-Bu,D-14,O,S,O,2-Adm,H),(10-375,i-Bu,D-15,O,S,O,2-Adm,H),(10-376,i-Bu,D-16,O,S,O,2-Adm,H),(10-377,i-Bu,D-17,O,S,O,2-Adm,H),(10-378,i-Bu,D-18,O,S,O,2-Adm,H),(10-379,i-Bu,D-19,O,S,O,2-Adm,H),(10-380,i-Bu,D-20,O,S,O,2-Adm,H),(10-381,i-Bu,D-21,O,S,O,2-Adm,H),(10-382,i-Bu,D-22,O,S,O,2-Adm,H),(10-383,i-Bu,D-23,O,S,O,2-Adm,H),(10-384,i-Bu,D-24,O,S,O,2-Adm,H),(10-385,i-Bu,D-25,O,S,O,2-Adm,H),(10-386,i-Bu,D-26,O,S,O,2-Adm,H),(10-387,i-Bu,D-27,O,S,O,2-Adm,H),(10-388,i-Bu,D-28,O,S,O,2-Adm,H),(10-389,i-Bu,D-29,O,S,O,2-Adm,H),(10-390,i-Bu,D-30,O,S,O,2-Adm,H),(10-391,i-Bu,D-31,O,S,O,2-Adm,H),(10-392,i-Bu,D-32,O,S,O,2-Adm,H),(10-393,i-Bu,D-33,O,S,O,2-Adm,H),(10-394,i-Bu,D-34,O,S,O,2-Adm,H),(10-395,i-Bu,D-35,O,S,O,2-Adm,H),(10-396,i-Bu,D-36,O,S,O,2-Adm,H),(10-397,i-Bu,D-1,O,S,O,5-OH-2-Adm,H),(10-398,i-Bu,D-2,O,S,O,5-OH-2-Adm,H),(10-399,i-Bu,D-3,O,S,O,5-OH-2-Adm,H),(10-400,i-Bu,D-4,O,S,O,5-OH-2-Adm,H),(10-401,i-Bu,D-5,O,S,O,5-OH-2-Adm,H),(10-402,i-Bu,D-6,O,S,O,5-OH-2-Adm,H),(10-403,i-Bu,D-7,O,S,O,5-OH-2-Adm,H),(10-404,i-Bu,D-8,O,S,O,5-OH-2-Adm,H),(10-405,i-Bu,D-9,O,S,O,5-OH-2-Adm,H),(10-406,i-Bu,D-10,O,S,O,5-OH-2-Adm,H),(10-407,i-Bu,D-11,O,S,O,5-OH-2-Adm,H),(10-408,i-Bu,D-12,O,S,O,5-OH-2-Adm,H),(10-409,i-Bu,D-13,O,S,O,5-OH-2-Adm,H),(10-410,i-Bu,D-14,O,S,O,5-OH-2-Adm,H),(10-411,i-Bu,D-15,O,S,O,5-OH-2-Adm,H),(10-412,i-Bu,D-16,O,S,O,5-OH-2-Adm,H),(10-413,i-Bu,D-17,O,S,O,5-OH-2-Adm,H),(10-414,i-Bu,D-18,O,S,O,5-OH-2-Adm,H),(10-415,i-Bu,D-19,O,S,O,5-OH-2-Adm,H),(10-416,i-Bu,D-20,O,S,O,5-OH-2-Adm,H),(10-417,i-Bu,D-21,O,S,O,5-OH-2-Adm,H),(10-418,i-Bu,D-22,O,S,O,5-OH-2-Adm,H),(10-419,i-Bu,D-23,O,S,O,5-OH-2-Adm,H),(10-420,i-Bu,D-24,O,S,O,5-OH-2-Adm,H),(10-421,i-Bu,D-25,O,S,O,5-OH-2-Adm,H),(10-422,i-Bu,D-26,O,S,O,5-OH-2-Adm,H),(10-423,i-Bu,D-27,O,S,O,5-OH-2-Adm,H),(10-424,i-Bu,D-28,O,S,O,5-OH-2-Adm,H),(10-425,i-Bu,D-29,O,S,O,5-OH-2-Adm,H),(10-426,i-Bu,D-30,O,S,O,5-OH-2-Adm,H),(10-427,i-Bu,D-31,O,S,O,5-OH-2-Adm,H), (10-428,i-Bu,D-32,O,S,O,5-OH-2-Adm,H),(10-

429,i-Bu,D-33,O,S,O,5-OH-2-Adm,H),(10-430,i-Bu,D-34,
O,S,O,5-OH-2-Adm,H),(10-431,i-Bu,D-35,O,S,O,5-OH-2-
Adm,H),(10-432,i-Bu,D-36,O,S,O,5-OH-2-Adm,H),(10-
433,i-Bu,E-1,O,S,O,1-Adm,H),(10-434,i-Bu,E-2,O,S,O,1-
Adm,H),(10-435,i-Bu,E-3,O,S,O,1-Adm,H),(10-436,i-Bu,
E-4,O,S,O,1-Adm,H),(10-437,i-Bu,E-5,O,S,O,1-Adm,H),
(10-438,i-Bu,E-6,O,S,O,1-Adm,H),(10-439,i-Bu,E-7,O,S,
O,1-Adm,H),(10-440,i-Bu,E-8,O,S,O,1-Adm,H),(10-441,i-
Bu,E-9,O,S,O,1-Adm,H),(10-442,i-Bu,E-10,O,S,O,1-Adm,
H),(10-443,i-Bu,E-11,O,S,O,1-Adm,H),(10-444,i-Bu,E-12,
O,S,O,1-Adm,H),(10-445,i-Bu,E-13,O,S,O,1-Adm,H),(10-
446,i-Bu,E-14,O,S,O,1-Adm,H),(10-447,i-Bu,E-15,O,S,O,
1-Adm,H),(10-448,i-Bu,E-16,O,S,O,1-Adm,H),(10-449,i-
Bu,E-17,O,S,O,1-Adm,H),(10-450,i-Bu,E-18,O,S,O,1-
Adm,H),(10-451,i-Bu,E-19,O,S,O,1-Adm,H),(10-452,i-Bu,
E-20,O,S,O,1-Adm,H),(10-453,i-Bu,E-21,O,S,O,1-Adm,
H),(10-454,i-Bu,E-22,O,S,O,1-Adm,H),(10-455,i-Bu,E-23,
O,S,O,1-Adm,H),(10-456,i-Bu,E-24,O,S,O,1-Adm,H),(10-
457,i-Bu,E-25,O,S,O,1-Adm,H),(10-458,i-Bu,E-26,O,S,O,
1-Adm,H),(10-459,i-Bu,E-27,O,S,O,1-Adm,H),(10-460,i-
Bu,E-28,O,S,O,1-Adm,H),(10-461,i-Bu,E-29,O,S,O,1-
Adm,H),(10-462,i-Bu,E-30,O,S,O,1-Adm,H),(10-463,i-Bu,
E-31,O,S,O,1-Adm,H),(10-464,i-Bu,E-32,O,S,O,1-Adm,
H),(10-465,i-Bu,E-33,O,S,O,1-Adm,H),(10-466,i-Bu,E-34,
O,S,O,1-Adm,H),(10-467,i-Bu,E-35,O,S,O,1-Adm,H),(10-
468,i-Bu,E-36,O,S,O,1-Adm,H),(10-469,i-Bu,E-1,O,S,O,2-
Adm,H),(10-470,i-Bu,E-2,O,S,O,2-Adm,H),(10-471,i-Bu,
E-3,O,S,O,2-Adm,H),(10-472,i-Bu,E-4,O,S,O,2-Adm,H),
(10-473,i-Bu,E-5,O,S,O,2-Adm,H),(10-474,i-Bu,E-6,O,S,
O,2-Adm,H),(10-475,i-Bu,E-7,O,S,O,2-Adm,H),(10-476,i-
Bu,E-8,O,S,O,2-Adm,H),(10-477,i-Bu,E-9,O,S,O,2-Adm,
H),(10-478,i-Bu,E-10,O,S,O,2-Adm,H),(10-479,i-Bu,E-11,
O,S,O,2-Adm,H),(10-480,i-Bu,E-12,O,S,O,2-Adm,H),(10-
481,i-Bu,E-13,O,S,O,2-Adm,H),(10-482,i-Bu,E-14,O,S,O,
2-Adm,H),(10-483,i-Bu,E-15,O,S,O,2-Adm,H),(10-484,i-
Bu,E-16,O,S,O,2-Adm,H),(10-485,i-Bu,E-17,O,S,O,2-
Adm,H),(10-486,i-Bu,E-18,O,S,O,2-Adm,H),(10-487,i-Bu,
E-19,O,S,O,2-Adm,H),(10-488,i-Bu,E-20,O,S,O,2-Adm,
H),(10-489,i-Bu,E-21,O,S,O,2-Adm,H),(10-490,i-Bu,E-22,
O,S,O,2-Adm,H),(10-491,i-Bu,E-23,O,S,O,2-Adm,H),(10-
492,i-Bu,E-24,O,S,O,2-Adm,H),(10-493,i-Bu,E-25,O,S,O,
2-Adm,H),(10-494,i-Bu,E-26,O,S,O,2-Adm,H),(10-495,i-
Bu,E-27,O,S,O,2-Adm,H),(10-496,i-Bu,E-28,O,S,O,2-
Adm,H),(10-497,i-Bu,E-29,O,S,O,2-Adm,H),(10-498,i-Bu,
E-30,O,S,O,2-Adm,H),(10-499,i-Bu,E-31,O,S,O,2-Adm,
H),(10-500,i-Bu,E-32,O,S,O,2-Adm,H),(10-501,i-Bu,E-33,
O,S,O,2-Adm,H),(10-502,i-Bu,E-34,O,S,O,2-Adm,H),(10-
503,i-Bu,E-35,O,S,O,2-Adm,H),(10-504,i-Bu,E-36,O,S,O,
2-Adm,H),(10-505,i-Bu,E-1,O,S,O,5-OH-2-Adm,H),(10-
506,i-Bu,E-2,O,S,O,5-OH-2-Adm,H),(10-507,i-Bu,E-3,O,
S,O,5-OH-2-Adm,H),(10-508,i-Bu,E-4,O,S,O,5-OH-2-
Adm,H),(10-509,i-Bu,E-5,O,S,O,5-OH-2-Adm,H),(10-510,
i-Bu,E-6,O,S,O,5-OH-2-Adm,H),(10-511,i-Bu,E-7,O,S,O,
5-OH-2-Adm,H),(10-512,i-Bu,E-8,O,S,O,5-OH-2-Adm,H),
(10-513,i-Bu,E-9,O,S,O,5-OH-2-Adm,H),(10-514,i-Bu,E-
10,O,S,O,5-OH-2-Adm,H),(10-515,i-Bu,E-11,O,S,O,5-OH-
2-Adm,H),(10-516,i-Bu,E-12,O,S,O,5-OH-2-Adm,H),(10-
517,i-Bu,E-13,O,S,O,5-OH-2-Adm,H),(10-518,i-Bu,E-14,
O,S,O,5-OH-2-Adm,H),(10-519,i-Bu,E-15,O,S,O,5-OH-2-
Adm,H),(10-520,i-Bu,E-16,O,S,O,5-OH-2-Adm,H),(10-
521,i-Bu,E-17,O,S,O,5-OH-2-Adm,H),(10-522,i-Bu,E-18,
O,S,O,5-OH-2-Adm,H),(10-523,i-Bu,E-19,O,S,O,5-OH-2-
Adm,H),(10-524,i-Bu,E-20,O,S,O,5-OH-2-Adm,H),(10-
525,i-Bu,E-21,O,S,O,5-OH-2-Adm,H),(10-526,i-Bu,E-22,
O,S,O,5-OH-2-Adm,H),(10-527,i-Bu,E-23,O,S,O,5-OH-2-
Adm,H),(10-528,i-Bu,E-24,O,S,O,5-OH-2-Adm,H),(10-
529,i-Bu, E-25,O,S,O,5-OH-2-Adm,H),(10-530,i-Bu,E-26,
O,S,O,5-OH-2-Adm,H),(10-531,i-Bu,E-27,O,S,O,5-OH-2-
Adm,H),(10-532,i-Bu,E-28,O,S,O,5-OH-2-Adm,H),(10-
533,i-Bu,E-29,O,S,O,5-OH-2-Adm,H),(10-534,i-Bu,E-30,
O,S,O,5-OH-2-Adm,H),(10-535,i-Bu,E-31,O,S,O,5-OH-2-
Adm,H),(10-536,i-Bu,E-32,O,S,O,5-OH-2-Adm,H),(10-
537,i-Bu,E-33,O,S,O,5-OH-2-Adm,H),(10-538,i-Bu,E-34,
O,S,O,5-OH-2-Adm,H),(10-539,i-Bu,E-35,O,S,O,5-OH-2-
Adm,H),(10-540,i-Bu,E-36,O,S,O,5-OH-2-Adm,H),(10-
541,i-Bu,F-1,O,S,O,1-Adm,H),(10-542,i-Bu,F-2,O,S,O,1-
Adm,H),(10-543,i-Bu,F-3,O,S,O,1-Adm,H),(10-544,i-Bu,
F-4,O,S,O,1-Adm,H),(10-545,i-Bu,F-5,O,S,O,1-Adm,H),
(10-546,i-Bu,F-6,O,S,O,1-Adm,H),(10-547,i-Bu,F-7,O,S,
O,1-Adm,H),(10-548,i-Bu,F-8,O,S,O,1-Adm,H),(10-549,i-
Bu,F-9,O,S,O,1-Adm,H),(10-550,i-Bu,F-10,O,S,O,1-Adm,
H),(10-551,i-Bu,F-11,O,S,O,1-Adm,H),(10-552,i-Bu,F-12,
O,S,O,1-Adm,H),(10-553,i-Bu,F-13,O,S,O,1-Adm,H),(10-
554,i-Bu,F-14,O,S,O,1-Adm,H),(10-555,i-Bu,F-15,O,S,O,
1-Adm,H),(10-556,i-Bu,F-16,O,S,O,1-Adm,H),(10-557,i-
Bu,F-17,O,S,O,1-Adm,H),(10-558,i-Bu,F-18,O,S,O,1-
Adm,H),(10-559,i-Bu,F-19,O,S,O,1-Adm,H),(10-560,i-Bu,
F-20,O,S,O,1-Adm,H),(10-561,i-Bu,F-21,O,S,O,1-Adm,H),
(10-562,i-Bu,F-22,O,S,O,1-Adm,H),(10-563,i-Bu,F-23,O,
S,O,1-Adm,H),(10-564,i-Bu,F-24,O,S,O,1-Adm,H),(10-
565,i-Bu,F-25,O,S,O,1-Adm,H),(10-566,i-Bu,F-26,O,S,O,
1-Adm,H),(10-567,i-Bu,F-27,O,S,O,1-Adm,H),(10-568,i-
Bu,F-28,O,S,O,1-Adm,H),(10-569,i-Bu,F-29,O,S,O,1-
Adm,H),(10-570,i-Bu,F-30,O,S,O,1-Adm,H),(10-571,i-Bu,
F-31,O,S,O,1-Adm,H),(10-572,i-Bu,F-32,O,S,O,1-Adm,H),
(10-573,i-Bu,F-33,O,S,O,1-Adm,H),(10-574,i-Bu,F-34,O,
S,O,1-Adm,H),(10-575,i-Bu,F-35,O,S,O,1-Adm,H),(10-
576,i-Bu,F-36,O,S,O,1-Adm,H),(10-577,i-Bu,F-1,O,S,O,2-
Adm,H),(10-578,i-Bu,F-2,O,S,O,2-Adm,H),(10-579,i-Bu,
F-3,O,S,O,2-Adm,H),(10-580,i-Bu,F-4,O,S,O,2-Adm,H),
(10-581,i-Bu,F-5,O,S,O,2-Adm,H),(10-582,i-Bu,F-6,O,S,
O,2-Adm,H),(10-583,i-Bu,F-7,O,S,O,2-Adm,H),(10-584,i-
Bu,F-8,O,S,O,2-Adm,H),(10-585,i-Bu,F-9,O,S,O,2-Adm,
H),(10-586,i-Bu,F-10,O,S,O,2-Adm,H),(10-587,i-Bu,F-11,
O,S,O,2-Adm,H),(10-588,i-Bu,F-12,O,S,O,2-Adm,H),(10-
589,i-Bu,F-13,O,S,O,2-Adm,H),(10-590,i-Bu,F-14,O,S,O,
2-Adm,H),(10-591,i-Bu,F-15,O,S,O,2-Adm,H),(10-592,i-
Bu,F-16,O,S,O,2-Adm,H),(10-593,i-Bu,F-17,O,S,O,2-
Adm,H),(10-594,i-Bu,F-18,O,S,O,2-Adm,H),(10-595,i-Bu,
F-19,O,S,O,2-Adm,H),(10-596,i-Bu,F-20,O,S,O,2-Adm,H),
(10-597,i-Bu,F-21,O,S,O,2-Adm,H),(10-598,i-Bu,F-22,O,
S,O,2-Adm,H),(10-599,i-Bu,F-23,O,S,O,2-Adm,H),(10-
600,i-Bu,F-24,O,S,O,2-Adm,H),(10-601,i-Bu,F-25,O,S,O,
2-Adm,H),(10-602,i-Bu,F-26,O,S,O,2-Adm,H),(10-603,i-
Bu,F-27,O,S,O,2-Adm,H),(10-604,i-Bu,F-28,O,S,O,2-
Adm,H),(10-605,i-Bu,F-29,O,S,O,2-Adm,H),(10-606,i-Bu,
F-30,O,S,O,2-Adm,H),(10-607,i-Bu,F-31,O,S,O,2-Adm,H),
(10-608,i-Bu,F-32,O,S,O,2-Adm,H),(10-609,i-Bu,F-33,O,
S,O,2-Adm,H),(10-610,i-Bu,F-34,O,S,O,2-Adm,H),(10-
611,i-Bu,F-35,O,S,O,2-Adm,H),(10-612,i-Bu,F-36,O,S,O,
2-Adm,H),(10-613,i-Bu,F-1,O,S,O,5-OH-2-Adm,H),(10-
614,i-Bu,F-2,O,S,O,5-OH-2-Adm,H),(10-615,i-Bu,F-3,O,
S,O,5-OH-2-Adm,H),(10-616,i-Bu,F-4,O,S,O,5-OH-2-
Adm,H),(10-617,i-Bu,F-5,O,S,O,5-OH-2-Adm,H),(10-618,
i-Bu,F-6,O,S,O,5-OH-2-Adm,H),(10-619,i-Bu,F-7,O,S,O,
5-OH-2-Adm,H),(10-620,i-Bu,F-8,O,S,O,5-OH-2-Adm,H),
(10-621,i-Bu,F-9,O,S,O,5-OH-2-Adm,H),(10-622,i-Bu,F-
10,O,S,O,5-OH-2-Adm,H),(10-623,i-Bu,F-11,O,S,O,5-OH-
2-Adm,H),(10-624,i-Bu,F-12,O,S,O,5-OH-2-Adm,H),(10-
625,i-Bu,F-13,O,S,O,5-OH-2-Adm,H),(10-626,i-Bu,F-14,
O,S,O,5-OH-2-Adm,H),(10-627,i-Bu,F-15,O,S,O,5-OH-2-
Adm,H),(10-628,i-Bu,F-16,O,S,O,5-OH-2-Adm,H),(10-
629,i-Bu,F-17,O,S,O,5-OH-2-Adm,H),(10-630,i-Bu,F-18,
O,S,O,5-OH-2-Adm,H), (10-631,i-Bu,F-19,O,S,O,5-OH-2-

Adm,H),(10-632,i-Bu,F-20,O,S,O,5-OH-2-Adm,H),(10-633,i-Bu,F-21,O,S,O,5-OH-2-Adm,H),(10-634,i-Bu,F-22,O,S,O,5-OH-2-Adm,H),(10-635,i-Bu,F-23,O,S,O,5-OH-2-Adm,H),(10-636,i-Bu,F-24,O,S,O,5-OH-2-Adm,H),(10-637,i-Bu,F-25,O,S,O,5-OH-2-Adm,H),(10-638,i-Bu,F-26,O,S,O,5-OH-2-Adm,H),(10-639,i-Bu,F-27,O,S,O,5-OH-2-Adm,H),(10-640,i-Bu,F-28,O,S,O,5-OH-2-Adm,H),(10-641,i-Bu,F-29,O,S,O,5-OH-2-Adm,H),(10-642,i-Bu,F-30,O,S,O,5-OH-2-Adm,H),(10-643,i-Bu,F-31,O,S,O,5-OH-2-Adm,H),(10-644,i-Bu,F-32,O,S,O,5-OH-2-Adm,H),(10-645,i-Bu,F-33,O,S,O,5-OH-2-Adm,H),(10-646,i-Bu,F-34,O,S,O,5-OH-2-Adm,H),(10-647,i-Bu,F-35,O,S,O,5-OH-2-Adm,H),(10-648,i-Bu,F-36,O,S,O,5-OH-2-Adm,H),(10-649,i-Bu,G-1,O,S,O,1-Adm,H),(10-650,i-Bu,G-2,O,S,O,1-Adm,H),(10-651,i-Bu,G-3,O,S,O,1-Adm,H),(10-652,i-Bu,G-4,O,S,O,1-Adm,H),(10-653,i-Bu,G-5,O,S,O,1-Adm,H),(10-654,i-Bu,G-6,O,S,O,1-Adm,H),(10-655,i-Bu,G-7,O,S,O,1-Adm,H),(10-656,i-Bu,G-8,O,S,O,1-Adm,H),(10-657,i-Bu,G-9,O,S,O,1-Adm,H),(10-658,i-Bu,G-1,O,S,O,2-Adm,H),(10-659,i-Bu,G-2,O,S,O,2-Adm,H),(10-660,i-Bu,G-3,O,S,O,2-Adm,H),(10-661,i-Bu,G-4,O,S,O,2-Adm,H),(10-662,i-Bu,G-5,O,S,O,2-Adm,H),(10-663,i-Bu,G-6,O,S,O,2-Adm,H),(10-664,i-Bu,G-7,O,S,O,2-Adm,H),(10-665,i-Bu,G-8,O,S,O,2-Adm,H),(10-666,i-Bu,G-9,O,S,O,2-Adm,H),(10-667,i-Bu,G-1,O,S,O,5-OH-2-Adm,H),(10-668,i-Bu,G-2,O,S,O,5-OH-2-Adm,H),(10-669,i-Bu,G-3,O,S,O,5-OH-2-Adm,H),(10-670,i-Bu,G-4,O,S,O,5-OH-2-Adm,H),(10-671,i-Bu,G-5,O,S,O,5-OH-2-Adm,H),(10-672,i-Bu,G-6,O,S,O,5-OH-2-Adm,H),(10-673,i-Bu,G-7,O,S,O,5-OH-2-Adm,H),(10-674,i-Bu,G-8,O,S,O,5-OH-2-Adm,H),(10-675,i-Bu,G-9,O,S,O,5-OH-2-Adm,H),(10-676,i-Bu,H-1,O,S,O,1-Adm,H),(10-677,i-Bu,H-2,O,S,O,1-Adm,H),(10-678,i-Bu,H-3,O,S,O,1-Adm,H),(10-679,i-Bu,H-4,O,S,O,1-Adm,H),(10-680,i-Bu,H-5,O,S,O,1-Adm,H),(10-681,i-Bu,H-6,O,S,O,1-Adm,H),(10-682,i-Bu,H-7,O,S,O,1-Adm,H),(10-683,i-Bu,H-8,O,S,O,1-Adm,H),(10-684,i-Bu,H-9,O,S,O,1-Adm,H),(10-685,i-Bu,H-1,O,S,O,2-Adm,H),(10-686,i-Bu,H-2,O,S,O,2-Adm,H),(10-687,i-Bu,H-3,O,S,O,2-Adm,H),(10-688,i-Bu,H-4,O,S,O,2-Adm,H),(10-689,i-Bu,H-5,O,S,O,2-Adm,H),(10-690,i-Bu,H-6,O,S,O,2-Adm,H),(10-691,i-Bu,H-7,O,S,O,2-Adm,H),(10-692,i-Bu,H-8,O,S,O,2-Adm,H),(10-693,i-Bu,H-9,O,S,O,2-Adm,H),(10-694,i-Bu,H-1,O,S,O,5-OH-2-Adm,H),(10-695,i-Bu,H-2,O,S,O,5-OH-2-Adm,H),(10-696,i-Bu,H-3,O,S,O,5-OH-2-Adm,H),(10-697,i-Bu,H-4,O,S,O,5-OH-2-Adm,H),(10-698,i-Bu,H-5,O,S,O,5-OH-2-Adm,H),(10-699,i-Bu,H-6,O,S,O,5-OH-2-Adm,H),(10-700,i-Bu,H-7,O,S,O,5-OH-2-Adm,H),(10-701,i-Bu,H-8,O,S,O,5-OH-2-Adm,H),(10-702,i-Bu,H-9,O,S,O,5-OH-2-Adm,H),(10-703,i-Bu,I-1,O,S,O,1-Adm,H),(10-704,i-Bu,I-2,O,S,O,1-Adm,H),(10-705,i-Bu,I-3,O,S,O,1-Adm,H),(10-706,i-Bu,I-4,O,S,O,1-Adm,H),(10-707,i-Bu,I-5,O,S,O,1-Adm,H),(10-708,i-Bu,I-6,O,S,O,1-Adm,H),(10-709,i-Bu,I-7,O,S,O,1-Adm,H),(10-710,i-Bu,I-8,O,S,O,1-Adm,H),(10-711,i-Bu,I-9,O,S,O,1-Adm,H),(10-712,i-Bu,I-1,O,S,O,2-Adm,H),(10-713,i-Bu,I-2,O,S,O,2-Adm,H),(10-714,i-Bu,I-3,O,S,O,2-Adm,H),(10-715,i-Bu,I-4,O,S,O,2-Adm,H),(10-716,i-Bu,I-5,O,S,O,2-Adm,H),(10-717,i-Bu,I-6,O,S,O,2-Adm,H),(10-718,i-Bu,I-7,O,S,O,2-Adm,H),(10-719,i-Bu,I-8,O,S,O,2-Adm,H),(10-720,i-Bu,I-9,O,S,O,2-Adm,H),(10-721,i-Bu,I-1,O,S,O,5-OH-2-Adm,H),(10-722,i-Bu,I-2,O,S,O,5-OH-2-Adm,H),(10-723,i-Bu,I-3,O,S,O,5-OH-2-Adm,H),(10-724,i-Bu,I-4,O,S,O,5-OH-2-Adm,H),(10-725,i-Bu,I-5,O,S,O,5-OH-2-Adm,H),(10-726,i-Bu,I-6,O,S,O,5-OH-2-Adm,H),(10-727,i-Bu,I-7,O,S,O,5-OH-2-Adm,H),(10-728,i-Bu,I-8,O,S,O,5-OH-2-Adm,H),(10-729,i-Bu,I-9,O,S,O,5-OH-2-Adm,H),(10-730,i-Bu,J-1,O,S,O,1-Adm,H),(10-731,i-Bu,J-2,O,S,O,1-Adm,H),(10-732,i-Bu,J-3,O,S,O,1-Adm,H),(10-733,i-Bu,J-4,O,S,O,1-Adm,H),(10-734,i-Bu,J-5,O,S,O,1-Adm,H),(10-735,i-Bu,J-6,O,S,O,1-Adm,H),(10-736,i-Bu,J-7,O,S,O,1-Adm,H),(10-737,i-Bu,J-8,O,S,O,1-Adm,H),(10-738,i-Bu,J-9,O,S,O,1-Adm,H),(10-739,i-Bu,J-1,O,S,O,2-Adm,H),(10-740,i-Bu,J-2,O,S,O,2-Adm,H),(10-741,i-Bu,J-3,O,S,O,2-Adm,H),(10-742,i-Bu,J-4,O,S,O,2-Adm,H),(10-743,i-Bu,J-5,O,S,O,2-Adm,H),(10-744,i-Bu,J-6,O,S,O,2-Adm,H),(10-745,i-Bu,J-7,O,S,O,2-Adm,H),(10-746,i-Bu,J-8,O,S,O,2-Adm,H),(10-747,i-Bu,J-9,O,S,O,2-Adm,H),(10-748,i-Bu,J-1,O,S,O,5-OH-2-Adm,H),(10-749,i-Bu,J-2,O,S,O,5-OH-2-Adm,H),(10-750,i-Bu,J-3,O,S,O,5-OH-2-Adm,H),(10-751,i-Bu,J-4,O,S,O,5-OH-2-Adm,H),(10-752,i-Bu,J-5,O,S,O,5-OH-2-Adm,H),(10-753,i-Bu,J-6,O,S,O,5-OH-2-Adm,H),(10-754,i-Bu,J-7,O,S,O,5-OH-2-Adm,H),(10-755,i-Bu,J-8,O,S,O,5-OH-2-Adm,H),(10-756,i-Bu,J-9,O,S,O,5-OH-2-Adm,H),(10-757,i-Bu,K-1,O,S,O,1-Adm,H),(10-758,i-Bu,K-2,O,S,O,1-Adm,H),(10-759,i-Bu,K-3,O,S,O,1-Adm,H),(10-760,i-Bu,K-4,O,S,O,1-Adm,H),(10-761,i-Bu,K-5,O,S,O,1-Adm,H),(10-762,i-Bu,K-6,O,S,O,1-Adm,H),(10-763,i-Bu,K-7,O,S,O,1-Adm,H),(10-764,i-Bu,K-8,O,S,O,1-Adm,H),(10-765,i-Bu,K-9,O,S,O,1-Adm,H),(10-766,i-Bu,K-1,O,S,O,2-Adm,H),(10-767,i-Bu,K-2,O,S,O,2-Adm,H),(10-768,i-Bu,K-3,O,S,O,2-Adm,H),(10-769,i-Bu,K-4,O,S,O,2-Adm,H),(10-770,i-Bu,K-5,O,S,O,2-Adm,H),(10-771,i-Bu,K-6,O,S,O,2-Adm,H),(10-772,i-Bu,K-7,O,S,O,2-Adm,H),(10-773,i-Bu,K-8,O,S,O,2-Adm,H),(10-774,i-Bu,K-9,O,S,O,2-Adm,H),(10-775,i-Bu,K-1,O,S,O,5-OH-2-Adm,H),(10-776,i-Bu,K-2,O,S,O,5-OH-2-Adm,H),(10-777,i-Bu,K-3,O,S,O,5-OH-2-Adm,H),(10-778,i-Bu,K-4,O,S,O,5-OH-2-Adm,H),(10-779,i-Bu,K-5,O,S,O,5-OH-2-Adm,H),(10-780,i-Bu,K-6,O,S,O,5-OH-2-Adm,H),(10-781,i-Bu,K-7,O,S,O,5-OH-2-Adm,H),(10-782,i-Bu,K-8,O,S,O,5-OH-2-Adm,H),(10-783,i-Bu,K-9,O,S,O,5-OH-2-Adm,H)

(Compound No., $R^2,R^3,X,Y,Z,R^4,R^5$)=(11-1,Bu,A-1,O,S,O,1-Adm,H),(11-2,Bu,A-2,O,S,O,1-Adm,H),(11-3,Bu,A-3,O,S,O,1-Adm,H),(11-4,Bu,A-4,O,S,O,1-Adm,H),(11-5,Bu,A-5,O,S,O,1-Adm,H),(11-6,Bu,A-6,O,S,O,1-Adm,H),(11-7,Bu,A-7,O,S,O,1-Adm,H),(11-8,Bu,A-8,O,S,O,1-Adm,H),(11-9,Bu,A-9,O,S,O,1-Adm,H),(11-10,Bu,A-10,O,S,O,1-Adm,H),(11-11,Bu,A-11,O,S,O,1-Adm,H),(11-12,Bu,A-12,O,S,O,1-Adm,H),(11-13,Bu,A-13,O,S,O,1-Adm,H),(11-14,Bu,A-14,O,S,O,1-Adm,H),(11-15,Bu,A-15,O,S,O,1-Adm,H),(11-16,Bu,A-16,O,S,O,1-Adm,H),(11-17,Bu,A-17,O,S,O,1-Adm,H),(11-18,Bu,A-18,O,S,O,1-Adm,H),(11-19,Bu,A-19,O,S,O,1-Adm,H),(11-20,Bu,A-20,O,S,O,1-Adm,H),(11-21,Bu,A-21,O,S,O,1-Adm,H),(11-22,Bu,A-22,O,S,O,1-Adm,H),(11-23,Bu,A-23,O,S,O,1-Adm,H),(11-24,Bu,A-24,O,S,O,1-Adm,H),(11-25,Bu,A-25,O,S,O,1-Adm,H),(11-26,Bu,A-26,O,S,O,1-Adm,H),(11-27,Bu,A-27,O,S,O,1-Adm,H),(11-28,Bu,A-28,O,S,O,1-Adm,H),(11-29,Bu,A-29,O,S,O,1-Adm,H),(11-30,Bu,A-30,O,S,O,1-Adm,H),(11-31,Bu,A-31,O,S,O,1-Adm,H),(11-32,Bu,A-32,O,S,O,1-Adm,H),(11-33,Bu,A-33,O,S,O,1-Adm,H),(11-34,Bu,A-34,O,S,O,1-Adm,H),(11-35,Bu,A-35,O,S,O,1-Adm,H),(11-36,Bu,A-36,O,S,O,1-Adm,H),(11-37,Bu,A-1,O,S,O,2-Adm,H),(11-38,Bu,A-2,O,S,O,2-Adm,H),(11-39,Bu,A-3,O,S,O,2-Adm,H),(11-40,Bu,A-4,O,S,O,2-Adm,H),(11-41,Bu,A-5,O,S,O,2-Adm,H),(11-42,Bu,A-6,O,S,O,2-Adm,H),(11-43,Bu,A-7,O,S,O,2-Adm,H),(11-44,Bu,A-8,O,S,O,2-Adm,H),(11-45,Bu,A-9,O,S,O,2-Adm,H),(11-46,Bu,A-11,O,S,O,2-Adm,H),(11-47,Bu,A-11,O,S,O,2-Adm,H),(11-48,Bu,A-12,O,S,O,2-Adm,H),(11-49,Bu,A-13,O,S,O,2-Adm,H),(11-50,Bu,A-14,O,S,O,2-Adm,H),(11-51,Bu,A-15,O,S,O,2-Adm,H),(11-52,Bu,A-16,O,S,O,2-Adm,H),(11-53,Bu,A-17,O,S,O,2-Adm,H),(11-54,Bu,A-18,O,S,O,2-Adm,H),(11-55,Bu,A-19,O,S,O,2-Adm,H),(11-56,Bu,A-20, O,S,O,2-Adm,H),(11-57,Bu, A-21,O,S,O,2-Adm,H),(11-58,Bu,A-22,O,S,O,2-Adm,H),(11-59,Bu,A-23,O,S,O,2-Adm,H),(11-60,Bu,A-24,O,S,O,2-Adm,H),(11-61,Bu,A-25,O,S,O,2-Adm,H),(11-62,Bu,A-26,O,S,O,2-Adm,H),(11-63,Bu,A-27,O,S,O,2-Adm,H),(11-64,Bu,A-28,O,S,O,2-Adm,H),(11-65,Bu,A-29,O,S,O,2-Adm,H),(11-66,Bu,A-30,O,S,O,2-Adm,H),(11-67,Bu,A-31,O,S,O,2-Adm,H),(11-68,Bu,A-32,O,S,O,2-Adm,H),(11-69,Bu,A-33,O,S,O,2-Adm,H),(11-70,Bu,A-34,O,S,O,2-Adm,H),(11-71,Bu,A-35,O,S,O,2-Adm,H),(11-72,Bu,A-36,O,S,O,2-Adm,H),(11-73,Bu,A-1,O,S,O,5-OH-2-Adm,H),(11-74,Bu,A-2,O,S,O,5-OH-2-Adm,H),(11-75,Bu,A-3,O,S,O,5-OH-2-Adm,H),(11-76,Bu,A-4,O,S,O,5-OH-2-Adm,H),(11-77,Bu,A-5,O,S,O,5-OH-2-Adm,H),(11-78,Bu,A-6,O,S,O,5-OH-2-Adm,H),(11-79,Bu,A-7,O,S,O,5-OH-2-Adm,H),(11-80,Bu,A-8,O,S,O,5-OH-2-Adm,H),(11-81,Bu,A-9,O,S,O,5-OH-2-Adm,H),(11-82,Bu,A-10,O,S,O,5-OH-2-Adm,H),(11-83,Bu,A-11,O,S,O,5-OH-2-Adm,H),(11-84,Bu,A-12,O,S,O,5-OH-2-Adm,H),(11-85,Bu,A-13,O,S,O,5-OH-2-Adm,H),(11-86,Bu,A-14,O,S,O,5-OH-2-Adm,H),(11-87,Bu,A-15,O,S,O,5-OH-2-Adm,H),(11-88,Bu,A-16,O,S,O,5-OH-2-Adm,H),(11-89,Bu,A-17,O,S,O,5-OH-2-Adm,H),(11-90,Bu,A-18,O,S,O,5-OH-2-Adm,H),(11-91,Bu,A-19,O,S,O,5-OH-2-Adm,H),(11-92,Bu,A-20,O,S,O,5-OH-2-Adm,H),(11-93,Bu,A-21,O,S,O,5-OH-2-Adm,H),(11-94,Bu,A-22,O,S,O,5-OH-2-Adm,H),(11-95,Bu,A-23,O,S,O,5-OH-2-Adm,H),(11-96,Bu,A-24,O,S,O,5-OH-2-Adm,H),(11-97,Bu,A-25,O,S,O,5-OH-2-Adm,H),(11-98,Bu,A-26,O,S,O,5-OH-2-Adm,H),(11-99,Bu,A-27,O,S,O,5-OH-2-Adm,H),(11-100,Bu,A-28,O,S,O,5-OH-2-Adm,H),(11-101,Bu,A-29,O,S,O,5-OH-2-Adm,H),(11-102,Bu,A-30,O,S,O,5-OH-2-Adm,H),(11-103,Bu,A-31,O,S,O,5-OH-2-Adm,H),(11-104,Bu,A-32,O,S,O,5-OH-2-Adm,H),(11-105,Bu,A-33,O,S,O,5-OH-2-Adm,H),(11-106,Bu,A-34,O,S,O,5-OH-2-Adm,H),(11-107,Bu,A-35,O,S,O,5-OH-2-Adm,H),(11-108,Bu,A-36,O,S,O,5-OH-2-Adm,H),(11-109,Bu,B-1,O,S,O,1-Adm,H),(11-110,Bu,B-2,O,S,O,1-Adm,H),(11-111,Bu,B-3,O,S,O,1-Adm,H),(11-112,Bu,B-4,O,S,O,1-Adm,H),(11-113,Bu,B-5,O,S,O,1-Adm,H),(11-114,Bu,B-6,O,S,O,1-Adm,H),(11-115,Bu,B-7,O,S,O,1-Adm,H),(11-116,Bu,B-8,O,S,O,1-Adm,H),(11-117,Bu,B-9,O,S,O,1-Adm,H),(11-118,Bu,B-10,O,S,O,1-Adm,H),(11-119,Bu,B-11,O,S,O,1-Adm,H),(11-120,Bu,B-12,O,S,O,1-Adm,H),(11-121,Bu,B-13,O,S,O,1-Adm,H),(11-122,Bu,B-14,O,S,O,1-Adm,H),(11-123,Bu,B-15,O,S,O,1-Adm,H),(11-124,Bu,B-16,O,S,O,1-Adm,H),(11-125,Bu,B-17,O,S,O,1-Adm,H),(11-126,Bu,B-18,O,S,O,1-Adm,H),(11-127,Bu,B-19,O,S,O,1-Adm,H),(11-128,Bu,B-20,O,S,O,1-Adm,H),(11-129,Bu,B-21,O,S,O,1-Adm,H),(11-130,Bu,B-22,O,S,O,1-Adm,H),(11-131,Bu,B-23,O,S,O,1-Adm,H),(11-132,Bu,B-24,O,S,O,1-Adm,H),(11-133,Bu,B-25,O,S,O,1-Adm,H),(11-134,Bu,B-26,O,S,O,1-Adm,H),(11-135,Bu,B-27,O,S,O,1-Adm,H),(11-136,Bu,B-28,O,S,O,1-Adm,H),(11-137,Bu,B-29,O,S,O,1-Adm,H),(11-138,Bu,B-30,O,S,O,1-Adm,H),(11-139,Bu,B-31,O,S,O,1-Adm,H),(11-140,Bu,B-32,O,S,O,1-Adm,H),(11-141,Bu,B-33,O,S,O,1-Adm,H),(11-142,Bu,B-34,O,S,O,1-Adm,H),(11-143,Bu,B-35,O,S,O,1-Adm,H),(11-144,Bu,B-36,O,S,O,1-Adm,H),(11-145,Bu,B-1,O,S,O,2-Adm,H),(11-146,Bu,B-2,O,S,O,2-Adm,H),(11-147,Bu,B-3,O,S,O,2-Adm,H),(11-148,Bu,B-4,O,S,O,2-Adm,H),(11-149,Bu,B-5,O,S,O,2-Adm,H),(11-150,Bu,B-6,O,S,O,2-Adm,H),(11-151,Bu,B-7,O,S,O,2-Adm,H),(11-152,Bu,B-8,O,S,O,2-Adm,H),(11-153,Bu,B-9,O,S,O,2-Adm,H),(11-154,Bu,B-10,O,S,O,2-Adm,H),(11-155,Bu,B-11,O,S,O,2-Adm,H),(11-156,Bu,B-12,O,S,O,2-Adm,H),(11-157,Bu,B-13,O,S,O,2-Adm,H),(11-158,Bu,B-14,O,S,O,2-Adm,H),(11-159,Bu,B-15,O,S,O,2-Adm,H),(11-160,Bu,B-16,O,S,O,2-Adm,H),(11-161,Bu,B-17,O,S,O,2-Adm,H),(11-162,Bu,B-18,O,S,O,2-Adm,H),(11-163,Bu,B-19,O,S,O,2-Adm,H), (11-164,Bu,B-20,O,S,O,2-Adm,H),(11-165,Bu,B-21,O,S,O,2-Adm,H),(11-166,Bu,B-22,O,S,O,2-Adm,H),(11-167,Bu,B-23,O,S,O,2-Adm,H),(11-168,Bu,B-24,O,S,O,2-Adm,H),(11-169,Bu,B-25,O,S,O,2-Adm,H),(11-170,Bu,B-26,O,S,O,2-Adm,H),(11-171,Bu,B-27,O,S,O,2-Adm,H),(11-172,Bu,B-28,O,S,O,2-Adm,H),(11-173,Bu,B-29,O,S,O,2-Adm,H),(11-174,Bu,B-30,O,S,O,2-Adm,H),(11-175,Bu,B-31,O,S,O,2-Adm,H),(11-176,Bu,B-32,O,S,O,2-Adm,H),(11-177,Bu,B-33,O,S,O,2-Adm,H),(11-178,Bu,B-34,O,S,O,2-Adm,H),(11-179,Bu,B-35,O,S,O,2-Adm,H),(11-180,Bu,B-36,O,S,O,2-Adm,H),(11-181,Bu,B-1,O,S,O,5-OH-2-Adm,H),(11-182,Bu,B-2,O,S,O,5-OH-2-Adm,H),(11-183,Bu,B-3,O,S,O,5-OH-2-Adm,H),(11-184,Bu,B-4,O,S,O,5-OH-2-Adm,H),(11-185,Bu,B-5,O,S,O,5-OH-2-Adm,H),(11-186,Bu,B-6,O,S,O,5-OH-2-Adm,H),(11-187,Bu,B-7,O,S,O,5-OH-2-Adm,H),(11-188,Bu,B-8,O,S,O,5-OH-2-Adm,H),(11-189,Bu,B-9,O,S,O,5-OH-2-Adm,H),(11-190,Bu,B-10,O,S,O,5-OH-2-Adm,H),(11-191,Bu,B-11,O,S,O,5-OH-2-Adm,H),(11-192,Bu,B-12,O,S,O,5-OH-2-Adm,H),(11-193,Bu,B-13,O,S,O,5-OH-2-Adm,H),(11-194,Bu,B-14,O,S,O,5-OH-2-Adm,H),(11-195,Bu,B-15,O,S,O,5-OH-2-Adm,H),(11-196,Bu,B-16,O,S,O,5-OH-2-Adm,H),(11-197,Bu,B-17,O,S,O,5-OH-2-Adm,H),(11-198,Bu,B-18,O,S,O,5-OH-2-Adm,H),(11-199,Bu,B-19,O,S,O,5-OH-2-Adm,H),(11-200,Bu,B-20,O,S,O,5-OH-2-Adm,H),(11-201,Bu,B-21,O,S,O,5-OH-2-Adm,H),(11-202,Bu,B-22,O,S,O,5-OH-2-Adm,H),(11-203,Bu,B-23,O,S,O,5-OH-2-Adm,H),(11-204,Bu,B-24,O,S,O,5-OH-2-Adm,H),(11-205,Bu,B-25,O,S,O,5-OH-2-Adm,H),(11-206,Bu,B-26,O,S,O,5-OH-2-Adm,H),(11-207,Bu,B-27,O,S,O,5-OH-2-Adm,H),(11-208,Bu,B-28,O,S,O,5-OH-2-Adm,H),(11-209,Bu,B-29,O,S,O,5-OH-2-Adm,H),(11-210,Bu,B-30,O,S,O,5-OH-2-Adm,H),(11-211,Bu,B-31,O,S,O,5-OH-2-Adm,H),(11-212,Bu,B-32,O,S,O,5-OH-2-Adm,H),(11-213,Bu,B-33,O,S,O,5-OH-2-Adm,H),(11-214,Bu,B-34,O,S,O,5-OH-2-Adm,H),(11-215,Bu,B-35,O,S,O,5-OH-2-Adm,H),(11-216,Bu,B-36,O,S,O,5-OH-2-Adm,H),(11-217,Bu,C-1,O,S,O,1-Adm,H),(11-218,Bu,C-2,O,S,O,1-Adm,H),(11-219,Bu,C-3,O,S,O,1-Adm,H),(11-220,Bu,C-4,O,S,O,1-Adm,H),(11-221,Bu,C-5,O,S,O,1-Adm,H),(11-222,Bu,C-6,O,S,O,1-Adm,H),(11-223,Bu,C-7,O,S,O,1-Adm,H),(11-224,Bu,C-8,O,S,O,1-Adm,H),(11-225,Bu,C-9,O,S,O,1-Adm,H),(11-226,Bu,C-10,O,S,O,1-Adm,H),(11-227,Bu,C-11,O,S,O,1-Adm,H),(11-228,Bu,C-12,O,S,O,1-Adm,H),(11-229,Bu,C-13,O,S,O,1-Adm,H),(11-230,Bu,C-14,O,S,O,1-Adm,H),(11-231,Bu,C-15,O,S,O,1-Adm,H),(11-232,Bu,C-16,O,S,O,1-Adm,H),(11-233,Bu,C-17,O,S,O,1-Adm,H),(11-234,Bu,C-18,O,S,O,1-Adm,H),(11-235,Bu,C-19,O,S,O,1-Adm,H),(11-236,Bu,C-20,O,S,O,1-Adm,H),(11-237,Bu,C-21,O,S,O,1-Adm,H),(11-238,Bu,C-22,O,S,O,1-Adm,H),(11-239,Bu,C-23,O,S,O,1-Adm,H),(11-240,Bu,C-24,O,S,O,1-Adm,H),(11-241,Bu,C-25,O,S,O,1-Adm,H),(11-242,Bu,C-26,O,S,O,1-Adm,H),(11-243,Bu,C-27,O,S,O,1-Adm,H),(11-244,Bu,C-28,O,S,O,1-Adm,H),(11-245,Bu,C-29,O,S,O,1-Adm,H),(11-246,Bu,C-30,O,S,O,1-Adm,H),(11-247,Bu,C-31,O,S,O,1-Adm,H),(11-248,Bu,C-32,O,S,O,1-Adm,H),(11-249,Bu,C-33,O,S,O,1-Adm,H),(11-250,Bu,C-34,O,S,O,1-Adm,H),(11-251,Bu,C-35,O,S,O,1-Adm,H),(11-252,Bu,C-36,O,S,O,1-Adm,H),(11-253,Bu,C-1,O,S,O,2-Adm,H),(11-254,Bu,C-2,O,S,O,2-Adm,H),(11-255,Bu,C-3,O,S,O,2-Adm,H),(11-256,Bu,C-4,O,S,O,2-Adm,H),(11-257,Bu,C-5,O,S,O,2-Adm,H),(11-258,Bu,C-6,O,S,O,2-Adm,H),(11-259,Bu,C-7,O,S,O,2-Adm,H),(11-260,Bu,C-8,O,S,O,2-Adm,H),(11-261,Bu,C-9,O,S,O,2-Adm,H),(11-262,Bu,C-10,O,S,O,2-Adm,H),(11-263,Bu,C-11,O,S,O,2-Adm,H),(11-264,Bu,C-12,O,S,O,2-Adm,H),(11-265,Bu,C-13,O,S,O,2-Adm,H),(11-266,Bu,C-14,O,S,O,2-Adm,H),(11-267,Bu,C-15,O,S,O,2-Adm,H),(11-268,Bu,C-16,O,S,O,2-Adm,H), (11-269,Bu,C-17,O,S, O,2-Adm,H),(11-270,Bu,C-18,O,S,O,2-Adm,H),(11-271, Bu,C-19,O,S,O,2-Adm,H),(11-272,Bu,C-20,O,S,O,2-Adm, H),(11-273,Bu,C-21,O,S,O,2-Adm,H),(11-274,Bu,C-22,O, S,O,2-Adm,H),(11-275,Bu,C-23,O,S,O,2-Adm,H),(11-276, Bu,C-24,O,S,O,2-Adm,H),(11-277,Bu,C-25,O,S,O,2-Adm, H),(11-278,Bu,C-26,O,S,O,2-Adm,H),(11-279,Bu,C-27,O, S,O,2-Adm,H),(11-280,Bu,C-28,O,S,O,2-Adm,H),(11-281, Bu,C-29,O,S,O,2-Adm,H),(11-282,Bu,C-30,O,S,O,2-Adm, H),(11-283,Bu,C-31,O,S,O,2-Adm,H),(11-284,Bu,C-32,O, S,O,2-Adm,H),(11-285,Bu,C-33,O,S,O,2-Adm,H),(11-286, Bu,C-34,O,S,O,2-Adm,H),(11-287,Bu,C-35,O,S,O,2-Adm, H),(11-288,Bu,C-36,O,S,O,2-Adm,H),(11-289,Bu,C-1,O,S, O,5-OH-2-Adm,H),(11-290,Bu,C-2,O,S,O,5-OH-2-Adm, H),(11-291,Bu,C-3,O,S,O,5-OH-2-Adm,H),(11-292,Bu,C-4,O,S,O,5-OH-2-Adm,H),(11-293,Bu,C-5,O,S,O,5-OH-2-Adm,H),(11-294,Bu,C-6,O,S,O,5-OH-2-Adm,H),(11-295, Bu,C-7,O,S,O,5-OH-2-Adm,H),(11-296,Bu,C-8,O,S,O,5-OH-2-Adm,H),(11-297,Bu,C-9,O,S,O,5-OH-2-Adm,H), (11-298,Bu,C-10,O,S,O,5-OH-2-Adm,H),(11-299,Bu,C-11, O,S,O,5-OH-2-Adm,H),(11-300,Bu,C-12,O,S,O,5-OH-2-Adm,H),(11-301,Bu,C-13,O,S,O,5-OH-2-Adm,H),(11-302, Bu,C-14,O,S,O,5-OH-2-Adm,H),(11-303,Bu,C-15,O,S,O, 5-OH-2-Adm,H),(11-304,Bu,C-16,O,S,O,5-OH-2-Adm,H), (11-305,Bu,C-17,O,S,O,5-OH-2-Adm,H),(11-306,Bu,C-18, O,S,O,5-OH-2-Adm,H),(11-307,Bu,C-19,O,S,O,5-OH-2-Adm,H),(11-308,Bu,C-20,O,S,O,5-OH-2-Adm,H),(11-309, Bu,C-21,O,S,O,5-OH-2-Adm,H),(11-310,Bu,C-22,O,S,O, 5-OH-2-Adm,H),(11-311,Bu,C-23,O,S,O,5-OH-2-Adm,H), (11-312,Bu,C-24,O,S,O,5-OH-2-Adm,H),(11-313,Bu,C-25, O,S,O,5-OH-2-Adm,H),(11-314,Bu,C-26,O,S,O,5-OH-2-Adm,H),(11-315,Bu,C-27,O,S,O,5-OH-2-Adm,H),(11-316, Bu,C-28,O,S,O,5-OH-2-Adm,H),(11-317,Bu,C-29,O,S,O, 5-OH-2-Adm,H),(11-318,Bu,C-30,O,S,O,5-OH-2-Adm,H), (11-319,Bu,C-31,O,S,O,5-OH-2-Adm,H),(11-320,Bu,C-32, O,S,O,5-OH-2-Adm,H),(11-321,Bu,C-33,O,S,O,5-OH-2-Adm,H),(11-322,Bu,C-34,O,S,O,5-OH-2-Adm,H),(11-323, Bu,C-35,O,S,O,5-OH-2-Adm,H),(11-324,Bu,C-36,O,S,O, 5-OH-2-Adm,H),(11-325,Bu,D-1,O,S,O,1-Adm,H),(11-326,Bu,D-2,O,S,O,1-Adm,H),(11-327,Bu,D-3,O,S,O,1-Adm,H),(11-328,Bu,D-4,O,S,O,1-Adm,H),(11-329,Bu,D-5, O,S,O,1-Adm,H),(11-330,Bu,D-6,O,S,O,1-Adm,H),(11-331,Bu,D-7,O,S,O,1-Adm,H),(11-332,Bu,D-8,O,S,O,1-Adm,H),(11-333,Bu,D-9,O,S,O,1-Adm,H),(11-334,Bu,D-10,O,S,O,1-Adm,H),(11-335,Bu,D-11,O,S,O,1-Adm,H), (11-336,Bu,D-12,O,S,O,1-Adm,H),(11-337,Bu,D-13,O,S, O,1-Adm,H),(11-338,Bu,D-14,O,S,O,1-Adm,H),(11-339, Bu,D-15,O,S,O,1-Adm,H),(11-340,Bu,D-16,O,S,O,1-Adm, H),(11-341,Bu,D-17,O,S,O,1-Adm,H),(11-342,Bu,D-18,O, S,O,1-Adm,H),(11-343,Bu,D-19,O,S,O,1-Adm,H),(11-344, Bu,D-20,O,S,O,1-Adm,H),(11-345,Bu,D-21,O,S,O,1-Adm, H),(11-346,Bu,D-22,O,S,O,1-Adm,H),(11-347,Bu,D-23,O, S,O,1-Adm,H),(11-348,Bu,D-24,O,S,O,1-Adm,H),(11-349, Bu,D-25,O,S,O,1-Adm,H),(11-350,Bu,D-26,O,S,O,1-Adm, H),(11-351,Bu,D-27,O,S,O,1-Adm,H),(11-352,Bu,D-28,O, S,O,1-Adm,H),(11-353,Bu,D-29,O,S,O,1-Adm,H),(11-354, Bu,D-30,O,S,O,1-Adm,H),(11-355,Bu,D-31,O,S,O,1-Adm, H),(11-356,Bu,D-32,O,S,O,1-Adm,H),(11-357,Bu,D-33,O, S,O,1-Adm,H),(11-358,Bu,D-34,O,S,O,1-Adm,H),(11-359, Bu,D-35,O,S,O,1-Adm,H),(11-360,Bu,D-36,O,S,O,1-Adm, H),(11-361,Bu,D-1,O,S,O,2-Adm,H),(11-362,Bu,D-2,O,S, O,2-Adm,H),(11-363,Bu,D-3,O,S,O,2-Adm,H),(11-364,Bu, D-4,O,S,O,2-Adm,H),(11-365,Bu,D-5,O,S,O,2-Adm,H), (11-366,Bu,D-6,O,S,O,2-Adm,H),(11-367,Bu,D-7,O,S,O,2-Adm,H),(11-368,Bu,D-8,O,S,O,2-Adm,H),(11-369,Bu,D-9, O,S,O,2-Adm,H),(11-370,Bu,D-10,O,S,O,2-Adm,H),(11-371,Bu,D-11,O,S,O,2-Adm,H),(11-372,Bu,D-12,O,S,O,2-Adm,H),(11-373,Bu,D-13,O,S,O,2-Adm,H),(11-374,Bu,D-14,O,S,O,2-Adm,H),(11-375,Bu,D-15,O,S,O,2-Adm,H), (11-376,Bu,D-16,O,S,O,2-Adm,H),(11-377,Bu,D-17,O,S, O,2-Adm,H),(11-378,Bu,D-18,O,S,O,2-Adm,H),(11-379, Bu,D-19,O,S,O,2-Adm,H),(11-380,Bu,D-20,O,S,O,2-Adm, H),(11-381,Bu,D-21,O,S,O,2-Adm,H),(11-382,Bu,D-22,O, S,O,2-Adm,H),(11-383,Bu,D-23,O,S,O,2-Adm,H),(11-384, Bu,D-24,O,S,O,2-Adm,H),(11-385,Bu,D-25,O,S,O,2-Adm, H),(11-386,Bu,D-26,O,S,O,2-Adm,H),(11-387,Bu,D-27,O, S,O,2-Adm,H),(11-388,Bu,D-28,O,S,O,2-Adm,H),(11-389, Bu,D-29,O,S,O,2-Adm,H),(11-390,Bu,D-30,O,S,O,2-Adm, H),(11-391,Bu,D-31,O,S,O,2-Adm,H),(11-392,Bu,D-32,O, S,O,2-Adm,H),(11-393,Bu,D-33,O,S,O,2-Adm,H),(11-394, Bu,D-34,O,S,O,2-Adm,H),(11-395,Bu,D-35,O,S,O,2-Adm, H),(11-396,Bu,D-36,O,S,O,2-Adm,H),(11-397,Bu,D-1,O,S, O,5-OH-2-Adm,H),(11-398,Bu,D-2,O,S,O,5-OH-2-Adm, H),(11-399,Bu,D-3,O,S,O,5-OH-2-Adm,H),(11-400,Bu,D-4,O,S,O,5-OH-2-Adm,H),(11-401,Bu,D-5,O,S,O,5-OH-2-Adm,H),(11-402,Bu,D-6,O,S,O,5-OH-2-Adm,H),(11-403, Bu,D-7,O,S,O,5-OH-2-Adm,H),(11-404,Bu,D-8,O,S,O,5-OH-2-Adm,H),(11-405,Bu,D-9,O,S,O,5-OH-2-Adm,H), (11-406,Bu,D-10,O,S,O,5-OH-2-Adm,H),(11-407,Bu,D-11,O,S,O,5-OH-2-Adm,H),(11-408,Bu,D-12,O,S,O,5-OH-2-Adm,H),(11-409,Bu,D-13,O,S,O,5-OH-2-Adm,H),(11-410,Bu,D-14,O,S,O,5-OH-2-Adm,H),(11-411,Bu,D-15,O, S,O,5-OH-2-Adm,H),(11-412,Bu,D-16,O,S,O,5-OH-2-Adm,H),(11-413,Bu,D-17,O,S,O,5-OH-2-Adm,H),(11-414, Bu,D-18,O,S,O,5-OH-2-Adm,H),(11-415,Bu,D-19,O,S,O, 5-OH-2-Adm,H),(11-416,Bu,D-20,O,S,O,5-OH-2-Adm,H), (11-417,Bu,D-21,O,S,O,5-OH-2-Adm,H),(11-418,Bu,D-22,O,S,O,5-OH-2-Adm,H),(11-419,Bu,D-23,O,S,O,5-OH-2-Adm,H),(11-420,Bu,D-24,O,S,O,5-OH-2-Adm,H),(11-421,Bu,D-25,O,S,O,5-OH-2-Adm,H),(11-422,Bu,D-26,O, S,O,5-OH-2-Adm,H),(11-423,Bu,D-27,O,S,O,5-OH-2-Adm,H),(11-424,Bu,D-28,O,S,O,5-OH-2-Adm,H),(11-425, Bu,D-29,O,S,O,5-OH-2-Adm,H),(11-426,Bu,D-30,O,S,O, 5-OH-2-Adm,H),(11-427,Bu,D-31,O,S,O,5-OH-2-Adm,H), (11-428,Bu,D-32,O,S,O,5-OH-2-Adm,H),(11-429,Bu,D-33,O,S,O,5-OH-2-Adm,H),(11-430,Bu,D-34,O,S,O,5-OH-2-Adm,H),(11-431,Bu,D-35,O,S,O,5-OH-2-Adm,H),(11-432,Bu,D-36,O,S,O,5-OH-2-Adm,H),(11-433,Bu,E-1,O,S, O,1-Adm,H),(11-434,Bu,E-2,O,S,O,1-Adm,H),(11-435,Bu, E-3,O,S,O,1-Adm,H),(11-436,Bu,E-4,O,S,O,1-Adm,H), (11-437,Bu,E-5,O,S,O,1-Adm,H),(11-438,Bu,E-6,O,S,O,1-Adm,H),(11-439,Bu,E-7,O,S,O,1-Adm,H),(11-440,Bu,E-8, O,S,O,1-Adm,H),(11-441,Bu,E-9,O,S,O,1-Adm,H),(11-442,Bu,E-10,O,S,O,1-Adm,H),(11-443,Bu,E-11,O,S,O,1-Adm,H),(11-444,Bu,E-12,O,S,O,1-Adm,H),(11-445,Bu,E-13,O,S,O,1-Adm,H),(11-446,Bu,E-14,O,S,O,1-Adm,H), (11-447,Bu,E-15,O,S,O,1-Adm,H),(11-448,Bu,E-16,O,S,O, 1-Adm,H),(11-449,Bu,E-17,O,S,O,1-Adm,H),(11-450,Bu, E-18,O,S,O,1-Adm,H),(11-451,Bu,E-19,O,S,O,1-Adm,H), (11-452,Bu,E-20,O,S,O,1-Adm,H),(11-453,Bu,E-21,O,S,O, 1-Adm,H),(11-454,Bu,E-22,O,S,O,1-Adm,H),(11-455,Bu, E-23,O,S,O,1-Adm,H),(11-456,Bu,E-24,O,S,O,1-Adm,H), (11-457,Bu,E-25,O,S,O,1-Adm,H),(11-458,Bu,E-26,O,S,O, 1-Adm,H),(11-459,Bu,E-27,O,S,O,1-Adm,H),(11-460,Bu, E-28,O,S,O,1-Adm,H),(11-461,Bu,E-29,O,S,O,1-Adm,H), (11-462,Bu,E-30,O,S,O,1-Adm,H),(11-463,Bu,E-31,O,S,O, 1-Adm,H),(11-464,Bu,E-32,O,S,O,1-Adm,H),(11-465,Bu, E-33,O,S,O,1-Adm,H),(11-466,Bu,E-34,O,S,O,1-Adm,H), (11-467,Bu,E-35,O,S,O,1-Adm,H),(11-468,Bu,E-36,O,S,O, 1-Adm,H),(11-469,Bu,E-1,O,S,O,2-Adm,H),(11-470,Bu,E-2,O,S,O,2-Adm,H),(11-471,Bu,E-3,O,S,O,2-Adm,H),(11-472,Bu,E-4,O,S,O,2-Adm,H),(11-473,Bu,E-5,O,S,O,2-Adm,H),(11-474,Bu,E-6,O,S,O,2-Adm,H),(11-475,Bu,E-7, O,S,O,2-Adm,H),(11-476,Bu,E-8,O,S,O,2-Adm,H),(11-477,Bu,E-9,O,S,O,2-Adm,H),    (11-478,Bu,E-10,O,S,O,2-

Adm,H),(11-479,Bu,E-11,O,S,O,2-Adm,H),(11-480,Bu,E-12,O,S,O,2-Adm,H),(11-481,Bu,E-13,O,S,O,2-Adm,H), (11-482,Bu,E-14,O,S,O,2-Adm,H),(11-483,Bu,E-15,O,S,O,2-Adm,H),(11-484,Bu,E-16,O,S,O,2-Adm,H),(11-485,Bu,E-17,O,S,O,2-Adm,H),(11-486,Bu,E-18,O,S,O,2-Adm,H), (11-487,Bu,E-19,O,S,O,2-Adm,H),(11-488,Bu,E-20,O,S,O,2-Adm,H),(11-489,Bu,E-21,O,S,O,2-Adm,H),(11-490,Bu,E-22,O,S,O,2-Adm,H),(11-491,Bu,E-23,O,S,O,2-Adm,H),(11-492,Bu,E-24,O,S,O,2-Adm,H),(11-493,Bu,E-25,O,S,O,2-Adm,H),(11-494,Bu,E-26,O,S,O,2-Adm,H),(11-495,Bu,E-27,O,S,O,2-Adm,H),(11-496,Bu,E-28,O,S,O,2-Adm,H), (11-497,Bu,E-29,O,S,O,2-Adm,H),(11-498,Bu,E-30,O,S,O,2-Adm,H),(11-499,Bu,E-31,O,S,O,2-Adm,H),(11-500,Bu,E-32,O,S,O,2-Adm,H),(11-501,Bu,E-33,O,S,O,2-Adm,H), (11-502,Bu,E-34,O,S,O,2-Adm,H),(11-503,Bu,E-35,O,S,O,2-Adm,H),(11-504,Bu,E-36,O,S,O,2-Adm,H),(11-505,Bu,E-1,O,S,O,5-OH-2-Adm,H),(11-506,Bu,E-2,O,S,O,5-OH-2-Adm,H),(11-507,Bu,E-3,O,S,O,5-OH-2-Adm,H),(11-508,Bu,E-4,O,S,O,5-OH-2-Adm,H),(11-509,Bu,E-5,O,S,O,5-OH-2-Adm,H),(11-510,Bu,E-6,O,S,O,5-OH-2-Adm,H), (11-511,Bu,E-7,O,S,O,5-OH-2-Adm,H),(11-512,Bu,E-8,O,S,O,5-OH-2-Adm,H),(11-513,Bu,E-9,O,S,O,5-OH-2-Adm,H),(11-514,Bu,E-10,O,S,O,5-OH-2-Adm,H),(11-515,Bu,E-11,O,S,O,5-OH-2-Adm,H),(11-516,Bu,E-12,O,S,O,5-OH-2-Adm,H),(11-517,Bu,E-13,O,S,O,5-OH-2-Adm,H),(11-518,Bu,E-14,O,S,O,5-OH-2-Adm,H),(11-519,Bu,E-15,S,O,5-OH-2-Adm,H),(11-520,Bu,E-16,O,S,O,5-OH-2-Adm,H),(11-521,Bu,E-17,O,S,O,5-OH-2-Adm,H),(11-522,Bu,E-18,O,S,O,5-OH-2-Adm,H),(11-523,Bu,E-19,O,S,O,5-OH-2-Adm,H),(11-524,Bu,E-20,O,S,O,5-OH-2-Adm,H),(11-525,Bu,E-21,O,S,O,5-OH-2-Adm,H),(11-526,Bu,E-22,O,S,O,5-OH-2-Adm,H),(11-527,Bu,E-23,O,S,O,5-OH-2-Adm,H),(11-528,Bu,E-24,O,S,O,5-OH-2-Adm,H),(11-529,Bu,E-25,O,S,O,5-OH-2-Adm,H),(11-530,Bu,E-26,O,S,O,5-OH-2-Adm,H),(11-531,Bu,E-27,O,S,O,5-OH-2-Adm,H),(11-532,Bu,E-28,O,S,O,5-OH-2-Adm,H),(11-533,Bu,E-29,O,S,O,5-OH-2-Adm,H),(11-534,Bu,E-30,O,S,O,5-OH-2-Adm,H),(11-535,Bu,E-31,O,S,O,5-OH-2-Adm,H),(11-536,Bu,E-32,O,S,O,5-OH-2-Adm,H),(11-537,Bu,E-33,O,S,O,5-OH-2-Adm,H),(11-538,Bu,E-34,O,S,O,5-OH-2-Adm,H),(11-539,Bu,E-35,O,S,O,5-OH-2-Adm,H),(11-540,Bu,E-36,O,S,O,5-OH-2-Adm,H),(11-541,Bu,F-1,O,S,O,1-Adm,H),(11-542,Bu,F-2,O,S,O,1-Adm,H),(11-543,Bu,F-3,O,S,O,1-Adm,H),(11-544,Bu,F-4,O,S,O,1-Adm,H),(11-545,Bu,F-5,O,S,O,1-Adm,H),(11-546,Bu,F-6,O,S,O,1-Adm,H),(11-547,Bu,F-7,O,S,O,1-Adm,H),(11-548,Bu,F-8,O,S,O,1-Adm,H),(11-549,Bu,F-9,O,S,O,1-Adm,H),(11-550,Bu,F-10,O,S,O,1-Adm,H),(11-551,Bu,F-11,O,S,O,1-Adm,H), (11-552,Bu,F-12,O,S,O,1-Adm,H),(11-553,Bu,F-13,O,S,O,1-Adm,H),(11-554,Bu,F-14,O,S,O,1-Adm,H),(11-555,Bu,F-15,O,S,O,1-Adm,H),(11-556,Bu,F-16,O,S,O,1-Adm,H), (11-557,Bu,F-17,O,S,O,1-Adm,H),(11-558,Bu,F-18,O,S,O,1-Adm,H),(11-559,Bu,F-19,O,S,O,1-Adm,H),(11-560,Bu,F-20,O,S,O,1-Adm,H),(11-561,Bu,F-21,O,S,O,1-Adm,H), (11-562,Bu,F-22,O,S,O,1-Adm,H),(11-563,Bu,F-23,O,S,O,1-Adm,H),(11-564,Bu,F-24,O,S,O,1-Adm,H),(11-565,Bu,F-25,O,S,O,1-Adm,H),(11-566,Bu,F-26,O,S,O,1-Adm,H), (11-567,Bu,F-27,O,S,O,1-Adm,H),(11-568,Bu,F-28,O,S,O,1-Adm,H),(11-569,Bu,F-29,O,S,O,1-Adm,H),(11-570,Bu,F-30,O,S,O,1-Adm,H),(11-571,Bu,F-31,O,S,O,1-Adm,H), (11-572,Bu,F-32,O,S,O,1-Adm,H),(11-573,Bu,F-33,O,S,O,1-Adm,H),(11-574,Bu,F-34,O,S,O,1-Adm,H),(11-575,Bu,F-35,O,S,O,1-Adm,H),(11-576,Bu,F-36,O,S,O,1-Adm,H), (11-577,Bu,F-1,O,S,O,2-Adm,H),(11-578,Bu,F-2,O,S,O,2-Adm,H),(11-579,Bu,F-3,O,S,O,2-Adm,H),(11-580,Bu,F-4,O,S,O,2-Adm,H),(11-581,Bu,F-5,O,S,O,2-Adm,H),(11-582,Bu,F-6,O,S,O,2-Adm,H),(11-583,Bu,F-7,O,S,O,2-Adm,H),(11-584,Bu, F-8,O,S,O,2-Adm,H),(11-585,Bu,F-9,O,S,O,2-Adm,H),(11-586,Bu,F-10,O,S,O,2-Adm,H),(11-587,Bu,F-11,O,S,O,2-Adm,H),(11-588,Bu,F-12,O,S,O,2-Adm,H),(11-589,Bu,F-13,O,S,O,2-Adm,H),(11-590,Bu,F-14,O,S,O,2-Adm,H),(11-591,Bu,F-15,O,S,O,2-Adm,H), (11-592,Bu,F-16,O,S,O,2-Adm,H),(11-593,Bu,F-17,O,S,O,2-Adm,H),(11-594,Bu,F-18,O,S,O,2-Adm,H),(11-595,Bu,F-19,O,S,O,2-Adm,H),(11-596,Bu,F-20,O,S,O,2-Adm,H), (11-597,Bu,F-21,O,S,O,2-Adm,H),(11-598,Bu,F-22,O,S,O,2-Adm,H),(11-599,Bu,F-23,O,S,O,2-Adm,H),(11-600,Bu,F-24,O,S,O,2-Adm,H),(11-601,Bu,F-25,O,S,O,2-Adm,H), (11-602,Bu,F-26,O,S,O,2-Adm,H),(11-603,Bu,F-27,O,S,O,2-Adm,H),(11-604,Bu,F-28,O,S,O,2-Adm,H),(11-605,Bu,F-29,O,S,O,2-Adm,H),(11-606,Bu,F-30,O,S,O,2-Adm,H), (11-607,Bu,F-31,O,S,O,2-Adm,H),(11-608,Bu,F-32,O,S,O,2-Adm,H),(11-609,Bu,F-33,O,S,O,2-Adm,H),(11-610,Bu,F-34,O,S,O,2-Adm,H),(11-611,Bu,F-35,O,S,O,2-Adm,H), (11-612,Bu,F-36,O,S,O,2-Adm,H),(11-613,Bu,F-1,O,S,O,5-OH-2-Adm,H),(11-614,Bu,F-2,O,S,O,5-OH-2-Adm,H), (11-615,Bu,F-3,O,S,O,5-OH-2-Adm,H),(11-616,Bu,F-4,O,S,O,5-OH-2-Adm,H),(11-617,Bu,F-5,O,S,O,5-OH-2-Adm,H),(11-618,Bu,F-6,O,S,O,5-OH-2-Adm,H),(11-619,Bu,F-7,O,S,O,5-OH-2-Adm,H),(11-620,Bu,F-8,O,S,O,5-OH-2-Adm,H),(11-621,Bu,F-9,O,S,O,5-OH-2-Adm,H),(11-622,Bu,F-10,O,S,O,5-OH-2-Adm,H),(11-623,Bu,F-11,O,S,O,5-OH-2-Adm,H),(11-624,Bu,F-12,O,S,O,5-OH-2-Adm,H), (11-625,Bu,F-13,O,S,O,5-OH-2-Adm,H),(11-626,Bu,F-14,O,S,O,5-OH-2-Adm,H),(11-627,Bu,F-15,O,S,O,5-OH-2-Adm,H),(11-628,Bu,F-16,O,S,O,5-OH-2-Adm,H),(11-629,Bu,F-17,O,S,O,5-OH-2-Adm,H),(11-630,Bu,F-18,O,S,O,5-OH-2-Adm,H),(11-631,Bu,F-19,O,S,O,5-OH-2-Adm,H), (11-632,Bu,F-20,O,S,O,5-OH-2-Adm,H),(11-633,Bu,F-21,O,S,O,5-OH-2-Adm,H),(11-634,Bu,F-22,O,S,O,5-OH-2-Adm,H),(11-635,Bu,F-23,O,S,O,5-OH-2-Adm,H),(11-636,Bu,F-24,O,S,O,5-OH-2-Adm,H),(11-637,Bu,F-25,O,S,O,5-OH-2-Adm,H),(11-638,Bu,F-26,O,S,O,5-OH-2-Adm,H), (11-639,Bu,F-27,O,S,O,5-OH-2-Adm,H),(11-640,Bu,F-28,O,S,O,5-OH-2-Adm,H),(11-641,Bu,F-29,O,S,O,5-OH-2-Adm,H),(11-642,Bu,F-30,O,S,O,5-OH-2-Adm,H),(11-643,Bu,F-31,O,S,O,5-OH-2-Adm,H),(11-644,Bu,F-32,O,S,O,5-OH-2-Adm,H),(11-645,Bu,F-33,O,S,O,5-OH-2-Adm,H), (11-646,Bu,F-34,O,S,O,5-OH-2-Adm,H),(11-647,Bu,F-35,O,S,O,5-OH-2-Adm,H),(11-648,Bu,F-36,O,S,O,5-OH-2-Adm,H),(11-649,Bu,G-1,O,S,O,1-Adm,H),(11-650,Bu,G-2,O,S,O,1-Adm,H),(11-651,Bu,G-3,O,S,O,1-Adm,H),(11-652,Bu,G-4,O,S,O,1-Adm,H),(11-653,Bu,G-5,O,S,O,1-Adm,H),(11-654,Bu,G-6,O,S,O,1-Adm,H),(11-655,Bu,G-7,O,S,O,1-Adm,H),(11-656,Bu,G-8,O,S,O,1-Adm,H),(11-657,Bu,G-9,O,S,O,1-Adm,H),(11-658,Bu,G-1,O,S,O,2-Adm,H),(11-659,Bu,G-2,O,S,O,2-Adm,H),(11-660,Bu,G-3,O,S,O,2-Adm,H),(11-661,Bu,G-4,O,S,O,2-Adm,H),(11-662,Bu,G-5,O,S,O,2-Adm,H),(11-663,Bu,G-6,O,S,O,2-Adm,H),(11-664,Bu,G-7,O,S,O,2-Adm,H),(11-665,Bu,G-8,O,S,O,2-Adm,H),(11-666,Bu,G-9,O,S,O,2-Adm,H),(11-667,Bu,G-1,O,S,O,5-OH-2-Adm,H),(11-668,Bu,G-2,O,S,O,5-OH-2-Adm,H),(11-669,Bu,G-3,O,S,O,5-OH-2-Adm,H),(11-670,Bu,G-4,O,S,O,5-OH-2-Adm,H),(11-671,Bu,G-5,O,S,O,5-OH-2-Adm,H),(11-672,Bu,G-6,O,S,O,5-OH-2-Adm,H),(11-673,Bu,G-7,O,S,O,5-OH-2-Adm,H),(11-674,Bu,G-8,O,S,O,5-OH-2-Adm,H),(11-675,Bu,G-9,O,S,O,5-OH-2-Adm,H),(11-676,Bu,H-1,O,S,O,1-Adm,H),(11-677,Bu,H-2,O,S,O,1-Adm,H),(11-678,Bu,H-3,O,S,O,1-Adm,H),(11-679,Bu,H-4,O,S,O,1-Adm,H),(11-680,Bu,H-5,O,S,O,1-Adm,H),(11-681,Bu,H-6,O,S,O,1-Adm,H),(11-682,Bu,H-7,O,S,O,1-Adm,H),(11-683,Bu,H-8,O,S,O,1-Adm,H), (11-684,Bu,H-9,O,S,O,1-Adm,H),(11-685,Bu,H-1,O,S,O,2-Adm,H),(11-686,Bu,H-2,O,S,O,2-Adm,H),(11-687,Bu,H-3,

O,S,O,2-Adm,H),(11-688,Bu,H-4,O,S,O,2-Adm,H),(11-689,Bu,H-5,O,S,O,2-Adm,H),(11-690,Bu,H-6,O,S,O,2-Adm,H),(11-691,Bu,H-7,O,S,O,2-Adm,H),(11-692,Bu,H-8,O,S,O,2-Adm,H),(11-693,Bu,H-9,O,S,O,2-Adm,H),(11-694,Bu,H-1,O,S,O,5-OH-2-Adm,H),(11-695,Bu,H-2,O,S,O,5-OH-2-Adm,H),(11-696,Bu,H-3,O,S,O,5-OH-2-Adm,H),(11-697,Bu,H-4,O,S,O,5-OH-2-Adm,H),(11-698,Bu,H-5,O,S,O,5-OH-2-Adm,H),(11-699,Bu,H-6,O,S,O,5-OH-2-Adm,H),(11-700,Bu,H-7,O,S,O,5-OH-2-Adm,H),(11-701,Bu,H-8,O,S,O,5-OH-2-Adm,H),(11-702,Bu,H-9,O,S,O,5-OH-2-Adm,H),(11-703,Bu,I-1,O,S,O,1-Adm,H),(11-704,Bu,I-2,O,S,O,1-Adm,H),(11-705,Bu,I-3,O,S,O,1-Adm,H),(11-706,Bu,I-4,O,S,O,1-Adm,H),(11-707,Bu,I-5,O,S,O,1-Adm,H),(11-708,Bu,I-6,O,S,O,1-Adm,H),(11-709,Bu,I-7,O,S,O,1-Adm,H),(11-710,Bu,I-8,O,S,O,1-Adm,H),(11-711,Bu,I-9,O,S,O,1-Adm,H),(11-712,Bu,I-1,O,S,O,2-Adm,H),(11-713,Bu,I-2,O,S,O,2-Adm,H),(11-714,Bu,I-3,O,S,O,2-Adm,H),(11-715,Bu,I-4,O,S,O,2-Adm,H),(11-716,Bu,I-5,O,S,O,2-Adm,H),(11-717,Bu,I-6,O,S,O,2-Adm,H),(11-718,Bu,I-7,O,S,O,2-Adm,H),(11-719,Bu,I-8,O,S,O,2-Adm,H),(11-720,Bu,I-9,O,S,O,2-Adm,H),(11-721,Bu,I-1,O,S,O,5-OH-2-Adm,H),(11-722,Bu,I-2,O,S,O,5-OH-2-Adm,H),(11-723,Bu,I-3,O,S,O,5-OH-2-Adm,H),(11-724,Bu,I-4,O,S,O,5-OH-2-Adm,H),(11-725,Bu,I-5,O,S,O,5-OH-2-Adm,H),(11-726,Bu,I-6,O,S,O,5-OH-2-Adm,H),(11-727,Bu,I-7,O,S,O,5-OH-2-Adm,H),(11-728,Bu,I-8,O,S,O,5-OH-2-Adm,H),(11-729,Bu,I-9,O,S,O,5-OH-2-Adm,H),(11-730,Bu,J-1,O,S,O,1-Adm,H),(11-731,Bu,J-2,O,S,O,1-Adm,H),(11-732,Bu,J-3,O,S,O,1-Adm,H),(11-733,Bu,J-4,O,S,O,1-Adm,H),(11-734,Bu,J-5,O,S,O,1-Adm,H),(11-735,Bu,J-6,O,S,O,1-Adm,H),(11-736,Bu,J-7,O,S,O,1-Adm,H),(11-737,Bu,J-8,O,S,O,1-Adm,H),(11-738,Bu,J-9,O,S,O,1-Adm,H),(11-739,Bu,J-1,O,S,O,2-Adm,H),(11-740,Bu,J-2,O,S,O,2-Adm,H),(11-741,Bu,J-3,O,S,O,2-Adm,H),(11-742,Bu,J-4,O,S,O,2-Adm,H),(11-743,Bu,J-5,O,S,O,2-Adm,H),(11-744,Bu,J-6,O,S,O,2-Adm,H),(11-745,Bu,J-7,O,S,O,2-Adm,H),(11-746,Bu,J-8,O,S,O,2-Adm,H),(11-747,Bu,J-9,O,S,O,2-Adm,H),(11-748,Bu,J-1,O,S,O,5-OH-2-Adm,H),(11-749,Bu,J-2,O,S,O,5-OH-2-Adm,H),(11-750,Bu,J-3,O,S,O,5-OH-2-Adm,H),(11-751,Bu,J-4,O,S,O,5-OH-2-Adm,H),(11-752,Bu,J-5,O,S,O,5-OH-2-Adm,H),(11-753,Bu,J-6,O,S,O,5-OH-2-Adm,H),(11-754,Bu,J-7,O,S,O,5-OH-2-Adm,H),(11-755,Bu,J-8,O,S,O,5-OH-2-Adm,H),(11-756,Bu,J-9,O,S,O,5-OH-2-Adm,H),(11-757,Bu,K-1,O,S,O,1-Adm,H),(11-758,Bu,K-2,O,S,O,1-Adm,H),(11-759,Bu,K-3,O,S,O,1-Adm,H),(11-760,Bu,K-4,O,S,O,1-Adm,H),(11-761,Bu,K-5,O,S,O,1-Adm,H),(11-762,Bu,K-6,O,S,O,1-Adm,H),(11-763,Bu,K-7,O,S,O,1-Adm,H),(11-764,Bu,K-8,O,S,O,1-Adm,H),(11-765,Bu,K-9,O,S,O,1-Adm,H),(11-766,Bu,K-1,O,S,O,2-Adm,H),(11-767,Bu,K-2,O,S,O,2-Adm,H),(11-768,Bu,K-3,O,S,O,2-Adm,H),(11-769,Bu,K-4,O,S,O,2-Adm,H),(11-770,Bu,K-5,O,S,O,2-Adm,H),(11-771,Bu,K-6,O,S,O,2-Adm,H),(11-772,Bu,K-7,O,S,O,2-Adm,H),(11-773,Bu,K-8,O,S,O,2-Adm,H),(11-774,Bu,K-9,O,S,O,2-Adm,H),(11-775,Bu,K-1,O,S,O,5-OH-2-Adm,H),(11-776,Bu,K-2,O,S,O,5-OH-2-Adm,H),(11-777,Bu,K-3,O,S,O,5-OH-2-Adm,H),(11-778,Bu,K-4,O,S,O,5-OH-2-Adm,H),(11-779,Bu,K-5,O,S,O,5-OH-2-Adm,H),(11-780,Bu,K-6,O,S,O,5-OH-2-Adm,H),(11-781,Bu,K-7,O,S,O,5-OH-2-Adm,H),(11-782,Bu,K-8,O,S,O,5-OH-2-Adm,H),(11-783,Bu,K-9,O,S,O,5-OH-2-Adm,H)

(Compound No., $R^2,R^3,X,Y,Z,R^4,R^5$)=(12-1,i-Pro,A-1,O,S,O,1-Adm,H),(12-2,i-Pro,A-2,O,S,O,1-Adm,H),(12-3,i-Pro,A-3,O,S,O,1-Adm,H),(12-4,i-Pro,A-4,O,S,O,1-Adm,H),(12-5,i-Pro,A-5,O,S,O,1-Adm,H),(12-6,i-Pro,A-6,O,S,O,1-Adm,H),(12-7,i-Pro,A-7,O,S,O,1-Adm,H),(12-8,i-Pro,A-8,O,S,O,1-Adm,H),(12-9,i-Pro,A-9,O,S,O,1-Adm,H),(12-10,i-Pro,A-10,O,S,O,1-Adm,H),(12-11,i-Pro,A-11,O,S,O,1-Adm,H),(12-12,i-Pro,A-12,O,S,O,1-Adm,H),(12-13,i-Pro,A-13,O,S,O,1-Adm,H),(12-14,i-Pro,A-14,O,S,O,1-Adm,H),(12-15,i-Pro,A-15,O,S,O,1-Adm,H),(12-16,i-Pro,A-16,O,S,O,1-Adm,H),(12-17,i-Pro,A-17,O,S,O,1-Adm,H),(12-18,i-Pro,A-18,O,S,O,1-Adm,H),(12-19,i-Pro,A-19,O,S,O,1-Adm,H),(12-20,i-Pro,A-20,O,S,O,1-Adm,H),(12-21,i-Pro,A-21,O,S,O,1-Adm,H),(12-22,i-Pro,A-22,O,S,O,1-Adm,H),(12-23,i-Pro,A-23,O,S,O,1-Adm,H),(12-24,i-Pro,A-24,O,S,O,1-Adm,H),(12-25,i-Pro,A-25,O,S,O,1-Adm,H),(12-26,i-Pro,A-26,O,S,O,1-Adm,H),(12-27,i-Pro,A-27,O,S,O,1-Adm,H),(12-28,i-Pro,A-28,O,S,O,1-Adm,H),(12-29,i-Pro,A-29,O,S,O,1-Adm,H),(12-30,i-Pro,A-30,O,S,O,1-Adm,H),(12-31,i-Pro,A-31,O,S,O,1-Adm,H),(12-32,i-Pro,A-32,O,S,O,1-Adm,H),(12-33,i-Pro,A-33,O,S,O,1-Adm,H),(12-34,i-Pro,A-34,O,S,O,1-Adm,H),(12-35,i-Pro,A-35,O,S,O,1-Adm,H),(12-36,i-Pro,A-36,O,S,O,1-Adm,H),(12-37,i-Pro,A-1,O,S,O,2-Adm,H),(12-38,i-Pro,A-2,O,S,O,2-Adm,H),(12-39,i-Pro,A-3,O,S,O,2-Adm,H),(12-40,i-Pro,A-4,O,S,O,2-Adm,H),(12-41,i-Pro,A-5,O,S,O,2-Adm,H),(12-42,i-Pro,A-6,O,S,O,2-Adm,H),(12-43,i-Pro,A-7,O,S,O,2-Adm,H),(12-44,i-Pro,A-9,O,S,O,2-Adm,H),(12-45,i-Pro,A-11,O,S,O,2-Adm,H),(12-46,i-Pro,A-12,O,S,O,2-Adm,H),(12-47,i-Pro,A-13,O,S,O,2-Adm,H),(12-48,i-Pro,A-14,O,S,O,2-Adm,H),(12-49,i-Pro,A-15,O,S,O,2-Adm,H),(12-50,i-Pro,A-16,O,S,O,2-Adm,H),(12-51,i-Pro,A-17,O,S,O,2-Adm,H),(12-52,i-Pro,A-18,O,S,O,2-Adm,H),(12-53,i-Pro,A-20,O,S,O,2-Adm,H),(12-54,i-Pro,A-21,O,S,O,2-Adm,H),(12-55,i-Pro,A-22,O,S,O,2-Adm,H),(12-56,i-Pro,A-23,O,S,O,2-Adm,H),(12-57,i-Pro,A-24,O,S,O,2-Adm,H),(12-58,i-Pro,A-26,O,S,O,2-Adm,H),(12-59,i-Pro,A-27,O,S,O,2-Adm,H),(12-60,i-Pro,A-28,O,S,O,2-Adm,H),(12-61,i-Pro,A-29,O,S,O,2-Adm,H),(12-62,i-Pro,A-30,O,S,O,2-Adm,H),(12-63,i-Pro,A-31,O,S,O,2-Adm,H),(12-64,i-Pro,A-32,O,S,O,2-Adm,H),(12-65,i-Pro,A-33,O,S,O,2-Adm,H),(12-66,i-Pro,A-34,O,S,O,2-Adm,H),(12-67,i-Pro,A-35,O,S,O,2-Adm,H),(12-68,i-Pro,A-36,O,S,O,2-Adm,H),(12-69,i-Pro,A-1,O,S,O,5-OH-2-Adm,H),(12-70,i-Pro,A-2,O,S,O,5-OH-2-Adm,H),(12-71,i-Pro,A-3,O,S,O,5-OH-2-Adm,H),(12-72,i-Pro,A-4,O,S,O,5-OH-2-Adm,H),(12-73,i-Pro,A-5,O,S,O,5-OH-2-Adm,H),(12-74,i-Pro,A-6,O,S,O,5-OH-2-Adm,H),(12-75,i-Pro,A-7,O,S,O,5-OH-2-Adm,H),(12-76,i-Pro,A-8,O,S,O,5-OH-2-Adm,H),(12-77,i-Pro,A-9,O,S,O,5-OH-2-Adm,H),(12-78,i-Pro,A-10,O,S,O,5-OH-2-Adm,H),(12-79,i-Pro,A-11,O,S,O,5-OH-2-Adm,H),(12-80,i-Pro,A-12,O,S,O,5-OH-2-Adm,H),(12-81,i-Pro,A-13,O,S,O,5-OH-2-Adm,H),(12-82,i-Pro,A-14,O,S,O,5-OH-2-Adm,H),(12-83,i-Pro,A-15,O,S,O,5-OH-2-Adm,H),(12-84,i-Pro,A-16,O,S,O,5-OH-2-Adm,H),(12-85,i-Pro,A-17,O,S,O,5-OH-2-Adm,H),(12-86,i-Pro,A-18,O,S,O,5-OH-2-Adm,H),(12-87,i-Pro,A-19,O,S,O,5-OH-2-Adm,H),(12-88,i-Pro,A-20,O,S,O,5-OH-2-Adm,H),(12-89,i-Pro,A-21,O,S,O,5-OH-2-Adm,H),(12-90,i-Pro,A-22,O,S,O,5-OH-2-Adm,H),(12-91,i-Pro,A-23,O,S,O,5-OH-2-Adm,H),(12-92,i-Pro,A-24,O,S,O,5-OH-2-Adm,H),(12-93,i-Pro,A-25,O,S,O,5-OH-2-Adm,H),(12-94,i-Pro,A-26,O,S,O,5-OH-2-Adm,H),(12-95,i-Pro,A-27,O,S,O,5-OH-2-Adm,H),(12-96,i-Pro,A-28,O,S,O,5-OH-2-Adm,H),(12-97,i-Pro,A-29,O,S,O,5-OH-2-Adm,H),(12-98,i-Pro,A-30,O,S,O,5-OH-2-Adm,H),(12-99,i-Pro,A-31,O,S,O,5-OH-2-Adm,H),(12-100,i-Pro,A-32,O,S,O,5-OH-2-Adm,H),(12-101,i-Pro,A-33,O,S,O,5-OH-2-Adm,H),(12-102,i-Pro,A-34,O,S,O,5-OH-2-Adm,H),(12-103,i-Pro,A-35,O,S,O,5-OH-2-Adm,H),(12-104,i-Pro,A-36,O,S,O,5-OH-2-Adm,H),(12-105,i-Pro,B-1,O,S,O,1-Adm,H),(12-106,i-Pro,B-2,O,S,O,1-Adm,H),(12-107,i-Pro,B-3,O,S,O,1-Adm,H),(12-108,i-Pro,B-4,O,S,O,1-Adm,H),(12-109,i-Pro,B-5,O,S,O,1-Adm,H),(12-110,i-Pro,B-6,O,S,O,1-Adm,H),(12-111,i-Pro,B-7,O,S,O,1-Adm,H),(12-112,i-Pro,B-8,O,S,O,1-Adm,H),(12-113,i-Pro,B-9,O,S,O,1-Adm,H),(12-114,i-

Pro,B-11,O,S,O,1-Adm,H),(12-115,i-Pro,B-11,O,S,O,1-Adm,H),(12-116,i-Pro,B-12,O,S,O,1-Adm,H),(12-117,i-Pro,B-13,O,S,O,1-Adm,H),(12-118,i-Pro,B-14,O,S,O,1-Adm,H),(12-119,i-Pro,B-15,O,S,O,1-Adm,H),(12-120,i-Pro,B-16,O,S,O,1-Adm,H),(12-121,i-Pro,B-17,O,S,O,1-Adm,H),(12-122,i-Pro,B-18,O,S,O,1-Adm,H),(12-123,i-Pro,B-19,O,S,O,1-Adm,H),(12-124,i-Pro,B-20,O,S,O,1-Adm,H),(12-125,i-Pro,B-21,O,S,O,1-Adm,H),(12-126,i-Pro,B-22,O,S,O,1-Adm,H),(12-127,i-Pro,B-23,O,S,O,1-Adm,H),(12-128,i-Pro,B-24,O,S,O,1-Adm,H),(12-129,i-Pro,B-25,O,S,O,1-Adm,H),(12-130,i-Pro,B-26,O,S,O,1-Adm,H),(12-131,i-Pro,B-27,O,S,O,1-Adm,H),(12-132,i-Pro,B-28,O,S,O,1-Adm,H),(12-133,i-Pro,B-29,O,S,O,1-Adm,H),(12-134,i-Pro,B-30,O,S,O,1-Adm,H),(12-135,i-Pro,B-31,O,S,O,1-Adm,H),(12-136,i-Pro,B-32,O,S,O,1-Adm,H),(12-137,i-Pro,B-33,O,S,O,1-Adm,H),(12-138,i-Pro,B-34,O,S,O,1-Adm,H),(12-139,i-Pro,B-35,O,S,O,1-Adm,H),(12-140,i-Pro,B-36,O,S,O,1-Adm,H),(12-141,i-Pro,B-1,O,S,O,2-Adm,H),(12-142,i-Pro,B-2,O,S,O,2-Adm,H),(12-143,i-Pro,B-3,O,S,O,2-Adm,H),(12-144,i-Pro,B-4,O,S,O,2-Adm,H),(12-145,i-Pro,B-5,O,S,O,2-Adm,H),(12-146,i-Pro,B-6,O,S,O,2-Adm,H),(12-147,i-Pro,B-7,O,S,O,2-Adm,H),(12-148,i-Pro,B-8,O,S,O,2-Adm,H),(12-149,i-Pro,B-9,O,S,O,2-Adm,H),(12-150,i-Pro,B-11,O,S,O,2-Adm,H),(12-151,i-Pro,B-11,O,S,O,2-Adm,H),(12-152,i-Pro,B-12,O,S,O,2-Adm,H),(12-153,i-Pro,B-13,O,S,O,2-Adm,H),(12-154,i-Pro,B-14,O,S,O,2-Adm,H),(12-155,i-Pro,B-15,O,S,O,2-Adm,H),(12-156,i-Pro,B-16,O,S,O,2-Adm,H),(12-157,i-Pro,B-17,O,S,O,2-Adm,H),(12-158,i-Pro,B-18,O,S,O,2-Adm,H),(12-159,i-Pro,B-19,O,S,O,2-Adm,H),(12-160,i-Pro,B-20,O,S,O,2-Adm,H),(12-161,i-Pro,B-21,O,S,O,2-Adm,H),(12-162,i-Pro,B-22,O,S,O,2-Adm,H),(12-163,i-Pro,B-23,O,S,O,2-Adm,H),(12-164,i-Pro,B-24,O,S,O,2-Adm,H),(12-165,i-Pro,B-25,O,S,O,2-Adm,H),(12-166,i-Pro,B-26,O,S,O,2-Adm,H),(12-167,i-Pro,B-27,O,S,O,2-Adm,H),(12-168,i-Pro,B-28,O,S,O,2-Adm,H),(12-169,i-Pro,B-29,O,S,O,2-Adm,H),(12-170,i-Pro,B-30,O,S,O,2-Adm,H),(12-171,i-Pro,B-31,O,S,O,2-Adm,H),(12-172,i-Pro,B-32,O,S,O,2-Adm,H),(12-173,i-Pro,B-33,O,S,O,2-Adm,H),(12-174,i-Pro,B-34,O,S,O,2-Adm,H),(12-175,i-Pro,B-35,O,S,O,2-Adm,H),(12-176,i-Pro,B-36,O,S,O,2-Adm,H),(12-177,i-Pro,B-1,O,S,O,5-OH-2-Adm,H),(12-178,i-Pro,B-2,O,S,O,5-OH-2-Adm,H),(12-179,i-Pro,B-3,O,S,O,5-OH-2-Adm,H),(12-180,i-Pro,B-4,O,S,O,5-OH-2-Adm,H),(12-181,i-Pro,B-5,O,S,O,5-OH-2-Adm,H),(12-182,i-Pro,B-6,O,S,O,5-OH-2-Adm,H),(12-183,i-Pro,B-7,O,S,O,5-OH-2-Adm,H),(12-184,i-Pro,B-8,O,S,O,5-OH-2-Adm,H),(12-185,i-Pro,B-9,O,S,O,5-OH-2-Adm,H),(12-186,i-Pro,B-10,O,S,O,5-OH-2-Adm,H),(12-187,i-Pro,B-11,O,S,O,5-OH-2-Adm,H),(12-188,i-Pro,B-12,O,S,O,5-OH-2-Adm,H),(12-189,i-Pro,B-13,O,S,O,5-OH-2-Adm,H),(12-190,i-Pro,B-14,O,S,O,5-OH-2-Adm,H),(12-191,i-Pro,B-15,O,S,O,5-OH-2-Adm,H),(12-192,i-Pro,B-16,O,S,O,5-OH-2-Adm,H),(12-193,i-Pro,B-17,O,S,O,5-OH-2-Adm,H),(12-194,i-Pro,B-18,O,S,O,5-OH-2-Adm,H),(12-195,i-Pro,B-19,O,S,O,5-OH-2-Adm,H),(12-196,i-Pro,B-20,O,S,O,5-OH-2-Adm,H),(12-197,i-Pro,B-21,O,S,O,5-OH-2-Adm,H),(12-198,i-Pro,B-22,O,S,O,5-OH-2-Adm,H),(12-199,i-Pro,B-23,O,S,O,5-OH-2-Adm,H),(12-200,i-Pro,B-24,O,S,O,5-OH-2-Adm,H),(12-201,i-Pro,B-25,O,S,O,5-OH-2-Adm,H),(12-202,i-Pro,B-26,O,S,O,5-OH-2-Adm,H),(12-203,i-Pro,B-27,O,S,O,5-OH-2-Adm,H),(12-204,i-Pro,B-28,O,S,O,5-OH-2-Adm,H),(12-205,i-Pro,B-29,O,S,O,5-OH-2-Adm,H),(12-206,i-Pro,B-30,O,S,O,5-OH-2-Adm,H),(12-207,i-Pro,B-31,O,S,O,5-OH-2-Adm,H),(12-208,i-Pro,B-32,O,S,O,5-OH-2-Adm,H),(12-209,i-Pro,B-33,O,S,O,5-OH-2-Adm,H),(12-210,i-Pro,B-34,O,S,O,5-OH-2-Adm,H),(12-211,i-Pro,B-35,O,S,O,5-OH-2-Adm,H),(12-212,i-Pro,B-36,O,S,O,5-OH-2-Adm,H),(12-213,i-Pro,C-1,O,S,O,1-Adm,H),(12-214,i-Pro,C-2,O,S,O,1-Adm,H),(12-215,i-Pro,C-3,O,S,O,1-Adm,H),(12-216,i-Pro,C-4,O,S,O,1-Adm,H),(12-217,i-Pro,C-5,O,S,O,1-Adm,H),(12-218,i-Pro,C-6,O,S,O,1-Adm,H),(12-219,i-Pro,C-7,O,S,O,1-Adm,H),(12-220,i-Pro,C-8,O,S,O,1-Adm,H),(12-221,i-Pro,C-9,O,S,O,1-Adm,H),(12-222,i-Pro,C-10,O,S,O,1-Adm,H),(12-223,i-Pro,C-11,O,S,O,1-Adm,H),(12-224,i-Pro,C-12,O,S,O,1-Adm,H),(12-225,i-Pro,C-13,O,S,O,1-Adm,H),(12-226,i-Pro,C-14,O,S,O,1-Adm,H),(12-227,i-Pro,C-15,O,S,O,1-Adm,H),(12-228,i-Pro,C-16,O,S,O,1-Adm,H),(12-229,i-Pro,C-17,O,S,O,1-Adm,H),(12-230,i-Pro,C-18,O,S,O,1-Adm,H),(12-231,i-Pro,C-19,O,S,O,1-Adm,H),(12-232,i-Pro,C-20,O,S,O,1-Adm,H),(12-233,i-Pro,C-21,O,S,O,1-Adm,H),(12-234,i-Pro,C-22,O,S,O,1-Adm,H),(12-235,i-Pro,C-23,O,S,O,1-Adm,H),(12-236,i-Pro,C-24,O,S,O,1-Adm,H),(12-237,i-Pro,C-25,O,S,O,1-Adm,H),(12-238,i-Pro,C-26,O,S,O,1-Adm,H),(12-239,i-Pro,C-27,O,S,O,1-Adm,H),(12-240,i-Pro,C-28,O,S,O,1-Adm,H),(12-241,i-Pro,C-29,O,S,O,1-Adm,H),(12-242,i-Pro,C-30,O,S,O,1-Adm,H),(12-243,i-Pro,C-31,O,S,O,1-Adm,H),(12-244,i-Pro,C-32,O,S,O,1-Adm,H),(12-245,i-Pro,C-33,O,S,O,1-Adm,H),(12-246,i-Pro,C-34,O,S,O,1-Adm,H),(12-247,i-Pro,C-35,O,S,O,1-Adm,H),(12-248,i-Pro,C-36,O,S,O,1-Adm,H),(12-249,i-Pro,C-1,O,S,O,2-Adm,H),(12-250,i-Pro,C-2,O,S,O,2-Adm,H),(12-251,i-Pro,C-3,O,S,O,2-Adm,H),(12-252,i-Pro,C-4,O,S,O,2-Adm,H),(12-253,i-Pro,C-5,O,S,O,2-Adm,H),(12-254,i-Pro,C-6,O,S,O,2-Adm,H),(12-255,i-Pro,C-7,O,S,O,2-Adm,H),(12-256,i-Pro,C-8,O,S,O,2-Adm,H),(12-257,i-Pro,C-9,O,S,O,2-Adm,H),(12-258,i-Pro,C-10,O,S,O,2-Adm,H),(12-259,i-Pro,C-11,O,S,O,2-Adm,H),(12-260,i-Pro,C-12,O,S,O,2-Adm,H),(12-261,i-Pro,C-13,O,S,O,2-Adm,H),(12-262,i-Pro,C-14,O,S,O,2-Adm,H),(12-263,i-Pro,C-15,O,S,O,2-Adm,H),(12-264,i-Pro,C-16,O,S,O,2-Adm,H),(12-265,i-Pro,C-17,O,S,O,2-Adm,H),(12-266,i-Pro,C-18,O,S,O,2-Adm,H),(12-267,i-Pro,C-19,O,S,O,2-Adm,H),(12-268,i-Pro,C-20,O,S,O,2-Adm,H),(12-269,i-Pro,C-21,O,S,O,2-Adm,H),(12-270,i-Pro,C-22,O,S,O,2-Adm,H),(12-271,i-Pro,C-23,O,S,O,2-Adm,H),(12-272,i-Pro,C-24,O,S,O,2-Adm,H),(12-273,i-Pro,C-25,O,S,O,2-Adm,H),(12-274,i-Pro,C-26,O,S,O,2-Adm,H),(12-275,i-Pro,C-27,O,S,O,2-Adm,H),(12-276,i-Pro,C-28,O,S,O,2-Adm,H),(12-277,i-Pro,C-29,O,S,O,2-Adm,H),(12-278,i-Pro,C-30,O,S,O,2-Adm,H),(12-279,i-Pro,C-31,O,S,O,2-Adm,H),(12-280,i-Pro,C-32,O,S,O,2-Adm,H),(12-281,i-Pro,C-33,O,S,O,2-Adm,H),(12-282,i-Pro,C-34,O,S,O,2-Adm,H),(12-283,i-Pro,C-35,O,S,O,2-Adm,H),(12-284,i-Pro,C-36,O,S,O,2-Adm,H),(12-285,i-Pro,C-1,O,S,O,5-OH-2-Adm,H),(12-286,i-Pro,C-2,O,S,O,5-OH-2-Adm,H),(12-287,i-Pro,C-3,O,S,O,5-OH-2-Adm,H),(12-288,i-Pro,C-4,O,S,O,5-OH-2-Adm,H),(12-289,i-Pro,C-5,O,S,O,5-OH-2-Adm,H),(12-290,i-Pro,C-6,O,S,O,5-OH-2-Adm,H),(12-291,i-Pro,C-7,O,S,O,5-OH-2-Adm,H),(12-292,i-Pro,C-8,O,S,O,5-OH-2-Adm,H),(12-293,i-Pro,C-9,O,S,O,5-OH-2-Adm,H),(12-294,i-Pro,C-10,O,S,O,5-OH-2-Adm,H),(12-295,i-Pro,C-11,O,S,O,5-OH-2-Adm,H),(12-296,i-Pro,C-12,O,S,O,5-OH-2-Adm,H),(12-297,i-Pro,C-13,O,S,O,5-OH-2-Adm,H),(12-298,i-Pro,C-14,O,S,O,5-OH-2-Adm,H),(12-299,i-Pro,C-15,O,S,O,5-OH-2-Adm,H),(12-300,i-Pro,C-16,O,S,O,5-OH-2-Adm,H),(12-301,i-Pro,C-17,O,S,O,5-OH-2-Adm,H),(12-302,i-Pro,C-18,O,S,O,5-OH-2-Adm,H),(12-303,i-Pro,C-19,O,S,O,5-OH-2-Adm,H),(12-304,i-Pro,C-20,O,S,O,5-OH-2-Adm,H),(12-305,i-Pro,C-21,O,S,O,5-OH-2-Adm,H),(12-306,i-Pro,C-22,O,S,O,5-OH-2-Adm,H),(12-307,i-Pro,C-23,O,S,O,5-OH-2-

Adm,H),(12-308,i-Pro,C-24,O,S,O,5-OH-2-Adm,H),(12-309,i-Pro,C-25,O,S,O,5-OH-2-Adm,H),(12-310,i-Pro,C-26,O,S,O,5-OH-2-Adm,H),(12-311,i-Pro,C-27,O,S,O,5-OH-2-Adm,H),(12-312,i-Pro,C-28,O,S,O,5-OH-2-Adm,H),(12-313,i-Pro,C-29,O,S,O,5-OH-2-Adm,H),(12-314,i-Pro,C-30,O,S,O,5-OH-2-Adm,H),(12-315,i-Pro,C-31,O,S,O,5-OH-2-Adm,H),(12-316,i-Pro,C-32,O,S,O,5-OH-2-Adm,H),(12-317,i-Pro,C-33,O,S,O,5-OH-2-Adm,H),(12-318,i-Pro,C-34,O,S,O,5-OH-2-Adm,H),(12-319,i-Pro,C-35,O,S,O,5-OH-2-Adm,H),(12-320,i-Pro,C-36,O,S,O,5-OH-2-Adm,H),(12-321,i-Pro,D-1,O,S,O,1-Adm,H),(12-322,i-Pro,D-2,O,S,O,1-Adm,H),(12-323,i-Pro,D-3,O,S,O,1-Adm,H),(12-324,i-Pro,D-4,O,S,O,1-Adm,H),(12-325,i-Pro,D-5,O,S,O,1-Adm,H),(12-326,i-Pro,D-6,O,S,O,1-Adm,H),(12-327,i-Pro,D-7,O,S,O,1-Adm,H),(12-328,i-Pro,D-8,O,S,O,1-Adm,H),(12-329,i-Pro,D-9,O,S,O,1-Adm,H),(12-330,i-Pro,D-11,O,S,O,1-Adm,H),(12-331,i-Pro,D-11,O,S,O,1-Adm,H),(12-332,i-Pro,D-12,O,S,O,1-Adm,H),(12-333,i-Pro,D-13,O,S,O,1-Adm,H),(12-334,i-Pro,D-14,O,S,O,1-Adm,H),(12-335,i-Pro,D-15,O,S,O,1-Adm,H),(12-336,i-Pro,D-16,O,S,O,1-Adm,H),(12-337,i-Pro,D-17,O,S,O,1-Adm,H),(12-338,i-Pro,D-18,O,S,O,1-Adm,H),(12-339,i-Pro,D-19,O,S,O,1-Adm,H),(12-340,i-Pro,D-20,O,S,O,1-Adm,H),(12-341,i-Pro,D-21,O,S,O,1-Adm,H),(12-342,i-Pro,D-22,O,S,O,1-Adm,H),(12-343,i-Pro,D-23,O,S,O,1-Adm,H),(12-344,i-Pro,D-24,O,S,O,1-Adm,H),(12-345,i-Pro,D-25,O,S,O,1-Adm,H),(12-346,i-Pro,D-26,O,S,O,1-Adm,H),(12-347,i-Pro,D-27,O,S,O,1-Adm,H),(12-348,i-Pro,D-28,O,S,O,1-Adm,H),(12-349,i-Pro,D-29,O,S,O,1-Adm,H),(12-350,i-Pro,D-30,O,S,O,1-Adm,H),(12-351,i-Pro,D-31,O,S,O,1-Adm,H),(12-352,i-Pro,D-32,O,S,O,1-Adm,H),(12-353,i-Pro,D-33,O,S,O,1-Adm,H),(12-354,i-Pro,D-34,O,S,O,1-Adm,H),(12-355,i-Pro,D-35,O,S,O,1-Adm,H),(12-356,i-Pro,D-36,O,S,O,1-Adm,H),(12-357,i-Pro,D-1,O,S,O,2-Adm,H),(12-358,i-Pro,D-2,O,S,O,2-Adm,H),(12-359,i-Pro,D-3,O,S,O,2-Adm,H),(12-360,i-Pro,D-4,O,S,O,2-Adm,H),(12-361,i-Pro,D-5,O,S,O,2-Adm,H),(12-362,i-Pro,D-6,O,S,O,2-Adm,H),(12-363,i-Pro,D-7,O,S,O,2-Adm,H),(12-364,i-Pro,D-8,O,S,O,2-Adm,H),(12-365,i-Pro,D-9,O,S,O,2-Adm,H),(12-366,i-Pro,D-11,O,S,O,2-Adm,H),(12-367,i-Pro,D-11,O,S,O,2-Adm,H),(12-368,i-Pro,D-12,O,S,O,2-Adm,H),(12-369,i-Pro,D-13,O,S,O,2-Adm,H),(12-370,i-Pro,D-14,O,S,O,2-Adm,H),(12-371,i-Pro,D-15,O,S,O,2-Adm,H),(12-372,i-Pro,D-16,O,S,O,2-Adm,H),(12-373,i-Pro,D-17,O,S,O,2-Adm,H),(12-374,i-Pro,D-18,O,S,O,2-Adm,H),(12-375,i-Pro,D-19,O,S,O,2-Adm,H),(12-376,i-Pro,D-20,O,S,O,2-Adm,H),(12-377,i-Pro,D-21,O,S,O,2-Adm,H),(12-378,i-Pro,D-22,O,S,O,2-Adm,H),(12-379,i-Pro,D-23,O,S,O,2-Adm,H),(12-380,i-Pro,D-24,O,S,O,2-Adm,H),(12-381,i-Pro,D-25,O,S,O,2-Adm,H),(12-382,i-Pro,D-26,O,S,O,2-Adm,H),(12-383,i-Pro,D-27,O,S,O,2-Adm,H),(12-384,i-Pro,D-28,O,S,O,2-Adm,H),(12-385,i-Pro,D-29,O,S,O,2-Adm,H),(12-386,i-Pro,D-30,O,S,O,2-Adm,H),(12-387,i-Pro,D-31,O,S,O,2-Adm,H),(12-388,i-Pro,D-32,O,S,O,2-Adm,H),(12-389,i-Pro,D-33,O,S,O,2-Adm,H),(12-390,i-Pro,D-34,O,S,O,2-Adm,H),(12-391,i-Pro,D-35,O,S,O,2-Adm,H),(12-392,i-Pro,D-36,O,S,O,2-Adm,H),(12-393,i-Pro,D-1,O,S,O,5-OH-2-Adm,H),(12-394,i-Pro,D-2,O,S,O,5-OH-2-Adm,H),(12-395,i-Pro,D-3,O,S,O,5-OH-2-Adm,H),(12-396,i-Pro,D-4,O,S,O,5-OH-2-Adm,H),(12-397,i-Pro,D-5,O,S,O,5-OH-2-Adm,H),(12-398,i-Pro,D-6,O,S,O,5-OH-2-Adm,H),(12-399,i-Pro,D-7,O,S,O,5-OH-2-Adm,H),(12-400,i-Pro,D-8,O,S,O,5-OH-2-Adm,H),(12-401,i-Pro,D-9,O,S,O,5-OH-2-Adm,H),(12-402,i-Pro,D-10,O,S,O,5-OH-2-Adm,H),(12-403,i-Pro,D-11,O,S,O,5-OH-2-Adm,H),(12-404,i-Pro,D-12,O,S,O,5-OH-2-Adm,H),(12-405,i-Pro,D-13,O,S,O,5-OH-2-Adm,H), (12-406,i-Pro,D-14,O,S,O,5-OH-2-Adm,H),(12-407,i-Pro,D-15,O,S,O,5-OH-2-Adm,H),(12-408,i-Pro,D-16,O,S,O,5-OH-2-Adm,H),(12-409,i-Pro,D-17,O,S,O,5-OH-2-Adm,H),(12-410,i-Pro,D-18,O,S,O,5-OH-2-Adm,H),(12-411,i-Pro,D-19,O,S,O,5-OH-2-Adm,H),(12-412,i-Pro,D-20,O,S,O,5-OH-2-Adm,H),(12-413,i-Pro,D-21,O,S,O,5-OH-2-Adm,H),(12-414,i-Pro,D-22,O,S,O,5-OH-2-Adm,H),(12-415,i-Pro,D-23,O,S,O,5-OH-2-Adm,H),(12-416,i-Pro,D-24,O,S,O,5-OH-2-Adm,H),(12-417,i-Pro,D-25,O,S,O,5-OH-2-Adm,H),(12-418,i-Pro,D-26,O,S,O,5-OH-2-Adm,H),(12-419,i-Pro,D-27,O,S,O,5-OH-2-Adm,H),(12-420,i-Pro,D-28,O,S,O,5-OH-2-Adm,H),(12-421,i-Pro,D-29,O,S,O,5-OH-2-Adm,H),(12-422,i-Pro,D-30,O,S,O,5-OH-2-Adm,H),(12-423,i-Pro,D-31,O,S,O,5-OH-2-Adm,H),(12-424,i-Pro,D-32,O,S,O,5-OH-2-Adm,H),(12-425,i-Pro,D-33,O,S,O,5-OH-2-Adm,H),(12-426,i-Pro,D-34,O,S,O,5-OH-2-Adm,H),(12-427,i-Pro,D-35,O,S,O,5-OH-2-Adm,H),(12-428,i-Pro,D-36,O,S,O,5-OH-2-Adm,H),(12-429,i-Pro,E-1,O,S,O,1-Adm,H),(12-430,i-Pro,E-2,O,S,O,1-Adm,H),(12-431,i-Pro,E-3,O,S,O,1-Adm,H),(12-432,i-Pro,E-4,O,S,O,1-Adm,H),(12-433,i-Pro,E-5,O,S,O,1-Adm,H),(12-434,i-Pro,E-6,O,S,O,1-Adm,H),(12-435,i-Pro,E-7,O,S,O,1-Adm,H),(12-436,i-Pro,E-8,O,S,O,1-Adm,H),(12-437,i-Pro,E-9,O,S,O,1-Adm,H),(12-438,i-Pro,E-11,O,S,O,1-Adm,H),(12-439,i-Pro,E-11,O,S,O,1-Adm,H),(12-440,i-Pro,E-12,O,S,O,1-Adm,H),(12-441,i-Pro,E-13,O,S,O,1-Adm,H),(12-442,i-Pro,E-14,O,S,O,1-Adm,H),(12-443,i-Pro,E-15,O,S,O,1-Adm,H),(12-444,i-Pro,E-16,O,S,O,1-Adm,H),(12-445,i-Pro,E-17,O,S,O,1-Adm,H),(12-446,i-Pro,E-18,O,S,O,1-Adm,H),(12-447,i-Pro,E-19,O,S,O,1-Adm,H),(12-448,i-Pro,E-20,O,S,O,1-Adm,H),(12-449,i-Pro,E-21,O,S,O,1-Adm,H),(12-450,i-Pro,E-22,O,S,O,1-Adm,H),(12-451,i-Pro,E-23,O,S,O,1-Adm,H),(12-452,i-Pro,E-24,O,S,O,1-Adm,H),(12-453,i-Pro,E-25,O,S,O,1-Adm,H),(12-454,i-Pro,E-26,O,S,O,1-Adm,H),(12-455,i-Pro,E-27,O,S,O,1-Adm,H),(12-456,i-Pro,E-28,O,S,O,1-Adm,H),(12-457,i-Pro,E-29,O,S,O,1-Adm,H),(12-458,i-Pro,E-30,O,S,O,1-Adm,H),(12-459,i-Pro,E-31,O,S,O,1-Adm,H),(12-460,i-Pro,E-32,O,S,O,1-Adm,H),(12-461,i-Pro,E-33,O,S,O,1-Adm,H),(12-462,i-Pro,E-34,O,S,O,1-Adm,H),(12-463,i-Pro,E-35,O,S,O,1-Adm,H),(12-464,i-Pro,E-36,O,S,O,1-Adm,H),(12-465,i-Pro,E-1,O,S,O,2-Adm,H),(12-466,i-Pro,E-2,O,S,O,2-Adm,H),(12-467,i-Pro,E-3,O,S,O,2-Adm,H),(12-468,i-Pro,E-4,O,S,O,2-Adm,H),(12-469,i-Pro,E-5,O,S,O,2-Adm,H),(12-470,i-Pro,E-6,O,S,O,2-Adm,H),(12-471,i-Pro,E-7,O,S,O,2-Adm,H),(12-472,i-Pro,E-8,O,S,O,2-Adm,H),(12-473,i-Pro,E-9,O,S,O,2-Adm,H),(12-474,i-Pro,E-10,O,S,O,2-Adm,H),(12-475,i-Pro,E-11,O,S,O,2-Adm,H),(12-476,i-Pro,E-12,O,S,O,2-Adm,H),(12-477,i-Pro,E-13,O,S,O,2-Adm,H),(12-478,i-Pro,E-14,O,S,O,2-Adm,H),(12-479,i-Pro,E-15,O,S,O,2-Adm,H),(12-480,i-Pro,E-16,O,S,O,2-Adm,H),(12-481,i-Pro,E-17,O,S,O,2-Adm,H),(12-482,i-Pro,E-18,O,S,O,2-Adm,H),(12-483,i-Pro,E-19,O,S,O,2-Adm,H),(12-484,i-Pro,E-20,O,S,O,2-Adm,H),(12-485,i-Pro,E-21,O,S,O,2-Adm,H),(12-486,i-Pro,E-22,O,S,O,2-Adm,H),(12-487,i-Pro,E-23,O,S,O,2-Adm,H),(12-488,i-Pro,E-24,O,S,O,2-Adm,H),(12-489,i-Pro,E-25,O,S,O,2-Adm,H),(12-490,i-Pro,E-26,O,S,O,2-Adm,H),(12-491,i-Pro,E-27,O,S,O,2-Adm,H),(12-492,i-Pro,E-28,O,S,O,2-Adm,H),(12-493,i-Pro,E-29,O,S,O,2-Adm,H),(12-494,i-Pro,E-30,O,S,O,2-Adm,H),(12-495,i-Pro,E-31,O,S,O,2-Adm,H),(12-496,i-Pro,E-32,O,S,O,2-Adm,H),(12-497,i-Pro,E-33,O,S,O,2-Adm,H),(12-498,i-Pro,E-34,O,S,O,2-Adm,H),(12-499,i-Pro,E-35,O,S,O,2-Adm,H),(12-500,i-Pro,E-36,O,S,O,2-Adm,H),(12-501,i-Pro,E-1,O,S,O,5-OH-2-Adm,H),(12-502,i-Pro,E-2,O,S,O,5-OH-2-Adm,H),(12-503,i-Pro,E-3,O,S,O,5-OH-2-Adm,H),(12-504,i-Pro, E-4,O,S,O,5-OH-2-Adm,H),(12-505,i-

Pro,E-5,O,S,O,5-OH-2-Adm,H),(12-506,i-Pro,E-6,O,S,O,
5-OH-2-Adm,H),(12-507,i-Pro,E-7,O,S,O,5-OH-2-Adm,
H),(12-508,i-Pro,E-8,O,S,O,5-OH-2-Adm,H),(12-509,i-
Pro,E-9,O,S,O,5-OH-2-Adm,H),(12-510,i-Pro,E-10,O,S,O,
5-OH-2-Adm,H),(12-511,i-Pro,E-11,O,S,O,5-OH-2-Adm,
H),(12-512,i-Pro,E-12,O,S,O,5-OH-2-Adm,H),(12-513,i-
Pro,E-13,O,S,O,5-OH-2-Adm,H),(12-514,i-Pro,E-14,O,S,
O,5-OH-2-Adm,H),(12-515,i-Pro,E-15,O,S,O,5-OH-2-
Adm,H),(12-516,i-Pro,E-16,O,S,O,5-OH-2-Adm,H),(12-
517,i-Pro,E-17,O,S,O,5-OH-2-Adm,H),(12-518,i-Pro,E-18,
O,S,O,5-OH-2-Adm,H),(12-519,i-Pro,E-19,O,S,O,5-OH-2-
Adm,H),(12-520,i-Pro,E-20,O,S,O,5-OH-2-Adm,H),(12-
521,i-Pro,E-21,O,S,O,5-OH-2-Adm,H),(12-522,i-Pro,E-22,
O,S,O,5-OH-2-Adm,H),(12-523,i-Pro,E-23,O,S,O,5-OH-2-
Adm,H),(12-524,i-Pro,E-24,O,S,O,5-OH-2-Adm,H),(12-
525,i-Pro,E-25,O,S,O,5-OH-2-Adm,H),(12-526,i-Pro,E-26,
O,S,O,5-OH-2-Adm,H),(12-527,i-Pro,E-27,O,S,O,5-OH-2-
Adm,H),(12-528,i-Pro,E-28,O,S,O,5-OH-2-Adm,H),(12-
529,i-Pro,E-29,O,S,O,5-OH-2-Adm,H),(12-530,i-Pro,E-30,
O,S,O,5-OH-2-Adm,H),(12-531,i-Pro,E-31,O,S,O,5-OH-2-
Adm,H),(12-532,i-Pro,E-32,O,S,O,5-OH-2-Adm,H),(12-
533,i-Pro,E-33,O,S,O,5-OH-2-Adm,H),(12-534,i-Pro,E-34,
O,S,O,5-OH-2-Adm,H),(12-535,i-Pro,E-35,O,S,O,5-OH-2-
Adm,H),(12-536,i-Pro,E-36,O,S,O,5-OH-2-Adm,H),(12-
537,i-Pro,F-1,O,S,O,1-Adm,H),(12-538,i-Pro,F-2,O,S,O,1-
Adm,H),(12-539,i-Pro,F-3,O,S,O,1-Adm,H),(12-540,i-Pro,
F-4,O,S,O,1-Adm,H),(12-541,i-Pro,F-5,O,S,O,1-Adm,H),
(12-542,i-Pro,F-6,O,S,O,1-Adm,H),(12-543,i-Pro,F-7,O,S,
O,1-Adm,H),(12-544,i-Pro,F-8,O,S,O,1-Adm,H),(12-545,i-
Pro,F-9,O,S,O,1-Adm,H),(12-546,i-Pro,F-10,O,S,O,1-
Adm,H),(12-547,i-Pro,F-11,O,S,O,1-Adm,H),(12-548,i-
Pro,F-12,O,S,O,1-Adm,H),(12-549,i-Pro,F-13,O,S,O,1-
Adm,H),(12-550,i-Pro,F-14,O,S,O,1-Adm,H),(12-551,i-
Pro,F-15,O,S,O,1-Adm,H),(12-552,i-Pro,F-16,O,S,O,1-
Adm,H),(12-553,i-Pro,F-17,O,S,O,1-Adm,H),(12-554,i-
Pro,F-18,O,S,O,1-Adm,H),(12-555,i-Pro,F-119,O,S,O,1-
Adm,H),(12-556,i-Pro,F-20,O,S,O,1-Adm,H),(12-557,i-
Pro,F-21,O,S,O,1-Adm,H),(12-558,i-Pro,F-22,O,S,O,1-
Adm,H),(12-559,i-Pro,F-23,O,S,O,1-Adm,H),(12-560,i-
Pro,F-24,O,S,O,1-Adm,H),(12-561,i-Pro,F-25,O,S,O,1-
Adm,H),(12-562,i-Pro,F-26,O,S,O,1-Adm,H),(12-563,i-
Pro,F-27,O,S,O,1-Adm,H),(12-564,i-Pro,F-28,O,S,O,1-
Adm,H),(12-565,i-Pro,F-29,O,S,O,1-Adm,H),(12-566,i-
Pro,F-30,O,S,O,1-Adm,H),(12-567,i-Pro,F-31,O,S,O,1-
Adm,H),(12-568,i-Pro,F-32,O,S,O,1-Adm,H),(12-569,i-
Pro,F-33,O,S,O,1-Adm,H),(12-570,i-Pro,F-34,O,S,O,1-
Adm,H),(12-571,i-Pro,F-35,O,S,O,1-Adm,H),(12-572,i-
Pro,F-36,O,S,O,1-Adm,H),(12-573,i-Pro,F-1,O,S,O,2-
Adm,H),(12-574,i-Pro,F-2,O,S,O,2-Adm,H),(12-575,i-Pro,
F-3,O,S,O,2-Adm,H),(12-576,i-Pro,F-4,O,S,O,2-Adm,H),
(12-577,i-Pro,F-5,O,S,O,2-Adm,H),(12-578,i-Pro,F-6,O,S,
O,2-Adm,H),(12-579,i-Pro,F-7,O,S,O,2-Adm,H),(12-580,i-
Pro,F-8,O,S,O,2-Adm,H),(12-581,i-Pro,F-9,O,S,O,2-Adm,
H),(12-582,i-Pro,F-100,O,S,O,2-Adm,H),(12-583,i-Pro,F-
11,O,S,O,2-Adm,H),(12-584,i-Pro,F-12,O,S,O,2-Adm,H),
(12-585,i-Pro,F-13,O,S,O,2-Adm,H),(12-586,i-Pro,F-14,O,
S,O,2-Adm,H),(12-587,i-Pro,F-15,O,S,O,2-Adm,H),(12-
588,i-Pro,F-16,O,S,O,2-Adm,H),(12-589,i-Pro,F-17,O,S,O,
2-Adm,H),(12-590,i-Pro,F-18,O,S,O,2-Adm,H),(12-591,i-
Pro,F-19,O,S,O,2-Adm,H),(12-592,i-Pro,F-20,O,S,O,2-
Adm,H),(12-593,i-Pro,F-21,O,S,O,2-Adm,H),(12-594,i-
Pro,F-22,O,S,O,2-Adm,H),(12-595,i-Pro,F-23,O,S,O,2-
Adm,H),(12-596,i-Pro,F-24,O,S,O,2-Adm,H),(12-597,i-
Pro,F-25,O,S,O,2-Adm,H),(12-598,i-Pro,F-26,O,S,O,2-
Adm,H),(12-599,i-Pro,F-27,O,S,O,2-Adm,H),(12-600,i-
Pro,F-28,O,S,O,2-Adm,H),(12-601,i-Pro,F-29,O,S,O,2-
Adm,H),(12-602, i-Pro,F-30,O,S,O,2-Adm,H),(12-603,i-
Pro,F-31,O,S,O,2-Adm,H),(12-604,i-Pro,F-32,O,S,O,2-
Adm,H),(12-605,i-Pro,F-33,O,S,O,2-Adm,H),(12-606,i-
Pro,F-34,O,S,O,2-Adm,H),(12-607,i-Pro,F-35,O,S,O,2-
Adm,H),(12-608,i-Pro,F-36,O,S,O,2-Adm,H),(12-609,i-
Pro,F-1,O,S,O,5-OH-2-Adm,H),(12-610,i-Pro,F-2,O,S,O,5-
OH-2-Adm,H),(12-611,i-Pro,F-3,O,S,O,5-OH-2-Adm,H),
(12-612,i-Pro,F-4,O,S,O,5-OH-2-Adm,H),(12-613,i-Pro,F-
5,O,S,O,5-OH-2-Adm,H),(12-614,i-Pro,F-6,O,S,O,5-OH-2-
Adm,H),(12-615,i-Pro,F-7,O,S,O,5-OH-2-Adm,H),(12-
616,i-Pro,F-8,O,S,O,5-OH-2-Adm,H),(12-617,i-Pro,F-9,O,
S,O,5-OH-2-Adm,H),(12-618,i-Pro,F-10,O,S,O,5-OH-2-
Adm,H),(12-619,i-Pro,F-11,O,S,O,5-OH-2-Adm,H),(12-
620,i-Pro,F-12,O,S,O,5-OH-2-Adm,H),(12-621,i-Pro,F-13,
O,S,O,5-OH-2-Adm,H),(12-622,i-Pro,F-14,O,S,O,5-OH-2-
Adm,H),(12-623,i-Pro,F-15,O,S,O,5-OH-2-Adm,H),(12-
624,i-Pro,F-16,O,S,O,5-OH-2-Adm,H),(12-625,i-Pro,F-17,
O,S,O,5-OH-2-Adm,H),(12-626,i-Pro,F-18,O,S,O,5-OH-2-
Adm,H),(12-627,i-Pro,F-19,O,S,O,5-OH-2-Adm,H),(12-
628,i-Pro,F-20,O,S,O,5-OH-2-Adm,H),(12-629,i-Pro,F-21,
O,S,O,5-OH-2-Adm,H),(12-630,i-Pro,F-22,O,S,O,5-OH-2-
Adm,H),(12-631,i-Pro,F-23,O,S,O,5-OH-2-Adm,H),(12-
632,i-Pro,F-24,O,S,O,5-OH-2-Adm,H),(12-633,i-Pro,F-25,
O,S,O,5-OH-2-Adm,H),(12-634,i-Pro,F-26,O,S,O,5-OH-2-
Adm,H),(12-635,i-Pro,F-27,O,S,O,5-OH-2-Adm,H),(12-
636,i-Pro,F-28,O,S,O,5-OH-2-Adm,H),(12-637,i-Pro,F-29,
O,S,O,5-OH-2-Adm,H),(12-638,i-Pro,F-30,O,S,O,5-OH-2-
Adm,H),(12-639,i-Pro,F-31,O,S,O,5-OH-2-Adm,H),(12-
640,i-Pro,F-32,O,S,O,5-OH-2-Adm,H),(12-641,i-Pro,F-33,
O,S,O,5-OH-2-Adm,H),(12-642,i-Pro,F-34,O,S,O,5-OH-2-
Adm,H),(12-643,i-Pro,F-35,O,S,O,5-OH-2-Adm,H),(12-
644,i-Pro,F-36,O,S,O,5-OH-2-Adm,H),(12-645,i-Pro,G-1,
O,S,O,1-Adm,H),(12-646,i-Pro,G-2,O,S,O,1-Adm,H),(12-
647,i-Pro,G-3,O,S,O,1-Adm,H),(12-648,i-Pro,G-4,O,S,O,1-
Adm,H),(12-649,i-Pro,G-5,O,S,O,1-Adm,H),(12-650,i-Pro,
G-6,O,S,O,1-Adm,H),(12-651,i-Pro,G-7,O,S,O,1-Adm,H),
(12-652,i-Pro,G-8,O,S,O,1-Adm,H),(12-653,i-Pro,G-9,O,S,
O,1-Adm,H),(12-654,i-Pro,G-1,O,S,O,2-Adm,H),(12-655,i-
Pro,G-2,O,S,O,2-Adm,H),(12-656,i-Pro,G-3,O,S,O,2-Adm,
H),(12-657,i-Pro,G-4,O,S,O,2-Adm,H),(12-658,i-Pro,G-5,
O,S,O,2-Adm,H),(12-659,i-Pro,G-6,O,S,O,2-Adm,H),(12-
660,i-Pro,G-7,O,S,O,2-Adm,H),(12-661,i-Pro,G-8,O,S,O,2-
Adm,H),(12-662,i-Pro,G-9,O,S,O,2-Adm,H),(12-663,i-Pro,
G-1,O,S,O,5-OH-2-Adm,H),(12-664,i-Pro,G-2,O,S,O,5-
OH-2-Adm,H),(12-665,i-Pro,G-3,O,S,O,5-OH-2-Adm,H),
(12-666,i-Pro,G-4,O,S,O,5-OH-2-Adm,H),(12-667,i-Pro,G-
5,O,S,O,5-OH-2-Adm,H),(12-668,i-Pro,G-6,O,S,O,5-OH-
2-Adm,H),(12-669,i-Pro,G-7,O,S,O,5-OH-2-Adm,H),(12-
670,i-Pro,G-8,O,S,O,5-OH-2-Adm,H),(12-671,i-Pro,G-9,O,
S,O,5-OH-2-Adm,H),(12-672,i-Pro,H-1,O,S,O,1-Adm,H),
(12-673,i-Pro,H-2,O,S,O,1-Adm,H),(12-674,i-Pro,H-3,O,S,
O,1-Adm,H),(12-675,i-Pro,H-4,O,S,O,1-Adm,H),(12-676,i-
Pro,H-5,O,S,O,1-Adm,H),(12-677,i-Pro,H-6,O,S,O,1-Adm,
H),(12-678,i-Pro,H-7,O,S,O,1-Adm,H),(12-679,i-Pro,H-8,
O,S,O,1-Adm,H),(12-680,i-Pro,H-9,O,S,O,1-Adm,H),(12-
681,i-Pro,H-1,O,S,O,2-Adm,H),(12-682,i-Pro,H-2,O,S,O,2-
Adm,H),(12-683,i-Pro,H-3,O,S,O,2-Adm,H),(12-684,i-Pro,
H-4,O,S,O,2-Adm,H),(12-685,i-Pro,H-5,O,S,O,2-Adm,H),
(12-686,i-Pro,H-6,O,S,O,2-Adm,H),(12-687,i-Pro,H-7,O,S,
O,2-Adm,H),(12-688,i-Pro,H-8,O,S,O,2-Adm,H),(12-689,i-
Pro,H-9,O,S,O,2-Adm,H),(12-690,i-Pro,H-1,O,S,O,5-OH-
2-Adm,H),(12-691,i-Pro,H-2,O,S,O,5-OH-2-Adm,H),(12-
692,i-Pro,H-3,O,S,O,5-OH-2-Adm,H),(12-693,i-Pro,H-4,O,
S,O,5-OH-2-Adm,H),(12-694,i-Pro,H-5,O,S,O,5-OH-2-
Adm,H),(12-695,i-Pro,H-6,O,S,O,5-OH-2-Adm,H),(12-
696,i-Pro,H-7,O,S,O,5-OH-2-Adm,H),(12-697,i-Pro,H-8,O,
S,O,5-OH-2-Adm,H),(12-698,i-Pro,H-9,O,S,O,5-OH-2-
Adm,H), (12-699,i-Pro,I-1,O,S,O,1-Adm,H),(12-700,i-Pro,

I-2,O,S,O,1-Adm,H),(12-701,i-Pro,I-3,O,S,O,1-Adm,H),
(12-702,i-Pro,I-4,O,S,O,1-Adm,H),(12-703,i-Pro,I-5,O,S,
O,1-Adm,H),(12-704,i-Pro,I-6,O,S,O,1-Adm,H),(12-705,i-
Pro,I-7,O,S,O,1-Adm,H),(12-706,i-Pro,I-8,O,S,O,1-Adm,
H),(12-707,i-Pro,I-9,O,S,O,1-Adm,H),(12-708,i-Pro,I-1,O,
S,O,2-Adm,H),(12-709,i-Pro,I-2,O,S,O,2-Adm,H),(12-710,
i-Pro,I-3,O,S,O,2-Adm,H),(12-711,i-Pro,I-4,O,S,O,2-Adm,
H),(12-712,i-Pro,I-5,O,S,O,2-Adm,H),(12-713,i-Pro,I-6,O,
S,O,2-Adm,H),(12-714,i-Pro,I-7,O,S,O,2-Adm,H),(12-715,
i-Pro,I-8,O,S,O,2-Adm,H),(12-716,i-Pro,I-9,O,S,O,2-Adm,
H),(12-717,i-Pro,I-1,O,S,O,5-OH-2-Adm,H),(12-718,i-Pro,
I-2,O,S,O,5-OH-2-Adm,H),(12-719,i-Pro,I-3,O,S,O,5-OH-
2-Adm,H),(12-720,i-Pro,I-4,O,S,O,5-OH-2-Adm,H),(12-
721,i-Pro,I-5,O,S,O,5-OH-2-Adm,H),(12-722,i-Pro,I-6,O,
S,O,5-OH-2-Adm,H),(12-723,i-Pro,I-7,O,S,O,5-OH-2-
Adm,H),(12-724,i-Pro,I-8,O,S,O,5-OH-2-Adm,H),(12-725,
i-Pro,I-9,O,S,O,5-OH-2-Adm,H),(12-726,i-Pro,J-1,O,S,O,
1-Adm,H),(12-727,i-Pro,J-2,O,S,O,1-Adm,H),(12-728,i-
Pro,J-3,O,S,O,1-Adm,H),(12-729,i-Pro,J-4,O,S,O,1-Adm,
H),(12-730,i-Pro,J-5,O,S,O,1-Adm,H),(12-731,i-Pro,J-6,O,
S,O,1-Adm,H),(12-732,i-Pro,J-7,O,S,O,1-Adm,H),(12-733,
i-Pro,J-8,O,S,O,1-Adm,H),(12-734,i-Pro,J-9,O,S,O,1-Adm,
H),(12-735,i-Pro,J-1,O,S,O,2-Adm,H),(12-736,i-Pro,J-2,O,
S,O,2-Adm,H),(12-737,i-Pro,J-3,O,S,O,2-Adm,H),(12-738,
i-Pro,J-4,O,S,O,2-Adm,H),(12-739,i-Pro,J-5,O,S,O,2-Adm,
H),(12-740,i-Pro,J-6,O,S,O,2-Adm,H),(12-741,i-Pro,J-7,O,
S,O,2-Adm,H),(12-742,i-Pro,J-8,O,S,O,2-Adm,H),(12-743,
i-Pro,J-9,O,S,O,2-Adm,H),(12-744,i-Pro,J-1,O,S,O,5-OH-
2-Adm,H),(12-745,i-Pro,J-2,O,S,O,5-OH-2-Adm,H),(12-
746,i-Pro,J-3,O,S,O,5-OH-2-Adm,H),(12-747,i-Pro,J-4,O,
S,O,5-OH-2-Adm,H),(12-748,i-Pro,J-5,O,S,O,5-OH-2-
Adm,H),(12-749,i-Pro,J-6,O,S,O,5-OH-2-Adm,H),(12-750,
i-Pro,J-7,O,S,O,5-OH-2-Adm,H),(12-751,i-Pro,J-8,O,S,O,
5-OH-2-Adm,H),(12-752,i-Pro,J-9,O,S,O,5-OH-2-Adm,H),
(12-753,i-Pro,K-1,O,S,O,1-Adm,H),(12-754,i-Pro,K-2,O,S,
O,1-Adm,H),(12-755,i-Pro,K-3,O,S,O,1-Adm,H),(12-756,i-
Pro,K-4,O,S,O,1-Adm,H),(12-757,i-Pro,K-5,O,S,O,1-Adm,
H),(12-758,i-Pro,K-6,O,S,O,1-Adm,H),(12-759,i-Pro,K-7,
O,S,O,1-Adm,H),(12-760,i-Pro,K-8,O,S,O,1-Adm,H),(12-
761,i-Pro,K-9,O,S,O,1-Adm,H),(12-762,i-Pro,K-1,O,S,O,2-
Adm,H),(12-763,i-Pro,K-2,O,S,O,2-Adm,H),(12-764,i-Pro,
K-3,O,S,O,2-Adm,H),(12-765,i-Pro,K-4,O,S,O,2-Adm,H),
(12-766,i-Pro,K-5,O,S,O,2-Adm,H),(12-767,i-Pro,K-6,O,S,
O,2-Adm,H),(12-768,i-Pro,K-7,O,S,O,2-Adm,H),(12-769,i-
Pro,K-8,O,S,O,2-Adm,H),(12-770,i-Pro,K-9,O,S,O,2-Adm,
H),(12-771,i-Pro,K-1,O,S,O,5-OH-2-Adm,H),(12-772,i-
Pro,K-2,O,S,O,5-OH-2-Adm,H),(12-773,i-Pro,K-3,O,S,O,
5-OH-2-Adm,H),(12-774,i-Pro,K-4,O,S,O,5-OH-2-Adm,
H),(12-775,i-Pro,K-5,O,S,O,5-OH-2-Adm,H),(12-776,i-
Pro,K-6,O,S,O,5-OH-2-Adm,H),(12-777,i-Pro,K-7,O,S,O,
5-OH-2-Adm,H),(12-778,i-Pro,K-8,O,S,O,5-OH-2-Adm,
H),(12-779,i-Pro,K-9,O,S,O,5-OH-2-Adm,H)

(Compound No., $R^2$,$R^3$,X,Y,Z,$R^4$,$R^5$)=(13-1,Pro,A-1,O,S,
O,1-Adm,H),(13-2,Pro,A-2,O,S,O,1-Adm,H),(13-3,Pro,A-
3,O,S,O,1-Adm,H),(13-4,Pro,A-4,O,S,O,1-Adm,H),(13-5,
Pro,A-5,O,S,O,1-Adm,H),(13-6,Pro,A-6,O,S,O,1-Adm,H),
(13-7,Pro,A-7,O,S,O,1-Adm,H),(13-8,Pro,A-8,O,S,O,1-
Adm,H),(13-9,Pro,A-9,O,S,O,1-Adm,H),(13-11,Pro,A-11,
O,S,O,1-Adm,H),(13-11,Pro,A-11,O,S,O,1-Adm,H),(13-
12,Pro,A-12,O,S,O,1-Adm,H),(13-13,Pro,A-13,O,S,O,1-
Adm,H),(13-14,Pro,A-14,O,S,O,1-Adm,H),(13-15,Pro,A-
15,O,S,O,1-Adm,H),(13-16,Pro,A-16,O,S,O,1-Adm,H),
(13-17,Pro,A-17,O,S,O,1-Adm,H),(13-18,Pro,A-18,O,S,O,
1-Adm,H),(13-19,Pro,A-19,O,S,O,1-Adm,H),(13-20,Pro,A-
20,O,S,O,1-Adm,H),(13-21,Pro,A-21,O,S,O,1-Adm,H),
(13-22,Pro,A-22,O,S,O,1-Adm,H),(13-23,Pro,A-23,O,S,O,
1-Adm,H),(13-24,Pro,A-24,O,S,O,1-Adm,H),(13-25,Pro,A-
25,O,S,O,1-Adm,H),(13-26,Pro,A-26,O,S,O,1-Adm,H),
(13-27,Pro,A-27,O,S,O,1-Adm,H),(13-28,Pro,A-28,O,S,O,
1-Adm,H),(13-29,Pro,A-29,O,S,O,1-Adm,H),(13-30,Pro,A-
30,O,S,O,1-Adm,H),(13-31,Pro,A-31,O,S,O,1-Adm,H),
(13-32,Pro,A-32,O,S,O,1-Adm,H),(13-33,Pro,A-33,O,S,O,
1-Adm,H),(13-34,Pro,A-34,O,S,O,1-Adm,H),(13-35,Pro,A-
35,O,S,O,1-Adm,H),(13-36,Pro,A-36,O,S,O,1-Adm,H),
(13-37,Pro,A-1,O,S,O,2-Adm,H),(13-38,Pro,A-2,O,S,O,2-
Adm,H),(13-39,Pro,A-3,O,S,O,2-Adm,H),(13-40,Pro,A-4,
O,S,O,2-Adm,H),(13-41,Pro,A-5,O,S,O,2-Adm,H),(13-42,
Pro,A-6,O,S,O,2-Adm,H),(13-43,Pro,A-7,O,S,O,2-Adm,
H),(13-44,Pro,A-9,O,S,O,2-Adm,H),(13-45,Pro,A-11,O,S,
O,2-Adm,H),(13-46,Pro,A-12,O,S,O,2-Adm,H),(13-47,Pro,
A-13,O,S,O,2-Adm,H),(13-48,Pro,A-14,O,S,O,2-Adm,H),
(13-49,Pro,A-15,O,S,O,2-Adm,H),(13-50,Pro,A-16,O,S,O,
2-Adm,H),(13-51,Pro,A-17,O,S,O,2-Adm,H),(13-52,Pro,A-
18,O,S,O,2-Adm,H),(13-53,Pro,A-20,O,S,O,2-Adm,H),
(13-54,Pro,A-21,O,S,O,2-Adm,H),(13-55,Pro,A-22,O,S,O,
2-Adm,H),(13-56,Pro,A-23,O,S,O,2-Adm,H),(13-57,Pro,A-
24,O,S,O,2-Adm,H),(13-58,Pro,A-26,O,S,O,2-Adm,H),
(13-59,Pro,A-27,O,S,O,2-Adm,H),(13-60,Pro,A-28,O,S,O,
2-Adm,H),(13-61,Pro,A-29,O,S,O,2-Adm,H),(13-62,Pro,A-
30,O,S,O,2-Adm,H),(13-63,Pro,A-31,O,S,O,2-Adm,H),
(13-64,Pro,A-32,O,S,O,2-Adm,H),(13-65,Pro,A-33,O,S,O,
2-Adm,H),(13-66,Pro,A-34,O,S,O,2-Adm,H),(13-67,Pro,A-
35,O,S,O,2-Adm,H),(13-68,Pro,A-36,O,S,O,2-Adm,H),
(13-69,Pro,A-1,O,S,O,5-OH-2-Adm,H),(13-70,Pro,A-2,O,
S,O,5-OH-2-Adm,H),(13-71,Pro,A-3,O,S,O,5-OH-2-Adm,
H),(13-72,Pro,A-4,O,S,O,5-OH-2-Adm,H),(13-73,Pro,A-5,
O,S,O,5-OH-2-Adm,H),(13-74,Pro,A-6,O,S,O,5-OH-2-
Adm,H),(13-75,Pro,A-7,O,S,O,5-OH-2-Adm,H),(13-76,
Pro,A-8,O,S,O,5-OH-2-Adm,H),(13-77,Pro,A-9,O,S,O,5-
OH-2-Adm,H),(13-78,Pro,A-10,O,S,O,5-OH-2-Adm,H),
(13-79,Pro,A-11,O,S,O,5-OH-2-Adm,H),(13-80,Pro,A-12,
O,S,O,5-OH-2-Adm,H),(13-81,Pro,A-13,O,S,O,5-OH-2-
Adm,H),(13-82,Pro,A-14,O,S,O,5-OH-2-Adm,H),(13-83,
Pro,A-15,O,S,O,5-OH-2-Adm,H),(13-84,Pro,A-16,O,S,O,
5-OH-2-Adm,H),(13-85,Pro,A-17,O,S,O,5-OH-2-Adm,H),
(13-86,Pro,A-18,O,S,O,5-OH-2-Adm,H),(13-87,Pro,A-19,
O,S,O,5-OH-2-Adm,H),(13-88,Pro,A-20,O,S,O,5-OH-2-
Adm,H),(13-89,Pro,A-21,O,S,O,5-OH-2-Adm,H),(13-90,
Pro,A-22,O,S,O,5-OH-2-Adm,H),(13-91,Pro,A-23,O,S,O,
5-OH-2-Adm,H),(13-92,Pro,A-24,O,S,O,5-OH-2-Adm,H),
(13-93,Pro,A-25,O,S,O,5-OH-2-Adm,H),(13-94,Pro,A-26,
O,S,O,5-OH-2-Adm,H),(13-95,Pro,A-27,O,S,O,5-OH-2-
Adm,H),(13-96,Pro,A-28,O,S,O,5-OH-2-Adm,H),(13-97,
Pro,A-29,O,S,O,5-OH-2-Adm,H),(13-98,Pro,A-30,O,S,O,
5-OH-2-Adm,H),(13-99,Pro,A-31,O,S,O,5-OH-2-Adm,H),
(13-100,Pro,A-32,O,S,O,5-OH-2-Adm,H),(13-101,Pro,A-
33,O,S,O,5-OH-2-Adm,H),(13-102,Pro,A-34,O,S,O,5-OH-
2-Adm,H),(13-103,Pro,A-35,O,S,O,5-OH-2-Adm,H),(13-
104,Pro,A-36,O,S,O,5-OH-2-Adm,H),(13-105,Pro,B-1,O,
S,O,1-Adm,H),(13-106,Pro,B-2,O,S,O,1-Adm,H),(13-107,
Pro,B-3,O,S,O,1-Adm,H),(13-108,Pro,B-4,O,S,O,1-Adm,
H),(13-109,Pro,B-5,O,S,O,1-Adm,H),(13-110,Pro,B-6,O,S,
O,1-Adm,H),(13-111,Pro,B-7,O,S,O,1-Adm,H),(13-112,
Pro,B-8,O,S,O,1-Adm,H),(13-113,Pro,B-9,O,S,O,1-Adm,
H),(13-114,Pro,B-11,O,S,O,1-Adm,H),(13-115,Pro,B-11,
O,S,O,1-Adm,H),(13-116,Pro,B-12,O,S,O,1-Adm,H),(13-
117,Pro,B-13,O,S,O,1-Adm,H),(13-118,Pro,B-14,O,S,O,1-
Adm,H),(13-119,Pro,B-15,O,S,O,1-Adm,H),(13-120,Pro,
B-16,O,S,O,1-Adm,H),(13-121,Pro,B-17,O,S,O,1-Adm,H),
(13-122,Pro,B-18,O,S,O,1-Adm,H),(13-123,Pro,B-19,O,S,
O,1-Adm,H),(13-124,Pro,B-20,O,S,O,1-Adm,H),(13-125,
Pro,B-21,O,S,O,1-Adm,H),(13-126,Pro,B-22,O,S,O,1-
Adm,H),(13-127,Pro,B-23,O,S,O,1-Adm,H),(13-128,Pro,
B-24,O,S,O,1-Adm,H),(13-129,Pro,B-25,O,S,O,1-Adm,H), (13-130,Pro,B-26,O,S,O,1-Adm,H),(13-131,Pro,B-27,O,S,O,1-Adm,H),(13-132,Pro,B-28,O,S,O,1-Adm,H),(13-133,Pro,B-29,O,S,O,1-Adm,H),(13-134,Pro,B-30,O,S,O,1-Adm,H),(13-135,Pro,B-31,O,S,O,1-Adm,H),(13-136,Pro,B-32,O,S,O,1-Adm,H),(13-137,Pro,B-33,O,S,O,1-Adm,H),(13-138,Pro,B-34,O,S,O,1-Adm,H),(13-139,Pro,B-35,O,S,O,1-Adm,H),(13-140,Pro,B-36,O,S,O,1-Adm,H),(13-141,Pro,B-1,O,S,O,2-Adm,H),(13-142,Pro,B-2,O,S,O,2-Adm,H),(13-143,Pro,B-3,O,S,O,2-Adm,H),(13-144,Pro,B-4,O,S,O,2-Adm,H),(13-145,Pro,B-5,O,S,O,2-Adm,H),(13-146,Pro,B-6,O,S,O,2-Adm,H),(13-147,Pro,B-7,O,S,O,2-Adm,H),(13-148,Pro,B-8,O,S,O,2-Adm,H),(13-149,Pro,B-9,O,S,O,2-Adm,H),(13-150,Pro,B-10,O,S,O,2-Adm,H),(13-151,Pro,B-11,O,S,O,2-Adm,H),(13-152,Pro,B-12,O,S,O,2-Adm,H),(13-153,Pro,B-13,O,S,O,2-Adm,H),(13-154,Pro,B-14,O,S,O,2-Adm,H),(13-155,Pro,B-15,O,S,O,2-Adm,H),(13-156,Pro,B-16,O,S,O,2-Adm,H),(13-157,Pro,B-17,O,S,O,2-Adm,H),(13-158,Pro,B-18,O,S,O,2-Adm,H),(13-159,Pro,B-19,O,S,O,2-Adm,H),(13-160,Pro,B-20,O,S,O,2-Adm,H),(13-161,Pro,B-21,O,S,O,2-Adm,H),(13-162,Pro,B-22,O,S,O,2-Adm,H),(13-163,Pro,B-23,O,S,O,2-Adm,H),(13-164,Pro,B-24,O,S,O,2-Adm,H),(13-165,Pro,B-25,O,S,O,2-Adm,H),(13-166,Pro,B-26,O,S,O,2-Adm,H),(13-167,Pro,B-27,O,S,O,2-Adm,H),(13-168,Pro,B-28,O,S,O,2-Adm,H),(13-169,Pro,B-29,O,S,O,2-Adm,H),(13-170,Pro,B-30,O,S,O,2-Adm,H),(13-171,Pro,B-31,O,S,O,2-Adm,H),(13-172,Pro,B-32,O,S,O,2-Adm,H),(13-173,Pro,B-33,O,S,O,2-Adm,H),(13-174,Pro,B-34,O,S,O,2-Adm,H),(13-175,Pro,B-35,O,S,O,2-Adm,H),(13-176,Pro,B-36,O,S,O,2-Adm,H),(13-177,Pro,B-1,O,S,O,5-OH-2-Adm,H),(13-178,Pro,B-2,O,S,O,5-OH-2-Adm,H),(13-179,Pro,B-3,O,S,O,5-OH-2-Adm,H),(13-180,Pro,B-4,O,S,O,5-OH-2-Adm,H),(13-181,Pro,B-5,O,S,O,5-OH-2-Adm,H),(13-182,Pro,B-6,O,S,O,5-OH-2-Adm,H),(13-183,Pro,B-7,O,S,O,5-OH-2-Adm,H),(13-184,Pro,B-8,O,S,O,5-OH-2-Adm,H),(13-185,Pro,B-9,O,S,O,5-OH-2-Adm,H),(13-186,Pro,B-10,O,S,O,5-OH-2-Adm,H),(13-187,Pro,B-11,O,S,O,5-OH-2-Adm,H),(13-188,Pro,B-12,O,S,O,5-OH-2-Adm,H),(13-189,Pro,B-13,O,S,O,5-OH-2-Adm,H),(13-190,Pro,B-14,O,S,O,5-OH-2-Adm,H),(13-191,Pro,B-15,O,S,O,5-OH-2-Adm,H),(13-192,Pro,B-16,O,S,O,5-OH-2-Adm,H),(13-193,Pro,B-17,O,S,O,5-OH-2-Adm,H),(13-194,Pro,B-18,O,S,O,5-OH-2-Adm,H),(13-195,Pro,B-19,O,S,O,5-OH-2-Adm,H),(13-196,Pro,B-20,O,S,O,5-OH-2-Adm,H),(13-197,Pro,B-21,O,S,O,5-OH-2-Adm,H),(13-198,Pro,B-22,O,S,O,5-OH-2-Adm,H),(13-199,Pro,B-23,O,S,O,5-OH-2-Adm,H),(13-200,Pro,B-24,O,S,O,5-OH-2-Adm,H),(13-201,Pro,B-25,O,S,O,5-OH-2-Adm,H),(13-202,Pro,B-26,O,S,O,5-OH-2-Adm,H),(13-203,Pro,B-27,O,S,O,5-OH-2-Adm,H),(13-204,Pro,B-28,O,S,O,5-OH-2-Adm,H),(13-205,Pro,B-29,O,S,O,5-OH-2-Adm,H),(13-206,Pro,B-30,O,S,O,5-OH-2-Adm,H),(13-207,Pro,B-31,O,S,O,5-OH-2-Adm,H),(13-208,Pro,B-32,O,S,O,5-OH-2-Adm,H),(13-209,Pro,B-33,O,S,O,5-OH-2-Adm,H),(13-210,Pro,B-34,O,S,O,5-OH-2-Adm,H),(13-211,Pro,B-35,O,S,O,5-OH-2-Adm,H),(13-212,Pro,B-36,O,S,O,5-OH-2-Adm,H),(13-213,Pro,C-1,O,S,O,1-Adm,H),(13-214,Pro,C-2,O,S,O,1-Adm,H),(13-215,Pro,C-3,O,S,O,1-Adm,H),(13-216,Pro,C-4,O,S,O,1-Adm,H),(13-217,Pro,C-5,O,S,O,1-Adm,H),(13-218,Pro,C-6,O,S,O,1-Adm,H),(13-219,Pro,C-7,O,S,O,1-Adm,H),(13-220,Pro,C-8,O,S,O,1-Adm,H),(13-221,Pro,C-9,O,S,O,1-Adm,H),(13-222,Pro,C-1,O,S,O,1-Adm,H),(13-223,Pro,C-11,O,S,O,1-Adm,H),(13-224,Pro,C-12,O,S,O,1-Adm,H),(13-225,Pro,C-13,O,S,O,1-Adm,H),(13-226,Pro,C-14,O,S,O,1-Adm,H),(13-227,Pro,C-15,O,S,O,1-Adm,H),(13-228,Pro,C-16,O,S,O,1-Adm,H),(13-229,Pro,C-17,O,S,O,1-Adm,H),(13-230,Pro,C-18, O,S,O,1-Adm,H),(13-231,Pro,C-19,O,S,O,1-Adm,H),(13-232,Pro,C-20,O,S,O,1-Adm,H),(13-233,Pro,C-21,O,S,O,1-Adm,H),(13-234,Pro,C-22,O,S,O,1-Adm,H),(13-235,Pro,C-23,O,S,O,1-Adm,H),(13-236,Pro,C-24,O,S,O,1-Adm,H),(13-237,Pro,C-25,O,S,O,1-Adm,H),(13-238,Pro,C-26,O,S,O,1-Adm,H),(13-239,Pro,C-27,O,S,O,1-Adm,H),(13-240,Pro,C-28,O,S,O,1-Adm,H),(13-241,Pro,C-29,O,S,O,1-Adm,H),(13-242,Pro,C-30,O,S,O,1-Adm,H),(13-243,Pro,C-31,O,S,O,1-Adm,H),(13-244,Pro,C-32,O,S,O,1-Adm,H),(13-245,Pro,C-33,O,S,O,1-Adm,H),(13-246,Pro,C-34,O,S,O,1-Adm,H),(13-247,Pro,C-35,O,S,O,1-Adm,H),(13-248,Pro,C-36,O,S,O,1-Adm,H),(13-249,Pro,C-1,O,S,O,2-Adm,H),(13-250,Pro,C-2,O,S,O,2-Adm,H),(13-251,Pro,C-3,O,S,O,2-Adm,H),(13-252,Pro,C-4,O,S,O,2-Adm,H),(13-253,Pro,C-5,O,S,O,2-Adm,H),(13-254,Pro,C-6,O,S,O,2-Adm,H),(13-255,Pro,C-7,O,S,O,2-Adm,H),(13-256,Pro,C-8,O,S,O,2-Adm,H),(13-257,Pro,C-9,O,S,O,2-Adm,H),(13-258,Pro,C-10,O,S,O,2-Adm,H),(13-259,Pro,C-11,O,S,O,2-Adm,H),(13-260,Pro,C-12,O,S,O,2-Adm,H),(13-261,Pro,C-13,O,S,O,2-Adm,H),(13-262,Pro,C-14,O,S,O,2-Adm,H),(13-263,Pro,C-15,O,S,O,2-Adm,H),(13-264,Pro,C-16,O,S,O,2-Adm,H),(13-265,Pro,C-17,O,S,O,2-Adm,H),(13-266,Pro,C-18,O,S,O,2-Adm,H),(13-267,Pro,C-19,O,S,O,2-Adm,H),(13-268,Pro,C-20,O,S,O,2-Adm,H),(13-269,Pro,C-21,O,S,O,2-Adm,H),(13-270,Pro,C-22,O,S,O,2-Adm,H),(13-271,Pro,C-23,O,S,O,2-Adm,H),(13-272,Pro,C-24,O,S,O,2-Adm,H),(13-273,Pro,C-25,O,S,O,2-Adm,H),(13-274,Pro,C-26,O,S,O,2-Adm,H),(13-275,Pro,C-27,O,S,O,2-Adm,H),(13-276,Pro,C-28,O,S,O,2-Adm,H),(13-277,Pro,C-29,O,S,O,2-Adm,H),(13-278,Pro,C-30,O,S,O,2-Adm,H),(13-279,Pro,C-31,O,S,O,2-Adm,H),(13-280,Pro,C-32,O,S,O,2-Adm,H),(13-281,Pro,C-33,O,S,O,2-Adm,H),(13-282,Pro,C-34,O,S,O,2-Adm,H),(13-283,Pro,C-35,O,S,O,2-Adm,H),(13-284,Pro,C-36,O,S,O,2-Adm,H),(13-285,Pro,C-1,O,S,O,5-OH-2-Adm,H),(13-286,Pro,C-2,O,S,O,5-OH-2-Adm,H),(13-287,Pro,C-3,O,S,O,5-OH-2-Adm,H),(13-288,Pro,C-4,O,S,O,5-OH-2-Adm,H),(13-289,Pro,C-5,O,S,O,5-OH-2-Adm,H),(13-290,Pro,C-6,O,S,O,5-OH-2-Adm,H),(13-291,Pro,C-7,O,S,O,5-OH-2-Adm,H),(13-292,Pro,C-8,O,S,O,5-OH-2-Adm,H),(13-293,Pro,C-9,O,S,O,5-OH-2-Adm,H),(13-294,Pro,C-10,O,S,O,5-OH-2-Adm,H),(13-295,Pro,C-11,O,S,O,5-OH-2-Adm,H),(13-296,Pro,C-12,O,S,O,5-OH-2-Adm,H),(13-297,Pro,C-13,O,S,O,5-OH-2-Adm,H),(13-298,Pro,C-14,O,S,O,5-OH-2-Adm,H),(13-299,Pro,C-15,O,S,O,5-OH-2-Adm,H),(13-300,Pro,C-16,O,S,O,5-OH-2-Adm,H),(13-301,Pro,C-17,O,S,O,5-OH-2-Adm,H),(13-302,Pro,C-18,O,S,O,5-OH-2-Adm,H),(13-303,Pro,C-19,O,S,O,5-OH-2-Adm,H),(13-304,Pro,C-20,O,S,O,5-OH-2-Adm,H),(13-305,Pro,C-21,O,S,O,5-OH-2-Adm,H),(13-306,Pro,C-22,O,S,O,5-OH-2-Adm,H),(13-307,Pro,C-23,O,S,O,5-OH-2-Adm,H),(13-308,Pro,C-24,O,S,O,5-OH-2-Adm,H),(13-309,Pro,C-25,O,S,O,5-OH-2-Adm,H),(13-310,Pro,C-26,O,S,O,5-OH-2-Adm,H),(13-311,Pro,C-27,O,S,O,5-OH-2-Adm,H),(13-312,Pro,C-28,O,S,O,5-OH-2-Adm,H),(13-313,Pro,C-29,O,S,O,5-OH-2-Adm,H),(13-314,Pro,C-30,O,S,O,5-OH-2-Adm,H),(13-315,Pro,C-31,O,S,O,5-OH-2-Adm,H),(13-316,Pro,C-32,O,S,O,5-OH-2-Adm,H),(13-317,Pro,C-33,O,S,O,5-OH-2-Adm,H),(13-318,Pro,C-34,O,S,O,5-OH-2-Adm,H),(13-319,Pro,C-35,O,S,O,5-OH-2-Adm,H),(13-320,Pro,C-36,O,S,O,5-OH-2-Adm,H),(13-321,Pro,D-1,O,S,O,1-Adm,H),(13-322,Pro,D-2,O,S,O,1-Adm,H),(13-323,Pro,D-3,O,S,O,1-Adm,H),(13-324,Pro,D-4,O,S,O,1-Adm,H),(13-325,Pro,D-5,O,S,O,1-Adm,H),(13-326,Pro,D-6,O,S,O,1-Adm,H),(13-327,Pro,D-7,O,S,O,1-Adm,H),(13-328,Pro,D-8,O,S,O,1-Adm,H),(13-329,Pro,D-9,O,S,O,1-Adm,H),(13-330,Pro,D-11,O,S,O,1-Adm,H),(13-331,Pro,D-11,O,S,O,1-Adm,H), (13-332,Pro,D-12,O,S,O,1-Adm,H),(13-

333,Pro,D-13,O,S,O,1-Adm,H),(13-334,Pro,D-14,O,S,O,1-Adm,H),(13-335,Pro,D-15,O,S,O,1-Adm,H),(13-336,Pro,D-16,O,S,O,1-Adm,H),(13-337,Pro,D-17,O,S,O,1-Adm,H),(13-338,Pro,D-18,O,S,O,1-Adm,H),(13-339,Pro,D-119,O,S,O,1-Adm,H),(13-340,Pro,D-20,O,S,O,1-Adm,H),(13-341,Pro,D-21,O,S,O,1-Adm,H),(13-342,Pro,D-22,O,S,O,1-Adm,H),(13-343,Pro,D-23,O,S,O,1-Adm,H),(13-344,Pro,D-24,O,S,O,1-Adm,H),(13-345,Pro,D-25,O,S,O,1-Adm,H),(13-346,Pro,D-26,O,S,O,1-Adm,H),(13-347,Pro,D-27,O,S,O,1-Adm,H),(13-348,Pro,D-28,O,S,O,1-Adm,H),(13-349,Pro,D-29,O,S,O,1-Adm,H),(13-350,Pro,D-30,O,S,O,1-Adm,H),(13-351,Pro,D-31,O,S,O,1-Adm,H),(13-352,Pro,D-32,O,S,O,1-Adm,H),(13-353,Pro,D-33,O,S,O,1-Adm,H),(13-354,Pro,D-34,O,S,O,1-Adm,H),(13-355,Pro,D-35,O,S,O,1-Adm,H),(13-356,Pro,D-36,O,S,O,1-Adm,H),(13-357,Pro,D-1,O,S,O,2-Adm,H),(13-358,Pro,D-2,O,S,O,2-Adm,H),(13-359,Pro,D-3,O,S,O,2-Adm,H),(13-360,Pro,D-4,O,S,O,2-Adm,H),(13-361,Pro,D-5,O,S,O,2-Adm,H),(13-362,Pro,D-6,O,S,O,2-Adm,H),(13-363,Pro,D-7,O,S,O,2-Adm,H),(13-364,Pro,D-8,O,S,O,2-Adm,H),(13-365,Pro,D-9,O,S,O,2-Adm,H),(13-366,Pro,D-110,O,S,O,2-Adm,H),(13-367,Pro,D-111,O,S,O,2-Adm,H),(13-368,Pro,D-12,O,S,O,2-Adm,H),(13-369,Pro,D-13,O,S,O,2-Adm,H),(13-370,Pro,D-14,O,S,O,2-Adm,H),(13-371,Pro,D-15,O,S,O,2-Adm,H),(13-372,Pro,D-16,O,S,O,2-Adm,H),(13-373,Pro,D-17,O,S,O,2-Adm,H),(13-374,Pro,D-18,O,S,O,2-Adm,H),(13-375,Pro,D-19,O,S,O,2-Adm,H),(13-376,Pro,D-20,O,S,O,2-Adm,H),(13-377,Pro,D-21,O,S,O,2-Adm,H),(13-378,Pro,D-22,O,S,O,2-Adm,H),(13-379,Pro,D-23,O,S,O,2-Adm,H),(13-380,Pro,D-24,O,S,O,2-Adm,H),(13-381,Pro,D-25,O,S,O,2-Adm,H),(13-382,Pro,D-26,O,S,O,2-Adm,H),(13-383,Pro,D-27,O,S,O,2-Adm,H),(13-384,Pro,D-28,O,S,O,2-Adm,H),(13-385,Pro,D-29,O,S,O,2-Adm,H),(13-386,Pro,D-30,O,S,O,2-Adm,H),(13-387,Pro,D-31,O,S,O,2-Adm,H),(13-388,Pro,D-32,O,S,O,2-Adm,H),(13-389,Pro,D-33,O,S,O,2-Adm,H),(13-390,Pro,D-34,O,S,O,2-Adm,H),(13-391,Pro,D-35,O,S,O,2-Adm,H),(13-392,Pro,D-36,O,S,O,2-Adm,H),(13-393,Pro,D-1,O,S,O,5-OH-2-Adm,H),(13-394,Pro,D-2,O,S,O,5-OH-2-Adm,H),(13-395,Pro,D-3,O,S,O,5-OH-2-Adm,H),(13-396,Pro,D-4,O,S,O,5-OH-2-Adm,H),(13-397,Pro,D-5,O,S,O,5-OH-2-Adm,H),(13-398,Pro,D-6,O,S,O,5-OH-2-Adm,H),(13-399,Pro,D-7,O,S,O,5-OH-2-Adm,H),(13-400,Pro,D-8,O,S,O,5-OH-2-Adm,H),(13-401,Pro,D-9,O,S,O,5-OH-2-Adm,H),(13-402,Pro,D-10,O,O,5-OH-2-Adm,H),(13-403,Pro,D-11,O,S,O,5-OH-2-Adm,H),(13-404,Pro,D-12,O,S,O,5-OH-2-Adm,H),(13-405,Pro,D-13,O,S,O,5-OH-2-Adm,H),(13-406,Pro,D-14,O,S,O,5-OH-2-Adm,H),(13-407,Pro,D-15,O,S,O,5-OH-2-Adm,H),(13-408,Pro,D-16,O,S,O,5-OH-2-Adm,H),(13-409,Pro,D-17,O,S,O,5-OH-2-Adm,H),(13-410,Pro,D-18,O,S,O,5-OH-2-Adm,H),(13-411,Pro,D-19,O,S,O,5-OH-2-Adm,H),(13-412,Pro,D-20,O,S,O,5-OH-2-Adm,H),(13-413,Pro,D-21,O,S,O,5-OH-2-Adm,H),(13-414,Pro,D-22,O,S,O,5-OH-2-Adm,H),(13-415,Pro,D-23,O,S,O,5-OH-2-Adm,H),(13-416,Pro,D-24,O,S,O,5-OH-2-Adm,H),(13-417,Pro,D-25,O,S,O,5-OH-2-Adm,H),(13-418,Pro,D-26,O,S,O,5-OH-2-Adm,H),(13-419,Pro,D-27,O,S,O,5-OH-2-Adm,H),(13-420,Pro,D-28,O,S,O,5-OH-2-Adm,H),(13-421,Pro,D-29,O,S,O,5-OH-2-Adm,H),(13-422,Pro,D-30,O,S,O,5-OH-2-Adm,H),(13-423,Pro,D-31,O,S,O,5-OH-2-Adm,H),(13-424,Pro,D-32,O,S,O,5-OH-2-Adm,H),(13-425,Pro,D-33,O,S,O,5-OH-2-Adm,H),(13-426,Pro,D-34,O,S,O,5-OH-2-Adm,H),(13-427,Pro,D-35,O,S,O,5-OH-2-Adm,H),(13-428,Pro,D-36,O,S,O,5-OH-2-Adm,H),(13-429,Pro,E-1,O,S,O,1-Adm,H),(13-430,Pro,E-2,O,S,O,1-Adm,H),(13-431,Pro,E-3,O,S,O,1-Adm,H),(13-432,Pro,E-4,O,S,O,1-Adm,H),(13-433,Pro,E-5,O,S,O,1-Adm,H), (13-434,Pro,E-6,O,S,O,1-Adm,H),(13-435,Pro,E-7,O,S,O,1-Adm,H),(13-436,Pro,E-8,O,S,O,1-Adm,H),(13-437,Pro,E-9,O,S,O,1-Adm,H),(13-438,Pro,E-11,O,S,O,1-Adm,H),(13-439,Pro,E-11,O,S,O,1-Adm,H),(13-440,Pro,E-12,O,S,O,1-Adm,H),(13-441,Pro,E-13,O,S,O,1-Adm,H),(13-442,Pro,E-14,O,S,O,1-Adm,H),(13-443,Pro,E-15,O,S,O,1-Adm,H),(13-444,Pro,E-16,O,S,O,1-Adm,H),(13-445,Pro,E-17,O,S,O,1-Adm,H),(13-446,Pro,E-18,O,S,O,1-Adm,H),(13-447,Pro,E-19,O,S,O,1-Adm,H),(13-448,Pro,E-20,O,S,O,1-Adm,H),(13-449,Pro,E-21,O,S,O,1-Adm,H),(13-450,Pro,E-22,O,S,O,1-Adm,H),(13-451,Pro,E-23,O,S,O,1-Adm,H),(13-452,Pro,E-24,O,S,O,1-Adm,H),(13-453,Pro,E-25,O,S,O,1-Adm,H),(13-454,Pro,E-26,O,S,O,1-Adm,H),(13-455,Pro,E-27,O,S,O,1-Adm,H),(13-456,Pro,E-28,O,S,O,1-Adm,H),(13-457,Pro,E-29,O,S,O,1-Adm,H),(13-458,Pro,E-30,O,S,O,1-Adm,H),(13-459,Pro,E-31,O,S,O,1-Adm,H),(13-460,Pro,E-32,O,S,O,1-Adm,H),(13-461,Pro,E-33,O,S,O,1-Adm,H),(13-462,Pro,E-34,O,S,O,1-Adm,H),(13-463,Pro,E-35,O,S,O,1-Adm,H),(13-464,Pro,E-36,O,S,O,1-Adm,H),(13-465,Pro,E-1,O,S,O,2-Adm,H),(13-466,Pro,E-2,O,S,O,2-Adm,H),(13-467,Pro,E-3,O,S,O,2-Adm,H),(13-468,Pro,E-4,O,S,O,2-Adm,H),(13-469,Pro,E-5,O,S,O,2-Adm,H),(13-470,Pro,E-6,O,S,O,2-Adm,H),(13-471,Pro,E-7,O,S,O,2-Adm,H),(13-472,Pro,E-8,O,S,O,2-Adm,H),(13-473,Pro,E-9,O,S,O,2-Adm,H),(13-474,Pro,E-10,O,S,O,2-Adm,H),(13-475,Pro,E-11,O,S,O,2-Adm,H),(13-476,Pro,E-12,O,S,O,2-Adm,H),(13-477,Pro,E-13,O,S,O,2-Adm,H),(13-478,Pro,E-14,O,S,O,2-Adm,H),(13-479,Pro,E-15,O,S,O,2-Adm,H),(13-480,Pro,E-16,O,S,O,2-Adm,H),(13-481,Pro,E-17,O,S,O,2-Adm,H),(13-482,Pro,E-18,O,S,O,2-Adm,H),(13-483,Pro,E-19,O,S,O,2-Adm,H),(13-484,Pro,E-20,O,S,O,2-Adm,H),(13-485,Pro,E-21,O,S,O,2-Adm,H),(13-486,Pro,E-22,O,S,O,2-Adm,H),(13-487,Pro,E-23,O,S,O,2-Adm,H),(13-488,Pro,E-24,O,S,O,2-Adm,H),(13-489,Pro,E-25,O,S,O,2-Adm,H),(13-490,Pro,E-26,O,S,O,2-Adm,H),(13-491,Pro,E-27,O,S,O,2-Adm,H),(13-492,Pro,E-28,O,S,O,2-Adm,H),(13-493,Pro,E-29,O,S,O,2-Adm,H),(13-494,Pro,E-30,O,S,O,2-Adm,H),(13-495,Pro,E-31,O,S,O,2-Adm,H),(13-496,Pro,E-32,O,S,O,2-Adm,H),(13-497,Pro,E-33,O,S,O,2-Adm,H),(13-498,Pro,E-34,O,S,O,2-Adm,H),(13-499,Pro,E-35,O,S,O,2-Adm,H),(13-500,Pro,E-36,O,S,O,2-Adm,H),(13-501,Pro,E-1,O,S,O,5-OH-2-Adm,H),(13-502,Pro,E-2,O,S,O,5-OH-2-Adm,H),(13-503,Pro,E-3,O,S,O,5-OH-2-Adm,H),(13-504,Pro,E-4,O,S,O,5-OH-2-Adm,H),(13-505,Pro,E-5,O,S,O,5-OH-2-Adm,H),(13-506,Pro,E-6,O,S,O,5-OH-2-Adm,H),(13-507,Pro,E-7,O,S,O,5-OH-2-Adm,H),(13-508,Pro,E-8,O,S,O,5-OH-2-Adm,H),(13-509,Pro,E-9,O,S,O,5-OH-2-Adm,H),(13-510,Pro,E-10,O,S,O,5-OH-2-Adm,H),(13-511,Pro,E-11,O,S,O,5-OH-2-Adm,H),(13-512,Pro,E-12,O,S,O,5-OH-2-Adm,H),(13-513,Pro,E-13,O,S,O,5-OH-2-Adm,H),(13-514,Pro,E-14,O,S,O,5-OH-2-Adm,H),(13-515,Pro,E-15,O,S,O,5-OH-2-Adm,H),(13-516,Pro,E-16,O,S,O,5-OH-2-Adm,H),(13-517,Pro,E-17,O,S,O,5-OH-2-Adm,H),(13-518,Pro,E-18,O,S,O,5-OH-2-Adm,H),(13-519,Pro,E-19,O,S,O,5-OH-2-Adm,H),(13-520,Pro,E-20,O,S,O,5-OH-2-Adm,H),(13-521,Pro,E-21,O,S,O,5-OH-2-Adm,H),(13-522,Pro,E-22,O,S,O,5-OH-2-Adm,H),(13-523,Pro,E-23,O,S,O,5-OH-2-Adm,H),(13-524,Pro,E-24,O,S,O,5-OH-2-Adm,H),(13-525,Pro,E-25,O,S,O,5-OH-2-Adm,H),(13-526,Pro,E-26,O,S,O,5-OH-2-Adm,H),(13-527,Pro,E-27,O,S,O,5-OH-2-Adm,H),(13-528,Pro,E-28,O,S,O,5-OH-2-Adm,H),(13-529,Pro,E-29,O,S,O,5-OH-2-Adm,H),(13-530,Pro,E-30,O,S,O,5-OH-2-Adm,H),(13-531,Pro,E-31,O,S,O,5-OH-2-Adm,H),(13-532,Pro,E-32,O,S,O,5-OH-2-Adm,H),(13-533,Pro,E-33,O,S,O,5-OH-2-Adm,H),(13-534,Pro,E-34,O,S,O,5-OH-2-Adm,H),(13-535,Pro,E-35,O,S,O,5-OH-2-Adm,H), (13-536,Pro,E-36,O,S,O,5-OH-

2-Adm,H),(13-537,Pro,F-1,O,S,O,1-Adm,H),(13-538,Pro,F-2,O,S,O,1-Adm,H),(13-539,Pro,F-3,O,S,O,1-Adm,H),(13-540,Pro,F-4,O,S,O,1-Adm,H),(13-541,Pro,F-5,O,S,O,1-Adm,H),(13-542,Pro,F-6,O,S,O,1-Adm,H),(13-543,Pro,F-7,O,S,O,1-Adm,H),(13-544,Pro,F-8,O,S,O,1-Adm,H),(13-545,Pro,F-9,O,S,O,1-Adm,H),(13-546,Pro,F-11,O,S,O,1-Adm,H),(13-547,Pro,F-11,O,S,O,1-Adm,H),(13-548,Pro,F-12,O,S,O,1-Adm,H),(13-549,Pro,F-13,O,S,O,1-Adm,H),(13-550,Pro,F-14,O,S,O,1-Adm,H),(13-551,Pro,F-15,O,S,O,1-Adm,H),(13-552,Pro,F-16,O,S,O,1-Adm,H),(13-553,Pro,F-17,O,S,O,1-Adm,H),(13-554,Pro,F-18,O,S,O,1-Adm,H),(13-555,Pro,F-19,O,S,O,1-Adm,H),(13-556,Pro,F-20,O,S,O,1-Adm,H),(13-557,Pro,F-21,O,S,O,1-Adm,H),(13-558,Pro,F-22,O,S,O,1-Adm,H),(13-559,Pro,F-23,O,S,O,1-Adm,H),(13-560,Pro,F-24,O,S,O,1-Adm,H),(13-561,Pro,F-25,O,S,O,1-Adm,H),(13-562,Pro,F-26,O,S,O,1-Adm,H),(13-563,Pro,F-27,O,S,O,1-Adm,H),(13-564,Pro,F-28,O,S,O,1-Adm,H),(13-565,Pro,F-29,O,S,O,1-Adm,H),(13-566,Pro,F-30,O,S,O,1-Adm,H),(13-567,Pro,F-31,O,S,O,1-Adm,H),(13-568,Pro,F-32,O,S,O,1-Adm,H),(13-569,Pro,F-33,O,S,O,1-Adm,H),(13-570,Pro,F-34,O,S,O,1-Adm,H),(13-571,Pro,F-35,O,S,O,1-Adm,H),(13-572,Pro,F-36,O,S,O,1-Adm,H),(13-573,Pro,F-1,O,S,O,2-Adm,H),(13-574,Pro,F-2,O,S,O,2-Adm,H),(13-575,Pro,F-3,O,S,O,2-Adm,H),(13-576,Pro,F-4,S,O,2-Adm,H),(13-577,Pro,F-5,O,S,O,2-Adm,H),(13-578,Pro,F-6,O,S,O,2-Adm,H),(13-579,Pro,F-7,O,S,O,2-Adm,H),(13-580,Pro,F-8,O,S,O,2-Adm,H),(13-581,Pro,F-9,O,S,O,2-Adm,H),(13-582,Pro,F-10,O,S,O,2-Adm,H),(13-583,Pro,F-11,O,S,O,2-Adm,H),(13-584,Pro,F-12,O,S,O,2-Adm,H),(13-585,Pro,F-13,O,S,O,2-Adm,H),(13-586,Pro,F-14,O,S,O,2-Adm,H),(13-587,Pro,F-15,O,S,O,2-Adm,H),(13-588,Pro,F-16,O,S,O,2-Adm,H),(13-589,Pro,F-17,O,S,O,2-Adm,H),(13-590,Pro,F-18,O,S,O,2-Adm,H),(13-591,Pro,F-19,O,S,O,2-Adm,H),(13-592,Pro,F-20,O,S,O,2-Adm,H),(13-593,Pro,F-21,O,S,O,2-Adm,H),(13-594,Pro,F-22,O,S,O,2-Adm,H),(13-595,Pro,F-23,O,S,O,2-Adm,H),(13-596,Pro,F-24,O,S,O,2-Adm,H),(13-597,Pro,F-25,O,S,O,2-Adm,H),(13-598,Pro,F-26,O,S,O,2-Adm,H),(13-599,Pro,F-27,O,S,O,2-Adm,H),(13-600,Pro,F-28,O,S,O,2-Adm,H),(13-601,Pro,F-29,O,S,O,2-Adm,H),(13-602,Pro,F-30,O,S,O,2-Adm,H),(13-603,Pro,F-31,O,S,O,2-Adm,H),(13-604,Pro,F-32,O,S,O,2-Adm,H),(13-605,Pro,F-33,O,S,O,2-Adm,H),(13-606,Pro,F-34,O,S,O,2-Adm,H),(13-607,Pro,F-35,O,S,O,2-Adm,H),(13-608,Pro,F-36,O,S,O,2-Adm,H),(13-609,Pro,F-1,O,S,O,5-OH-2-Adm,H),(13-610,Pro,F-2,O,S,O,5-OH-2-Adm,H),(13-611,Pro,F-3,O,S,O,5-OH-2-Adm,H),(13-612,Pro,F-4,O,S,O,5-OH-2-Adm,H),(13-613,Pro,F-5,O,S,O,5-OH-2-Adm,H),(13-614,Pro,F-6,O,S,O,5-OH-2-Adm,H),(13-615,Pro,F-7,O,S,O,5-OH-2-Adm,H),(13-616,Pro,F-8,O,S,O,5-OH-2-Adm,H),(13-617,Pro,F-9,O,S,O,5-OH-2-Adm,H),(13-618,Pro,F-10,O,S,O,5-OH-2-Adm,H),(13-619,Pro,F-11,O,S,O,5-OH-2-Adm,H),(13-620,Pro,F-12,O,S,O,5-OH-2-Adm,H),(13-621,Pro,F-13,O,S,O,5-OH-2-Adm,H),(13-622,Pro,F-14,O,S,O,5-OH-2-Adm,H),(13-623,Pro,F-15,O,S,O,5-OH-2-Adm,H),(13-624,Pro,F-16,O,S,O,5-OH-2-Adm,H),(13-625,Pro,F-17,O,S,O,5-OH-2-Adm,H),(13-626,Pro,F-18,O,S,O,5-OH-2-Adm,H),(13-627,Pro,F-19,O,S,O,5-OH-2-Adm,H),(13-628,Pro,F-20,O,S,O,5-OH-2-Adm,H),(13-629,Pro,F-21,O,S,O,5-OH-2-Adm,H),(13-630,Pro,F-22,O,S,O,5-OH-2-Adm,H),(13-631,Pro,F-23,O,S,O,5-OH-2-Adm,H),(13-632,Pro,F-24,O,S,O,5-OH-2-Adm,H),(13-633,Pro,F-25,O,S,O,5-OH-2-Adm,H),(13-634,Pro,F-26,O,S,O,5-OH-2-Adm,H),(13-635,Pro,F-27,O,S,O,5-OH-2-Adm,H),(13-636,Pro,F-28,O,S,O,5-OH-2-Adm,H),(13-637,Pro,F-29,O,S,O,5-OH-2-Adm,H),(13-638,Pro,F-30,O,S,O,5-OH-2-Adm,H),(13-639,Pro,F-31,O,S,O,5-OH-2-Adm,H),(13-640,Pro,F-32,O,S,O,5-OH-2-Adm,H), (13-641,Pro,F-33,O,S,O,5-OH-2-Adm,H),(13-642,Pro,F-34,O,S,O,5-OH-2-Adm,H),(13-643,Pro,F-35,O,S,O,5-OH-2-Adm,H),(13-644,Pro,F-36,O,S,O,5-OH-2-Adm,H),(13-645,Pro,G-1,O,S,O,1-Adm,H),(13-646,Pro,G-2,O,S,O,1-Adm,H),(13-647,Pro,G-3,O,S,O,1-Adm,H),(13-648,Pro,G-4,O,S,O,1-Adm,H),(13-649,Pro,G-5,O,S,O,1-Adm,H),(13-650,Pro,G-6,O,S,O,1-Adm,H),(13-651,Pro,G-7,O,S,O,1-Adm,H),(13-652,Pro,G-8,O,S,O,1-Adm,H),(13-653,Pro,G-9,O,S,O,1-Adm,H),(13-654,Pro,G-1,O,S,O,2-Adm,H),(13-655,Pro,G-2,O,S,O,2-Adm,H),(13-656,Pro,G-3,O,S,O,2-Adm,H),(13-657,Pro,G-4,O,S,O,2-Adm,H),(13-658,Pro,G-5,O,S,O,2-Adm,H),(13-659,Pro,G-6,O,S,O,2-Adm,H),(13-660,Pro,G-7,O,S,O,2-Adm,H),(13-661,Pro,G-8,O,S,O,2-Adm,H),(13-662,Pro,G-9,O,S,O,2-Adm,H),(13-663,Pro,G-1,O,S,O,5-OH-2-Adm,H),(13-664,Pro,G-2,O,S,O,5-OH-2-Adm,H),(13-665,Pro,G-3,O,S,O,5-OH-2-Adm,H),(13-666,Pro,G-4,O,S,O,5-OH-2-Adm,H),(13-667,Pro,G-5,O,S,O,5-OH-2-Adm,H),(13-668,Pro,G-6,O,S,O,5-OH-2-Adm,H),(13-669,Pro,G-7,O,S,O,5-OH-2-Adm,H),(13-670,Pro,G-8,O,S,O,5-OH-2-Adm,H),(13-671,Pro,G-9,O,S,O,5-OH-2-Adm,H),(13-672,Pro,H-1,O,S,O,1-Adm,H),(13-673,Pro,H-2,O,S,O,1-Adm,H),(13-674,Pro,H-3,O,S,O,1-Adm,H),(13-675,Pro,H-4,O,S,O,1-Adm,H),(13-676,Pro,H-5,O,S,O,1-Adm,H),(13-677,Pro,H-6,O,S,O,1-Adm,H),(13-678,Pro,H-7,O,S,O,1-Adm,H),(13-679,Pro,H-8,O,S,O,1-Adm,H),(13-680,Pro,H-9,O,S,O,1-Adm,H),(13-681,Pro,H-1,O,S,O,2-Adm,H),(13-682,Pro,H-2,O,S,O,2-Adm,H),(13-683,Pro,H-3,O,S,O,2-Adm,H),(13-684,Pro,H-4,O,S,O,2-Adm,H),(13-685,Pro,H-5,O,S,O,2-Adm,H),(13-686,Pro,H-6,O,S,O,2-Adm,H),(13-687,Pro,H-7,O,S,O,2-Adm,H),(13-688,Pro,H-8,O,S,O,2-Adm,H),(13-689,Pro,H-9,O,S,O,2-Adm,H),(13-690,Pro,H-1,O,S,O,5-OH-2-Adm,H),(13-691,Pro,H-2,O,S,O,5-OH-2-Adm,H),(13-692,Pro,H-3,O,S,O,5-OH-2-Adm,H),(13-693,Pro,H-4,O,S,O,5-OH-2-Adm,H),(13-694,Pro,H-5,O,S,O,5-OH-2-Adm,H),(13-695,Pro,H-6,O,S,O,5-OH-2-Adm,H),(13-696,Pro,H-7,O,S,O,5-OH-2-Adm,H),(13-697,Pro,H-8,O,S,O,5-OH-2-Adm,H),(13-698,Pro,H-9,O,S,O,5-OH-2-Adm,H),(13-699,Pro,I-1,O,S,O,1-Adm,H),(13-700,Pro,I-2,O,S,O,1-Adm,H),(13-701,Pro,I-3,O,S,O,1-Adm,H),(13-702,Pro,I-4,O,S,O,1-Adm,H),(13-703,Pro,I-5,O,S,O,1-Adm,H),(13-704,Pro,I-6,O,S,O,1-Adm,H),(13-705,Pro,I-7,O,S,O,1-Adm,H),(13-706,Pro,I-8,O,S,O,1-Adm,H),(13-707,Pro,I-9,O,S,O,1-Adm,H),(13-708,Pro,I-1,O,S,O,2-Adm,H),(13-709,Pro,I-2,O,S,O,2-Adm,H),(13-710,Pro,I-3,O,S,O,2-Adm,H),(13-711,Pro,I-4,O,S,O,2-Adm,H),(13-712,Pro,I-5,O,S,O,2-Adm,H),(13-713,Pro,I-6,O,S,O,2-Adm,H),(13-714,Pro,I-7,O,S,O,2-Adm,H),(13-715,Pro,I-8,O,S,O,2-Adm,H),(13-716,Pro,I-9,O,S,O,2-Adm,H),(13-717,Pro,I-1,O,S,O,5-OH-2-Adm,H),(13-718,Pro,I-2,O,S,O,5-OH-2-Adm,H),(13-719,Pro,I-3,O,S,O,5-OH-2-Adm,H),(13-720,Pro,I-4,O,S,O,5-OH-2-Adm,H),(13-721,Pro,I-5,O,S,O,5-OH-2-Adm,H),(13-722,Pro,I-6,O,S,O,5-OH-2-Adm,H),(13-723,Pro,I-7,O,S,O,5-OH-2-Adm,H),(13-724,Pro,I-8,O,S,O,5-OH-2-Adm,H),(13-725,Pro,I-9,O,S,O,5-OH-2-Adm,H),(13-726,Pro,J-1,O,S,O,1-Adm,H),(13-727,Pro,J-2,O,S,O,1-Adm,H),(13-728,Pro,J-3,O,S,O,1-Adm,H),(13-729,Pro,J-4,O,S,O,1-Adm,H),(13-730,Pro,J-5,O,S,O,1-Adm,H),(13-731,Pro,J-6,O,S,O,1-Adm,H),(13-732,Pro,J-7,O,S,O,1-Adm,H),(13-733,Pro,J-8,O,S,O,1-Adm,H),(13-734,Pro,J-9,O,S,O,1-Adm,H),(13-735,Pro,J-1,O,S,O,2-Adm,H),(13-736,Pro,J-2,O,S,O,2-Adm,H),(13-737,Pro,J-3,O,S,O,2-Adm,H),(13-738,Pro,J-4,O,S,O,2-Adm,H),(13-739,Pro,J-5,O,S,O,2-Adm,H),(13-740,Pro,J-6,O,S,O,2-Adm,H),(13-741,Pro,J-7,O,S,O,2-Adm,H),(13-742,Pro,J-8,O,S,O,2-Adm,H),(13-743,Pro,J-9,O,S,O,2-Adm,H),(13-744,Pro,J-1,O,S,O,5-OH-2-Adm,H),(13-745,Pro,J-2,O,S,O,5-OH-2-Adm,H),(13-746,Pro,J-3,O,S,O,5-OH-2-Adm,H),(13-747,Pro,J-4,O,S,O,

5-OH-2-Adm,H),(13-748,Pro,J-5,O,S,O,5-OH-2-Adm,H),(13-749,Pro,J-6,O,S,O,5-OH-2-Adm,H),(13-750,Pro,J-7,O,S,O,5-OH-2-Adm,H),(13-751,Pro,J-8,O,S,O,5-OH-2-Adm,H),(13-752,Pro,J-9,O,S,O,5-OH-2-Adm,H),(13-753,Pro,K-1,O,S,O,1-Adm,H),(13-754,Pro,K-2,O,S,O,1-Adm,H),(13-755,Pro,K-3,O,S,O,1-Adm,H),(13-756,Pro,K-4,O,S,O,1-Adm,H),(13-757,Pro,K-5,O,S,O,1-Adm,H),(13-758,Pro,K-6,O,S,O,1-Adm,H),(13-759,Pro,K-7,O,S,O,1-Adm,H),(13-760,Pro,K-8,O,S,O,1-Adm,H),(13-761,Pro,K-9,O,S,O,1-Adm,H),(13-762,Pro,K-1,O,S,O,2-Adm,H),(13-763,Pro,K-2,O,S,O,2-Adm,H),(13-764,Pro,K-3,O,S,O,2-Adm,H),(13-765,Pro,K-4,O,S,O,2-Adm,H),(13-766,Pro,K-5,O,S,O,2-Adm,H),(13-767,Pro,K-6,O,S,O,2-Adm,H),(13-768,Pro,K-7,O,S,O,2-Adm,H),(13-769,Pro,K-8,O,S,O,2-Adm,H),(13-770,Pro,K-9,O,S,O,2-Adm,H),(13-771,Pro,K-1,O,S,O,5-OH-2-Adm,H),(13-772,Pro,K-2,O,S,O,5-OH-2-Adm,H),(13-773,Pro,K-3,O,S,O,5-OH-2-Adm,H),(13-774,Pro,K-4,O,S,O,5-OH-2-Adm,H),(13-775,Pro,K-5,O,S,O,5-OH-2-Adm,H),(13-776,Pro,K-6,O,S,O,5-OH-2-Adm,H),(13-777,Pro,K-7,O,S,O,5-OH-2-Adm,H),(13-778,Pro,K-8,O,S,O,5-OH-2-Adm,H),(13-779,Pro,K-9,O,S,O,5-OH-2-Adm,H)

(Compound No., $R^2,R^3,X,Y,Z,R^4,R^5$)=(14-1,Et,A-1,O,S,O,1-Adm,H),(14-2,Et,A-2,O,S,O,1-Adm,H),(14-3,Et,A-3,O,S,O,1-Adm,H),(14-4,Et,A-4,O,S,O,1-Adm,H),(14-5,Et,A-5,O,S,O,1-Adm,H),(14-6,Et,A-6,O,S,O,1-Adm,H),(14-7,Et,A-7,O,S,O,1-Adm,H),(14-8,Et,A-8,O,S,O,1-Adm,H),(14-9,Et,A-9,O,S,O,1-Adm,H),(14-11,Et,A-11,O,S,O,1-Adm,H),(14-11,Et,A-1,O,S,O,1-Adm,H),(14-12,Et,A-12,O,S,O,1-Adm,H),(14-13,Et,A-13,O,S,O,1-Adm,H),(14-14,Et,A-14,O,S,O,1-Adm,H),(14-15,Et,A-15,O,S,O,1-Adm,H),(14-16,Et,A-16,O,S,O,1-Adm,H),(14-17,Et,A-17,O,S,O,1-Adm,H),(14-18,Et,A-18,O,S,O,1-Adm,H),(14-19,Et,A-19,O,S,O,1-Adm,H),(14-20,Et,A-20,O,S,O,1-Adm,H),(14-21,Et,A-21,O,S,O,1-Adm,H),(14-22,Et,A-22,O,S,O,1-Adm,H),(14-23,Et,A-23,O,S,O,1-Adm,H),(14-24,Et,A-24,O,S,O,1-Adm,H),(14-25,Et,A-25,O,S,O,1-Adm,H),(14-26,Et,A-26,O,S,O,1-Adm,H),(14-27,Et,A-27,O,S,O,1-Adm,H),(14-28,Et,A-28,O,S,O,1-Adm,H),(14-29,Et,A-29,O,S,O,1-Adm,H),(14-30,Et,A-30,O,S,O,1-Adm,H),(14-31,Et,A-31,O,S,O,1-Adm,H),(14-32,Et,A-32,O,S,O,1-Adm,H),(14-33,Et,A-33,O,S,O,1-Adm,H),(14-34,Et,A-34,O,S,O,1-Adm,H),(14-35,Et,A-35,O,S,O,1-Adm,H),(14-36,Et,A-36,O,S,O,1-Adm,H),(14-37,Et,A-1,O,S,O,2-Adm,H),(14-38,Et,A-2,O,S,O,2-Adm,H),(14-39,Et,A-3,O,S,O,2-Adm,H),(14-40,Et,A-4,O,S,O,2-Adm,H),(14-41,Et,A-5,O,S,O,2-Adm,H),(14-42,Et,A-6,O,S,O,2-Adm,H),(14-43,Et,A-7,O,S,O,2-Adm,H),(14-44,Et,A-8,O,S,O,2-Adm,H),(14-45,Et,A-9,O,S,O,2-Adm,H),(14-46,Et,A-10,O,S,O,2-Adm,H),(14-47,Et,A-11,O,S,O,2-Adm,H),(14-48,Et,A-12,O,S,O,2-Adm,H),(14-49,Et,A-13,O,S,O,2-Adm,H),(14-50,Et,A-14,O,S,O,2-Adm,H),(14-51,Et,A-15,O,S,O,2-Adm,H),(14-52,Et,A-16,O,S,O,2-Adm,H),(14-53,Et,A-17,O,S,O,2-Adm,H),(14-54,Et,A-18,O,S,O,2-Adm,H),(14-55,Et,A-19,O,S,O,2-Adm,H),(14-56,Et,A-20,O,S,O,2-Adm,H),(14-57,Et,A-21,O,S,O,2-Adm,H),(14-58,Et,A-22,O,S,O,2-Adm,H),(14-59,Et,A-23,O,S,O,2-Adm,H),(14-60,Et,A-24,O,S,O,2-Adm,H),(14-61,Et,A-25,O,S,O,2-Adm,H),(14-62,Et,A-26,O,S,O,2-Adm,H),(14-63,Et,A-27,O,S,O,2-Adm,H),(14-64,Et,A-28,O,S,O,2-Adm,H),(14-65,Et,A-29,O,S,O,2-Adm,H),(14-66,Et,A-30,O,S,O,2-Adm,H),(14-67,Et,A-31,O,S,O,2-Adm,H),(14-68,Et,A-32,O,S,O,2-Adm,H),(14-69,Et,A-33,O,S,O,2-Adm,H),(14-70,Et,A-34,O,S,O,2-Adm,H),(14-71,Et,A-35,O,S,O,2-Adm,H),(14-72,Et,A-36,O,S,O,2-Adm,H),(14-73,Et,A-1,O,S,O,5-OH-2-Adm,H),(14-74,Et,A-2,O,S,O,5-OH-2-Adm,H),(14-75,Et,A-3,O,S,O,5-OH-2-Adm,H),(14-76,Et,A-4,O,S,O,5-OH-2-Adm,H),(14-77,Et,A-5,O,S,O,5-OH-2-Adm,H), (14-78,Et,A-6,O,S,O,5-OH-2-Adm,H),(14-79,Et,A-7,O,S,O,5-OH-2-Adm,H),(14-80,Et,A-8,O,S,O,5-OH-2-Adm,H),(14-81,Et,A-9,O,S,O,5-OH-2-Adm,H),(14-82,Et,A-10,O,S,O,5-OH-2-Adm,H),(14-83,Et,A-11,O,S,O,5-OH-2-Adm,H),(14-84,Et,A-12,O,S,O,5-OH-2-Adm,H),(14-85,Et,A-13,O,S,O,5-OH-2-Adm,H),(14-86,Et,A-14,O,S,O,5-OH-2-Adm,H),(14-87,Et,A-15,O,S,O,5-OH-2-Adm,H),(14-88,Et,A-16,O,S,O,5-OH-2-Adm,H),(14-89,Et,A-17,O,S,O,5-OH-2-Adm,H),(14-90,Et,A-18,O,S,O,5-OH-2-Adm,H),(14-91,Et,A-19,O,S,O,5-OH-2-Adm,H),(14-92,Et,A-20,O,S,O,5-OH-2-Adm,H),(14-93,Et,A-21,O,S,O,5-OH-2-Adm,H),(14-94,Et,A-22,O,S,O,5-OH-2-Adm,H),(14-95,Et,A-23,O,S,O,5-OH-2-Adm,H),(14-96,Et,A-24,O,S,O,5-OH-2-Adm,H),(14-97,Et,A-25,O,S,O,5-OH-2-Adm,H),(14-98,Et,A-26,O,S,O,5-OH-2-Adm,H),(14-99,Et,A-27,O,S,O,5-OH-2-Adm,H),(14-100,Et,A-28,O,S,O,5-OH-2-Adm,H),(14-101,Et,A-29,O,S,O,5-OH-2-Adm,H),(14-102,Et,A-30,O,S,O,5-OH-2-Adm,H),(14-103,Et,A-31,O,S,O,5-OH-2-Adm,H),(14-104,Et,A-32,O,S,O,5-OH-2-Adm,H),(14-105,Et,A-33,O,S,O,5-OH-2-Adm,H),(14-106,Et,A-34,O,S,O,5-OH-2-Adm,H),(14-107,Et,A-35,O,S,O,5-OH-2-Adm,H),(14-108,Et,A-36,O,S,O,5-OH-2-Adm,H),(14-119,Et,B-1,O,S,O,1-Adm,H),(14-111,Et,B-2,O,S,O,1-Adm,H),(14-111,Et,B-3,O,S,O,1-Adm,H),(14-112,Et,B-4,O,S,O,1-Adm,H),(14-113,Et,B-5,O,S,O,1-Adm,H),(14-114,Et,B-6,O,S,O,1-Adm,H),(14-115,Et,B-7,O,S,O,1-Adm,H),(14-116,Et,B-8,O,S,O,1-Adm,H),(14-117,Et,B-9,O,S,O,1-Adm,H),(14-118,Et,B-11,O,S,O,1-Adm,H),(14-119,Et,B-11,O,S,O,1-Adm,H),(14-120,Et,B-12,O,S,O,1-Adm,H),(14-121,Et,B-13,O,S,O,1-Adm,H),(14-122,Et,B-14,O,S,O,1-Adm,H),(14-123,Et,B-15,O,S,O,1-Adm,H),(14-124,Et,B-16,O,S,O,1-Adm,H),(14-125,Et,B-17,O,S,O,1-Adm,H),(14-126,Et,B-18,O,S,O,1-Adm,H),(14-127,Et,B-19,O,S,O,1-Adm,H),(14-128,Et,B-20,O,S,O,1-Adm,H),(14-129,Et,B-21,O,S,O,1-Adm,H),(14-130,Et,B-22,O,S,O,1-Adm,H),(14-131,Et,B-23,O,S,O,1-Adm,H),(14-132,Et,B-24,O,S,O,1-Adm,H),(14-133,Et,B-25,O,S,O,1-Adm,H),(14-134,Et,B-26,O,S,O,1-Adm,H),(14-135,Et,B-27,O,S,O,1-Adm,H),(14-136,Et,B-28,O,S,O,1-Adm,H),(14-137,Et,B-29,O,S,O,1-Adm,H),(14-138,Et,B-30,O,S,O,1-Adm,H),(14-139,Et,B-31,O,S,O,1-Adm,H),(14-140,Et,B-32,O,S,O,1-Adm,H),(14-141,Et,B-33,O,S,O,1-Adm,H),(14-142,Et,B-34,O,S,O,1-Adm,H),(14-143,Et,B-35,O,S,O,1-Adm,H),(14-144,Et,B-36,O,S,O,1-Adm,H),(14-145,Et,B-1,O,S,O,2-Adm,H),(14-146,Et,B-2,O,S,O,2-Adm,H),(14-147,Et,B-3,O,S,O,2-Adm,H),(14-148,Et,B-4,O,S,O,2-Adm,H),(14-149,Et,B-5,O,S,O,2-Adm,H),(14-150,Et,B-6,O,S,O,2-Adm,H),(14-151,Et,B-7,O,S,O,2-Adm,H),(14-152,Et,B-8,O,S,O,2-Adm,H),(14-153,Et,B-9,O,S,O,2-Adm,H),(14-154,Et,B-10,O,S,O,2-Adm,H),(14-155,Et,B-11,O,S,O,2-Adm,H),(14-156,Et,B-12,O,S,O,2-Adm,H),(14-157,Et,B-13,O,S,O,2-Adm,H),(14-158,Et,B-14,O,S,O,2-Adm,H),(14-159,Et,B-15,O,S,O,2-Adm,H),(14-160,Et,B-16,O,S,O,2-Adm,H),(14-161,Et,B-17,O,S,O,2-Adm,H),(14-162,Et,B-18,O,S,O,2-Adm,H),(14-163,Et,B-19,O,S,O,2-Adm,H),(14-164,Et,B-20,O,S,O,2-Adm,H),(14-165,Et,B-21,O,S,O,2-Adm,H),(14-166,Et,B-22,O,S,O,2-Adm,H),(14-167,Et,B-23,O,S,O,2-Adm,H),(14-168,Et,B-24,O,S,O,2-Adm,H),(14-169,Et,B-25,O,S,O,2-Adm,H),(14-170,Et,B-26,O,S,O,2-Adm,H),(14-171,Et,B-27,O,S,O,2-Adm,H),(14-172,Et,B-28,O,S,O,2-Adm,H),(14-173,Et,B-29,O,S,O,2-Adm,H),(14-174,Et,B-30,O,S,O,2-Adm,H),(14-175,Et,B-31,O,S,O,2-Adm,H),(14-176,Et,B-32,O,S,O,2-Adm,H),(14-177,Et,B-33,O,S,O,2-Adm,H),(14-178,Et,B-34,O,S,O,2-Adm,H),(14-179,Et,B-35,O,S,O,2-Adm,H),(14-180,Et,B-36,O,S,O,2-Adm,H),(14-181,Et,B-1,O,S,O,5-OH-2-Adm,H),(14-182,Et,B-2,O,S,O,5-OH-2-Adm,H),(14-183,Et,B-3,O,S,O,5-OH-2-Adm,H),(14-184,Et,B-4,O,S,O,5-OH-2-Adm,H),(14-185,Et,B-5,O,S,O,5-OH-2-Adm,H), (14-186,Et,B-6,O,S,O, 5-OH-2-Adm,H),(14-187,Et,B-7,O,S,O,5-OH-2-Adm,H),(14-188,Et,B-8,O,S,O,5-OH-2-Adm,H),(14-189,Et,B-9,O,S,O,5-OH-2-Adm,H),(14-190,Et,B-10,O,S,O,5-OH-2-Adm,H),(14-191,Et,B-11,O,S,O,5-OH-2-Adm,H),(14-192,Et,B-12,O,S,O,5-OH-2-Adm,H),(14-193,Et,B-13,O,S,O,5-OH-2-Adm,H),(14-194,Et,B-14,O,S,O,5-OH-2-Adm,H),(14-195,Et,B-15,O,S,O,5-OH-2-Adm,H),(14-196,Et,B-16,O,S,O,5-OH-2-Adm,H),(14-197,Et,B-17,O,S,O,5-OH-2-Adm,H),(14-198,Et,B-18,O,S,O,5-OH-2-Adm,H),(14-199,Et,B-19,O,S,O,5-OH-2-Adm,H),(14-200,Et,B-20,O,S,O,5-OH-2-Adm,H),(14-201,Et,B-21,O,S,O,5-OH-2-Adm,H),(14-202,Et,B-22,O,S,O,5-OH-2-Adm,H),(14-203,Et,B-23,O,S,O,5-OH-2-Adm,H),(14-204,Et,B-24,O,S,O,5-OH-2-Adm,H),(14-205,Et,B-25,O,S,O,5-OH-2-Adm,H),(14-206,Et,B-26,O,S,O,5-OH-2-Adm,H),(14-207,Et,B-27,O,S,O,5-OH-2-Adm,H),(14-208,Et,B-28,O,S,O,5-OH-2-Adm,H),(14-209,Et,B-29,O,S,O,5-OH-2-Adm,H),(14-210,Et,B-30,O,S,O,5-OH-2-Adm,H),(14-211,Et,B-31,O,S,O,5-OH-2-Adm,H),(14-212,Et,B-32,O,S,O,5-OH-2-Adm,H),(14-213,Et,B-33,O,S,O,5-OH-2-Adm,H),(14-214,Et,B-34,O,S,O,5-OH-2-Adm,H),(14-215,Et,B-35,O,S,O,5-OH-2-Adm,H),(14-216,Et,B-36,O,S,O,5-OH-2-Adm,H),(14-217,Et,C-1,O,S,O,1-Adm,H),(14-218,Et,C-2,O,S,O,1-Adm,H),(14-219,Et,C-3,O,S,O,1-Adm,H),(14-220,Et,C-4,O,S,O,1-Adm,H),(14-221,Et,C-5,O,S,O,1-Adm,H),(14-222,Et,C-6,O,S,O,1-Adm,H),(14-223,Et,C-7,O,S,O,1-Adm,H),(14-224,Et,C-8,O,S,O,1-Adm,H),(14-225,Et,C-9,O,S,O,1-Adm,H),(14-226,Et,C-11,O,S,O,1-Adm,H),(14-227,Et,C-11,O,S,O,1-Adm,H),(14-228,Et,C-12,O,S,O,1-Adm,H),(14-229,Et,C-13,O,S,O,1-Adm,H),(14-230,Et,C-14,O,S,O,1-Adm,H),(14-231,Et,C-15,O,S,O,1-Adm,H),(14-232,Et,C-16,O,S,O,1-Adm,H),(14-233,Et,C-17,O,S,O,1-Adm,H),(14-234,Et,C-18,O,S,O,1-Adm,H),(14-235,Et,C-19,O,S,O,1-Adm,H),(14-236,Et,C-20,O,S,O,1-Adm,H),(14-237,Et,C-21,O,S,O,1-Adm,H),(14-238,Et,C-22,O,S,O,1-Adm,H),(14-239,Et,C-23,O,S,O,1-Adm,H),(14-240,Et,C-24,O,S,O,1-Adm,H),(14-241,Et,C-25,O,S,O,1-Adm,H),(14-242,Et,C-26,O,S,O,1-Adm,H),(14-243,Et,C-27,O,S,O,1-Adm,H),(14-244,Et,C-28,O,S,O,1-Adm,H),(14-245,Et,C-29,O,S,O,1-Adm,H),(14-246,Et,C-30,O,S,O,1-Adm,H),(14-247,Et,C-31,O,S,O,1-Adm,H),(14-248,Et,C-32,O,S,O,1-Adm,H),(14-249,Et,C-33,O,S,O,1-Adm,H),(14-250,Et,C-34,O,S,O,1-Adm,H),(14-251,Et,C-35,O,S,O,1-Adm,H),(14-252,Et,C-36,O,S,O,1-Adm,H),(14-253,Et,C-1,O,S,O,2-Adm,H),(14-254,Et,C-2,O,S,O,2-Adm,H),(14-255,Et,C-3,O,S,O,2-Adm,H),(14-256,Et,C-4,O,S,O,2-Adm,H),(14-257,Et,C-5,O,S,O,2-Adm,H),(14-258,Et,C-6,O,S,O,2-Adm,H),(14-259,Et,C-7,O,S,O,2-Adm,H),(14-260,Et,C-8,O,S,O,2-Adm,H),(14-261,Et,C-9,O,S,O,2-Adm,H),(14-262,Et,C-10,O,S,O,2-Adm,H),(14-263,Et,C-11,O,S,O,2-Adm,H),(14-264,Et,C-12,O,S,O,2-Adm,H),(14-265,Et,C-13,O,S,O,2-Adm,H),(14-266,Et,C-14,O,S,O,2-Adm,H),(14-267,Et,C-15,O,S,O,2-Adm,H),(14-268,Et,C-16,O,S,O,2-Adm,H),(14-269,Et,C-17,O,S,O,2-Adm,H),(14-270,Et,C-18,O,S,O,2-Adm,H),(14-271,Et,C-19,O,S,O,2-Adm,H),(14-272,Et,C-20,O,S,O,2-Adm,H),(14-273,Et,C-21,O,S,O,2-Adm,H),(14-274,Et,C-22,O,S,O,2-Adm,H),(14-275,Et,C-23,O,S,O,2-Adm,H),(14-276,Et,C-24,O,S,O,2-Adm,H),(14-277,Et,C-25,O,S,O,2-Adm,H),(14-278,Et,C-26,O,S,O,2-Adm,H),(14-279,Et,C-27,O,S,O,2-Adm,H),(14-280,Et,C-28,O,S,O,2-Adm,H),(14-281,Et,C-29,O,S,O,2-Adm,H),(14-282,Et,C-30,O,S,O,2-Adm,H),(14-283,Et,C-31,O,S,O,2-Adm,H),(14-284,Et,C-32,O,S,O,2-Adm,H),(14-285,Et,C-33,O,S,O,2-Adm,H),(14-286,Et,C-34,O,S,O,2-Adm,H),(14-287,Et,C-35,O,S,O,2-Adm,H),(14-288,Et,C-36,O,S,O,2-Adm,H),(14-289,Et,C-1,O,S,O,5-OH-2-Adm,H),(14-290,Et,C-2,O,S,O,5-OH-2-Adm,H),(14-291,Et,C-3,O,S,O,5-OH-2-Adm,H),(14-292,Et,C-4,O,S,O,5-OH-2-Adm,H),(14-293,Et,C-5,O,S,O,5-OH-2-Adm,H),(14-294,Et,C-6,O,S,O,5-OH-2-Adm,H),(14-295,Et,C-7,O,S,O,5-OH-2-Adm,H),(14-296,Et,C-8,O,S,O,5-OH-2-Adm,H),(14-297,Et,C-9,O,S,O,5-OH-2-Adm,H),(14-298,Et,C-10,O,S,O,5-OH-2-Adm,H),(14-299,Et,C-11,O,S,O,5-OH-2-Adm,H),(14-300,Et,C-12,O,S,O,5-OH-2-Adm,H),(14-301,Et,C-13,O,S,O,5-OH-2-Adm,H),(14-302,Et,C-14,O,S,O,5-OH-2-Adm,H),(14-303,Et,C-15,O,S,O,5-OH-2-Adm,H),(14-304,Et,C-16,O,S,O,5-OH-2-Adm,H),(14-305,Et,C-17,O,S,O,5-OH-2-Adm,H),(14-306,Et,C-18,O,S,O,5-OH-2-Adm,H),(14-307,Et,C-19,O,S,O,5-OH-2-Adm,H),(14-308,Et,C-20,O,S,O,5-OH-2-Adm,H),(14-309,Et,C-21,O,S,O,5-OH-2-Adm,H),(14-310,Et,C-22,O,S,O,5-OH-2-Adm,H),(14-311,Et,C-23,O,S,O,5-OH-2-Adm,H),(14-312,Et,C-24,O,S,O,5-OH-2-Adm,H),(14-313,Et,C-25,O,S,O,5-OH-2-Adm,H),(14-314,Et,C-26,O,S,O,5-OH-2-Adm,H),(14-315,Et,C-27,O,S,O,5-OH-2-Adm,H),(14-316,Et,C-28,O,S,O,5-OH-2-Adm,H),(14-317,Et,C-29,O,S,O,5-OH-2-Adm,H),(14-318,Et,C-30,O,S,O,5-OH-2-Adm,H),(14-319,Et,C-31,O,S,O,5-OH-2-Adm,H),(14-320,Et,C-32,O,S,O,5-OH-2-Adm,H),(14-321,Et,C-33,O,S,O,5-OH-2-Adm,H),(14-322,Et,C-34,O,S,O,5-OH-2-Adm,H),(14-323,Et,C-35,O,S,O,5-OH-2-Adm,H),(14-324,Et,C-36,O,S,O,5-OH-2-Adm,H),(14-325,Et,D-1,O,S,O,1-Adm,H),(14-326,Et,D-2,O,S,O,1-Adm,H),(14-327,Et,D-3,O,S,O,1-Adm,H),(14-328,Et,D-4,O,S,O,1-Adm,H),(14-329,Et,D-5,O,S,O,1-Adm,H),(14-330,Et,D-6,O,S,O,1-Adm,H),(14-331,Et,D-7,O,S,O,1-Adm,H),(14-332,Et,D-8,O,S,O,1-Adm,H),(14-333,Et,D-9,O,S,O,1-Adm,H),(14-334,Et,D-11,O,S,O,1-Adm,H),(14-335,Et,D-11,O,S,O,1-Adm,H),(14-336,Et,D-12,O,S,O,1-Adm,H),(14-337,Et,D-13,O,S,O,1-Adm,H),(14-338,Et,D-14,O,S,O,1-Adm,H),(14-339,Et,D-15,O,S,O,1-Adm,H),(14-340,Et,D-16,O,S,O,1-Adm,H),(14-341,Et,D-17,O,S,O,1-Adm,H),(14-342,Et,D-18,O,S,O,1-Adm,H),(14-343,Et,D-19,O,S,O,1-Adm,H),(14-344,Et,D-20,O,S,O,1-Adm,H),(14-345,Et,D-21,O,S,O,1-Adm,H),(14-346,Et,D-22,O,S,O,1-Adm,H),(14-347,Et,D-23,O,S,O,1-Adm,H),(14-348,Et,D-24,O,S,O,1-Adm,H),(14-349,Et,D-25,O,S,O,1-Adm,H),(14-350,Et,D-26,O,S,O,1-Adm,H),(14-351,Et,D-27,O,S,O,1-Adm,H),(14-352,Et,D-28,O,S,O,1-Adm,H),(14-353,Et,D-29,O,S,O,1-Adm,H),(14-354,Et,D-30,O,S,O,1-Adm,H),(14-355,Et,D-31,O,S,O,1-Adm,H),(14-356,Et,D-32,O,S,O,1-Adm,H),(14-357,Et,D-33,O,S,O,1-Adm,H),(14-358,Et,D-34,O,S,O,1-Adm,H),(14-359,Et,D-35,O,S,O,1-Adm,H),(14-360,Et,D-36,O,S,O,1-Adm,H),(14-361,Et,D-1,O,S,O,2-Adm,H),(14-362,Et,D-2,O,S,O,2-Adm,H),(14-363,Et,D-3,O,S,O,2-Adm,H),(14-364,Et,D-4,O,S,O,2-Adm,H),(14-365,Et,D-5,O,S,O,2-Adm,H),(14-366,Et,D-6,O,S,O,2-Adm,H),(14-367,Et,D-7,O,S,O,2-Adm,H),(14-368,Et,D-8,O,S,O,2-Adm,H),(14-369,Et,D-9,O,S,O,2-Adm,H),(14-370,Et,D-10,O,S,O,2-Adm,H),(14-371,Et,D-11,O,S,O,2-Adm,H),(14-372,Et,D-12,O,S,O,2-Adm,H),(14-373,Et,D-13,O,S,O,2-Adm,H),(14-374,Et,D-14,O,S,O,2-Adm,H),(14-375,Et,D-15,O,S,O,2-Adm,H),(14-376,Et,D-16,O,S,O,2-Adm,H),(14-377,Et,D-17,O,S,O,2-Adm,H),(14-378,Et,D-18,O,S,O,2-Adm,H),(14-379,Et,D-19,O,S,O,2-Adm,H),(14-380,Et,D-20,O,S,O,2-Adm,H),(14-381,Et,D-21,O,S,O,2-Adm,H),(14-382,Et,D-22,O,S,O,2-Adm,H),(14-383,Et,D-23,O,S,O,2-Adm,H),(14-384,Et,D-24,O,S,O,2-Adm,H),(14-385,Et,D-25,O,S,O,2-Adm,H),(14-386,Et,D-26,O,S,O,2-Adm,H),(14-387,Et,D-27,O,S,O,2-Adm,H),(14-388,Et,D-28,O,S,O,2-Adm,H),(14-389,Et,D-29,O,S,O,2-Adm,H),(14-390,Et,D-30,O,S,O,2-Adm,H),(14-391,Et,D-31,O,S,O,2-Adm,H),(14-392,Et,D-32,O,S,O,2-Adm,H),(14-393,Et,D-33,O,S,O,2-Adm,H),(14-394,Et,D-34,O,S,O,2-Adm,H),(14-395,Et,D-35,O,S,O,2-Adm,H),(14-396,Et,D-36,O,S,O,2-Adm,H),(14-397,Et,D-1,O,S,O,5-OH-2-Adm,H), (14-398,Et,D-2,O,S,O,5-OH-2-

Adm,H),(14-399,Et,D-3,O,S,O,5-OH-2-Adm,H),(14-400,Et,D-4,O,S,O,5-OH-2-Adm,H),(14-401,Et,D-5,O,S,O,5-OH-2-Adm,H),(14-402,Et,D-6,O,S,O,5-OH-2-Adm,H),(14-403,Et,D-7,O,S,O,5-OH-2-Adm,H),(14-404,Et,D-8,O,S,O,5-OH-2-Adm,H),(14-405,Et,D-9,O,S,O,5-OH-2-Adm,H),(14-406,Et,D-10,O,S,O,5-OH-2-Adm,H),(14-407,Et,D-11,O,S,O,5-OH-2-Adm,H),(14-408,Et,D-12,O,S,O,5-OH-2-Adm,H),(14-409,Et,D-13,O,S,O,5-OH-2-Adm,H),(14-410,Et,D-14,O,S,O,5-OH-2-Adm,H),(14-411,Et,D-15,O,S,O,5-OH-2-Adm,H),(14-412,Et,D-16,O,S,O,5-OH-2-Adm,H),(14-413,Et,D-17,O,S,O,5-OH-2-Adm,H),(14-414,Et,D-18,O,S,O,5-OH-2-Adm,H),(14-415,Et,D-19,O,S,O,5-OH-2-Adm,H),(14-416,Et,D-20,O,S,O,5-OH-2-Adm,H),(14-417,Et,D-21,O,S,O,5-OH-2-Adm,H),(14-418,Et,D-22,O,S,O,5-OH-2-Adm,H),(14-419,Et,D-23,O,S,O,5-OH-2-Adm,H),(14-420,Et,D-24,O,S,O,5-OH-2-Adm,H),(14-421,Et,D-25,O,S,O,5-OH-2-Adm,H),(14-422,Et,D-26,O,S,O,5-OH-2-Adm,H),(14-423,Et,D-27,O,S,O,5-OH-2-Adm,H),(14-424,Et,D-28,O,S,O,5-OH-2-Adm,H),(14-425,Et,D-29,O,S,O,5-OH-2-Adm,H),(14-426,Et,D-30,O,S,O,5-OH-2-Adm,H),(14-427,Et,D-31,O,S,O,5-OH-2-Adm,H),(14-428,Et,D-32,O,S,O,5-OH-2-Adm,H),(14-429,Et,D-33,O,S,O,5-OH-2-Adm,H),(14-430,Et,D-34,O,S,O,5-OH-2-Adm,H),(14-431,Et,D-35,O,S,O,5-OH-2-Adm,H),(14-432,Et,D-36,O,S,O,5-OH-2-Adm,H),(14-433,Et,E-1,O,S,O,1-Adm,H),(14-434,Et,E-2,O,S,O,1-Adm,H),(14-435,Et,E-3,O,S,O,1-Adm,H),(14-436,Et,E-4,O,S,O,1-Adm,H),(14-437,Et,E-5,O,S,O,1-Adm,H),(14-438,Et,E-6,O,S,O,1-Adm,H),(14-439,Et,E-7,O,S,O,1-Adm,H),(14-440,Et,E-8,O,S,O,1-Adm,H),(14-441,Et,E-9,O,S,O,1-Adm,H),(14-442,Et,E-10,O,S,O,1-Adm,H),(14-443,Et,E-11,O,S,O,1-Adm,H),(14-444,Et,E-12,O,S,O,1-Adm,H),(14-445,Et,E-13,O,S,O,1-Adm,H),(14-446,Et,E-14,O,S,O,1-Adm,H),(14-447,Et,E-15,O,S,O,1-Adm,H),(14-448,Et,E-16,O,S,O,1-Adm,H),(14-449,Et,E-17,O,S,O,1-Adm,H),(14-450,Et,E-18,O,S,O,1-Adm,H),(14-451,Et,E-19,O,S,O,1-Adm,H),(14-452,Et,E-20,O,S,O,1-Adm,H),(14-453,Et,E-21,O,S,O,1-Adm,H),(14-454,Et,E-22,O,S,O,1-Adm,H),(14-455,Et,E-23,O,S,O,1-Adm,H),(14-456,Et,E-24,O,S,O,1-Adm,H),(14-457,Et,E-25,O,S,O,1-Adm,H),(14-458,Et,E-26,O,S,O,1-Adm,H),(14-459,Et,E-27,O,S,O,1-Adm,H),(14-460,Et,E-28,O,S,O,1-Adm,H),(14-461,Et,E-29,O,S,O,1-Adm,H),(14-462,Et,E-30,O,S,O,1-Adm,H),(14-463,Et,E-31,O,S,O,1-Adm,H),(14-464,Et,E-32,O,S,O,1-Adm,H),(14-465,Et,E-33,O,S,O,1-Adm,H),(14-466,Et,E-34,O,S,O,1-Adm,H),(14-467,Et,E-35,O,S,O,1-Adm,H),(14-468,Et,E-36,O,S,O,1-Adm,H),(14-469,Et,E-1,O,S,O,2-Adm,H),(14-470,Et,E-2,O,S,O,2-Adm,H),(14-471,Et,E-3,O,S,O,2-Adm,H),(14-472,Et,E-4,O,S,O,2-Adm,H),(14-473,Et,E-5,O,S,O,2-Adm,H),(14-474,Et,E-6,O,S,O,2-Adm,H),(14-475,Et,E-7,O,S,O,2-Adm,H),(14-476,Et,E-8,O,S,O,2-Adm,H),(14-477,Et,E-9,O,S,O,2-Adm,H),(14-478,Et,E-10,O,S,O,2-Adm,H),(14-479,Et,E-11,O,S,O,2-Adm,H),(14-480,Et,E-12,O,S,O,2-Adm,H),(14-481,Et,E-13,O,S,O,2-Adm,H),(14-482,Et,E-14,O,S,O,2-Adm,H),(14-483,Et,E-15,O,S,O,2-Adm,H),(14-484,Et,E-16,O,S,O,2-Adm,H),(14-485,Et,E-17,O,S,O,2-Adm,H),(14-486,Et,E-18,O,S,O,2-Adm,H),(14-487,Et,E-19,O,S,O,2-Adm,H),(14-488,Et,E-20,O,S,O,2-Adm,H),(14-489,Et,E-21,O,S,O,2-Adm,H),(14-490,Et,E-22,O,S,O,2-Adm,H),(14-491,Et,E-23,O,S,O,2-Adm,H),(14-492,Et,E-24,O,S,O,2-Adm,H),(14-493,Et,E-25,O,S,O,2-Adm,H),(14-494,Et,E-26,O,S,O,2-Adm,H),(14-495,Et,E-27,O,S,O,2-Adm,H),(14-496,Et,E-28,O,S,O,2-Adm,H),(14-497,Et,E-29,O,S,O,2-Adm,H),(14-498,Et,E-30,O,S,O,2-Adm,H),(14-499,Et,E-31,O,S,O,2-Adm,H),(14-500,Et,E-32,O,S,O,2-Adm,H),(14-501,Et,E-33,O,S,O,2-Adm,H),(14-502,Et,E-34,O,S,O,2-Adm,H),(14-503,Et,E-35,O,S,O,2-Adm,H),(14-504,Et,E-36,O,S,O,2-Adm,H),(14-505,Et,E-1,O,S,O,5-OH-2-Adm,H),(14-506,Et,E-2,O,S,O,5-OH-2-Adm,H),(14-507,Et,E-3,O,S,O,5-OH-2-Adm,H),(14-508,Et,E-4,O,S,O,5-OH-2-Adm,H),(14-509,Et,E-5,O,S,O,5-OH-2-Adm,H),(14-510,Et,E-6,O,S,O,5-OH-2-Adm,H),(14-511,Et,E-7,O,S,O,5-OH-2-Adm,H),(14-512,Et,E-8,O,S,O,5-OH-2-Adm,H),(14-513,Et,E-9,O,S,O,5-OH-2-Adm,H),(14-514,Et,E-10,O,S,O,5-OH-2-Adm,H),(14-515,Et,E-11,O,S,O,5-OH-2-Adm,H),(14-516,Et,E-12,O,S,O,5-OH-2-Adm,H),(14-517,Et,E-13,O,S,O,5-OH-2-Adm,H),(14-518,Et,E-14,O,S,O,5-OH-2-Adm,H),(14-519,Et,E-15,O,S,O,5-OH-2-Adm,H),(14-520,Et,E-16,O,S,O,5-OH-2-Adm,H),(14-521,Et,E-17,O,S,O,5-OH-2-Adm,H),(14-522,Et,E-18,O,S,O,5-OH-2-Adm,H),(14-523,Et,E-19,O,S,O,5-OH-2-Adm,H),(14-524,Et,E-20,O,S,O,5-OH-2-Adm,H),(14-525,Et,E-21,O,S,O,5-OH-2-Adm,H),(14-526,Et,E-22,O,S,O,5-OH-2-Adm,H),(14-527,Et,E-23,O,S,O,5-OH-2-Adm,H),(14-528,Et,E-24,O,S,O,5-OH-2-Adm,H),(14-529,Et,E-25,O,S,O,5-OH-2-Adm,H),(14-530,Et,E-26,O,S,O,5-OH-2-Adm,H),(14-531,Et,E-27,O,S,O,5-OH-2-Adm,H),(14-532,Et,E-28,O,S,O,5-OH-2-Adm,H),(14-533,Et,E-29,O,S,O,5-OH-2-Adm,H),(14-534,Et,E-30,O,S,O,5-OH-2-Adm,H),(14-535,Et,E-31,O,S,O,5-OH-2-Adm,H),(14-536,Et,E-32,O,S,O,5-OH-2-Adm,H),(14-537,Et,E-33,O,S,O,5-OH-2-Adm,H),(14-538,Et,E-34,O,S,O,5-OH-2-Adm,H),(14-539,Et,E-35,O,S,O,5-OH-2-Adm,H),(14-540,Et,E-36,O,S,O,5-OH-2-Adm,H),(14-541,Et,F-1,O,S,O,1-Adm,H),(14-542,Et,F-2,O,S,O,1-Adm,H),(14-543,Et,F-3,O,S,O,1-Adm,H),(14-544,Et,F-4,O,S,O,1-Adm,H),(14-545,Et,F-5,O,S,O,1-Adm,H),(14-546,Et,F-6,O,S,O,1-Adm,H),(14-547,Et,F-7,O,S,O,1-Adm,H),(14-548,Et,F-8,O,S,O,1-Adm,H),(14-549,Et,F-9,O,S,O,1-Adm,H),(14-550,Et,F-10,O,S,O,1-Adm,H),(14-551,Et,F-11,O,S,O,1-Adm,H),(14-552,Et,F-12,O,S,O,1-Adm,H),(14-553,Et,F-13,O,S,O,1-Adm,H),(14-554,Et,F-14,O,S,O,1-Adm,H),(14-555,Et,F-15,O,S,O,1-Adm,H),(14-556,Et,F-16,O,S,O,1-Adm,H),(14-557,Et,F-17,O,S,O,1-Adm,H),(14-558,Et,F-18,O,S,O,1-Adm,H),(14-559,Et,F-19,O,S,O,1-Adm,H),(14-560,Et,F-20,O,S,O,1-Adm,H),(14-561,Et,F-21,O,S,O,1-Adm,H),(14-562,Et,F-22,O,S,O,1-Adm,H),(14-563,Et,F-23,O,S,O,1-Adm,H),(14-564,Et,F-24,O,S,O,1-Adm,H),(14-565,Et,F-25,O,S,O,1-Adm,H),(14-566,Et,F-26,O,S,O,1-Adm,H),(14-567,Et,F-27,O,S,O,1-Adm,H),(14-568,Et,F-28,O,S,O,1-Adm,H),(14-569,Et,F-29,O,S,O,1-Adm,H),(14-570,Et,F-30,O,S,O,1-Adm,H),(14-571,Et,F-31,O,S,O,1-Adm,H),(14-572,Et,F-32,O,S,O,1-Adm,H),(14-573,Et,F-33,O,S,O,1-Adm,H),(14-574,Et,F-34,O,S,O,1-Adm,H),(14-575,Et,F-35,O,S,O,1-Adm,H),(14-576,Et,F-36,O,S,O,1-Adm,H),(14-577,Et,F-1,O,S,O,2-Adm,H),(14-578,Et,F-2,O,S,O,2-Adm,H),(14-579,Et,F-3,O,S,O,2-Adm,H),(14-580,Et,F-4,O,S,O,2-Adm,H),(14-581,Et,F-5,O,S,O,2-Adm,H),(14-582,Et,F-6,O,S,O,2-Adm,H),(14-583,Et,F-7,O,S,O,2-Adm,H),(14-584,Et,F-8,O,S,O,2-Adm,H),(14-585,Et,F-9,O,S,O,2-Adm,H),(14-586,Et,F-10,O,S,O,2-Adm,H),(14-587,Et,F-11,O,S,O,2-Adm,H),(14-588,Et,F-12,O,S,O,2-Adm,H),(14-589,Et,F-13,O,S,O,2-Adm,H),(14-590,Et,F-14,O,S,O,2-Adm,H),(14-591,Et,F-15,O,S,O,2-Adm,H),(14-592,Et,F-16,O,S,O,2-Adm,H),(14-593,Et,F-17,O,S,O,2-Adm,H),(14-594,Et,F-18,O,S,O,2-Adm,H),(14-595,Et,F-19,O,S,O,2-Adm,H),(14-596,Et,F-20,O,S,O,2-Adm,H),(14-597,Et,F-21,O,S,O,2-Adm,H),(14-598,Et,F-22,O,S,O,2-Adm,H),(14-599,Et,F-23,O,S,O,2-Adm,H),(14-600,Et,F-24,O,S,O,2-Adm,H),(14-601,Et,F-25,O,S,O,2-Adm,H),(14-602,Et,F-26,O,S,O,2-Adm,H),(14-603,Et,F-27,O,S,O,2-Adm,H),(14-604,Et,F-28,O,S,O,2-Adm,H),(14-605,Et,F-29,O,S,O,2-Adm,H),(14-606,Et,F-30,O,S,O,2-Adm,H),(14-607,Et,F-31,O,S,O,2-Adm,H),(14-608,Et,F-32,O,S,O,2-Adm,H),(14-609,Et,F-33,O,S,O,2-Adm,H), (14-610,Et,F-34,O,S,O,2-Adm,H),(14-611,Et,F-

35,O,S,O,2-Adm,H),(14-612,Et,F-36,O,S,O,2-Adm,H),(14-613,Et,F-1,O,S,O,5-OH-2-Adm,H),(14-614,Et,F-2,O,S,O,5-OH-2-Adm,H),(14-615,Et,F-3,O,S,O,5-OH-2-Adm,H),(14-616,Et,F-4,O,S,O,5-OH-2-Adm,H),(14-617,Et,F-5,O,S,O,5-OH-2-Adm,H),(14-618,Et,F-6,O,S,O,5-OH-2-Adm,H),(14-619,Et,F-7,O,S,O,5-OH-2-Adm,H),(14-620,Et,F-8,O,S,O,5-OH-2-Adm,H),(14-621,Et,F-9,O,S,O,5-OH-2-Adm,H),(14-622,Et,F-10,O,S,O,5-OH-2-Adm,H),(14-623,Et,F-11,O,S,O,5-OH-2-Adm,H),(14-624,Et,F-12,O,S,O,5-OH-2-Adm,H),(14-625,Et,F-13,O,S,O,5-OH-2-Adm,H),(14-626,Et,F-14,O,S,O,5-OH-2-Adm,H),(14-627,Et,F-15,O,S,O,5-OH-2-Adm,H),(14-628,Et,F-16,O,S,O,5-OH-2-Adm,H),(14-629,Et,F-17,O,S,O,5-OH-2-Adm,H),(14-630,Et,F-18,O,S,O,5-OH-2-Adm,H),(14-631,Et,F-19,O,S,O,5-OH-2-Adm,H),(14-632,Et,F-20,O,S,O,5-OH-2-Adm,H),(14-633,Et,F-21,O,S,O,5-OH-2-Adm,H),(14-634,Et,F-22,O,S,O,5-OH-2-Adm,H),(14-635,Et,F-23,O,S,O,5-OH-2-Adm,H),(14-636,Et,F-24,O,S,O,5-OH-2-Adm,H),(14-637,Et,F-25,O,S,O,5-OH-2-Adm,H),(14-638,Et,F-26,O,S,O,5-OH-2-Adm,H),(14-639,Et,F-27,O,S,O,5-OH-2-Adm,H),(14-640,Et,F-28,O,S,O,5-OH-2-Adm,H),(14-641,Et,F-29,O,S,O,5-OH-2-Adm,H),(14-642,Et,F-30,O,S,O,5-OH-2-Adm,H),(14-643,Et,F-31,O,S,O,5-OH-2-Adm,H),(14-644,Et,F-32,O,S,O,5-OH-2-Adm,H),(14-645,Et,F-33,O,S,O,5-OH-2-Adm,H),(14-646,Et,F-34,O,S,O,5-OH-2-Adm,H),(14-647,Et,F-35,O,S,O,5-OH-2-Adm,H),(14-648,Et,F-36,O,S,O,5-OH-2-Adm,H),(14-649,Et,G-1,O,S,O,1-Adm,H),(14-650,Et,G-2,O,S,O,1-Adm,H),(14-651,Et,G-3,O,S,O,1-Adm,H),(14-652,Et,G-4,O,S,O,1-Adm,H),(14-653,Et,G-5,O,S,O,1-Adm,H),(14-654,Et,G-6,O,S,O,1-Adm,H),(14-655,Et,G-7,O,S,O,1-Adm,H),(14-656,Et,G-8,O,S,O,1-Adm,H),(14-657,Et,G-9,O,S,O,1-Adm,H),(14-658,Et,G-1,O,S,O,2-Adm,H),(14-659,Et,G-2,O,S,O,2-Adm,H),(14-660,Et,G-3,O,S,O,2-Adm,H),(14-661,Et,G-4,O,S,O,2-Adm,H),(14-662,Et,G-5,O,S,O,2-Adm,H),(14-663,Et,G-6,O,S,O,2-Adm,H),(14-664,Et,G-7,O,S,O,2-Adm,H),(14-665,Et,G-8,O,S,O,2-Adm,H),(14-666,Et,G-9,O,S,O,2-Adm,H),(14-667,Et,G-1,O,S,O,5-OH-2-Adm,H),(14-668,Et,G-2,O,S,O,5-OH-2-Adm,H),(14-669,Et,G-3,O,S,O,5-OH-2-Adm,H),(14-670,Et,G-4,O,S,O,5-OH-2-Adm,H),(14-671,Et,G-5,O,S,O,5-OH-2-Adm,H),(14-672,Et,G-6,O,S,O,5-OH-2-Adm,H),(14-673,Et,G-7,O,S,O,5-OH-2-Adm,H),(14-674,Et,G-8,O,S,O,5-OH-2-Adm,H),(14-675,Et,G-9,O,S,O,5-OH-2-Adm,H),(14-676,Et,H-1,O,S,O,1-Adm,H),(14-677,Et,H-2,O,S,O,1-Adm,H),(14-678,Et,H-3,O,S,O,1-Adm,H),(14-679,Et,H-4,O,S,O,1-Adm,H),(14-680,Et,H-5,O,S,O,1-Adm,H),(14-681,Et,H-6,O,S,O,1-Adm,H),(14-682,Et,H-7,O,S,O,1-Adm,H),(14-683,Et,H-8,O,S,O,1-Adm,H),(14-684,Et,H-9,O,S,O,1-Adm,H),(14-685,Et,H-1,O,S,O,2-Adm,H),(14-686,Et,H-2,O,S,O,2-Adm,H),(14-687,Et,H-3,O,S,O,2-Adm,H),(14-688,Et,H-4,O,S,O,2-Adm,H),(14-689,Et,H-5,O,S,O,2-Adm,H),(14-690,Et,H-6,O,S,O,2-Adm,H),(14-691,Et,H-7,O,S,O,2-Adm,H),(14-692,Et,H-8,O,S,O,2-Adm,H),(14-693,Et,H-9,O,S,O,2-Adm,H),(14-694,Et,H-1,O,S,O,5-OH-2-Adm,H),(14-695,Et,H-2,O,S,O,5-OH-2-Adm,H),(14-696,Et,H-3,O,S,O,5-OH-2-Adm,H),(14-697,Et,H-4,O,S,O,5-OH-2-Adm,H),(14-698,Et,H-5,O,S,O,5-OH-2-Adm,H),(14-699,Et,H-6,O,S,O,5-OH-2-Adm,H),(14-700,Et,H-7,O,S,O,5-OH-2-Adm,H),(14-701,Et,H-8,O,S,O,5-OH-2-Adm,H),(14-702,Et,H-9,O,S,O,5-OH-2-Adm,H),(14-703,Et,I-1,O,S,O,1-Adm,H),(14-704,Et,I-2,O,S,O,1-Adm,H),(14-705,Et,I-3,O,S,O,1-Adm,H),(14-706,Et,I-4,O,S,O,1-Adm,H),(14-707,Et,I-5,O,S,O,1-Adm,H),(14-708,Et,I-6,O,S,O,1-Adm,H),(14-709,Et,I-7,O,S,O,1-Adm,H),(14-710,Et,I-8,O,S,O,1-Adm,H),(14-711,Et,I-9,O,S,O,1-Adm,H),(14-712,Et,I-1,O,S,O,2-Adm,H),(14-713,Et,I-2,O,S,O,2-Adm,H),(14-714,Et,I-3,O,S,O,2-Adm,H),(14-715,Et,I-4,O,S,O,2-Adm,H),(14-716,Et,I-5,O,S,O,2-Adm,H),(14-717,Et,I-6,O,S,O,2-Adm,H),(14-718,Et,I-7,O,S,O,2-Adm,H),(14-719,Et,I-8,O,S,O,2-Adm,H),(14-720,Et,I-9,O,S,O,2-Adm,H),(14-721,Et,I-1,O,S,O,5-OH-2-Adm,H),(14-722,Et,I-2,O,S,O,5-OH-2-Adm,H),(14-723,Et,I-3,O,S,O,5-OH-2-Adm,H),(14-724,Et,I-4,O,S,O,5-OH-2-Adm,H),(14-725,Et,I-5,O,S,O,5-OH-2-Adm,H),(14-726,Et,I-6,O,S,O,5-OH-2-Adm,H),(14-727,Et,I-7,O,S,O,5-OH-2-Adm,H),(14-728,Et,I-8,O,S,O,5-OH-2-Adm,H),(14-729,Et,I-9,O,S,O,5-OH-2-Adm,H),(14-730,Et,J-1,O,S,O,1-Adm,H),(14-731,Et,J-2,O,S,O,1-Adm,H),(14-732,Et,J-3,O,S,O,1-Adm,H),(14-733,Et,J-4,O,S,O,1-Adm,H),(14-734,Et,J-5,O,S,O,1-Adm,H),(14-735,Et,J-6,O,S,O,1-Adm,H),(14-736,Et,J-7,O,S,O,1-Adm,H),(14-737,Et,J-8,O,S,O,1-Adm,H),(14-738,Et,J-9,O,S,O,1-Adm,H),(14-739,Et,J-1,O,S,O,2-Adm,H),(14-740,Et,J-2,O,S,O,2-Adm,H),(14-741,Et,J-3,O,S,O,2-Adm,H),(14-742,Et,J-4,O,S,O,2-Adm,H),(14-743,Et,J-5,O,S,O,2-Adm,H),(14-744,Et,J-6,O,S,O,2-Adm,H),(14-745,Et,J-7,O,S,O,2-Adm,H),(14-746,Et,J-8,O,S,O,2-Adm,H),(14-747,Et,J-9,O,S,O,2-Adm,H),(14-748,Et,J-1,O,S,O,5-OH-2-Adm,H),(14-749,Et,J-2,O,S,O,5-OH-2-Adm,H),(14-750,Et,J-3,O,S,O,5-OH-2-Adm,H),(14-751,Et,J-4,O,S,O,5-OH-2-Adm,H),(14-752,Et,J-5,O,S,O,5-OH-2-Adm,H),(14-753,Et,J-6,O,S,O,5-OH-2-Adm,H),(14-754,Et,J-7,O,S,O,5-OH-2-Adm,H),(14-755,Et,J-8,O,S,O,5-OH-2-Adm,H),(14-756,Et,J-9,O,S,O,5-OH-2-Adm,H),(14-757,Et,K-1,O,S,O,1-Adm,H),(14-758,Et,K-2,O,S,O,1-Adm,H),(14-759,Et,K-3,O,S,O,1-Adm,H),(14-760,Et,K-4,O,S,O,1-Adm,H),(14-761,Et,K-5,O,S,O,1-Adm,H),(14-762,Et,K-6,O,S,O,1-Adm,H),(14-763,Et,K-7,O,S,O,1-Adm,H),(14-764,Et,K-8,O,S,O,1-Adm,H),(14-765,Et,K-9,O,S,O,1-Adm,H),(14-766,Et,K-1,O,S,O,2-Adm,H),(14-767,Et,K-2,O,S,O,2-Adm,H),(14-768,Et,K-3,O,S,O,2-Adm,H),(14-769,Et,K-4,O,S,O,2-Adm,H),(14-770,Et,K-5,O,S,O,2-Adm,H),(14-771,Et,K-6,O,S,O,2-Adm,H),(14-772,Et,K-7,O,S,O,2-Adm,H),(14-773,Et,K-8,O,S,O,2-Adm,H),(14-774,Et,K-9,O,S,O,2-Adm,H),(14-775,Et,K-1,O,S,O,5-OH-2-Adm,H),(14-776,Et,K-2,O,S,O,5-OH-2-Adm,H),(14-777,Et,K-3,O,S,O,5-OH-2-Adm,H),(14-778,Et,K-4,O,S,O,5-OH-2-Adm,H),(14-779,Et,K-5,O,S,O,5-OH-2-Adm,H),(14-780,Et,K-6,O,S,O,5-OH-2-Adm,H),(14-781,Et,K-7,O,S,O,5-OH-2-Adm,H),(14-782,Et,K-8,O,S,O,5-OH-2-Adm,H),(14-783,Et,K-9,O,S,O,5-OH-2-Adm,H)

EXPERIMENTAL EXAMPLE 1

Evaluation of 11β-HSD1 Inhibitors (Enzyme Activity Assay on Human 11β-HSD1)

Enzymatic activity for human 11β-HSD1 was determined in a 10 µl final volume of assay mixture containing 50 mM sodium phosphate buffer (pH 7.6), 1 mg/ml bovine serum albumin, 0.42 mg/ml NADPH, 1.26 mg/ml glucose-6-phosphate, glucose-6-phosphate dehydrogenase, test compound, recombinant human 11β-HSD1, and 5 µM cortisone as substrate. The reaction was started with the addition of cortisone. After incubation for 2 hours at 37° C., 5 µl of europium cryptate-labelled anti-cortisol antibody and 5 µl of XL665-labeled cortisol were added. After further incubation for 2 hours at room temperature, the homogeneous time-resolved fluorescence (HTRF) signal was measured. The cortisol production was quantitated by a standard curve generated with several known concentrations of cortisol in each assay.

The amount of cortisol production without compounds served as control, and the percent inhibition by test compound at each concentration was calculated. The IC50 value of the compound for 11β-HSD1 was obtained using the inhibition curve generated by plotting the percent inhibition versus the concentration of test compound.

EXPERIMENTAL EXAMPLE 2

Evaluation of 11β-HSD1 Inhibitors (Enzyme Activity Assay on Mouse 11β-HSD1)

Enzymatic activity for mouse 11β-HSD1 activity was determined in a 10 µl final volume of assay mixture containing 50 mM sodium phosphate buffer (pH 7.6), 1 mg/ml bovine serum albumin, 0.42 mg/ml NADPH, 1.26 mg/ml glucose-6-phosphate, glucose-6-phosphate dehydrogenase, test compound, recombinant mouse 11β-HSD1, and 2 µM 11-dehydrocorticosterone as substrate. The reaction was started with the addition of 11-dehydrocorticosterone. After incubation for 2 hours at 37° C., 5 µl of europium cryptate-labelled anti-cortisol antibody and 5 µl of XL665-labeled cortisol were added. After further incubation for 2 hours at room temperature, the HTRF signal was measured. The corticosterone production was quantitated by a standard curve generated with several known concentrations of corticosterone in each assay.

The amount of corticosterone production without compounds served as control, and the percent inhibition by compound at each concentration was calculated. The IC50 value of the compound for 11β-HSD1 was obtained using the inhibition curve generated by plotting the percent inhibition versus the concentration of test compound.

The results of experimental example 1 and 2 are shown in the following table.

TABLE 29

| No. | humanIC$_{50}$ (µM) | mouseIC$_{50}$ (µM) |
| --- | --- | --- |
| 9c | 0.18 | 0.5 |
| 12b | 0.14 | 1.6 |
| 24b | 0.82 | 0.17 |
| 29 | 0.043 | 0.33 |
| 27 | 0.26 | 0.038 |
| II-18 | 0.035 | 0.049 |
| II-25 | 0.051 | 0.16 |
| II-49 | 0.071 | 0.023 |
| II-72 | 0.077 | 0.0065 |
| II-117 | 0.095 | 0.021 |
| II-130 | 0.086 | 0.033 |
| II-150 | 0.010 | 0.027 |
| II-153 | 0.025 | 0.014 |

EXPERIMENTAL EXAMPLE 3

Materials and Methods in Oral Absorption of 11β-HSD1 Inhibitor (1) Animals

Male C57BL/6J Jcl mice were purchased from CLEA Japan at the age of 6 weeks. After 1-week preliminary rearing, the mice were used for this study at the age of 7 weeks (2) Rearing Conditions The mice were placed at an animal room, where was set at room temperature of 23±2° C. and humidity of 55±10%, and lighting cycle time was 12 hours [light (8:00-20:00)/dark (20:00-8:00)]. The mice were allowed free access to solid laboratory food (CE-2, CLEA Japan) and sterile tap water through the preliminary rearing and experimental periods.

(3) Identification of Animals and Cages

The mice were identified by tail marking with an oil marker pen. Labels identifying the study director, purchased date, strain, sex and supplier were placed on each cage. The mice were housed by 20 mice/cage in the preliminary rearing period, and 3 mice/cage in the experimental period.

(4) Group Composition

Oral administration: 20 mg/kg (n=3)

Intravenous administration: 5 mg/kg (n=3)

(5) Preparation of Dosing Formulation Dosing suspension for oral administration was prepared using 0.5% methyl cellulose (1500 cP) aqueous solution. Dosing solution for intravenous administration was prepared using N-dimethylacetamide/polyethyleneglycol 400 (½).

(6) Dosing Method

As to oral administration, the dosing suspension at 10 mL/kg was administered into the stomach using a feeding tube. As to intravenous administration, the dosing solution at 2.5 mL/kg was administered into the caudal vein using a glass syringe.

(7) Evaluation Items

The blood samples were collected from the heart at each sampling point. The drug concentration in plasma was measured using HPLC or LC/MS/MS.

(8) Statistical Analysis

The area under the plasma concentration-time curve (AUC) was calculated by WinNonlin®, and the bioavailability was calculated by the AUC values after oral and intravenous administration.

FORMULATION EXAMPLES

The following formulation examples 1 to 8 are provided to further illustrate the present invention and are not intended to limit the scope of the present invention. The term of "active ingredient" means a compound of the present invention, a pharmaceutical acceptable salt, or a hydrate thereof.

Formulation Example 1

Hard gelatin capsules are prepared with the following ingredients:

|  | Dose (mg/capsule) |
| --- | --- |
| Active ingredient | 250 |
| Starch (dried) | 200 |
| Magnesium stearate | 10 |
| Total | 460 mg |

Formulation Example 2

Tablets are prepared with the following ingredients:

|  | Dose (mg/tablet) |
| --- | --- |
| Active ingredient | 250 |
| Cellulose (microcrystal) | 400 |
| Silicon dioxide, fumed | 10 |
| Stearic acid | 5 |
| Total | 665 mg |

The ingredients are blended and compressed to form tablets each weighing 665 mg.

Formulation Example 3

An aerosol solution is prepared containing the following ingredients:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient is mixed with ethanol and the admixture is added to a portion of the propellant 22, cooled to −30° C. and transferred to a filling device. Then the required amount is provided in a stainless steel container and diluted with the reminder of the propellant. The valve units are then attached to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the obtained powder, and then the admixture is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are added to the granules, mixed, and then compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution and flavor are diluted with a portion of the water, added and stirred. Then sufficient water is added to produce the required volume.

Formulation Example 8

An intravenous formulation may be prepared as follows:

| Active ingredient | 100 mg |
| --- | --- |
| Saturated fatty acid glycerides | 1000 mL |

The solution of the above ingredients is generally administered intravenously to a patient at a rate of 1 mL per minute.

INDUSTRIAL APPLICABILITY

As is apparent from the experiment as described above, the compounds according to the invention have an inhibitory activity on 11-hydroxysteroid dehydrogenase type 1. Thus, the compounds according to the invention are useful as pharmaceutical compositions for treating diabetes.

The invention claimed is:
1. A compound represented by the formula (I):

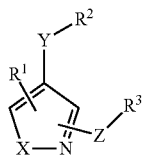

or a pharmaceutically acceptable salt thereof,
wherein
R$^1$ is a group of the formula: —C(═O)NR$^4$R$^5$,
wherein R$^4$ and R$^5$ are each independently, hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or R$^4$ and R$^5$ taken together with the adjacent nitrogen atom to which they are attached may form an optionally substituted ring or
a group of the formula: —NR$^6$C(═O)R$^7$,
wherein R$^6$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted aralkyl or a group of the formula: —C(═O)R$^8$, R$^7$ and R$^8$ are each independently, hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or R$^7$ and R$^8$ taken together with the adjacent carbon atom to which they are attached may form an optionally substituted ring,
X and Y are each independently, —O— or —S—,
Z is a bond, —O— or —S—,
R$^2$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl or optionally substituted carbamoyl,
R$^3$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted amino, optionally substituted sulfamoyl or a group of the formula: —R$^9$—C(R$^{10}$R$^{11}$)—R$^{12}$—R$^{13}$,
R$^9$ is —(CH$_2$)$_m$—, wherein m is an integer of 0 to 3,
R$^{10}$ and R$^{11}$ are each independently, hydrogen, optionally substituted alkyl or halogen; or R$^{10}$ and R$^{11}$ taken together with the adjacent carbon atom to which they are attached may form an optionally substituted ring,
R$^{12}$ is —(CH$_2$)$_n$—, wherein n is an integer of 0 to 3,
R$^{13}$ is hydrogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkoxycarbonyl, optionally substituted aralkylcarbonyl, optionally substituted carbamoyl, optionally substituted thiocarbamoyl, optionally substituted alkylsulfonyl, optionally substituted arylsulfonyl, optionally substituted sulfamoyl, optionally substituted amino, optionally substituted carbamoyloxy, optionally substituted alkoxy, optionally substituted alkylthio,
a group of the formula: —C(═O)—NR$^{14}$R$^{15}$,
wherein R$^{14}$ and R$^{15}$ are each independently, hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted arylsulfonyl, optionally substituted heteroarylsulfonyl or optionally substituted heterocycle sulfonyl; or R$^{14}$ and R$^{15}$ taken together with the adjacent nitrogen atom to which they are attached may form an optionally substituted ring or
a group of the formula: —NR$^{16}$R$^{17}$,
wherein R$^{16}$ and R$^{17}$ are each independently, hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted arylsulfonyl, optionally substituted alkyloxycarbonyl or optionally substituted sulfamoyl; or R$^{16}$ and R$^{17}$ taken together with the adjacent nitrogen atom to which they are attached may form an optionally substituted ring,
provided that, when R$^2$ encompasses a cyclic group and Y is —S—, then the compound is any one of compounds shown as follows

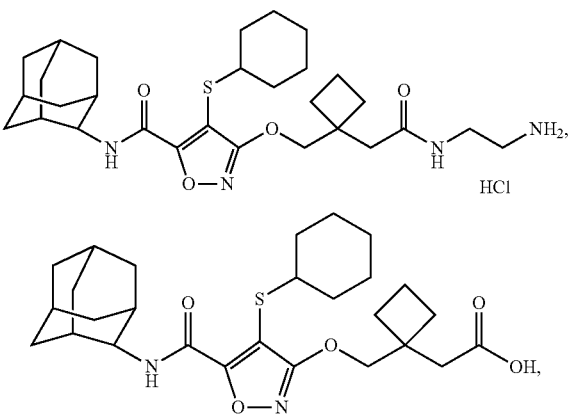

243
-continued
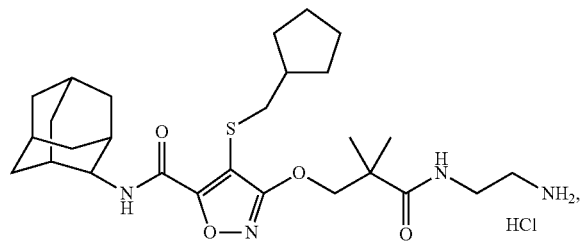
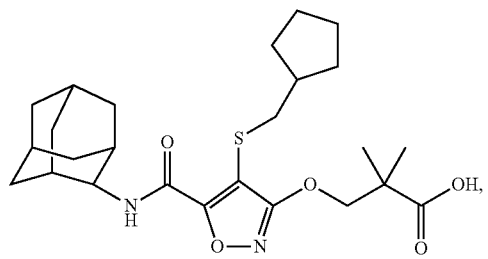
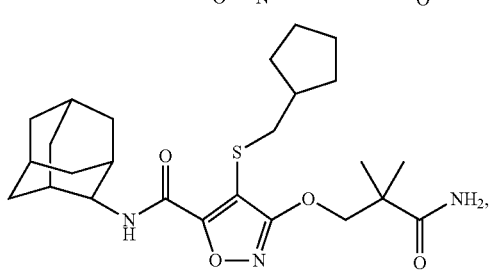
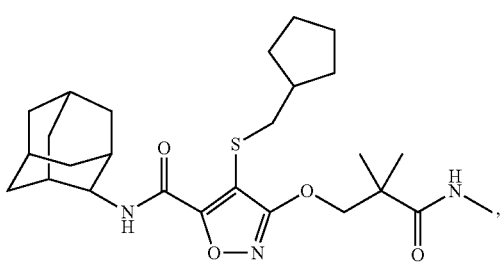
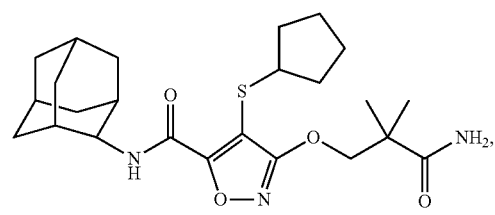
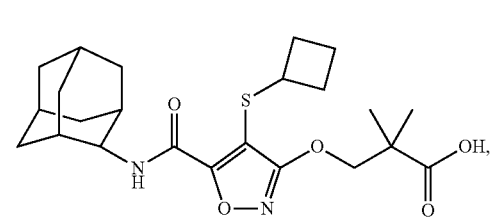
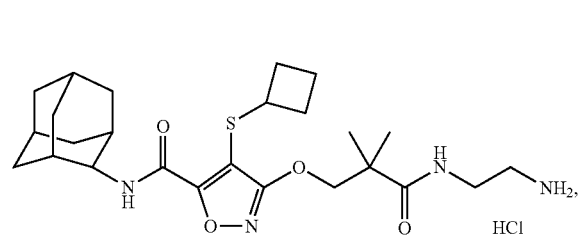
244
-continued
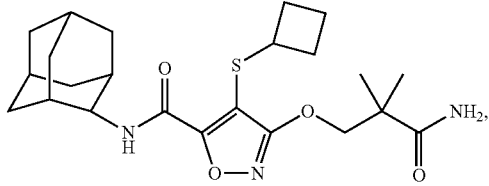
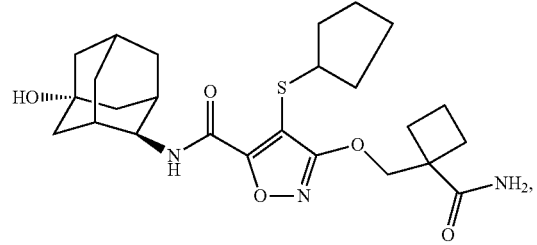
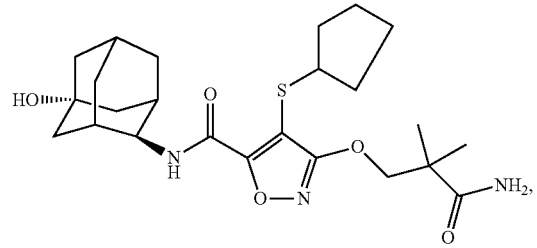
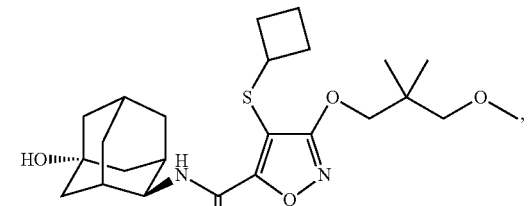
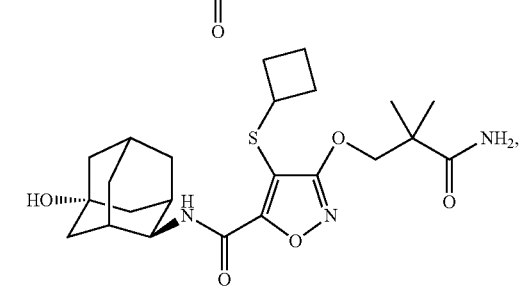
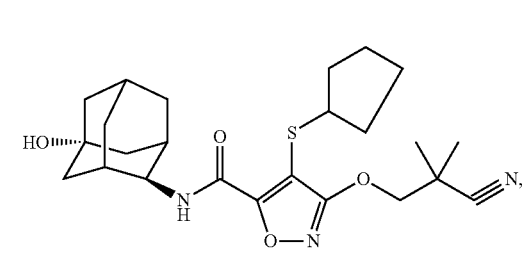
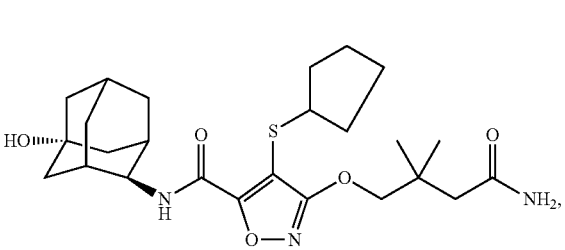

245
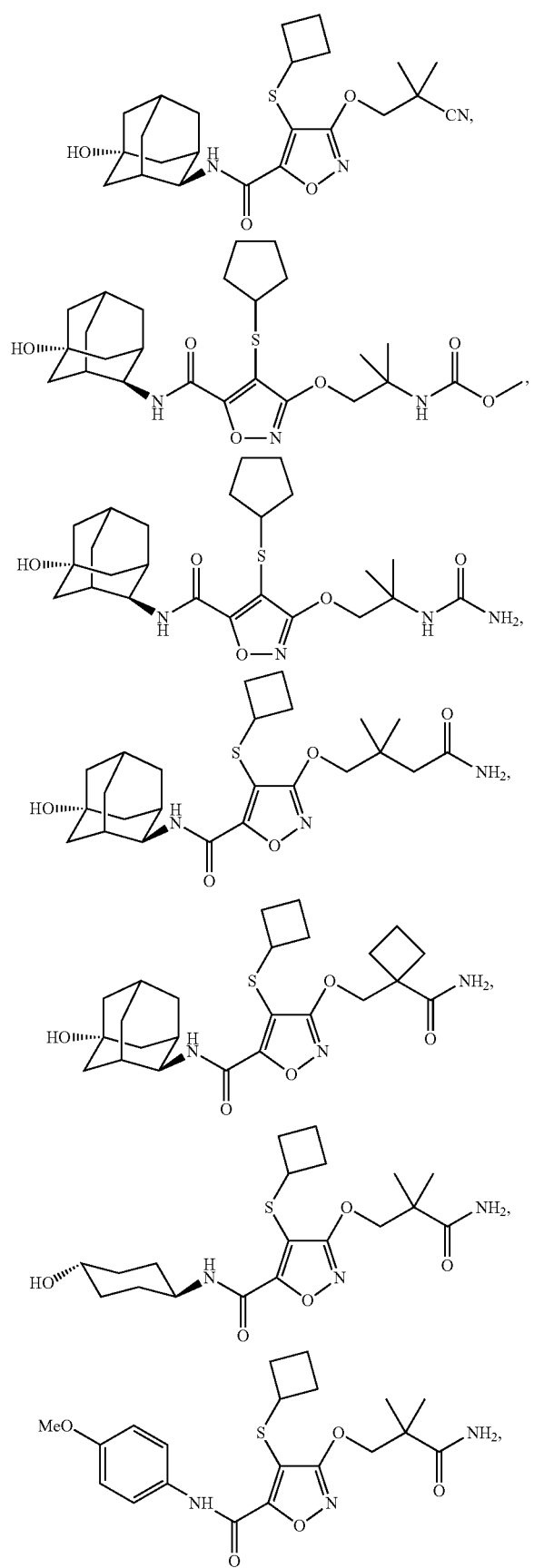
246
-continued
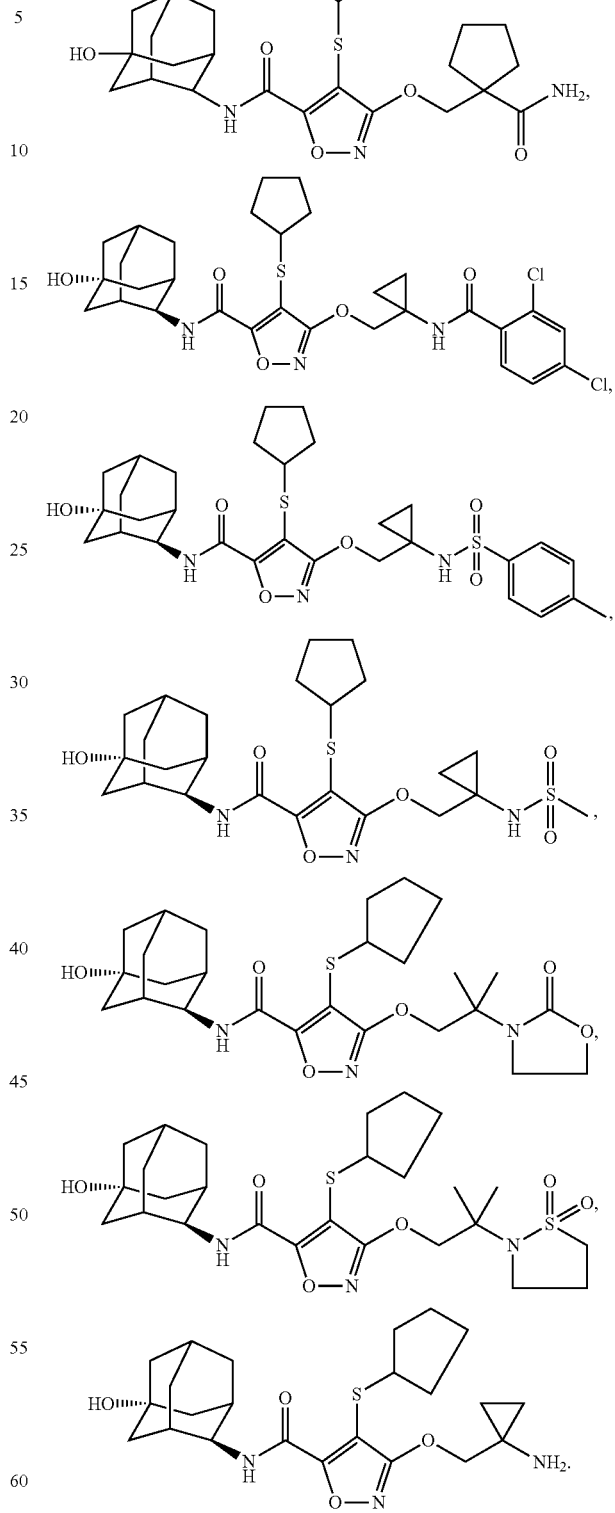
2. The compound according to claim 1, or a pharmaceutically acceptable salt thereof, wherein the compound of the formula (I):

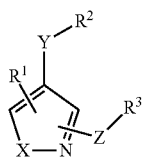

is a compound of the formula (II) represented below.

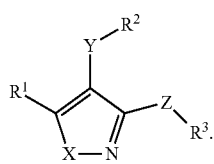

3. The compound according to claim 2, or a pharmaceutically acceptable salt thereof, wherein $R^1$ is a group of the formula: —C(=O)NR$^4$R$^5$, Y is —S— and z is 0.

4. The compound according to claim 1, or a pharmaceutically acceptable salt thereof, wherein $R^1$ is a group of the formula; —C(=O)NR$^4$R$^5$ wherein $R^4$ and $R^5$ have the same meaning as defined in claim 1.

5. The compound according to claim 4, or a pharmaceutically acceptable salt thereof, wherein either one of $R^4$ and $R^5$ is optionally substituted cycloalkyl.

6. The compound according to claim 5, or a pharmaceutically acceptable salt thereof, wherein either one of $R^4$ and $R^5$ is optionally substituted adamantyl.

7. The compound according to claim 4, or a pharmaceutically acceptable salt thereof,
wherein $R^1$ is a group of the formula (III):

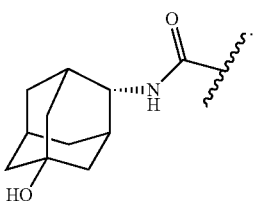

8. The compound according to a one of claim 1, a pharmaceutically acceptable salt or a solvate thereof, wherein $R^2$ is optionally substituted alkyl, optionally substituted cycloalkyl, optionally substituted aryl, optionally substituted heteroaryl or optionally substituted heterocycle.

9. The compound according to claim 1, or a pharmaceutically acceptable salt thereof, wherein $R^2$ is
optionally substituted alkyl wherein the substituent of said optionally substituted alkyl does not encompass a cyclic group,
optionally substituted alkenyl wherein the substituent of said optionally substituted alkenyl does not encompass a cyclic group,
optionally substituted alkynyl wherein the substituent of said optionally substituted alkynyl does not encompass a cyclic group,
optionally substituted acyl wherein the substituent of said optionally substituted acyl does not encompass a cyclic group or
optionally substituted carbamoyl wherein the substituent of said optionally substituted carbamoyl does not encompass a cyclic group.

10. The compound according to claim 9, or a pharmaceutically acceptable salt thereof, wherein $R^2$ is optionally substituted alkyl wherein the substituent of said optionally substituted alkyl does not encompass a cyclic group.

11. The compound according to claim 10, or a pharmaceutically acceptable salt thereof, wherein $R^2$ is branched alkyl.

12. The compound according to claim 1, or a pharmaceutically acceptable salt or a solvate thereof, wherein $R^3$ is a group of the formula: —R$^9$—C(R$^{10}$R$^{11}$)—R$^{12}$—R$^{13}$ wherein $R^9$, $R^{10}$, $R^{11}$, $R^{12}$ and $R^{13}$ have the same meaning as defined in claim 1.

13. The compound according to claim 12, a pharmaceutically acceptable salt thereof, wherein $R^9$ is —CH$_2$—.

14. The compound according to claim 12, or a pharmaceutically acceptable salt thereof, wherein $R^{10}$ and $R^{11}$ are each independently optionally substituted alkyl; or
$R^{10}$ and $R^{11}$ taken together with the adjacent carbon atom to which they are attached may form an optionally substituted ring.

15. The compound according to claim 12, or a pharmaceutically acceptable salt thereof, wherein $R^{12}$ is —(CH$_2$)$_n$— wherein n is an integer of 0 to 1.

16. The compound according to claim 12, or a pharmaceutically acceptable salt thereof, wherein $R^{13}$ is carboxy, cyano or heterocycle.

17. The compound according to claim 12, or a pharmaceutically acceptable salt or a solvate thereof, wherein $R^{13}$ is a group of the formula: —C(=O)—NR$^{14}$R$^{15}$, wherein $R^{14}$ and $R^{15}$ are each independently hydrogen, optionally substituted alkyl, optionally substituted aryl, optionally substituted cycloalkyl, optionally substituted alkylsulfonyl, optionally substituted arylsulfonyl, optionally substituted heteroarylsulfonyl, optionally substituted heterocycle sulfonyl or optionally substituted heterocycle; or $R^{14}$ and $R^{15}$ taken together with the adjacent nitrogen atom to which they are attached may form an optionally substituted ring.

18. The compound according to claim 12, or a pharmaceutically acceptable salt or a solvate thereof, wherein $R^{13}$ is a group of the formula: —NR$^{16}$R$^{17}$.

19. The compound according to claim 18, or a pharmaceutically acceptable salt thereof, wherein $R^{16}$ is a group of the formula: —C(=O)R', wherein R' is optionally substituted alkyl, optionally substituted alkenyl, optionally substituted cycloalkyl, optionally substituted aryl, optionally substituted amino or optionally substituted alkoxy.

20. The compound according to claim 1, or a pharmaceutically acceptable salt thereof, wherein X and/or Z is(are) —O—.

21. The compound according to claim 1, or a pharmaceutically acceptable salt thereof, wherein Y is —S—.

22. A pharmaceutical composition which comprises the compound according to claim 1, or a pharmaceutically acceptable salt thereof.

23. The pharmaceutical composition according to claim 22, which has an inhibitory activity on 11β-hydroxysteroid dehydrogenase type 1.

24. The pharmaceutical composition according to claim 22 for treating diabetes.

25. A method for treating diabetes, comprising administering the compound of claim 1, a pharmaceutically acceptable salt thereof.

* * * * *